US012371701B2

(12) United States Patent
Kelliher et al.

(10) Patent No.: US 12,371,701 B2
(45) **Date of Patent: *Jul. 29, 2025**

(54) HAPLOID INDUCTION COMPOSITIONS AND METHODS FOR USE THEREFOR

(71) Applicant: Syngenta Participations AG, Basel (CH)

(72) Inventors: Timothy Kelliher, RTP, NC (US); Satya Chintamanani, Slater, IA (US); Brent Delzer, Janesville, WI (US); Michael L Nuccio, Durham, NC (US); Robert Arthur Dietrich, RTP, NC (US); Suresh Babu Kadaru, Hydrabad (IN); Todd Lee Warner, Stanton, MN (US); William Paul Bullock, Slater, IA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/524,717

(22) Filed: Nov. 30, 2023

(65) Prior Publication Data

US 2024/0099213 A1 Mar. 28, 2024

Related U.S. Application Data

(62) Division of application No. 17/691,549, filed on Mar. 10, 2022, now Pat. No. 12,035,666, which is a division of application No. 17/174,515, filed on Feb. 12, 2021, now Pat. No. 11,840,697, which is a division of application No. 16/218,529, filed on Dec. 13, 2018, now Pat. No. 10,954,523, which is a division of application No. 15/586,649, filed on May 4, 2017, now Pat. No. 10,190,125, which is a division of application No. 14/212,504, filed on Mar. 14, 2014, now Pat. No. 9,677,082.

(60) Provisional application No. 61/852,428, filed on Mar. 15, 2013.

(51) Int. Cl.

| | |
|---|---|
| ***C12N 15/82*** | (2006.01) |
| ***A01H 1/04*** | (2006.01) |
| ***A01H 1/08*** | (2006.01) |
| ***C12N 9/18*** | (2006.01) |
| ***C12Q 1/6895*** | (2018.01) |
| *C12Q 1/686* | (2018.01) |

(52) U.S. Cl.

CPC ......... *C12N 15/8216* (2013.01); *A01H 1/045* (2021.01); *A01H 1/08* (2013.01); *C12N 9/18* (2013.01); *C12N 15/8218* (2013.01); *C12N 15/8247* (2013.01); *C12N 15/8261* (2013.01); *C12N 15/8287* (2013.01); *C12Q 1/6895* (2013.01); *C12Y 301/01002* (2013.01); *C12N 2310/14* (2013.01); *C12N 2310/20* (2017.05); *C12Q 1/686* (2013.01); *Y02A 40/146* (2018.01)

(58) Field of Classification Search

CPC .................................................. C12N 15/8216
USPC .......................................................... 800/285
See application file for complete search history.

(56) References Cited

U.S. PATENT DOCUMENTS

| | | | | |
|---|---|---|---|---|
| 7,411,117 | B2 | 8/2008 | Bohning | |
| 8,207,092 | B2 | 6/2012 | Bhatti et al. | |
| 9,677,082 | B2 * | 6/2017 | Chintamanani | C12Q 1/6895 |
| 10,190,125 | B2 * | 1/2019 | Chintamanani | C12N 15/8261 |
| 10,954,523 | B2 * | 3/2021 | Kelliher | C12N 15/8216 |
| 10,954,532 | B2 | 3/2021 | Groenestijin et al. | |
| 11,840,697 | B2 * | 12/2023 | Kelliher | C12N 15/8218 |
| 2006/0123505 | A1 | 7/2006 | Kikuchi et al. | |
| 2009/0029860 | A1 | 1/2009 | Moffatt et al. | |
| 2012/0090047 | A1 | 4/2012 | Ren et al. | |
| 2014/0298532 | A1 | 10/2014 | Dhawan et al. | |
| 2015/0184194 | A1 | 7/2015 | Bidney et al. | |

FOREIGN PATENT DOCUMENTS

| | | | |
|---|---|---|---|
| CN | 102440179 | A | 5/2012 |
| CN | 104726449 | A | 6/2015 |
| CN | 109837295 | A | 6/2019 |
| EP | 0127313 | A1 | 12/1984 |
| EP | 3091076 | A1 | 11/2016 |
| WO | 201230893 | A1 | 3/2012 |
| WO | 2013169802 | A1 | 11/2013 |
| WO | 2014093718 | A1 | 6/2014 |
| WO | 2014/151749 | A1 | 9/2014 |
| WO | 2016075255 | A1 | 11/2015 |

(Continued)

OTHER PUBLICATIONS

Alexandrov et al, Plant Mol. Biology, 69(1-2), pp. 179-194, 2009.

(Continued)

*Primary Examiner* — Li Zheng
(74) *Attorney, Agent, or Firm* — Amanda Bublitz

(57) ABSTRACT

Provided here are methods of using a mutated patatin-like phospholipase IIα ("pPLAIIα," renamed here MATRILINEAL) to induce haploid induction in plants, cloning a pPLAIIα to induce haploid induction in plants, and genetically engineering a plant to contain a mutated pPLAIIα. Also provided are methods of applying topical and spray chemicals, lipids, and RNAi molecules to plants during pollination in order to induce haploid production. Further provided are methods of chemically treating plants during pollination to induce haploids while also reducing embryo abortion and increasing seed set.

2 Claims, 16 Drawing Sheets

Specification includes a Sequence Listing.

(56) References Cited

FOREIGN PATENT DOCUMENTS

| | | | |
|---|---|---|---|
| WO | 2016177887 | A1 | 11/2016 |
| WO | 2018/102816 | A1 | 7/2018 |

OTHER PUBLICATIONS

Hae Jin Kim et al: "Endoplasmic Reticulum- and Golgi-Localized Phospholipase A2 Plays Critical Roles in Arabidopsis Pollen Development and Germination", The American Society of Plant Biologists, The Plant Cell, Jan. 2011, vol. 23 (p. 94-110).
Li et al.: "Overexpression of Patatin-Related Phospholipase Allidella Altered Plant Growth and Increased Seed Oil Content in Camelina", Plant Biotechnology Journal, vol. 13, pp. 766-778, Dec. 29, 2014.
McConn et al.: "The Critical Requirement for Linolenic Acid is Pollen Development, Not Photosynthesis in an *Arabidopsis* Mutant", The Plant Cell, vol. 8, pp. 403-416, Mar. 1996.
International Search report mailed Apr. 20, 2017 in international application No. PCT/US2016/62548, filed Nov. 17, 2016.
Extended ESR for EP16867143.6, mailed on May 15, 2019.
Luo, Yi-Ching et al: "Irreversible inhibition of Ca-2+independent phospholipase A-2 by methyl arachidonyl fluorophosphonate", Biochimica Et Biophysica Acta, val. 1302, No. 1, 1996, pp. 55-60, XP55584054, ISSN: 0006-3002.
Hu, G. et al: "Chemical Induction of Apomictic Seed Formation in Maize", Euphytica, vol. 56, No. 2,1991, pp. 97-106, ISSN: 0014-2336.
Trewavas, "How do plant growth substances work? II"; Plant, Cell and Environment, 14, pp. 1-12.
Sigma-Aldrich online catalog, 2020, Merck KGaA.
Kim et al. "Endoplasmic Reticulum and Golgi-Localized Phospholipase A2 Plays Critical Roles in Arabidopsis Pollen Development and Germination by" , The Plant Cell, vol. 23. 94-110, Jan. 2011; p. 94, col. 2, para 1, p. 95, col. 2, para 3, p. 101, col. 2, para 2, p. 107, col. para 2 to col. 2, para 1.
Chellappan P. et al., siRNAs from miRNA sites mediate DNA methylation of target genes, Nucleic Acids Research, Mar. 2010, V. 38, N. 20, pp. 6883-6894.
Eder J et al: "In vivo haploid induction in maize", Theoretical & Applied Genetics: Int. Journal of Plant Breeding Res., Springer, Berlin, De, vol. 104(4), pp. 703-708, Mar. 1, 2002.
Timothy Kelliher et al: "MATRILINEAL, a sperm-specific phospholipase, triggers maize haploid induction", NATURE, vol. 542(7639), pp. 105-109, Jan. 23, 2017.
Chen G et al, "Plant phospholipase A: advances in molecular biology, biochemistry, and cellular function", Biomolecular Concepts, 2013, 4(5):527-532. doi: 10.1515/bmc-2013-0011.
Serrat X et al, "EMS mutagenesis in mature seed-derived rice calli as a new method for rapidly obtaining TILLING mutant populations", Plant Methods, 2014, 10(1):5. doi: 10.1186/1746-4811-10-5.
Cheng WH et al, "The Miniature1 Seed Locus of Maize Encodes a Cell Wall Invertase Required for Normal Development of Endosperm and Maternal Cells in the Pedicel", Plant Cell, 1996, 8(6):971-983. doi: 10.1105/tpc.8.6.971.
Liu G et al, "Patatin-related phospholipase A, pPLAIIIa, modulates the longitudinal growth of vegetative tissues and seeds in rice", Journal of Experimental Botany, 2015, 66(21):6945-6955. doi: 10.1093/jxb/erv402. Epub Aug. 18, 2015.
Zhang Z et al, "Chromosome elimination and in vivo haploid production induced by Stock 6-derived inducer line in maize (*Zea mays* L.)", Plant Cell Reports, 2008, 27(12):1851-1860. doi: 10.1007/s00299-008-0601-2.
Sarkar KR et al, "A genetic analysis of the origin of maternal haploids in maize", Genetics, 1966, 54(2):453-464. doi: 10.1093/genetics/54.2.453.
Accession No. AAP04195.1, NCBI_GenBank.
Accession No. EU973572.1, NCBI_GenBank.
Scherer G.F.E et al: "Patatin-related phospholipase A: nomenclature, subfamilies and functions in plants", Trends in Plant Science, Elsevier, Amsterdam, NL, vol. 15(12), Dec. 1, 2010, pp. 693-700, XP027533639.
Colliver et al, 1997, Plant Molecular Bioogy 35, pp. 509-522.
Thomas et al, The Plant Journal Issue 25, vol. 4, pp. 417-425.
EMBO "Hybrid Plant Breeding: Secrets Behind Haploid Inducers, A Powerful Tool In Maize Breeding", pp. 1-3, Feb. 22, 2017.
Yibrah et al., Hereditas, "Antisense RNA Inhibition of uidA Gene Expression In Transgenic Plants: Evidence for Interaction Between First and Second Trasformation Events", vol. 118, pp. 273-280, 1993.
Dong et al., "Fine mapping of qhir1 influencing in vivo haploid induction in maize.", Theor. Appl. Genet. Vol. 126: 2013, pp. 1713-1720.
Kelliher et al., "Unresolved issues in pre-meiotic anther development", Frontiers in Plant Science, Plant Evolution and Development, published Jul. 21, 2014, vol. 5, Article 341, pp. 1-9.
Qiu et al., "Morphological, cellular and molecular evidences of chromosomerandom elimination in vivo upon haploid induction in malze", Current Plant Biology 1 (2014) pp. 83-90.
Schnable et al., "The B73 Maize Genome: Complexity, Diversity, and Dynamics", Downloaded from www.sciencemag.org on Nov. 16, 2015, Science Magizine, vol. 326, Nov. 20, 20019.
Hu et al., "The Genetic Basis of Haploid Induction in Maize Identified with a Novel Genome-Wide Association Method", Genetics, vol. 202, pp. 1267-1276, Apr. 2016.

* cited by examiner

SEQUENCE LISTING

```
Sequence total quantity: 144
SEQ ID NO: 1           moltype = DNA  length = 1302
FEATURE                Location/Qualifiers
source                 1..1302
                       mol_type = genomic DNA
                       organism = Zea mays
SEQUENCE: 1
cccgctacct gttcaccgcg cgccagcgaa acctccgcac gcccactgcc catctgttcc  60
ccgtgcgcca gcgaaacatc cgcacgcccg cggcccgcct gttccccgcg catcccgctg  120
cacgacttct gctaccgcaa cggccaccca cgcacgcccg cctgttcacc gcgcatcccg  180
```

-continued

```
ctgacctccc cttcacgctc gcacacgctc cgttccccca ccccaccgca atccccgacg  240
aactcattac cagtagaatc agttactaac tgcttttctt tttcttggat tagaatggct  300
ggggctatct ctcaccatgc gctagcattt tcacaatccc actggtgcag tgcgaagaac  360
tctagattcg gaaagaggac gggcaatgct cgcctggttt atctaaaagg aagatgtggt  420
tcaggcagca gaaaactggg tttgatgtgg gcctcgagct cgcagtcttc tgtcatggag  480
ccgacgcacc taccatctga tggcaacagc agccacaccc caaaaaaatc aagtgaaagc  540
gctcttatat tgatttggca tggtgaatcc ctgtggaacg agaaaaatct atttcctggc  600
tgcatcgatg taccccctgac accgaagggt gttgaggagg ccattgaggc aggtaaaagg  660
atatgcaata tcccaatcga tgtgatatat acttcatcac tgatttgtgc tcagatgacc  720
gcaatgcttg ccatgatgca gcatcgacgc aagaagatcc tagttatcac gcataatgag  780
agtgaacaag ctcacaggtg gagtcagata tacagtgagg agacaatgaa acagtccatt  840
cctgtcatca cagcttggca attgaatgaa cggatgtatg gtgagctaca aggccttaac  900
aagcaagaaa ctgtagatcg atttggcaaa gaacaagttc atgagtggcg ccgcagttat  960
gatattcctc cgccaaatgg agaaagtcta gagaagtgtg ctgagagagc tgttgcttat  1020
ttcaaagatc agattattcc acaacttgtg gctggaaaac atgtgatggt tgctgcacat  1080
gggaattcac ttcgttcaat tataatgcat ctggacaaat taacttctca gaaggtaata  1140
agccttgagc tgtctactgg cattcccatg ctttacatat tcaaagaggg aaagtttatt  1200
cgacgtggga ctccagtagg accttcggag gccagtgttt atgcttatac caggaccaaa  1260
cgatttgctg agcacattac atttcagaac aaattggcct ag                    1302

SEQ ID NO: 2           moltype = AA  length = 335
FEATURE                Location/Qualifiers
source                 1..335
                       mol_type = protein
                       organism = Zea mays
SEQUENCE: 2
MAGAISHHAL AFSQSHWCSA KNSRFGKRTG NARLVYLKGR CGSGSRKLGL MWASSSQSSV  60
MEPTHLPSDG NSSHTPKKSS ESALILIWHG ESLWNEKNLF PGCIDVPLTP KGVEEAIEAG  120
KRICNIPIDV IYTSSLICAQ MTAMLAMMQH RRKKILVITH NESEQAHRWS QIYSEETMKQ  180
SIPVITAWQL NERMYGELQG LNKQETVDRF GKEQVHEWRR SYDIPPPNGE SLEKCAERAV  240
AYFKDQIIPQ LVAGKHVMVA AHGNSLRSII MHLDKLTSQK VISLELSTGI PMLYIFKEGK  300
FIRRGTPVGP SEASVYAYTR TKRFAEHITF QNKLA                              335

SEQ ID NO: 3           moltype = DNA  length = 2992
FEATURE                Location/Qualifiers
source                 1..2992
                       mol_type = genomic DNA
                       organism = Zea mays
SEQUENCE: 3
ttcaaccacc aaaatcaatt aggaaaaggt gtaagcctat ttccctttca ggaggcgtac  60
gtgagaggga gaggtgaaaa ggaacaacgc gtataccaga taaggtccca cagcctaagt  120
aggtagcctt ctgatatctc tactaactat taaggagaga gtgtagactg cccccgctcc  180
ctacccaacg ccccccgcta cctgttcacc gcgcgccagc gaaacctccg cacgcccact  240
gcccatctgt tccccgtgcg ccagcgaaac atccgcacgc ccgcggcccg cctgttcccc  300
gcgcatcccg ctgcacgact tctgctaccg caacggccac ccccgcacgc ccgcctgttc  360
accgcgcatc ccgctgacct ccccttcacg ctcgcacacg ctccgttccc ccacccccacc  420
gcaatccccg acgctataag agcggtaacc aactccatct ccctggtgcc acgcattgtt  480
gagttcttaa ggtgcgtttc gttgaggact tgttcatttt tgttggtcat gtattccatt  540
ttactgctct accattttgt ggaataaagg gaggaatgtt ttcactagaa gagttcatca  600
atcttatgtt ggtttcttgg atcagttttg ctctatggct aaatggtcga attgagccta  660
tttcattata aagttagcga gcgaataatt gttcagcctc ttcctagaac tcattaccag  720
tagaatcagt tactaactgc ttttcttttt cttggattag aatggctggg gctatctctc  780
accatgcgct agcattttca caatcccact ggtgcagtgc gaagaactct agattcggaa  840
agaggacggg caatgctcgc ctggtttatc taaaaggaag atgtggttca ggcagcagaa  900
aactgggttt gatgtgggcc tcgagctcgc agtcttctgt catggagccg acgcacctac  960
catctgatgg caacagcagc cacaccccaa aaaaatcaag taattttaac gacctcctat  1020
ggtggttatt tgtttttaat ttgagaaaac tatccatttg acacatttaa ctttgggctt  1080
ctcagaattt ggggcatata ataagatctg ctaatctgtt atctctatgt cgttgtaggt  1140
gaaagcgctc ttatattgat ttggcatggt gaatccctgt ggaacgagaa aaatctattt  1200
actggctgca tcgatgtacc ccctgacaccg aagggtgttg aggaggccat tgaggcaggt  1260
aaaaggatat gcaatatccc aatcgatgtg atatatactt catcactgat ttgtgctcag  1320
atgaccgcaa tgcttgccat gatgcagcat cgacgcaaga aggtttgtgt ctttcctttg  1380
aaattccagt aatttcttct agcatttgta tgaacttgcc ggagaaatca tgctttgctg  1440
gtgatatatg tatttataga tcccagttat cacgcataat gagagtgaac aagctcacag  1500
gtggagtcag atatacagtg aggagacaat gaaacagtcc attcctgtca tcacagcttg  1560
gcaattgaat gaacggatgt aatactttct ccatactctt tgatttgcta attactccct  1620
ctgtctcaaa atagtattaa ttttagctct tgatttttat gtctatattc aaatagatga  1680
tgataaatct agattctaga cacaaatata aaacatatac atcaagtatt atatgaatct  1740
attaatttac taagaccaat tttaatttgg gacagaggga gtatacgatt ataatagttg  1800
tttgactgtg cttctcttta aatatccctt gacatttcta ggtatggtga gctacaaggc  1860
cttaacaagc aagaaactgt agatcgattt ggcaaagaac aagttcatga gtggcaccgc  1920
agttatgata ttcctccgcc aaatggagaa agtctagaga agtgtgctga gagagctgtt  1980
gcttatttca aagatcaggc acatctagca aggccacttt acactaattg aaagatacac  2040
tttttacttg ggttattggt cttgctgcag tattggtatg catgctaaag gttattcttg  2100
aatcgatgaa ttcctctact atgggatgca gaaatgcatg tgcttagttt tctttctatt  2160
gtgctagctc atatcaaatt tataacctga attttttatt tatgttcgac tctaaaaaac  2220
agttttttct agctcgattt gacctatagt aatttttccg taatagatta ttccacaact  2280
tgtggctgga aaacatgtga tggttgctgc acatgggaat tcacttcgtt caattataat  2340
gcatctggac aaattaactt ctcagaaggt aattcactgt cgtttttgtc tttccatcaa  2400
```

```
aaaggactcg gctaaacaga acatgtagca ttatgttaag tttgggagtg agcctttcgt  2460
cccttcaggt aataagcctt gagctgtcta ctggcattcc catgctttac atattcaaag  2520
agggaaagtt tattcgacgt gggactccag taggaccttc ggaggccagt gtttatgctt  2580
ataccagggt aagattcttt cccccacatg ttctaccata ggacgatact ccagtttaca  2640
aaccttatct gtacagacca aacgatttgc tgagcacatt acatttcaga acaaattggc  2700
ctagaagata aggggtgttt ggtttgagaa atcactctat tcaaaatgag atggtgtatc  2760
atgggtccat ttctcaaatt tggtgggatg accctattcc tcatattagt actaactagg  2820
tgagtgtccg tgcgttgcaa cgggaacata taataacatg ataacttata tacaaaatgt  2880
gtcttatatt gttataagaa aatgtttcat aatctatttg tgatcctggc catacataaa  2940
ttttgttatt ttaatttaac tgtttcacta ctacattgaa atcatcagta tc          2992

SEQ ID NO: 4            moltype = DNA  length = 6916
FEATURE                 Location/Qualifiers
misc_feature            1..6916
                        note = Synthetic
source                  1..6916
                        mol_type = other DNA
                        organism = synthetic construct
SEQUENCE: 4
cctcgggacc cttgtcgcgt tgttcgttcc attgccgcat cacctccttt ctcatcgtgc  60
attacgaggt cttcaaaggg cttttggtca tcagccggga gcgcctccat cgccggcttg  120
atgatgttgg tagtggagat cttggtgtga tccttaaaac cggccattta tgggccgatt  180
tttagcagat ctagacacct attccccagc ggagtcgcca aaagtatgtt gacgcttttt  240
cggagcgcca atcactcaag aagaaccggc ggcggtgccc tctgcacagg ggcggacgct  300
ccgcgcgcag gggccggacg ctccgcggcc tggtgcgagg cggcggcgct ctctggttag  360
acgcggacgg tgcgcggcac agggccggac ggtgcgcgac ctagtgcagg agcacgggtt  420
ccctgcctga cggccggacg ctccgcgctc tagggccgga cggtgcgcgc gtgcgcaggg  480
gcggcggaag atcgccggcg gcgcctggat ctcgctcccg ggagggagcc cgtcggggag  540
gagagatcct aggagttgtc taggctcggg ccggccgacc tagactcctc taatcgacgt  600
agagtcgagg agaggcagag aatttgggga ttggaatact aaactagggc taaactagaa  660
ctagactaga actactccta attgtgctga aaataaatgc gagatagaag ttgtattggt  720
tcgattgttg ggggtcaatc ggccgtagcc cttcatctat ataaagggga ggtctggatc  780
cgtttccaac tgatttccga gttaatcccg cggttttagg taacaaatcc cgcgagaaac  840
taggaaccct aactgactct gcgcacgcgc cgaccgtccg cgccaccacc gcggacggtc  900
ccgaccgcgg agcgtccggc ctccgggccg gagcgtccgc acggtcattt tgggttcgaa  960
cagagtccca acgaggttag taaatgtagt gatgaaatta agttttgtac gaagtttgta  1020
aatttaagga cctgttttac ataactattg gagaagagtt ttctctgaaa aattcttaaa  1080
tttatattta gggagttgtt tatataacta ttggcatttg agatgctcta aggaagcgaa  1140
ggaaataact tggcggcgat cctagtcgac aaccgttgaa ttcgtgagaa tcaatcattc  1200
tgtaggagta aaaaaataaa ataaaatatg catttcctcg ttcctatacg cttaaattag  1260
acgaccctgg actggaacca ggaactagga aggggcaccg atgtcatttg cgaagcaaca  1320
acaacatgcg tgaggacgac caagtcaaac gttgcgtcgc gttgcctcgc cggcgggccg  1380
gtcccaccaa gacgtggcgc catgcaagtg cgtcgtcgac cctcttctct ctctctcttg  1440
tagtcttgtt cctgttatct ctctcggctg tccgctgccc cgtgatctga gcgcgtttct  1500
ctcccgtcct ctcttctccc tctcccgcaa caaacacctg ctatccggtc tccctctccc  1560
ctgccatctc tctctagcgc attgctagcg cgagcgcaga aggcacacac gtagagcctt  1620
ggtgatacct cctcctcctc ctcctcctcc tcctgatctc ctctcctcct ccggcctccg  1680
tatacctata actaaaagat gatcatcgtg cgatgcaggc gaactcgtcg tccgaaaacc  1740
atggatccaa ctcattacca gtagaatcag ttactaactg cttttctttt tcttggatta  1800
gaatggctgg ggctatctct caccatgcgc tagcattttc acaatcccac tggtgcagtg  1860
cgaagaactc tagattcgga aagaggacgg gcaatgctcg cctggtttat ctaaaaggaa  1920
gatgtggttc aggcagcaga aaactgggtt tgatgtgggc ctcgtgctcg cagtcttctg  1980
tcatggagcc gacgcaccta ccatctgatg gcaacagcag ccacacccca aaaaaatcaa  2040
gtgaaagcgc tcttatattg atttggcatg gtgaatccct gtggaacgag aaaaatctat  2100
ttcctggctg catcgatgta cccctgacac cgaagggtgt tgaggaggcc attgaggcag  2160
gtaaaaggat atgcaatatc ccaatcgatg tgatatatac ttcatcactg atttgtgctc  2220
agatgaccgc aatgcttgcc atgatgcact cgagaaatct gaagaagaga catcagtagg  2280
aaaaccatga aacaactcac caagtgataa aactttgata aattcattca aaagtatcat  2340
gttctacgtg attcgcttgt atgccaaatt atctaaatat tagtaagaat taactactcg  2400
gacgatcatc agcaaatgaa aatgaaacag cacaccaatt gagactgatc agatcagaaa  2460
ccagaaaaac atctcaacat ggataaattc atcagcaata ctgtagcatt gatatatttg  2520
tgtttcttga aagaaagaca tcaaagaaac tttgcaatta tgtagtattg tttatttttc  2580
tgttacaaac ttaatcaact gacatgtaat gtgtctctat tgtcagttca agtattagac  2640
tatccattgt caccttttaa atgtaccttt actgtcagcg tacgagataa agttggccga  2700
ttgaattcta agctactata aaagcaactt tattatatag acatggcaaa caatcgttaa  2760
caaactgttt ttctttttga ttgattagga cttggaaaca cactgaacat gatcaaagtc  2820
acaaaagtca cttggttgcc tagtctgaca gcaagcgcag gtgtaaattc agaatgatag  2880
tgaaccaaaa ctcatctgct tccagtacca aattcgtcag aaggcagaac ggaggcataa  2940
gcacaaaggg catgctcacc cgagtcgagt gcatcatggc aagcattgcg gtcatctgag  3000
cacaaatcag tgatgaagta tatatcacat cgattgggat attgcatatc cttttacctg  3060
cctcaatggc ctcctcaaca cccttcggtg tcaggggtac atcgatgcag ccaggaaata  3120
gatttttctc gttccacagg gattcaccat gccaaatcaa tataagagcg ctttcacttg  3180
attttttttgg ggtgtggctg ctgttgccat cagatggtag gtgcgtcggc tccatgacag  3240
aagactgcga gcacgaggcc cacatcaaac ccagttttct gctgcctgaa ccacatcttc  3300
cttttagata aaccaggcga gcattgcccg tcctctttcc gaatctagag ttcttcgcac  3360
tgcaccagtg ggattgtgaa aatgctagcg catggtgaga gatagcccca gccattctaa  3420
tccaagaaaa agaaaagcag ttagtaactg attctactgg taatgagttg gatctccatg  3480
ggagctctcg tcatcgtcct actatcaagc aacacgatcg accaccacct cgattatata  3540
tgcatcatta tagtatcgtt tattaatttc agacccaccc actgctaacc acatcgtcca  3600
```

-continued

```
cgagagatta tattcatccg tggactacgc tctcgatctt acaatttgaa acctttctat  3660
tttcctaatt actatgtatt ccaggttcat tttgattgtg accattcttc agttctttct  3720
gtaaggatcg gagcatatta tatactctat gtggctatgc caattatatt gttgggtata  3780
agaatgcatt ttgtttctgt aatacggaaa aatatatttt ctttaagcaa caacaaggta  3840
aaaacttgcc tcgttgcata ttttctttat gtcaatctcc ttttgttcgt tgtatgatcc  3900
tctgtttgga aactgaatac tgatcgaaca actgatcagg agttaaaaca tattgtaaat  3960
atatataaaa acttgctgtg tacaactctt ctttattgta taagtttctt gaggtaaccg  4020
aaatagatag taaatcccaa tacaaataga ttcctccgtt actaactaat ctgaacataa  4080
atgctaataa aaaaagtata aatttctatc tgcgtatgta ccttgacctt acctttattc  4140
tattaactcc tgattttcta ttcagatttt gaacggtctg ttacttcctt tctattctgt  4200
tctggtttcg tcgtcgtttg tttccgaacg gtctgctact tctgattttc tatttgttct  4260
tacgtttggt tttgccgttc tagtttcttg cgtttttcca tataaatata gaaacacaaa  4320
ataaatgtaa tgttgtagat acttgaacta tcgatctttt cctttaaaaa atgatattgc  4380
taccactaat gtagttttaa ttaggaacaa aacttacaac caatgatcaa ctaatgaacc  4440
ggtctagaac agtctatatg gacatggtga gcaagcgtac gtaattccgg accgcgcggg  4500
cggccgcact agtcccgggc ccatcgatga tatcagatct ggttctatag tgtcacctaa  4560
atcgtatgtg tatgatacat aaggttatgt attaattgta gccgcgttct aacgacaata  4620
tgtccatatg gtgcactctc agtacaatct gctctgatgc cgcatagtta agccagcccc  4680
gacacccgcc aacacccgct gacgcgccct gacgggcttg tctgctcccg gcatccgctt  4740
acagacaagc tgtgaccgtc tccgggagct gcatgtgtca gaggttttca ccgtcatcac  4800
cgaaacgcgc gagacgaaag ggcctcgtga tacgcctatt tttataggtt aatgtcatga  4860
taataatggt ttcttagacg tcaggtggca cttttcgggg aaatgtgcgc ggaaccccta  4920
tttgtttatt tttctaaata cattcaaata tgtatccgct catgagacaa taaccctgat  4980
aaatgcttca ataatattga aaaaggaaga gtatgagtat tcaacatttc cgtgtcgccc  5040
ttattccctt ttttgcggca ttttgccttc ctgtttttgc tcacccagaa acgctggtga  5100
aagtaaaaga tgctgaagat cagttgggtg cacgagtggg ttacatcgaa ctggatctca  5160
acagcggtaa gatccttgag agttttcgcc ccgaagaacg ttttccaatg atgagcactt  5220
ttaaagttct gctatgtggc gcggtattat cccgtattga cgccgggcaa gagcaactcg  5280
gtcgccgcat acactattct cagaatgact tggttgagta ctcaccagtc acagaaaagc  5340
atcttacgga tggcatgaca gtaagagaat tatgcagtgc tgccataacc atgagtgata  5400
acactgcggc caacttactt ctgacaacga tcggaggacc gaaggagcta accgcttttt  5460
tgcacaacat gggggatcat gtaactcgcc ttgatcgttg ggaaccggag ctgaatgaag  5520
ccataccaaa cgacgagcgt gacaccacga tgcctgtagc aatggcaaca acgttgcgca  5580
aactattaac tggcgaacta cttactctag cttcccggca acaattaata gactggatgg  5640
aggcggataa agttgcagga ccacttctgc gctcggccct tccggctggc tggtttattg  5700
ctgataaatc tggagccggt gagcgtgggt ctcgcggtat cattgcagca ctggggccag  5760
atggtaagcc ctcccgtatc gtagttatct acacgacggg gagtcaggca actatggatg  5820
aacgaaatag acagatcgct gagataggtg cctcactgat taagcattgg taactgtcag  5880
accaagttta ctcatatata ctttagattg atttaaaact tcatttttaa tttaaaagga  5940
tctaggtgaa gatccttttt gataatctca tgaccaaaat cccttaacgt gagttttcgt  6000
tccactgagc gtcagacccc gtagaaaaga tcaaaggatc ttcttgagat cctttttttc  6060
tgcgcgtaat ctgctgcttg caaacaaaaa aaccaccgct accagcggtg gtttgtttgc  6120
cggatcaaga gctaccaact ctttttccga aggtaactgg cttcagcaga gcgcagatac  6180
caaatactgt tcttctagtg tagccgtagt taggccacca cttcaagaac tctgtagcac  6240
cgcctacata cctcgctctg ctaatcctgt taccagtggc tgctgccagt ggcgataagt  6300
cgtgtcttac cgggttggac tcaagacgat agttaccgga taaggcgcag cggtcgggct  6360
gaacgggggg ttcgtgcaca cagcccagct tggagcgaac gacctacacc gaactgagat  6420
acctacagcg tgagctatga gaaagcgcca cgcttcccga agggagaaag gcggacaggt  6480
atccggtaag cggcagggtc ggaacaggag agcgcacgag ggagcttcca gggggaaacg  6540
cctggtatct ttatagtcct gtcgggtttc gccacctctg acttgagcgt cgatttttgt  6600
gatgctcgtc aggggggcgg agcctatgga aaaacgccag caacgcggcc tttttacggt  6660
tcctggcctt ttgctggcct tttgctcaca tgttctttcc tgcgttatcc cctgattctg  6720
tggataaccg tattaccgcc tttgagtgag ctgataccgc tcgccgcagc cgaacgaccg  6780
agcgcagcga gtcagtgagc gaggaagcgg aagagcgccc aatacgcaaa ccgcctctcc  6840
ccgcgcgttg gccgattcat taatgcaggt taacctggct tatcgaaatt aatacgactc  6900
actataggga gaccgg                                                 6916
```

```
SEQ ID NO: 5            moltype = AA  length = 335
FEATURE                 Location/Qualifiers
source                  1..335
                        mol_type = protein
                        organism = Zea mays
SEQUENCE: 5
MAGAISHHAL AFSQSHWCSA KNSRFGKRTG NARLVYLKGR CGSGSRKLGL MWASSSQSSV  60
MEPTHLPSDG NSSHTPKKSS ESALILIWHG ESLWNEKNLF TGCIDVPLTP KGVEEAIEAG  120
KRICNIPIDV IYTSSLICAQ MTAMLAMMQH RRKKIPVITH NESEQAHRWS QIYSEETMKQ  180
SIPVITAWQL NERMYGELQG LNKQETVDRF GKEQVHEWHR SYDIPPPNGE SLEKCAERAV  240
AYFKDQIIPQ LVAGKHVMVA AHGNSLRSII MHLDKLTSQK VISLELSTGI PMLYIFKEGK  300
FIRRGTPVGP SEASVYAYTR TKRFAEHITF QNKLA                            335
```

```
SEQ ID NO: 6            moltype = AA  length = 335
FEATURE                 Location/Qualifiers
source                  1..335
                        mol_type = protein
                        organism = Zea mays
SEQUENCE: 6
MAGAISHHAL AFSQSHWCSA KNSRFGKRTG NARLVYLKGR CGSGSRKLGL MWASSSQSSV  60
MEPTHLPSDG NSSHTPKKSS ESALILIWHG ESLWNEKNLF PGCIDVPLTP KGVEEAIEAG  120
KRICNIPIDV IYTSSLICAQ MTAMLAMMQH RRKKIPVITH NESEQAHRWS QIYSEETMKQ  180
```

-continued

```
SIPVITAWQL NERMYGELQG LNKQETVDRF GKEQVHEWHR SYDIPPPNGE SLEKCAERAV  240
AYFKDQIIPQ LVAGKHVMVA AHGNSLRSII MHLDKLTSQK VISLELSTGI PMLYIFKEGK  300
FIRRGTPVGP SEASVYAYTR TKRFAEHITF QNKLA                             335

SEQ ID NO: 7           moltype = AA  length = 335
FEATURE                Location/Qualifiers
source                 1..335
                       mol_type = protein
                       organism = Zea mays
SEQUENCE: 7
MAGAISHHAL AFSQSHWCSA KNSRFGKRTG NARLVYLKGR CGSGSRKLGL MWASSSQSSV  60
MEPTHLPSDG NSSHTPKKSS ESALILIWHG ESLWNEKNLF TGCIDVPLTP KGVEEAIEAG  120
KRICNIPIDV IYTSSLICAQ MTSMLAMMQH RRKKIPVITH NESEQAHRWS QIYSEETMKQ  180
SIPVITAWQL NERMYGELQG LNKQETVDRF GKEQVHEWHR SYDIPPPNGE SLEKCAERAV  240
AYFKDQIIPQ LVAGKHVMVA AHGNSLRSII MHLDKLTSQK VISLELSTGI PMLYIFKEGK  300
FIRRGTPVGP SEASVYAYTR TKRFAEHITF QNKLA                             335

SEQ ID NO: 8           moltype = AA  length = 335
FEATURE                Location/Qualifiers
source                 1..335
                       mol_type = protein
                       organism = Zea mays
SEQUENCE: 8
MAGAISHHAL AFSQSHWCSA KNSRFGKRTG NARLVYLKGR CGSGSRKLGL MWASSSQSSV  60
MEPTHLPSDG NSSHTPKKSS ESALILIWHG ESLWNEKNLF TGCIDVPLTP KGVEEAIEAG  120
KRICNIPIDV IYTSSLICAQ MTSMLAMMQH RRKKIPVITH NESEQAHRWS QIYSEETMKQ  180
SIPVITAWQL NERMYGELQG LNKQETVDRF GKEQVHEWRR SYDIPPPNGE SLEKCAERAV  240
AYFKDQIIPQ LVAGKHVMVA AHGNSLRSII MHLDKLTSQK VISLELSTGI PMLYIFKEGK  300
FIRRGTPVGP SEASVYAYTR TKRFAEHITF QNKLA                             335

SEQ ID NO: 9           moltype = DNA  length = 4921
FEATURE                Location/Qualifiers
source                 1..4921
                       mol_type = genomic DNA
                       organism = Zea mays
SEQUENCE: 9
attgctataa gtataataat atctaagaga tggaagaaga ctggccggcc gggtagtgac  60
aataatgaat gaccaacggc agaaaagttg gtgcgaagat gttttaggtg aatgcaagtc  120
acaaaaggaa aaggctggca tctcgaatag aactcctata ccacggatca agaaacaatt  180
aaaaccatac ataattgtcg gagtaatatg ctaatcctag taattttagt cacatcattg  240
gaggtccttc gttccattca attttttttc tttcttcatg aacatttgtt caagatttat  300
ctcccacatg tttcaaagca tgcattattt attattattg gcaaatttca tgatctttca  360
aaagatatct cttgggcctg gcatggatat gctctatctc tagtaagtaa ttggctctgc  420
aataatgagt tggatattgc cacgaagaac cacgccttgc ttggaagaaa cttgatgaat  480
gccaaatctt gctctttttc aacatgttga tttaggaaat tatttggcaa ccaaacataa  540
tgtgactaga attagcacac ttctaatgac aaaaatataa tcacatttct gcgcgcacaa  600
aatatttgct tgccaaaatg caatcatgtt ttgatgtaca gttcgataga cattgaaaaa  660
gaatgcattt aggaaccttt tagtaccact ttgatcaatt tctgccatct acacgtcaaa  720
ctagataaaa agaataatgg cagccacatc ctacagaaaa aaaaagacat atcaagaatt  780
caacttaatt tcagaatata caagatttca tagtgacctt taacattgat ttttcgactc  840
acatcttata agcgggtgaa gcagtatata aaagaattcc acaaaaaaat ctacaacagc  900
cataagcatt aattacacat aaacgctcac caccctataa aacacccaga ccttcacatt  960
tcttcttcag acctccaaca agcagcagat agatagagaa atgaagagat agattagagt  1020
taccatcata tccccaacaa tggcatagcc aacaagttgg atccttcgga ccctgtagct  1080
cctggtccat gaattgccaa gagaacacct tttagtttct ttgagcaacc tcgatctcgc  1140
catggggttc cgctgtggcc gtgcctcctc ttcgctgctg tgtgaagagg acgtggccgg  1200
catgtttgga tgcaatgggc acgacgacga agaggtgggg cttctggtgt tggggatgga  1260
cacgactttt gctgcgctgc catcacagag cgacgaggtc gtagcatccc tgatggagaa  1320
ggagaaggag cagctgcata gcgttgcgac gggggattac ctccagaggc tgagcagtgg  1380
aggactggag tcatcttgta ggattgccgc cattgattgg ataaaaaagg tttctgcttc  1440
tccatccata ctatatagta tgtatatgat ttctcgcgca tcgatcctag ttagaatctc  1500
atgtttctgt gttttgcagc aaaatgcaat ttatttgact ccaagtttga cttaaacttc  1560
agtttgttca aaaaaaaaaa gtttgccctt gcttgaccaa aacctcgttt tgcatatata  1620
gataaatata tagttactga aatgtgtact acttgtctct tacatgtgta ttaattgcag  1680
gcccaggctt atcacgactt tggaccgttg tctgcttatc ttgctgttaa ctaccttgat  1740
agggtcctct ccacaaatca agtcccagtg agttctacaa atgtacccaa cttgtttatt  1800
ctttttttcta catgtccaat cagcatgtgg ttgtcagagg tctttgcctc tccctctcta  1860
gaaaacctta tggcatgttt ggttcagcgg cggaccagga actaaagaca gcctatgcga  1920
gattataagt gtcaataact atagctaatt tcatataaaa aaatacatgc atatttggat  1980
ttgagatgca ctttcgtccg atcagtagat aaggtcattt ggtttaggat catgagttga  2040
gttaggactt agcactattg gaatcgagct ctttgtcaat tgtctgaagc actcggcaaa  2100
gctgggaaaa cactcgacga cgtctttgcc gagtgtagca ctcggcaaag agagctcggc  2160
gaacagtata tcgacacggc ttctttgccg agtatttttt atcgggcact cgacaaagac  2220
tttgccgagt gtcactcggt actcggcaaa gaaaagtcgc cgtcaaggcg accggaaacg  2280
gagacagcgc ctttgccgag tgttctaggt gacactcggc aaagagatta cctttgtcga  2340
gtgtccgcca gtctacactc gccaaagggg ctaccagcgg accccttttgt cagtttcttt  2400
gccgagtgcg ctagaaggca ctcggcaaag cttgcttctt tgtcgagtgc caaggccaca  2460
gcactcggca aataagcttt accggtgccc aggaatggca ctcggcaaaa tgttctttat  2520
cgagtgtcag gcgataggac actcggcaaa gtagcttctt tgccgaatgc caaagcctag  2580
```

```
cgttcggcat agataacagc cgtcagctat agacggctgc tgacggttct ttgcctagca  2640
ccgaattgtg tcgagtgttt ggcactcgac aaagtagtct ttgccactac tttgccgagt  2700
gtctttctgt gccgagagtc ctattatcgg caaacgcgat cgttatcgag agtgaaactt  2760
tgtcgagtgt ggcactcggc aaagaagtgt cgagtgcccg ataaaaaaca cttggcaaag  2820
agccaaattc cgatagcgta gcattcgtgc agccgtacgt tagaattgga cagacgaggg  2880
atgtgactgt gctcggctgt tccagctata tcctgcaacc aaacacaacc ttacattttg  2940
atggggcaca aatcttatgt gagtttcttg gtgtaggctg atgctgacca ccagccctgg  3000
atgccacagc tgctgtccgt tgcttgccta accattgcag ccaagatgga ggagaccgtg  3060
gttcctcgcc gtctggacat ccatcagaat caggtggaca aaattggata tatagtacag  3120
tttcacgttt gagttcacca aatctttatc tttattatat atatatatat gtcacaggtt  3180
ctcagcgaga agtacagatt cgatttagat gctattcaga ggatggagat ttacattcta  3240
gactctctga attggaggat gcaagctgtg acgccattct cttacatcaa ctatttcgtg  3300
gacaagttca ctgatgggaa gccgctaagt tgcggattca tttctcggtg caccgagatc  3360
atacttggca gtcttgaagg tacatcagat tacttcatgc atgagcgagc gaatcggact  3420
tacccgcctt ttccattcga taagcaattg ttactatgtg attggaacat gcatctaaat  3480
agatgtctgt gtgcatttga tttgcagcaa cgaagctcct acagttcagg ccttctgaga  3540
tggcagcagc agtggttctg tcagcagctg ctgagtctca agtcattgcc ttcagcggcg  3600
ctcttttagc ttctaatatc cttgtcaata aggtgtagat cctctctctc tatgaaggtt  3660
tagtattttt tttaatgtac gtatttacat ttctaggaaa atgtaaggag atgccatgaa  3720
gcattgcaag aagtgggatt agtgaagaag aaaacagact acagtgcgag tccatctcgc  3780
gtgctagatg cctcatgctt cagcttcaag actgacgata accagacagc cggttcatcc  3840
caatcccaag caaacaacaa tggcaactac aaccaggctt actctccagc tagcaagagg  3900
acaaggctag acatctagac tcaatcagga aaaattgcat gagatcatag acgtacacat  3960
atacacacaa agtttcttta gataaaggat acataaagtt aaatttgatt ctggctacat  4020
ttctgagtac gtgcttctca actcagaaga gttcataggg aacattatac atgcatgcat  4080
gctaacaggc aaaagaaggc tgaattatta agagcaatcc tatttatttc ctcctttgtt  4140
cctttgttaa ctttttcttt cttcttgtct actttaaatc atggcattag caaagacatt  4200
tgcgtgtatg ggacaggtga tgcaatgata caacataaaa gaaggctagg cattgttttc  4260
aacataagca gaggtaatct cgtttcagga aaaaaatgag cgccaggaac tttgatatct  4320
gatcaaggga gaagcaaagt tagttgttgt gggaatctgt ggctgagttc ttggttctcg  4380
atttcttgtt tgtttgtttg tctgtgatga atatttttca gatttattca atgaactgac  4440
catgttatgc tatagagcaa gtacaacaat aggttctaag caggataaat gatgaggtac  4500
aggagagaga agatgagaga gaggataagc gagctataaa cttacaacca tctaagactt  4560
agatataaga ataaaaaaac tttgagagag acaaatgagt tatgtattag tagtgaacgg  4620
ttaactatta tgtagatgga ctaagagata ggacgcaaat agccaatagt cagctatatt  4680
attagcctcg ctcttattca gcacccgggc aattttatcg tccaaatttg ttagcatgca  4740
tgctacttct tatagaatga atattagata tgcattaggc ttcacatcct attcaaaata  4800
aggtgctaga ggccttaaaa tttaagtgtt ttagatgagt tccatggatg aatcttagtt  4860
gcgccataca tataattaat ttaaaacaca caaaaaaaac actagccata tacttactat  4920
g                                                                 4921

SEQ ID NO: 10          moltype = DNA  length = 1071
FEATURE                Location/Qualifiers
source                 1..1071
                       mol_type = genomic DNA
                       organism = Zea mays
SEQUENCE: 10
atgaagagat agattagagt taccatcata tccccaacaa tggcatagcc aacaagttgg  60
atccttcgga ccctgtagct cctggtccat gaattgccaa gagaacacct tttagtttct  120
ttgagcaacc tcgatctcgc catggggttc cgctgtggcc gtgcctcctc ttcgctgctg  180
tgtgaagagg acgtggccgg catgtttgga tgcaatgggc acgacgacga agaggtgggg  240
cttctggtgt tggggatgga cacgactttt gctgcgctgc catcacagag cgacgaggtc  300
gtagcatccc tgatggagaa ggagaaggag cagctgcata gcgttgcgac gggggattac  360
ctccagaggc tgagcagtgg aggactggag tcatcttgta ggattgccgc cattgattgg  420
ataaaaaagg cccaggctta tcacgacttt ggaccgttgt ctgcttatct tgctgttaac  480
taccttgata gggtcctctc cacaaatcaa gtcccagtga gttctacaaa taagtacaga  540
ttcgatttag atgctattca gaggatggag atttacattc tagactctct gaattggagg  600
atgcaagctg tgacgccatt ctcttacatc aactatttcg tggacaagtt cactgatggg  660
aagccgctaa gttgcggatt catttctcgg tgcaccgaga tcatacttgg cagtcttgaa  720
gcaacgaagc tcctacagtt caggccttct gagatggcag cagcagtggt tctgtcagca  780
gctgctgagt ctcaagtcat tgccttcagc ggcgctcttt tagcttctaa tatccttgtc  840
aataaggaaa atgtaaggag atgccatgaa gcattgcaag aagtgggatt agtgaagaag  900
aaaacagact acagtgcgag tccatctcgc gtgctagatg cctcatgctt cagcttcaag  960
actgacgata accagacagc cggttcatcc caatcccaag caaacaacaa tggcaactac  1020
aaccaggctt actctccagc tagcaagagg acaaggctag acatctagac t           1071

SEQ ID NO: 11          moltype = DNA  length = 5918
FEATURE                Location/Qualifiers
source                 1..5918
                       mol_type = genomic DNA
                       organism = Zea mays
SEQUENCE: 11
ttggtagtgg aattagctag ctaacaaata actatctaac tattaactaa tttaccaaaa  60
atagctaata gttgaactat taactaaagt gtttggatgt ctcaactaat tttagctact  120
aactattagc tctagtgcat tcaaacaccc cttaagtgaa tgtcatggta tgggctgaca  180
tttcgagagg tggagagtgt catggtatgg gctgccatgt gggccgagag tccgagaccg  240
ggctaaatga gctgggctga ataggactga ctgcaggtag aaaggcaagc gcaacatttg  300
gcaccgttag ctctccacta aacttgtcag atgcaataat ttatgttttt attaatggca  360
aagccctcct gccagccagt gccttccttc cgggtcaacc actggtacag tcacatcacg  420
```

-continued

```
aattcccact ggcagtacga taacctcact gagcggtagg gcctcccgtc ccagaatcct  480
gcaggaccca tcgatcatgg ccccacgggt cctgctcctg cgtgggttcc aattccaagt  540
cgcccaccgt gacgcccatc gagtcaaccg aacccaagcc gtgtggcgac tggcgaggcg  600
agtgccccag ttcctaactc cggtgggcgc gctcccaccg ccgcgcggct caaaacccgc  660
cctcagcctc ccgcgctcca gtccacacgg gagcgggtgg tgtcgtctga agcggcgcga  720
tcaaggagtc ttcgggcgct ccggtgagct atctagatct caacatcctc tcccctctgt  780
agtctgtagt tgtactctcc cgcccgatgg ttcagttaag ttatatcctc tccccttatt  840
tttactcggt cgataccatt tcgttgtgga ttgggcgccc ccgcaggttg aaatgctgcc  900
catcatgctg cggccctgta ctatgaggat ggttctagtt ttgcgtctgg caatttgggg  960
cgtacatgct tttggctgcg tactgttact gatcggagaa aatgtttgta acgtatgatt  1020
cgtttttcag gacgtaacgt gctggcggtt gcttatctcc ggatgtatat ataagcggaa  1080
atgttctcct tgttctatgg cctgtggaag tatgtgttcg ccaaggacga gttccgtgtt  1140
ctgattcttg gtgttgacag agctggcaag acggtagctg ctagctccca gccttcatat  1200
atatatttcc ctttctgaac tagaaattga tgatacttac ctgtacacga tgtttctgga  1260
accgttgcca tagactttgc tggagaagtt gaaatcgata tatctcaagg gggaaggact  1320
tccgcctgac cgtgtcgttc caacagttgg gctcaacatt ggccgcatcg aagacgcaaa  1380
ggcaaaactt gttttctggg atctaggtgg tcaggtaaga acgtttacgt acgtagtaaa  1440
gtgagccttc tgttgccgtg gcaccaccct acgatcgttg atatttgagt cttgtcagtt  1500
tggtgctata tcagggtttc taatgcctgg gaaatacatg tcataaattc aaattactag  1560
gatgtggttg ctttagttat taacctagca tctttttgcg ttccagcaga atatatataa  1620
tctagttata tggaatgctc aatagaattt tcagaaagca aagatatgct ctgttggcta  1680
acattcacag tactcaatag aattgtttac tagtagaaca gcatcagctt ctctgctatg  1740
ttataagaat tagtgtaaaa ctaacttcag tatcactgct tgctagtatg ataattaagc  1800
ttccatgcca agttcagtat ttcttacaca cttgcctgct tggcaggtta gcctacgaac  1860
aatctgggag aaatactatg aagaggccca tgccataatg tacgttattg acgctgccac  1920
agcatcgtca tttgaagatt ccaaatctgc tctgggtaag gttcttattt gtgttaatta  1980
taaactactc cctccattcc aaattataag acattttggc ctttttttcta gataaataaa  2040
ttttgctatg gacttaaata ttatttatat atatatatat atatatataa aatgtcctgg  2100
tacatagtta aaacattata tcttaaaaag ctaaaacatt gtcttataac ttggaacaag  2160
ggagtactgg tttgtttcta ttgctagatc ttccgagaag atgcattgcc tctctggtaa  2220
atgggatgag aactcattct agctagagaa cctaacctaa atttcttact tcagagaagg  2280
ttattcgcca tgaacatctg agaggagcac cactcttgat agttgcaaac aaacaggtga  2340
agggtttact tccactttct atattttgta ccacagtaca taattatgat tgaaagattc  2400
agtgcttaca ataaagttgc catcgtagta aaataaagat tttgtttttg tcatgtgccc  2460
atgctgtgag gcatacaaat ctaaattcct acgttgcaaa gcgcctatgc gccattgcga  2520
ggttgaatac cagatgtagt ttggccaatt gtgatgtaca gatgtgccac attgacaatt  2580
gacacgcagt ttaaaggaga gtcagactac tagttttttc attgcccaac atataccttt  2640
ggccacttat tgaaaatgtg agagatcatt tgagtttgaa cagtaagttt tgtgagatat  2700
cattttattt agtaatcatg cacacatgtc tagaattgtg aaatgcacaa taaagacgca  2760
aactcccacg agcatgcagg tacacccgat tgaggattct cagcgaatgt tccagtttcg  2820
agaatcaaac aacatataac aatgatgaat tttttaaatc aattaaaact tcctgaaaag  2880
atcacatgga aaccaatgac tacatgcact gtctgtttct gttaagctgg gtacacatta  2940
ttctatcaaa ttgtttatta tttacctctt gttctcatgt ttggagggtg cttctggatt  3000
tcttttggca ggatttacct ggagccattg atgaggaaga attggctaaa tttctgcata  3060
aagaactgga tgagaggcca tatacatttc aggctgtatc tgcatatgat gggtgagcgc  3120
agaaactcaa ctggttcctg aggaaatttg actcgccatg aaaaaaaatg acaattttac  3180
tcaaagatac aaaaaattca cacattcgtc tgttatattg tttcctgggt gcatgaaact  3240
caactggttc gtgaggaaat ttgactcgcc atgaaaaaaa tgacaatttt actcaaagat  3300
acaaaaaatt cacacattcg tctgttatat tgtttcctgg gtgcatgata ttctaaagat  3360
ctgttatatt gtttaaatgt gacaccggct cttgcagcag ggggatcaaa tctggcatag  3420
actggctggt ggaacaaatg gaaaaaagca aacgtaccga gacactgcag gctcgtgctg  3480
gcgtagctgg acaaatttag aatggggtga atttgttaaa gaacaaagca ttggatagga  3540
cggcttcctt cgtatcgcgt aagcagccat ttgctgcatt ccgggattat cgttccaggt  3600
cgcccagagt gctgcaagaa atgtttggct ggttgctcct gtggtggtgg tgattggtga  3660
ggcgattcgt ttggtattat tgaggttgca ttcatatgta cctaaaggtc gcaagcatac  3720
atgtctatat gatgcttttc aattttcgta gcaaactagt agcttcaata cagaggatca  3780
aagagagccg tgttctttaa cttgtttgtg ataaaaaaaa aggaagaaag gaaagcgaag  3840
aaggaattat tggtgcatct gaaagtcttt attgcatatg tctaaaccat tttaaccgat  3900
gctggatgag cttttcttcg caccgatgtt acatctagtc tatcatatgt atcctcgttt  3960
catactcgca ccgatgttac atctagtcta tcatatgtat cctcgtttca tactcgatcc  4020
tttttatgg ccaaactcca acacaacata tacatttctg tagcgcatac gtattgaaca  4080
tgtcttttttt agactaacat tctgcaccga acaatatagc agatcgaatt gtcatcctat  4140
aaagattatt tttaactttt gtggtatcct attgtcatat ttattgaggt tgcattcata  4200
tgtacctaaa ggtcgcaagc atacatgtct atatgatgct tttcaatttt cgtagcaaac  4260
tagtagcttc aatacagagg atcaaagaga gccgtgttct ttaacttgtt tgtgataaaa  4320
aaaaaggaag aaaggaaagc gaagaaggaa ttattggtgc atctgaaagt ctttattgca  4380
tatgtctaaa ccattttaac cgatgctgga tgagcttttc ttcgcaccga tgttacatct  4440
agtctatcat atgtatcctc gtttcatact cgcaccgatg ttacatctag tctatcatat  4500
gtatcctcgt ttcatactcg atccttttt atggccaaac tccaacacaa catatacatt  4560
tctgtagcgc atacgtattg aacatgtctt ttttagacta acattctgca ccgaacaata  4620
tagcagatcg aattgtcatc ctataaagat tctttttaac ttttgtggta tcctattgtc  4680
atatagaaca tcaaatgttt ggcgccacct catcctttga ctaatacctt tatcactatc  4740
tctacgtagc ctttcgtagc atagatccta aatatctatg catagatcct aaatatctat  4800
gcatagatcc taaatatcta aagatgtcct ttcagaacac tacttgattt ttcaaactaa  4860
catgtctttc ctcatatgta gtagcataga ttctaaatat ctaaagatgt ccttccggac  4920
actacttgat ttttcaaact aacatgtctt tcctcatatg tagtagtgtt gaaatcacat  4980
cttttatatt caatttgagt tctactgatc gagtccaaaa tcgtccaaaa cctttaaact  5040
ctagaatctc ccacgacaac tctagtttc catttactcg tgcttagctt tcatcaacta  5100
acactacatc cataaaaaca tatgttaaga gatccctttg tgatcttatc catagactca  5160
```

-continued

```
aagctaattt ttttatgtag tcatattcta atcggaaagt cacatgtgtc tccatcattt  5220
attcaaacat attcataaca ttgttgttgg aactttgctt cctcaaaaaa tagggataaa  5280
aaaaacagta aaaggaattg gcccttcagg ctagggctgc tgatatcccc actaagctgg  5340
gccaatcggc caagaaactt tgcttcattc agggcatggt atggacaacc cactgcgggt  5400
tgccaaacaa aggagttagt aagaaaccac aaaatgctta gtctgagctt tgaagagttc  5460
tacttggtga gtaaaacagt taatcttaac tactgcttgg ctaagataag atgttagtca  5520
aaagaattct gtagatgtgc aatctcaaac caatctgcct ttgcatcatt tagaaaactg  5580
ctttaaaatt cgaaatattt tgcttaccat agctcatagc acagaagaat attatagaac  5640
aaaccaaggc aagtgacttt ctgaaacaca gttttcaaga acaggttcag attaaactag  5700
ataacaggat gccagcgttg gtaataagtg tactccccaa gagaagtcgc tgttttgttc  5760
tatctcaatg aaaaataacg acacgaaaat gaactatggc cgtctgcatt aatatggata  5820
ctcagcaaaa atggacatga gtaactcaaa atcgtcaatt gcttgctatg ttaggcaccc  5880
aagtcaatga tttctattcc atgctatcac aaagatta                          5918

SEQ ID NO: 12          moltype = DNA  length = 1288
FEATURE                Location/Qualifiers
source                 1..1288
                       mol_type = genomic DNA
                       organism = Zea mays
SEQUENCE: 12
ttccaagtcg cccaccgtga cgcccatcga gtcaaccgaa cccaagccgt gtggcgactg  60
gcgaggcgag tgccccagtt cctaactccg gtgggcgcgc tcccaccgcc gcgcggctca  120
aaacccgccc tcagcctccc gcgctccagt ccacacggga gcgggtggtg tcgtctgaag  180
cggcgcgatc aaggagtctt cgggcgctcc ggacgtaacg tgctggcggt tgcttatctc  240
cggatgtata tataagcgga aatgttctcc ttgttctatg gcctgtggaa gtatgtgttc  300
gccaaggacg agttccgtgt tctgattctt ggtgttgaca gagctggcaa gacgactttg  360
ctggagaagt tgaaatcgat atatctcaag gggggaaggac ttccgcctga ccgtgtcgtt  420
ccaacagttg ggctcaacat tggccgcatc gaagacgcaa aggcaaaact tgttttctgg  480
gatctaggtg gtcaggttag cctacgaaca atctgggaga aatactatga agaggcccat  540
gccataatgt acgttattga cgctgccaca gcatcgtcat ttgaagattc caaatctgct  600
ctggagaagg ttattcgcca tgaacatctg agaggagcac cactcttgat agttgcaaac  660
aaacaggatt tacctggagc cattgatgag gaagaattgg ctaaatttct gcataaagaa  720
ctggatgaga ggccatatac atttcaggct gtatctgcat atgatggcag gggggatcaaa  780
tctggcatag actggctggt ggaacaaatg gaaaaaagca aacgtaccga gacactgcag  840
gctcgtgctg gcgtagctgg acaaatttag aatggggtga atttgttaaa gaacaaagca  900
ttggatagga cggcttcctt cgtatcgcgt aagcagccat ttgctgcatt ccgggattat  960
cgttccaggt cgcccagagt gctgcaagaa atgtttggct ggttgctcct gtggtggtgg  1020
tgattggtga ggcgattcgt ttggtattat tgaggttgca ttcatatgta cctaaaggtc  1080
gcaagcatac atgtctatat gatgcttttc aattttcgta gcaaactagt agcttcaata  1140
cagaggatca aagagagccg tgttctttaa cttgtttgtg ataaaaaaaa aggaagaaag  1200
gaaagcgaag aaggaattat tggtgcatct gaaagtcttt attgcatatg tctaaaccat  1260
tttaaccgat gctggatgag cttttctt                                    1288

SEQ ID NO: 13          moltype = DNA  length = 979
FEATURE                Location/Qualifiers
source                 1..979
                       mol_type = genomic DNA
                       organism = Zea mays
SEQUENCE: 13
aatcgagtca accgaaccca agccgtgtgg cgactggcga ggcgagtgcc ccagttccta  60
actccggtgg gcgcgctccc accgccgcgc ggctcaaaac ccgccctcag cctcccgcgc  120
tccagtccac acgggagcgg gtggtgtcgt ctgaagcggc gcgatcaagg agtcttcggg  180
cgctccggac gtaacgtgct ggcggttgct tatcaccgga tatatatata taagcggaaa  240
tgttctcctt gttctatggc ctgtggaagt atgtgttcgc caaggacgag ttccgtgttc  300
tgattcttgg tgttgacaga gctggcaaga cgactttgct ggagaagttg aaatcgatat  360
atctcaaggg ggaaggactt ccgcctgacc gtgtcgttcc aacagttggg ctcaacattg  420
gccgcatcga agacgcaaag gcaaaacttg ttttctggga tctaggtggt caggttagcc  480
tacgaacaat ctgggagaaa tactatgaag aggcccatgc cataatgtac gttattgacg  540
ctgccacagc atcgtcattt gaagattcca aatctgctct ggagaaggtt attcgccatg  600
aacatctgag aggagcacca ctcttgatag ttgcaaacaa acaggattta cctggagcca  660
ttgatgagga agaattggct aaatttctgc ataaagaact ggatgagagg ccatatacat  720
ttcaggctgt atctgcatat gatgggtgag cgcagaaact caactggttc ctgaggaaat  780
ttgactcgcc atgaaaaaaa atgacaattt tactcaaaga tacaaaaaat tcacacattc  840
gtctgttata ttgtttcctg ggtgcatgaa actcaactgg ttcgtgagga aatttgactc  900
gccatgaaaa aaatgacaat tttactcaaa gatacaaaaa attcacacat tcgtcaaaaa  960
aaaaaaaaaa aaaaaaaaa                                               979

SEQ ID NO: 14          moltype = DNA  length = 1305
FEATURE                Location/Qualifiers
source                 1..1305
                       mol_type = genomic DNA
                       organism = Zea mays
SEQUENCE: 14
aaccgaaccc aagccgtgtg gcgactggcg aggcgagtgc cccagttcct aactccggtg  60
ggcgcgctcc caccgtcgcg cggctcaaaa cccgccctca gcctcccgcg ctccagtcca  120
cacgggagcg ggtggtgtcg tctgaagcgg cgcgatcaag gagtcttcgg gcgctccgga  180
cgtaacgtgc tggcggttgc ttatcaccgg atatatatat ataagcggaa atgttctcct  240
tgttctatgg cctgtggaag tatgtgttcg ccaaggacga gttccgtgtt ctgattcttg  300
gtgttgacag agctggcaag acgactttgc tggagaagtt gaaatcgata tatctcaagg  360
```

-continued

```
gggaaggact tccgcctgac cgtgtcgttc caacagttgg gctcaacatt ggccgcatcg  420
aagacgcaaa ggcaaaactt gttttctggg atctaggtgg tcaggttagc ctacgaacaa  480
tctgggagaa atactatgaa gaggcccatg ccataatgta cgttattgac gctgccacag  540
catcgtcatt tgaagattcc aaatctgctc tggagaaggt tattcgccat gaacatctga  600
gaggagcacc actcttgata gttgcaaaca aacaggattt acctggagcc attgatgagg  660
aagaattggc taaatttctg cataaagaac tggatgagag gccatataca tttcaggctg  720
tatctgcata tgatgggagg gggatcaaat ctggcataga ctggctggtg gaacaaatgg  780
aaaaaagcaa acgtaccgag acactgcagg ctcgtgctgg cgtagctgga caaatttaga  840
atggtaagct tgcagctgcg accggatgaa tttgttaaaa gaacaaagca ttggatagga  900
cggcttcctt cgtatcgcgt aagcagccat ttgctggatt acagggatta tcgttccagg  960
ccgcccagag tgctgcaaga aatgtttggc tggttgctcc tgtggtggtg gtgattggtg  1020
aggcgattcg tttggtatta gaggttgcat tcatatgtac ctaaaggtca cgagcataca  1080
tgtctatatg atgcttttca attttcgtag caaactagta gcttcaacac agaggatcaa  1140
agagagccgt gttctttaac ttgtttgtga taaaaaaaag gaagaaagga aagcgaagaa  1200
ggaatcactg gtgcatctga aagtctttat tggatatgtc taaaccattt caactgatgc  1260
tggataagtt tttcttaaaa aaaaaaaata aaaaaaaaaa aaaaa                  1305
```

```
SEQ ID NO: 15          moltype = DNA  length = 3993
FEATURE                Location/Qualifiers
variation              2094
                       note = n is a, c, g, or t
source                 1..3993
                       mol_type = genomic DNA
                       organism = Zea mays
SEQUENCE: 15
tgaaaatata tattgaataa cttttaacgg cttttagtgg tttccatcaa acggttttta  60
gctttttaac atctcacagc ccacagtaac tttttccaca gctcacaacc tatagcagct  120
tttttcacag ccacatccca actaaaaaga ccctaagtga atgtcatggt atggctgac  180
atttcgagag gtggacaaat ggagaatggc atgatatggg ctgccatgtg ggccgagggt  240
ctgagaccgg gctaaatgag ctgggctgaa gaggactgac tgtaggtaga aaggcaagcg  300
caacatttgg caccgttagc tctccactaa acttgtcaga tgcaataatt tatgtttttt  360
aaatggcaaa gccctcctgc cagccagtgc cttccttccg ggtcaaccac tggtaccgtc  420
acatcacgaa ttcccactgg cagtacgata acctcactga gcggtagggc ctcccgtccc  480
agaatcctgc aggacccatc gatcatggcc ccacgggtcc tgctcctgcg tgggttccaa  540
ttccaagtcg cccaccgtga cgcccatcga gtcaaccgaa cccaagccgt gtggcgactg  600
gcgaggcgag tgccccagtt cctaactccg gtgggcgcgc tcccaccgcc gcgcggctca  660
aaacccgccc tcagcctccc gcgctccagt ccacacggga gcgggtggtg tcgtctgaag  720
cggcgcgatc aaggagtctt cgggcgctcc ggtgagctat ctagatctca acatcctctc  780
ccctctgtag tctgtagttg tactctcccg cccgatggtt cagttaagtt atatcctctc  840
cccttatttt tactcggtcg ataccatttc gttgtggatt gggcgccccc gcaggttgaa  900
atgctgccca tcatgctgcg gccctgtact atgaggatgg ttctagtttt gcgtctggca  960
atttggggcg tacatgcttt tggctgcgta ctgttactga tcggagaaaa tgtttgtaac  1020
gtatgattcg tttttcagga cgtaacgtgc tggcggttgc ttatctccgg atgtatatat  1080
aagcggaaat gttctccttg ttctatggcc tgtggaagta tgtgttcgcc aaggacgagt  1140
tccgtgttct gattcttggt gttgacagag ctggcaagac ggtagctgct agctcccagc  1200
cttcatatat atatttccct ttctgaacta gaaattgatg atacttacct gtacacgatg  1260
tttctggaac cgttgccata gactttgctg gagaagttga aatcgatata tctcaagggg  1320
gaaggacttc cgcctgaccg tgtcgttcca acagttgggc tcaacattgg ccgcatcgaa  1380
gacgcaaagg caaaacttgt tttctgggat ctaggtggtc aggtaagaac gtttacgtac  1440
gtagtaaagt gagccttctg ttgccgtggc accaccctac gatcgttgat atttgagtct  1500
tgtcagtttg gtgctatatc agggtttcta atgcctggga aatacatgtc ataaattcaa  1560
attactagga tgtggttgct ttagttatta acctagcatc tttttgcgtt ccagcagaat  1620
atatataatc tagttatatg gaatgctcaa tagaattttc agaaagcaaa gatatgctct  1680
gttggctaac attcacagta ctcaatagaa ttgtttacta gtagaacagc atcagcttct  1740
ctgctatgtt ataagaatta gtgtaaaact aacttcagta tcactgcttg ctagtatgat  1800
aattaagctt ccatgccaag ttcagtattt cttacacact tgcctgcttg gcaggttagc  1860
ctacgaacaa tctgggagaa atactatgaa gaggcccatg ccataatgta cgttattgac  1920
gctgccacag catcgtcatt tgaagattcc aaatctgctc tgggtaaggt tcttatttgt  1980
gttaattata aactactccc tccattccaa attataagac attttggcct tttttctaga  2040
taaataaatt ttgctatgga cttaaatatt atttatatat atatatatat atantatata  2100
tatatatata tataaaatgt cctggtacat agttaaaaca ttatatctta aaaagctaaa  2160
acattgtctt ataacttgga acaagggagt actggtttgt ttctattgct agatcttccg  2220
agaagatgca ttgcctctct ggtaaatggg atgagaactc attctagcta gagaacctaa  2280
cctaaatttc ttacttcaga gaaggttatt cgccatgaac atctgagagg agcaccactc  2340
ttgatagttg caaacaaaca ggtgaagggt ttacttccac tttctatatt ttgtaccaca  2400
gtacataatt atgattgaaa gattcagtgc ttacaataaa gttgccatcg tagtaaaata  2460
aagattttgt ttttgtcatg tgcccatgct gtgaggcata caaatctaaa ttcctacgtt  2520
gcaaagcgcc tatgcgccat tgcgaggttg aataccagat gtagtttggc caattgtgat  2580
gtacagatgt gccacattga caattgacac gcagtttaaa ggagagtcag actactagtt  2640
ttttcattgc ccaacatata cctttggcca cttattgaaa atgtgagaga tcatttgagt  2700
ttgaacagta agttttgtga gatatcattt tatttagtaa tcatgcacac atgtctagaa  2760
ttgtgaaatg cacaataaag acgcaaactc ccacgagcat gcaggtacac ccgattgagg  2820
attctcagcg aatgttccag tttcgagaat caaacaacat ataacaatga tgaatttttt  2880
aaatcaatta aaacttcctg aaaagatcac atggaaacca atgactacat gcactgtctg  2940
tttctgttaa gctgggtaca cattattcta tcaaattgtt tattatttac ctcttgttct  3000
catgtttgga gggtgcttct ggatttcttt tggcaggatt tacctggagc cattgatgag  3060
gaagaattgg ctaaatttct gcataaagaa ctggatgaga ggccatatac atttcaggct  3120
gtatctgcat atgatgggtg agcgcagaaa ctcaactggt tcctgaggaa atttgactcg  3180
ccatgaaaaa aaatgacaat tttactcaaa gatacaaaaa attcacacat tcgtctgtta  3240
```

-continued

```
tattgtttcc tgggtgcatg aaactcaact ggttcgtgag gaaatttgac tcgccatgaa  3300
aaaaatgaca attttactca aagatacaaa aaattcacac attcgtctgt tatattgttt  3360
cctgggtgca tgatattcta aagatctgtt atattgttta aatgtgacac cggctcttgc  3420
agcaggggga tcaaatctgg catagactgg ctggtggaac aaatggaaaa aagcaaacgt  3480
accgagacac tgcaggctcg tgctggcgta gctggacaaa tttagaatgg ggtgaatttg  3540
ttaaagaaca aagcattgga taggacggct tccttcgtat cgcgtaagca gccatttgct  3600
gcattccggg attatcgttc caggtcgccc agagtgctgc aagaaatgtt tggctggttg  3660
ctcctgtggt ggtggtgatt ggtgaggcga ttcgtttggt attattgagg ttgcattcat  3720
atgtacctaa aggtcgcaag catacatgtc tatatgatgc ttttcaattt tcgtagcaaa  3780
ctagtagctt caatacagag gatcaaagag agccgtgttc tttaacttgt ttgtgataaa  3840
aaaaaaggaa gaaaggaaag cgaagaagga attattggtg catctgaaag tctttattgc  3900
atatgtctaa accattttaa ccgatgctgg atgagctttt cttcgcaccg atgttacatc  3960
tagtctatca tatgtatcct cgtttcatac tcg                                3993

SEQ ID NO: 16          moltype = DNA  length = 6492
FEATURE                Location/Qualifiers
source                 1..6492
                       mol_type = genomic DNA
                       organism = Zea mays
SEQUENCE: 16
cgaagaacaa ggaaagcact tgtccatcaa ttgcacttga gtagcaaagg tttcaggttg  60
tcggtgctga catctcttct actctgttaa gaccaggcta agggggtgtt tgaatgcact  120
agaactaata gttagttggc taaaaattgg tagtggaatt agctagctaa caaataacta  180
tctaactatt aactaattta ccaaaaatag ctaatagttg aactattaac taaagtgttt  240
ggatgtctca actaatttta gctactaact attagctcta gtgcattcaa acacccctta  300
agtgaatgtc atggtatggg ctgacatttc gagaggtgga gagtgtcatg gtatgggctg  360
ccatgtgggc cgagagtccg agaccgggct aaatgagctg ggctgaatag gactgactgc  420
aggtagaaag gcaagcgcaa catttggcac cgttagctct ccactaaact tgtcagatgc  480
aataatttat gtttttatta atggcaaagc cctcctgcca gccagtgcct tccttccggg  540
tcaaccactg gtacagtcac atcacgaatt cccactggca gtacgataac ctcactgagc  600
ggtagggcct cccgtcccag aatcctgcag gacccaccga tcatagcccc acgggtcctg  660
ctcctgcgtg ggttccagtt ccaagtcgcc caccgtgacg cccatcgagt caaccgaacc  720
caagccgtgt ggcgactggc gaggcgagtg ccccagttcc taactccggt gggcgcgctc  780
ccaccgccgc gcggctcaaa acccgccctc agcctcccgc gctccagtcc acacgggagc  840
gggtggtgtc gtctgaagcg gcgcgatcaa ggagccttcg agcgctccgg tgagctatct  900
agatctcaac atcctctccc ctctgtagtc tgtagttgta ctctcccgcc cgatggttca  960
gttaagttat atcctctccc cttattttta ctcggtcgat accatttcgt tgtggattga  1020
aatgctgcgg ccctgtacta tgaggatggt tcctagtttt gcgtctggca atttggggcg  1080
tacatgcttt tggctgcgta ctgttactga tcggagaaaa tgtttgtaac gtatgattcg  1140
tttttcagga cgtaacgtgc tggcggttgc ttatcgccgg atatatatat ataagcggaa  1200
atgttctcct tgttctatgg cctgtggaag tatgtgttcg ccaaggacga gttccgtgtt  1260
ctgattcttg gtgttgacag agctggcaag acggtagctg ctagctccca gccttcatat  1320
atatatattt ccctttctga actagaaatt gatgaaactt acctgtacac aatgtttctg  1380
gaaccgttgc catagacttt gctggagaag ttgaaatcga tatatctcaa gggggaagga  1440
cttccgcctg accgtgtcgt tccaacagtt gggctcaaca ttggccgcat cgaagacgca  1500
aaggcaaaac ttgttttctg ggatctaggt ggtcaggtaa gaacgtttac gtacgtagta  1560
aagtgagcct tctgttgccg tggcaccacc ctacgatcgt tgatatttga gtcttgtcag  1620
tttggtgcta tatcagggtt tctaatgcct gggaaataca tgtcataaaa tcaaattact  1680
aggatgtggt tgctttagtt attaacctag catctttttg cgttccagca gaatatatat  1740
aatctagtta tatggaatgc tcaatagaat tttcagaaag caaagatatg ctctgttggc  1800
taacattcac agtactcaat agaattgggt ggctagtaga acagcatcag cttctctgct  1860
atgttataag aattagtgta aaactaactt cagtatcact gcttgctagt atgataatta  1920
agcttccatg ccaagttcag tatttcttac acacttgcct gcttggcagg ttagcctacg  1980
aacaatctgg gagaaatact atgaagaggc ccatgccata atgtacgtta ttgacgctgc  2040
cacagcatcg tcatttgaag attccaaatc tgctttgggt aaggttctta tttgtgtcaa  2100
ttataaacta cgccatccat tccaaattat aagacatttt ggccttttttc tagataaata  2160
aattttgcta tggacttaaa tattaaaaat atatataatg tcctggtaca tagttaaaac  2220
aatatatcta gaaaagctaa aacatcgtct tataacttgg aacagaggga gtactggttt  2280
gtttctattg ctagatcttt ccagaagatg caatgcctct ctggtaaatg ggatgagaac  2340
tcattctaga gaacctaacc taaatttctt acttcagaga aggttattcg ccatgaacat  2400
ctgagaggag caccactctt gatagttgca aacaaacagg tgaagggttt acttccactt  2460
tctatatttt gtaccacagt acataattat gattgaaaga tttagtgctt acaataaagt  2520
tgccatcgta gttaaaataa agattttgtt tttgtcatgt gcacatgctg tgaggcatac  2580
aaatataaat tcctacgttg caaagcgcct atgcgccatt gcgaggttga ataccagatg  2640
tagtttttaa atcaattaaa acttcctgaa aagatcacat ggaaaccaat gactacatgc  2700
actgtctgtt tctgttaagc tggtacacaa ttattctatc aaattgttta ttatttacct  2760
ctagcttgtt ctcatgtttg gagggtgctt ctggatttct tttggcagga tttacctgga  2820
gccattgatg aggaagaatt ggctaaattt ctgcataaag aactggatga gaggacatat  2880
acatttcagg ctgtatctgc atatgatggg tgagcgcaga aactcaactg gttcctgagg  2940
aaatttgact cgccatgaaa aaaatgacaa ttttactcaa agatacaaaa aaattcacac  3000
attcgtctgt tatattgttt cctgggtgca tgatattcta aagatctgtt atattgttta  3060
aatgtgacac cggctcttgc aggaggggga tcaaatctgg catagactgg ctggtggaac  3120
aaatggaaaa aagcaaacgt accgagacac tgcaggctcg tgctggcgta gctggacaaa  3180
tttagaatgg ggtgaatttg ttaaagaaca aagcattgga taggaccgct tccttcgtat  3240
cgcgtaagca gccatttgct gcattccggg attatcgttc caggtcgccc agagtgctgc  3300
aagaaatgtt tggctggttg ctcctgtggt ggtggtgatt ggtgaggcga ttcgtttggt  3360
attattgagg ttgcattctt atgtacctaa aggtcgcaag catacatgtt tatatgatgc  3420
ttttcaattt tcgtagcaaa ctagtagctt caatacagag gatcaaagag agccgtgttc  3480
tttaacttgt ttgtgataaa aaaaaggaag aaaggaaagc gaagaaggaa ttattggtgc  3540
```

```
atctgaaagt ctttattgat atgtctaaac catttcaacc gatgttggat gaggttttct  3600
tcgcaccggt gttacatcta gtctatcata tgtatcgtcg tttcatactc gatccttttt  3660
tatggccaaa ctccaacaca acatatgcat ttctgtagcg catatgtatt gaacatgtct  3720
tttttagact aacattttgc accgaacaac atagcagatc gaattgtcat cctataaaac  3780
ttctttttaa cttttgtggt atcctattgt catatagaat atcaaatgtt tggcgctacc  3840
tcatccattg actaatacct ttatcaatat ctctacgtag catagatcct aaatatctaa  3900
agatgtcctt catggacact acttgatttt tcaaactaac atgtctttcc taatatgtag  3960
tagcatagat cctaaatatc taaagatgtc cttcctggac actacttgat tttcaaact   4020
aacatgtctt tcctcatatg tagtagtgtt gaaatcacat cttttatatt caatttgagt  4080
tctactgatc gagtccaaaa tcgtccaaaa cctttaaact ctagaatctc ccaccacaac  4140
tctagttttc tatttactcg tgcttagctt tcatcaacta acactacatc cataaaaaac  4200
atatgttaag agatatccct ttgtgatctt atccatagac tcagctaatt ttttatgtag  4260
tcatattcta atcgaaaagt cacatgtgtc tccatcattt attcaaacat attcataaca  4320
ttgttgttgg aactttgctt cctcaaaaaa cagggataaa aaacagtaaa aggaattggc  4380
ccttcaggct agagctgctg atatccccac taagctgggc caatcggcca agaaactttg  4440
cttcattcag ggcatgatat ggacaaccca ctgcggattg ccaaacaaag aagttagtaa  4500
gaaaccacaa aatgcttagt ctgagctttg aagagttcta cttggtgagt aaaacagtta  4560
atcttaacta ctgcttggct aagataagat gttagctaaa agaattctgt agatgtgcaa  4620
tctcaaacca atctgccttt gcatcattta gaaaactgct ttaaaattcg aaatattttg  4680
cttacaatag ctcatagcac agaagaatat tatagaacaa accaaggcaa gtgactttct  4740
gaaacacagt tttcaagaac aggttcagat taaactagat aacaggatgc cagcgttggt  4800
aataagtcta ctccccaaga gaagtcactg ttttgttctt tctcaatgaa aaataacgac  4860
acaaaaatga actatggccg tctgcattaa tatggatacg cagcaaaaat ggacatgagt  4920
aactcaaaat cgtcaagtgc ttgctatgtt aagcacccaa gtcaatgatt tatattccat  4980
gatatcgcaa agattatcta taacaagttc tgagtgtgtt tcaaacatta aatgatccat  5040
gaaaggtaag cacttgtatt tagcggacag tactagtctg ctgtgggatt aacccatttt  5100
ttatggttct cgatggcctt ttgcttcaag ataatatctg atccaattaa tagacaaaat  5160
cacaagtaat ctttgttaca tgtcatcatc gaatcctatc ttctgtagga gcaaacttaa  5220
acggtgacat atcaagcaac actatgagaa ttcatgtgta tctgataaag gatcattcac  5280
ttcacatgta gacatatatg actacaaaag tggtatgaat attgttaaca gaatcaatgg  5340
aaaatggaat atatctcatt aggtaacata tggaattgta agcaggctat aaaaaatcag  5400
aggtattaag tatcaattca gacagcagaa tgatgcaatg atcacaacca agtcaacaag  5460
ttatcataac taagattagt ccttttgtag ccaaagaagt ttaccgaact cagaaagcag  5520
aacataattc acttacttga tctcaacaac attttgtgtc accatgccag gaagaaacca  5580
gaagtggcat ggtaagcatt gccagtccaa ccagacctct gtgaagcatt atcccatcac  5640
tggaaacctc cacaaagcgt gtttgctaag gcaaatggca tgtatctcca tctaatgaac  5700
atacaaattt tgccctgcct gatgttaagt aactacaggt accaggtaga ctacaagtct  5760
acaactacaa cattacataa cagggatgga acaattacac tcaaatgaac acttgaacag  5820
caagagccag tctctgagac atctgcttcg gcctggctaa tcatagcccc agtaaaccat  5880
aacaacagtt aaatcatccg tccaagattg tccaccctca agaagtgcat gttgtgcaaa  5940
ttccccaata tatcctcaga tgcatcaaca tcgatatgaa agttgctgat atcttcaact  6000
ccgccagcac cgctaacatt aaccctacca gtgccatctg tagcatgtgc tgcctcattt  6060
atgttaattc tcctcacctc ctcggccctt ccatctccag cgttctcatc cccagcccag  6120
ccttcctgcc cgagcatcga agaatcaatg ccactctcca caccaagaga acgtctcctg  6180
agccctaccc cgaccttctt gcgggccgtc gtcttcttga tcctacctct agaagagcca  6240
ccacgagcac tgtcattctg tggctgccta ccaccatggt ttccgtgact cctaccacca  6300
ccaccttggc cactgggagc cgtgttccaa ggaaacatct tgtagaatgg cttccagttg  6360
gcacccaggt cggccgcgtt gggaaatccg agggggaaga acccccaggc gcagtggtac  6420
atttcagtgc ccggcacaac ggtgggtggg gtcgggagct cagaagccac gaatccgcgg  6480
cggcagcccg cg                                                     6492

SEQ ID NO: 17          moltype = DNA  length = 10054
FEATURE                Location/Qualifiers
source                 1..10054
                       mol_type = genomic DNA
                       organism = Zea mays
SEQUENCE: 17
tttggatgtc tcaactaatt ttagctacta actattagct ctagtgcatt caaacacccc  60
ttaagtgaat gtcatggtat gggctgacat ttcgagaggt ggagagtgtc atggtatggg  120
ctgccatgtg ggccgagagt ccgagaccgg gctaaatgag ctgggctgaa taggactgac  180
tgcaggtaga aaggcaagcg caacatttgg caccgttagc tctccactaa acttgtcaga  240
tgcaataatt tatgttttta ttaatggcaa agccctcctg ccagccagtg ccttccttcc  300
gggtcaacca ctggtacagt cacatcacga attcccactg gcagtacgat aacctcactg  360
agcggtaggg cctcccgtcc cagaatcctg caggacccac cgatcatagc cccacgggtc  420
ctgctcctgc gtgggttcca gttccaagtc gcccaccgtg acgcccatcg agtcaaccga  480
acccaagccg tgtggcgact ggcgaggcga gtgccccagt tcctaactcc ggtgggcgcg  540
ctcccaccgc cgcgcggctc aaaacccgcc ctcagcctcc cgcgctccag tccacacggg  600
agcgggtggt gtcgtctgaa gcggcgcgat caaggagcct tcgagcgctc cggtgagcta  660
tctagatctc aacatcctct cccctctgta gtctgtagtt gtactctccc gcccgatggt  720
tcagttaagt tatatcctct ccccttattt ttactcggtc gataccattt cgttgtggat  780
tgaaatgctg cggccctgta ctatgaggat ggttcctagt tttgcgtctg gcaatttggg  840
gcgtacatgc ttttggctgc gtactgttac tgatcggaga aaatgtttgt aacgtatgat  900
tcgtttttca ggacgtaacg tgctggcggt tgcttatcgc cggatatata tatataagcg  960
gaaatgttct ccttgttcta tggcctgtgg aagtatgtgt tcgccaagga cgagttccgt  1020
gttctgattc ttggtgttga cagagctggc aagacggtag ctgctagctc ccagccttca  1080
tatatatata tttccctttc tgaactagaa attgatgaaa cttacctgta cacaatgttt  1140
ctggaaccgt tgccatagac tttgctggag aagttgaaat cgatatatct caagggggaa  1200
ggacttccgc ctgaccgtgt cgttccaaca gttgggctca acattggccg catcgaagac  1260
gcaaaggcaa aacttgtttt ctgggatcta ggtggtcagg taagaacgtt tacgtacgta  1320
```

-continued

```
gtaaagtgag ccttctgttg ccgtggcacc accctacgat cgttgatatt tgagtcttgt  1380
cagtttggtg ctatatcagg gtttctaatg cctgggaaat acatgtcata aaatcaaatt  1440
actaggatgt ggttgcttta gttattaacc tagcatcttt ttgcgttcca gcagaatata  1500
tataatctag ttatatggaa tgctcaatag aattttcaga aagcaaagat atgctctgtt  1560
ggctaacatt cacagtactc aatagaattg ggtggctagt agaacagcat cagcttctct  1620
gctatgttat aagaattagt gtaaaactaa cttcagtatc actgcttgct agtatgataa  1680
ttaagcttcc atgccaagtt cagtatttct tacacacttg cctgcttggc aggttagcct  1740
acgaacaatc tgggagaaat actatgaaga ggcccatgcc ataatgtacg ttattgacgc  1800
tgcccacagca tcgtcatttg aagattccaa atctgctttg ggtaaggttc ttatttgtgt  1860
caattataaa ctacgccatc cattccaaat tataagacat tttggccttt ttctagataa  1920
ataaattttg ctatggactt aaatattaaa aatatatata atgtcctggt acatagttaa  1980
aacaatatat ctagaaaagc taaaacatcg tcttataact tggaacagag ggagtactgg  2040
tttgtttcta ttgctagatc tttccagaag atgcaatgcc tctctggtaa atgggatgag  2100
aactcattct agagaaccta acctaaattt cttacttcag agaaggttat tcgccatgaa  2160
catctgagag gagcaccact cttgatagtt gcaaacaaac aggtgaaggg tttacttcca  2220
ctttctatat tttgtaccac agtacataat tatgattgaa agatttagtg cttacaataa  2280
agttgccatc gtagttaaaa taaagatttt gtttttgtca tgtgcacatg ctgtgaggca  2340
tacaaatata aattcctacg ttgcaaagcg cctatgcgcc attgcgaggt tgaataccag  2400
atgtagtttt taaatcaatt aaaacttcct gaaaagatca catggaaacc aatgactaca  2460
tgcactgtct gtttctgtta agctgggtac acattattct atcaaattgt ttattattta  2520
cctctagctt gttctcatgt ttggagggtg cttctggatt tcttttggca ggatttacct  2580
ggagccattg atgaggaaga attggctaaa tttctgcata aagaactgga tgagaggaca  2640
tatacatttc aggctgtatc tgcatatgat gggtgagcgc agaaactcaa ctggttcctg  2700
aggaaatttg actcgccatg aaaaaaatga caattttact caaagataca aaaaaattca  2760
cacattcgtc tgttatattg tttcctgggt gcatgatatt ctaaagatct gttatattgt  2820
ttaaatgtga caccggctct tgcaggaggg ggatcaaatc tggcatagac tggctggtgg  2880
aacaaatgga aaaaagcaaa cgtaccgaga cactgcaggc tcgtgctggc gtagctggac  2940
aaatttagaa tggggtgaat ttgttaaaga acaaagcatt ggataggacc gcttccttcg  3000
tatcgcgtaa gcagccattt gctgcattcc gggattatcg ttccaggtcg cccagagtgc  3060
tgcaagaaat gtttggctgg ttgctcctgt ggtggtggtg attggtgagg cgattcgttt  3120
ggtattattg aggttgcatt cttatgtacc taaaggtcgc aagcatacat gtttatatga  3180
tgcttttcaa ttttcgtagc aaactagtag cttcaataca gaggatcaaa gagagccgtg  3240
ttctttaact tgtttgtgat aaaaaaaagg aagaaaggaa agcgaagaag gaattattgg  3300
tgcatctgaa agtctttatt gatatgtcta aaccatttca accgatgttg gatgaggttt  3360
tcttcgcacc ggtgttacat ctagtctatc atatgtatcg tcgtttcata ctcgatcctt  3420
ttttatggcc aaactccaac acaacatatg catttctgta gcgcatatgt attgaacatg  3480
tcttttttag actaacattt tgcaccgaac aacatagcag atcgaattgt catcctataa  3540
aacttctttt taacttttgt ggtatcctat tgtcatatag aatatcaaat gtttggcgct  3600
acctcatcca ttgactaata cctttatcaa tatctctacg tagcatagat cctaaatatc  3660
taaagatgtc cttcatggac actacttgat ttttcaaact aacatgtctt tcctaatatg  3720
tagtagcata gatcctaaat atctaaagat gtccttcctg gacactactt gatttttcaa  3780
actaacatgt ctttcctcat atgtagtagt gttgaaatca catcttttat attcaatttg  3840
agttctactg atcgagtcca aaatcgtcca aaacctttaa actctagaat ctcccaccac  3900
aactctagtt ttctatttac tcgtgcttag ctttcatcaa ctaacactac atccataaaa  3960
aacatatgtt aagagatatc cctttgtgat cttatccata gactcagcta attttttatg  4020
tagtcatatt ctaatcgaaa agtcacatgt gtctccatca tttattcaaa catattcata  4080
acattgttgt tggaactttg cttcctcaaa aaacagggat aaaaaacagt aaaaggaatt  4140
ggcccttcag gctagagctg ctgatatccc cactaagctg ggccaatcgg ccaagaaact  4200
ttgcttcatt cagggcatga tatggacaac ccactgcgga ttgccaaaca aagaagttag  4260
taagaaacca caaaatgctt agtctgagct ttgaagagtt ctacttggtg agtaaaacag  4320
ttaatcttaa ctactgcttg gctaagataa gatgttagct aaaagaattc tgtagatgtg  4380
caatctcaaa ccaatctgcc tttgcatcat ttagaaaact gctttaaaat tcgaaatatt  4440
ttgcttacaa tagctcatag cacagaagaa tattatagaa caaaccaagg caagtgactt  4500
tctgaaacac agttttcaag aacaggttca gattaaacta gataacagga tgccagcgtt  4560
ggtaataagt ctactcccca agagaagtca ctgttttgtt ctttctcaat gaaaaataac  4620
gacacaaaaa tgaactatgg ccgtctgcat taatatggat acgcagcaaa aatggacatg  4680
agtaactcaa aatcgtcaag tgcttgctat gttaagcacc caagtcaatg atttatattc  4740
catgatatcg caaagattat ctataacaag ttctgagtgt gtttcaaaca ttaaatgatc  4800
catgaaaggt aagcacttgt atttagcgga cagtactagt ctgctgtggg attaacccat  4860
tttttatggt tctcgatggc cttttgcttc aagataatat ctgatccaat taatagacaa  4920
aatcacaagt aatctttgtt acatgtcatc atcgaatcct atcttctgta ggagcaaact  4980
taaacggtga catatcaagc aacactatga gaattcatgt gtatctgata aaggatcatt  5040
cacttcacat gtagacatat atgactacaa aagtggtatg aatattgtta acagaatcaa  5100
tggaaaatgg aatatatctc attaggtaac atatggaatt gtaagcaggc tataaaaaat  5160
cagaggtatt aagtatcaat tcagacagca gaatgatgca atgatcacaa ccaagtcaac  5220
aagttatcat aactaagatt agtccttttg tagccaaaga agtttaccga actcagaaag  5280
cagaacataa ttcacttact tgatctcaac aacattttgt gtcaccatgc caggaagaaa  5340
ccagaagtgg catggtaagc attgccagtc caaccagacc tctgtgaagc attatcccat  5400
cactggaaac ctccacaaag cgtgtttgct aaggcaaatg gcatgtatct ccatctaatg  5460
aacatacaaa ttttgccctg cctgatgtta agtaactaca ggtaccaggt agactacaag  5520
tctacaacta caacattaca taacagggat ggaacaatta cactcaaatg aacacttgaa  5580
cagcaagagc cagtctctga gacatctgct tcggcctggc taatcatagc cccagtaaac  5640
cataacaaca gttaaatcat ccgtccaaga ttgtccaccc tcaagaagtg catgttgtgc  5700
aaattcccca atatatcctc agatgcatca acatcgatat gaaagttgct gatatcttca  5760
actccgccag caccgctaac attaacccta ccagtgccat ctgtagcatg tgctgcctca  5820
tttatgttaa ttctcctcac ctcctcggcc cttccatctc cagcgttctc atccccagcc  5880
cagccttcct gcccgagcat cgaagaatca atgccactct ccacaccaag agaacgtctc  5940
ctgagcccta ccccgacctt cttgcgggcc gtcgtcttct tgatcctacc tctagaagag  6000
ccaccacgag cactgtcatt ctgtggctgc ctaccaccat ggtttccgtg actcctacca  6060
```

-continued

```
ccaccacctt ggccactggg agccgtgttc caaggaaaca tcttgtagaa tggcttccag  6120
ttggcaccca ggtcggccgc gttgggaaat ccgagggggga agaaccccca ggcgcagtgg  6180
tacatttcag tgcccggcac aacggtgggt ggggtcggga gctcagaagc cacgaatccg  6240
cggcggcagc ccgcgttggg gcacttgagg gcgcgcccga tcaggctgcg cgggtactgg  6300
tgcacgtagc agcagaaggg gcacgccgtc cagaactccg gggtgtccga ggcgggagcg  6360
gccgcggcgg gatactggga ggagtaaggg gtaccagtgg cgggatcggc gggcggcggg  6420
gggcggcgag agggatccga gaggaaggcg taggcgtcgt tgacgaggcg gagcgccatc  6480
tcggctcccg ggtgcgggtt gctggggccg aggaggagcg cgaggcggcg gaaggcgcgg  6540
gacacggcgg cctggtcggg gctgactccg ggcggcagct ggaggatggc gagcgggtcc  6600
ggctggcccg aggggcccat gaactgggaa gcgaggagga cgtcggcgac ggcgaggagc  6660
tcgtcaacgc cagcgaggag cgggttcgcc tccatcgacc gctccgcgaa gcgcttgcag  6720
ccgacgaggt cgcgcgccgc gaggagcttc tcggcgatct ccagccagcg ctccgcctgc  6780
gcggggccgt cgctggcgcc tccgccgccc ccgctcacgc tcccgccggt ggagaagtcc  6840
atggtttggg ggaggaaaag gtggatgctg tcggaggcag ctggtttggt tttggggagg  6900
gggaagatcc tgctgcccga ggggctcttg actggcgact gtctgtcagt ccgagagtat  6960
tttgttgggc agcacattta ttttaaggac aactgtgatt atacgttttc aacttcgtga  7020
attattgatt acgaaaatta aaaatgaggg gtaaaatcat aattgtaagg gaagagaagg  7080
atatactcaa aattaatctg aaaataatat taaacttttt atggttaatt gtgattatag  7140
ccttctctca ctttacaatt gtgattttac cccttatttt tatttttaat cactaattct  7200
gatttttatt aacgttgata aggcggtgca aacaacggct ttgttttcaa aacagagggg  7260
taacaaagtt aaaaaagaag ggataaaatc acaattaaaa tattagaaaa gggtataatc  7320
acaattatcc cttgatttta ttaggctctc tccaatcatt ctccatctca aatcccacat  7380
ttggactttc tattcatatt taaatatcct catcttcact attatttccc tattttacct  7440
cctctccaag catccctcta ttcagctctc cctttaccct ttaactaagc tatttgactt  7500
ttctacatca gtttttagag tttttaatat ttataatatc ataatacaca ttgtcactta  7560
accaaactta tagcagatta attttatagt taaaaacact aattagtgaa gagtagggtt  7620
ctatctttct cgttttacaa ggtgttttcc ttctctcacc ctacaagagg gaggagaggg  7680
acctgttgaa gctctctcga tgtacgaaat caccgaatac gtcgtgaagg ggaggggaaa  7740
ggatccgttg gagagcgtct tatagcctgt tagcttcgaa ttaaagtcag ttgtttagat  7800
tattgtagct gcaattcaca gagaccaaaa cactacagaa atagtaaaag ccgtttcgaa  7860
ttaaaaccaa gggaacgggc tattagtttt cccatatgca aacataccag accattgtag  7920
cgccccaccg cagagcaagt tttgcataca atcaatgtat aattggacta ccaaaaacca  7980
taaaaaattc taaaaatata taaatataat ttattgttta ctttattaga ttataaaatt  8040
ttaagtttaa atttatacaa tagtaaaaga aaaaatatat tcaattagat aaaaaaaatt  8100
ccctcaattc cgtaaaataa ggcctgcatt ttaaaaaaaa aagactcaat gttttaaaac  8160
ttttgactag taattcagcc aaaagcatat attttagtat atacatgtta tatacttgat  8220
ttgtattcaa aaattacttt aatttaatgc tcgttatgtt tttattgata gcatattttg  8280
aaataaacaa atagtcaaag tttcgctcca aagactgtac caaaaatata taccttgtta  8340
tataagatga atgaattata tattaacata gcataaatca atctaggatc ttaaatatga  8400
tatattgata aagtaaataa tatatatgta taatttttta aatattttg tgacttttga  8460
tagttggatt gtatagaatg tttggttgca caatagtatt ttcctcaagt gaaagatctt  8520
catcaatgtt gtaatacagt gacatgtcat catcaagcct ggttagatct atcctcaaaa  8580
tctactccat aaatttaagg gccaattccc tgtatgccac tagaaaatat actcattcct  8640
tgtatgccac tgaccccaca tgtcatagac accaaaaaat atacctatat gccactcagt  8700
ggcacacaag gaatgagtat aaaatttgat ggcataccag gaattttctc taaatttaat  8760
ttagagtttc tagagtactt ctcttttaac ttcacctttt ttagctacac ttgtttggtt  8820
gaaatataga gccgcacagt cccaaacaaa ctctaaggat gagttgatgt atccccaagt  8880
atatcttaca aaaaatgata taatgactct atttatctta tagggtattt gtgattatac  8940
cctctctggt cttgaaattg tgattttacc catcgttttt caactttgtg atattttatc  9000
ccttcatttt gaaaacgaag agttgccata cccttgtgcc gttagatgca gttaacaatg  9060
ttaaatttga tgcaaaagat aaaaataccc aagcaattta ttttgatttt accctcgtta  9120
tattatgtaa tagtgatttc accccctatta gggttgtgcc cataaagaat agaaaaaggt  9180
agtttgaacc tttcacccat ttattttctc atttttttat ttttaatcac taattctgat  9240
tttcactaac gatgttgaga gtgaagggca aatggtagct tcgtatttaa aacggaggtg  9300
taaaattaga aagttgaaaa tgcagagtaa aatcacaatt gcaaggccaa cgaagggtat  9360
aatcacaatt atctcttatc ttactagtag taattattag attgtgagga ataaagtaat  9420
ggcagattat ttcattctat tttataaacc aaacaaaact tggaaaagta aaaatatgat  9480
ggagtgtatg tgggggtggt tagggaggaa aggcccaaaa caaagggttt tcgaatctta  9540
cctaaataaa aatcatggca agctaaattg ctaaaacaag aatctaacgt gtttgtttgg  9600
cacttgcata aagatggtat cttttctatt aattatatgt ataaattctt agttactaat  9660
ggaattaatg ttttatgaat aatttggtgt ctaaagatac ctttaaagat aaaaatcttc  9720
atgtagttct ttcaaaaaaa gagggtcatt ctcacaatct cacaaaaggt aattttatca  9780
aaaagaaatt gaaatagtga cacaacttgc tcttttgagc cacaaaccat ctgatacata  9840
ttttctttga gtgcacttat gctaggttac tatagagaga agtttatatt tttttttctc  9900
gaacacgcag gaaaactgcg catcattata ttgaaagaga gaaaggtccg aaatggacca  9960
aagtacaaag ccaagcaggc aaaaaataaa aaggaaaaat agtacagcct catgcactag  10020
gaatagccct gatcctagca aaagcagcca gaag                             10054
```

```
SEQ ID NO: 18          moltype = DNA  length = 5714
FEATURE                Location/Qualifiers
source                 1..5714
                       mol_type = genomic DNA
                       organism = Zea mays
SEQUENCE: 18
atcacgcctc gcccgagcct agcctcgggc aagggcagcc gaccccgaag gggtttccgt  60
ctcgcccgag gccccccttc aacggcggac acatctccgg cttgcccgag gccttgcctt  120
cgctgagaag caaccctgac tgaatcgccg caccgaccgg ccaagtcgca ggagcattta  180
acgcaaagga aaccaggccc tgccaaaggc accataggaa actccgctcc gcccaaccca  240
gggctcggac tcgggcaaag ccccggaaga cggcgaactc cgctccgccc gacccagggc  300
```

-continued

```
tcggactcgg gctaagcccc ggaagacggc gaactccgct ccgcccgacc cagggctcgg  360
actcgggcta agccccggaa gacggcgaac tccgctccgc ccgaccaagg gctcggactc  420
gggctaagcc ccggaagacg gcgaactccg ctccgcccga ccaagggctc ggactcgggc  480
taagccccgg aagacggcga actccgctcc gcccgaccaa gggctcggac tcgggctaag  540
ccccggaaga cgacgaactc cgcctcgccc gacctagggg ctcggactcg gcctctgctg  600
acgaactctg cctcgcccga cccaggggct cggactcggc ctctgctgac gaactccgcc  660
tcgcccgacc caggggctcg gactcggcct ctgctgacga actccgcctc gcccgacccg  720
ggggctcgga ctcggcctct gctgacgacc tccgcctcgc ccgacccagg ggctcggact  780
cggcttctgc tgacgacctc cgcctcgccc gacccagggg ctcggactcg gcctcggcca  840
tggaagacag actcgacccc ggcttcggag gagcctccac gtcgcccaac ctagggccca  900
ggccagccac gtcgacagga agcgccatca tcaccctacc ccgagccgac tcgggtcgca  960
gagaacaaga cctgtgtccc atctggctgg ctccgccaga taggcaatga tggcgccccg  1020
ctagccccgt gacgacggcg gctctcagct ctcttacgga agcagggcga cgtcagcaag  1080
gacacaaccg ttccaacagc tgtccctccg ccaggctccg ttgctcctcc gacagccacg  1140
acatcacgcc agcagggtgc caagatctct ccggctgcca tattggcatg tacttagggc  1200
actagctctc cccccgctag acacgtagca ctccgctaca ccccattgta cgcctggatc  1260
ctctccttac gcctataaaa ggaaggacca gggccttctt agagaaggtt ggccgcgcgg  1320
ggacgaggac ggggacaggc actctcttgc ggccgctcgc ttccctcacc cgtgtggacg  1380
cttgtaaccc cctattgcaa gcgcacccga cctgggcgcg ggacgaacac gaaggccgcg  1440
ggattcccac ctctctctcg ccggactccg gcctcctcgc tcctttcccc cttcgcgctc  1500
gcccacgcgc tcgacccatc tgggctgggg cacgcagcac actcactcgt cggcttaggg  1560
accccccggt ctcgaaacgc cgacactact cttgaggaga ttattagatt atcataatct  1620
aggctttaga ttatataatc tgaacacata atctagttgt ttgtttatct aatggattat  1680
ttacgctaga ttatataatc tggagagatt ataatctgaa acaaacatgg ccttagtgat  1740
taaaaataaa aataaggggt aaaatcacaa ttgtaaagtg agagaaggct ataatcacaa  1800
ttaaccataa aaagtttaat attattttca ggttaatttt gagtatatcc ttctcttccc  1860
ttacagttat gatttaccc cttattttta atttttgtaa tcaataattc acaaagttga  1920
aaacgtataa tcacagttgt ccttaaaatt aaatgtgctg cccaacaaaa tactctcgga  1980
ctgacagaca gtcgccagtc aagagcccct cgggcagcag gatcttcccc ctccccaaaa  2040
ccaaaccagc tgcctccgac agcatccacc ttttcctccc ccaaaccatg gacttctcca  2100
ccggcgggag cgtgagcggg ggcggcggag gcgccagcga cggcccccgcg caggcggagc  2160
gctggctgga gatcgccgag aagctcctcg cggcgcgcga cctcgtcggc tgcaagcgct  2220
tcgcggagcg gtcggtggag gcgaacccgc tcctcgccgg cgttgacgaa ctcctcgccg  2280
tcgccgacgt cctcctcgct tcccagttca tgggcacctc gggccagccg gacccgctcg  2340
ccatcctcca gctgccgccc ggagtcagcc ccgaccaggc cgccgtgtcc cgcgccttcc  2400
gccgcctcgc gctcctcctc ggtcccagca acccgcaccc gggagccgag atggcgctcc  2460
gcctcgtcaa cgacgcctac gccttcctct cggatccctc tcgccgcccc ccgccgcccg  2520
ccgatcccgc cactggtacc ccttactcct cccagtatcc cgccgcggcc gctcccgcct  2580
ccgacacccc ggagttctgg acggcgtgcc ccttctgctg ctacgtgcac cagtacccgc  2640
gcagcctgat cggcgcgcc ctcaagtgcc ccaacgcggg ctgccgccgc ggattcgtgg  2700
cttctgagct cccgacccca cccacggttg tgccgggcac tgaaatgtac cactgcgcct  2760
gggggttctt ccccctcgga tttcccaacg cggccgacct gggtgccaac tggaagccat  2820
tctacaagat gttcccttgg aacacggctc ccagtggcca aggtggtggt ggtaggagtc  2880
acggaaacca tggtggtagg cagccacaga atgacagtgc tcgtggtggc tcttctagag  2940
gtaggatcaa gaagacgacg gcccgcaaga aggtcggggt agggctcagg agacgttctc  3000
ttggtgtgga gagtggcatt gattcttcga tgctcgggca ggaaggctgg gctggggatg  3060
agaacgctgg agatggaagg gccgaggagg tgaggagaat taacataaat gaggcagcac  3120
atgctacaga tggcactggt agggttaatg ttagcggtgc tggcggagtt gaagatatcg  3180
gcaactttca tatcgatgtt gatgcatccg aggatatatt ggggaatttg cacaacatgc  3240
acttcttgag ggtggacaat cttggacgga tgatttaact gttgttatgg tttactgggg  3300
ctatgattag ccaggccgac tcttgctgtt caagtgttca tttgagtgta attgttccat  3360
ccctgttatg taatgttgta gttgtagact tgtagtctac ctggtacctg tagttactta  3420
acatcaggca gggaaaaatt tgtatgttca ttagatggag atacatgcca tttgccttag  3480
caaacacact ttgtggaggt ttccagtgat gggataatgc ttcgcagagg tgtggttgga  3540
ctggcaatgc ttaccatgcc acttctggtt tcttcctggc atggtgacac aaaatgttgt  3600
tgagatcaag taagtgaatt atgttctgct ttctgagttc ggtaaacttc tttggctaca  3660
aaaggactaa gcttagttat gctaacttgt tgatttggtt gtgatcattg catcattctg  3720
ctgtgtgaat tgatacttaa tacctctgat tttttatagc ctgcttacaa ttacatatgt  3780
tacctaatga gatatattcc attttccatt gattctgtta acaatattca taccactttg  3840
gtcgtgataa attcatttga ctattgtata gaagtcatat atgtctacat gtgaagtgaa  3900
tgatccatta tcagatacac atgaattctc atagtgttgc ttgatatgtc accgtttaag  3960
tttgctccta cagaagatag gattcgatga ttacatgtaa caaagattag ttgtgatttt  4020
gtctattaat tggatgagat attatcttga agcaaaaggt catcgagaac cataaaaaat  4080
gggttaatcc cacagcagac tagtactgtc cgctaaatac aagtgcttac ctttcctgga  4140
ccatttaatc tttgaaacac acgcagaact tgttatagat aatctttgtg atagcatgga  4200
atagaaatca ttgacttggg tgcctaacat agcaagcaat tgacgatttt gagttactca  4260
tgtccatttt tgctgagtat ccatattaat gcagacggcc atagttcatt ttcgtgtcgt  4320
tatttttcat tgagatagaa caaaacagcg acttctcttg gggagtacac ttattaccaa  4380
cgctggcatc ctgttatcta gtttaatctg aacctgttct tgaaaactgt gtttcagaaa  4440
gtcacttgcc ttggtttgtt ctataatatt cttctgtgct atgagctatg gtaagcaaaa  4500
tatttcgaat tttaaagcag ttttctaaat gatgcaaagg cagattggtt tgagattgca  4560
catctacaga attcttttga ctaacatctt atcttagcca agcagtagtt aagattaact  4620
gttttactca ccaagtagaa ctcttcaaag ctcagactaa gcattttgtg gtttcttact  4680
aactcctttg tttggcaacc cgcagtgggt tgtccatacc atgccctgaa tgaagcaaag  4740
tttcttggcc gattggccca gcttagtggg gatatcagca gccctagcct gaagggccaa  4800
ttccttttac tgttttttt atccctattt tttgaggaag caaagttcca acaacaatgt  4860
tatgaatatg tttgaataaa tgatggagac acatgtgact ttccgattag aatatgacta  4920
cataaaaaaa ttagctttga gtctatggat aagatcacaa agggatctct taacatatgt  4980
ttttatggat gtagtgttag ttgatgaaag ctaagcacga gtaaatggaa aactagagtt  5040
```

-continued

```
gtcgtgggag attctagagt ttaaaggttt tggacgattt tggactcgat cagtagaact  5100
caaattgaat ataaaagatg tgatttcaac actactacat atgaggaaag acatgttagt  5160
ttgaaaaatc aagtagtgtc cggaaggaca tctttagata tttagaatct atgctactac  5220
atatgaggaa agacatgtta gtttgaaaaa tcaagtagtg ttctgaaagg acatctttag  5280
atatttagga tctatgcata gatatttagg atctatgcat agatatttag gatctatgct  5340
acgaaaggct acgtagagat agtgataaag gtattagtca aaggatgagg tggcgccaaa  5400
catttgatgt tctatatgac aataggatac cacaaaagtt aaaaagaatc tttataggat  5460
gacaattcga tctgctatat tgttcggtgc agaatgttag tctaaaaaag acatgttcaa  5520
tacgtatgcg ctacagaaat gtatatgttg tgttggagtt tggccataaa aaaggatcga  5580
gtatgaaacg aggatacata tgatagacta gatgtaacat cggtgcgagt atgaaacgag  5640
gatacatatg atagactaga tgtaacatcg gtgcgaagaa aagctcatcc agcatcggtt  5700
aaaatggttt agac                                                   5714

SEQ ID NO: 19          moltype = DNA  length = 577
FEATURE                Location/Qualifiers
source                 1..577
                       mol_type = genomic DNA
                       organism = Zea mays
SEQUENCE: 19
actcgatcct tcctcttcct caaccgtgcg ggcgatcgat cgcaccgccc cctcgcccga  60
ccccatgcct tccacgtcgc ggtcggggta gggctcagga gacgttctct tggtgtggag  120
agtggcattg attcttcgat gctcgggcag gaaggctggg ctggggatga gaacgctgga  180
gatggaaggg ccgaggaggt gaggagaatt aacataaatg aggcagcaca tgctacagat  240
ggcactggta gggttaatgt tagcggtgct ggcggagttg aagatatcgg caactttcat  300
atcgatgttg atgcatccga ggatatattg gggaatttgc acaacatgca cttcttgagg  360
gtggacaatc ttggacggat gatttaactg ttgttatggt ttactggggc tatgattagc  420
caggccgact cttgctgttc aagtgttcat ttgagtgtaa ttgttccatc cctgttatgt  480
aatgttgtag ttgtagactt gtagtctacc tggtacctgt agttacttaa catcaggcag  540
ggaaaaattt gtatgttcat taaaaaaaaa aaaaaaa                          577

SEQ ID NO: 20          moltype = DNA  length = 4090
FEATURE                Location/Qualifiers
source                 1..4090
                       mol_type = genomic DNA
                       organism = Zea mays
SEQUENCE: 20
cacactcact cgtcggctta gggacccccc ggtctcgaaa cgccgacact actcttgagg  60
agattattag attatcataa tctaggcttt agattatata atctgaacac ataatctagt  120
tgtttgttta tctaatggat tatttacgct agattatata atctggagag attataatct  180
gaaacaaaca tggccttagt gattaaaaat aaaaataagg ggtaaaatca caattgtaaa  240
gtgagagaag gctataatca caattaacca taaaaagtta atattatttt caggttaatt  300
ttgagtatat ccttctcttc ccttacagtt atgattttac cccttatttt taatttttgt  360
aatcaataat tcacaaagtt gaaaacgtat aatcacagtt gtccttaaaa ttaaatgtgc  420
tgcccaacaa aatactctcg gactgacaga cagtcgccag tcaagagccc ctcgggcagc  480
aggatcttcc ccctccccaa aaccaaacca gctgcctccg acagcatcca cctttcctc  540
ccccaaacca tggacttctc caccggcggg agcgtgagcg ggggcggcgg aggcgccagc  600
gacggccccg cgcaggcgga gcgctggctg gagatcgccg agaagctcct cgcggcgcgc  660
gacctcgtcg gctgcaagcg cttcgcggag cggtcggtgg aggcgaaccc gctcctcgcc  720
ggcgttgacg aactcctcgc cgtcgccgac gtcctcctcg cttcccagtt catgggcacc  780
tcgggccagc cggacccgct cgccatcctc cagctgccgc ccggagtcag ccccgaccag  840
gccgccgtgt cccgcgcctt ccgccgcctc gcgctcctcc tcggtcccag caacccgcac  900
ccgggagccg agatggcgct ccgcctcgtc aacgacgcct acgccttcct ctcggatccc  960
tctcgccgcc ccccgccgcc cgccgatccc gccactggta ccccttactc ctcccagtat  1020
cccgccgcgg ccgctcccgc ctccgacacc ccggagttct ggacggcgtg cccccttctgc  1080
tgctacgtgc accagtaccc gcgcagcctg atcgggcgcg ccctcaagtg ccccaacgcg  1140
ggctgccgcc gcggattcgt ggcttctgag ctcccgaccc cacccacggt tgtgccgggc  1200
actgaaatgt accactgcgc ctgggggttc ttccccctcg gatttcccaa cgcggccgac  1260
ctgggtgcca actggaagcc attctacaag atgttccctt ggaacacggc tcccagtggc  1320
caaggtggtg gtggtaggag tcacggaaac catggtggta ggcagccaca gaatgacagt  1380
gctcgtggtg gctcttctag aggtaggatc aagaagacga cggcccgcaa gaaggtcggg  1440
gtagggctca ggagacgttc tcttggtgtg gagagtggca ttgattcttc gatgctcggg  1500
caggaaggct gggctgggga tgagaacgct ggagatggaa gggccgagga ggtgaggaga  1560
attaacataa atgaggcagc acatgctaca gatggcactg gtagggttaa tgttagcggt  1620
gctggcggag ttgaagatat cggcaacttt catatcgatg ttgatgcatc cgaggatata  1680
ttggggaatt tgcacaacat gcacttcttg agggtggaca atcttggacg gatgatttaa  1740
ctgttgttat ggtttactgg ggctatgatt agccaggccg actcttgctg ttcaagtgtt  1800
catttgagtg taattgttcc atccctgtta tgtaatgttg tagttgtaga cttgtagtct  1860
acctggtacc tgtagttact taacatcagg cagggaaaaa tttgtatgtt cattagatgg  1920
agatacatgc catttgcctt agcaaacaca ctttgtggag gtttccagtg atgggataat  1980
gcttcgcaga ggtgtggttg gactggcaat gcttaccatg ccacttctgg tttcttcctg  2040
gcatggtgac acaaaatgtt gttgagatca agtaagtgaa ttatgttctg ctttctgagt  2100
tcggtaaact tctttggcta caaaaggact aagcttagtt atgctaactt gttgatttgg  2160
ttgtgatcat tgcatcattc tgctgtgtga attgatactt aatacctctg atttttttata  2220
gcctgcttac aattacatat gttacctaat gagatatatt ccattttcca ttgattctgt  2280
taacaatatt cataccactt tggtcgtgat aaattcattt gactattgta tagaagtcat  2340
atatgtctac atgtgaagtg aatgatccat tatcagatac acatgaattc tcatagtgtt  2400
gcttgatatg tcaccgttta agtttgctcc tacagaagat aggattcgat gattacatgt  2460
aacaaagatt agttgtgatt ttgtctatta attggatgag atattatctt gaagcaaaag  2520
gtcatcgaga accataaaaa atgggttaat cccacagcag actagtactg tccgctaaat  2580
```

-continued

```
acaagtgctt acctttcctg gaccatttaa tctttgaaac acacgcagaa cttgttatag  2640
ataatctttg tgatagcatg gaatagaaat cattgacttg ggtgcctaac atagcaagca  2700
attgacgatt ttgagttact catgtccatt tttgctgagt atccatatta atgcagacgg  2760
ccatagttca ttttcgtgtc gttatttttc attgagatag aacaaaacag cgacttctct  2820
tggggagtac acttattacc aacgctggca tcctgttatc tagtttaatc tgaacctgtt  2880
cttgaaaact gtgtttcaga aagtcacttg ccttggtttg ttctataata ttcttctgtg  2940
ctatgagcta tggtaagcaa aatatttcga attttaaagc agttttctaa atgatgcaaa  3000
ggcagattgg tttgagattg cacatctaca gaattctttt gactaacatc ttatcttagc  3060
caagcagtag ttaagattaa ctgttttact caccaagtag aactcttcaa agctcagact  3120
aagcattttg tggtttctta ctaactcctt tgtttggcaa cccgcagtgg gttgtccata  3180
ccatgccctg aatgaagcaa agtttcttgg ccgattggcc cagcttagtg gggatatcag  3240
cagccctagc ctgaagggcc aattcctttt actgtttttt ttatccctat tttttgagga  3300
agcaaagttc caacaacaat gttatgaata tgtttgaata aatgatggag acacatgtga  3360
ctttccgatt agaatatgac tacataaaaa aattagcttt gagtctatgg ataagatcac  3420
aaagggatct cttaacatat gtttttatgg atgtagtgtt agttgatgaa agctaagcac  3480
gagtaaatgg aaaactagag ttgtcgtggg agattctaga gtttaaaggt tttggacgat  3540
tttggactcg atcagtagaa ctcaaattga atataaaaga tgtgatttca acactactac  3600
atatgaggaa agacatgtta gtttgaaaaa tcaagtagtg tccggaagga catctttaga  3660
tatttagaat ctatgctact acatatgagg aaagacatgt tagtttgaaa aatcaagtag  3720
tgttctgaaa ggacatcttt agatatttag gatctatgca tagatattta ggatctatgc  3780
atagatattt aggatctatg ctacgaaagg ctacgtagag atagtgataa aggtattagt  3840
caaaggatga ggtggcgcca aacatttgat gttctatatg acaataggat accacaaaag  3900
ttaaaaagaa tctttatagg atgacaattc gatctgctat attgttcggt gcagaatgtt  3960
agtctaaaaa agacatgttc aatacgtatg cgctacagaa atgtatatgt tgtgttggag  4020
tttggccata aaaaaggatc gagtatgaaa cgaggataca tatgatagac tagatgtaac  4080
atcggtgcga                                                         4090

SEQ ID NO: 21          moltype = DNA  length = 10452
FEATURE                Location/Qualifiers
source                 1..10452
                       mol_type = genomic DNA
                       organism = Zea mays
SEQUENCE: 21
tgcggataga cttcagagga aaggactacc gcacccggtg gtttgtccat tatgtgatca  60
agagcaggaa actatcttgc acctcttgtg ctcttgcagt ttcgctagac aattttggca  120
tgttatattt tcagctttga ggatgggcca tcttacgcct actagagagg cgggctcttt  180
tgtggattgg tgggaaaagg tgcataggag agtccccaaa catatcagaa aaaggttttc  240
atagtctcat tatcctaggg gcctggtgtt tatggctaca tcgcaataag gcggtttttg  300
atggtgtcaa cccttcattg agcaccattc agaggctttt catggatgag gtggaatgct  360
ggtatatggc tggtgcaaag cagctcgaga gtctcggact tctggctgct tttgctagga  420
tcagggctat tcctagtgca tgaggctgta ctatttttcc tttttatttt ttgcctgctt  480
ggctttgtac tttggtccat ttcggacctt tctctctttc aatataatga tgcgcagttt  540
tcctgcgtgt tcgagaaaaa aaaatataaa cttctctcta tagtaaccta gcataagtgc  600
actcaaagaa aatatgtatc agatggtttg tggctcaaaa gagcaagttg tgtcactatt  660
tcaatttctt tttgataaaa ttacctttg tgagattgtg agaatgaccc tcttttttttg  720
aaagaactac atgaagattt ttatctttaa aggtatcttt agacaccaaa ttattcataa  780
aacattaatt ccattagtaa ctaagaattt atacatataa ttaatagaaa agataccatc  840
tttatgcaag tgccaaacaa acacgttaga ttcttgtttt agcaatttag cttgccatga  900
tttttattta ggtaagattc gaaaaccctt tgttttgggc ctttcctccc taaccacccc  960
cacatacact ccatcatatt tttacttttc caagttttgt ttggtttata aaatagaatg  1020
aaataatctg ccattacttt attcctcaca atctaataat tactactagt aagataagag  1080
ataattgtga ttataccctt cgttggcctt gcaattgtga ttttactctg cattttcaac  1140
tttctaattt tacacctccg ttttaaatac gaagctacca tttgcccttc actctcaaca  1200
tcgttagtga aaatcagaat tagtgattaa aaataaaaaa atgagaaaat aaatgggtga  1260
aaggttcaaa ctaccttttt ctattcttta tgggcacaac cctaataggg gtgaaatcac  1320
tattacataa tataacgagg gtaaaatcaa aataaattgc ttgggtattt ttatcttttg  1380
catcaaattt aacattgtta actgcatcta acggcacaag ggtatggcaa ctcttcgttt  1440
tcaaaatgaa gggataaaat atcacaaagt tgaaaaacga tgggtaaaat cacaatttca  1500
agaccagaga gggtataatc acaaataccc tataagataa atagagtcat tatatcattt  1560
tttgtaagat atacttgggg atacatcaac tcatccttag agtttgtttg ggactgtgcg  1620
gctctatatt tcaaccaaac aagtgtagct aaaaaaggtg aagttaaaag agaagtactc  1680
tagaaactct aaattaaatt tagagaaaat tcctggtatg ccatcaaatt ttatactcat  1740
tccttgtgtg ccactgagtg gcatataggt atattttttg gtgtctatga catgtggggt  1800
cagtggcata caaggaatga gtatattttc tagtggcata cagggaattg gcccttaaat  1860
ttatggagta gattttgagg atagatctaa ccaggcttga tgatgacatg tcactgtatt  1920
acaacattga tgaagatctt tcacttgagg aaaatactat tgtgcaacca aacattctat  1980
acaatccaac tatcaaaagt cacaaaaata tttaaaaaat tatacatata tattatttac  2040
tttatcaata tatcatattt aagatcctag attgatttat gctatgttaa tatataattc  2100
attcatctta tataacaagg tatatatttt tggtacagtc tttggagcga aactttgact  2160
atttgtttat ttcaaaatat gctatcaata aaaacataac gagcattaaa ttaaagtaat  2220
ttttgaatac aaatcaagta tataacatgt atatactaaa atatatgctt ttggctgaat  2280
tactagtcaa aagttttaaa acattgagtc tttttttttt aaaatgcagg ccttatttta  2340
cggaattgag ggaatttttt ttatctaatt gaatatattt tttcttttac tattgtataa  2400
atttaaactt aaaattttat aatctaataa agtaaacaat aaattatatt tatatatttt  2460
tagaattttt tatggttttt ggtagtccaa ttatacattg attgtatgca aaacttgctc  2520
tgcggtgggg cgctacaatg gtctggtatg tttgcatatg ggaaaactaa tagcccgttc  2580
ccttggtttt aattcgaaac ggcttttact atttctgtag tgttttggtc tctgtgaatt  2640
gcagctacaa taatctaaac aactgacttt aattcgaagc taacaggcta taagacgctc  2700
tccaacggat cctttcccct ccccttcacg acgtattcgg tgatttcgta catcgagaga  2760
```

-continued

```
gcttcaacag gtccctctcc tccctcttgt agggtgagag aaggaaaaca ccttgtaaaa  2820
cgagaaagat agaaccctac tcttcactaa ttagtgtttt taactataaa attaatctgc  2880
tataagtttg gttaagtgac aatgtgtatt atgatattat aaatattaaa aactctaaaa  2940
actgatgtag aaaagtcaaa tagcttagtt aaagggtaaa gggagagctg aatagaggga  3000
tgcttggaga ggaggtaaaa tagggaaata atagtgaaga tgaggatatt taaatatgaa  3060
tagaaagtcc aaatgtggga tttgagatgg agaatgattg gagagagcct aataaaatca  3120
agggataatt gtgattatac ccttttctaa tattttaatt gtgattttat cccttctttt  3180
ttaactttgt taccccctctg ttttgaaaac aaagccgttg tttgcaccgc cttatcaacg  3240
ttaataaaaa tcagaattag tgattaaaaa taaaaataag gggtaaaatc acaattgtaa  3300
agtgagagaa ggctataatc acaattaacc ataaaaagtt taatattatt ttcagattaa  3360
ttttgagtat atccttctct tcccttacaa ttatgatttt acccctcatt tttaattttc  3420
gtaatcaata attcacgaag ttgaaaacgt ataatcacag ttgtccttaa aataaatgtg  3480
ctgcccaaca aaatactctc ggactgacag acagtcgcca gtcaagagcc cctcgggcag  3540
caggatcttc cccctcccca aaaccaaacc agctgcctcc gacagcatcc accttttcct  3600
cccccaaacc atggacttct ccaccggcgg gagcgtgagc gggggcggcg gaggcgccag  3660
cgacggcccc gcgcaggcgg agcgctggct ggagatcgcc gagaagctcc tcgcggcgcg  3720
cgacctcgtc ggctgcaagc gcttcgcgga gcggtcgatg gaggcgaacc cgctcctcgc  3780
tggcgttgac gagctcctcg ccgtcgccga cgtcctcctc gcttcccagt tcatgggccc  3840
ctcgggccag ccggacccgc tcgccatcct ccagctgccg cccggagtca gccccgacca  3900
ggccgccgtg tcccgcgcct tccgccgcct cgcgctcctc ctcggcccca gcaacccgca  3960
cccgggagcc gagatggcgc tccgcctcgt caacgacgcc tacgccttcc tctcggatcc  4020
ctctcgccgc cccccgccgc ccgccgatcc cgccactggt acccccttact cctcccagta  4080
tcccgccgcg gccgctcccg cctcggacac ccgggagttc tggacggcgt gccccttctg  4140
ctgctacgtg caccagtacc cgcgcagcct gatcgggcgc gccctcaagt gccccaacgc  4200
gggctgccgc cgcggattcg tggcttctga gctcccgacc ccacccaccg ttgtgccggg  4260
cactgaaatg taccactgcg cctgggggtt cttcccccctc ggatttccca acgcggccga  4320
cctgggtgcc aactggaagc cattctacaa gatgtttcct tggaacacgg ctcccagtgg  4380
ccaaggtggt ggtggtagga gtcacggaaa ccatggtggt aggcagccac agaatgacag  4440
tgctcgtggt ggctcttcta gaggtaggat caagaagacg acggcccgca agaaggtcgg  4500
ggtagggctc aggagacgtt ctcttggtgt ggagagtggc attgattctt cgatgctcgg  4560
gcaggaaggc tgggctgggg atgagaacgc tggagatgga agggccgagg aggtgaggag  4620
aattaacata aatgaggcag cacatgctac agatggcact ggtagggtta atgttagcgg  4680
tgctggcgga gttgaagata tcagcaactt tcatatcgat gttgatgcat ctgaggatat  4740
attggggaat ttgcacaaca tgcacttctt gagggtggac aatcttggac ggatgattta  4800
actgttgtta tggtttactg gggctatgat tagccaggcc gaagcagatg tctcagagac  4860
tggctcttgc tgttcaagtg ttcatttgag tgtaattgtt ccatccctgt tatgtaatgt  4920
tgtagttgta gacttgtagt ctacctggta cctgtagtta cttaacatca ggcagggcaa  4980
aatttgtatg ttcattagat ggagatacat gccatttgcc ttagcaaaca cgctttgtgg  5040
aggtttccag tgatgggata atgcttcaca gaggtctggt tggactggca atgcttacca  5100
tgccacttct ggtttcttcc tggcatggtg acacaaaatg ttgttgagat caagtaagtg  5160
aattatgttc tgctttctga gttcggtaaa cttctttggc tacaaaagga ctaatcttag  5220
ttatgataac ttgttgactt ggttgtgatc attgcatcat tctgctgtct gaattgatac  5280
ttaatacctc tgatttttta tagcctgctt acaattccat atgttaccta atgagatata  5340
ttccattttc cattgattct gttaacaata ttcataccac ttttgtagtc atatatgtct  5400
acatgtgaag tgaatgatcc tttatcagat acacatgaat tctcatagtg ttgcttgata  5460
tgtcaccgtt taagtttgct cctacagaag ataggattcg atgatgacat gtaacaaaga  5520
ttacttgtga ttttgtctat taattggatc agatattatc ttgaagcaaa aggccatcga  5580
gaaccataaa aaatgggtta atcccacagc agactagtac tgtccgctaa atacaagtgc  5640
ttacctttca tggatcattt aatgtttgaa acacactcag aacttgttat agataatctt  5700
tgcgatatca tggaatataa atcattgact tgggtgctta acatagcaag cacttgacga  5760
ttttgagtta ctcatgtcca tttttgctgc gtatccatat taatgcagac ggccatagtt  5820
catttttgtg tcgttatttt tcattgagaa agaacaaaac agtgacttct cttggggagt  5880
agacttatta ccaacgctgg catcctgtta tctagtttaa tctgaacctg ttcttgaaaa  5940
ctgtgtttca gaaagtcact tgccttggtt tgttctataa tattcttctg tgctatgagc  6000
tattgtaagc aaaatatttc gaattttaaa gcagttttct aaatgatgca aaggcagatt  6060
ggtttgagat tgcacatcta cagaattctt ttagctaaca tcttatctta gccaagcagt  6120
agttaagatt aactgtttta ctcaccaagt agaactcttc aaagctcaga ctaagcattt  6180
tgtggtttct tactaacttc tttgtttggc aatccgcagt gggttgtcca tatcatgccc  6240
tgaatgaagc aaagtttctt ggccgattgg cccagcttag tggggatatc agcagctcta  6300
gcctgaaggg ccaattcctt ttactgtttt ttatccctgt tttttgagga agcaaagttc  6360
caacaacaat gttatgaata tgtttgaata aatgatggag acacatgtga cttttcgatt  6420
agaatatgac tacataaaaa attagctgag tctatggata agatcacaaa gggatatctc  6480
ttaacatatg ttttttatgg atgtagtgtt agttgatgaa agctaagcac gagtaaatag  6540
aaaactagag ttgtggtggg agattctaga gtttaaaggt tttggacgat tttggactcg  6600
atcagtagaa ctcaaattga atataaaaga tgtgatttca acactactac atatgaggaa  6660
agacatgtta gtttgaaaaa tcaagtagtg tccaggaagg acatctttag atatttagga  6720
tctatgctac tacatattag gaaagacatg ttagtttgaa aaatcaagta gtgtccatga  6780
aggacatctt tagatattta ggatctatgc tacgtagaga tattgataaa ggtattagtc  6840
aatggatgag gtagcgccaa acatttgata ttctatatga caataggata ccacaaaagt  6900
taaaaagaag ttttatagga tgacaattcg atctgctatg ttgttcggtg caaaatgtta  6960
gtctaaaaaa gacatgttca atacatatgc gctacagaaa tgcatatgtt gtgttggagt  7020
ttggccataa aaaaggatcg agtatgaaac gacgatacat atgatagact agatgtaaca  7080
ccggtgcgaa gaaaacctca tccaacatcg gttgaaatgg tttagacata tcaataaaga  7140
ctttcagatg caccaataat tccttcttcg ctttcctttc ttcctttttt ttatcacaaa  7200
caagttaaag aacacggctc tctttgatcc tctgtattga agctactagt ttgctacgaa  7260
aattgaaaag catcatataa acatgtatgc ttgcgacctt taggtacata agaatgcaac  7320
ctcaataata ccaaacgaat cgcctcacca atcaccacca ccacaggagc aaccagccaa  7380
acatttcttg cagcactctg ggcgacctgg aacgataatc ccggaatgca gcaaatggct  7440
gcttacgcga tacgaaggaa gcggtcctat ccaatgcttt gttctttaac aaattcaccc  7500
```

```
cattctaaat ttgtccagct acgccagcac gagcctgcag tgtctcggta cgtttgcttt  7560
tttccatttg ttccaccagc cagtctatgc cagatttgat ccccctcctg caagagccgg  7620
tgtcacattt aaacaatata acagatcttt agaatatcat gcacccagga aacaatataa  7680
cagacgaatg tgtgaatttt tttgtatctt tgagtaaaat tgtcattttt ttcatggcga  7740
gtcaaatttc ctcaggaacc agttgagttt ctgcgctcac ccatcatatg cagatacagc  7800
ctgaaatgta tatgtcctct catccagttc tttatgcaga aatttagcca attcttcctc  7860
atcaatggct ccaggtaaat cctgccaaaa gaaatccaga agcaccctcc aaacatgaga  7920
acaagctaga ggtaaataat aaacaatttg atagaataat gtgtacccag cttaacagaa  7980
acagacagtg catgtagtca ttggtttcca tgtgatcttt tcaggaagtt ttaattgatt  8040
taaaaactac atctggtatt caacctcgca atggcgcata ggcgctttgc aacgtaggaa  8100
tttatatttg tatgcctcac agcatgtgca catgacaaaa acaaaatctt tattttaact  8160
acgatggcaa ctttattgta agcactaaat ctttcaatca taattatgta ctgtggtaca  8220
aaatatagaa agtggaagta aacccttcac ctgtttgttt gcaactatca agagtggtgc  8280
tcctctcaga tgttcatggc gaataacctt ctctgaagta agaaatttag gttaggttct  8340
ctagaatgag ttctcatccc atttaccaga gaggcattgc atcttctgga aagatctagc  8400
aatagaaaca aaccagtact ccctctgttc caagttataa gacgatgttt tagcttttct  8460
agatatattg ttttaactat gtaccaggac attatatata tttttaatat ttaagtccat  8520
agcaaaattt atttatctag aaaaaggcca aaatgtctta taatttggaa tggatggcgt  8580
agtttataat tgacacaaat aagaacctta cccaaagcag atttggaatc ttcaaatgac  8640
gatgctgtgg cagcgtcaat aacgtacatt atggcatggg cctcttcata gtatttctcc  8700
cagattgttc gtaggctaac ctgccaagca ggcaagtgtg taagaaatac tgaacttggc  8760
atggaagctt aattatcata ctagcaagca gtgatactga agttagtttt acactaattc  8820
ttataacata gcagagaagc tgatgctgtt ctactagcca cccaattcta ttgagtactg  8880
tgaatgttag ccaacagagc atatctttgc tttctgaaaa ttctattgag cattccatat  8940
aactagatta tatatattct gctggaacgc aaaaagatgc taggttaata actaaagcaa  9000
ccacatccta gtaatttgat tttatgacat gtatttccca ggcattagaa accctgatat  9060
agcaccaaac tgacaagact caaatatcaa cgatcgtagg gtggtgccac ggcaacagaa  9120
ggctcacttt actacgtacg taaacgttct tacctgacca cctagatccc agaaaacaag  9180
ttttgccttt gcgtcttcga tgcggccaat gttgagccca actgttggaa cgacacggtc  9240
aggcggaagt ccttcccccct tgagatatat cgatttcaac ttctccagca aagtctatgg  9300
caacggttcc agaaacattg tgtacaggta agtttcatca atttctagtt cagaaaggga  9360
aatatatata tatgaaggct gggagctagc agctaccgtc ttgccagctc tgtcaacacc  9420
aagaatcaga acacggaact cgtccttggc gaacacatac ttccacaggc catagaacaa  9480
ggagaacatt tccgcttata tatatatatc cggcgataag caaccgccag cacgttacgt  9540
cctgaaaaac gaatcatacg ttacaaacat tttctccgat cagtaacagt acgcagccaa  9600
aagcatgtac gccccaaatt gccagacgca aaactaggaa ccatcctcat agtacagggc  9660
cgcagcattt caatccacaa cgaaatggta tcgaccgagt aaaaataagg ggagaggata  9720
taacttaact gaaccatcgg gcgggagagt acaactacag actacagagg ggagaggatg  9780
ttgagatcta gatagctcac cggagcgctc gaaggctcct tgatcgcgcc gcttcagacg  9840
acaccacccg ctcccgtgtg gactggagcg cgggaggctg agggcgggtt ttgagccgcg  9900
cggcggtggg agcgcgccca ccggagttag gaactggggc actcgcctcg ccagtcgcca  9960
cacggcttgg gttcggttga ctcgatgggc gtcacggtgg gcgacttgga actggaaccc  10020
acgcaggagc aggacccgtg gggctatgat cggtgggtcc tgcaggattc tgggacggga  10080
ggccctaccg ctcagtgagg ttatcgtact gccagtggga attcgtgatg tgactgtacc  10140
agtggttgac ccggaaggaa ggcactggct ggcaggaggg ctttgccatt aataaaaaca  10200
taaattattg catctgacaa gtttagtgga gagctaacgg tgccaaatgt tgcgcttgcc  10260
tttctacctg cagtcagtcc tattcagccc agctcattta gcccggtctc ggactctcgg  10320
cccacatggc agcccatacc atgacactct ccacctctcg aaatgtcagc ccataccatg  10380
acattcactt aaggggtgtt tgaatgcact agagctaata gttagtagct aaaattagtt  10440
gagacatcca aa                                                     10452

SEQ ID NO: 22           moltype = DNA  length = 6816
FEATURE                 Location/Qualifiers
source                  1..6816
                        mol_type = genomic DNA
                        organism = Zea mays
SEQUENCE: 22
tgtcccgcgc ctcccgccgc ctcgcgctcc tcctcggccc cagcaacccg cacccgggag  60
ccgagatggc gctccgcctc gtcaacgacg cctacgcctt cctctcggat ccctctcgcc  120
gccccccgcc gcccgccgat cccgccactg gtacccctta ctcctcccag tatcccgccg  180
cggccgctcc cgcctcggac accccggagt tctggacggc gtgccccttc tgctgctacg  240
tgcaccagta cccgcgcagc ctgatcgggc gcgccctcaa gtgccccaac gcgggctgcc  300
gccgcggatt cgtggcttct gcgacgcggg ctgccgccgc ggattcgtgg cttctgagct  360
cccgacccca cccaccgttg tgccgggcac tgaaatgtac cactgcgcct gggggttctt  420
ccccctcgga tttcccaacg cggccgacct gggtgccaac tggaagccat tctacaagat  480
gtttccttgg aacacggctc ccagtggcca aggtggtggt ggtaggagtc acggaaacca  540
tggtggtagg cagccacaga atgacagtgc tcgtggtggc tcttctagag gtaggatcaa  600
gaagacgacg gccccgcaaga aggtcggggt agggctcagg agacgttctc ttggtgtgga  660
gagtggcatt gattcttcga tgctcgggca ggaaggctgg gctggggatg agaacgctgg  720
agatggaagg gccgaggagg tgaggagaat taacataaat gaggcagcac atgctacaga  780
tggcactggt agggttaatg ttagcggtgc tggcggagtt gaagatatca gcaactttca  840
tatcgatgtt gatgcatctg aggatatatt ggggaatttg cacaacatgc acttcttgag  900
ggtggacaat cttggacgga tgatttaact gttgttatgg tttactgggg ctatgattag  960
ccaggccgaa gcagatgtct cagagactgg ctcttgctgt tcaagtgttc atttgagtgt  1020
aattgttcca tccctgttat gtaatgttgt agttgtagac ttgtagtcta cctggtacct  1080
gtagttactt aacatcaggc agggcaaaat ttgtatgttc attagatgga gatacatgcc  1140
atttgcctta gcaaacacgc tttgtggagg tttccagtga tgggataatg cttcacagag  1200
gtctggttgg actggcaatg cttaccatgc cacttctggt ttcttcctgg catggtgaca  1260
caaaatgttg ttgagatcaa gtaagtgaat tatgttctgc tttctgagtt cggtaaactt  1320
```

-continued

```
ctttggctac aaaaggacta atcttagtta tgataacttg ttgacttggt tgtgatcatt  1380
gcatcattct gctgtctgaa ttgatactta atacctctga ttttttatag cctgcttaca  1440
attccatatg ttacctaatg agatatattc cattttccat tgattctgtt aacaatattc  1500
ataccacttt tgtagtcata tatgtctaca tgtgaagtga atgatccttt atcagataca  1560
catgaattct catagtgttg cttgatatgt caccgtttaa gtttgctcct acagaagata  1620
ggattcgatg atgacatgta acaaagatta cttgtgattt tgtctattaa ttggatcaga  1680
tattatcttg aagcaaaagg ccatcgagaa ccataaaaaa tgggttaatc ccacagcaga  1740
ctagtactgt ccgctaaata caagtgctta cctttcatgg atcatttaat gtttgaaaca  1800
cactcagaac ttgttataga taatctttgc gatatcatgg aatataaatc attgacttgg  1860
gtgcttaaca tagcaagcac ttgacgattt tgagttactc atgtccattt ttgctgcgta  1920
tccatattaa tgcagacggc catagttcat ttttgtgtcg ttatttttca ttgagaaaga  1980
acaaaacagt gacttctctt ggggagtaga cttattacca acgctggcat cctgttatct  2040
agtttaatct gaacctgttc ttgaaaactg tgtttcagaa agtcacttgc cttggtttgt  2100
tctataatat tcttctgtgc tatgagctat tgtaagcaaa atatttcgaa ttttaaagca  2160
gttttctaaa tgatgcaaag gcagattggt ttgagattgc acatctacag aattctttta  2220
gctaacatct tatcttagcc aagcagtagt taagattaac tgttttactc accaagtaga  2280
actcttcaaa gctcagacta agcattttgt ggtttcttac taacttcttt gtttggcaat  2340
ccgcagtggg ttgtccatat catgccctga atgaagcaaa gtttcttggc cgattggccc  2400
agcttagtgg ggatatcagc agctctagcc tgaagggcca attcctttta ctgtttttta  2460
tccctgtttt ttgaggaagc aaagttccaa caacaatgtt atgaatatgt ttgaataaat  2520
gatggagaca catgtgactt ttcgattaga atatgactac ataaaaaatt agctgagtct  2580
atggataaga tcacaaaggg atatctctta acatatgttt tttatggatg tagtgttagt  2640
tgatgaaagc taagcacgag taaatagaaa actagagttg tggtgggaga ttctagagtt  2700
taaaggtttt ggacgatttt ggactcgatc agtagaactc aaattgaata taaaagatgt  2760
gatttcaaca ctactacata tgaggaaaga catgttagtt tgaaaaatca agtagtgtcc  2820
aggaaggaca tctttagata tttaggatct atgctactac atattaggaa agacatgtta  2880
gtttgaaaaa tcaagtagtg tccatgaagg acatctttag atatttagga tctatgctac  2940
gtagagatat tgataaaggt attagtcaat ggatgaggta gcgccaaaca tttgatattc  3000
tatatgacaa taggatacca caaaagttaa aaagaagttt tataggatga caattcgatc  3060
tgctatgttg ttcggtgcaa aatgttagtc taaaaaagac atgttcaata catatgcgct  3120
acagaaatgc atatgttgtg ttggagtttg gccataaaaa aggatcgagt atgaaacgac  3180
gatacatatg atagactaga tgtaacaccg gtgcgaagaa aacctcatcc aacatcggtt  3240
gaaatggttt agacatatca ataaagactt tcagatgcac caataattcc ttcttcgctt  3300
tcctttcttc cttttttttta tcacaaacaa gttaaagaac acggctctct ttgatcctct  3360
gtattgaagc tactagtttg ctacgaaaat tgaaaagcat catataaaca tgtatgcttg  3420
cgacctttag gtacataaga atgcaacctc aataatacca aacgaatcgc ctcaccaatc  3480
accaccacca caggagcaac cagccaaaca tttcttgcag cactctgggc gacctggaac  3540
gataatcccg gaatgcagca aatggctgct tacgcgatac gaaggaagcg gtcctatcca  3600
atgctttgtt ctttaacaaa ttcaccccat tctaaatttg tccagctacg ccagcacgag  3660
cctgcagtgt ctcggtacgt ttgctttttt ccatttgttc caccagccag tctatgccag  3720
atttgatccc cctcctgcaa gagccggtgt cacatttaaa caatataaca gatctttaga  3780
atatcatgca cccaggaaac aatataacag acgaatgtgt gaattttttt gtatctttga  3840
gtaaaattgt catttttttc atggcgagtc aaatttcctc aggaaccagt tgagtttctg  3900
cgctcaccca tcatatgcag atacagcctg aaatgtatat gtcctctcat ccagttcttt  3960
atgcagaaat ttagccaatt cttcctcatc aatggctcca ggtaaatcct gccaaaagaa  4020
atccagaagc accctccaaa catgagaaca agctagaggt aaataataaa caatttgata  4080
gaataatgtg tacccagctt aacagaaaca gacagtgcat gtagtcattg gtttccatgt  4140
gatcttttca ggaagtttta attgatttaa aaactacatc tggtattcaa cctcgcaatg  4200
gcgcataggc gctttgcaac gtaggaattt atatttgtat gcctcacagc atgtgcacat  4260
gacaaaaaca aaatctttat tttaactacg atggcaactt tattgtaagc actaaatctt  4320
tcaatcataa ttatgtactg tggtacaaaa tatagaaagt ggaagtaaac ccttcacctg  4380
tttgtttgca actatcaaga gtggtgctcc tctcagatgt tcatggcgaa taaccttctc  4440
tgaagtaaga aatttaggtt aggttctcta gaatgagttc tcatcccatt taccagagag  4500
gcattgcatc ttctggaaag atctagcaat agaaacaaac cagtactccc tctgttccaa  4560
gttataagac gatgttttag cttttctaga tatattgttt taactatgta ccaggacatt  4620
atatatattt ttaatattta agtccatagc aaaatttatt tatctagaaa aaggccaaaa  4680
tgtcttataa tttggaatgg atggcgtagt ttataattga cacaaataag aaccttaccc  4740
aaagcagatt tggaatcttc aaatgacgat gctgtggcag cgtcaataac gtacattatg  4800
gcatgggcct cttcatagta tttctcccag attgttcgta ggctaacctg ccaagcaggc  4860
aagtgtgtaa gaaatactga acttggcatg gaagcttaat tatcatacta gcaagcagtg  4920
atactgaagt tagttttaca ctaattctta taacatagca gagaagctga tgctgttcta  4980
ctagccaccc aattctattg agtactgtga atgttagcca acagagcata tctttgcttt  5040
ctgaaaattc tattgagcat tccatataac tagattatat atattctgct ggaacgcaaa  5100
aagatgctag gttaataact aaagcaacca catcctagta atttgatttt atgacatgta  5160
tttcccaggc attagaaacc ctgatatagc accaaactga caagactcaa atatcaacga  5220
tcgtagggtg gtgccacggc aacagaaggc tcactttact acgtacgtaa acgttcttac  5280
ctgaccacct agatcccaga aaacaagttt tgcctttgcg tcttcgatgc ggccaatgtt  5340
gagcccaact gttggaacga cacggtcagg cggaagtcct tccccccttga gatatatcga  5400
tttcaacttc tccagcaaag tctatggcaa cggttccaga aacattgtgt acaggtaagt  5460
ttcatcaatt tctagttcag aaagggaaat atatatatat gaaggctggg agctagcagc  5520
taccgtcttg ccagctctgt caacaccaag aatcagaaca cggaactcgt ccttggcgaa  5580
cacatacttc cacaggccat agaacaagga gaacatttcc gcttatatat atatatccgg  5640
cgataagcaa ccgccagcac gttacgtcct gaaaaacgaa tcatacgtta caaacatttt  5700
ctccgatcag taacagtacg cagccaaaag catgtacgcc ccaaattgcc agacgcaaaa  5760
ctaggaacca tcctcatagt acagggccgc agcatttcaa tccacaacga aatggtatcg  5820
accgagtaaa aataaggggga gaggatataa cttaactgaa ccatcgggcg ggagagtaca  5880
actacagact acagagggga gaggatgttg agatctagat agctcaccgg agcgctcgaa  5940
ggctccttga tcgcgccgct tcagacgaca ccacccgctc ccgtgtggac tggagcgcgg  6000
gaggctgagg gcgggttttg agccgcgcgg cggtgggagc gcgcccaccg gagttaggaa  6060
```

-continued

```
ctggggcact cgcctcgcca gtcgccacac ggcttgggtt cggttgactc gatgggcgtc  6120
acggtgggcg acttggaact ggaacccacg caggagcagg acccgtgggg ctatgatcgg  6180
tgggtcctgc aggattctgg gacgggaggc cctaccgctc agtgaggtta tcgtactgcc  6240
agtgggaatt cgtgatgtga ctgtaccagt ggttgacccg gaaggaaggc actggctggc  6300
aggagggctt tgccattaat aaaaacataa attattgcat ctgacaagtt tagtggagag  6360
ctaacggtgc caaatgttgc gcttgccttt ctacctgcag tcagtcctat tcagcccagc  6420
tcatttagcc cggtctcgga ctctcggccc acatggcagc ccataccatg acactctcca  6480
cctctcgaaa tgtcagccca taccatgaca ttcacttaag gggtgtttga atgcactaga  6540
gctaatagtt agtagctaaa attagttgag acatccaaac actttagtta atagttcaac  6600
tattagctat ttttggtaaa ttagttaata gttagatagt tatttgttag ctagctaatt  6660
ccactaccaa tttttagcca actaactatt agttctagtg cattcaaaca ccccccttagc  6720
ctggtcttaa cagagtagaa gagatgtcag caccgacaac ctgaaacctt tgctactcaa  6780
gtgcaattga tggacaagtg ctttccttgt tcttcg                              6816

SEQ ID NO: 23          moltype = DNA  length = 3904
FEATURE                Location/Qualifiers
source                 1..3904
                       mol_type = genomic DNA
                       organism = Zea mays
SEQUENCE: 23
tgcggataga cttcagagga aaggactacc gcacccggtg gtttgtccat tatgtgatca  60
agagcaggaa actatcttgc acctcttgtg ctcttgcagt ttcgctagac aattttggca  120
tgttatattt tcagctttga ggatgggcca tcttacgcct actagagagg cgggctcttt  180
tgtggattgg tgggaaaagg tgcataggag agtccccaaa catatcagaa aaaggttttc  240
atagtctcat tatcctaggg gcctggtgtt tatggctaca tcgcaataag gcggtttttg  300
atggtgtcaa cccttcattg agcaccattc agaggctttt catggatgag gtggaatgct  360
ggtatatggc tggtgcaaag cagctcgaga gtctcggact tctggctgct tttgctagga  420
tcagggctat tcctagtgca tgaggctgta ctatttttcc tttttatttt ttgcctgctt  480
ggctttgtac tttggtccat ttcggacctt tctctctttc aatataatga tgcgcagttt  540
tcctgcgtgt tcgagaaaaa aaaatataaa cttctctcta tagtaaccta gcataagtgc  600
actcaaagaa aatatgtatc agatggtttg tggctcaaaa gagcaagttg tgtcactatt  660
tcaatttctt tttgataaaa ttaccttttg tgagattgtg agaatgaccc tctttttttg  720
aaagaactac atgaagattt ttatctttaa aggtatcttt agacaccaaa ttattcataa  780
aacattaatt ccattagtaa ctaagaattt atacatataa ttaatagaaa agataccatc  840
tttatgcaag tgccaaacaa acacgttaga ttcttgtttt agcaatttag cttgccatga  900
tttttattta ggtaagattc gaaaaccctt tgttttgggc ctttcctccc taaccacccc  960
cacatacact ccatcatatt tttacttttc caagttttgt ttggtttata aaatagaatg  1020
aaataatctg ccattacttt attcctcaca atctaataat tactactagt aagataagag  1080
ataattgtga ttataccctt cgttggcctt gcaattgtga ttttactctg cattttcaac  1140
tttctaattt tacacctccg ttttaaatac gaagctacca tttgcccttc actctcaaca  1200
tcgttagtga aaatcagaat tagtgattaa aaataaaaaa atgagaaaat aaatgggtga  1260
aaggttcaaa ctacctttt ctattcttta tgggcacaac cctaataggg gtgaaatcac  1320
tattacataa tataacgagg gtaaaatcaa aataaattgc ttgggtattt ttatcttttg  1380
catcaaattt aacattgtta actgcatcta acggcacaag ggtatggcaa ctcttcgttt  1440
tcaaaatgaa gggataaaat atcacaaagt tgaaaaacga tgggtaaaat cacaatttca  1500
agaccagaga gggtataatc acaaataccc tataagataa atagagtcat tatatcattt  1560
tttgtaagat atacttgggg atacatcaac tcatccttag agtttgtttg ggactgtgcg  1620
gctctatatt tcaaccaaac aagtgtagct aaaaaaggtg aagttaaaag agaagtactc  1680
tagaaactct aaattaaatt tagagaaaat tcctggtatg ccatcaaatt ttatactcat  1740
tccttgtgtg ccactgagtg gcatataggt atattttttg gtgtctatga catgtggggt  1800
cagtggcata caaggaatga gtatattttc tagtggcata cagggaattg gcccttaaat  1860
ttatggagta gattttgagg atagatctaa ccaggcttga tgatgacatg tcactgtatt  1920
acaacattga tgaagatctt tcacttgagg aaaatactat tgtgcaacca aacattctat  1980
acaatccaac tatcaaaagt cacaaaaata tttaaaaaat tatacatata tattatttac  2040
tttatcaata tatcatattt aagatcctag attgatttat gctatgttaa tatataattc  2100
attcatctta tataacaagg tatatatttt tggtacagtc tttggagcga aactttgact  2160
atttgtttat ttcaaaatat gctatcaata aaaacataac gagcattaaa ttaaagtaat  2220
ttttgaatac aaatcaagta tataacatgt atatactaaa atatatgctt ttggctgaat  2280
tactagtcaa aagttttaaa acattgagtc tttttttttt aaaatgcagg ccttatttta  2340
cggaattgag ggaatttttt ttatctaatt gaatatattt tttcttttac tattgtataa  2400
atttaaactt aaaatttat aatctaataa agtaaacaat aaattatatt tatatatttt  2460
tagaattttt tatggttttt ggtagtccaa ttatacattg attgtatgca aaacttgctc  2520
tgcggtgggg cgctacaatg gtctggtatg tttgcatatg ggaaaactaa tagcccgttc  2580
ccttggtttt aattcgaaac ggcttttact atttctgtag tgttttggtc tctgtgaatt  2640
gcagctacaa taatctaaac aactgacttt aattcgaagc taacaggcta taagacgctc  2700
tccaacggat cctttcccct cccctccacg acgtattcgg tgatttcgta catcgagaga  2760
gcttcaacag gtccctctcc tccctcttgt agggtgagag aaggaaaaca ccttgtaaaa  2820
cgagaaagat agaaccctac tcttcactaa ttagtgtttt taactataaa attaatctgc  2880
tataagtttg gttaagtgac aatgtgtatt atgatattat aaatattaaa aactctaaaa  2940
actgatgtag aaaagtcaaa tagcttagtt aaagggtaaa gggagagctg aatagaggga  3000
tgcttggaga ggaggtaaaa tagggaaata atagtgaaga tgaggatatt taaatatgaa  3060
tagaaagtcc aaatgtggga tttgagatgg agaatgattg gagagagcct aataaaatca  3120
agggataatt gtgattatac ccttttctaa tattttaatt gtgattttat cccttctttt  3180
ttaactttgt taccccctctg ttttgaaaac aaagccgttg tttgcaccgc cttatcaacg  3240
ttaataaaaa tcagaattag tgattaaaaa taaaaataag gggtaaaatc acaattgtaa  3300
agtgagagaa ggctataatc acaattaacc ataaaaagtt taatattatt ttcagattaa  3360
ttttgagtat atccttctct tcccttacaa ttatgatttt acccctcatt tttaattttc  3420
gtaatcaata attcacgaag ttgaaaacgt ataatcacag ttgtccttaa aataaatgtg  3480
ctgcccaaca aaatactctc ggactgacag acagtcgcca gtcaagagcc cctcgggcag  3540
```

-continued

```
caggatcttc cccctcccca aaaccaaacc agctgcctcc gacagcatcc accttttcct  3600
cccccaaacc atggacttct ccaccggcgg gagcgtgagc gggggcggcg gaggcgccag  3660
cgacggcccc gcgcaggcgg agcgctggct ggagatcgcc gagaagctcc tcgcggcgcg  3720
cgacctcgtc ggctgcaagc gcttcgcgga gcggtcgatg gaggcgaacc cgctcctcgc  3780
tggcgttgac gagctcctcg ccgtcgccga cgtcctcctc gcttcccagt tcatgggccc  3840
ctcgggccag ccggacccgc tcgccatcct ccagctgccg cccggagtca gccccgacca  3900
ggcc                                                              3904

SEQ ID NO: 24          moltype = DNA  length = 1191
FEATURE                Location/Qualifiers
source                 1..1191
                       mol_type = genomic DNA
                       organism = Zea mays
SEQUENCE: 24
atggacttct ccaccggcgg gagcgtgagc gggggcggcg gaggcgccag cgacggcccc  60
gcgcaggcgg agcgctggct ggagatcgcc gagaagctcc tcgcggcgcg cgacctcgtc  120
ggctgcaagc gcttcgcgga gcggtcgatg gaggcgaacc cgctcctcgc tggcgttgac  180
gagctcctcg ccgtcgccga cgtcctcctc gcttcccagt tcatgggccc ctcgggccag  240
ccggacccgc tcgccatcct ccagctgccg cccggagtca gccccgacca ggccgccgtg  300
tcccgcgcct tccgccgcct cgcgctcctc ctcggcccca gcaacccgca cccgggagcc  360
gagatggcgc tccgcctcgt caacgacgcc tacgccttcc tctcggatcc ctctcgccgc  420
cccccgccgc ccgccgatcc cgccactggt acccctact cctcccagta tcccgccgcg  480
gccgctcccg cctcggacac cccggagttc tggacggcgt gccccttctg ctgctacgtg  540
caccagtacc cgcgcagcct gatcgggcgc gccctcaagt gccccaacgc gggctgccgc  600
cgcggattcg tggcttctga gctcccgacc ccacccaccg ttgtgccggg cactgaaatg  660
taccactgcg cctgggggtt cttcccctc ggatttccca acgcggccga cctgggtgcc  720
aactggaagc cattctacaa gatgtttcct tggaacacgg ctcccagtgg ccaaggtggt  780
ggtggtagga gtcacggaaa ccatggtggt aggcagccac agaatgacag tgctcgtggt  840
ggctcttcta gaggtaggat caagaagacg acggcccgca agaaggtcgg ggtagggctc  900
aggagacgtt ctcttggtgt ggagagtggc attgattctt cgatgctcgg gcaggaaggc  960
tgggctgggg atgagaacgc tggagatgga agggccgagg aggtgaggag aattaacata  1020
aatgaggcag cacatgctac agatggcact ggtagggtta atgttagcgg tgctggcgga  1080
gttgaagata tcagcaactt tcatatcgat gttgatgcat ctgaggatat attggggaat  1140
ttgcacaaca tgcacttctt gagggtggac aatcttggac ggatgattta a          1191

SEQ ID NO: 25          moltype = DNA  length = 5776
FEATURE                Location/Qualifiers
source                 1..5776
                       mol_type = genomic DNA
                       organism = Zea mays
SEQUENCE: 25
acctagaggg ggtaaataga tgatcctgca aaattagctt taaacaacac aaacttggtt  60
tgtaaaatat gttagtgaga actaaaacca agttaggtta cgaagagagg agaaaagaga  120
actcttcact tgattgctcc tttaaaataa gtattaaagt tagtagcaat attataaata  180
aatatgagaa ttaaatagat aataatcgca ataagcagaa tggtccctct caggccaacc  240
gttccatccg tatccatttc tatcacatca tctctcacgt ctgcatgaac atgtgcacat  300
ggtatttcct tctcaaattt aacccgcgat atgaaaaaca tcgttatcaa tctttcacat  360
ctcaaaataa ctctacataa attttagtat ttgttttatt tagttcaatg agaaaaagat  420
ttgattatat acattgtagt acacctcacg ttctgcttgg acacctctat atatcttcct  480
ctaggcccta tactccctgg cccaattaaa caacacggca tcatgcagta ccaaaagaca  540
aaaacaattt ctagtagtcg agtgcctcct ctctctcctc gataccacat aatatgatat  600
atcacatggc agacggtaga taaagtaggc ggactttgct gggcatagaa aaaaaaaagg  660
atcggcgcca attaccatgg caccgatctt ctgtcacgta gacgccagat cagcgtgaaa  720
gagtgagatc tcgacgccat cttatattgg cgcgcgagac atgcaaactc ggtactaata  780
ataatggcgc cggagtaaag gttcattttt tgaattgaaa cttaaaaaga cgtatttgta  840
ataatcttac aaaaaaatat caaaataaaa aaaaagtcag cgaaacaacg cttcacctat  900
tttaaaacgg gcctcggcgc tcgccctctt ggccacagcg cgcctcacag cgacacccac  960
aagaccacgc ccccggtcgt gcatcatcat catcgctcgc gtcttcgagt tcgaggacat  1020
ggagaggccg cgttgctact ctccgcttgc cctgcacctc ctcctctgcc tcttctcgct  1080
ccgcgcctgt tccgccgcgt ccatcacagc cggcaccccc gacgagtcgg agctgtgggg  1140
gtacgtcgag gtccggccaa gtacgtaaca acccctccct atctcgttgc gcttcagagc  1200
ctctcctcgt cgaaggcgag gtgtcgccgt tgacgacgct ttgccgcctt gtcgcagagg  1260
cgcacctgtt ctggtggtac tacaagagcc cgcagaagac gtcgacgccg tccaagccat  1320
ggcccacggt cctctggctg cagggcggcc cggtaggcag ctgctgcctc gttctctctt  1380
tccctcctca caccaccaca atttctcggc ttcggcacag gagggcatga tccggcctct  1440
gtgcttcatt acgggagcac ggtctagcta cctgatgagc gagagcgagt gatcaaccat  1500
ggttgttttg tccctctcgc agggcgcgtc cggggtcggg ctcggcaact tcctggagat  1560
ggggccgctg gacgtggacc tgaagccgcg caactcgacg tggctccaca aggccgacct  1620
catctttgtg gtcagaccag agagcgatag ctgatgcctg atggcggctc tcttctcctc  1680
tcttctgccc cccgctcttc tacacctttc gctgtcgtga tgtcctcgct gaccgacttc  1740
ttccatggcc gggcgcgcgc gcgcaggaca acccggtcgg cacagggtac agctacgtgg  1800
aggacgacag cctgttcgtg accagcgact ggcagcaggc cgcggacatg acgacggtgg  1860
tcagggcgct ggcgaaggag gtgcccaccc tggcgagcag cccgctgttc ctggtcgccg  1920
agtcctacgg cggcaagtac gccgccacgc tcggcgcgtc cattgccagg gccgtccgcg  1980
ctggcgagct caacgtcacg ctcggaggtt cgtaaggtta cttccgttcc atctccgggc  2040
tccgactcga tgaaccaaat cgacgttggg ggagcagagc agctgactcg atgaaattct  2100
cgttccctcc tgctgcaggt gtggcggttg gagatagctg gatctcgccg gaggatttca  2160
cggtgaggtt gaccattcct agtttcgtta gtgcagaaat aaaccacgga cacattacag  2220
agctaatagt tacctgctaa aattagctaa atacatttag tctagctaat aatttaacta  2280
```

-continued

```
ttagctattt tagtaaacta gcgtatagcc tgtactaata tattatctag ccaaacaata  2340
atttatattg tttgtttacc ctttaactta tttaagtttg attatataat ctagaggata  2400
tccaaaccta taaaactaat agctagaagc taaaactagc tatctcaacc tagctaaaac  2460
cagctaataa gtgattggcg attaaattgc tccgaaccat ttctacctat tagcttatta  2520
gaaaaaggga cgtggatagc ttatcagaat aatctagggt attagcttta gatttagaac  2580
atcctcagct aataatagtt agccagtaac aattagttgt agaggtttgg cttcatctag  2640
actaatgcta ctaaccgaga ctaaattaga ccagtgattt tagtcttgtt ttccatctga  2700
tcgggactaa aagatgaaga cttgttctgt actagtgttc tcttggataa atcacaaatg  2760
atgaatacgc atgtgataat taaagtgagg cctgagtgct gctgcagctt tcctacacac  2820
cgctgcttct gagcgtgtcg aggctggacg acaacgccgg cgacgaagca aacaagtaag  2880
gcagcaacaa cacgcacact gcaccaccac catttgcatg cataaatttc tcttgacgct  2940
tagcgcaccc ccatcacata tatgggcatg cgaatttgag ttcaggaagg cggagacggt  3000
gaaggagcaa atcgtggcgg ggcagtgggc cgcctcgcag aagtcatggg gcagcctgct  3060
agatttcatc gacacaaaga gcggcaacgt cgtaagacta gtttacttat cttcgttctt  3120
atattcaaac ttcactcttc gaacaatata atctacagtg caatctcttt tttttggcag  3180
gacgtttaca atttcatgct cgactccggc atggacccgg tggcactgcc cgtgggttct  3240
tcatcactga tgagcagctt gcaggcgatg aagtactcga cgtacggcca ggactcccag  3300
cctggctcca acaccattga cggcatcatg aatggggtca tcaagcaaaa gctcaagata  3360
atccccaaga acttcacgta tgtcagtcca tagcagtgct catatcgcat cacaagtcac  3420
agccggtttc ctgctgctaa tataatgctg cctgtgacgc tggctgcgct tccaaattaa  3480
acgtctacag gtggggggag caatccgact cggtctacaa cgcgctggtc aacgatttca  3540
tgaaaccgaa gatcgatgag gtaaacggat cgagcagatc aatgaaaagc gccctcgatc  3600
agtttctgaa atttatccct ctttgtttc ttattcagat tgatgagctg ctgtcttatg  3660
gcattaatgt gacggtgtac aatggccagg tcagtaacag tctgcaactt cttcttacga  3720
tccccagcag ctcaaaacta ctcggagctc gtcatcggtt tttactgcat gcatgcgttc  3780
tgttagttcg attagtatta cactgcctgg catcctatct gctataaagc cgtccactct  3840
ttgtaattaa aaaaaaaaca cagatcatga aaactagaag acagaccagg ataaggtcat  3900
tggatagtgg cttagtgaat gattggcatt gactataata atattcgaag ttgagattat  3960
tagcatttac taataagact gcattttttt cattactgaa cttgatatat acatgacttt  4020
tcctctatct gaagctcgac gtaatctgct cgaccaacgg agcagaagca tgggttcaga  4080
agctcaagta agtttttttt tgcgacctat tcccttccct cccctttctct ggcaggattt  4140
caacgatgca tctggattgc tcgttttcag atgggatggt ctgaggacct tcctgagcct  4200
gccaaggcag cccctctact gtggcgccag caagggtacc aaggcctttg tcaggtccca  4260
caagaacctg catttctact ggatacttgg agcagggcac tatgtaagtc ccaagtctga  4320
accccaactg tgccgtctca tctgagatct gcttcccatg tctgtgagag tgtgaggttc  4380
ttaggtttgg atgaaccaaa taaaacctta tttgttttct cgtgggatca tctctctgat  4440
tgcattgcag gtgcctgcag accagccctg catcgcgcta agcatgatca gcagcataac  4500
ccagtcgcca gcaagctagt tcactgactc tatgtggtgt atgccaagaa caaaggaggc  4560
gttgaagcag gtagcgcaag gtcccggagg accattcggc gttcttgaag tgcggtatag  4620
gttggatacc tgaaagacga tgcagttgac aaggacattt tttttacaga aaaagatccg  4680
ataaaaacat atatgatcta cgtattacaa aatattgtaa agaggccgga acttgttttt  4740
ttaataatag aaatgtatct ggcttcatcc tggtccaaat aacgtgccaa ataacgtgaa  4800
aaatacattg ccgcattctc tagcttgcgg aatgcctgca acatcggctc ctgctcctca  4860
gacattgtat ttgggcccaa gatccaagcc aatgcattcg actgaaaatg acatacaaga  4920
gattttggtc agcaaagttg tcaaattttg acagcttcgt ttcttgttag ctagatagat  4980
taacagatca cagacgtcat gtccataaaa aatggatctt tgtagggtat taatcattga  5040
aacagttttg gatattcagc ggcggagagg tcttcgtcag ggagaccctc tcttccctat  5100
gttgtttgtg ctgatcatgg acgtgcttag cagtcttttc aggactgctg aatgtagggg  5160
attgctgcac agtttggaaa gggcaagagt ccataacagg ctttctatct atgttgatga  5220
tgtggtcctt tttgttaaac ccattgagga agatctgaaa tgtgttagat tgattctgaa  5280
ttgttttggg tcggcctccg gattggttac caatatgaat aagagttatg ctattcctat  5340
cagatgtgag gagcatgtgg ttcaagaggg ctgcaatatg ctgaggtgca gtgtggcctc  5400
atttccttgt tcttacttgg gtctgccaat ctcagacagg aagctgaagc gagatgatct  5460
taagttgtgg atagataaaa ttgcagacag actccctaac tggaaggctc gtttattgaa  5520
cctagccggg aggacaacat tagtgcggtt tgtcttatcg gtcatcccaa tttatcttct  5580
tattgccatt aaaattccca aatgggttat taaatcaatt gacaagattc gaagagagtt  5640
tctttggaaa gggtgaaagg aggtgaatgg tggaagttgt attgttccct gggaaactgt  5700
gacaaggcca taagtttagg gggtcttggt gttcctaatt tgcaattgaa gagttgggca  5760
ctgcaggcta agtggc                                                   5776

SEQ ID NO: 26          moltype = DNA  length = 1653
FEATURE                Location/Qualifiers
source                 1..1653
                       mol_type = genomic DNA
                       organism = Zea mays
SEQUENCE: 26
gtcttcgagt tcgaggacat ggagaggccg cgttgctact ctccgcttgc cctgcacctc  60
ctcctctgcc tcttctcgct ccgcgcctgt tccgccgcgt ccatcacagc cggcaccccc  120
gacgagtcgg agctgtgggg gtacgtcgag gtccggccaa aggcgcacct gttctggtgg  180
tactacaaga gcccgcagaa gacgtcgacg ccgtccaagc catggcccac ggtcctctgg  240
ctgcagggcg gcccgggcgc gtccggggtc gggctcggca acttcctgga gatggggccg  300
ctggacgtgg acctgaagcc gcgcaactcg acgtggctcc acaaggccga cctcatcttt  360
gtggacaacc cggtcggcac agggtacagc tacgtggagg acgacagcct gttcgtgacc  420
agcgactggc agcaggccgc ggacatgacg acggtggtca gggcgctggc gaaggaggtg  480
cccacccctgg cgagcagccc gctgttcctg gtcgccgagt cctacggcgg caagtacgcc  540
gccacgctcg gcgcgtccat tgccagggcc gtccgcgctg gcgagctcaa cgtcacgctc  600
ggaggtgtgg cggttggaga tagctggatc tcgccggagg atttcacgct ttcctacaca  660
ccgctgcttc tgagcgtgtc gaggctggac gacaacgccg gcgacgaagc aaacaagaag  720
gcggagacgg tgaaggagca aatcgtggcg gggcagtggg ccgcctcgca gaagtcatgg  780
```

-continued

```
ggcagcctgc tagatttcat cgacacaaag agcggcaacg tcgacgttta caatttcatg  840
ctcgactccg gcatggaccc ggtggcactg cccgtgggtt cttcatcact gatgagcagc  900
ttgcaggcga tgaagtactc gacgtacggc caggactccc agcctggctc caacaccatt  960
gacggcatca tgaatggggt catcaagcaa aagctcaaga taatccccaa gaacttcacg  1020
tggggggagc aatccgactc ggtctacaac gcgctggtca acgatttcat gaaaccgaag  1080
atcgatgaga ttgatgagct gctgtcttat ggcattaatg tgacggtgta caatggccag  1140
ctcgacgtaa tctgctcgac caacggagca gaagcatggg ttcagaagct caaatgggat  1200
ggtctgagga ccttcctgag cctgccaagg cagcccctct actgtggcgc cagcaagggt  1260
accaaggcct ttgtcaggtc ccacaagaac ctgcatttct actggatact tggagcaggg  1320
cactatgtgc ctgcagacca gccctgcatc gcgctaagca tgatcagcag cataacccag  1380
tcgccagcaa gctagttcac tgactctatg tggtgtatgc caagaacaaa ggaggcgttg  1440
aagcaggtag cgcaaggtcc cggaggacca ttcggcgttc ttgaagtgcg gtataggttg  1500
gatacctgaa agacgatgca gttgacaagg acattttttt tacagaaaaa gatccgataa  1560
aaacatatat gatctacgta ttacaaaata ttgtaaagag gccggaactt gttttttaa  1620
taatagaaat gtatctggct tcatcctggt cca                              1653
```

```
SEQ ID NO: 27           moltype = DNA  length = 1800
FEATURE                 Location/Qualifiers
source                  1..1800
                        mol_type = genomic DNA
                        organism = Zea mays
SEQUENCE: 27
acgtgggaga ccacgccccc ggtcgtgcat catcatcatc gctcgcgtct acgagttcga  60
ggacatggag aggccgcgtt gctactctcc gcttgccctg cacctcctcc tctgcctctt  120
ctcgctccgc gcctgttccg ccgcgtccat cacagccggc acccccgacg agtcggagct  180
gtgggggtac gtcgaggtcc ggccaaaggc gcacctgttc tggtggtact acaagagccc  240
gcagaagacg tcgacgccgt ccaagccatg gcccacggtc ctctggctgc agggcggccc  300
gggcgcgtcc ggggtcgggc tcggcaactt cctggagatg ggcccgctgg acgtggacct  360
gaagccgcgc aactcgacgt ggctccacaa ggccgacctc atctttgtgg acaacccggt  420
cggcacaggg tacagctacg tggaggacga cagcctgttc gtgaccagcg actggcagca  480
ggccgcggac atgacgacgg tggtcagggc gctggcgaag gaggtgccca ccctggcgag  540
cagcccgctg ttcctggtcg ccgagtccta cggcggcaag tacgccgcca cgctcggcgc  600
gtccattgcc agggccgtcc gcgctggcga gctcaacgtc acgctcggag gtgtggcggt  660
tggagatagc tggatctcgc cggaggattt cacgctttcc tacacaccgc tgcttctgag  720
cgtgtcgagg ctggacgaca acgccggcga cgaagcaaac aagaaggcgg agacggtgaa  780
ggagcaaatc gtggcggggc agtgggccgc ctcgcagaag tcatggggca gcctgctaga  840
tttcatcgac acaaagagcg gcaacgtcga aggacaaatt caggctgagc agtgggccgc  900
ctcgcagaag tcaaacggca ccctgcgaac aatataatcg acacagcaag agcggcaacg  960
tggcaggacg tttacaattt catgctcgac tccggcatgg acccggtggc actgcccgtg  1020
ggttcttcat cactgatgag cagcttgcag gcgatgaagt actcgacgta cggccaggac  1080
tcccagcctg gctccaacac cattgacggc atcatgaatg gggtcatcaa gcaaaagctc  1140
aagataatcc ccaagaactt cacgtggggg gagcaatccg actcggtcta caacgcgctg  1200
gtcaacgatt tcatgaaacc gaagatcgat gagattgatg agctgctgtc ttatggcatt  1260
aatgtgacgg tgtacaatgg ccagctcgac gtaatctgct cgaccaacgg agcagaagca  1320
tgggttcaga agctcaaatg ggatggtctg aggaccttcc tgagcctgcc aaggcagccc  1380
ctctactgtg gcgccagcaa gggtaccaag gcctttgtca ggtcccacaa gaacctgcat  1440
ttctactgga tacttggagc agggcactat gtgcctgcag accagccctg catcgcgcta  1500
agcatgatca gcagcataac ccagtcgcca gcaagctagt tcactgactc tatgtggtgt  1560
atgccaagaa caaaggaggc gttgaagcag gtagcgcaag gtcccggagg accattcggc  1620
gttcttgaag tgcggtatag gttggatacc tgaaagacga tgcagttgac aaggacattt  1680
tttttacag aaaaagatcc gataaaaaca tatatgatct acgtattaca aaatattgta  1740
aagaggccgg aacttgtttt tttaataata gaaatgtatc tggcttcatc ctggtccaaa  1800
```

```
SEQ ID NO: 28           moltype = DNA  length = 1150
FEATURE                 Location/Qualifiers
source                  1..1150
                        mol_type = genomic DNA
                        organism = Zea mays
SEQUENCE: 28
tcacaaatga tgaatacgca tgtgataatt aaagtgaggc ctgagtgctg ctgcagcttt  60
cctacacacc gctgcttctg agcgtgtcga ggctggacga caacgccggc gacgaagcaa  120
acaagaaggc ggagacggtg aaggagcaaa tcgtggcggg gcagtgggcc gcctcgcaga  180
agtcatgggg cagcctgcta gatttcatcg acacaaagag cggcaacgtc gtaagactag  240
tttacttatc ttcgttctta tattcaaact tcactcttcg aacaatataa tctacagtgc  300
aatctctttt ttttggcagg acgtttacaa tttcatgctc gactccggca tggacccggt  360
ggcactgccc gtgggttctt catcactgat gagcagcttg caggcgatga agtactcgac  420
gtacggccag gactcccagc ctggctccaa caccattgac ggcaccatga atggggtcat  480
caagcaaaag ctcaagataa tccccaagaa cttcacgtgg ggggagcaat ccgactcggt  540
ctacaacgcg ctggtcaacg atttcatgaa accgaagatc gatgagattg atgagctgct  600
gtcttatggc attaatgtga cggtgtacaa tggccagctc gacgtaatct gctcgaccaa  660
cggagcagaa gcatgggttc agaagctcaa atgggatggt ctgaggacct tcctgagcct  720
gccaaggcag cccctctact gtggcgccag caagggtacc aaggcctttg tcaggtccca  780
caagaacctg catttctact ggatacttgg agcagggcac tatgtgcctg cagaccagcc  840
ctgcatcgcg ctaagcatga tcagcagcat aacccagtcg ccagcaagct agttcactga  900
ctctatgtgg tgtatgccaa gaacaaagga ggcgttgaag caggtagcgc aaggtcccgg  960
aggaccattc ggcgttcttg aagtgcggta taggttggat acctgaaaga cgatgcagtt  1020
gacaaggaca ttttttttac agaaaaagat ccgataaaaa catatatgat ctacgtatta  1080
caaaatattg taaagaggcc ggaacttgtt tttttaataa tagaaatgta tctggcttca  1140
tcctggtcca                                                        1150
```

-continued

```
SEQ ID NO: 29          moltype = DNA  length = 4215
FEATURE                Location/Qualifiers
source                 1..4215
                       mol_type = genomic DNA
                       organism = Zea mays
SEQUENCE: 29
aaggacatat ttgtaataat ctttccaaaa aagtgtcaaa atacaaaaaa aaaagtcagc  60
gaaacaacgc ttcacctatt ttaaaacggg tctcggcgct cgccctcttg gccacaggcc  120
cacagcgcgc ctcacagcga cacccaccac gcccccggtc gtgcatcatc atcatcactc  180
gcgtcttcga gttcgaggac atggacaggc cgcgttgcta ctccccgctt gccctgcacc  240
tcctcctctg cctcgtctcg ctccgcgcct gttccgccgc gtccatcact gccggcaccc  300
ccgacgagtc ggagctgtgg gggtacgtcg aggtccggcc aagtacgtaa cacccccctcc  360
ctagctcgtt gcgcttcaga gcctctcttc gtcgaaggcg aggtgtcgcc gttgacgacg  420
ctttgccgcc ttgtcgcaga ggcgcacctg ttctggtggt actacaagag cccgcagagg  480
acgtcgacgc cgtccaagcc atggcccacg gtcctctggc tgcagggcgg cccggtaggc  540
agctgctgcc tcgttctctc tttccctcct cacaccacca caatttctcg gcttcggcac  600
aggaggacat gatccggcct ctgtgcttca ttacgggagc acggtctagc tacctgatga  660
gcaagagcga gtaatcaacc atggttgtct tgtccctctc gcagggcgcg tccggggtcg  720
ggctcggcaa cttcctggag atggggccgc tggacgtgga cctgaagccg cgcaactcga  780
cgtggctcca caaggccgac ctcatctttg tggtcagacc agagagcgat agctgatggc  840
ggctctcttc tccgatcctc tcttctgccc cccgctcttc ttctacacct ttcgctgtcg  900
tgatgtcctc actgaccgac ttcttccatg gccgggcgcg cgcgcaggac aacccggtcg  960
gcacagggta cagctacgtg gaggacgaca gcctgttcgt gaccagcgac tggcagcagg  1020
ccgcggacat gacgacggtg gtcagggcgc tggcgaagga ggtgcccacc ctggcgagca  1080
gcccgctgtt cctggtcgcc gagtcctacg gcggcaagta cgccgccacg ctcggcgcgt  1140
ccatcgccag ggccgtccgc gctggcgagc tcaacgtcac gctcggaggt tcgtaaggtt  1200
gcttccgttc catctccggg ctccgactcg atgaaccaaa tcgacgttgg gggagcagag  1260
cagagcagag cagctgactc gatgaaattc tcgttccctc ctgctgcagg tgtggcggtt  1320
ggagatagct ggatctcgcc ggaggatttc acggtgaggt tgaccgttct tagtttcgtt  1380
agtgcagaaa taaactgcgg ctacgttgca gagctaatag ttagctgata aaattagcta  1440
aaaacattta aatagtctag ctaataattt aactattagc tattttagta aactagcgtg  1500
tagcatgtac taatatatta tctaaaagcc aaataataat ctatattgtt tgtttaccct  1560
ttaacttatt taagtttaat tatataatct agaggatatc caaacttata aaattaatag  1620
ctagaagcta aaactagcta tcccaaccta gctaaaacca gctaataagt gattgacgat  1680
taaattgctt cgaaccattt ctacctatta gcttattaga aaaagggacg tggatagctt  1740
atcagaataa tctagggtat tagctttaga tttagaacat cctcaactaa taatagttcc  1800
agtaacaatt agttctagag gtttggcttg atctagacta atgctactaa ccgagactaa  1860
attagaccag tgattttagt cttgtttggt agcttcaatc gagactaatg cttccatctg  1920
atcgggacta aaagatgaag acttgttctg tactagtgtt ctcttggata aatcacaaat  1980
gatgaatatg catgtgataa ttaaagtgag gcctgaatgc tgctgcagct ttcctacaca  2040
ccgctgcttc tgagcgtgtc gaggctggac gacaacgccg gcgacgaagc aaacaagtaa  2100
gggggtgttt ggtttctagg gactaatgtt tagtcccttc attttattcc tttttagtgt  2160
ataaattgat aaacatagaa attaaaataa agttttagtt tctatatttg gtaattttgg  2220
accaaaaatg gaataaaatc tagggactaa acattagtcc ctagaaacca aacaccctct  2280
aaggcagcaa caacacgcac actgcaccac caccatttgc atgcataaat ttctcttgac  2340
gcttagcgca cccccatcac atatatgggc atgcgaattt gagttcagga aggcggagac  2400
ggtgaaggag caaatcgtgg cggggcagtg ggccgcctcg cagaagtcat ggagcagcct  2460
gctagatttc atcgacacaa agagcggcaa cgtcgtaagg ctagtttact tatcttcatt  2520
cttatattta aacttcactc ttcgaacaat ataatctaca gtgcaatctc ttttttttgg  2580
caggacgttt acaatttcat gctcgactcc ggcatggacc cggtggcact gctgcccgtg  2640
ggttcttcat cactgatgag cagcttgcag gcgatgaaga agtactcgac gtacggccag  2700
gactcccagc ctggctccaa caccattgac ggcatcatga atggggtcat caagcaaaag  2760
ctcaagataa tccccaagaa cttcacgtat gtcagtccat agcagtgctc atatcgcatc  2820
acaagtcaca gccggtttcc tgctgctaat gtaatgctgc ctgtgacgct ggctgcgctt  2880
ccaaattaaa cgtctacagg tgggggcagc aatccgactc ggtctacaac gcgctggtca  2940
acgatttcat gaaaccgagg atcgatgagg taaactggtc gagcagataa atgaaaagcg  3000
ccctcgatca gtttctgaaa ttaatccctc ttcattttct cattcagatt gatgagctgc  3060
tgtcttatgg cattaatgtg acggtgtaca atggccaggt cagtaacagt ctgcaacttc  3120
aattcttacg atccccagca gctcaaaact actcggaaaa aaatttgctg cagcccggct  3180
gcaaaacagt atgtttacag cccctcacaa aaaggaggat agatctctac tcttttttttt  3240
ctcgaatata caggagacct gcatatctgt tagttcgatt agtattacac tgccatccta  3300
tctgctataa agccgtccac tctttgtaat taaaaaaaac acagatcatg aaaactagaa  3360
gacagaccag gataaggtca ttggatagtg gcttagtgaa tgattggcat tgactaataa  3420
tattcgaagt tgagattgag attattagca tttactaata agactgcatt tttttcatta  3480
ctgaacttga tatatacatg acttttcctc tatctgaagc tcgacgtaat ctgctcgacc  3540
aacggagcag aagcatgggt tcagaagctc aagtaagttt tttttttggc aacctattcc  3600
ctcccattct ctggcaggat ttcaacgatg catctggatt gctcgttttc agatgggatg  3660
gtctgaggac cttcctgagc ctgccaaggc agcccctcta ctgtggcgcc agcaagggca  3720
ccaaggcctt tgtcaggtcc cacaagaacc tgcatttcta ctggattctt ggagcagggc  3780
actatgtaag tcccaagtct gaaccctaac tgtgccgtct catctgagat ctgcttccca  3840
tgtctgtgag agtgggaggt tcttaggttt ggatgaacca aaaccttatt tgttttctcg  3900
tgggatcatc tctctgattg cattgcaggt gcctgcagac cagccctgca tcgcgctaag  3960
catgatcagc agcataaccc agtcgccagc aagctagttg actgactcta tgtggtgtat  4020
gccaaaaaca aaggaggcgt tgaagcaggt agcgcaaggt cccggaggac cattcggcgt  4080
tcttgaagtg cggtataggt tggataccctg aaaaaataca taagattata ttataaaaag  4140
gaagaatata cactaaatgg tagtataatt aattataaaa tgtttgtagt ccttttcttg  4200
cgaagaaaat ctttt                                                   4215
```

-continued

```
SEQ ID NO: 30          moltype = DNA  length = 5108
FEATURE                Location/Qualifiers
source                 1..5108
                       mol_type = genomic DNA
                       organism = Zea mays
SEQUENCE: 30
tataatccga ctacatttaa tacccggaac ggaggttcaa acattcgatg ggacagggac  60
taaattttag cggggtgtaa ccaaacaccc ccttagtagc aatattacaa gtgaatatga  120
gaacttaaga agacaataat cgcaataaga agaatggtcc ctctccggcc aaccgttcca  180
tccatatcca tttctatcac atcatctctc acgtctccat gaacatgtgc acatggtatt  240
tccttctcaa atttttaccc gcgatatgaa aaacatcgtt atcaatcttt cacatctcaa  300
aataactcta ctataaattt ttagtatttg ttatatttag ttcaatgaga aaaggatttg  360
attatataca ttgtagtaca cgtcatgttc tgcttggaca cctctgtata tctccctcta  420
ggctctatac tccctgcccc aattaaacaa cacggcatca tgccaaaaac aatttctagt  480
agtcgagtgc ctactctctc tcctcgttct ctctccccag tggcatcgaa ggaaaagtat  540
atatgattgt acccatgatg tgatatacca tatgacagac ggtagataaa gcaggcggac  600
tttgatgggc atagaaaaca gggtcggcgc caattaccat ggcgccgatc tcatgtcaca  660
tagacgccac atcagcgtga gagagtgaga tctcgacagt cgacgccatc tatattgccg  720
cgcgagacgt gcaaactcgg tactaataat aatggcgccg ggtaaaggtc tattttttta  780
attgaaactt aaaaggacat atttgtaata atctttccaa aaaagtgtca aaatacaaaa  840
aaaaaagtca gcgaaacaac gcttcaccta ttttaaaacg ggtctcggcg ctcgccctct  900
tggccacagg cccacagcgc gcctcacagc gacacccacc acgcccccgg tcgtgcatca  960
tcatcatcac tcgcgtcttc gagttcgagg acatggacag gccgcgttgc tactccccgc  1020
ttgccctgca cctcctcctc tgcctcgtct cgctccgcgc ctgttccgcc gcgtccatca  1080
ctgccggcac ccccgacgag tcggagctgt gggggtacgt cgaggtccgg ccaagtacgt  1140
aacacccccct ccctagctcg ttgcgcttca gagcctctct tcgtcgaagg cgaggtgtcg  1200
ccgttgacga cgctttgccg ccttgtcgca gaggcgcacc tgttctggtg gtactacaag  1260
agcccgcaga ggacgtcgac gccgtccaag ccatggccca cggtcctctg gctgcagggc  1320
ggcccggtag gcagctgctg cctcgttctc tctttccctc ctcacaccac cacaatttct  1380
cggcttcggc acaggaggac atgatccggc ctctgtgctt cattacggga gcacggtcta  1440
gctacctgat gagcaagagc gagtaatcaa ccatggttgt cttgtccctc tcgcagggcg  1500
cgtccggggt cgggctcggc aacttcctgg agatggggcc gctggacgtg gacctgaagc  1560
cgcgcaactc gacgtggctc cacaaggccg acctcatctt tgtggtcaga ccagagagcg  1620
atagctgatg gcggctctct tctccgatcc tctcttctgc cccccgctct tcttctacac  1680
ctttcgctgt cgtgatgtcc tcactgaccg acttcttcca tggccgggcg cgcgcgcagg  1740
acaacccggt cggcacaggg tacagctacg tggaggacga cagcctgttc gtgaccagcg  1800
actggcagca ggccgcggac atgacgacgg tggtcagggc gctggcgaag gaggtgccca  1860
ccctggcgag cagcccgctg ttcctggtcg ccgagtccta cggcggcaag tacgccgcca  1920
cgctcggcgc gtccatcgcc agggccgtcc gcgctggcga gctcaacgtc acgctcggag  1980
gttcgtaagg ttgcttccgt tccatctccg ggctccgact cgatgaacca aatcgacgtt  2040
gggggagcag agcagagcag agcagctgac tcgatgaaat tctcgttccc tcctgctgca  2100
ggtgtggcgg ttggagatag ctggatctcg ccggaggatt tcacggtgag gttgaccgtt  2160
cttagtttcg ttagtgcaga aataaactgc ggctacgttg cagagctaat agttagctga  2220
taaaattagc taaaaacatt taaatagtct agctaataat ttaactatta gctattttag  2280
taaactagcg tgtagcatgt actaatatat tatctaaaag ccaaataata atctatattg  2340
tttgtttacc ctttaactta tttaagttta attatataat ctagaggata tccaaactta  2400
taaaattaat agctagaagc taaaactagc tatcccaacc tagctaaaac cagctaataa  2460
gtgattgacg attaaattgc ttcgaaccat ttctacctat tagcttatta gaaaaaggga  2520
cgtggatagc ttatcagaat aatctagggt attagcttta gatttagaac atcctcaact  2580
aataatagtt ccagtaacaa ttagttctag aggtttggct tgatctagac taatgctact  2640
aaccgagact aaattagacc agtgatttta gtcttgtttg gtagcttcaa tcgagactaa  2700
tgcttccatc tgatcgggac taaaagatga agacttgttc tgtactagtg ttctcttgga  2760
taaatcacaa atgatgaata tgcatgtgat aattaaagtg aggcctgaat gctgctgcag  2820
ctttcctaca caccgctgct tctgagcgtg tcgaggctgg acgacaacgc cggcgacgaa  2880
gcaaacaagt aagggggtgt ttggtttcta gggactaatg tttagtccct tcattttatt  2940
ccttttagt gtataaattg ataaacatag aaattaaaat aaagttttag tttctatatt  3000
tggtaatttt ggaccaaaaa tggaataaaa tctagggact aaacattagt ccctagaaac  3060
caaacaccct ctaaggcagc aacaacacgc acactgcacc accaccattt gcatgcataa  3120
atttctcttg acgcttagcg cacccccatc acatatatgg gcatgcgaat ttgagttcag  3180
gaaggcggag acggtgaagg agcaaatcgt ggcggggcag tgggccgcct cgcagaagtc  3240
atggagcagc ctgctagatt tcatcgacac aaagagcggc aacgtcgtaa ggctagttta  3300
cttatcttca ttcttatatt taaacttcac tcttcgaaca atataatcta cagtgcaatc  3360
tcttttttttt ggcaggacgt ttacaatttc atgctcgact ccggcatgga cccggtggca  3420
ctgctgcccg tgggttcttc atcactgatg agcagcttgc aggcgatgaa gaagtactcg  3480
acgtacggcc aggactccca gcctggctcc aacaccattg acggcatcat gaatggggtc  3540
atcaagcaaa agctcaagat aatccccaag aacttcacgt atgtcagtcc atagcagtgc  3600
tcatatcgca tcacaagtca cagccggttt cctgctgcta atgtaatgct gcctgtgacg  3660
ctggctgcgc ttccaaatta aacgtctaca ggtgggggca gcaatccgac tcggtctaca  3720
acgcgctggt caacgatttc atgaaaccga ggatcgatga ggtaaactgg tcgagcagat  3780
aaatgaaaag cgccctcgat cagtttctga aattaatccc tcttcatttt ctcattcaga  3840
ttgatgagct gctgtcttat ggcattaatg tgacggtgta caatggccag gtcagtaaca  3900
gtctgcaact tcaattctta cgatccccag cagctcaaaa ctactcggaa aaaaatttgc  3960
tgcagcccgg ctgcaaaaca gtatgtttac agcccctcac aaaaaggagg atagatctct  4020
actctttttt ttctcgaata tacaggagac ctgcatatct gttagttcga ttagtattac  4080
actgccatcc tatctgctat aaagccgtcc actctttgta attaaaaaaa acacagatca  4140
tgaaaactag aagacagacc aggataaggt cattggatag tggcttagtg aatgattggc  4200
attgactaat aatattcgaa gttgagattg agattattag catttactaa taagactgca  4260
tttttttcat tactgaactt gatatataca tgacttttcc tctatctgaa gctcgacgta  4320
atctgctcga ccaacggagc agaagcatgg gttcagaagc tcaagtaagt tttttttttg  4380
```

-continued

```
gcaacctatt ccctcccatt ctctggcagg atttcaacga tgcatctgga ttgctcgttt  4440
tcagatggga tggtctgagg accttcctga gcctgccaag gcagcccctc tactgtggcg  4500
ccagcaaggg caccaaggcc tttgtcaggt cccacaagaa cctgcatttc tactggattc  4560
ttggagcagg gcactatgta agtcccaagt ctgaacccta actgtgccgt ctcatctgag  4620
atctgcttcc catgtctgtg agagtgggag gttcttaggt ttggatgaac caaaacctta  4680
tttgttttct cgtgggatca tctctctgat tgcattgcag gtgcctgcag accagccctg  4740
catcgcgcta agcatgatca gcagcataac ccagtcgcca gcaagctagt tgactgactc  4800
tatgtggtgt atgccaaaaa caaaggaggc gttgaagcag gtagcgcaag gtcccggagg  4860
accattcggc gttcttgaag tgcggtatag gttggatacc tgaaaaaata cataagatta  4920
tattataaaa aggaagaata tacactaaat ggtagtataa ttaattataa aatgtttgta  4980
gtccttttct tgcgaagaaa atcttttaaa tggcatttgt gtgaagcaca atgtttagag  5040
tcctaaaaat gcaattgtct ctgttgggga cttgctctca aatgctatga atcaagagca  5100
agacaaca                                                            5108

SEQ ID NO: 31          moltype = DNA  length = 1659
FEATURE                Location/Qualifiers
source                 1..1659
                       mol_type = genomic DNA
                       organism = Zea mays
SEQUENCE: 31
gtcttcgagt tcgaggacat ggacaggccg cgttgctact ctccgcttgc cctgcacctc  60
ctcctctgcc tcttctcgct ccgcgcctgt tccgccgcgt ccatcacagc cggcaccccc  120
gacgagtcgg agctgtgggg gtacgtcgag gtccggccaa aggcgcacct gttctggtgg  180
tactacaaga gcccgcagaa gacgtcgacg ccgtccaagc catggcccac ggtcctctgg  240
ctgcagggcg gcccgggcgc gtccggggtc gggctcggca acttcctgga gatggggccg  300
ctggacgtgg acctgaagcc gcgcaactcg acgtggctcc acaaggccga cctcatcttt  360
gtggacaacc cggtcggcac agggtacagc tacgtggagg acgacagcct gttcgtgacc  420
agcgactggc agcaggccgc ggacatgacg acggtggtca gggcgctggc gaaggaggtg  480
cccaccctgg cgagcagccc gctgttcctg gtcgccgagt cctacggcgg caagtacgcc  540
gccacgctcg gcgcgtccat tgccagggcc gtccgcgctg gcgagctcaa cgtcacgctc  600
ggaggtgtgg cggttggaga tagctggatc tcgccggagg atttcacgct ttcctacaca  660
ccgctgcttc tgagcgtgtc gaggctggac gacaacgccg gcgacgaagc aaacaagaag  720
gcggagacgg tgaaggagca aatcgtggcg gggcagtggg ccgcctcgca gaagtcatgg  780
ggcagcctgc tagatttcat cgacacaaag agcggcaacg tcgacgttta caatttcatg  840
ctcgactccg gcatggaccc ggtggcactg ctgcccgtgg gttcttcatc actgatgagc  900
agcttgcagg cgatgaagaa gtactcgacg tacggccagg actcccagcc tggctccaac  960
accattgacg gcatcatgaa tggggtcatc aagcaaaagc tcaagataat ccccaagaac  1020
ttcacgtggg gggagcaatc cgactcggtc tacaacgcgc tggtcaacga tttcatgaaa  1080
ccgaagatcg atgagattga tgagctgctg tcttatggca ttaatgtgac ggtgtacaat  1140
ggccagctcg acgtaatctg ctcgaccaac ggagcagaag catgggttca gaagctcaaa  1200
tgggatggtc tgaggacctt cctgagcctg ccaaggcagc ccctctactg tggcgccagc  1260
aagggtacca aggcctttgt caggtcccac aagaacctgc atttctactg gatacttgga  1320
gcagggcact atgtgcctgc agaccagccc tgcatcgcgc taagcatgat cagcagcata  1380
acccagtcgc cagcaagcta gttcactgac tctatgtggt gtatgccaag aacaaaggag  1440
gcgttgaagc aggtagcgca aggtcccgga ggaccattcg gcgttcttga agtgcggtat  1500
aggttggata cctgaaagac gatgcagttg acaaggacat ttttttaca gaaaaagatc  1560
cgataaaaac atatatgatc tacgtattac aaaatattgt aaagaggccg gaacttgttt  1620
ttttaataat agaaatgtat ctggcttcat cctggtcca                          1659

SEQ ID NO: 32          moltype = DNA  length = 1795
FEATURE                Location/Qualifiers
source                 1..1795
                       mol_type = genomic DNA
                       organism = Zea mays
SEQUENCE: 32
agttcatcac taatcacact tattgtgccc tcgacgagta tctatagcta gctcattaat  60
cgattcgggg gtgtgttgtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
cagaactgcc cgcgcatctt tcctcagaag tgagtccgat gctgccgcca ttgttcttgc  480
atccatccag catcgtacgt acgtcctcta tacatctgcg gatcatcatg tgcgcatgtt  540
tgtggcatgc atgcatgcat gtgagcagga gcaggcttgc ggccgccatg tccgcgctga  600
ggaagccaaa gtacaacggc aagtgcatgc gcagcctgat taggagcatc ctcggcgaga  660
cgagggtaag cgagacgctg accaacgtca tcatccctgc cttcgacatc aggctgctgc  720
agcctatcat cttctctacc tacgacgtac gtacgtcgtc acgaatgatt catctgtacg  780
tcgtcgcatg cgaatggctg cctacgtacg ccgtgcgcta acatactcag ctctttccta  840
tctgctgcgc caatttgcag gccaagagca cgcctctgaa gaacgctctg ctctcggacg  900
tgtgcattgg cacgtccgcc gcgccgacct acctcccggc gcactacttc cagactgaag  960
acgccaacgg caaggagcgc gaatacaacc tcatcgacgg cggtgtggcg gccaacaacc  1020
cggtaactga ctagctaact ggaaaacgga cgcacagact ccatgtccat ggcggcccac  1080
aaggtcgatg ctaattgttg cttatgtatg tcgcccgatt gcacatgcgt agacgatggt  1140
tgcgatgacg cagatcacca aaaagatgct tgccagcaag gacaaggccg aggagctgta  1200
cccagtgaag ccgtcgaact gccgcaggtt cctggtgctg tccatcggga cggggtcgac  1260
gtccgagcag ggcctctaca cggcgcggca gtgctcccgg tggggtatct gccggtggct  1320
ccgcaacaac ggcatggccc ccatcatcga catcttcatg gcggccagct cggacctggt  1380
ggacatccac gtcgccgcga tgttccagtc gctccacagc gacggcgact acctgcgcat  1440
```

```
ccaggacaac tcgctccgtg gcgccgcggc caccgtggac gcggcgacgc cggagaacat  1500
gcggacgctc gtcgggatcg gggagcggat gctggcacag agggtgtcca gggtcaacgt  1560
ggagacaggg aggtacgaac cggtgactgg cgaaggaagc aatgccgatg ccctcggtgg  1620
gctcgctagg cagctctccg aggagaggag aacaaggctc gcgcgccgcg tctctgccat  1680
caacccaaga ggctctagat gtgcgtcgta cgatatctaa gacaagtggc tttactgtca  1740
gtcacatgct tgtaaataag tagactttat tttaataaaa cataaaaata tatat       1795

SEQ ID NO: 33           moltype = DNA  length = 1452
FEATURE                 Location/Qualifiers
source                  1..1452
                        mol_type = genomic DNA
                        organism = Zea mays
SEQUENCE: 33
agttcatcac taatcacact tattgtgccc tcgacgagta tctatagcta gctcattaat  60
cgattcgggg gtgtgttgtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
cagaactgcc cgcgcatctt tcctcagaag agcaggcttg cggccgccat gtccgcgctg  480
aggaagccaa agtacaacgg caagtgcatg cgcagcctga ttaggagcat cctcggcgag  540
acgagggtaa gcgagacgct gaccaacgtc atcatccctg ccttcgacat caggctgctg  600
cagcctatca tcttctctac ctacgacgcc aagagcacgc ctctgaagaa cgctctgctc  660
tcggacgtgt gcattggcac gtccgccgcg ccgacctacc tcccggcgca ctacttccag  720
actgaagacg ccaacggcaa ggagcgcgaa tacaacctca tcgacggcgg tgtggcggcc  780
aacaacccga cgatggttgc gatgacgcag atcaccaaaa agatgcttgc cagcaaggac  840
aaggccgagg agctgtaccc agtgaagccg tcgaactgcc gcaggttcct ggtgctgtcc  900
atcgggacgg ggtcgacgtc cgagcagggc ctctacacgg cgcggcagtg ctcccggtgg  960
ggtatctgcc ggtggctccg caacaacggc atggccccca tcatcgacat cttcatggcg  1020
gccagctcgg acctggtgga catccacgtc gccgcgatgt tccagtcgct ccacagcgac  1080
ggcgactacc tgcgcatcca ggacaactcg ctccgtggcg ccgcggccac cgtggacgcg  1140
gcgacgccgg agaacatgcg gacgctcgtc gggatcgggg agcggatgct ggcacagagg  1200
gtgtccaggg tcaacgtgga gacagggagg tacgaaccgg tgactggcga aggaagcaat  1260
gccgatgccc tcggtgggct cgctaggcag ctctccgagg agaggagaac aaggctcgcg  1320
cgccgcgtct ctgccatcaa cccaagaggc tctagatgtg cgtcgtacga tatctaagac  1380
aagtggcttt actgtcagtc acatgcttgt aaataagtag actttatttt aataaaacat  1440
aaaaatatat at                                                      1452

SEQ ID NO: 34           moltype = DNA  length = 4564
FEATURE                 Location/Qualifiers
source                  1..4564
                        mol_type = genomic DNA
                        organism = Zea mays
SEQUENCE: 34
aaggaaaggt cacacatcct agctagcttc actggttcta gctccttcca attttgcaaa  60
aaagtcacaa aggataagcc atttttccaa atgatttgtg aaatgcctat gctaaaaagc  120
ctacttttcc gaaaaaccag agctagagcc atttttgaca agtcagaacc ctaccaaata  180
gtccctcagt ttaagcaaag tgaggccata ctgaagctaa attatgccaa attgggccta  240
catctccata ttttcaacca aatgctttag ggtttcttgt aatcgacatg atttgtttct  300
tcataaatag tatatggacc gctccaaaat actccatccg tttcaattta tatttcgttt  360
gatcttttta ccctaaattt gatcgactcg tcttattaaa aaaagttcat aactattaat  420
aatctttact gtgatatcat ttagcatata atatacttta attgtggctt tgattttttt  480
ccgcaaaaat taaatgaaac gacccaatca aacttgataa aaaagtaaaa ctaattataa  540
atttggacag aaggagtagg agggtgtttg aatacactag agttaatagt tagttgcctt  600
aaaatttgct agtacaatta gctagctaac aaatatttag gtaactatta gctaatttgc  660
taaaaacagc taatagttaa actattagct agactgtttg gatgtattca gctaatttta  720
gcagctaact attagctata gtataatatt caaacacctc ctaattaaaa tggacaaata  780
tctcttccct tggtcccttg cgttagattt ccatatctcc ttatttagta taaaaagaat  840
catcaaaaag tggacaaccc ctagtggaac accattttag tagtggttgc atgaaacctt  900
tcgcgcatca gttactatgt gtcactctaa aaatggggca gcatgtacgc agtgcctata  960
tttatacaag gcatctatcg ttgcctcctc agttcatcac taatcacact tattgttccc  1020
tcgacgagta tctagctagc tcattaatcg atcaatcggg gtgtgcggtc gaaggcggca  1080
atggcgagct actcgtcgcg gcgtccatgc aatacctgta gcacgaaggc gatggccggg  1140
agcgtggtcg gcgagcccgt cgtgctgggg cagagggtga cggtgctgac ggtggacggc  1200
ggcggcgtcc ggggtctcat cccgggaacc atcctcgcct tcctcgaggc caggctgcag  1260
gagctggacg gaccggaggc gaggctggcg gactacttcg actacatcgc cggaaccagc  1320
accggcggtc tcatcaccgc catgctcacc gcgcccggca aggacaagcg gcctctctac  1380
gctgccaagg acatcaacca cttttacatg gagaactgcc cgcgcatctt ccctcagaag  1440
tgagtccgat gctgccgcca ttgttcttgc atccatgcat ccagcatcgt acgtcctcta  1500
tacatctgcg gatgatcatt tgcgcatgtt tgtggcatgc atgcatgtga tgtgagcagg  1560
agcaggcttg cggccgccat gtccgcgctg aggaagccaa agtacaacgg caagtgcatg  1620
cgcagcctga ttaggagcat cctcggcgag acgagggtaa gcgagacgct gaccaacgtc  1680
atcatccctg ccttcgacat caggctgctg cagcctatca tcttctctac ctacgacgta  1740
cgtacgtcgt cacgaatgat tcatctgtac gtcgtcgcat gcgaatggct gcctacgtac  1800
gccgtgcgct aacatactca gctctttcct atctgctgcg ccaatttgca ggccaagagc  1860
acgcctctga agaacgctct gctctcggac gtgtgcattg gcacgtccgc cgcgccgacc  1920
tacctcccgg cgcactactt ccagactgaa gacgccaacg gcaaggagcg cgaatacaac  1980
ctcatcgacg gcggtgtggc ggccaacaac ccggtaactg actagctaac tggaaaacgg  2040
```

-continued

```
acgcacagac tccatgtcca tggcggccca caaggtcgat gctaattgtt gcttatgtat  2100
gtcgcccgat tgcacatgcg tagacgatgg ttgcgatgac gcagatcacc aaaaagatgc  2160
ttgccagcaa ggacaaggcc gaggagctgt acccagtgaa gccgtcgaac tgccgcaggt  2220
tcctggtgct gtccatcggg acggggtcga cgtccgagca gggcctctac acggcgcggc  2280
agtgctcccg gtggggtatc tgccggtggc tccgcaacaa cggcatggcc cccatcatcg  2340
acatcttcat ggcggccagc tcggacctgg tggacatcca cgtcgccgcg atgttccagt  2400
cgctccacag cgacggcgac tacctgcgca tccaggacaa ctcgctccgt ggcgccgcgg  2460
ccaccgtgga cgcggcgacg ccggagaaca tgcggacgct cgtcgggatc ggggagcgga  2520
tgctggcaca gagggtgtcc agggtcaacg tggagacagg gaggtacgaa ccggtgactg  2580
gcgaaggaag caatgccgat gccctcggtg ggctcgctag gcagctctcc gaggagagga  2640
gaacaaggct cgcgcgccgc gtgtctgcca tcaacccaag aggctctaga tgtgcgtcgt  2700
acgatatcta agacaagtgg ctttactgtc agtcacatgc ttgtaaataa gtagacttta  2760
ttttaataaa acataaaaat atatatatgt tcttgaatat aaaattgata accaaaattc  2820
gaaccatcac ttatacataa ttttacttta tttttttataa aacgtgaacg ggaaggacta  2880
ccatgaatga ctatagaacc aatcatacta gtataaaata tatgatgaca ctacgagaga  2940
gacaaacttt gtctggcgct aaatattttg ccgagtgtga attcacgggc actaggcaaa  3000
gatcttcttt gccgagtgtt acgctgggca aagtaagaca ctaggtaaat cagtcatttg  3060
ccgagtgtcc gccactaggc aaagcaaaac actggcaaat caaaagttta cctagtgcca  3120
gacactaggc aaaaaaaaac gctcggcaaa tcggaagttt ccctagtgcc agacactaga  3180
caaagaaaaa cacttgataa actagcgtcg tcagctaaca ccatccacca accgttaacg  3240
ttgccgagta tctgacttcg acactcggca aagaaggtct ctttgcctag tgtcggtctg  3300
gaacactagg caaagaggca ctttacctag tgtcgtattt tgacactcag taaaataatt  3360
tttttctttt ctgcttccaa actttttatg atgtgttcct atagcaccta gaactacatg  3420
tcaagttttg gtaaaatttt tgaagttttt gctatattta cttaatttat tttatttaat  3480
tgaatttctt ttgataattc aaatttgaac tcggcaaggt aagaagcgag ggtagcctgg  3540
aaacacactt tgcctagtgt tacactcggt acaggagcct cccctgccta gtgctgcact  3600
cgacaaaaga ttcgcctttg cctagcgctg cactcggcac aggagtcgcc tttgcctagt  3660
gctgcactag gcaaagcctc cgttaccgtg ccttccatcg tcatggaaac ttttcttcgc  3720
cgagtgacgt gtggcactag gcaaagtttt tgccgagtgc ccgagaaatg gcactcggca  3780
aggactcttt gtcgatccct tcgttgccga cttctttttg ccgagtgcaa cactaggcaa  3840
accatttgcc gagtgtaaaa gaggctttgc ctagtgtctg tggcactagg caaagaagac  3900
gagtcctgta gtgaacctag taggccagtg cgggaccatt ccaaaaaaata cctataaaaa  3960
taaatttaat attaaattaa acatatggtc cacgtaccaa gatattaaac tcaaaagaac  4020
aattattaca atttatctta gctaaaaggc cgagaaaagt atatgttaaa aaggagtgtg  4080
atcccatttt tatagctcgc tcggtcgatc gcccgtccac ttttaggtaa cgaggtggta  4140
ccatgtagga gtgttgcgtt gcgtgcgact tcctatcatg ttgggcttag gtggcttctc  4200
acgacccaat gataggcgag aagtgtggaa gatgaacaaa cctacttgtt tcgtgcacga  4260
cgcatgtgtt tgaacaacga gttagattag aaaaaaaaata taatgacttt tttttgcaa  4320
aagtgaggat aatgaaaacc agaaaaactg gtgcttcata agagtagaga tttgatggta  4380
aatatagtag taatgcaatg gctatactac acgcgagagt ccaatggcaa gccggtgtgt  4440
tggggcgaag gcgaagacgc tacccttcgc tccaggcctt tgtcaactcg ctgcaccaac  4500
agaggcaaga tgaccggcgc ggcccaccct tcgtcctctt cactgcaaga cgaaggccta  4560
cgac                                                              4564

SEQ ID NO: 35          moltype = DNA  length = 2089
FEATURE                Location/Qualifiers
source                 1..2089
                       mol_type = genomic DNA
                       organism = Zea mays
SEQUENCE: 35
caccggcggt ctcatcaccg ccatgctcac cgcgcccggc aaggacaagc ggcctctcta  60
cgctgccaag gacatcaact acttttacat ggagaactgc ccgcgcatct tccctcagaa  120
gtgagtccga tgctgccgcc attgttctcg catccatcca gcatcgtacg tcctctatac  180
atctgcggat gatcatttgc gcatgtttgt ggcatgcatg tgagcaggag caggcttgcg  240
gccgccatgt ccgcgctgag gaagccaaag tacaacggca agtgcatgcg cagcctgatt  300
aggagcatcc tcggcgagac gagggtaagc gagacgctga ccaacgtcat catccctgcc  360
ttcgacatca ggctgctgca gcctatcatc ttctctacct acgacgtacg tacgtcgtca  420
cgaatgattc atctgtacgt cgtcgcatgc gaatggctgc ctacgccgtg cgctaacata  480
ctcagctctt tccgatctgc tgcgccaatt tgcaggccaa gagcacgcct ctgaagaacg  540
cgctgctctc ggacgtgtgc attggcacgt ccgccgcgcc gacctacctc ccggcgcact  600
acttccagac tgaagacgcc aacggcaagg agcgcgaata caacctcatc gacggcggtg  660
tggcggccaa caacccggta actgactagc taactgcaaa acgaacgcac agactccatg  720
tccatggcgg cccacaaggt cgatgctaat tgttgcttat gtatgtcgcc cgattgcaca  780
tgcgtagacg atggttgcga tgacgcagat caccaaaaag atgcttgcca gcaaggacaa  840
ggccgaggag ctgtacccag tgaacccgtc gaactgccgc aggttcctgg tgctgtccat  900
cgggacgggg tcgacgtccg agcagggcct ctacacggcg cggcagtgct cccggtgggg  960
catctgccgg tggctccgca acaacggcat ggcccccatc atcgacatct tcatggcggc  1020
cagctcggac ctggtggaca tccacgtcgc cgcgatgttc cagtcgctcc acagcgacgg  1080
cgactaccta cgcatccagg acaactcgct ccgtggcgcc gcggcaaccg tggacgcggc  1140
gacgccggag aacatgcgga cgctcgtcgg gatcggggag cggatgctgg cacagcgggt  1200
gtccagggtc aacgtggaga cagggagcga ggtacgaacc ggtgaccgga gaaggaagca  1260
atgccgatgc cctcggtggg ctcgctaggc agctctccga ggagaggaga acaaggctcg  1320
cgcgccgcgt ctctgccatc aaccccagaa gctctagatg tgcgccctac gatatctaag  1380
acaagtggct ttactgtcaa tcacatgctt gtaaataagt agactttatt ttaataaaat  1440
ataaatatat atatattctg ataaccaaga ttcgaaccct cacttataca caattttatc  1500
ttattttttta taaaatgaga atggaaagga ctaccgtgaa cgactataga accaatcata  1560
ctagtttaaa atgctcgtaa gctatgacga acctagtagg ccggtgctgg accattccaa  1620
aaaacctata aaaataaatt taatattaaa ttaaacatat ggtctatata tcagatatta  1680
aactcaaaag aataattatt ataatttatc ttagctaaaa ggttgagaaa ggtatgcgtt  1740
```

-continued

```
aaaaaagagt tttaacccat ttttatagct tatttgatcg cccgtccact tttagggagc  1800
gaggtggtac tatgcagaag tgttgcgctg tgtgcgactt actatcatgt tgggtttagg  1860
tggattctca cgacccaatg atagacgaga agtgtgggag atgaacaaac ctacgcattt  1920
cgcgtacgac acatgtgttt gaacaacgag ttagattgga aaaaatataa tgaccttttt  1980
tgcaaaaatg actacaatga aaaccaggaa aaccggtgct tcataggagt agagatttga  2040
cggtaaattg ttacgatcta ctggtatttg ctgcgaggat gtattcgct             2089

SEQ ID NO: 36          moltype = DNA  length = 3557
FEATURE                Location/Qualifiers
source                 1..3557
                       mol_type = genomic DNA
                       organism = Zea mays
SEQUENCE: 36
tgacgtttgg taaaacgact tcttccgaaa aacacccaaa aacccaagat attttatact  60
acgaaggaaa ggtcacacat cctagttagc ttcactggtt ctagctcctt ccaattttgc  120
aaaaaagtca caaaggataa gccatttttt caaatgattt gtgaaatgcc tacgctaaaa  180
agtctacttt tccaaaaaaa ctagagctag agccgttttt ggcaagtcag aaccctacca  240
aatagtccct cagtttaagc aaagtgaggc tatactgaag ctaaattatg ccaaattggg  300
cctacatctc catattttca accaaatgct ttagggtttc ttgtaatcga catgatttgt  360
ttcttcataa atagtatatg gaccgctcca aaatactcca tccgtttcaa tttatattac  420
gtttgatctt tttaccctaa atttgatcga ctcgtcttat taaaaaagtt cataactatt  480
aataatcttt actgtgatat catttagcat ataatatact ttaagtgtag ctttgatttt  540
ttttttgcaa aaattaaatg aaacgaccca atcaaacttg ataaaaaagt aaaactaatt  600
ataaatttgg acataaggag taggagggtg tttgaataca ctagagttaa tagttagttg  660
tcttaaaatt tgctagtaca attagctagc taacaaatat ttaggtaact attagctaat  720
ttgctaaaaa cagctaatag ttgaactatt agttgaacta ttagctagac tgtttggatg  780
tattcaacta attttagcag ctaactatta gttatagtat aatattcaaa cacctcctaa  840
ttaaaatgga caaatatcta ttcccttggt cccttgcgtt agattttcca tatatcctca  900
tttagtataa aaagaatcat caaaaagtgg acaaccccta gtggaacacc attttagtag  960
tggttgcatg aaacctttcg cgcatcagtt actatgtgtc actctaaaaa tggggcagca  1020
tgtacgcagt gcctatattt atacaaggca tctatcgttg cctcctcagt tcatcactaa  1080
tcacacttat tgtgccctcg acgagtatct agctagctca ttaatcgatc aatcggggtg  1140
tgcggtcgaa ggcggcaatg gcgagctact cgtcgcggcg tccatgcaat acctgtagca  1200
cgaaggcgat ggccgggagc gtggtcggcg agcccgtcgt gctggggcag agggtgacgg  1260
tgctgacggt ggacggcggc ggcgtccggg gtctcatccc gggaaccatc ctcgccttcc  1320
tggaggccag gctgcaggag ctggacggac cggaggcgag gctggcggac tacttcgact  1380
acatcgccgg aaccagcacc ggcggtctca tcaccgccat gctcaccgcg cccggcaagg  1440
acaagcggcc tctctacgct gccaaggaca tcaactactt ttacatggag aactgcccgc  1500
gcatcttccc tcagaagtga gtccgatgct gccgccattg ttctcgcatc catccagcat  1560
cgtacgtcct ctatacatct gcggatgatc atttgcgcat gtttgtggca tgcatgtgag  1620
caggagcagg cttgcggccg ccatgtccgc gctgaggaag ccaaagtaca acggcaagtg  1680
catgcgcagc ctgattagga gcatcctcgg cgagacgagg gtaagcgaga cgctgaccaa  1740
cgtcatcatc cctgccttcg acatcaggct gctgcagcct atcatcttct ctacctacga  1800
cgtacgtacg tcgtcacgaa tgattcatct gtacgtcgtc gcatgcgaat ggctgcctac  1860
gccgtgcgct aacatactca gctctttccg atctgctgcg ccaatttgca ggccaagagc  1920
acgcctctga agaacgcgct gctctcggac gtgtgcattg gcacgtccgc cgcgccgacc  1980
tacctcccgg cgcactactt ccagactgaa gacgccaacg gcaaggagcg cgaatacaac  2040
ctcatcgacg gcggtgtggc ggccaacaac ccggtaactg actagctaac tgcaaaacga  2100
acgcacagac tccatgtcca tggcggccca caaggtcgat gctaattgtt gcttatgtat  2160
gtcgcccgat tgcacatgcg tagacgatgg ttgcgatgac gcagatcacc aaaaagatgc  2220
ttgccagcaa ggacaaggcc gaggagctgt acccagtgaa cccgtcgaac tgccgcaggt  2280
tcctggtgct gtccatcggg acggggtcga cgtccgagca gggcctctac acggcgcggc  2340
agtgctcccg gtggggcatc tgccggtggc tccgcaacaa cggcatggcc cccatcatcg  2400
acatcttcat ggcggccagc tcggacctgg tggacatcca cgtcgccgcg atgttccagt  2460
cgctccacag cgacggcgac tacctacgca tccaggacaa ctcgctccgt ggcgccgcgg  2520
caaccgtgga cgcggcgacg ccggagaaca tgcggacgct cgtcgggatc ggggagcgga  2580
tgctggcaca gcgggtgtcc agggtcaacg tggagacagg gagcgaggta cgaaccggtg  2640
accggagaag gaagcaatgc cgatgccctc ggtgggctcg ctaggcagct ctccgaggag  2700
aggagaacaa ggctcgcgcg ccgcgtctct gccatcaacc ccagaagctc tagatgtgcg  2760
ccctacgata tctaagacaa gtggctttac tgtcaatcac atgcttgtaa ataagtagac  2820
tttattttaa taaaatataa atatatatat attctgataa ccaagattcg aaccctcact  2880
tatacacaat tttatcttat tttttataaa atgagaatgg aaaggactac cgtgaacgac  2940
tatagaacca atcatactag tttaaaatgc tcgtaagcta tgacgaacct agtaggccgg  3000
tgctggacca ttccaaaaaa cctataaaaa taaatttaat attaaattaa acatatggtc  3060
tatatatcag atattaaact caaaagaata attattataa tttatcttag ctaaaaggtt  3120
gagaaaggta tgcgttaaaa aagagtttta acccattttt atagcttatt tgatcgcccg  3180
tccactttta gggagcgagg tggtactatg cagaagtgtt gcgctgtgtg cgacttacta  3240
tcatgttggg tttaggtgga ttctcacgac ccaatgatag acgagaagtg tgggagatga  3300
acaaacctac gcatttcgcg tacgacacat gtgtttgaac aacgagttag attggaaaaa  3360
atataatgac ctttttttgca aaaatgacta caatgaaaac caggaaaacc ggtgcttcat  3420
aggagtagag atttgacggt aaattgttac gatctactgg tatttgctgc gaggatgtat  3480
tcgcttggtg aaaacagaat tacagagtag cagtagcagg gaagacagta gcgagaggag  3540
aagaagaaac ttgagga                                                3557

SEQ ID NO: 37          moltype = DNA  length = 1382
FEATURE                Location/Qualifiers
source                 1..1382
                       mol_type = genomic DNA
                       organism = Zea mays
```

```
SEQUENCE: 37
agttcatcac taatcacact tattgtgccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacta cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gcgctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaacccgt cgaactgccg caggttcctg gtgctgtcca tcgggacggg gtcgacgtcc  840
gagcagggcc tctacacggc gcggcagtgc tcccggtggg gcatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct acgcatccag  1020
gacaactcgc tccgtggcgc cgcggcaacc gtggacgcgg cgacgccgga gaacatgcgg  1080
acgctcgtcg ggatcgggga gcggatgctg gcacagcggg tgtccagggt caacgtggag  1140
acagggagcg aggtacgaac cggtgaccgg agaaggaagc aatgccgatg ccctcggtgg  1200
gctcgctagg cagctctccg aggagaggag aacaaggctc gcgcgccgcg tctctgccat  1260
caaccccaga agctctagat gtgcgcccta cgatatctaa gacaagtggc tttactgtca  1320
atcacatgct tgtaaataag tagactttat tttaataaaa tataaatata tatatattct  1380
ga                                                                 1382

SEQ ID NO: 38          moltype = DNA  length = 10843
FEATURE                Location/Qualifiers
source                 1..10843
                       mol_type = genomic DNA
                       organism = Zea mays
SEQUENCE: 38
cgcacacact gtctttctct gcctttcttt ccctagcgcc gcgccggcgc cgccattcga  60
tcaggccgct tcgccggcga cagcatattc caggtatgcc gtcccttctg ctccttctgc  120
gagaattcaa acaccccgaa ctccccaaat ctagtatttg tattcggatc tgaccatttt  180
tcactgggcc cgcccctgat tcgcaggtcg gttggttttg gcacttcgga ccggcggcca  240
tggcttccga cggcatcggc cccagaggta taactgtttc atctcttctt tgtgttcaaa  300
cagacagacg tcaaaccgcc gagaggaggt acaaatatag atttgggct atgagcacgc  360
cattgcgctt ccagcgatct gacatattgg gaattcttgt tttttttttg ggtaccttgc  420
aaggccgaaa tttgacgctt ttctgtttaa ttctagtgcc tgtctgcatc cattagggca  480
tcctagctgc tccatgctcg tgatctcgtc cgtttgcttg attgaatcca ttgttttcca  540
aagttcattg ctactgcgaa atacgtttat atgattacca caatttgtgt ttttgccttt  600
tcgggttgca cagagggtac tgccatcatt gttgttttag cgccatttgg aacaagtgat  660
tcactggtac tagtacagta tgtgcttttc atgtgtgttt ggtttgtacc atcagatgga  720
attttgagcg cggtttacaa attagtacta tagatatact gtgaggtgca cactagatgg  780
ttctgctttg ttctacagtc agtaactttt tcttccttgc tcacagatgt atgtgttgtt  840
ggggttgcac gcaccccaat gggcggtttc cttggtgcct tgtctccctt gcctgctacg  900
aaacttggct ctatagtaat tcaaggtgag atccgaatct tctctgcatt tacatccgag  960
ctctgaacat ggtcatggct gggggctgtt agctgctctg gaaagagcaa acgtggatcc  1020
agccctcgtg caggaggtct actttggaaa cgtcttgagt gctaatttgg ggcaagctcc  1080
tgcaaggcaa gctgctctgg gtgccgggat accaaactct gttgtttgca ccactgttaa  1140
caaagtctgt gcatctggca tgaaaggttt gaatcgaatt tatctgtctg tccttgtgta  1200
ctctgctcag agttcacaga agtgagagat tacctgacca tgctcttgtt ttcctttcct  1260
atatgcagct actatgtttg cagcacagtc aattcaattg ggtatcaatg atattgttgt  1320
ggctggtggc atggaaagca tgtccaatgc cccaaagtac attgctgaag ctaggtatgc  1380
aattattact tggtggatat attcaatatc gagctgcata aaccaaatga tagtcttaag  1440
ttatttggta gatacatgca tgcttactta tcttcattgc attttctaaa tttgtttgta  1500
agaaatgttg attcaccagc agcgaggcta ttaacgaagt ggccagtttt gttgtgaaag  1560
tatattctgt tcatgtttaa agtgcatttc aactgcttat aagcttgcta attacaattg  1620
caggaagggg tctcgtttg gtcatgacac acttgttgat gccatgctta aggatgggct  1680
ttgggatgta tacaatgatt gtgccatggg aatgtgtgcc gagctttgtg ctgacaacca  1740
tgccctcaca agagaagacc aggtctctta atacagatag cagtaaatgc tgtttgttat  1800
aatattccca tatttttcaa gatataagtt gtgctataca acatgtcaat gctggcaatt  1860
cttttgagac tgccctggaa tcttcgtgct ttatcttggt catcatcata aatggtctag  1920
agactctaga ccagcatctg cattccttgt ctgatgaact agtaacttgg atcctttcta  1980
gcaatgattt tctgttatgt tgtgacatga ttgatagggt gggcttttat gcatgctctg  2040
ggtctgtgaa ctgaccattc atctgcttcc agagatgaaa gtagatgtgc cacacaaaaa  2100
tgagcactct tttgtattcc tgttagagct atacaagtat aatctcttaa aagctgctca  2160
tcagtacatg acactagtac cttgatgatt ttactgtatc tgtttatgta atttttttct  2220
taataaattt gatatagtat aattaaaatt gagttgcctt ttaattttca cttatatgtt  2280
gcaatttatt tttgtctata ttgcaataaa tatatttcca atttctggta tatttaattt  2340
tacttattct tgaataggat gcatttgcta tccaaagcaa cgagcgtgga attgctgctc  2400
gtgacagtgg tgcttttgca tgggagatta ttccggtaat ttctccctc attgatgata  2460
ctagacatgc ttttcttggt tttctgatgg tcagtgttgt cacccaggtt caagttcctg  2520
ttggtagagg aaaacccccca acattaattg agagagatga aagcctggat aaggtatttt  2580
ttctgacgtg acaaaatatt tttaacaaaa taaagcttgt agttgatcaa aggcaaaaag  2640
actggcaggc actttgattt attgttcttg cttcctccaa atgcaacgtt ccttgcataa  2700
tgagctttgc tagcagttat ttgtaagatc aatgcatgac agttttattt atgtcttgtg  2760
ctattccttt tgtgtcttag tttgacccag taaaactaaa gaaacttcgc ccaagtttca  2820
```

-continued

```
aggagaatgg tggtacagtt acagctggaa atgcttctag tataaggtag ctgcttgaaa  2880
tatttctgag gccttttgtc ctacaaagtc tttctgagac cttgtttttc ggccatatgt  2940
tgtttagctg acagatatga aggacaacct atttcattgt tgacagttaa attatattat  3000
tgtattatgc atgcattttt aactgatata ttatgcttgc attttgtcaa cttcattgtt  3060
tctctatttg tttttagact gcttgggtat gctctactcc gttaaataga tggtaatttt  3120
ttctttagat ttggtaccca attggtgtga atgatttatc acaatatcac ataagaaagt  3180
aaaaacattt taaatgcctt attatgccca ttcaaacaac aaaagttgcc ctacctttta  3240
aatttcttca tggttgccct agaccttgtt tgtctcactt tgtactgtgt ctatttttag  3300
ctgacaagta ctgtccggtg tactgcctac tatggcttgt gtagccttct gcaaccagtc  3360
atctaatttg ttttatatgg atcagtgatg gagctgctgc attagtttta gtgagtgggc  3420
agaaggctca agagcttggc cttcaagtcc ttgcaaggat caaaggttat gctgatgcag  3480
ctcaagtaag ccacagaaac aattgttagc tctcctaaga gtagaatgcg cttattctaa  3540
tttacactgt gatctaaata ttttaggata taggaagtta tttttatctg gaacgatttt  3600
atgttactat tttagatatc gaaatttatc aactattgga acttgtgatc tggaatatta  3660
ttttgtaatg tggatgctgt ttatacaggc tccggagctt tttacaacca ctccagcact  3720
tgcaatacca aaggctatcg caaatgctgg attagagtca tcccgtgttg atttctatga  3780
gattaatgaa gccttttcgg tatgcattga gtttctttta ctcacatttt ttgtaagcct  3840
tttgttatgc attgagagtt tattttactt attacttttt ttgtaataat gtctttttta  3900
cttgtcaata taggctgttg cgcttgcaaa tcaaaaactt cttggaattc cttcagtaag  3960
tgtcacctgt attaaactgc cattctttgt ggattttaga agttaaacaa tcactttcag  4020
aaagtacata ttgtctcttt tttgttattt gctatgcagc agcaacgtgt aattgcatta  4080
taacagtatt atctgtacta acagcatatg tgtttgcagg aaaagattaa tgttcatgga  4140
ggagctgtat ccttaggaca tcctctcggg tgcagtggtg ctcgcatttt ggttaccctt  4200
attggtgtaa gttctatctt aagatgcttg ttttaccttt tgagttacaa tccctttttgt  4260
ttaaaaaaaa tgtgcaatgt ttttctagta aaaaaataga tggtctttga gtaaataatg  4320
aattctgaca tatgttacca tatcatcata gggttcgtga tgaacagtaa gcatcttcac  4380
tattgctact aggtctactt cctctatccc aaattataag acgtcttggg atgttggcat  4440
tgttagattt atagctttta ctacgtgtac tgagacataa tgtttatcgc aataaaaact  4500
acaaatctag aaaaagtaaa aacatcttat aatttgaaac atagggagta tgttggatca  4560
agccacccca tccctgcacc aaacactacc ttaggccatg ttcggttaca agtggttcga  4620
gggggattga aggggattaa atccccttct agttaaaatt gaataggagg ggatttaatc  4680
cccctcaatc ccctccaatc ctctcgcaac cgaacaagcc cttagtgatt tccaatgtgc  4740
aaattatctg caaatagaat cttgtataaa gctgcaaatg tagagtttca cattgatatc  4800
ggctcatccc ttgtttcact tgttgctggt gatcaatagt ttctttttct cttcattttc  4860
tttaagcaaa acgttgggca caatatagtg ccatcatgtt gggacatcaa aatatattgt  4920
gcttgaccct cctaatcatt gtttcttgtt aacaggttct cagggcgaag agtggcaaga  4980
tcggagttgc tggtgtctgc aacggtggag gcggagcatc agctcttgtt ctggagctcg  5040
cataagaaat ctagaccttg taagactcaa aacaccgaat atatctcaac tcaaattgat  5100
tcttttacta gctggcagta ggagctaacc agtataaggt gctattatca aactgtaata  5160
tggtcgcata ttcagctagg cctaattaag ttgtattttt tcctttttaca actgttgtgc  5220
aatttgacta actgctgcac cttgatattg caggtagtta gcaaaagctc cctgaggtga  5280
tcttgtagtc ttattttccg ttgtagtagt cccatagaac atttcttaat ttaatttggc  5340
aataaagcaa aagctccctg aggagatatt gcttctgttg gttgcatagt agagtatcat  5400
gtaataagag ctacagaaat atttttgata tatttgtgag gatactacag aaatatttta  5460
tatatttgtg atgtgtcttg tacatttatc taggtcacat caactatcct gccgcccggg  5520
atctggaact ccgacagccc gatttcaaat agtttgaaag aacatcagca aacacccaag  5580
gcaaatacaa agatcagaga agctggaggg ttagttacag gagcatcagg ttaccgagaa  5640
tgcaaccatg cacggcaaaa ggcgcctacc ccgcatcaaa atttctgcca gaaacaaaca  5700
agaaacgaaa gaatcacacg cacactatct acatccagaa acgtgatgtt atactagata  5760
gtcagcggca ttcaggaagc cctcgtactg ggtaccgttg agggcgctgt agacctcgtc  5820
ccagttctcg atctgctccg acagcggctt cgtgtgtatc ttcacgtgcc ggctcaccag  5880
cttcctcctc ggcactccga ggaaatccag gacatccaag agcttctgca gtgcagcagc  5940
gatggtaagc gacacaacca acggaaggga acagacaagg gaagggcatc agcgagaacg  6000
cactgttctg ttgcggacga cgtcctcgta gtagacgctc atgtgccggg tgttgtttag  6060
gttctcaaga gcgtcgcgag tgtactcgtc agctcgtttc agctgccata tcagtgacgt  6120
cgtgttgagc ctgggcctgt atcttgccag tatatgggcc tgtggagcga gaacgaacga  6180
cacgtcaaac acagagagag atcagatcag ctcagagact tgctgccata tccgtttctt  6240
agctagcatt actaacctca cgcttcgtgt ggacatgggc cttgtgcgtt ccgtttagtt  6300
gcttaagtaa cctgtcgtgg ttgttcgcta cctgtgatac caactggcgg agcaggttcc  6360
ttctgaaaag aaatatcgca gagactcctc ttcggttgaa gtagtcgact acgtccgcat  6420
ggtttgccac gaggccctga aaacatacac cccaaccccg ttcagaagaa atgctccttt  6480
gtttccactc tctagctaca atgcctgttt tgtttccagt ctctaaacct atgtttggcc  6540
aatattcatg gtttggttag gcaatctgtc taccaggaaa aaagttcgtt ctcgcacaaa  6600
ttagatgaag ccctgaaaca aacatgcttg acatgtagat tataatcagt ctactggaca  6660
cactacagaa tctatcaaat attactccat atgcatttgc agttctcatg catgttcgag  6720
agagagaaaa tttgtctaaa atgcaggatc tgacagcaag tcagaaaact aaactagcta  6780
ccgacagttc cataaggcct tgttcggtta ttcgcatccc acatggattg gaagagattg  6840
gaaaatttta agaaggattt tgacttctta tggatttaaa ctcatccaat ctcgtccaat  6900
ccacatggat tggcactaaa acgagcaagc cctaaagtgg attcccaaaa aaaaatagtt  6960
acatggactt gaggaaagtt tggcgcaata tgcaataaca tttagcatct acagttgaga  7020
acatgtaggc cgtttaggag actacacata ctaataattg aaacatactg gaactaaatg  7080
gaaaaataaa tgaaaaagga tcatccaaat aaattatcta tactgcatgt tttagtccgc  7140
acctgattta gcatccactt gaagccaata gctgcagtgc actcattctt ggaagcgcta  7200
ctgttccagt ccaaattgta cactttatcc agggtatcta ttatagagga aatgttactc  7260
ctcctttctt ttctagagaa aatttcacca ttggagctaa cattcatgtg gctgttaaga  7320
agtgtttcaa accagccact tccagatcgc tgcgatgata taattgcaaa ggaccggaca  7380
gcattgcact tgcattcctc cctagaaata aaaaattatg cattaggcat taaacaaacg  7440
agattgctca atcttaccac agtgcagatc tcacctgctg taaatatagg aagttatttt  7500
tatctggaac gattttatgt tactatttta gatatcgaaa tttatcaact attggaactt  7560
```

-continued

```
gtgatctgga atattatttt gtaatgtgga tgctgtttat acaggctccg gagcttttta  7620
caaccactcc agcacttgca ataccaaagg ctatcgcaaa tgctggatta gagtcatccc  7680
gtgttgattt ctatgagatt aatgaagcct tttcggtatg cattgagttt cttttactca  7740
catttttgt aagcctttg ttatgcattg agagtttatt ttacttatta ctttttttgt  7800
aataatgtct tttttacttg tcaatatagg ctgttgcgct tgcaaatcaa aaacttcttg  7860
gaattccttc agtaagtgtc acctgtatta aactgccatt ctttgtggat tttagaagtt  7920
aaacaatcac tttcagaaag tacatattgt ctctttttttg ttatttgcta tgcagcagca  7980
acgtgtaatt gcattataac agtattatct gtactaacag catatgtgtt tgcaggaaaa  8040
gattaatgtt catggaggag ctgtatcctt aggacatcct ctcgggtgca gtggtgctcg  8100
cattttggtt acccttattg gtgtaagttc tatcttaaga tgcttgtttt accttttgag  8160
ttacaatccc ttttgtttaa aaaaaatgtg caatgttttt ctagtaaaaa aatagatggt  8220
ctttgagtaa ataatgaatt ctgacatatg ttaccatatc atcatagggt tcgtgatgaa  8280
cagtaagcat cttcactatt gctactaggt ctacttcctc tatcccaaat tataagacgt  8340
cttgggatgt tggcattgtt agatttatag cttttactac gtgtactgag acataatgtt  8400
tatcgcaata aaaactacaa atctagaaaa agtaaaaaca tcttataatt tgaaacatag  8460
ggagtatgtt ggatcaagcc accccatccc tgcaccaaac actaccttag gccatgttcg  8520
gttacaagtg gttcgagggg gattgaaggg gattaaatcc ccttctagtt aaaattgaat  8580
aggaggggat ttaatccccc tcaatcccct ccaatcctct cgcaaccgaa caagccctta  8640
gtgatttcca atgtgcaaat tatctgcaaa tagaatcttg tataaagctg caaatgtaga  8700
gtttcacatt gatatcggct catcccttgt ttcacttgtt gctggtgatc aatagtttct  8760
ttttctcttc attttcttta agcaaaacgt tgggcacaat atagtgccat catgttggga  8820
catcaaaata tattgtgctt gaccctccta atcattgttt cttgttaaca ggttctcagg  8880
gcgaagagtg gcaagatcgg agttgctggt gtctgcaacg gtggaggcgg agcatcagct  8940
cttgttctgg agctcgcata agaaatctag accttgtaag actcaaaaca ccgaatatat  9000
ctcaactcaa attgattctt ttactagctg gcagtaggag ctaaccagta taaggtgcta  9060
ttatcaaact gtaatatggt cgcatattca gctaggccta attaagttgt atttttcct  9120
tttacaactg ttgtgcaatt tgactaactg ctgcaccttg atattgcagg tagttagcaa  9180
aagctccctg aggtgatctt gtagtcttat tttccgttgt agtagtccca tagaacattt  9240
cttaatttaa tttggcaata aagcaaaagc tccctgagga gatattgctt ctgttggttg  9300
catagtagag tatcatgtaa taagagctac agaaatattt ttgatatatt tgtgaggata  9360
ctacagaaat attttatata tttgtgatgt gtcttgtaca tttatctagg tcacatcaac  9420
tatcctgccg cccgggatct ggaactccga cagcccgatt tcaaatagtt tgaaagaaca  9480
tcagcaaaca cccaaggcaa atacaaagat cagagaacgr mmgtgagcat caggttaccg  9540
agaatgcaac catgcacggc aaaaggcgcc taccccgcat caaaatttct gccagaaaca  9600
aacaagaaac gaaagaatca cacgcacact atctacatcc agaaacgtga tgttatacta  9660
gatagtcagc ggcattcagg aagccctcgt actgggtacc gttgagggcg ctgtagacct  9720
cgtcccagtt ctcgatctgc tccgacagcg gcttcgtgtg tatcttcacg tgccggctca  9780
ccagcttcct cctcggcact ccgaggaaat ccaggacatc caagagcttc tgcagtgcag  9840
cagcgatggt aagcgacaca accaacggaa gggaacagac aagggaaggg catcagcgag  9900
aacgcactgt tctgttgcgg acgacgtcct cgtagtagac gctcatgtgc cgggtgttgt  9960
ttaggttctc aagagcgtcg cgagtgtact cgtcagctcg tttcagctgc catatcagtg  10020
acgtcgtgtt gagcctgggc ctgtatcttg ccagtatatg ggcctgtgga gcgagaacga  10080
acgacacgtc aaacacagag agagatcaga tcagctcaga gacttgctgc catatccgtt  10140
tcttagctag cattactaac ctcacgcttc gtgtggacat gggccttgtg cgttccgttt  10200
agttgcttaa gtaacctgtc gtggttgttc gctacctgtg ataccaactg gcggagcagg  10260
ttccttctga aaagaaatat cgcagagact cctcttcggt tgaagtagtc gactacgtcc  10320
gcatggtttg ccacgaggcc ctgaaaacat acaccccaac cccgttcaga agaaatgctc  10380
ctttgtttcc actctctagc tacaatgcct gttttgtttc cagtctctaa acctatgttt  10440
ggccaatatt catggtttgg ttaggcaatc tgtctaccag gaaaaaagtt cgttctcgca  10500
caaattagat gaagccctga aacaaacatg cttgacatgt agattataat cagtctactg  10560
gacacactac agaatctatc aaatattact ccatatgcat ttgcagttct catgcatgtt  10620
cgagagagag aaaatttgtc taaaatgcag gatctgacag caagtcagaa aactaaacta  10680
gctaccgaca gttccataag gccttgttcg gttattcgca tcccacatgg attggaagag  10740
attggaaaat tttaagaagg attttgactt cttatggatt taaactcatc caatctcgtc  10800
caatccacat ggattggcac taaaacgagc aagccctaaa gtg                     10843
```

```
SEQ ID NO: 39          moltype = DNA  length = 1704
FEATURE                Location/Qualifiers
source                 1..1704
                       mol_type = genomic DNA
                       organism = Zea mays
SEQUENCE: 39
gtgttgcgtt ccctacttgc tcttttcttc ctccgcttca acctgtcccg agcgcccccc  60
gcgcacacac tgtctttctc tgcctttctt tccctagcgc cgcgccggcg ccgccattcg  120
atcaggccgc ttcgccggcg acagcatatt ccaggtcggt tggttttggc acttcggacc  180
ggcggccatg gcttccgacg gcatcggccc cagagatgta tgtgttgttg gggttgcacg  240
caccccaatg ggcggtttcc ttggtgcctt gtctcccttg cctgctacga aacttggctc  300
tatagtaatt caaggtgaga tccgaatctt ctctgcattt acatccgagc tctgaacatg  360
gtcatggctg ggggctgtta gctgctctgg aaagagcaaa cgtggatcca gccctcgtgc  420
aggaggtcta ctttggaaac gtcttgagtg ctaatttggg gcaagctcct gcaaggcaag  480
ctgctctggg tgccgggata ccaaactctg ttgtttgcac cactgttaac aaagtctgtg  540
catctggcat gaaagctact atgtttgcag cacagtcaat tcaattgggt atcaatgata  600
ttgttgtggc tggtggcatg gaaagcatgt ccaatgcccc aaagtacatt gctgaagcta  660
ggaaggggtc tcgttttggt catgacacac ttgttgatgc catgcttaag gatgggcttt  720
gggatgtata caatgattgt gccatgggaa tgtgtgccga gctttgtgct gacaaccatg  780
ccctcacaag agaagaccag gatgcatttg ctatccaaag caacgagcgt ggaattgctg  840
ctcgtgacag tggtgctttt gcatgggaga ttattccggt tcaagttcct gttggtagag  900
gaaaaccccc aacattaatt gagagagatg aaagcctgga taagtttgac ccagtaaaac  960
taaagaaact tcgcccaagt ttcaaggaga atggtggtac agttacagct ggaaatgctt  1020
```

-continued

```
ctagtataag tgatggagct gctgcattag ttttagtgag tgggcagaag gctcaagagc  1080
ttggccttca agtccttgca aggatcaaag gttatgctga tgcagctcaa gctccggagc  1140
tttttacaac cactccagca cttgcaatac caaaggctat cgcaaatgct ggattagagt  1200
catcccgtgt tgatttctat gagattaatg aagccttttc ggctgttgcg cttgcaaatc  1260
aaaaacttct tggaattcct tcagaaaaga ttaatgttca tggaggagct gtatccttag  1320
gacatcctct cgggtgcagt ggtgctcgca ttttggttac ccttattggt gttctcaggg  1380
cgaagagtgg caagatcgga gttgctggtg tctgcaacgg tggaggcgga gcatcagctc  1440
ttgttctgga gctcgcataa gaaatctaga ccttgtagtt agcaaaagct ccctgaggtg  1500
atcttgtagt cttattttcc gttgtagtag tcccatagaa catttcttaa tttaatttgg  1560
caataaagca aaagctccct gaggagatat tgcttctgtt ggttgcatag tagagtatca  1620
tgtaataaga gctacagaaa tatttttgat atatttgtga ggatactaca gaaatatttt  1680
atatatttgt gatgtgtctt gtac                                         1704
```

```
SEQ ID NO: 40          moltype = DNA  length = 1637
FEATURE                Location/Qualifiers
source                 1..1637
                       mol_type = genomic DNA
                       organism = Zea mays
SEQUENCE: 40
gtgttgcgtt ccctacttgc tcttttcttc ctccgcttca acctgtcccc agcgcccccc  60
gcgcacacac tgtctttctc tgcctttctt tccctagcgc cgcgccggcg ccgccattcg  120
atcaggccgc ttcgccggcg acagcatatt ccaggtcggt tggttttggc acttcggacc  180
ggcggccatg gcttccgacg gcatcggccc cagagatgta tgtgttgttg gggttgcacg  240
caccccaatg ggcggtttcc ttggtgcctt gtctcccttg cctgctacga aacttggctc  300
tatagtaatt caagctgctc tggaaagagc aaacgtggat ccagccctcg tgcaggaggt  360
ctactttgga aacgtcttga gtgctaattt ggggcaagct cctgcaaggc aagctgctct  420
gggtgccggg ataccaaact ctgttgtttg caccactgtt aacaaagtct gtgcatctgg  480
catgaaagct actatgtttg cagcacagtc aattcaattg ggtatcaatg atattgttgt  540
ggctggtggc atggaaagca tgtccaatgc ccccaaagtac attgctgaag ctaggaaggg  600
gtctcgtttt ggtcatgaca cacttgttga tgccatgctt aaggatgggc tttgggatgt  660
atacaatgat tgtgccatgg gaatgtgtgc cgagctttgt gctgacaacc atgccctcac  720
aagagaagac caggatgcat ttgctatcca aagcaacgag cgtggaattg ctgctcgtga  780
cagtggtgct tttgcatggg agattattcc ggttcaagtt cctgttggta gaggaaaacc  840
cccaacatta attgagagag atgaaagcct ggataagttt gacccagtaa aactaaagaa  900
acttcgccca agtttcaagg agaatggtgg tacagttaca gctggaaatg cttctagtat  960
aagtgatgga gctgctgcat tagttttagt gagtgggcag aaggctcaag agcttggcct  1020
tcaagtcctt gcaaggatca aaggttatgc tgatgcagct caagctccgg agctttttac  1080
aaccactcca gcacttgcaa taccaaaggc tatcgcaaat gctggattag agtcatcccg  1140
tgttgatttc tatgagatta atgaagcctt ttcggctgtt gcgcttgcaa atcaaaaact  1200
tcttggaatt ccttcagaaa agattaatgt tcatggagga gctgtatcct taggacatcc  1260
tctcgggtgc agtggtgctc gcattttggt taccctttatt ggtgttctca gggcgaagag  1320
tggcaagatc ggagttgctg gtgtctgcaa cggtggaggc ggagcatcag ctcttgttct  1380
ggagctcgca taagaaatct agaccttgta gttagcaaaa gctccctgag gtgatcttgt  1440
agtcttattt tccgttgtag tagtcccata gaacatttct taatttaatt tggcaataaa  1500
gcaaaagctc cctgaggaga tattgcttct gttggttgca tagtagagta tcatgtaata  1560
agagctacag aaatattttt gatatatttg tgaggatact acagaaatat tttatatatt  1620
tgtgatgtgt cttgtac                                                 1637
```

```
SEQ ID NO: 41          moltype = DNA  length = 1780
FEATURE                Location/Qualifiers
source                 1..1780
                       mol_type = genomic DNA
                       organism = Zea mays
SEQUENCE: 41
cagagcacca gctcaccgcc ccaccgattc aaaggcgctc ggatcctctg acgtcgacgt  60
tccctgccag ctcccggctg ccgccctcgc tccttccgcc atctgcgctg ctctgcggcg  120
ccagagccgg cgcccgcccg ctgccgccct cgacggaccg ggacacgggg ccccaccgtt  180
ctctttcctg cgctgcgctg cgcggcggct gtgctgctga tcagttaatg tgcctgtgag  240
gctgtgacag gcggcgtcga gcgagtccga ggcgggctaa ctaaacccgc cgtctctcga  300
ggcggcgccc gcggagggcc aggtggaggg ccgaggaagg tggaggcggt gaggcgatgg  360
ggggcgccaa ggcggaggac aagcccgccg ccgccaccgc tgaagacgat tggtgttacc  420
agtttggaaa caagaatgcg tttgactcga aggccccgaa aaaatcacca cttgcattga  480
gagtggttgt ctttgccatg actgtgttat gtgggatatc tatttggtca atgtgtatga  540
agcagctagg gagtgatggc tggtcaagaa tagtgaagat cgaagttgtg gaacaaccat  600
gtaataagtc tacagttcct ccttctgagg ttcaatttgc gcattaccct caaccgacaa  660
cttacagcag ggaggaatgc aagtgcaatg ctgtccggtt ctttgcgatt atatcatcac  720
agcgatctgg aagtggctgg tttgaaaccc ttcttaacag ccacatgaat gttagctcca  780
acggtgaaat ttctctaga aaagaaagga gaagtaacat ttcctctata atagataccc  840
tggataaagt gtacaatttg gactggaaca gtagcgcttc caagaatgag tgcactgcag  900
ctattggctt caagtggatg ctaaatcagg gcctcgtggc aaaccatgcg gacgtagtcg  960
actacttcaa ccgaagagga gtctctgcga tatttctttt cagaaggaac ctgctccgcc  1020
agttggtatc acaggtagcg aacaaccacg acaggttact taagcaacta aacggaacgc  1080
acaaggccca tgtccacacg aagcgtgagg cccatatact ggcaagatac aggcccaggc  1140
tcaacacgac gtcactgata tggcagctga aacgagctga cgagtacact cgcgacgctc  1200
ttgagaacct aaacaacacc cggcacatga gcgtctacta cgaggacgtc gtccgcaaca  1260
gaacaaagct cttggatgtc ctggatttcc tcggagtgcc gaggaggaag ctggtgagcc  1320
ggcacgtgaa gatacacacg aagccgctgt cggagcagat cgagaactgg gacgaggtct  1380
acagcgccct caacggtacc cagtacgagg gcttcctgaa tgccgctgac tatctagtat  1440
aacatcacgt ttctggatgt agatagtgtg cgtgtgattc tttcgtttct tgtttgtttc  1500
```

-continued

```
tggcagaaat tttgatgcgg ggtaggcgcc ttttgccgtg catggttgca ttctcggtaa  1560
cctgatgctc ctgtaactaa ccctccagct tctctgatct ttgtatttgc cttgggtgtt  1620
tgctgatgtt ctttcaaact atttgaaatc gggctgtcgg agttccagat cccgggcggc  1680
aggatagttg atgtgaccta gataaatgta caagacacat cacaaatata taaaatattt  1740
ctgtagtatc ctcaaaaaaa aaaaaaaaaa aaaaaaaaag                        1780

SEQ ID NO: 42          moltype = DNA  length = 11900
FEATURE                Location/Qualifiers
source                 1..11900
                       mol_type = genomic DNA
                       organism = Zea mays
SEQUENCE: 42
aacgccatgg agaaatcaca catgagacac caattactca aggagtttac ttaattatat  60
tttacttaaa ttgagtatag gattcatcgt actaccaagg ggatccaaaa ataaggttgg  120
tgtttgccaa agctcaagcc tctatattca aaagctattt tttgaaaatc aaaaatctct  180
ttaaaattct atggttgact atggttaggt ttgagaaacc tagagtgttt ttgttgaaaa  240
gcagctgagc ttttcagctg aactaaactt cagctgagtt gagcttcttc agctgcagtt  300
gagcttttca gctgagctaa acttcagctg tgtcgagctt tctcaactcc agttgaactt  360
caacttcaac tggggtccag tcaagttcaa ccggggtcca ggcaggttca accggggtcc  420
aaggcaagtt caaccggggt ccagagaggt tcaactgggg tccaggaaaa gttcaaccgg  480
ggtttagaga ggttcaacca gggatgggct gtacgcaacg cgtctaagaa ttgtacgtgt  540
gttctctcgt aaccagaagc agcctcacct cctttgtata tataaacgag cagagggagg  600
cgaacggata gtaacggtca ccatcagagc tatcattaca gccagccaga aacggacgcc  660
attagtgacg tccgttaata gctgacaagc attataactc gttcgttact atccataaca  720
taggaaacga ccaataacgt acaacagtaa tggacggtca tcactttagg caaaatgtgc  780
aaccgttagg aaggaatatt cggaccaagg tccgatctac cacggccacg gcccggcggc  840
gcgcgcgtgt ggcagtcctt catcattttc tcaacttctc actagatgca ccaaagatcc  900
gcctatttaa gttgattgaa ttgtcccttg tacttccggt atggtactaa agtactagta  960
caccgtagca ttaaagtggg cctttagcat tgactattat tgaatattaa tttgggttag  1020
gccctcatta attcaacagt agcttctagg cctaaccatc ccaccccca aactaagcat  1080
agatgaacta tgtttaggtt gctacaaaaa tattccaaaa aataattccc tccgtcctaa  1140
aatactaacc gttttagcat tttaatagat tcataaaaat atgtcagatc cacaagtcat  1200
acgaggcaac tgtctcgagc atgatggatg gagaaccaat atcccccttg taaaatgtct  1260
tcttcctcca cttccaatgc atgcaatcta tactcaatat cataatagaa aatccccttt  1320
ccacctcctt agctaagata agcctaagtc attgacaatg gcatgataat tgtactccgc  1380
cctgaaacat gcaataccac ctctacagaa tagaccaaaa actccactcg taggggaaat  1440
actgccccca cggtaagaag aagcttaatc ggagccctga tcgagaaagg tcacgaaaga  1500
tgtacccctc cccccatgca acatgagagt ccgcccccta taggccagat ctttactcgt  1560
gctttgagcc ctactagccc ttacacgagg atccgcccca taggtcagcc catctcatgt  1620
gcacacaact agggaaacta gtgagtgacc ttgttaacct cagcctaaaa ttcgctccca  1680
ccgggattca aacttaggac ctgaggagtg ctactcagac gacctaacca acttaactag  1740
ggacccttc acacagaata gtccaaggca ctctgaggtg gaactttcct catttgatg  1800
tactcatcga tggagtcagc aatgctacag tacgcaagca tgcttaggcc aattgtgcac  1860
ttctggtggg ggaggaaaca ctgcggttga atgcatcggt tcaaaaagtg aagtatggga  1920
agtgctcacc caatctctct aagatatgaa ggaagagact tctctagatg cggtaacttt  1980
gacaaaagta gagcagtggg tagacacaca ggtcgttgaa atggtcttgc attaaccggt  2040
cgtatgcaac tacatagtcg cagtcaatgt atctctgatg ttgccttggc cacctcatcg  2100
acctaggaga ctcggatcca agctctgacg cctgttgcat tatattttgt tgtaataact  2160
tgaataactc ttttcagtca tattgatgtc caagctgaac gaaaacatca caacaatgct  2220
tgatttgatt gaaacgagtg taagaggatt ataaggggtg gtagagaaat ttgaagtgtg  2280
ggttgtgtga atgagatcaa acactcctct atttatagac caagttctag tttttttatt  2340
tttgaaaaaa aatcaaaata aagcgaagca attagaacct gccacatggc aagaggcgat  2400
cgttatcgac atggccgcaa tagctgttca gtaccaacca gtcagtatcg accgacgcgg  2460
tcccaacacg gtcaatagta accctggcgg ccgatcagta gcctcgacaa ccacaagcga  2520
ggctattagt gctggcacca tgtcgggtga tactgaccat ttggttgtgc cacatgggtg  2580
ggcgggcagt agagccaagc gccggcactc gcctaacatg atctaaaaca atcgataaaa  2640
ctgacagatt ggttgcggtt catgactacc tagacctggt cgaccacaag tagaaaatga  2700
gtcgagccga gcttgactcg gctcgtccat ttcacgagct agagagttag gctcggctca  2760
gctcgaagtc ggctcgcgag ctacaccccg atatatatta tttcattata tagtaaatta  2820
ttaatatata aacataaaat ataaaaatat tattcaccat tatgaattat cttatattta  2880
tcatcaaagg ctaagaaata agccgactat ctataaatta tctaatatct atcattattc  2940
tacatattga ttaatttggt acaactagct cgctcgcaga cgctccgaac ttgatctgac  3000
tcgtgagcct caagtttttt ttctagcctt aaccacatgc ccgcgaggat gattgttcga  3060
ggtgattagc aaacgcaaac gatatcaatt gacatttttt attagtttca ttaggtttag  3120
agataaaatt atatcatgta tgtcactcgt ctagtatctt atttgttatc ataaatgttc  3180
taatcctttt tacgtcaccc gaatacaatt ttttactctt tcatgtcata gtaagggact  3240
aagacataca acattttaca tttaacattt ggccacgaca tgtaagagtg agatattgaa  3300
ttcgagtaac atacgaggta cgatgaataa ggtattacac aaaattacag tggcatatag  3360
tgaattgaat tgttctattt ttactttttt tttgcctaac ataaagccta ttttatttag  3420
tactttctct gattcagctt taatttttat gatttattaa ttttattata tatctatata  3480
ttgtatagat taaaaaataa aataaattat agatttagga aaaattacat tcgggtgatt  3540
tggctgttgg gtgttgcgtt ccctacttgc tcttttcttc ctccgcttca acctgtcccc  3600
agcgcccccc gcgcacacac tgtctttctc tgcctttctt tccctagcgc cgcgccggcg  3660
ccgccattcg atcaggccgc ttcgccggcg acagcatatt ccaggtatgc cgtcccttct  3720
gctccttctg cgagaattca aacaccccga actccccaaa tctagtattt gtattcggat  3780
ctgaccattt ttcactgggc ccgcccctga ttcgcaggtc ggttggtttt ggcacttcgg  3840
accggcggcc atggcttccg acggcatcgg ccccagaggt ataactgttt catctcttct  3900
ttgtgttcaa acagacagac gtcaaaccgc cgagaggagg tacaaatata gatttgggc  3960
tatgagcacg ccattgcgct tccagcgatc tgacatattg ggaattcttg ttttttttt  4020
```

-continued

```
gggtaccttg caaggccgaa atttgacgct tttctgttta attctagtgc ctgtctgcat  4080
ccattagggc atcctagctg ctccatgctc gtgatctcgt ccgtttgctt gattgaatcc  4140
attgttttcc aaagttcatt gctactgcga aatacgttta tatgattacc acaatttgtg  4200
tttttgcctt ttcgggttgc acagagggta ctgccatcat tgttgtttta gcgccatttg  4260
gaacaagtga ttcactggta ctagtacagt atgtgctttt catgtgtgtt tggtttgtac  4320
catcagatgg aattttgagc gcggtttaca aattagtact atagatatac tgtgaggtgc  4380
acactagatg gttctgcttt gttctacagt cagtaacttt ttcttccttg ctcacagatg  4440
tatgtgttgt tggggttgca cgcaccccaa tgggcggttt ccttggtgcc ttgtctccct  4500
tgcctgctac gaaacttggc tctatagtaa ttcaaggtga gatccgaatc ttctctgcat  4560
ttacatccga gctctgaaca tggtcatggc tgggggctgt tagctgctct ggaaagagca  4620
aacgtggatc cagccctcgt gcaggaggtc tactttggaa acgtcttgag tgctaatttg  4680
gggcaagctc ctgcaaggca agctgctctg ggtgccggga taccaaactc tgttgtttgc  4740
accactgtta acaaagtctg tgcatctggc atgaaaggtt tgaatcgaat ttatctgtct  4800
gtccttgtgt actctgctca gagttcacag aagtgagaga ttacctgacc atgctcttgt  4860
tttcctttcc tatatgcagc tactatgttt gcagcacagt caattcaatt gggtatcaat  4920
gatattgttg tggctggtgg catggaaagc atgtccaatg ccccaaagta cattgctgaa  4980
gctaggtatg caattattac ttggtggata tattcaatat cgagctgcat aaaccaaatg  5040
atagtcttaa gttatttggt agatacatgc atgcttactt atcttcattg catttttctaa  5100
atttgtttgt aagaaatgtt gattcaccag cagcgaggct attaacgaag tggccagttt  5160
tgttgtgaaa gtatattctg ttcatgttta aagtgcattt caactgctta taagcttgct  5220
aattacaatt gcaggaaggg gtctcgtttt ggtcatgaca cacttgttga tgccatgctt  5280
aaggatgggc tttgggatgt atacaatgat tgtgccatgg gaatgtgtgc cgagctttgt  5340
gctgacaacc atgccctcac aagagaagac caggtctctt aatacagata gcagtaaatg  5400
ctgtttgtta taatattccc atatttttca agatataagt tgtgctatac aacatgtcaa  5460
tgctggcaat tcttttgaga ctgccctgga atcttcgtgc tttatcttgg tcatcatcat  5520
aaatggtcta gagactctag accagcatct gcattccttg tctgatgaac tagtaacttg  5580
gatcctttct agcaatgatt ttctgttatg ttgtgacatg attgataggg tgggctttta  5640
tgcatgctct gggtctgtga actgaccatt catctgcttc cagagatgaa agtagatgtg  5700
ccacacaaaa atgagcactc ttttgtattc ctgttagagc tatacaagta taatctctta  5760
aaagctgctc atcagtacat gacactagta ccttgatgat tttactgtat ctgtttatgt  5820
aattttttttc ttaataaatt tgatatagta taattaaaat tgagttgcct tttaattttc  5880
acttatatgt tgcaatttat ttttgtctat attgcaataa atatatttcc aatttctggt  5940
atatttaatt ttacttattc ttgaatagga tgcatttgct atccaaagca acgagcgtgg  6000
aattgctgct cgtgacagtg gtgcttttgc atgggagatt attccggtaa ttttctccct  6060
cattgatgat actagacatg cttttcttgg ttttctgatg gtcagtgttg tcacccaggt  6120
tcaagttcct gttggtagag gaaaaccccc aacattaatt gagagagatg aaagcctgga  6180
taaggtattt tttctgacgt gacaaaatat ttttaacaaa ataaagcttg tagttgatca  6240
aaggcaaaaa gactggcagg cactttgatt tattgttctt gcttcctcca aatgcaacgt  6300
tccttgcata atgagctttg ctagcagtta tttgtaagat caatgcatga cagttttatt  6360
tatgtcttgt gctattcctt ttgtgtctta gtttgaccca gtaaaactaa agaaacttcg  6420
cccaagtttc aaggagaatg gtggtacagt tacagctgga aatgcttcta gtataaggta  6480
gctgcttgaa atatttctga ggccttttgt cctacaaagt ctttctgaga ccttgttttt  6540
cggccatatg ttgtttagct gacagatatg aaggacaacc tatttcattg ttgacagtta  6600
aattatatta ttgtattatg catgcatttt taactgatat attatgcttg catttttgtca  6660
acttcattgt ttctctattt gtttttagac tgcttgggta tgctctactc cgttaaatag  6720
atggtaattt tttctttaga tttggtaccc aattggtgtg aatgatttat cacaatatca  6780
cataagaaag taaaaacatt ttaaatgcct tattatgccc attcaaacaa caaaagttgc  6840
cctacctttt aaatttcttc atggttgccc tagaccttgt ttgtctcact ttgtactgtg  6900
tctattttta gctgacaagt actgtccggt gtactgccta ctatggcttg tgtagccttc  6960
tgcaaccagt catctaattt gttttatatg gatcagtgat ggagctgctg cattagtttt  7020
agtgagtggg cagaaggctc aagagcttgg ccttcaagtc cttgcaagga tcaaaggtta  7080
tgctgatgca gctcaagtaa gccacagaaa caattgttag ctctcctaag agtagaatgc  7140
gcttattcta atttacactg tgatctaaat attttaggat ataggaagtt atttttatct  7200
ggaacgattt tatgttacta ttttagatat cgaaatttat caactattgg aacttgtgat  7260
ctggaatatt attttgtaat gtggatgctg tttatacagg ctccggagct tttacaacc  7320
actccagcac ttgcaatacc aaaggctatc gcaaatgctg gattagagtc atcccgtgtt  7380
gatttctatg agattaatga agccttttcg gtatgcattg agtttctttt actcacattt  7440
tttgtaagcc ttttgttatg cattgagagt ttattttact tattactttt tttgtaataa  7500
tgtcttttttt acttgtcaat ataggctgtt gcgcttgcaa atcaaaaact tcttggaatt  7560
ccttcagtaa gtgtcacctg tattaaactg ccattctttg tggattttag aagttaaaca  7620
atcactttca gaaagtacat attgtctctt ttttgttatt tgctatgcag cagcaacgtg  7680
taattgcatt ataacagtat tatctgtact aacagcatat gtgtttgcag gaaaagatta  7740
atgttcatgg aggagctgta tccttaggac atcctctcgg gtgcagtggt gctcgcattt  7800
tggttaccct tattggtgta agttctatct taagatgctt gttttacctt ttgagttaca  7860
atccctttttg tttaaaaaaa atgtgcaatg tttttctagt aaaaaaaatag atggtctttg  7920
agtaaataat gaattctgac atatgttacc atatcatcat agggttcgtg atgaacagta  7980
agcatcttca ctattgctac taggtctact tcctctatcc caaattataa gacgtcttgg  8040
gatgttggca ttgttagatt tatagctttt actacgtgta ctgagacata atgtttatcg  8100
caataaaaac tacaaatcta gaaaaagtaa aaacatctta taatttgaaa catagggagt  8160
atgttggatc aagccacccc atccctgcac caaacactac cttaggccat gttcggttac  8220
aagtggttcg agggggattg aaggggatta aatccccttc tagttaaaat tgaataggag  8280
gggatttaat ccccctcaat cccctccaat cctctcgcaa ccgaacaagc ccttagtgat  8340
ttccaatgtg caaattatct gcaaatagaa tcttgtataa agctgcaaat gtagagtttc  8400
acattgatat cggctcatcc cttgtttcac ttgttgctgg tgatcaatag tttctttttc  8460
tcttcatttt ctttaagcaa aacgttgggc acaatatagt gccatcatgt tgggacatca  8520
aaatatattg tgcttgaccc tcctaatcat tgtttcttgt taacaggttc tcagggcgaa  8580
gagtggcaag atcggagttg ctggtgtctg caacggtgga ggcggagcat cagctcttgt  8640
tctggagctc gcataagaaa tctagacctt gtaagactca aaacaccgaa tatatctcaa  8700
ctcaaattga ttcttttact agctggcagt aggagctaac cagtataagg tgctattatc  8760
```

```
aaactgtaat atggtcgcat attcagctag gcctaattaa gttgtatttt ttccttttac  8820
aactgttgtg caatttgact aactgctgca ccttgatatt gcaggtagtt agcaaaagct  8880
ccctgaggtg atcttgtagt cttattttcc gttgtagtag tcccatagaa catttcttaa  8940
tttaatttgg caataaagca aaagctccct gaggagatat tgcttctgtt ggttgcatag  9000
tagagtatca tgtaataaga gctacagaaa tatttttgat atatttgtga ggatactaca  9060
gaaatatttt atatatttgt gatgtgtctt gtacatttat ctaggtcaca tcaactatcc  9120
tgccgcccgg gatctggaac tccgacagcc cgatttcaaa tagtttgaaa gaacatcagc  9180
aaacacccaa ggcaaataca aagatcagag aagctggagg gttagttaca ggagcatcag  9240
gttaccgaga atgcaaccat gcacggcaaa aggcgcctac cccgcatcaa aatttctgcc  9300
agaaacaaac aagaaacgaa agaatcacac gcacactatc tacatccaga aacgtgatgt  9360
tatactagat agtcagcggc attcaggaag ccctcgtact gggtaccgtt gagggcgctg  9420
tagacctcgt cccagttctc gatctgctcc gacagcggct tcgtgtgtat cttcacgtgc  9480
cggctcacca gcttcctcct cggcactccg aggaaatcca ggacatccaa gagcttctgc  9540
agtgcagcag cgatggtaag cgacacaacc aacggaaggg aacagacaaa gggcatcagc  9600
gagaacgcac tgttctgttg cggacgacat cctcgtagta gacgctcatg tgccgggtgt  9660
tgtttaggtt ctcaagagcg tcgcgagtgt actcgtcagc tcgtttcagc tgccatatca  9720
gtgacgtcgt gttgagcctg ggcctgtatc ttgccagtat atgggcctgt ggagcgagaa  9780
cgaacgacac gtcaaacaca gacagagatc agctcagctc agagacttgc tgtgagagtg  9840
agacattagc cgcgaacacg tttcttagct agcattacta acctcacgct tcgtgtggac  9900
atgggccttg tgcgttccgt ttagttgctt aagtaacctg tcgtgattgt tcgctacttg  9960
tgataccaac tggcggagca ggttccttct gaaaagaaat attgcagaga ctcctcttcg  10020
attgaagtag tcgactacgt ccgcatggtt tgccacgagg ccctgaaaac atacacccca  10080
accccaaccc cgttcagaag aaatgctcct ttgtttccac tctctagcta cagtgcctgt  10140
tttgtttcca gtctctaact ctatgtttgg ccaacattca tggtttggtt aggcaatctg  10200
tctaccagga aaaaagtttg ttctcacaca aattagatga agccctgaaa caaacatgct  10260
tgacatgtag attataatca gtctactgga cacactacag aatctatcaa atattactcc  10320
atatgcattt gcagttctca tgcacgttcg agagaaaaaa attgtctaaa atgcaggatc  10380
tgacagcaag tcacaaaact aaactagcta tccgacagtc ccataaggtt attcgcatcc  10440
cacatagatt ggaagggatt ggaaaatttt aagaaggatt ttgacttctt acggatttaa  10500
acccgttcaa tctcgtccaa tccacatgga ttggcactaa gacgagcaag ccctaaagtg  10560
gattcccaaa aaaaaatagt tccatggact tgaggaaagt ttggagcaat atgcaatact  10620
ggaactaaat ggaaaaataa atgaaaaagg gtcatccaaa taaatctata ctgcatgttt  10680
tagtccgcac ctgatttagc atccacttga agccaatagc tgcagtgcac tcattcttgg  10740
aagcgctact gttccagtcc aaattgtaca ctttatccag ggtatctatt atagaggaaa  10800
tgttactcct cctttctttt ctagagaaaa tttcaccatt ggagctaaca ttcatgtggc  10860
tgttaagaag agtttcaaac cagccacttc cagatcgctg cgatgatata attgcaaagg  10920
accggacagc attgcacttg cattcctccc tagaaattaa aaattatgta ttaggcatta  10980
aacaaacgag attgctcaat cttaccacag ttgcagatct cacctgctgt aagttatcgg  11040
ttgaggatag cgcacaaatt gagcctccga aagaggagca atggacttat tacatggttg  11100
tcccacaact tcaatcttga caactcttga ccagccatca ctccctagtt gcttcatgca  11160
cattgagcaa atagatatcc cgcataacat agtcatagca aagacaaccg ttctcaacgc  11220
gatcggtgat tttttcgggg gcttcaagtc aaatgcatcc tgcaaacaga tccgaccagt  11280
acaaaaccaa tcagcaggtt gcactgcgca tacgcggttc agtgccagta tatatacatt  11340
gcagcccttt tttgaggtaa gatctgttat tttgtaacct tctgctacag taaaaaaacc  11400
tttcagcaaa caacacaaac attaatgttc aatgtgagct gagaagcatc catttggcta  11460
catctatata agcagaaata aaaagaaata aacaaataaa acttcaaggt ctatctagtc  11520
ctcagggaag ttaaaatgag cacgtactat tcaattcagc tactagcctt tttaccaaca  11580
tggaagacac ggcaagggat gaaaaggccc ttttttgata agttcaagta cattcccata  11640
tattctgtcg cccagctgcc ttagggggcg tttggttgcc ttctccagtg gtgcagctgc  11700
atctacacat gcaaaaagta gtgtttgttt ggttcgttgt atcgcacgag acaggctagc  11760
acggaactta aagcgccgcg agccaggccc ggcagaaacg catcgcgcga ccgcacgcgc  11820
gcggccaggc tccgctcagc cagctcttta ctcgtgcacg catatcgaga cacgttttta  11880
attggttttt tcattatatc                                          11900

SEQ ID NO: 43           moltype = DNA  length = 1411
FEATURE                 Location/Qualifiers
source                  1..1411
                        mol_type = genomic DNA
                        organism = Zea mays
SEQUENCE: 43
gtgttgcgtt ccctacttgc tcttttcttc ctccgcttca acctgtcccc agcgcccccc  60
gcgcacacac tgtctttctc tgcctttctt tccctagcgc cgcgccggcg ccgccattcg  120
atcaggccgc ttcgccggcg acagcatatt ccaggtcggt tggttttggc acttcggacc  180
ggcggccatg gcttccgacg gcatcggccc cagaggatgt atgtgttgtt ggggttgcac  240
gcaccccaat gggcggtttc cttggtgcct tgtctccctt gcctgctacg aaacttggct  300
ctatagtaat tcaagctgct ctggaaagag caaacgtgga tccagccctc gtgcaggagg  360
tctactttgg aaacgtcttg agtgctaatt tggggcaagc tcctgcaagg caagctgctc  420
tgggtgccgg gataccaaac tctgttgttt gcaccactgt taacaaagtc tgtgcatctg  480
gcatgaaagc tactatgttt gcagcacagt caattcaatt gggtatcaat gatattgttg  540
tggctggtgg catggaaagc atgtccaatg ccccaaagta cattgctgaa gctaggaagg  600
ggtctcgttt tggtcatgac acacttgttg atgccatgct taaggatggg ctttgggatg  660
tatacaatga ttgtgccatg ggaatgtgtg ccgagctttg tgctgacaac catgccctca  720
caagagaaga ccaggatgca tttgctatcc aaagcaacga gcgtggaatt gctgctcgtg  780
acagtggtgc ttttgcatgg gagattattc cggttcaagt tcctgttggt agaggaaaac  840
ccccaacatt aattgagaga gatgaaagcc tggataagtt tgacccagta aaactaaaga  900
aacttcgccc aagtttcaag gagaatggtg gtacagttac agctggaaat gcttctagta  960
taagtgatgg agctgctgca ttagttttag tgagtgggca gaaggctcaa gagcttggcc  1020
ttcaagtcct tgcaaggatc aaaggttatg ctgatgcagc tcaagctccg gagcttttta  1080
caaccactcc agcacttgca ataccaaagg ctatcgcaaa tgctggatta gagtcatccc  1140
```

-continued

```
gtgttgattt ctatgagatt aatgaagcct tttcggctgt tgcgcttgca aatcaaaaac  1200
ttcttggaat tccttcagaa aagattaatg ttcatggagg agctgtatcc ttaggacatc  1260
ctctcgggtg cagtggtgct cgcattttgg ttacccttat tggtgttctc agggcgaaga  1320
gtggcaagat cggagttgct ggtgtctgca acggtggagg cggagcatca gctcttgttc  1380
tggagctcgc ataagaaatc tagaccttgt a                                  1411

SEQ ID NO: 44          moltype = DNA  length = 5790
FEATURE                Location/Qualifiers
source                 1..5790
                       mol_type = genomic DNA
                       organism = Zea mays
SEQUENCE: 44
gggggcagtc tatactgccc ccttaatagt tagtagagat ttggtacaac tcacgagcta  60
gctcgctcgc agacgctccg aacttgatct gactcgtgag cctcaagttt tttttctagc  120
cttaaccaca tgcccacgag gatgattgtt cgaggtgatt agcaaacgca aacgatatca  180
attgacattt tttattagtt tcattaggtt tagagataaa attatatcat gtatgtcact  240
catctagtat cttatttgtt atcataaatg ttctaatcct ttttacgtca cccgaataca  300
atttttttact ctttcatgtc atcgttgatg acatagtaag ggactaagac atacaacatt  360
ttacatttaa catttggcca cgacatgtaa gagtgagata ttgaattcga gtaacatacg  420
aggtacgatg aataaggtat tacacaaaat tacagtggca tatagtgaat tgaattgttc  480
tatttttact tttttttgc ctaacataaa gcctatttta tttagtactt tctctgattc  540
agctttaatt tttatgattt attaatttta ttatatatct atatattgta tagattaaaa  600
aataaaatag attatagatt taggaaaaat tacattcggg tgatttggct gttgggtgtt  660
gcgttcccta cttgctcttt tcttcctccg cttcaacctg tccccagcgc cccccgcgca  720
cacactgtct ttctctgcct ttctttccct agcgccgcgc cggcgacgcc attcgatcag  780
gccgcttcgc cggcgacagc atattccagg tatgccgtcc cttctgctcc ttctgcgaga  840
attcaaacac cccgaactcc ccaaatctag tatttgtatt cggatctgac cattttttcac  900
tgggcccgcc cctgattcgc aggtcggttg gttttggcac ttcggaccgg cggccatggc  960
ttccgacggc atcggcccca gaggtattac tgtttcatct cttcttgtgt tcaaacagac  1020
agacgtcaag ccgccgagag gaggtacaaa tatagatttt gggtaatgag cacgccattg  1080
cgcttccagc gatctgacat attgggaatt cttgcttttt tttgggtacc ttgcaaggcc  1140
gaaatttgac gcttttctgt ttaattctag tgcctgtctg catccattag ggcatcctag  1200
ctgctccatg ctcgtgatct cgtccgtttg cttgattgaa tccattgttt tccaaagttc  1260
attgctactg cgaaatacgt ttatatgatt accacaagtt gtgttttttc cttttcgggt  1320
tgcacagagg gtactgccat cattgttgtt atagcgccat ttggaacaag tgattcactg  1380
gtactagtac agtatgtgct tttcatgtgt gtttggtttg taccatcaga tggaattttg  1440
agcgcggttt acaaattagt actatagata tactgtgagg tgcacactag atggttctgc  1500
tttgttctac agtcagtaac tttttcttcc ttgctcacag atgtatgtgt tgttggggtt  1560
gcacgcaccc caatgggcgg tttccttggt gccttgtctc ccttgcctgc tacgaaactt  1620
ggctctatag taattcaagg tgagatccga atcttctctg catttacatc cgagctctga  1680
acatggtcat ggctgggggc tgttagctgc tctggaaaga gcaaacgtgg atccagccct  1740
cgtgcaggag gtctactttg gaaacgtctt gagtgctaat ttggggcaag cgcctgcaag  1800
gcaagctgct ctgggtgccg ggataccaaa ctctgttgtt tgcaccactg ttaacaaagt  1860
ctgtgcatct ggcatgaaag gtttgaatcg aatttatctg tctgtccttg tgtactctgc  1920
tcagagttca cagaagtgag agattacctg accatgctct tgtttccctt tcctatatgc  1980
agctactatg tttgcagcac agtcaattca attgggtatc aatgatattg ttgtggctgg  2040
tggcatggaa agcatgtcca atgccccaaa gtacattgct gaagctaggt atgcaattat  2100
tacttggtgg atatattcaa tatcgagctg cataaaccaa atgatagtct taagttattt  2160
ggtagataca tgcatgctta cttatcttca ttgcattttc taaatttgtt tgtaagaaat  2220
gttgattcac cagcagcgag gctattaacg aagtggccag ttttgttgtg aaagtatatt  2280
ctgttcatgt ttaaagtgca tttcaactgc tttaatccaa taagcttgct acttacaatt  2340
gcaggaaggg gtctcgtttt ggtcatgaca cacttgttga tgccatgctt aaggatgggc  2400
tttgggatgt atacaatgat tgtgccatgg gaatgtgtgc cgagctttgt gctgacaatc  2460
atgccctcac aagagaagac caggtctctt aatacagata gcagtaaatg ctgtttgtta  2520
taatattccc atatttttca agatataagt tgtgctatac aacatgtcaa tgctggcaat  2580
tattttgaga gtgccctgga atcttcgtgc tttatcttgg ttatcatcat aaatggtcta  2640
gagactctag accagcatct gcattccttg tccgatgaac tagtaacttg gatcctttct  2700
ggcaatgatt ttctgttagg ttgtgacatg attgataggg tgggcttatg catgctctgg  2760
gtctgtgaac tgaccattca tttgcttcca gagatgaaag tagatgtgcc acacaaaaat  2820
gagcactctt ttgcattctt gttagagcta tacaagtata atctcttaaa agctgctcat  2880
cagtacatga cactagtacc ttgatgattt tactgtatct gtttatgtaa tttttttctt  2940
aataaatttg atatagtata attaaaattg agttgccttt gaattttcac ttatatgttg  3000
caatgtattt ttgtctatat tgcaataaat atattcccaa tttctggtat atttacttat  3060
tcttgaatag gatgcatttg ctatccaaag caatgagcgt ggaattgctg ctcgtgacag  3120
tggtgctttt gcatgggaga ttattccggt aattttctcc ctcattgatg atactagaca  3180
tgcttttctt ggttttctga tggtcaatgt tgtcgcccag gttcaagttc ctgttggtag  3240
aggaaaaccc ccaacattaa ttgagagaga tgaaagcctg gataaggttt tttttctgat  3300
ttgacaaaat atttttaaca aaataaagct tgtagttgat caaaggcaaa aagactggca  3360
ggcactttga tttattgttc ttgcttcctc caaatgcaac gttcctcgca taatgagctt  3420
tgctagcagt tatttgtaag atcaatgcat gacagtttta tttatgtctt gtgctattcc  3480
ttttgtgtct tagtttgacc cagtaaaact aaagaaactt cgcccaagtt tcaaggagaa  3540
tgatggtaca gttacagctg gaaatgcttc tagtataagg tagctgcttg aaatatttct  3600
gagacctttt tgtcctacaa agtctttctg agaccttgtt tttcggccat atgttgttta  3660
gctgacagat atgaaggaca acctatttca ttgttgacag ttaaattata ttattgtatt  3720
atgcatgcat ttttaactga tatattatgc ttgcattttg tcaacttcat tgtttctcta  3780
tttgttttta gactgcttgg gtatgctcta ctctgtgaaa tagatggtaa ttttttcttt  3840
agaattggta cccaatcgat gtgaatgatt tatcacataa gaaagtaaaa acattttaaa  3900
tgccttatta tgcccattca aacaacaaaa gttgccctag accttgtctg tctcactttg  3960
tactgtgtct atttttagct gaccagtact gtccggtgta ctgcctacta tggcttgtct  4020
```

-continued

```
agccttctgc aaccagtcat atctaatttg ttttatatgg atcagtgatg gagctgctgc  4080
attagttttg gtgagtgggc agaaggctca agagcttggc cttcaagtcc ttgcaaggat  4140
caaaggttat gctgatgcag ctcaagtaag ccacagtaac aattgttagc tctcctaaga  4200
gtagaatgcg cttattctaa ttcacattgt gatctaaata ttttaggata taggaagtta  4260
tttttatctg gaacgatttt atgttactat tttagatatc gaaatttatc aactattgga  4320
acttgtgatc tggaatatta ttttgtaatg tggatgctgt ttatacaggc tccggagctt  4380
tttacaacca ctccagcact tgcaatacca aaggctatcg caaatgctgg attagagtca  4440
tcccatgttg atttctatga gattaatgaa gccttttcgg tatgcattgg gtttctttat  4500
ttgtaagcct tttgttatgc attgagagct tattttactt attacttttt ttttgtaata  4560
atgtcttttt tacttatcaa tataggctgt tgcacttgca aatcaaaagc ttcttggaat  4620
tccttcagta agtgtcacct gtattaaact gccattcttt gtgcatttta gaagttaaaa  4680
catcactttc agaaagtaca tattggccct tttttgttat ttgctatgca gcagcaacat  4740
gtaattgcat tataacagca ttatatgtac taacaacata tgtgtttgca ggaaaagatt  4800
aatgttcatg gaggagctgt atctttagga catcctctcg ggtgcagtgg tgctcgcatt  4860
ttggttaccc ttattggtgt aagttctatc ttaagatgct tgttttatct tttgagttac  4920
aatccctttt gtttaaaaaa atgtgcaatg tttttctagt aaaaaaatag atgatggtct  4980
ttgagtaatt gatgaattct gacatatgtt accgtatcat catagggttc gtgatgaaca  5040
gtaagcatct tcactattgc tactaagtct acttccttag tgttttccaa tgtgcaatgt  5100
ttttcttgta taaagctgca aatgtagagt ttcacttgtt gctggtgatc agtagtttct  5160
cttcattttc tttaagcaaa accttgagaa caatatggtg ccatcatgtt gggacatcaa  5220
atatatggtg cttgaccctc ctaatcattg tttcttgtta acaggttctc agggcgaaga  5280
gtggcaagat cggagttgct ggtgtctgca acggtggagg cggagcatca gctcttgttc  5340
tggagctcgc ataagaaatc tagaccttgt aaggctcaaa acaccgaata tatctcaact  5400
caaattgatt cttttactag ctggcaggag ctaaccagta taaggtgcta ttactgttgt  5460
gcaatttgac taactgctgc aactgatatt gcaggtattt agcaaaagtt ccctgaggtg  5520
atcttgtagt cttattttcc gttgtagtag tcccatagaa catttcttaa tttaatttgg  5580
caataaagcg aagtcgtgct tctgttggtt gcatagtaga gtatcatgta ataagagcaa  5640
tggggatgtt tcatagatat ttttgaggat gctacagaaa tattttatat actagtgagt  5700
gctcgtgcgt tgcaacggga atatataatt ctatgataac ttatatacaa aatgtgtgct  5760
acattgttat aagaaaatgt ttcataatct                                   5790

SEQ ID NO: 45          moltype = DNA  length = 5881
FEATURE                Location/Qualifiers
source                 1..5881
                       mol_type = genomic DNA
                       organism = Zea mays
SEQUENCE: 45
gggcagtcta tactgccccc ttaatagtta gtagagattt ggtacaactc acgagctagc  60
tcgctcgcag acgctccgaa cttgatctga ctcgtgagcc tcaagttttt tttctagcct  120
taaccacatg cccacgagga tgattgttcg aggtgattag caaacgcaaa cgatatcaat  180
tgacattttt tattagtttc attaggttta gagataaaat tatatcatgt atgtcactca  240
tctagtatct tatttgttat cataaatgtt ctaatccttt ttacgtcacc cgaatacaat  300
tttttactct ttcatgtcat cgttgatgac atagtaaggg actaagacat acaacatttt  360
acatttaaca tttggccacg acatgtaaga gtgagatatt gaattcgagt aacatacgag  420
gtacgatgaa taaggtatta cacaaaatta cagtggcata tagtgaattg aattgttcta  480
tttttacttt ttttttgcct aacataaagc ctattttatt tagtactttc tctgattcag  540
ctttaatttt tatgatttat taattttatt atatatctat atattgtata gattaaaaaa  600
taaaatagat tatagattta ggaaaaatta cattcgggtg atttggctgt tgggtgttgc  660
gttccctact tgctctttc ttcctccgct tcaacctgtc cccagcgccc cccgcgcaca  720
cactgtcttt ctctgccttt ctttccctag cgccgcgccg gcgacgccat tcgatcaggc  780
cgcttcgccg gcgacagcat attccaggta tgccgtccct tctgctcctt ctgcgagaat  840
tcaaacaccc cgaactcccc aaatctagta tttgtattcg gatctgacca tttttcactg  900
ggcccgcccc tgattcgcag gtcggttggt tttggcactt cggaccggcg gccatggctt  960
ccgacggcat cggccccaga ggtattactg tttcatctct tcttgtgttc aaacagacag  1020
acgtcaagcc gccgagagga ggtacaaata tagattttgg gtaatgagca cgccattgcg  1080
cttccagcga tctgacatat tgggaattct tgcttttttt tgggtacctt gcaaggccga  1140
aatttgacgc ttttctgttt aattctagtg cctgtctgca tccattaggg catcctagct  1200
gctccatgct cgtgatctcg tccgtttgct tgattgaatc cattgttttc caaagttcat  1260
tgctactgcg aaatacgttt atatgattac cacaagttgt gttttttcct tttcgggttg  1320
cacagagggt actgccatca ttgttgttat agcgccattt ggaacaagtg attcactggt  1380
actagtacag tatgtgcttt tcatgtgtgt ttggtttgta ccatcagatg gaattttgag  1440
cgcggtttac aaattagtac tatagatata ctgtgaggtg cacactagat ggttctgctt  1500
tgttctacag tcagtaactt tttcttcctt gctcacagat gtatgtgttg ttggggttgc  1560
acgcacccca atgggcggtt tccttggtgc cttgtctccc ttgcctgcta cgaaacttgg  1620
ctctatagta attcaaggtg agatccgaat cttctctgca tttacatccg agctctgaac  1680
atggtcatgg ctgggggctg ttagctgctc tggaaagagc aaacgtggat ccagccctcg  1740
tgcaggaggt ctactttgga aacgtcttga gtgctaattt ggggcaagcg cctgcaaggc  1800
aagctgctct gggtgccggg ataccaaact ctgttgtttg caccactgtt aacaaagtct  1860
gtgcatctgg catgaaaggt ttgaatcgaa tttatctgtc tgtccttgtg tactctgctc  1920
agagttcaca gaagtgagag attacctgac catgctcttg tttccctttc ctatatgcag  1980
ctactatgtt tgcagcacag tcaattcaat tgggtatcaa tgatattgtt gtggctggtg  2040
gcatggaaag catgtccaat gccccaaagt acattgctga agctaggtat gcaattatta  2100
cttggtggat atattcaata tcgagctgca taaaccaaat gatagtctta agttatttgg  2160
tagatacatg catgcttact tatcttcatt gcattttcta aatttgtttg taagaaatgt  2220
tgattcacca gcagcgaggc tattaacgaa gtggccagtt ttgttgtgaa agtatattct  2280
gttcatgttt aaagtgcatt tcaactgctt taatccaata agcttgctac ttacaattgc  2340
aggaaggggt ctcgttttgg tcatgacaca cttgttgatg ccatgcttaa ggatgggctt  2400
tgggatgtat acaatgattg tgccatggga atgtgtgccg agctttgtgc tgacaatcat  2460
gccctcacaa gagaagacca ggtctcttaa tacagatagc agtaaatgct gtttgttata  2520
```

```
atattcccat atttttcaag atataagttg tgctatacaa catgtcaatg ctggcaatta  2580
ttttgagagt gccctggaat cttcgtgctt tatcttggtt atcatcataa atggtctaga  2640
gactctagac cagcatctgc attccttgtc cgatgaacta gtaacttgga tcctttctgg  2700
caatgatttt ctgttaggtt gtgacatgat tgatagggtg ggcttatgca tgctctgggt  2760
ctgtgaactg accattcatt tgcttccaga gatgaaagta gatgtgccac acaaaaatga  2820
gcactctttt gcattcttgt tagagctata caagtataat ctcttaaaag ctgctcatca  2880
gtacatgaca ctagtacctt gatgatttta ctgtatctgt ttatgtaatt tttttcttaa  2940
taaatttgat atagtataat taaaattgag ttgcctttga attttcactt atatgttgca  3000
atgtattttt gtctatattg caataaatat attcccaatt tctggtatat ttacttattc  3060
ttgaatagga tgcatttgct atccaaagca atgagcgtgg aattgctgct cgtgacagtg  3120
gtgcttttgc atgggagatt attccggtaa ttttctccct cattgatgat actagacatg  3180
cttttcttgg ttttctgatg gtcaatgttg tcgcccaggt tcaagttcct gttggtagag  3240
gaaaaccccc aacattaatt gagagagatg aaagcctgga taaggttttt tttctgattt  3300
gacaaaatat ttttaacaaa ataaagcttg tagttgatca aaggcaaaaa gactggcagg  3360
cactttgatt tattgttctt gcttcctcca aatgcaacgt tcctcgcata atgagctttg  3420
ctagcagtta tttgtaagat caatgcatga cagttttatt tatgtcttgt gctattcctt  3480
ttgtgtctta gtttgaccca gtaaaactaa agaaacttcg cccaagtttc aaggagaatg  3540
atggtacagt tacagctgga aatgcttcta gtataaggta gctgcttgaa atatttctga  3600
gaccttttg tcctacaaag tctttctgag accttgtttt tcggccatat gttgtttagc  3660
tgacagatat gaaggacaac ctatttcatt gttgacagtt aaattatatt attgtattat  3720
gcatgcattt ttaactgata tattatgctt gcattttgtc aacttcattg tttctctatt  3780
tgtttttaga ctgcttgggt atgctctact ctgtgaaata gatggtaatt ttttctttag  3840
aattggtacc caatcgatgt gaatgattta tcacataaga aagtaaaaac attttaaatg  3900
ccttattatg cccattcaaa caacaaaagt tgccctagac cttgtctgtc tcactttgta  3960
ctgtgtctat ttttagctga ccagtactgt ccggtgtact gcctactatg gcttgtctag  4020
ccttctgcaa ccagtcatat ctaatttgtt ttatatggat cagtgatgga gctgctgcat  4080
tagttttggt gagtgggcag aaggctcaag agcttggcct tcaagtcctt gcaaggatca  4140
aaggttatgc tgatgcagct caagtaagcc acagtaacaa ttgttagctc tcctaagagt  4200
agaatgcgct tattctaatt cacattgtga tctaaatatt ttaggatata ggaagttatt  4260
tttatctgga acgattttat gttactattt tagatatcga aatttatcaa ctattggaac  4320
ttgtgatctg gaatattatt ttgtaatgtg gatgctgttt atacaggctc cggagctttt  4380
tacaaccact ccagcacttg caataccaaa ggctatcgca aatgctggat tagagtcatc  4440
ccatgttgat ttctatgaga ttaatgaagc cttttcggta tgcattgggt ttctttattt  4500
gtaagccttt tgttatgcat tgagagctta ttttacttat tacttttttt ttgtaataat  4560
gtcttttta cttatcaata taggctgttg cacttgcaaa tcaaaagctt cttggaattc  4620
cttcagtaag tgtcacctgt attaaactgc cattctttgt gcattttaga agttaaaaca  4680
tcactttcag aaagtacata ttggcccttt tttgttattt gctatgcagc agcaacatgt  4740
aattgcatta taacagcatt atatgtacta acaacatatg tgtttgcagg aaaagattaa  4800
tgttcatgga ggagctgtat ctttaggaca tcctctcggg tgcagtggtg ctcgcatttt  4860
ggttaccctt attggtgtaa gttctatctt aagatgcttg ttttatcttt tgagttacaa  4920
tcccttttgt ttaaaaaaat gtgcaatgtt tttctagtaa aaaaatagat gatggtcttt  4980
gagtaattga tgaattctga catatgttac cgtatcatca tagggttcgt gatgaacagt  5040
aagcatcttc actattgcta ctaagtctac ttccttagtg ttttccaatg tgcaatgttt  5100
ttcttgtata aagctgcaaa tgtagagttt cacttgttgc tggtgatcag tagtttctct  5160
tcattttctt taagcaaaac cttgagaaca atatggtgcc atcatgttgg gacatcaaat  5220
atatggtgct tgaccctcct aatcattgtt tcttgttaac aggttctcag ggcgaagagt  5280
ggcaagatcg gagttgctgg tgtctgcaac ggtggaggcg gagcatcagc tcttgttctg  5340
gagctcgcat aagaaatcta gaccttgtaa ggctcaaaac accgaatata tctcaactca  5400
aattgattct tttactagct ggcaggagct aaccagtata aggtgctatt actgttgtgc  5460
aatttgacta actgctgcaa ctgatattgc aggtatttag caaaagttcc ctgaggtgat  5520
cttgtagtct tattttccgt tgtagtagtc ccatagaaca tttcttaatt taatttggca  5580
ataaagcgaa gtcgtgcttc tgttggttgc atagtagagt atcatgtaat aagagcaatg  5640
gggatgtttc atagatattt ttgaggatgc tacagaaata ttttatatac tagtgagtgc  5700
tcgtgcgttg caacgggaat atataattct atgataactt atatacaaaa tgtgtgctac  5760
attgttataa gaaaatgttt cataatctat acacaaagat gagatttctg caaagaatac  5820
catgccacat cactaaaata tgaatggctc acttatccct tataacagca gccttgtctt  5880
t                                                                  5881
```

```
SEQ ID NO: 46          moltype = DNA  length = 1628
FEATURE                Location/Qualifiers
source                 1..1628
                       mol_type = genomic DNA
                       organism = Zea mays
SEQUENCE: 46
gtgttgcgtt ccctacttgc tcttttcttc ctccgcttca acctgtcccc agcgcccccc  60
gcgcacacac tgtctttctc tgcctttctt tccctagcgc cgcgccggcg acgccattcg  120
atcaggccgc ttcgccggcg acagcatatt ccaggtcggt tggttttggc acttcggacc  180
ggcggccatg gcttccgacg gcatcggccc cagagatgta tgtgttgttg gggttgcacg  240
caccccaatg ggcggtttcc ttggtgcctt gtctcccttg cctgctacga aacttggctc  300
tatagtaatt caagctgctc tggaaagagc aaacgtggat ccagccctcg tgcaggaggt  360
ctactttgga aacgtcttga gtgctaattt ggggcaagcg cctgcaaggc aagctgctct  420
gggtgccggg ataccaaact ctgttgtttg caccactgtt aacaaagtct gtgcatctgg  480
catgaaagct actatgtttg cagcacagtc aattcaattg ggtatcaatg atattgttgt  540
ggctggtggc atggaaagca tgtccaatgc cccaaagtac attgctgaag ctaggaaggg  600
gtctcgtttt ggtcatgaca cacttgttga tgccatgctt aaggatgggc tttgggatgt  660
atacaatgat tgtgccatgg gaatgtgtgc cgagctttgt gctgacaatc atgccctcac  720
aagagaagac caggatgcat ttgctatcca aagcaatgag cgtggaattg ctgctcgtga  780
cagtggtgct tttgcatggg agattattcc ggttcaagtt cctgttggta gaggaaaacc  840
cccaacatta attgagagag atgaaagcct ggataagttt gacccagtaa aactaaagaa  900
```

-continued

```
acttcgccca agtttcaagg agaatgatgg tacagttaca gctggaaatg cttctagtat  960
aagtgatgga gctgctgcat tagttttggt gagtgggcag aaggctcaag agcttggcct  1020
tcaagtcctt gcaaggatca aaggttatgc tgatgcagct caagctccgg agctttttac  1080
aaccactcca gcacttgcaa taccaaaggc tatcgcaaat gctggattag agtcatccca  1140
tgttgatttc tatgagatta atgaagcctt ttcggctgtt gcacttgcaa atcaaaagct  1200
tcttggaatt ccttcagaaa agattaatgt tcatggagga gctgtatctt taggacatcc  1260
tctcgggtgc agtggtgctc gcattttggt taccctattt ggtgttctca gggcgaagag  1320
tggcaagatc ggagttgctg gtgtctgcaa cggtggaggc ggagcatcag ctcttgttct  1380
ggagctcgca taagaaatct agaccttgta tttagcaaaa gttccctgag gtgatcttgt  1440
agtcttattt tccgttgtag tagtcccata gaacatttct taatttaatt tggcaataaa  1500
gcgaagtcgt gcttctgttg gttgcatagt agagtatcat gtaataagag caatggggat  1560
gtttcataga tatttttgag gatgctacag aaatatttta tatactagtg agtgctcgtg  1620
cgttgcaa                                                            1628

SEQ ID NO: 47          moltype = DNA  length = 1714
FEATURE                Location/Qualifiers
source                 1..1714
                       mol_type = genomic DNA
                       organism = Zea mays
SEQUENCE: 47
aagagcccct cgggcagcag gatcttcccc ctccccaaaa ccaaaccagc tgcctccgac  60
agcatccacc ttttcctccc ccaaaccatg gacttctcca ccggcgggag cgtgagcggg  120
ggcggcggag gcgccagcga cggccccgcg caggcggagc gctggctgga gatcgccgag  180
aagctcctcg cggcgcgcga cctcgtcggc tgcaagcgct tcgcggagcg gtcggtggag  240
gcgaacccgc tcctcgccgg cgttgacgaa ctcctcgccg tcgccgacgt cctcctcgct  300
tcccagttca tgggcacctc gggccagccg gacccgctcg ccatcctcca gctgccgccc  360
ggagtcagcc ccgaccaggc cgccgtgtcc cgcgccttcc gccgcctcgc gctcctcctc  420
ggtcccagca acccgcaccc gggagccgag atggcgctcc gcctcgtcaa cgacgcctac  480
gccttcctct cggatccctc tcgccgcccc ccgccgcccg ccgatcccgc cactggtacc  540
ccttactcct cccagtatcc cgccgcggcc gctcccgcct ccgacacccc ggagttctgg  600
acggcgtgcc ccttctgctg ctacgtgcac cagtacccgc gcagcctgat cgggcgcgcc  660
ctcaagtgcc ccaacgcggg ctgccgccgc ggattcgtgg cttctgagct cccgacccca  720
cccacggttg tgccgggcac tgaaatgtac cactgcgcct gggggttctt ccccctcgga  780
tttcccaacg cggccgacct gggtgccaac tggaagccat tctacaagat gttcccttgg  840
aacacggctc ccagtggcca aggtggtggt ggtaggagtc acggaaacca tggtggtagg  900
cagccacaga atgacagtgc tcgtggtggc tcttctagag gtaggatcaa gaagacgacg  960
gcccgcaaga aggtcggggt agggctcagg agacgttctc ttggtgtgga gagtggcatt  1020
gattcttcga tgctcgggca ggaaggctgg gctggggatg agaacgctgg agatggaagg  1080
gccgaggagg tgaggagaat taacataaat gaggcagcac atgctacaga tggcactggt  1140
agggttaatg ttagcggtgc tggcggagtt gaagatatcg gcaactttca tatcgatgtt  1200
gatgcatccg aggatatatt ggggaatttg cacaacatgc acttcttgag ggtggacaat  1260
cttggacgga tgatttaact gttgttatgg tttactgggg ctatgattag ccaggccgac  1320
tcttgctgtt caagtgttca tttgagtgta attgttccat ccctgttatg taatgttgta  1380
gttgtagact tgtagtctac ctggtacctg tagttactta acatcaggca gggaaaaatt  1440
tgtatgttca ttagatggag atacatgcca tttgccttag caaacacact ttgtggaggt  1500
ttccagtgat gggataatgc ttcgcagagg tgtggttgga ctggcaatgc ttaccatgcc  1560
acttctggtt tyttcctggc atggtgacac aaaatgttgt tgagatcaag taagtgaatt  1620
atgttctgct ttctgagttc ggtaaacttc tttggctaca aaaggactaa gcttagttat  1680
gctaacttgt tgatttggtt gtgatcattg catc                               1714

SEQ ID NO: 48          moltype = DNA  length = 9828
FEATURE                Location/Qualifiers
source                 1..9828
                       mol_type = genomic DNA
                       organism = Zea mays
SEQUENCE: 48
tggcctcagc atgtttgcaa aatgaatcag taaggaaaaa gaacacggct gcatcatcta  60
tatgatacct ccaagtgaac ataaaggaca acatcatcga ccaatttaat ataaatccaa  120
agcaaaccac atgaaaatca aactcgcagc aggtataaca tgaacaacac actgtaccaa  180
accctaactc atgaagcatg aaccagaaaa tagaacgatt gggggttgat ttcaccttgg  240
ggtcaaggtc gtagcaacgg agacggagca gacctagaag tataggaagc aaatcgacca  300
gagacgaagc gacgaagcag atgcccaacg ccacggagtc ctggcaccag gcggagctgg  360
acgcagccgc gacgcacagc cactcgccgc cggtctctca cgagggaggg agggggtgga  420
agaagaacga gcagcgagag gaggggaaaa ggagggtgca ccgtcgccat atatagccgc  480
aagaggattc accggagcgc tccttcccgc gcgcgcgaaa acctcaccat tcccgcgcga  540
gcccgcgcga gctcccgcca gccacctcgc ccgccgccac attccgccag tgcgccgcgc  600
gcagccgagc tcccaggaaa cgaaccctag ccgcgtttcc tgggagccac ccaggaaaca  660
ggctgttttc agccaggctg cgaaacgggc caaccttgca aacaaggtta gttgtagccc  720
acgggcacaa tcgggctact gggccatcct ccgaaacacg cccttggtga tctctggtgg  780
cgaagcgata cgatacgatg gccggccgta gtacgtcccg tgggtggccg ctgacgtgac  840
gagaaacagt cggtcggcgg ccagccagta acgtgacact cgccatctgc ttccatcttt  900
tgtggttttt tcttctctag acttgactgc atgcagccaa gaaccagaaa ccggacgacc  960
gaccgacgac ggcgacgggt cgtcgtgcac cgccacacgg gggtcatacg atacgacacg  1020
acacgttccg ccgcgagatc gaggtcgatg agtccgaggc tctcggctcc caagtcccaa  1080
caagctgcac cggctcgacg aggacgacgt actgtacgaa cagaacaaca gccagaggcc  1140
ggccggccgg acgaccgacg gtcgccgtcg tgcaccgtgc acggtgcacc acgtctcatg  1200
ccgtctggcg tgtgggtgac gaatcactga aactgaaagg gtaggcagca cagcacatcc  1260
acacacatgt tctttgccta tcacacgctc tttgtaaaat tttagtacac tggtgacaat  1320
aggcggaccg agtccaacat caacaaaaaa atatatatat actggacgtt cgttagccgg  1380
```

-continued gaccatttt cccccaaaag gaaccaacta cagcaggctg aaataaacgt tcctccctct 1440
atgccaaaat aaaattcgta ttagtaaatt agtggttcat ataacatttg atgtatgtgt 1500
tttgtatata tatacatgcc tatatttatt aacatttatt tgaatataga tataaaaaca 1560
cagagctaaa acgattacta ataaagttaa cttgacgctg cagtgttgtt tttttttata 1620
aactctgttc aagttagaga aatctgattt gtagcagctc ttgacttcaa cagagggatc 1680
agaataacta taaagctcca gtaaatagat tacagaatac agcttccctg tttctttcaa 1740
caatacggca gtttagaatt ttttatgtaa caaagctaga gagtttgtgt tttatgtaac 1800
taagccaaag tgtgggtaag tgatatacga taaagtagca tgacacacgg aagttccact 1860
catggaatgg ctttgttcgt ttacaccaat cccgctctag attagcatgg attggaatta 1920
aatccatgcc tcaatccatg ccccaaaata atccatgact acttaatttt ttttattcgg 1980
ttaaacccat catggaatat aacccaaagg tttgggaatt ttttaaacta tggaagacat 2040
ggattctatc catagcccat taggtatgga acaaatccat gagatattgc acaagtttac 2100
attagaattc atggatcaaa agaataacta gctttgaaag tcacatggat ttgttgatgg 2160
atttaatccc accatgggat taggtgtgag atatggattc acccaatcca tacccagatt 2220
aaatccatgg tgggattata tcccatataa ccgaacaaga ccttatgtgg aaatataact 2280
aaataggagg acaacaagct tacttctatt caagcacagc tctagcaagg gactatgaca 2340
atacagataa accaagatat agtaaggtag gacacaatag cattccaggg tgcaccacga 2400
gcgctatgct ttaacaaata gacctaacat catggagtac atagattagg gataaaaaca 2460
ggtacccgaa ctcttaaaac aaatctaata ttttaaaata gatatgtata aaatttaatc 2520
ataatctttc cttctgttat aagcacacta ttatatataa gaataaattt tacatagatt 2580
gttttataca ttatttactc tttacaacaa aaagatgaaa aaatgtttgt atccgtatcc 2640
gaatgctacc caaattttat atctatcatt ttaaaaaata tgataaattt gatgtttatt 2700
ttttataaat ctttacaagt tcaatgctaa aaacaagaat attaatttgt ctagcagatt 2760
ctatatcata tttattcact atcaaagaaa aaaataccaa aaaactggta tgcgaatagg 2820
tacccgtttt catccctaca taggatggac atggttgtca ccaccttcca actatcatta 2880
actatttaga ggcctaacca cattccggta cccggtagag taaacaccac tgaaaggccc 2940
tagtttgatt ttggtaaccg agtgacaacc taggtggact aatatatttt ctatgttgag 3000
atacacaggt gattagtcca caagtagact agtttgagat acttaaatca tgatggtgaa 3060
atgcttggat ttattgtaaa cctcaactag gtgtatgtga gacatcacat ggtgtcttgt 3120
ggataggtgc aggcagtggc ggagccagga tttctgtaag tgtagggcca atataacact 3180
aacaaatatt tatatcagct agaaaatctt aaatcatgca aatgtataga taatgacaca 3240
tatgaccatg aacggattat acaaattctc tcattccttc agaacatatt tgggtcccta 3300
gcaatttttc ggctcaagag tagggcccaa gccctaatgg ccctatgcct gtctccgcca 3360
ctgggtgtag gatatcaaga gacatggttt gggtatgaag gactgattgt aaaagtgatt 3420
gacaagttag atactttgag gcgatggacc acatgtggca gagaagcttg agcaaggact 3480
tggcaccgat cgaccaagga aacaataaag accaaatgaa gttgcgataa ataaagtaat 3540
gaggccacaa tggtaacatg aagtggacca tatcattcaa agaagatcaa gccaattgtt 3600
tattcatgtt gatggtcaag tggcttgatg aagtatgatg gaggaacttc atgatatggt 3660
taatgatcaa aggtagcatg gttggctaca tctatggatg atcattgccc atcatgtgat 3720
gaggttggat gcttgtataa catcatcaac attaagatga aatggaatgt gcaagacaaa 3780
ggtattgtcc aagattgttc tgtagtgatt atgcaggtat gtcacgagat cgagagcata 3840
gtgattatgt aggtatttca cgagatcgat agcatatata gtgattatac gggatatgtc 3900
atgggatcga gagctaaagg ttagggcatg agagacatga ggatttatac atgtttggac 3960
tctcaatgtc agacaatact ttttgtcttg tgtgtgttgt tatatgttcg gaacgatcac 4020
agagttttcc cgtccctctt tttatattct aaggagggat agatgttaca cggtaagcat 4080
agagccgatt atcaagttca tgatggaatc aagtcaattg ccaagttgta cacaagtcca 4140
atttacggct tatctcatat tcagttgaga tctttaaaat ctatcctagt ttaatcattg 4200
attctttgga cttatggccg gacgcatagg tccttctgct tagcctcttc tttataaagc 4260
ttgatttagg tactcatgca tattattgac aatagcttca gactttgttt gacgataaaa 4320
aagactctct atatatgaga gcatccatac aaggtttga ccactttagg acgaaacttg 4380
aagatggaga gatatgagaa aatacaatgt cgtttccatc tctactcaca gccgtgagtc 4440
catacacgag ttgtttttat gttcaatttc cacggtcatg tccctgtatt taaatgataa 4500
aaaaactaaa attatattta aatataagat atgacatatg gatgttggct ataaacctat 4560
attcacacac ctaactcatg gttctatagt cgtcgtgcat cacccttctc attcccgttt 4620
atgcaaaaat aaagagaaaa tatgcatgat tggggatttg aactttagtt gtaggatcta 4680
agttcatacc ctcctatcca acagagcaca tatattttta tgtttcatta aaaacaaagt 4740
atactcatgt cttatataaa aaccgtttca acgaatgaac atctcattag tgatatttaa 4800
aaactatagc aatgcataag caactaacta ctcaaaaaaa tgcaacctga atacttcctt 4860
tgcttctcca cacatgaaat gaaagaaact gaaataagaa acgggcaaac ggcgctgcaa 4920
aagcgggaaa tcccttttcc ttgctgatag tgatacccgg tcaaaaccca ccgagacggc 4980
gagacgcggg gagcgggtac atacacactg acacacctca cgcgagccga gacgcccagc 5040
tcaccgcccc accgagtccc acagtctcag aggccacctc gagccccccc tgccccgcaa 5100
gccgcacccg ccgctccctc cgccatctgc gctgcgctgc tctgctctgc ggtgccaggc 5160
tgccagccag tgccggcgcg cgcccgctgc cgccccgacg ggcccaccgt tctcttctct 5220
ccgcgctgcg cgccggctgg gctgcaggtc agttaatgcg cccgtgacag gcggcgtcgg 5280
ggaggccaag ggcggtgccg ggttaatccc gccgtctctc gaggcggcgc ccgcggagga 5340
ccaggcggga gggggagacg gtgaggcgcg gccatggggg gcgccaaggc ggaggacaaa 5400
cccgccgccg ccgctgcaga agattggtgc taccaatttg gaaacaaggt tcgatttctt 5460
caccatttgc actcctctgc aagactggga cacgtttccg ggtttcgttc tgcctgggcg 5520
gcgacaaatc tcatggcaaa ttgcctttgt ggggctcatt ccctgggttc acactccaaa 5580
tccttccttg cgaccttctc tcagccgtcg cgctttccgt ggcaagcctt ttggaaccct 5640
gatctgaagt gtcactcaga tcaatgcagt cgcattgatt ctattcgttt cctgtttccg 5700
tttccccctt ttaacgtgtc tgctagttcc aagtcccgag cgttttccgt tctctgtttc 5760
agaattgaag cttgttaagt tctgtttttt ttacaatcct tcgtttttgt cccagtcctt 5820
tctattcctg gagaagttag gaatctgttg ttctcctgtt ccatttctcc tttctattcc 5880
tggagaagtt aggaatctgt tgttctcctg ttccatttct cggtgcagta ttagttgcag 5940
aacaggaatc cacttgattt gtcagtttaa ttatgcttgt gtcacctcag atgtgtcata 6000
ttgattatga ctgcattttt gtcagctgta atatgcgtgt tggcttgcat ttgtttctct 6060
ctttattagt actaccagca ttttcggtca gtattttttg tcttccttgc tgaagaatga 6120

-continued

```
gaaggaaagc tgtcatactc ctcgtcggga tagcttcatt tattaaggca gctgggcgac  6180
agaatatatg ggaatgtact tgaacttcac aaaaaagggc cttttcatcc cttgccgtgt  6240
cttccatgtt ggtaaaaagg ctagtagctg aattgaatag tacgtgctca ttttaactac  6300
cctgaggact agatagatct tgaagtttta tttgtttatt tctttttatt tctgcttata  6360
tagatgtagg atgtagccaa atggatgctt ctcagctcac attgaacatt aatgtttgtg  6420
ttgtttgctg aaaggttttt tactgtagca gaaggttaca aaataacaga tcttacctca  6480
aaaaagggct gcaatgtata tatactggca ctgaaccgcg tatgcgcagt gcaacctgct  6540
gattggtttt gtactggtcg gatctgtttg caggatgcat ttgacttgaa gcccccgaaa  6600
aaatcaccga tcgcgttgag aacggttgtc ttcgctatga ctatgttatg cgggatatct  6660
atttgctcaa tgtgcatgaa gcaactaggg agtgatggct ggtcaagagt tgtcaagatt  6720
gaagttgtgg aacaaccatg taataagtcc attgctcctc tttcggaggc tcaatttgtg  6780
cgctatcctc aaccgataac ttacagcagg tgagatctgc actgtggtaa gattgagcaa  6840
tctcgtttgt ttaatgccta atgcataatt ttttatttct agggaggaat gcaagtgcaa  6900
tgctgtccgg tcctttgcaa ttatatcatc gcagcgatct ggaagtggct ggtttgaaac  6960
acttcttaac agccacatga atgttagctc caatggtgaa attttctcta gaaaagaaag  7020
gaggagtaac atttcctcta taatagatac cctggataaa gtgtacaatt tggactggaa  7080
cagtagcgct tccaagaatg agtgcactgc agctattggc ttcaagtgga tgctaaatca  7140
ggtgcggact aaaacatgca gtatagataa tttatttgga tgatcctttt tcatttattt  7200
ttccatttag ttccagtatg tttcaattat tagtatgtgt agtctcctaa acggcctaca  7260
tgttctcaac tgtagatgct aaatgttatt gcatattgcg ccaaactttc ctcaagtcca  7320
tgtaactatt ttttttgggg aatccacttt agggcttgct cgttttagtg ccaatccatg  7380
tggattggac gagattggat gagtttaaat ccataagaag tcaaaatcct tcttaaaatt  7440
ttccaatctc ttccaatcca tgtgggatgc gaataaccga acaaggcctt atggaactgt  7500
cggtagctag tttagttttc tgacttgctg tcagatcctg cattttagac aaattttctc  7560
tctctcgaac atgcatgaga actgcaaatg catatggagt aatatttgat agattctgta  7620
gtgtgtccag tagactgatt ataatctaca tgtcaagcat gtttgtttca gggcttcatc  7680
taatttgtgc gagaacgaac ttttttcctg gtagacagat tgcctaacca aaccatgaat  7740
attggccaaa cataggttta gagactggaa acaaaacagg cattgtagct agagagtgga  7800
aacaaaggag catttcttct gaacggggtt ggggtgtatg ttttcagggc ctcgtggcaa  7860
accatgcgga cgtagtcgac tacttcaacc gaagaggagt ctctgcgata tttcttttca  7920
gaaggaacct gctccgccag ttggtatcac aggtagcgaa caaccacgac aggttactta  7980
agcaactaaa cggaacgcac aaggcccatg tccacacgaa gcgtgaggtt agtaatgcta  8040
gctaagaaac ggatatggca gcaagtctct gagctgatct gatctctctc tgtgtttgac  8100
gtgtcgttcg ttctcgctcc acaggcccat atactggcaa gatacaggcc caggctcaac  8160
acgacgtcac tgatatggca gctgaaacga gctgacgagt acactcgcga cgctcttgag  8220
aacctaaaca acacccggca catgagcgtc tactacgagg acgtcgtccg caacagaaca  8280
gtgcgttctc gctgatgccc ttcccttgtc tgttcccttc cgttggttgt gtcgcttacc  8340
atcgctgctg cactgcagaa gctcttggat gtcctggatt tcctcggagt gccgaggagg  8400
aagctggtga gccggcacgt gaagatacac acgaagccgc tgtcggagca gatcgagaac  8460
tgggacgagg tctacagcgc cctcaacggt acccagtacg agggcttcct gaatgccgct  8520
gactatctag tataacatca cgtttctgga tgtagatagt gtgcgtgtga ttctttcgtt  8580
tcttgtttgt ttctggcaga aattttgatg cggggtaggc gccttttgcc gtgcatggtt  8640
gcattctcgg taacctgatg ctcctgtaac taaccctcca gcttctctga tctttgtatt  8700
tgccttgggt gtttgctgat gttctttcaa actatttgaa atcgggctgt cggagttcca  8760
gatcccgggc ggcaggatag ttgatgtgac ctagataaat gtacaagaca catcacaaat  8820
atataaaata tttctgtagt atcctcacaa atatatcaaa aatatttctg tagctcttat  8880
tacatgatac tctactatgc aaccaacaga agcaatatct cctcagggag cttttgcttt  8940
attgccaaat taaattaaga aatgttctat gggactacta caacggaaaa taagactaca  9000
agatcacctc agggagcttt tgctaactac ctgcaatatc aaggtgcagc agttagtcaa  9060
attgcacaac agttgtaaaa ggaaaaaata caacttaatt aggcctagct gaatatgcga  9120
ccatattaca gtttgataat agcaccttat actggttagc tcctactgcc agctagtaaa  9180
agaatcaatt tgagttgaga tatattcggt gttttgagtc ttacaaggtc tagatttctt  9240
atgcgagctc cagaacaaga gctgatgctc cgcctccacc gttgcagaca ccagcaactc  9300
cgatcttgcc actcttcgcc ctgagaacct gttaacaaga aacaatgatt aggagggtca  9360
agcacaatat attttgatgt cccaacatga tggcactata ttgtgcccaa cgttttgctt  9420
aaagaaaatg aagagaaaaa gaaactattg atcaccagca acaagtgaaa caagggatga  9480
gccgatatca atgtgaaact ctacatttgc agctttatac aagattctat ttgcagataa  9540
tttgcacatt ggaaatcact aagggcttgt tcggttgcga gaggattgga ggggattgag  9600
ggggattaaa tcccctccta ttcaatttta actagaaggg gatttaatcc ccttcaatcc  9660
ccctcgaacc acttgtaacc gaacatggcc taaggtagtg tttggtgcag ggatggggtg  9720
gcttgatcca acatactccc tatgtttcaa attataagat gtttttactt tttctagatt  9780
tgtagttttt attgcgataa acattatgtc tcagtacacg tagtaaaa             9828
```

```
SEQ ID NO: 49          moltype = DNA  length = 11900
FEATURE                Location/Qualifiers
source                 1..11900
                       mol_type = genomic DNA
                       organism = Zea mays
SEQUENCE: 49
gatataatga aaaaaccaat taaaaacgtg tctcgatatg cgtgcacgag taaagagctg  60
gctgagcgga gcctggccgc gcgcgtgcgg tcgcgcgatg cgtttctgcc gggcctggct  120
cgcggcgctt taagttccgt gctagcctgt ctcgtgcgat acaacgaacc aaacaaacac  180
tactttttgc atgtgtagat gcagctgcac cactggagaa ggcaaccaaa cgccccctaa  240
ggcagctggg cgacagaata tatgggaatg tacttgaact tatcaaaaaa gggccttttc  300
atcccttgcc gtgtcttcca tgttggtaaa aaggctagta gctgaattga atagtacgtg  360
ctcattttaa cttccctgag gactagatag accttgaagt tttatttgtt tatttctttt  420
tatttctgct tatatagatg tagccaaatg gatgcttctc agctcacatt gaacattaat  480
gtttgtgttg tttgctgaaa ggttttttta ctgtagcaga aggttacaaa ataacagatc  540
ttacctcaaa aaagggctgc aatgtatata tactggcact gaaccgcgta tgcgcagtgc  600
```

```
aacctgctga ttggttttgt actggtcgga tctgtttgca gratgcattt gacttgaagc  660
ccccgaaaaa atcaccgatc gcgttgagaa cggttgtctt tgctatgact atgttatgcg  720
ggatatctat ttgctcaatg tgcatgaagc aactagggag tgatggctgg tcaagagttg  780
tcaagattga agttgtggaa caaccatgta ataagtccat tgctcctctt tcggaggctc  840
aatttgtgcg ctatcctcaa ccgataactt acagcaggtg agatctgcaa ctgtggtaag  900
attgagcaat ctcgtttgtt taatgcctaa tacataattt ttaatttcta gggaggaatg  960
caagtgcaat gctgtccggt cctttgcaat tatatcatcg cagcgatctg gaagtggctg  1020
gtttgaaach cttcttaaca gccacatgaa tgttagctcc aatggtgaaa ttttctctag  1080
aaaagaaagg aggagtaaca tttcctctat aatagatacc ctggataaag tgtacaattt  1140
ggactggaac agtagcgctt ccaagaatga gtgcactgca gctattggct tcaagtggat  1200
gctaaatcag gtgcggacta aaacatgcag tatagattta tttggatgac cctttttcat  1260
ttatttttcc atttagttcc agtattgcat attgctccaa actttcctca agtccatgga  1320
actatttttt tttgggaatc cactttaggg cttgctcgtc ttagtgccaa tccatgtgga  1380
ttggacgaga ttgaacgggt ttaaatccgt aagaagtcaa aatccttctt aaaatttttcc  1440
aatcccttcc aatctatgtg ggatgcgaat aaccttatgg gactgtcgga tagctagttt  1500
agttttgtga cttgctgtca gatcctgcat tttagacaat ttttttctct cgaacgtgca  1560
tgagaactgc aaatgcatat ggagtaatat ttgatagatt ctgtagtgtg tccagtagac  1620
tgattataat ctacatgtca agcatgtttg tttcagggct tcatctaatt tgtgtgagaa  1680
caaacttttt tcctggtaga cagattgcct aaccaaacca tgaatgttgg ccaaacatag  1740
agttagagac tggaaacaaa acaggcactg tagctagaga gtggaaacaa aggagcattt  1800
cttctgaacg gggttggggt tggggtgtat gttttcaggg cctcgtggca aaccatgcgg  1860
acgtagtcga ctacttcaac cgaagaggag tctctgcgat atttcttttc agaaggaacc  1920
tgctccgcca gttggtatca caggtagcga acaaccacga caggttactt aagcaactaa  1980
acggaacgca caaggcccat gtccacacga agcgtgaggt tagtaatgct agctaagaaa  2040
cgtgttcgcg gctaatgtct cactctcaca gcaagtctct gagctgagct gatctctgtc  2100
tgtgtttgac gtgtcgttcg ttctcgctcc acaggcccat atactggcaa gatacaggcc  2160
caggctcaac acgacgtcac tgatatggca gctgaaacga gctgacgagt acactcgcga  2220
cgctcttgag aacctaaaca acacccggca catgagcgtc tactacgagg acgtcgtccg  2280
caacagaaca gtgcgttctc gctgatgccc tttgtctgtt cccttccgtt ggttgtgtcg  2340
cttaccatcg ctgctgcact gcagaagctc ttggatgtcc tggatttcct cggagtgccg  2400
aggaggaagc tggtgagccg gcacgtgaag atacacacga agccgctgtc ggagcagatc  2460
gagaactggg acgaggtcta cagcgccctc aacggtaccc agtacgaggg cttcctgaat  2520
gccgctgact atctagtata acatcacgtt tctggatgta gatagtgtgc gtgtgattct  2580
ttcgtttctt gtttgtttct ggcagaaatt ttgatgcggg gtaggcgcct tttgccgtgc  2640
atggttgcat tctcggtaac ctgatgctcc tgtaactaac cctccagctt ctctgatctt  2700
tgtatttgcc ttgggtgttt gctgatgttc tttcaaacta tttgaaatcg ggctgtcgga  2760
gttccagatc ccgggcggca ggatagttga tgtgacctag ataaatgtac aagacacatc  2820
acaaatatat aaaatatttc tgtagtatcc tcamaaaatat atcaaaaata tttctgtagc  2880
tcttattaca tgatactcta ctatgcaacc aacagaagca atatctcctc agggagcttt  2940
tgctttattg ccaaattaaa ttaagaaatg ttctatggga ctactacaac ggaaaataag  3000
actacaagat cacctcaggg agcttttgct aactacctgc aatatcaagg tgcagcagtt  3060
agtcaaattg cacaacagtt gtaaaaggaa aaaatacaac ttaattaggc ctagctgaat  3120
atgcgaccat attacagttt gataatagca ccttatactg gttagctcct actgccagct  3180
agtaaaagaa tcaatttgag ttgagatata ttcggtgttt tgagtcttac aaggtctaga  3240
tttcttatgc gagctccaga acaagagctg atgctccgcc tccaccgttg cagacaccag  3300
caactccgat cttgccactc ttcgccctga gaacctgtta acaagaaaca atgattagga  3360
gggtcaagca caatatattt tgatgtccca acatgatggc actatattgt gcccaacgtt  3420
ttgcttaaag aaaatgaaga gaaaaagaaa ctattgatca ccagcaacaa gtgaaacaag  3480
ggatgagccg atatcaatgt gaaactctac atttgcagct ttatacaaga ttctatttgc  3540
agataatttg cacattggaa atcactaagg gcttgttcgg ttgcgagagg attggagggg  3600
attgaggggg attaaatccc ctcctattca attttaacta gaaggggatt taatcccctt  3660
caatccccct cgaaccactt gtaaccgaac atggcctaag gtagtgtttg gtgcagggat  3720
ggggtggctt gatccaacat actccctatg tttcaaatta taagatgttt ttactttttc  3780
tagatttgta gtttttattg cgataaacat tatgtctcag tacacgtagt aaaagctata  3840
aatctaacaa tgccaacatc ccaagacgtc ttataatttg ggatagagga agtagaccta  3900
gtagcaatag tgaagatgct tactgttcat cacgaaccct atgatgatat ggtaacatat  3960
gtcagaattc attatttact caaagaccat ctattttttt actagaaaaa cattgcacat  4020
tttttttaaa caaaagggat tgtaactcaa aaggtaaaac aagcatctta agatagaact  4080
tacaccaata agggtaacca aaatgcgagc accactgcac ccgagaggat gtcctaagga  4140
tacagctcct ccatgaacat taatcttttc ctgcaaacac atatgctgtt agtacagata  4200
atactgttat aatgcaatta cacgttgctg ctgcatagca aataacaaaa aagagacaat  4260
atgtactttc tgaaagtgat tgtttaactt ctaaaatcca caaagaatgg cagtttaata  4320
caggtgacac ttactgaagg aattccaaga agtttttgat ttgcaagcgc aacagcctat  4380
attgacaagt aaaaaagaca ttattacaaa aaaagtaata agtaaaataa actctcaatg  4440
cataacaaaa ggcttacaaa aaatgtgagt aaaagaaact caatgcatac cgaaaaggct  4500
tcattaatct catagaaatc aacacgggat gactctaatc cagcatttgc gatagccttt  4560
ggtattgcaa gtgctggagt ggttgtaaaa agctccggag cctgtataaa cagcatccac  4620
attacaaaat aatattccag atcacaagtt ccaatagttg ataaatttcg atatctaaaa  4680
tagtaacata aaatcgttcc agataaaaat aacttcctat atcctaaaat atttagatca  4740
cagtgtaaat tagaataagc gcattctact cttaggagag ctaacaattg tttctgtggc  4800
ttacttgagc tgcatcagca taacctttga tccttgcaag gacttgaagg ccaagctctt  4860
gagccttctg cccactcact aaaactaatg cagcagctcc atcactgatc catataaaac  4920
aaattagatg actggttgca gaaggctaca caagccatag taggcagtac accggacagt  4980
acttgtcagc taaaaataga cacagtacaa agtgagacaa acaaggtcta gggcaaccat  5040
gaagaaattt aaaaggtagg gcaacttttg ttgtttgaat gggcataata aggcatttaa  5100
aatgttttta ctttcttatg tgatattgtg ataaatcatt cacaccaatt gggtaccaaa  5160
tctaaagaaa aaattaccat ctatttaacg gagtagagca tacccaagca gtctaaaaac  5220
aaatagagaa acaatgaagt tgacaaaatg caagcataat atatcagtta aaaatgcatg  5280
cataatacaa taatataatt taactgtcaa caatgaaata ggttgtcctt catatctgtc  5340
```

-continued

```
agctaaacaa catatggccg aaaaacaagg tctcagaaag actttgtagg acaaaaggcc  5400
tcagaaatat ttcaagcagc taccttatac tagaagcatt tccagctgta actgtaccac  5460
cattctcctt gaaacttggg cgaagtttct ttagttttac tgggtcaaac taagacacaa  5520
aaggaatagc acaagacata aataaaactg tcatgcattg atcttacaaa taactgctag  5580
caaagctcat tatgcaagga acgttgcatt tggaggaagc aagaacaata aatcaaagtg  5640
cctgccagtc tttttgcctt tgatcaacta caagctttat tttgttaaaa atattttgtc  5700
acgtcagaaa aaatacctta tccaggcttt catctctctc aattaatgtt gggggttttc  5760
ctctaccaac aggaacttga acctgggtga caacactgac catcagaaaa ccaagaaaag  5820
catgtctagt atcatcaatg agggagaaaa ttaccggaat aatctcccat gcaaaagcac  5880
cactgtcacg agcagcaatt ccacgctcgt tgctttggat agcaaatgca tcctattcaa  5940
gaataagtaa aattaaatat accagaaatt ggaaatatat ttattgcaat atagacaaaa  6000
ataaattgca acatataagt gaaaattaaa aggcaactca attttaatta tactatatca  6060
aatttattaa gaaaaaaatt acataaacag atacagtaaa atcatcaagg tactagtgtc  6120
atgtactgat gagcagcttt taagagatta tacttgtata gctctaacag gaatacaaaa  6180
gagtgctcat ttttgtgtgg cacatctact ttcatctctg gaagcagatg aatggtcagt  6240
tcacagaccc agagcatgca taaaagccca ccctatcaat catgtcacaa cataacagaa  6300
aatcattgct agaaaggatc caagttacta gttcatcaga caaggaatgc agatgctggt  6360
ctagagtctc tagaccattt atgatgatga ccaagataaa gcacgaagat tccagggcag  6420
tctcaaaaga attgccagca ttgacatgtt gtatagcaca acttatatct tgaaaaatat  6480
gggaatatta taacaaacag catttactgc tatctgtatt aagagacctg gtcttctctt  6540
gtgagggcat ggttgtcagc acaaagctcg gcacacattc ccatggcaca atcattgtat  6600
acatcccaaa gcccatcctt aagcatggca tcaacaagtg tgtcatgacc aaaacgagac  6660
cccttcctgc aattgtaatt agcaagctta taagcagttg aaatgcactt taaacatgaa  6720
cagaatatac tttcacaaca aaactggcca cttcgttaat agcctcgctg ctggtgaatc  6780
aacatttctt acaaacaaat ttagaaaatg caatgaagat aagtaagcat gcatgtatct  6840
accaaataac ttaagactat catttggttt atgcagctcg atattgaata tatccaccaa  6900
gtaataattg catacctagc ttcagcaatg tactttgggg cattggacat gctttccatg  6960
ccaccagcca caacaatatc attgataccc aattgaattg actgtgctgc aaacatagta  7020
gctgcatata ggaaaggaaa acaagagcat ggtcaggtaa tctctcactt ctgtgaactc  7080
tgagcagagt acacaaggac agacagataa attcgattca aacctttcat gccagatgca  7140
cagactttgt taacagtggt gcaaacaaca gagtttggta tcccggcacc cagagcagct  7200
tgccttgcag gagcttgccc caaattagca ctcaagacgt ttccaaagta gacctcctgc  7260
acgagggctg gatccacgtt tgctctttcc agagcagcta acagccccca gccatgacca  7320
tgttcagagc tcggatgtaa atgcagagaa gattcggatc tcaccttgaa ttactataga  7380
gccaagtttc gtagcaggca agggagacaa ggcaccaagg aaaccgccca ttggggtgcg  7440
tgcaacccca acaacacata catctgtgag caaggaagaa aaagttactg actgtagaac  7500
aaagcagaac catctagtgt gcacctcaca gtatatctat agtactaatt tgtaaaccgc  7560
gctcaaaatt ccatctgatg gtacaaacca aacacacatg aaaagcacat actgtactag  7620
taccagtgaa tcacttgttc caaatggcgc taaaacaaca atgatggcag taccctctgt  7680
gcaacccgaa aaggcaaaaa cacaaattgt ggtaatcata taaacgtatt tcgcagtagc  7740
aatgaacttt ggaaaacaat ggattcaatc aagcaaacgg acgagatcac gagcatggag  7800
cagctaggat gccctaatgg atgcagacag gcactagaat taaacagaaa agcgtcaaat  7860
ttcggccttg caaggtaccc aaaaaaaaaa caagaattcc caatatgtca gatcgctgga  7920
agcgcaatgg cgtgctcata gcccaaaatc tatatttgta cctcctctcg gcggtttgac  7980
gtctgtctgt ttgaacacaa agaagagatg aaacagttat acctctgggg ccgatgccgt  8040
cggaagccat ggccgccggt ccgaagtgcc aaaaccaacc gacctgcgaa tcaggggcgg  8100
gcccagtgaa aaatggtcag atccgaatac aaatactaga tttggggagt tcggggtgtt  8160
tgaattctcg cagaaggagc agaagggacg gcatacctgg aatatgctgt cgccggcgaa  8220
gcggcctgat cgaatggcgg cgccggcgcg gcgctaggga aagaaaggca gagaaagaca  8280
gtgtgtgcgc ggggggcgct ggggacaggt tgaagcggag gaagaaaaga gcaagtaggg  8340
aacgcaacac ccaacagcca aatcacccga atgtaatttt tcctaaatct ataatttatt  8400
ttattttta atctatacaa tatatagata tataataaaa ttaataaatc ataaaaatta  8460
aagctgaatc agagaaagta ctaaataaaa taggctttat gttaggcaaa aaaaaagtaa  8520
aaatagaaca attcaattca ctatatgcca ctgtaatttt gtgtaatacc ttattcatcg  8580
tacctcgtat gttactcgaa ttcaatatct cactcttaca tgtcgtggcc aaatgttaaa  8640
tgtaaaatgt tgtatgtctt agtcccttac tatgacatga aagagtaaaa aattgtattc  8700
gggtgacgta aaaaggatta gaacatttat gataacaaat aagatactag acgagtgaca  8760
tacatgatat aattttatct ctaaacctaa tgaaactaat aaaaaatgtc aattgatatc  8820
gtttgcgttt gctaatcacc tcgaacaatc atcctcgcgg gcatgtggtt aaggctagaa  8880
aaaaaacttg aggctcacga gtcagatcaa gttcggagcg tctgcgagcg agctagttgt  8940
accaaattaa tcaatatgta gaataatgat agatattaga taatttatag atagtcggct  9000
tatttcttag cctttgatga taaatataag ataattcata atggtgaata atatttttat  9060
attttatgtt tatatattaa taatttacta tataatgaaa taatatatat cggggtgtag  9120
ctcgcgagcc gacttcgagc tgagccgagc ctaactctct agctcgtgaa atggacgagc  9180
cgagtcaagc tcggctcgac tcattttcta cttgtggtcg accaggtcta ggtagtcatg  9240
aaccgcaacc aatctgtcag ttttatcgat tgttttagat catgttaggc gagtgccggc  9300
gcttggctct actgcccgcc cacccatgtg gcacaaccaa atggtcagta tcacccgaca  9360
tggtgccagc actaatagcc tcgcttgtgg ttgtcgaggc tactgatcgg ccgccagggt  9420
tactattgac cgtgttggga ccgcgtcggt cgatactgac tggttggtac tgaacagcta  9480
ttgcggccat gtcgataacg atcgcctctt gccatgtggc aggttctaat tgcttcgctt  9540
tattttgatt ttttttcaaa aataaaaaaa ctagaacttg gtctataaat agaggagtgt  9600
ttgatctcat tcacacaacc cacacttcaa atttctctac cacccctat aatcctctta  9660
cactcgtttc aatcaaatca agcattgttg tgatgttttc gttcagcttg gacatcaata  9720
tgactgaaaa gagttattca agttattaca acaaaatata atgcaacagg cgtcagagct  9780
tggatccgag tctcctaggt cgatgaggtg gccaaggcaa catcagagat acattgactg  9840
cgactatgta gttgcatacg accggttaat gcaagaccat ttcaacgacc tgtgtgtcta  9900
cccactgctc tacttttgtc aaagttaccg catctagaga agtctcttcc ttcatatctt  9960
agagagattg ggtgagcact tcccatactt cactttttga accgatgcat tcaaccgcag  10020
tgtttcctcc cccaccagaa gtgcacaatt ggcctaagca tgcttgcgta ctgtagcatt  10080
```

-continued

```
gctgactcca tcgatgagta catcaaaatg aggaaagttc cacctcagag tgccttggac  10140
tattctgtgt gaaagggtcc ctagttaagt tggttaggtc gtctgagtag cactcctcag  10200
gtcctaagtt tgaatcccgg tgggagcgaa ttttaggctg aggttaacaa ggtcactcac  10260
tagtttccct agttgtgtgc acatgagatg ggctgaccta tggggcggat cctcgtgtaa  10320
gggctagtag ggctcaaagc acgagtaaag atctggccta tagggggcgg actctcatgt  10380
tgcatggggg gaggggtaca tctttcgtga cctttctcga tcagggctcc gattaagctt  10440
cttcttaccg tgggggcagt atttccccta cgagtggagt tttggtctta ttctgtagag  10500
gtggtattgc atgtttcagg gcggagtaca attatcatgc cattgtcaat gacttaggct  10560
tatcttagct aaggaggtgg aaaggggatt ttctattatg atattgagta tagattgcat  10620
gcattggaag tggaggaaga agacatttta caagggggat attggttctc catccatcat  10680
gctcgagaca gttgcctcgt atgacttgtg gatctgacat atttttatga atctattaaa  10740
atgctaaaac ggttagtatt ttaggacgga gggaattatt ttttggaata tttttgtagc  10800
aacctaaaca tagttcatct atgcttagtt tggggggtgg gatggttagg cctagaagct  10860
actgttgaat taatgagggc ctaacccaaa ttaatattca ataatagtca atgctaaagg  10920
cccactttaa tgctacggtg tactagtact ttagtaccat accggaagta caagggacaa  10980
ttcaatcaac ttaaataggc ggatctttgg tgcatctagt gagaagttga gaaaatgatg  11040
aaggactgcc acacgcgcgc gccgccgggc cgtggccgtg gtagatcgga ccttggtccg  11100
aatattcctt cctaacggtt gcacattttg cctaaagtga tgaccgtcca ttactgttgt  11160
acgttattgg tcgtttccta tgttatggat agtaacgaac gagttataat gcttgtcagc  11220
tattaacgga cgtcactaat ggcgtccgtt tctggctggc tgtaatgata gctctgatgg  11280
tgaccgttac tatccgttcg cctccctctg ctcgtttata tatacaaagg aggtgaggct  11340
gcttctggtt acgagagaac acacgtacaa ttcttagacg cgttgcgtac agcccatccc  11400
tggttgaacc tctctaaacc ccggttgaac ttttcctgga ccccagttga acctctctgg  11460
accccggttg aacttgcctt ggaccccggt tgaacctgcc tggaccccgg ttgaacttga  11520
ctggacccca gttgaagttg aagttcaact ggagttgaga aagctcgaca cagctgaagt  11580
ttagctcagc tgaaaagctc aactgcagct gaagaagctc aactcagctg aagtttagtt  11640
cagctgaaaa gctcagctgc ttttcaacaa aaacactcta ggtttctcaa acctaaccat  11700
agtcaaccat agaattttaa agagattttt gattttcaaa aaatagcttt tgaatataga  11760
ggcttgagct ttggcaaaca ccaaccttat ttttggatcc ccttggtagt acgatgaatc  11820
ctatactcaa tttaagtaaa atataattaa gtaaactcct tgagtaattg gtgtctcatg  11880
tgtgatttct ccatggcgtt                                              11900

SEQ ID NO: 50          moltype = DNA  length = 3571
FEATURE                Location/Qualifiers
variation              1933
                       note = n is a, c, g, or t
source                 1..3571
                       mol_type = genomic DNA
                       organism = Zea mays
SEQUENCE: 50
ggagggggag acggtgaggc gcggccatgg ggggcgccaa ggcggaggac aaaccggccg  60
ccgctgcaga agattggtgc taccaatttg gaaacaaggt tcgatttctt caccatttgc  120
actcctctgc aagactggga cacgtttccg ggtttcgttc tgcctgggcg gcgacaaatc  180
tcatggcaaa ttgcctttgg ggggctcatt ccctgggttc acactccaaa tccttccttg  240
cgaccttctc tcagccgtcg cgctttccgt ggcaagcctt ttggaaccct gatctgaagt  300
gtcactcaga tcaatgcagt cgcattgatt ctattcgttt cctgtttccg tttcccctt  360
ttaacgtgtc tgctagttcc aagtcccgag cgttttccgt tctctgtttc agaattgaag  420
cttgttaagt tctgtttttt tttacaatcc ttcgtttttg tcccagtcct ttctattcct  480
ggagaagtta ggaatctgtt gttctcctgt tccatttctc ggtgcagtat tagttgcaga  540
acaggaatcc acttgatttg tcagtttaat tatgcttgtg tcacctcaga tgtgtcatat  600
tgatgatgac tgcatttttt tttcagctgt aatatgcgtg ttggcttgca tttgtttctc  660
tctttattag tactaccagc attttcggtc agtatttttt gtcttccttg ctgaagaatg  720
agaaggaaag ctgtcatact cctcgtcggg atagcttcat ttattatggc agctgggcga  780
cagaatatat gggaatgtac ttgaacttca caaaaaaggg ccttttcatc ccttgccgtg  840
tcttccatgt tggtaaaaag gctagtagct gaattgaata gtacgtgctc attttaacta  900
ccctgaggac tagatagatc ttgaagtttt atttgtttat ttctttttac ttctgcttat  960
atagatgtag ccaaatatat gcttcttcag ctcacgttga acattaatgt ttgtgttgtt  1020
tgctgaaagg ttttttactg tagcagaagg ttacaaaata acagatctta cctcaaaaaa  1080
gggctgcaat gcatatatac tggcactgaa ccgcgtatgc gcagtgcaac ctgctgattg  1140
gttttgtact ggtcggatct gtttgcagga tgcatttgac ttgaagcccc cgaaaaaatc  1200
accgatcgcg ttgagaacgg ttgtctttgc tatgactatg ttatgcggga tatctatttg  1260
ctcaatgtgc atgaagcaac tagggagtga tggctggtca agagttgtca agattgaagt  1320
tgtggaacaa ccatgtaata agtccattgc tcctctttcg gaggctcaat ttgtgcgcta  1380
tcctcaaccg ataacttaca gcaggtgaga tttgcactgt ggtaagattg agcaatctcg  1440
tttgtttaat gcctaatata taatttttaa tttctaggga ggaatgcaag tgcaatgctg  1500
tccggtcctt tgcaattata tcatcgcagc gatctggaag tggctggttt gaaacacttc  1560
ttaacagcca catgaatgtt agctccaatg gtgaaatttt ctctagaaaa gaaaggagga  1620
gtaacatttc ctctatagta gataccctgg ataaagtgta caatttggac tggaatagta  1680
gtgcttccaa gaatgagtgc actgcagcta ttggcttcaa gtggatgctg aatcaggtgc  1740
ggactaaaac atgcagtata gataatttat ttggatgatc ctttttcatt tattgttcca  1800
tttagttcca gtatgtttca attattacta tctgtagtct cctaaacggc ctacatgttc  1860
tcaactgtag atgctagatg ttattgcata ttgcgccaaa ctttcctcaa gaccatggaa  1920
ctttttttt ttntttttt ttttggaaac cactttaggg cttgttcgtt ttagtgccaa  1980
tccatatgga ttggatgggt ttaaatacat aagaagtcaa aatccttctt aaaattttc  2040
aatctcttcc aatccatgtg ggtgggatgc gattccaatc catgtgggat gcgaataacc  2100
gaacaaggcc ttataggact gtcgaatagc tagtttagtt ttctgacttg ctgtcagatc  2160
ctgcatttta gacaatttct ctctctcgaa catgcatgag aactgcaaat gcatatggag  2220
taatatttga tagattctgt agtgtgtcca gtagactgat tataatctac atgtcaagca  2280
tgtttgtttc agggcttcat ctaatttgtg cgagaacaaa ctttttcct ggtagacaga  2340
```

-continued

```
ttgcctaacc aaaccatgaa tattggccaa acagagagtt agagactgga aacaaaacag  2400
gcactctagc tagggagtgg aaacaaagga gcatttcttc tgaacggggt tggggttggg  2460
gtgtatgttt tcagggcctc gtggcaaacc atgcggacgt agtcgactac ttcaaccgaa  2520
gaggagtctc tgcaatattt cttttcagaa ggaacctgct ccgtcagttg gtatcacaag  2580
tagcgaacaa tcacgacagg ttacttaagc aactaaacgg aacgcacaag gcccatgtcc  2640
acacgaagcg tgaggttagt aatgctagct aagaaacgtg ttcgcggcta atgtctcact  2700
ctcacagcaa gtctctgagc tgagctgatc tctgtctgtg tttgacgtgt cgttcgttct  2760
cgctccacag gcccatatac tggcaagata caggcccagg ctcaacacga cgtcactgat  2820
atggcagctg aaacgagctg acgagtacac tcgcgacgct cttgagaacc taaacaacac  2880
ccggcacatg agcgtctact acgaggacgt cgtccgcaac agaacagtgc gttctcgctg  2940
atgccctttg tctgttccct tccgttggtt gtatcgctta ccatcgctgc tgcactgcag  3000
aagctcttgg atgtcctgga tttcctcgga gtgccgagga ggaagctggt gagccggcac  3060
gtgaagatac acacgaagcc gctgtcggag cagatcgaga actgggacga ggtctacagc  3120
gccctcaacg gtacccagta cgagggcttc ctgaatgccg ctgactatct agtataacat  3180
cacgtttctg gatgtagata gtgtgcgtgt gattctttcg tttcttgttt gtttctggca  3240
gaaattttga tgcggggtag gcgccttttg ccgtgcatgg ttgcattctc ggtaacctga  3300
tgctcctgta actaaccctc cagcttctct ggtctttgta tttgccttgg gtgtttgctg  3360
atgttctttc aaactatttg aaatcgggct gtcggagttc cagatcacgg gcggcaggat  3420
aggtgatgtg acctagataa atgtacgaga cacatgacaa atctatacta cttattaaaa  3480
gtgtaatagc agtctgccgt tctgccatcc tgcaacctca accgtccatt ccattgttct  3540
gcaatttcaa ccgttcgatc ccacccacca g                                 3571

SEQ ID NO: 51          moltype = DNA  length = 1896
FEATURE                Location/Qualifiers
source                 1..1896
                       mol_type = genomic DNA
                       organism = Zea mays
SEQUENCE: 51
ccaaggcgga ggacaaaccg gccgccgctg cagaagattg gtgctaccaa tttggaaaca  60
aggttcgatt tcttcaccat ttgcactcct ctgcaagact gggacacgtt tccgggtttc  120
gttctgcctg ggcggcgaca aatctcatgg caaattgcct ttggggggct cattccctgg  180
gttcacactc caaatccttc cttgcgacct tctctcagcc gtcgcgcttt ccgtggcaag  240
ccttttggaa ccctgatctg aagtgtcact cagatcaatg cagtcgcatt gattctattc  300
gtttcctgtt tccgtttccc ccttttaacg tgtctgctag ttccaagtcc cgagcgtttt  360
ccgttctctg tttcagaatt gaagcttgtt aagttctgtt ttttttaca atccttcgtt   420
tttgtcccag tcctttctat tcctggagaa gttaggaatc tgttgttctc ctgttccatt  480
tctcggtgca gtattagttg cagaacagga atccacttga tttgtcagtt taattatgct  540
tgtgtcacct cagatgtgtc atattgatga tgactgcatt ttttttcag ctgtaatatg   600
cgtgttggct tgcatttgtt tctctcttta ttagtactac cagcattttc ggtcagtatt  660
ttttgtcttc cttgctgaag aatgagaagg aaagctgtca tactcctcgt cgggatagct  720
tcatttatta tggcagctgg gcgacagaat atatgggaat gtacttgaac ttcacaaaaa  780
agggcctttt catcccttgc cgtgtcttcc atgttggtaa aaaggctagt agctgaattg  840
aatagtacgt gctcatttta actaccctga ggactagata gatcttgaag ttttatttgt  900
ttatttcttt ttacttctgc ttatatagat gtagccaaat atatgcttct tcagctcacg  960
ttgaacatta atgtttgtgt tgtttgctga aaggtttttt actgtagcag aaggttacaa  1020
aataacagat cttacctcaa aaaagggctg caatgcatat atactggcac tgaaccgcgt  1080
atgcgcagtg caacctgctg attggttttg tactggtcgg atctgtttgc aggatgcatt  1140
tgacttgaag cccccgaaaa aatcaccgat cgcgttgaga acggttgtct ttgctatgac  1200
tatgttatgc gggatatcta tttgctcaat gtgcatgaag caactaggga gtgatggctg  1260
gtcaagagtt gtcaagattg aagttgtgga acaaccatgt aataagtcca ttgctcctct  1320
ttcggaggct caatttgtgc gctatcctca accgataact tacagcaggt gagatttgca  1380
ctgtggtaag attgagcaat ctcgtttgtt taatgcctaa tatataattt ttaatttcta  1440
gggaggaatg caagtgcaat gctgtccggt cctttgcaat tatatcatcg cagcgatctg  1500
gaagtggctg gtttgaaaca cttcttaaca gccacatgaa tgttagctcc aatggtgaaa  1560
ttttctctag aaaagaaagg aggagtaaca tttcctctat agtagatacc ctggataaag  1620
tgtacaattt ggactggaat agtagtgctt ccaagaatga gtgcactgca gctattggct  1680
tcaagtggat gctgaatcag gtgcggacta aaacatgcag tatagataat ttatttggat  1740
gatccttttt catttattgt tccatttagt tccagtatgt ttcaattatt actatctgta  1800
gtctcctaaa cggcctacat gttctcaact gtagatgcta gatgttattg catattgcgc  1860
caaactttcc tcaagaccat ggaacttttt tttttt                            1896

SEQ ID NO: 52          moltype = DNA  length = 1371
FEATURE                Location/Qualifiers
source                 1..1371
                       mol_type = genomic DNA
                       organism = Zea mays
SEQUENCE: 52
agttcatcac taatcacact tattgtgccc tcgacgagta tctatagcta gctcattaat  60
cgattcgggg gtgtgttgtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
cagaactgcc cgcgcatctt tcctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
```

```
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtctc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 53          moltype = DNA  length = 1458
FEATURE                Location/Qualifiers
source                 1..1458
                       mol_type = genomic DNA
                       organism = Zea mays
SEQUENCE: 53
agttcatcac taatcacact tattgtgccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacta cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggtaa gcgagacgct gaccaacgtc atcatccctg ccttcgacat caggctgctg  600
cagcctatca tcttctctac ctacgacgcc aagagcacgc ctctgaagaa cgcgctgctc  660
tcggacgtgt gcattggcac gtccgccgcg ccgacctacc tcccggcgca ctacttccag  720
actgaagacg ccaacggcaa ggagcgcgaa tacaacctca tcgacggcgg tgtggcggcc  780
aacaacccga cgatggttgc gatgacgcag atcaccaaaa agatgcttgc cagcaaggac  840
aaggccgagg agctgtaccc agtgaacccg tcgaactgcc gcaggttcct ggtgctgtcc  900
atcgggacgg ggtcgacgtc cgagcagggc ctctacacgg cgcggcagtg ctcccggtgg  960
ggcatctgcc ggtggctccg caacaacggc atggccccca tcatcgacat cttcatggcg  1020
gccagctcgg acctggtgga catccacgtc gccgcgatgt tccagtcgct ccacagcgac  1080
ggcgactacc tacgcatcca ggacaactcg ctccgtggcg ccgcggcaac cgtggacgcg  1140
gcgacgccgg agaacatgcg gacgctcgtc gggatcgggg agcggatgct ggcacagcgg  1200
gtgtccaggg tcaacgtgga gacagggagc gaggtacgaa ccggtgaccg gagaaggaag  1260
caatgccgat gccctcggtg ggctcgctag gcagctctcc gaggagagga gaacaaggct  1320
cgcgcgccgc gtctctgcca tcaaccccag aagctctaga tgtgcgccct acgatatcta  1380
agacaagtgg ctttactgtc aatcacatgc ttgtaaataa gtagacttta ttttaataaa  1440
atataaatat atatatat                                                1458

SEQ ID NO: 54          moltype = AA  length = 401
FEATURE                Location/Qualifiers
source                 1..401
                       mol_type = protein
                       organism = Zea mays
SEQUENCE: 54
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                      401

SEQ ID NO: 55          moltype = AA  length = 428
FEATURE                Location/Qualifiers
source                 1..428
                       mol_type = protein
                       organism = Zea mays
SEQUENCE: 55
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGR YEPVTGEGSN ADALGGLARQ LSEERRTRLA RRVSAINPRG  420
SRCASYDI                                                           428

SEQ ID NO: 56          moltype = AA  length = 372
FEATURE                Location/Qualifiers
source                 1..372
                       mol_type = protein
                       organism = Zea mays
SEQUENCE: 56
```

```
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINYFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VNPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGSEVRTGDR  360
RRKQCRCPRW AR                                                     372

SEQ ID NO: 57          moltype = AA  length = 399
FEATURE                Location/Qualifiers
source                 1..399
                       mol_type = protein
                       organism = Zea mays
SEQUENCE: 57
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINYFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGS EVRTGDRRRK QCRCPRWAR                         399

SEQ ID NO: 58          moltype = DNA  length = 2088
FEATURE                Location/Qualifiers
source                 1..2088
                       mol_type = genomic DNA
                       organism = Zea mays
SEQUENCE: 58
tatttgtact cattccatgt ctcataaact ttgggcacca tccatccaac acatccaatc  60
taaacacacc aaacgatggg gaatggaaag agcagtattc gattcaacaa tggcaaacaa  120
atatcactga attagaccaa gaataaacct aattagacaa cgacctccca accatcattc  180
gtcaggctgt aaagaagata aagctgcctt ggggcatgga tcaagcagaa caccagagat  240
gaatccaaac acacagaaaa tcacgcgcgc tgtctacaat gacaacaagc cccacatttc  300
attgcagtac actgggctac aaaggcacgt acaacaaaga gctagggaaa cattgcggag  360
ggcacgagag agcagctaac ttgacaatat agcagactga gcttgcactg ttagcaggcg  420
aggaagggaa tcatggggac ggagaatggg gtccatgccc gcgaaggaga aggcggacgc  480
cgccacggtg gcaccggcgc acgcgcacac agggaacccg cacaggcagc caaggatgct  540
gcctcgccat tgcgccggtc gtctctgcca cgctcctctc tctctcccgc tgcatcgccg  600
tggatggggc aagcagagag cagggactgc gacgatctgg gcggaggact cgccttggag  660
agcgcggacg cagacgggat tctagggaga gagcgaagac ggggcgcgcg cggcgctcgc  720
gcggcgtggt ggcggcgaga ttagcggggg tggggggagg gcggagccgt ggtgagggtg  780
tggacgccct ccttaccctc ttaagtagta gtagagatat aatccgttcc aaaatatcca  840
tccgttcaat ttatatttcg tttgatcttt ttaccctaaa tttgattgac tcatcttatt  900
aaaaaagttc ataactatta ttaatcttta ttgagatatc atttagcata taatatactt  960
taagtgtggt tttagatttt ttttaaaaaa aaaaattcgc aaaaattaaa tgaaacgacc  1020
caatcaaact tgaaaagtaa aactaattat aaatttgaac ggaaggagta agaggatgtt  1080
tgaatgtact agagctaata gttggttgct ttaaaatttg ctagtagaat tagctagcta  1140
ataaatatct agataactat tagctaattt gctaaaacag ctaatagttg aactattagc  1200
tagattgttt ggatgtattc ggctaatttt aatggctaac tattagctat agtacaatat  1260
tcaaacacct cctaattaaa atggacaaat atctcttctt ttggtccctt gcgttagatt  1320
tttcatatct ccttatttag tataaaagaa tcatcaaaaa gtggacaacc cctagtggaa  1380
caccatttta gtagtggttg catgaaacct ttcgcgcacc agtttctatg tgtcactcta  1440
aaaatgggac agcatgtacg tagtgcctat atatatacaa gtcatctatc gttgcctcct  1500
cagttcatca ctaatcacac ttattgtgcc ctcgacgagt atctatagct agctcattaa  1560
tcgattcggg ggtgtgttgt cgaaggcggc attggcgagc tactcgtcgc ggcgtccaag  1620
caatacctgt agcacgaagg cgatcgccgg gagcgtggtc ggcgagcccg tcgtgctggg  1680
gcagagggtg acggtgctga cggtggacgg cggcggcgtc cggggtctca tcccgggaac  1740
catcctcgcc ttcctggagg ccaggctgca ggagctggac gcaccggagg cgaggctggc  1800
ggactacttc gactacatcg ccggaaccag caccggcggt ctcatcaccg ccttgctgac  1860
cgcgcccggc aaggacaagc ggcctctcta ggctgccaag gacatcaacc acttttacat  1920
ccataactgc ccgcgcatct ttcctcagaa gtgagtccga tgctgccgcc attgttcttg  1980
catccatcca gcatcgtacg tacgtcctct atacatctgc ggatcatcat gtgcgcatgt  2040
ttgtggcatg catgcatgca tgtgagcagg agcaggcttg cgaaaacc               2088

SEQ ID NO: 59          moltype = DNA  length = 996
FEATURE                Location/Qualifiers
source                 1..996
                       mol_type = genomic DNA
                       organism = Zea mays
SEQUENCE: 59
gacaagtggc tttactgtca gtcacatgct tgtaaataag tagactttat tttaataaaa  60
cataaaaata tatatatgtt cttgaatata aaattgataa ccaaattaaa attcgaacca  120
tcacttatac ataattttac tttatttttt ataaaacgtg aacgggaagg actaccgtga  180
atgactatag aaccaatcat actagtataa aatatatgat gacactacgg gagagacaaa  240
ctttgtctgg cgctaaatat tttgccgagt gtgaattcac gggcactagg caaagatctt  300
ctttgccgag tgttacgctg ggcaaagtaa gacactaggt aaatcagtca tttgccgagt  360
gtccgccact aggcaaagca aaacactggc aaatcaaaag tttacctagt gccagacact  420
aggcaaaaaa aaaacgctcg gcaaatcgga agtttcccta gtgccagaca ctagacaaag  480
aaaaacactt gataaactag cgtcgtcagc taacaccatc caccaaccgt taacgttgcc  540
```

```
gagtatctga cttcgacact cggcaaagaa ggtctctttg cctagtgtcg gtctggaaca  600
ctaggcaaag aggcacttta cctagtgtcg tattttgaca ctcagtaaaa taattttttt  660
tctttctgct tccaaacttt ttatgatgtg ttcctatagc acctagaact acatgtcaag  720
ttttggtaaa atttttgaag tttttgctat atttacttaa tttattttat ttaattgaat  780
ttcttttgat aattcaaatt tgaactcggc aaggtaagaa gcgagggtag cctggaaaca  840
cactttgcct agtgttacac tcggtacagg agcctcccct gcctagtgct gcactcgaca  900
aaagattcgc ctttgcctag cgctgcactc ggcacaggag tcgcctttgc ctagtgctgc  960
actaggcaaa gcctccgtta ccgtgccttc catcgt                            996

SEQ ID NO: 60          moltype = DNA  length = 1089
FEATURE                Location/Qualifiers
misc_feature           1..1089
                       note = Synthetic
source                 1..1089
                       mol_type = other DNA
                       organism = synthetic construct
SEQUENCE: 60
ttgcgatggc gcagatcacc aaaaagatgc ttgccaacaa ggacaaggcc gaggagctgt  60
acccagtgaa gccgtcgaac tgccgcaggt tcctggtgct gtccatcggg acggggtcga  120
cgtccgagca gggcctctac acggcgcggc agtgctcccg gtggggtatc tgccggtggc  180
tccgcgtcga ctcgggagca tgccctttgt gcttatgcct ccgttctgcc ttctgacgaa  240
tttggtactg gaagcagatg agttttggtt cactatcatt ctgaatttac acctgcgctt  300
gctgtcagac taggcaacca agtgactttt gtgactttga tcatgttcag tgtgtttcca  360
agtcctaatc aatcaaaaag aaaaacagtt tgttaacgat tgtttgccat gtctatataa  420
taaagttgct tttatagtag cttagaattc aatcggccaa ctttatctcg tacgctgaca  480
gtaaaggtac atttaaaagg tgacaatgga tagtctaata cttgaactga caatagagac  540
acattacatg tcagttgatt aagtttgtaa cagaaaaata aacaatacta cataattgca  600
aagtttcttt gatgtctttc tttcaagaaa cacaaatata tcaatgctac agtattgctg  660
atgaatttat ccatgttgag atgtttttct ggtttctgat ctgatcagtc tcaattggtg  720
tgctgtttca ttttcatttg ctgatgatcg tccgagtagt taattcttac taatatttag  780
ataatttggc atacaagcga atcacgtaga acatgatact tttgaatgaa tttatcaaag  840
ttttatcact tggtgagttg tttcatggtt ttcctactga tgtctcttct tcagatttct  900
cgaggcggag ccaccggcag ataccccacc gggagcactg ccgcgccgtg tagaggccct  960
gctcggacgt cgaccccgtc ccgatggaca gcaccaggaa cctgcggcag ttcgacggct  1020
tcactgggta cagctcctcg gccttgtcct tgctggcaag catctttttg gtgatctgcg  1080
tcatcgcaa                                                          1089

SEQ ID NO: 61          moltype = DNA  length = 915
FEATURE                Location/Qualifiers
misc_feature           1..915
                       note = Synthetic
source                 1..915
                       mol_type = other DNA
                       organism = synthetic construct
SEQUENCE: 61
gaacaggctt gcggccgccg tgtccgcgct gaggaagcca aagtacaacg gcaagtgcat  60
gcgcagcctg attaggagca tcctcggcga gacgaggggt cgactcggga gcatgccctt  120
tgtgcttatg cctccgttct gccttctgac gaatttggta ctggaagcag atgagttttg  180
gttcactatc attctgaatt tacacctgcg cttgctgtca gactaggcaa ccaagtgact  240
tttgtgactt tgatcatgtt cagtgtgttt ccaagtccta atcaatcaaa aagaaaaaca  300
gtttgttaac gattgtttgc catgtctata taataaagtt gcttttatag tagcttagaa  360
ttcaatcggc caactttatc tcgtacgctg acagtaaagg tacatttaaa aggtgacaat  420
ggatagtcta atacttgaac tgacaataga gacacattac atgtcagttg attaagtttg  480
taacagaaaa ataaacaata ctacataatt gcaaagtttc tttgatgtct ttctttcaag  540
aaacacaaat atatcaatgc tacagtattg ctgatgaatt tatccatgtt gagatgtttt  600
tctggtttct gatctgatca gtctcaattg gtgtgctgtt tcattttcat ttgctgatga  660
tcgtccgagt agttaattct tactaatatt tagataattt ggcatacaag cgaatcacgt  720
agaacatgat acttttgaat gaatttatca aagttttatc acttggtgag ttgtttcatg  780
gttttcctac tgatgtctct tcttcagatt tctcgagccc tcgtctcgcc gaggatgctc  840
ctaatcaggc tgcgcatgca cttgccgttg tactttggct tcctcagcgc ggacatggcg  900
gccgcaagcc tgctc                                                   915

SEQ ID NO: 62          moltype = DNA  length = 1452
FEATURE                Location/Qualifiers
source                 1..1452
                       mol_type = genomic DNA
                       organism = Zea mays
SEQUENCE: 62
atatatattt ttatgtttta ttaaaataaa gtctacttat ttacaagcat gtgactgaca  60
gtaaagccac ttgtcttaga tatcgtacga cgcacatcta gagcctcttg ggttgatggc  120
agagacgcgg cgcgcgagcc ttgttctcct ctcctcggag agctgcctag cgagccccacc  180
gagggcatcg gcattgcttc cttcgccagt caccggttcg tacctccctg tctccacgtt  240
gaccctggac accctctgtg ccagcatccg ctccccgatc ccgacgagcg tccgcatgtt  300
ctccggcgtc gccgcgtcca cggtggccgc ggcgccacgg agcgagttgt cctggatgcg  360
caggtagtcg ccgtcgctgt ggagcgactg gaacatcgcg gcgacgtgga tgtccaccag  420
gtccgagctg gccgccatga agatgtcgat gatgggggcc atgccgttgt tgcggagcca  480
ccggcagata ccccaccggg agcactgccg cgccgtgtag aggccctgct cggacgtcga  540
ccccgtcccg atggacagca ccaggaacct gcggcagttc gacggcttca ctgggtacag  600
ctcctcggcc ttgtccttgc tggcaagcat ctttttggtg atctgcgtca tcgcaaccat  660
```

```
cgtcgggttg ttggccgcca caccgccgtc gatgaggttg tattcgcgct ccttgccgtt  720
ggcgtcttca gtctggaagt agtgcgccgg gaggtaggtc ggcgcggcgg acgtgccaat  780
gcacacgtcc gagagcagag cgttcttcag aggcgtgctc ttggcgtcgt aggtagagaa  840
gatgataggc tgcagcagcc tgatgtcgaa ggcagggatg atgacgttgg tcagcgtctc  900
gcttaccctc gtctcgccga ggatgctcct aatcaggctg cgcatgcact tgccgttgta  960
ctttggcttc ctcagcgcgg acatggcggc cgcaagcctg ctcttctgag gaaagatgcg  1020
cgggcagttc tgcatgtaaa agtggttgat gtccttggca gcgtagagag gccgcttgtc  1080
cttgccgggc gcggtgagca tggcggtgat gagaccgccg gtgctggttc cggcgatgta  1140
gtcgaagtag tccgccagcc tcgcctccgg tccgtccagc tcctgcagcc tggcctccag  1200
gaaggcgagg atggttcccg ggatgagacc ccggacgccg ccgccgtcca ccgtcagcac  1260
cgtcaccctc tgccccagca cgacgggctc gccgaccacg ctcccggcca tcgccttcgt  1320
gctacaggta ttgcatggac gccgcgacga gtagctcgcc attgccgcct tcgacaacac  1380
acccccgaat cgattaatga gctagctata gatactcgtc gagggcacaa taagtgtgat  1440
tagtgatgaa ct                                                        1452
```

```
SEQ ID NO: 63           moltype = DNA  length = 1382
FEATURE                 Location/Qualifiers
source                  1..1382
                        mol_type = genomic DNA
                        organism = Zea mays
SEQUENCE: 63
tcagaatata tatatattta tattttatta aaataaagtc tacttattta caagcatgtg  60
attgacagta aagccacttg tcttagatat cgtagggcgc acatctagag cttctggggt  120
tgatggcaga gacgcggcgc gcgagccttg ttctcctctc ctcggagagc tgcctagcga  180
gcccaccgag ggcatcggca ttgcttcctt ctccggtcac cggttcgtac ctcgctccct  240
gtctccacgt tgaccctgga cacccgctgt gccagcatcc gctccccgat cccgacgagc  300
gtccgcatgt tctccggcgt cgccgcgtcc acggttgccg cggcgccacg gagcgagttg  360
tcctggatgc gtaggtagtc gccgtcgctg tggagcgact ggaacatcgc ggcgacgtgg  420
atgtccacca ggtccgagct ggccgccatg aagatgtcga tgatgggggc catgccgttg  480
ttgcggagcc accggcagat gccccaccgg gagcactgcc gcgccgtgta gaggccctgc  540
tcggacgtcg accccgtccc gatggacagc accaggaacc tgcggcagtt cgacgggttc  600
actgggtaca gctcctcggc cttgtccttg ctggcaagca tctttttggt gatctgcgtc  660
atcgcaacca tcgtcgggtt gttggccgcc acaccgccgt cgatgaggtt gtattcgcgc  720
tccttgccgt tggcgtcttc agtctggaag tagtgcgccg ggaggtaggt cggcgcggcg  780
gacgtgccaa tgcacacgtc cgagagcagc gcgttcttca gaggcgtgct cttggccctc  840
gtctcgccga ggatgctcct aatcaggctg cgcatgcact tgccgttgta ctttggcttc  900
ctcagcgcgg acatggcggc cgcaagcctg ctcttctgag ggaagatgcg cgggcagttc  960
tccatgtaaa agtagttgat gtccttggca gcgtagagag gccgcttgtc cttgccgggc  1020
gcggtgagca tggcggtgat gagaccgccg gtgctggttc cggcgatgta gtcgaagtag  1080
tccgccagcc tcgcctccgg tccgtccagc tcctgcagcc tggcctccag gaaggcgagg  1140
atggttcccg ggatgagacc ccggacgccg ccgccgtcca ccgtcagcac cgtcaccctc  1200
tgccccagca cgacgggctc gccgaccacg ctcccggcca tcgccttcgt gctacaggta  1260
ttgcatggac gccgcgacga gtagctcgcc attgccgcct tcgaccgcac accccgattg  1320
atcgattaat gagctagcta gatactcgtc gagggcacaa taagtgtgat tagtgatgaa  1380
ct                                                                   1382

SEQ ID NO: 64           moltype = DNA  length = 19
FEATURE                 Location/Qualifiers
source                  1..19
                        mol_type = genomic DNA
                        organism = Zea mays
SEQUENCE: 64
tacgccgtgc gctaacata                                                 19

SEQ ID NO: 65           moltype = DNA  length = 20
FEATURE                 Location/Qualifiers
source                  1..20
                        mol_type = genomic DNA
                        organism = Zea mays
SEQUENCE: 65
gtacctcgct ccctgtctcc                                                20

SEQ ID NO: 66           moltype = DNA  length = 18
FEATURE                 Location/Qualifiers
source                  1..18
                        mol_type = genomic DNA
                        organism = Zea mays
SEQUENCE: 66
gtacgccgtg cgctaaca                                                  18

SEQ ID NO: 67           moltype = DNA  length = 20
FEATURE                 Location/Qualifiers
source                  1..20
                        mol_type = genomic DNA
                        organism = Zea mays
SEQUENCE: 67
tcgtacctcc ctgtctccac                                                20

SEQ ID NO: 68           moltype = DNA  length = 1371
```

```
FEATURE                Location/Qualifiers
source                 1..1371
                       mol_type = genomic DNA
                       organism = Zea mays
SEQUENCE: 68
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 69          moltype = AA  length = 401
FEATURE                Location/Qualifiers
source                 1..401
                       mol_type = protein
                       organism = Zea mays
SEQUENCE: 69
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                      401

SEQ ID NO: 70          moltype = DNA  length = 1375
FEATURE                Location/Qualifiers
source                 1..1375
                       mol_type = genomic DNA
                       organism = Zea mays
SEQUENCE: 70
agttcatcac taatcacact tattgtgccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacta cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gcgctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaacccgt cgaactgccg caggttcctg gtgctgtcca tcgggacggg gtcgacgtcc  840
gagcagggcc tctacacggc gcggcagtgc tcccggtggg gcatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct acgcatccag  1020
gacaactcgc tccgtggcgc cgcggcaacc gtggacgcgg cgacgccgga gaacatgcgg  1080
acgctcgtcg ggatcgggga gcggatgctg gcacagcggg tgtccagggt caacgtggag  1140
acagggagcg aggtacgaac cggtgaccgg agaaggaagc aatgccgatg ccctcggtgg  1200
gctcgctagg cagctctccg aggagaggag aacaaggctc gcgcgccgcg tctctgccat  1260
caaccccaga agctctagat gtgcgcccta cgatatctaa gacaagtggc tttactgtca  1320
atcacatgct tgtaaataag tagactttat tttaataaaa tataaaaata tatat       1375

SEQ ID NO: 71          moltype = AA  length = 372
FEATURE                Location/Qualifiers
source                 1..372
                       mol_type = protein
                       organism = Zea mays
SEQUENCE: 71
```

```
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINYFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VNPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGSEVRTGDR  360
RRKQCRCPRW AR                                                     372

SEQ ID NO: 72           moltype = DNA  length = 1358
FEATURE                 Location/Qualifiers
misc_feature            1..1358
                        note = TALEN-induced MTL mutation in Event 39A individual
                         ID 22808-3954 allele 1
source                  1..1358
                        mol_type = other DNA
                        organism = synthetic construct
SEQUENCE: 72
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
aaccggtgac tggcgaagga agcaatgccg atgccctcgg tgggctcgct aggcagctct  1200
ccgaggagag gagaacaagg ctcgcgcgcc gcgtctctgc catcaaccca agaggctcta  1260
gatgtgcgtc gtacgatatc taagacaagt ggctttactg tcagtcacat gcttgtaaat  1320
aagtagactt tattttaata aaacataaaa atatatat                         1358

SEQ ID NO: 73           moltype = DNA  length = 1366
FEATURE                 Location/Qualifiers
misc_feature            1..1366
                        note = TALEN-induced MTL mutation in Event 23A individual
                         ID 22808-3924 allele 1
source                  1..1366
                        mol_type = other DNA
                        organism = synthetic construct
SEQUENCE: 73
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggagaa ccggtgactg gcgaaggaag caatgccgat gccctcggtg ggctcgctag  1200
gcagctctcc gaggagagga gaacaaggct cgcgcgccgc gtctctgcca tcaacccaag  1260
aggctctaga tgtgcgtcgt acgatatcta agacaagtgg ctttactgtc agtcacatgc  1320
ttgtaaataa gtagacttta ttttaataaa acataaaaat atatat                1366

SEQ ID NO: 74           moltype = DNA  length = 1358
FEATURE                 Location/Qualifiers
misc_feature            1..1358
                        note = TALEN-induced MTL mutation in Event 81A
source                  1..1358
```

mol_type = other DNA
organism = synthetic construct
SEQUENCE: 74
agttcatcac taatcacact tattgttccc tcgacgagta tctagctagc tcattaatcg 60
atcaatcggg gtgtgcggtc gaaggcggca atggcgagct actcgtcgcg gcgtccatgc 120
aatacctgta gcacgaaggc gatggccggg agcgtggtcg gcgagcccgt cgtgctgggg 180
cagagggtga cggtgctgac ggtggacggc ggcggcgtcc ggggtctcat cccgggaacc 240
atcctcgcct tcctcgaggc caggctgcag gagctggacg gaccggaggc gaggctggcg 300
gactacttcg actacatcgc cggaaccagc accggcggtc tcatcaccgc catgctcacc 360
gcgcccggca aggacaagcg gcctctctac gctgccaagg acatcaacca cttttacatg 420
gagaactgcc cgcgcatctt ccctcagaag agcaggcttg cggccgccat gtccgcgctg 480
aggaagccaa agtacaacgg caagtgcatg cgcagcctga ttaggagcat cctcggcgag 540
acgagggcca agagcacgcc tctgaagaac gctctgctct cggacgtgtg cattggcacg 600
tccgccgcgc cgacctacct cccggcgcac tacttccaga ctgaagacgc caacggcaag 660
gagcgcgaat acaacctcat cgacggcggt gtggcggcca acaacccgac gatggttgcg 720
atgacgcaga tcaccaaaaa gatgcttgcc agcaaggaca aggccgagga gctgtaccca 780
gtgaagccgt cgaactgccg caggttcctg gtgctgtcca tcgggacggg gtcgacgtcc 840
gagcagggcc tctacacggc gcggcagtgc tcccggtggg gtatctgccg gtggctccgc 900
aacaacggca tggcccccat catcgacatc ttcatggcgg ccagctcgga cctggtggac 960
atccacgtcg ccgcgatgtt ccagtcgctc cacagcgacg gcgactacct gcgcatccag 1020
gacaactcgc tccgtggcgc cgcggccacc gtggacgcgg cgacgccgga gaacatgcgg 1080
acgctcgtcg ggatcgggga gcggatgctg gcacagaggg tgtccagggt caacgtggag 1140
aaccggtgac tggcgaagga agcaatgccg atgccctcgg tgggctcgct aggcagctct 1200
ccgaggagag gagaacaagg ctcgcgcgcc gcgtctctgc catcaaccca agaggctcta 1260
gatgtgcgtc gtacgatatc taagacaagt ggctttactg tcagtcacat gcttgtaaat 1320
aagtagactt tattttaata aaacataaaa atatatat 1358

SEQ ID NO: 75 moltype = DNA length = 1343
FEATURE Location/Qualifiers
misc_feature 1..1343
note = TALEN-induced MTL mutation in Event 39A individual
ID 22808-3954 allele 2
source 1..1343
mol_type = other DNA
organism = synthetic construct
SEQUENCE: 75
agttcatcac taatcacact tattgttccc tcgacgagta tctagctagc tcattaatcg 60
atcaatcggg gtgtgcggtc gaaggcggca atggcgagct actcgtcgcg gcgtccatgc 120
aatacctgta gcacgaaggc gatggccggg agcgtggtcg gcgagcccgt cgtgctgggg 180
cagagggtga cggtgctgac ggtggacggc ggcggcgtcc ggggtctcat cccgggaacc 240
atcctcgcct tcctcgaggc caggctgcag gagctggacg gaccggaggc gaggctggcg 300
gactacttcg actacatcgc cggaaccagc accggcggtc tcatcaccgc catgctcacc 360
gcgcccggca aggacaagcg gcctctctac gctgccaagg acatcaacca cttttacatg 420
gagaactgcc cgcgcatctt ccctcagaag agcaggcttg cggccgccat gtccgcgctg 480
aggaagccaa agtacaacgg caagtgcatg cgcagcctga ttaggagcat cctcggcgag 540
acgagggcca agagcacgcc tctgaagaac gctctgctct cggacgtgtg cattggcacg 600
tccgccgcgc cgacctacct cccggcgcac tacttccaga ctgaagacgc caacggcaag 660
gagcgcgaat acaacctcat cgacggcggt gtggcggcca acaacccgac gatggttgcg 720
atgacgcaga tcaccaaaaa gatgcttgcc agcaaggaca aggccgagga gctgtaccca 780
gtgaagccgt cgaactgccg caggttcctg gtgctgtcca tcgggacggg gtcgacgtcc 840
gagcagggcc tctacacggc gcggcagtgc tcccggtggg gtatctgccg gtggctccgc 900
aacaacggca tggcccccat catcgacatc ttcatggcgg ccagctcgga cctggtggac 960
atccacgtcg ccgcgatgtt ccagtcgctc cacagcgacg gcgactacct gcgcatccag 1020
gacaactcgc tccgtggcgc cgcggccacc gtggacgcgg cgacgccgga gaacatgcgg 1080
acgctcgtcg ggatcgggga gcggatgctg gcacagaggg tgtccagggt caacgtggag 1140
acggaagcaa tgccgatgcc ctcggtgggc tcgctaggca gctctccgag gagaggagaa 1200
caaggctcgc gcgccgcgtc tctgccatca acccaagagg ctctagatgt gcgtcgtacg 1260
atatctaaga caagtggctt tactgtcagt cacatgcttg taaataagta gactttattt 1320
taataaaaca taaaaatata tat 1343

SEQ ID NO: 76 moltype = DNA length = 1363
FEATURE Location/Qualifiers
misc_feature 1..1363
note = TALEN-induced MTL mutation in Event 23A ID
22808-3924 allele 2
source 1..1363
mol_type = other DNA
organism = synthetic construct
SEQUENCE: 76
agttcatcac taatcacact tattgttccc tcgacgagta tctagctagc tcattaatcg 60
atcaatcggg gtgtgcggtc gaaggcggca atggcgagct actcgtcgcg gcgtccatgc 120
aatacctgta gcacgaaggc gatggccggg agcgtggtcg gcgagcccgt cgtgctgggg 180
cagagggtga cggtgctgac ggtggacggc ggcggcgtcc ggggtctcat cccgggaacc 240
atcctcgcct tcctcgaggc caggctgcag gagctggacg gaccggaggc gaggctggcg 300
gactacttcg actacatcgc cggaaccagc accggcggtc tcatcaccgc catgctcacc 360
gcgcccggca aggacaagcg gcctctctac gctgccaagg acatcaacca cttttacatg 420
gagaactgcc cgcgcatctt ccctcagaag agcaggcttg cggccgccat gtccgcgctg 480
aggaagccaa agtacaacgg caagtgcatg cgcagcctga ttaggagcat cctcggcgag 540
acgagggcca agagcacgcc tctgaagaac gctctgctct cggacgtgtg cattggcacg 600

```
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaggaaccg gtgactggcg aaggaagcaa tgccgatgcc ctcggtgggc tcgctaggca  1200
gctctccgag gagaggagaa caaggctcgc gcgccgcgtc tctgccatca acccaagagg  1260
ctctagatgt gcgtcgtacg atatctaaga caagtggctt tactgtcagt cacatgcttg  1320
taaataagta gactttattt taataaaaca taaaaatata tat                  1363
```

```
SEQ ID NO: 77          moltype = DNA  length = 1360
FEATURE                Location/Qualifiers
misc_feature           1..1360
                       note = TALEN-induced MTL mutation in Event 38A individual
                        ID 22808-4108 allele 1
source                 1..1360
                       mol_type = other DNA
                       organism = synthetic construct
SEQUENCE: 77
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaaccggtg actggcgaag gaagcaatgc cgatgccctc ggtgggctcg ctaggcagct  1200
ctccgaggag aggagaacaa ggctcgcgcg ccgcgtctct gccatcaacc caagaggctc  1260
tagatgtgcg tcgtacgata tctaagacaa gtggctttac tgtcagtcac atgcttgtaa  1320
ataagtagac tttattttaa taaaacataa aaatatatat                       1360
```

```
SEQ ID NO: 78          moltype = DNA  length = 1363
FEATURE                Location/Qualifiers
misc_feature           1..1363
                       note = CRISPR-induced MTL mutation in Event 18A ID
                        22807-4016
source                 1..1363
                       mol_type = other DNA
                       organism = synthetic construct
SEQUENCE: 78
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaggaaccg gtgactggcg aaggaagcaa tgccgatgcc ctcggtgggc tcgctaggca  1200
gctctccgag gagaggagaa caaggctcgc gcgccgcgtc tctgccatca acccaagagg  1260
ctctagatgt gcgtcgtacg atatctaaga caagtggctt tactgtcagt cacatgcttg  1320
taaataagta gactttattt taataaaaca taaaaatata tat                  1363
```

```
SEQ ID NO: 79          moltype = DNA  length = 1372
FEATURE                Location/Qualifiers
misc_feature           1..1372
                       note = CRISPR-induced MTL mutation in Event 27A individual
                        ID 22807-4801 allele 1
source                 1..1372
                       mol_type = other DNA
                       organism = synthetic construct
SEQUENCE: 79
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaagggagg tacgaaccgg tgactggcga aggaagcaat gccgatgccc tcggtgggct  1200
cgctaggcag ctctccgagg agaggagaac aaggctcgcg cgccgcgtct ctgccatcaa  1260
cccaagaggc tctagatgtg cgtcgtacga tatctaagac aagtggcttt actgtcagtc  1320
acatgcttgt aaataagtag actttatttt aataaaacat aaaaatatat at          1372

SEQ ID NO: 80          moltype = DNA  length = 1372
FEATURE                Location/Qualifiers
misc_feature           1..1372
                       note = CRISPR-induced mutation in Event 27A individual ID
                        22807-4081 allele 1
source                 1..1372
                       mol_type = other DNA
                       organism = synthetic construct
SEQUENCE: 80
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaagggagg tacgaaccgg tgactggcga aggaagcaat gccgatgccc tcggtgggct  1200
cgctaggcag ctctccgagg agaggagaac aaggctcgcg cgccgcgtct ctgccatcaa  1260
cccaagaggc tctagatgtg cgtcgtacga tatctaagac aagtggcttt actgtcagtc  1320
acatgcttgt aaataagtag actttatttt aataaaacat aaaaatatat at          1372

SEQ ID NO: 81          moltype = DNA  length = 1373
FEATURE                Location/Qualifiers
misc_feature           1..1373
                       note = CRISPR-induced MTL mutation in Event 76A individual
                        ID 22873-3999
source                 1..1373
                       mol_type = other DNA
                       organism = synthetic construct
SEQUENCE: 81
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
```

```
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaaagggag gtacgaaccg gtgactggcg aaggaagcaa tgccgatgcc ctcggtgggc  1200
tcgctaggca gctctccgag gagaggagaa caaggctcgc gcgccgcgtc tctgccatca  1260
acccaagagg ctctagatgt gcgtcgtacg atatctaaga caagtggctt tactgtcagt  1320
cacatgcttg taaataagta gactttattt taataaaaca taaaaatata tat         1373
```

```
SEQ ID NO: 82           moltype = DNA  length = 1370
FEATURE                 Location/Qualifiers
misc_feature            1..1370
                        note = CRISPR-induced mutation in Event 32A individual ID
                         22873-3991
source                  1..1370
                        mol_type = other DNA
                        organism = synthetic construct
SEQUENCE: 82
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acgggaggta cgaaccggtg actggcgaag gaagcaatgc cgatgccctc ggtgggctcg  1200
ctaggcagct ctccgaggag aggagaacaa ggctcgcgcg ccgcgtgtct gccatcaacc  1260
caagaggctc tagatgtgcg tcgtacgata tctaagacaa gtggctttac tgtcagtcac  1320
atgcttgtaa ataagtagac tttattttaa taaaacataa aaatatatat             1370

SEQ ID NO: 83           moltype = DNA  length = 18
FEATURE                 Location/Qualifiers
misc_feature            1..18
                        note = nucleotide sequence encoding guide RNA
source                  1..18
                        mol_type = other DNA
                        organism = synthetic construct
SEQUENCE: 83
gtcaacgtgg agacaggg                                                18

SEQ ID NO: 84           moltype = DNA  length = 1823
FEATURE                 Location/Qualifiers
5'UTR                   1..78
exon                    79..444
                        note = exon 1
misc_feature            445..536
                        note = Intron - intron 1
exon                    537..717
                        note = exon 2
misc_feature            718..803
                        note = Intron - intron 2
exon                    804..967
                        note = exon 3
misc_feature            968..1074
                        note = Intron - intron 3
```

-continued

```
exon                    1075..1662
                        note = exon 4
3'UTR                   1663..1823
source                  1..1823
                        mol_type = genomic DNA
                        organism = Oryza sativa
SEQUENCE: 84
acagtgacta gtgacaaacg atcgatcgat ccctccatcc acaaaccctc ctcgatctca  60
tcttccttcg tctcgtcaat ggcggcgagc tactcgtgcc ggcggacatg cgaggcgtgc  120
agcacgaggg cgatggccgg gtgcgtggtg ggcgagccgg cgtcggcgcc ggggcagcgg  180
gtgacgttgc tggcgatcga cggcggcggc atcaggggcc tcatcccggg caccatcctc  240
gccttcctcg aggccaggct gcaggagctg gatggccccg acgcgcgcct cgccgattac  300
ttcgactgca tcgccgggac cagcaccggc ggcctcatca ccgccatgct cgccgcgccc  360
ggcgaccacg gccgcccgct cttcgccgcc agcgacatca accgcttcta cctcgacaac  420
ggcccactca tcttcccaca aaagtaactg atcacctcga attcgatctc ctctcttcga  480
tctctgcatt atttgatttg attggggatt gtgggcggcg tggcgtggcg tccaggaggt  540
gcggcatggc ggcggccatg gcggcgctga cgaggccgag gtacaacggc aagtacctgc  600
aggggaagat caggaagatg ctgggcgaga cgagggtgcg cgacacgctg acgaacgtcg  660
tcatccccac gttcgacgtc aggctgctcc agccaaccat cttctccaca tacgacgtgc  720
gtgcgttgat tccatccgca ttggcgttgg aatcagctga ttgtttgatt gatcgaacaa  780
ttgatcggtt aaaattttgc aggcgaagag catgccgctc aagaacgcgc tcctctccga  840
catctgcatc agcacatccg cggcgccgac ctacctcccc gcgcactgct tccagaccac  900
cgacgacgcc accggcaagg tccgcgagtt cgacctcatc gacggcggcg tcgccgccaa  960
caacccggta actaatcaat caagcaatcc atcaaacgaa gatccacatg tgcattcctg  1020
tggtacaaat gctgatcgat cgatggatgg atcgattttc gcgagaacgt acagacgatg  1080
gtggccatga cgcagatcac caagaagata atggtgaagg acaaggagga gctgtacccg  1140
gtaaagccgt cggactgcgg taagttcctg gtgctgtccg tgggcaccgg gtcgacgtcg  1200
gaccagggga tgtacacggc gaggcagtgc tcgcggtggg ggatcgtccg gtggctgcgc  1260
aacaagggga tggcgcccat catcgacatc ttcatggcgg ccagctccga cctcgtcgac  1320
atccacgccg ccgtcatgtt ccagtcgctg cacagcgacg gcgactacct ccgcatccag  1380
gacaacacgc tccacggcga cgccgccacg gtggacgccg ccaccaggga caacatgcgg  1440
gcgctcgtcg ggatcggcga gcggatgctg gcgcagcggg tgtcgagggt caacgtcgag  1500
accggcaggt acgtcgaggt gcccggcgcc ggcagcaacg ccgacgcgct gaggggcttc  1560
gccaggcagc tctccgagga gaggagggcg aggctaggtc ggcgaaacgc ctgcggcggc  1620
ggcggcgaag gagagcccag cggcgtggcg tgcaagcgtt agtaactgta cacgcatcat  1680
gctgacgcga tctttttat ttttcttttt tttttttac ctttctagcg gacatgggga  1740
ataacaagac gtgacagtag tgcaatcggt ttgtaacgtg cgtataccaa cattgatcca  1800
tttcttcatc acagtttcag ttc                                          1823

SEQ ID NO: 85           moltype = DNA  length = 1299
FEATURE                 Location/Qualifiers
source                  1..1299
                        mol_type = genomic DNA
                        organism = Oryza sativa
SEQUENCE: 85
atggcggcga gctactcgtg ccggcggaca tgcgaggcgt gcagcacgag ggcgatggcc  60
gggtgcgtgg tgggcgagcc ggcgtcggcg ccggggcagc gggtgacgtt gctggcgatc  120
gacggcggcg gcatcagggg cctcatcccg ggcaccatcc tcgccttcct cgaggccagg  180
ctgcaggagc tggatggccc cgacgcgcgc ctcgccgatt acttcgactg catcgccggg  240
accagcaccg gcggcctcat caccgccatg ctcgccgcgc ccggcgacca cggccgcccg  300
ctcttcgccg ccagcgacat caaccgcttc tacctcgaca acggcccact catcttccca  360
caaaagaggt gcggcatggc ggcggccatg gcggcgctga cgaggccgag gtacaacggc  420
aagtacctgc aggggaagat caggaagatg ctgggcgaga cgagggtgcg cgacacgctg  480
acgaacgtcg tcatccccac gttcgacgtc aggctgctcc agccaaccat cttctccaca  540
tacgacgcga agagcatgcc gctcaagaac gcgctcctct ccgacatctg catcagcaca  600
tccgcggcgc cgacctacct ccccgcgcac tgcttccaga ccaccgacga cgccaccggc  660
aaggtccgcg agttcgacct catcgacggc ggcgtcgccg ccaacaaccc gacgatggtg  720
gccatgacgc agatcaccaa gaagataatg gtgaaggaca aggaggagct gtacccggta  780
aagccgtcgg actgcggtaa gttcctggtg ctgtccgtgg gcaccgggtc gacgtcggac  840
caggggatgt acacggcgag gcagtgctcg cggtggggga tcgtccggtg gctgcgcaac  900
aaggggatgg cgcccatcat cgacatcttc atggcggcca gctccgacct cgtcgacatc  960
cacgccgccg tcatgttcca gtcgctgcac agcgacggcg actacctccg catccaggac  1020
aacacgctcc acggcgacgc cgccacggtg gacgccgcca ccagggacaa catgcgggcg  1080
ctcgtcggga tcggcgagcg gatgctggcg cagcgggtgt cgagggtcaa cgtcgagacc  1140
ggcaggtacg tcgaggtgcc cggcgccggc agcaacgccg acgcgctgag gggcttcgcc  1200
aggcagctct ccgaggagag gagggcgagg ctaggtcggc gaaacgcctg cggcggcggc  1260
ggcgaaggag agcccagcgg cgtggcgtgc aagcgttag                         1299

SEQ ID NO: 86           moltype = AA  length = 432
FEATURE                 Location/Qualifiers
source                  1..432
                        mol_type = protein
                        organism = Oryza sativa
SEQUENCE: 86
MAASYSCRRT CEACSTRAMA GCVVGEPASA PGQRVTLLAI DGGGIRGLIP GTILAFLEAR  60
LQELDGPDAR LADYFDCIAG TSTGGLITAM LAAPGDHGRP LFAASDINRF YLDNGPLIFP  120
QKRCGMAAAM AALTRPRYNG KYLQGKIRKM LGETRVRDTL TNVVIPTFDV RLLQPTIFST  180
YDAKSMPLKN ALLSDICIST SAAPTYLPAH CFQTTDDATG KVREFDLIDG GVAANNPTMV  240
AMTQITKKIM VKDKEELYPV KPSDCGKFLV LSVGTGSTSD QGMYTARQCS RWGIVRWLRN  300
```

-continued

```
KGMAPIIDIF MAASSDLVDI HAAVMFQSLH SDGDYLRIQD NTLHGDAATV DAATRDNMRA  360
LVGIGERMLA QRVSRVNVET GRYVEVPGAG SNADALRGFA RQLSEERRAR LGRRNACGGG  420
GEGEPSGVAC KR                                                     432

SEQ ID NO: 87          moltype = DNA  length = 1371
FEATURE                Location/Qualifiers
source                 1..1371
                       mol_type = genomic DNA
                       organism = Zea mays
SEQUENCE: 87
agttcatcac taatcacact tattgtgccc tcgacgagta tctatagcta gctcattaat  60
cgattcgggg gtgtgttgtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
cagaactgcc cgcgcatctt tcctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtctc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 88          moltype = DNA  length = 1375
FEATURE                Location/Qualifiers
source                 1..1375
                       mol_type = genomic DNA
                       organism = Zea mays
SEQUENCE: 88
agttcatcac taatcacact tattgtgccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacta cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gcgctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaacccgt cgaactgccg caggttcctg gtgctgtcca tcgggacggg gtcgacgtcc  840
gagcagggcc tctacacggc gcggcagtgc tcccggtggg gcatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct acgcatccag  1020
gacaactcgc tccgtggcgc cgcggcaacc gtggacgcgg cgacgccgga gaacatgcgg  1080
acgctcgtcg ggatcgggga gcggatgctg gcacagcggg tgtccagggt caacgtggag  1140
acagggagcg aggtacgaac cggtgaccgg agaaggaagc aatgccgatg ccctcggtgg  1200
gctcgctagg cagctctccg aggagaggag aacaaggctc gcgcgccgcg tctctgccat  1260
caaccccaga agctctagat gtgcgcccta cgatatctaa gacaagtggc tttactgtca  1320
atcacatgct tgtaaataag tagactttat tttaataaaa tataaaaata tatat       1375

SEQ ID NO: 89          moltype = DNA  length = 1375
FEATURE                Location/Qualifiers
source                 1..1375
                       mol_type = genomic DNA
                       organism = Zea mays
SEQUENCE: 89
agttcatcac taatcacact tattgtgccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctggaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacta cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
```

```
acgagggcca agagcacgcc tctgaagaac gcgctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaacccgt cgaactgccg caggttcctg gtgctgtcca tcgggacggg gtcgacgtcc  840
gagcagggcc tctacacggc gcggcagtgc tcccggtggg gcatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct acgcatccag  1020
gacaactcgc tccgtggcgc cgcggcaacc gtggacgcgg cgacgccgga gaacatgcgg  1080
acgctcgtcg ggatcgggga gcggatgctg gcacagcggg tgtccagggt caacgtggag  1140
acagggagcg aggtacgaac cggtgaccgg agaaggaagc aatgccgatg ccctcggtgg  1200
gctcgctagg cagctctccg aggagaggag aacaaggctc gcgcgccgcg tctctgccat  1260
caaccccaga agctctagat gtgcgcccta cgatatctaa gacaagtggc tttactgtca  1320
atcacatgct tgtaaataag tagactttat tttaataaaa tataaaaata tatat       1375

SEQ ID NO: 90          moltype = AA  length = 401
FEATURE                Location/Qualifiers
source                 1..401
                       mol_type = protein
                       organism = Zea mays
SEQUENCE: 90
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                    401

SEQ ID NO: 91          moltype = AA  length = 372
FEATURE                Location/Qualifiers
source                 1..372
                       mol_type = protein
                       organism = Zea mays
SEQUENCE: 91
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINYFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VNPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGSEVRTGDR  360
RRKQCRCPRW AR                                                    372

SEQ ID NO: 92          moltype = AA  length = 372
FEATURE                Location/Qualifiers
source                 1..372
                       mol_type = protein
                       organism = Zea mays
SEQUENCE: 92
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINYFYM QNCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VNPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGSEVRTGDR  360
RRKQCRCPRW AR                                                    372

SEQ ID NO: 93          moltype = DNA  length = 15463
FEATURE                Location/Qualifiers
misc_feature           1..15463
                       note = Expression cassette of construct 22466
regulatory             214..2339
                       regulatory_class = promoter
gene                   2341..3018
                       note = PLA2 gene
regulatory             3024..4036
                       regulatory_class = terminator
regulatory             4044..4237
                       note = enhancer - eFMV
                       regulatory_class = enhancer
regulatory             4244..4536
                       note = enhancer - e35S
                       regulatory_class = enhancer
regulatory             4544..8537
                       note = promoter - Ubi
                       regulatory_class = promoter
regulatory             10009..11008
                       note = terminator - Ubi
                       regulatory_class = terminator
```

-continued

```
regulatory           11028..12618
                     note = promoter - pPLA2
                     regulatory_class = promoter
exon                 12619..12977
                     note = PLA2 exon1
intron               12978..13096
                     note = PLA2 intron 1
exon                 13097..13193
                     note = PLA2 exon2
intron               13194..13388
                     note = PLA2 intron 2
exon                 13389..13550
                     note = PLA2 exon3
intron               13551..13660
                     note = PLA2 intron 3
exon                 13661..14248
                     note = PLA2 exon4
regulatory           14249..15244
                     note = terminator - tPLA2
                     regulatory_class = terminator
source               1..15463
                     mol_type = other DNA
                     organism = synthetic construct
SEQUENCE: 93
cctgtggttg gcatgcacat acaaatggac gaacggataa accttttcac gccctttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga cccgaaagta gcaaacaaca ggttcatgtg  240
cactataaaa agacaaaatt ctcgagtttc atcttttatt ccacataagc cttatatttt  300
ccattttcat atgattttta gtttaagttt gtgtcttaac tttttcgtta atacgtaatt  360
ctatgcatta tggatgcgtg aagtattttt gtttaaaaaa atgaaatgtc aaaatacgtt  420
ttgtgatcta tttccatgtt ttcacctaac aggtggtttt tactatatat tctgccataa  480
ctctagcctt agatgtaaat cgaaaaaaaa tgagagatga gctggagata gccttagatg  540
aagcgtctga aatataaaag aaagagtaat gttgaacgca gtaggtgtag cagctgtagt  600
tccatctcta ggaaagggaa ctgcaatccg ggctccgggc ctcgcgcaat ctggcctgtc  660
gtgtagatgc agccctgtcc atgacggccc aagcaacgcc cgcggctctc gatccaccac  720
ggaacccact ccgacacaca ctgacacaca catgctggat gtggatgtgc tgtccaatta  780
ttagtagcaa ttcggtaggc acaggcacgt actggccggt gttttagctg taagtaccga  840
accaatcacg gttaagaacc gattaatccg tgcccagccg ccgagtgcgt tcgtacgtgc  900
atcggatgca ctgcatgaat tgagagcatc atcatatcat acgcaggagt agtacgacgc  960
cgctgctgtc ttgtccggct aatgctttgc tcacagatta gtccatcgcc cacggtcggt  1020
gtggtgtgga tcgctgatgc cactgctttt tgtttggttt ttattcccct gataatcctc  1080
cgcgtccctg aatgtatcta tttattttca ttccgaaatc cctttcacga aaaagaaaac  1140
gaataaaaag agagttacga atacgcttcc ggcggcccac atcaccttcc agcgaacatc  1200
gcgccgcgct gacgtgtcgc ccatcgcggc cgtccatatc gccatccgac gaccgtggaa  1260
gctggcagcg gccgctccgt tccgtcgaag gggcaggtca gtcaggtcac ccacacggcc  1320
acacccgcgc gggggatacg cggtggaaaa cccggcgacc acatcaaaac acgaggcgtc  1380
tcccgcagga ctggtcactc ggcacgcagg cagaggcagc acagcagcag ccagctccat  1440
ccatcctctt tcccctcctc gcttcgcttc ctcggcggat tcctcctccc tcggccgtcc  1500
ccgtcccctt cttcgccgcg ccagctcgcc cgagttggta cgcccatcct ctgctgtact  1560
ccccccgttc ctgctgtgcg aaaccgagca cccaaaccct agcctaagct attcgcatcg  1620
caaactctat tgagcgacgg atcgcgaaac gcgcgccgcc gcattcggac gagacctcgt  1680
ggcccgtacc ttcctactct accgtcgtcg ccggagacca gctcaccggt tagggtttcg  1740
ggattagggg cttggggctt ggattcccgg gggactccat acccggtggc cttagaaggg  1800
gaagggggcc cagcggtggt ggtggttcga ctgtcagcga gcgagacggc ggggcaccgc  1860
cgatcgggcg tcgctggaca tttgattgag ctgggcaggc gaaggcgtgg agcttgctct  1920
tcgattggga ttagaggagg gcggaggtgg tatggtgggc ggctcggctg gctcaatgga  1980
gccgctggcc ggtggtgggg caggcgagat cacgctctct catagagcgt aatgggttgc  2040
gtaacacact cctgtttgta tttcgatccg atctaataat taaagtttat ttacgtggtg  2100
cacatgtaga attttcccat gcccactgct aacttggatt ggatttttgc caaaaaaacg  2160
ggtgtgcacc caatcactta tagtgaaacc gttgtgtgtt tgatgtgctt ctaaccaagt  2220
acaaatccag tgaaaacaca cctaccattc aacaatccac attttggttg caattatcag  2280
cattctagaa aggtgcatgt gcccattgat acacttgcta ttggtgcagg caaacccacc  2340
atggcctcct ccgagaacgt catcaccgag ttcatgcgct tcaaggtgcg catggagggc  2400
accgtgaacg gccacgagtt cgagatcgag ggcgagggcg agggccgccc ctacgagggc  2460
cacaacaccg tgaagctgaa ggtgaccaag ggcggccccc tgcccttcgc ctgggacatc  2520
ctgtcccccc agttccagta cggctccaag gtgtacgtga agcaccccgc cgacatcccc  2580
gactacaaga agctgtcctt ccccgagggc ttcaagtggg agcgcgtgat gaacttcgag  2640
gacggcggcg tggcgaccgt gacccaggac tcctccctgc aggacggctg cttcatctac  2700
aaggtgaagt tcatcggcgt gaacttcccc tccgacggcc ccgtgatgca gaagaagacc  2760
atgggctggg aggcctccac cgagcgcctg tacccccgcg acggcgtgct gaagggcgag  2820
acccacaagg ccctgaagct gaaggacggc ggccactacc tggtggagtt caagtccatc  2880
tacatggcca agaagcccgt gcagctgccc ggctactact acgtggacgc caagctggac  2940
atcacctccc acaacgagga ctacaccatc gtggagcagt acgagcgcac cgagggccgc  3000
caccacctgt tcctgtagga gctcgcatca tgatcatgca tcatggactc ggcctactac  3060
tgtggatttg tatgccatta tagacttggt gctgtgaaag actgcttgat gatttgcggg  3120
tttgttgctg tgtaaaaaaa ggtcccttgg ctcccagaag accatgaagg ttcggatcta  3180
tcatgtaatt ccttgttatc tgccaattat gtatggacta tggacatgtg ttgcgctgtt  3240
caacttacta ctacaaataa gtaatcgata tgttcccttc ccatgtctcg gtgacaattg  3300
```

-continued

```
tctggagaag cttaggggtc gtttgtttgg gattatgtct ggagaaactt attttaaact  3360
aagtgtgagt tcaagttaag ttagattata taatctaggc agattataat tccaagcgaa  3420
caggtcctta gtgtttttgg aaaatcctag gtgttctttt ggctacattg ttgtgtgtgc  3480
agatcccttg ttggtctgta agcgtgggga agtaagaatc gtccgtttct actgaagacc  3540
tgctcgagtt aggcaccgag gatgccggta accaaacaga gcaatagtgt ctctgtgggc  3600
acagtggagt gtgaatctgt gtgatgcaaa tccgtcattt gtttagcaaa atttccagcg  3660
ttgcatgatg cagtttcttt aacacggact taagggaagg gaaaaaaatg ttgagccagg  3720
agatccttca atgtgttaga ctgacgtgat agccaactaa accacgacgc aatgttgtcg  3780
ttaatgacaa aaaaactatt tgttcctaaa tccttggcga cattgcatgg ctgtctcatg  3840
agataatggt ctcatctctt atttatctct tatttatagc cggaagtggt agtgacccct  3900
gcttgattgc tcgtatgcca tctcaagttc tcaaccgtgt cgagcagcca ttttcccatc  3960
tcaagcgcat catcgtttcg tttgacctca tctgctatcc tgctcctagt gcaaatcaca  4020
tgcgacagaa agtgtgcgga cccagctgct tgtggggacc agacaaaaaa ggaatggtgc  4080
agaattgtta ggcgcaccta ccaaaagcaa ctttgccttt attgcaaaga taaagcagat  4140
tcctctagta caagtgggga acaaaataac gtggaaaaga gctgtcctga cagcccactc  4200
actattgcgt ttgacgaacg cagtgacgac cacaaaactc gagacttttc aacaaagggt  4260
attatccgga aacctcctcg gattccattg cccagctatc tgtcacttta ttgtgaagat  4320
agtggaaaag gaaggtggct cctacaaatg ccatcattgc gataaaggaa aggctatcgt  4380
tgaagatgcc tctgccgaca gtggtcccaa agatggaccc ccacccacga ggagcatcgt  4440
ggaaaaagaa gacgttccaa ccacgtcttc aaagcaagtg gattgatgtg atatctccac  4500
tgacgtaagg gttgacgaac aatcccacta tccttcaagc tttggaaaac caaaacaacg  4560
aataagcaaa ctgcaggaaa agtatgcagt ggaaaccaac ccagattcgg acgataggaa  4620
agtatcaagt gaatgatttg ccaggaaaag gagaggggta aaaaggggcg aagatttaga  4680
agatctaaag cacaagaacc agagattaga ttgaacaata gggaacttgg agcatccttt  4740
ttttcttcag ggaaaaactg aaaatccaaa ccatgttgag caaaaccgag tgggattgga  4800
aaccaaaaaa cccgagataa agaaactcga gaaaaagcat gaaatcgaaa ccaacttcag  4860
taaaacaaaa ggaggacaga aaagaaagtc ggaagctata aagaatacat taacattcag  4920
tgaaacagca tgctgtcttc ttcttttttt atgcacaaca gagcatacat atataccttc  4980
ccaggctgag gacttggcgg aggagagccg cggataggtt ggcggtgcag acggtctgga  5040
cgggcccgaa gacggagacg aacagcgggc ccttcctgcc caggcaccac gcttggaacg  5100
ccaagcacgc gccaaccgcg gccccgccga ggacgacgat ccccgcgaca agcgtggcgt  5160
cgatcctggg cgaccccaag ccgaggaacc tcccttccag gacgagccgt aggacggcgg  5220
tgagagaggc acccgtcgcg gaggtggcgc agcacaaggt gagcagcgcg gggaaggcgg  5280
cgagcgtggc ggcctgcagg acggtgacga gcgcgaagac ggtgacgccg gcgacgaggc  5340
agcagcagcc gaggatccag tcgtaggagg aagccggacc aaaccgggca atgcaacctg  5400
cagatgcact agacggaggt aacgaggagg aggagaaaac agagcaagag caggcggaga  5460
gaagatagag caaaacacga gtgaggcaca gcgtaagcac tcggtagaag tctccagagg  5520
cgaggtgcgc acaggagaac agatgagtaa agtcagccaa ggatccacga tccaacggct  5580
acgaattttt ggagtgacgt ggataggctc aaaggcgcca tttccatccg gctttatagt  5640
attttaaaaa aattcatttt cctccctcta gtgtgtgcgg aggcgtgagc ccgtttaacg  5700
gcgttgagaa gtctaacgga caccaaccac aaccaggaac cagcgccggc cgcgccgccg  5760
agtgaagcag actgcatacg gcacggcgcg gcatctctct ggctgcctct cgagagttcc  5820
gcccccacct tcccgcggta gcgtggtggt ttcgctttcc gctgtcggca tccggaagtt  5880
gcgtggcaga gtggacggag acgaggccgg gtcctccagc tcctctcaaa cgtcacggca  5940
ccggcatccg gcagccagcg cggtccttcc caaccactcg ttcccaaccc atcccccttc  6000
ctcgcccgcc gtcataaata gccagcccca tccccagctt ctttccccaa cctcatcttc  6060
tctccttttg ctctgaacgc acacaccgcc cggtctccga tctccgatcc ccgatcccct  6120
cgtcgatcct aggtacggcg accatcctac cccccccccc ccccctctc tctctgcctt  6180
ctctagatcg gcgatccgat ccatgcttac ttggttaggg cctgctaact atgttcatgt  6240
ttgcgttaga tccgtgcatg gacgcgatct gtacacacca gacgcgttct gattgctagc  6300
taactcgcca gtacctggga atcctgggat ggctgtagcc ggccccgcac gcagacggga  6360
ccgatttcat gattctctat tttttcttt gtttcgttgc ctagggtttc gttcgatcga  6420
tccgcgttat tctttatttc catatattct ggtacgatgt tgatacggtt cgaccgtgct  6480
gcttacgttc tgtgcgcttg tttgccgggt catttttacc ttgccttttt tgtatggttt  6540
ggttgtggcg atgtggtctg gtcgggctgt cgttctagat cggagtagag tgctgtttca  6600
aactgtctag cggatctatt agatttggat ctgcatgtgt gacatatatc ttcgtagtta  6660
agatgatgca tctgtatgtg tgacatgcgg atctattaga tttggatctg tatgtgtgac  6720
atatatcttc gtagttgaga tgatgcatct gtatgtgtga catatatctt cgtagttaag  6780
attatgcatg gaaatatcaa tcctttagat aaggacgggt atacttgttg ctgtgggttt  6840
tactggtact tcgatagatg catatacatg atctaacatg cttagataca tgaagtaaca  6900
tgctgctacg gtttaataat tcttgagttg atttttactg gtacttagat agatgtatat  6960
acatgcttag atacatgaag taacatgctc ctacagttcc tttaatcatt attgagtacc  7020
tatatattct aataaatcag tatgttttaa attattttga ttttactggt acttagatag  7080
atgtatatat acatgctcaa acatgcttag atacatgaag taacatgctg ctacggttta  7140
gtcattattg agtgcctata tattctaata aatcagtatg ttttaaatta ttttgatttt  7200
actggtactt agatagatgt atatatacat gctcaaacat gcttagatac atgaagtaat  7260
atgctactac ggtttaattg ttcttgagta cctatatatt ctaataaatc agtatgtttt  7320
aaattatttc gattttactg gtacttagat agatgtatat atacatgctt agatacatga  7380
agtaacatgc tactacggtt taattgttct tgaataccta tatattctaa taaatcagta  7440
tgttttaaat tatttcgatt ttactggtac ttagatagat gtatatatac atgctcgaac  7500
atgcttagat acatgaagta acatgctaca tatatattat aataaatcag tatgtcttaa  7560
attattttga ttttactggt acttagatag atgtatatac atgctcaaac atgcttagat  7620
acatgaagta acatgctact acggtttaat cattattgag tacctatata ttctaataaa  7680
tcagtatgtt ttcaattgtt ttgattttac tggtacttag atatatgtat atatacatgc  7740
tcgaacatgc ttagatacgt gaagtaacat gctactatgg ttaattgttc ttgagtacct  7800
atatattcta ataaatcagt atgttttaaa ttatttcgat tttactggta cttagataga  7860
tgtatatata catgctcgaa catgcttaga tacatgaagt aacatgctac tacggtttaa  7920
tcgttcttga gtacctatat attctaataa atcagtatgt cttaaattat cttgatttta  7980
ctggtactta gatagatgta tatacatgct tagatacatg aagtaacatg ctactatgat  8040
```

-continued

```
ttaatcgttc ttgagtacct atatattcta ataaatcagt atgtttttaa ttattttgat  8100
tttactggta cttagataga tgtatatata catgctcgaa catgcttaga tacatgaagt  8160
aacatgctac tacggtttaa tcattcttga gtacctatat attctaataa atcagtatgt  8220
ttttaattat tttgatatta ctggtactta acatgtttag atacatcata tagcatgcac  8280
atgctgctac tgtttaatca ttcgtgaata cctatatatt ctaatatatc agtatgtctt  8340
ctaattatta tgattttgat gtacttgtat ggtggcatat gctgcagcta tgtgtagatt  8400
ttgaataccc agtgtgatga gcatgcatgg cgccttcata gttcatatgc tgtttatttc  8460
ctttgagact gttctttttt gttgatagtc accctgttgt ttggtgattc ttatgcagat  8520
ccagatcttc gtaaaccatg gctctggtgg ctaggccagt gctgtctgct agagtggctg  8580
cttctaggcc aagggtggcc gctagaaagg ctgtgagggt gagcgctgcc agtcacggcg  8640
ctagctctag gccagccacc gctaggaagt ccagcggcct gagcggcacc gtgcgcatcc  8700
caggcgacaa gagcatcagt caccgcagct tcatgttcgg cggcctggcc agcggcgaga  8760
ctaggatcac cggcctgctc gagggcgagg acgtgatcaa caccggcaag gccatgcagg  8820
ctatgggcgc tcgcatccgc aaggagggcg acacctggat catcgacggc gtgggtaatg  8880
gcggcctgct ggccccagag gccccactgg acttcggcaa cgccgccacc ggctgcaggc  8940
tgactatggg cctggtgggc gtgtacgact tcgacagcac ctttatcggc gacgccagcc  9000
tgaccaagag gccgatgggc agggtgctga acccgctgcg cgagatgggc gtgcaggtca  9060
agagcgagga cggcgacagg ctgccggtga ccctgagggg cccaaagacc ccgaccccga  9120
tcacctaccg cgtgccaatg gccagcgccc aggtgaagtc agccgtgctg ctggccggcc  9180
tgaacacccc aggcatcacc accgtgatcg agccgatcat gacccgcgat cacaccgaga  9240
agatgctgca gggcttcggc gccaacctga ccgtcgagac tgacgctgac ggcgtgagga  9300
ccatcaggct cgagggcagg ggcaagctga ccggccaggt gatcgacgtg ccgggcgacc  9360
caagcagcac cgccttccca ctggtggccg ccctgctggt gccaggctct gacgtgacca  9420
tcctgaacgt gctgatgaac ccgagccgca ccggcctgat cctgaccctg caggagatgg  9480
gcgccgatat cgaggtgatc aacccgaggc tggctggcgg cgaggacgtc gccgacctga  9540
gggtgaggtc cagcaccctg aagggcgtga ccgtgccaga ggacagggcc ccgagtatga  9600
ttgacgagta cccgatcctg gccgtggccg ctgccttcgc cgagggcgcc accgtgatga  9660
acggcctcga ggagctgcgc gtgaaggaga gcgacaggct gagcgctgtg gccaacggcc  9720
tgaagctgaa cggcgtggac tgcgacgagg gcgagactag cctggtggtg aggggcaggc  9780
cagacggcaa gggcctgggc aacgcttccg gcgctgccgt ggccacccac ctggatcaca  9840
ggatcgccat gtcgttcctc gtgatgggcc tcgtgagcga gaacccggtg accgtggacg  9900
acgccaccat gatcgccacc agcttccccg agttcatgga cctgatggcc ggcctgggcg  9960
ctaagatcga gctgagcgac accaaggccg cctgatcatc tagagctcgc caaggttcaa  10020
ttaagctgct gctgtacctg ggtatctgcg tcgtctggtg ccctctggtg tacctctata  10080
tggatgtcgt cgtctaataa acatctgtgg tttgtgtgtc atgaatcgtg gttgtggctt  10140
cgttggttta atggacctgt tgtgtcctct gtgttgtacc caaaactctt ctgcagcagt  10200
atggcttgaa tccttatgaa gtttgatatt tgaacttaaa agtctgctca ttatgttttt  10260
ttctggttat atctcctaat taactgcctg ggatcaaatt tgattcgctg gtgtttattg  10320
gacccctccc aggttcttgc tttctaccgt ttcttgctga atgttaactt gattctgtca  10380
ggctcagttt cccactatgg cttacagctt aacgtgtttg gtttgttgaa tgttaacttg  10440
gttttgtcaa gctcagtttt ttactctggc ttacagcata acatgtttga cttttggttt  10500
tgctgctttg ttattgggtt ctgggtagtt cttgatgaat ccaaaagatc atgtgcacag  10560
ccatattatc tatttaagcg atccaggtta ttactatgaa aggatgcctt ctagctaagg  10620
agtagttagg tttttttcttc aaggttaaat ttctcgatg ctctagtgtt cctgtgacca  10680
taatcataat aattcctttg aaagctctat ggtccctgga agcagggcat acaatgcaag  10740
acagcaactt gatcacatca actgaagtat acagggttct cttaactctt ggtgacttcg  10800
gtttaatgga ccggttgtac tcgtgttcta tccgtaaccg ttgtgatgtc ttgtgtgttt  10860
ggttgcggga tagctgggac cacgacgttt ccgtctaatt ctgatggata gctatagacg  10920
gcactgagat ggttatatta taacctctga tcctgaactc tacgagatcg tctcatccgt  10980
cattgccacc aaatacacca ttaaattact aattagctaa cggaccctat ttgtactcat  11040
tccatgtctc ataaactttg ggcaccatcc atccaacaca tccaatctaa acacaccaaa  11100
cgatggggaa tggaaagagc agtattcgat tcaacaatgg caaacaaata tcactgaatt  11160
agaccaagaa taaacctaat tagacaacga cctcccaacc atcattcgtc aggctgtaaa  11220
gaagataaag ctgccatggg gcatggatca agcagaacac cagagatgaa tccaaacaca  11280
cagaaaatca cgcgcgctgt ctacaatgac aacaagcccc acatttcatt gcagtacact  11340
gggctacaaa ggcacgtaca acaaagagct agggaaacat tgcggagggc acgagagagc  11400
agctaacttg acaatatagc agactgagct tgcactgtta gcaggcgagg aagggaatca  11460
tggggacgga gaatggggtc catgcccgcg aaggagaagg cggacgccgc cacggtggca  11520
ccggcgcacg cgcacacagg gaacccgcac aggcagccat ggatgctgcc tcgccattgc  11580
gccggtcgtc tctgccacgc tcctctctct ctcccgctgc atcgccgtgg atggggcaag  11640
cagagagcag ggactgcgac gatctgggcg gaggactcgc cttggagagc gcggacgcag  11700
acgggattct agggagagag cgaagacggg gcgcgcgcgg cgctcgcgcg gcgtggtggc  11760
ggcgagatta gcgggggtgg ggggagggcg gagccgtggt gagggtgtgg acgccctcct  11820
taccctctta agtagtagta gagatataat ccgttccaaa atatccatcc gttcaattta  11880
tatttcgttt gatcttttta ccctaaattt gattgactca tcttattaaa aaagttcata  11940
actattatta atctttattg agatatcatt tagcatataa tatactttaa gtgtggtttt  12000
agattttttt taaaaaaaaa aattcgcaaa aattaaatga aacgacccaa tcaaacttga  12060
aaagtaaaac taattataaa tttgaacgga aggagtaaga ggatgtttga atgtactaga  12120
gctaatagtt ggttgcttta aaatttgcta gtagaattag ctagctaata aatatctaga  12180
taactattag ctaatttgct aaaacagcta atagttgaac tattagctag attgtttgga  12240
tgtattcggc taattttaat ggctaactat tagctatagt acaatattca aacacctcct  12300
aattaaaatg gacaaatatc tcttcttttg gtcccttgcg ttagattttt catatctcct  12360
tatttagtat aaaagaatca tcaaaaagtg gacaacccct agtggaacac catttagta  12420
gtggttgcat gaaacctttc gcgcaccagt ttctatgtgt cactctaaaa atgggacagc  12480
atgtacgtag tgcctatata tatacaagtc atctatcgtt gcctcctcag ttcatcacta  12540
atcacactta ttgtgccctc gacgagtatc tatagctagc tcattaatcg attcgggggt  12600
gtgttgtcga aggcggcaat ggcgagctac tcgtcgcggc gtccatgcaa tacctgtagc  12660
acgaaggcga tggccgggag cgtggtcggc gagcccgtcg tgctggggca gagggtgacg  12720
gtgctgacgg tggacggcgg cggcgtccgg ggtctcatcc cgggaaccat cctcgccttc  12780
```

-continued

```
ctggaggcca ggctgcagga gctggacggg ccggaggcga ggctggcgga ctacttcgac  12840
tacatcgccg gaaccagcac cggcggtctc atcaccgcca tgctcaccgc gcccggcaag  12900
gacaagcggc ctctctacgc tgccaaggac atcaaccact tttacatgca gaactgcccg  12960
cgcatctttc ctcagaagtg agtccgatgc tgccgccatt gttcttgcat ccatccagca  13020
tcgtacgtac gtcctctata catctgcgga tcatcatgtg cgcatgtttg tggcatgcat  13080
gcatgcatgt gagcaggagc aggcttgcgg ccgccatgtc cgcgctgagg aagccaaagt  13140
acaacggcaa gtgcatgcgc agcctgatta ggagcatcct cggcgagacg agggtaagcg  13200
agacgctgac caacgtcatc atccctgcct tcgacatcag gctgctgcag cctatcatct  13260
tctctaccta cgacgtacgt acgtcgtcac gaatgattca tctgtacgtc gtcgcatgcg  13320
aatggctgcc tacgtacgcc gtgcgctaac atactcagct ctttcctatc tgctgcgcca  13380
atttgcaggc caagagcacg cctctgaaga acgctctgct ctcggacgtg tgcattggca  13440
cgtccgccgc gccgacctac ctcccggcgc actacttcca gactgaagac gccaacggca  13500
aggagcgcga atacaacctc atcgacggcg gtgtggcggc caacaacccg gtaactgact  13560
agctaactgg aaaacggacg cacagactcc atgtccatgg cggcccacaa ggtcgatgct  13620
aattgttgct tatgtatgtc gcccgattgc acatgcgtag acgatggttg cgatgacgca  13680
gatcaccaaa aagatgcttg ccagcaagga caaggccgag gagctgtacc cagtgaagcc  13740
gtcgaactgc cgcaggttcc tggtgctgtc catcgggacg gggtcgacgt ccgagcaggg  13800
cctctacacg gcgcggcagt gctcccggtg gggtatctgc cggtggctcc gcaacaacgg  13860
catggccccc atcatcgaca tcttcatggc ggccagctcg gacctggtgg acatccacgt  13920
cgccgcgatg ttccagtcgc tccacagcga cggcgactac ctgcgcatcc aggacaactc  13980
gctccgtggc gccgcggcca ccgtggacgc ggcgacgccg gagaacatgc ggacgctcgt  14040
cgggatcggg gagcggatgc tggcacagag ggtgtccagg gtcaacgtgg agacagggag  14100
gtacgaaccg gtgactggcg aaggaagcaa tgccgatgcc ctcggtgggc tcgctaggca  14160
gctctccgag gagaggagaa caaggctcgc gcgccgcgtc tctgccatca acccaagagg  14220
ctctagatgt gcgtcgtacg atatctaaga caagtggctt tactgtcagt cacatgcttg  14280
taaataagta gactttattt taataaaaca taaaaatata tatatgttct tgaatataaa  14340
attgataacc aaattaaaat tcgaaccatc acttatacat aattttactt tattttttat  14400
aaaacgtgaa cgggaaggac taccgtgaat gactatagaa ccaatcatac tagtataaaa  14460
tatatgatga cactacggga gagacaaact ttgtctggcg ctaaatattt tgccgagtgt  14520
gaattcacgg gcactaggca aagatcttct ttgccgagtg ttacgctggg caaagtaaga  14580
cactaggtaa atcagtcatt tgccgagtgt ccgccactag gcaaagcaaa acactggcaa  14640
atcaaaagtt tacctagtgc cagacactag gcaaaaaaaa aacgctcggc aaatcggaag  14700
tttccctagt gccagacact agacaaagaa aaacacttga taaactagcg tcgtcagcta  14760
acaccatcca ccaaccgtta acgttgccga gtatctgact tcgacactcg gcaaagaagg  14820
tctctttgcc tagtgtcggt ctggaacact aggcaaagag gcactttacc tagtgtcgta  14880
ttttgacact cagtaaaata atttttttc tttctgcttc caaacttttt atgatgtgtt  14940
cctatagcac ctagaactac atgtcaagtt ttggtaaaat ttttgaagtt tttgctatat  15000
ttacttaatt tattttattt aattgaattt cttttgataa ttcaaatttg aactcggcaa  15060
ggtaagaagc gagggtagcc tggaaacaca ctttgcctag tgttacactc ggtacaggag  15120
cctcccctgc ctagtgctgc actcgacaaa agattcgcct ttgcctagcg ctgcactcgg  15180
cacaggagtc gcctttgcct agtgctgcac taggcaaagc ctccgttacc gtgccttcca  15240
tcgtcggacc gcctgcaggc ccgggggcgc gccctaatta gctaacggcc aggatcgccg  15300
cgtgagcctt tagcaactag ctagattaat taacgcaatc tgttattaag ttgtctaagc  15360
gtcaatttgt ttacaccaca atatatcctg ccaccagcca gccaacagct ccccgaccgg  15420
cagctcggca caaaatcacc actcgataca ggcagcccat cag                   15463
```

```
SEQ ID NO: 94          moltype = DNA  length = 15757
FEATURE                Location/Qualifiers
misc_feature           1..15757
                       note = Expression cassette of construct 22467
regulatory             214..2339
                       regulatory_class = promoter
gene                   2341..3018
regulatory             3024..4036
                       regulatory_class = terminator
regulatory             4044..4237
                       note = enhancer - eFMV
                       regulatory_class = enhancer
regulatory             4244..4536
                       note = enhancer - e35S
                       regulatory_class = enhancer
regulatory             4544..8537
                       note = promoter - Ubi
                       regulatory_class = promoter
gene                   8538..9995
                       note = EPSPS
regulatory             10009..11008
                       note = terminator - Ubi
                       regulatory_class = terminator
gene                   11028..15538
                       note = GRMZM2G062320
regulatory             11028..12596
                       note = promoter - pPGM
                       regulatory_class = promoter
exon                   12597..12834
                       note = PGM exon1
misc_feature           12835..12974
                       note = Intron - PGM intron1
exon                   12975..13198
```

```
                        note = PGM exon2
misc_feature            13199..13295
                        note = Intron - PGM intron2
exon                    13296..13382
                        note = PGM exon3
misc_feature            13383..13718
                        note = Intron - PGM intron3
exon                    13719..13787
                        note = PGM exon4
misc_feature            13788..14102
                        note = Intron - PGM intron4
exon                    14103..14204
                        note = PGM exon5
misc_feature            14205..14304
                        note = Intron - PGM intron5
exon                    14305..14424
                        note = PGM exon6
misc_feature            14425..14492
                        note = Intron - PGM intron6
exon                    14493..14540
                        note = PGM exon7
regulatory              14541..15538
                        note = terminator - tPGM
                        regulatory_class = terminator
source                  1..15757
                        mol_type = other DNA
                        organism = synthetic construct
SEQUENCE: 94
cctgtggttg gcatgcacat acaaatggac gaacggataa acctttcac gccctttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga cccgaaagta gcaaacaaca ggttcatgtg  240
cactataaaa agacaaaatt ctcgagtttc atcttttatt ccacataagc cttatatttt  300
ccattttcat atgattttta gtttaagttt gtgtcttaac tttttcgtta atacgtaatt  360
ctatgcatta tggatgcgtg aagtattttt gtttaaaaaa atgaaatgtc aaaatacgtt  420
ttgtgatcta tttccatgtt ttcacctaac aggtggtttt tactatatat tctgccataa  480
ctctagcctt agatgtaaat cgaaaaaaaa tgagagatga gctggagata gccttagatg  540
aagcgtctga aatataaaag aaagagtaat gttgaacgca gtaggtgtag cagctgtagt  600
tccatctcta ggaaagggaa ctgcaatccg ggctccgggc ctcgcgcaat ctggcctgtc  660
gtgtagatgc agccctgtcc atgacggccc aagcaacgcc cgcggctctc gatccaccac  720
ggaacccact ccgacacaca ctgacacaca catgctggat gtggatgtgc tgtccaatta  780
ttagtagcaa ttcggtaggc acaggcacgt actggccggt gttttagctg taagtaccga  840
accaatcacg gttaagaacc gattaatccg tgcccagccg ccgagtgcgt tcgtacgtgc  900
atcggatgca ctgcatgaat tgagagcatc atcatatcat acgcaggagt agtacgacgc  960
cgctgctgtc ttgtccggct aatgctttgc tcacagatta gtccatcgcc cacggtcggt  1020
gtggtgtgga tcgctgatgc cactgctttt tgtttggttt ttattcccct gataatcctc  1080
cgcgtccctg aatgtatcta tttattttca ttccgaaatc cctttcacga aaaagaaaac  1140
gaataaaaag agagttacga atacgcttcc ggcggcccac atcaccttcc agcgaacatc  1200
gcgccgcgct gacgtgtcgc ccatcgcggc cgtccatatc gccatccgac gaccgtggaa  1260
gctggcagcg gccgctccgt tccgtcgaag gggcaggtca gtcaggtcac ccacacggcc  1320
acacccgcgc gggggatacg cggtggaaaa cccggcgacc acatcaaaac acgaggcgtc  1380
tcccgcagga ctggtcactc ggcacgcagg cagaggcagc acagcagcag ccagctccat  1440
ccatcctctt tcccctcctc gcttcgcttc ctcggcggat tcctcctccc tcggccgtcc  1500
ccgtcccctt cttcgccgcg ccagctcgcc cgagttggta cgcccatcct ctgctgtact  1560
ccccccgttc ctgctgtgcg aaaccgagca cccaaaccct agcctaagct attcgcatcg  1620
caaactctat tgagcgacgg atcgcgaaac gcgcgccgcc gcattcggac gagacctcgt  1680
ggcccgtacc ttcctactct accgtcgtcg ccggagacca gctcaccggt tagggtttcg  1740
ggattagggg cttggggctt ggattcccgg gggactccat acccggtggc cttagaaggg  1800
gaagggggcc cagcggtggt ggtggttcga ctgtcagcga gcgagacggc ggggcaccgc  1860
cgatcgggcg tcgctggaca tttgattgag ctgggcaggc gaaggcgtgg agcttgctct  1920
tcgattggga ttagaggagg gcggaggtgg tatggtgggc ggctcggctg gctcaatgga  1980
gccgctggcc ggtggtgggg caggcgagat cacgctctct catagagcgt aatgggttgc  2040
gtaacacact cctgtttgta tttcgatccg atctaataat taaagtttat ttacgtggtg  2100
cacatgtaga atttcccat gcccactgct aacttggatt ggatttttgc caaaaaaacg  2160
ggtgtgcacc caatcactta tagtgaaacc gttgtgtgtt tgatgtgctt ctaaccaagt  2220
acaaatccag tgaaaacaca cctaccattc aacaatccac attttggttg caattatcag  2280
cattctagaa aggtgcatgt gcccattgat acacttgcta ttggtgcagg caaacccacc  2340
atggcctcct ccgagaacgt catcaccgag ttcatgcgct tcaaggtgcg catggagggc  2400
accgtgaacg gccacgagtt cgagatcgag ggcgagggcg agggccgccc ctacgagggc  2460
cacaacaccg tgaagctgaa ggtgaccaag ggcggccccc tgcccttcgc ctgggacatc  2520
ctgtccccc agttccagta cggctccaag gtgtacgtga agcaccccgc cgacatcccc  2580
gactacaaga agctgtcctt ccccgagggc ttcaagtggg agcgcgtgat gaacttcgag  2640
gacggcggcg tggcgaccgt gacccaggac tcctccctgc aggacggctg cttcatctac  2700
aaggtgaagt tcatcggcgt gaacttcccc tccgacggcc ccgtgatgca gaagaagacc  2760
atgggctggg aggcctccac cgagcgcctg tacccccgcg acggcgtgct gaagggcgag  2820
acccacaagg ccctgaagct gaaggacggc ggccactacc tggtggagtt caagtccatc  2880
tacatggcca agaagcccgt gcagctgccc ggctactact acgtggacgc caagctggac  2940
atcacctccc acaacgagga ctacaccatc gtggagcagt acgagcgcac cgagggccgc  3000
caccacctgt tcctgtagga gctcgcatca tgatcatgca tcatggactc ggcctactac  3060
```

```
tgtggatttg tatgccatta tagacttggt gctgtgaaag actgcttgat gatttgcggg  3120
tttgttgctg tgtaaaaaaa ggtcccttgg ctcccagaag accatgaagg ttcggatcta  3180
tcatgtaatt ccttgttatc tgccaattat gtatggacta tggacatgtg ttgcgctgtt  3240
caacttacta ctacaaataa gtaatcgata tgttcccttc ccatgtctcg gtgacaattg  3300
tctggagaag cttaggggtc gtttgtttgg gattatgtct ggagaaactt attttaaact  3360
aagtgtgagt tcaagttaag ttagattata taatctaggc agattataat tccaagcgaa  3420
caggtcctta gtgtttttgg aaaatcctag gtgttctttt ggctacattg ttgtgtgtgc  3480
agatcccttg ttggtctgta agcgtgggga agtaagaatc gtccgtttct actgaagacc  3540
tgctcgagtt aggcaccgag gatgccggta accaaacaga gcaatagtgt ctctgtgggc  3600
acagtggagt gtgaatctgt gtgatgcaaa tccgtcattt gtttagcaaa atttccagcg  3660
ttgcatgatg cagtttcttt aacacggact taagggaagg gaaaaaaatg ttgagccagg  3720
agatccttca atgtgttaga ctgacgtgat agccaactaa accacgacgc aatgttgtcg  3780
ttaatgacaa aaaaactatt tgttcctaaa tccttggcga cattgcatgg ctgtctcatg  3840
agataatggt ctcatctctt atttatctct tatttatagc cggaagtggt agtgacccct  3900
gcttgattgc tcgtatgcca tctcaagttc tcaaccgtgt cgagcagcca ttttcccatc  3960
tcaagcgcat catcgtttcg tttgacctca tctgctatcc tgctcctagt gcaaatcaca  4020
tgcgacagaa agtgtgcgga cccagctgct tgtggggacc agacaaaaaa ggaatggtgc  4080
agaattgtta ggcgcaccta ccaaaagcaa ctttgccttt attgcaaaga taaagcagat  4140
tcctctagta caagtgggga acaaaataac gtggaaaaga gctgtcctga cagcccactc  4200
actattgcgt ttgacgaacg cagtgacgac cacaaaactc gagacttttc aacaaagggt  4260
attatccgga aacctcctcg gattccattg cccagctatc tgtcacttta ttgtgaagat  4320
agtggaaaag gaaggtggct cctacaaatg ccatcattgc gataaaggaa aggctatcgt  4380
tgaagatgcc tctgccgaca gtggtcccaa agatggaccc ccacccacga ggagcatcgt  4440
ggaaaaagaa gacgttccaa ccacgtcttc aaagcaagtg gattgatgtg atatctccac  4500
tgacgtaagg gttgacgaac aatcccacta tccttcaagc tttggaaaac caaaacaacg  4560
aataagcaaa ctgcaggaaa agtatgcagt ggaaaccaac ccagattcgg acgataggaa  4620
agtatcaagt gaatgatttg ccaggaaaag gagaggggta aaaaggggcg aagatttaga  4680
agatctaaag cacaagaacc agagattaga ttgaacaata gggaacttgg agcatccttt  4740
ttttcttcag ggaaaaactg aaaatccaaa ccatgttgag caaaaccgag tgggattgga  4800
aaccaaaaaa cccgagataa agaaactcga gaaaaagcat gaaatcgaaa ccaacttcag  4860
taaaacaaaa ggaggacaga aaagaaagtc ggaagctata aagaatacat taacattcag  4920
tgaaacagca tgctgtcttc ttcttttttt atgcacaaca gagcatacat atataccttc  4980
ccaggctgag gacttggcgg aggagagccg cggataggtt ggcggtgcag acggtctgga  5040
cgggcccgaa gacggagacg aacagcgggc ccttcctgcc caggcaccac gcttggaacg  5100
ccaagcacgc gccaaccgcg gccccgccga ggacgacgat ccccgcgaca agcgtggcgt  5160
cgatcctggg cgaccccaag ccgaggaacc tcccttccag gacgagccgt aggacggcgg  5220
tgagagaggc acccgtcgcg gaggtggcgc agcacaaggt gagcagcgcg gggaaggcgg  5280
cgagcgtggc ggcctgcagg acggtgacga gcgcgaagac ggtgacgccg gcgacgaggc  5340
agcagcagcc gaggatccag tcgtaggagg aagccggacc aaaccgggca atgcaacctg  5400
cagatgcact agacggaggt aacgaggagg aggagaaaac agagcaagag caggcggaga  5460
gaagatagag caaaacacga gtgaggcaca gcgtaagcac tcggtagaag tctccagagg  5520
cgaggtgcgc acaggagaac agatgagtaa agtcagccaa ggatccacga tccaacggct  5580
acgaattttt ggagtgacgt ggataggctc aaaggcgcca tttccatccg gctttatagt  5640
attttaaaaa aattcatttt cctccctcta gtgtgtgcgg aggcgtgagc ccgtttaacg  5700
gcgttgagaa gtctaacgga caccaaccac aaccaggaac cagcgccggc cgcgccgccg  5760
agtgaagcag actgcatacg gcacggcgcg gcatctctct ggctgcctct cgagagttcc  5820
gcccccacct tcccgcggta gcgtggtggt ttcgctttcc gctgtcggca tccggaagtt  5880
gcgtggcaga gtggacggag acgaggccgg gtcctccagc tcctctcaaa cgtcacggca  5940
ccggcatccg gcagccagcg cggtccttcc caaccactcg ttcccaaccc atccccctc  6000
ctcgcccgcc gtcataaata gccagcccca tccccagctt ctttccccaa cctcatcttc  6060
tctccttttg ctctgaacgc acacaccgcc cggtctccga tctccgatcc ccgatcccct  6120
cgtcgatcct aggtacggcg accatcctac cccccccccc ccccctctc tctctgcctt  6180
ctctagatcg gcgatccgat ccatgcttac ttggttaggg cctgctaact atgttcatgt  6240
ttgcgttaga tccgtgcatg gacgcgatct gtacacacca gacgcgttct gattgctagc  6300
taactcgcca gtacctggga atcctgggat ggctgtagcc ggccccgcac gcagacggga  6360
ccgatttcat gattctctat tttttctttt gtttcgttgc ctagggtttc gttcgatcga  6420
tccgcgttat tctttatttc catatattct ggtacgatgt tgatacggtt cgaccgtgct  6480
gcttacgttc tgtgcgcttg tttgccgggt catttttacc ttgccttttt tgtatggttt  6540
ggttgtggcg atgtggtctg gtcgggctgt cgttctagat cggagtagag tgctgtttca  6600
aactgtctag cggatctatt agatttggat ctgcatgtgt gacatatatc ttcgtagtta  6660
agatgatgca tctgtatgtg tgacatgcgg atctattaga tttggatctg tatgtgtgac  6720
atatatcttc gtagttgaga tgatgcatct gtatgtgtga catatatctt cgtagttaag  6780
attatgcatg gaaatatcaa tcctttagat aaggacgggt atacttgttg ctgtgggttt  6840
tactggtact tcgatagatg catatacatg atctaacatg cttagataca tgaagtaaca  6900
tgctgctacg gtttaataat tcttgagttg atttttactg gtacttagat agatgtatat  6960
acatgcttag atacatgaag taacatgctc ctacagttcc tttaatcatt attgagtacc  7020
tatatattct aataaatcag tatgttttaa attattttga ttttactggt acttagatag  7080
atgtatatat acatgctcaa acatgcttag atacatgaag taacatgctg ctacggttta  7140
gtcattattg agtgcctata tattctaata aatcagtatg ttttaaatta ttttgatttt  7200
actggtactt agatagatgt atatatacat gctcaaacat gcttagatac atgaagtaat  7260
atgctactac ggtttaattg ttcttgagta cctatatatt ctaataaatc agtatgtttt  7320
aaattatttc gattttactg gtacttagat agatgtatat atacatgctt agatacatga  7380
agtaacatgc tactacggtt taattgttct tgaataccta tatattctaa taaatcagta  7440
tgttttaaat tatttcgatt ttactggtac ttagatagat gtatatatac atgctcgaac  7500
atgcttagat acatgaagta acatgctaca tatatattat aataaatcag tatgtcttaa  7560
attattttga ttttactggt acttagatag atgtatatac atgctcaaac atgcttagat  7620
acatgaagta acatgctact acggtttaat cattattgag tacctatata ttctaataaa  7680
tcagtatgtt ttcaattgtt ttgattttac tggtacttag atatatgtat atatacatgc  7740
tcgaacatgc ttagatacgt gaagtaacat gctactatgg ttaattgttc ttgagtacct  7800
```

-continued

```
atatattcta ataaatcagt atgttttaaa ttatttcgat tttactggta cttagataga  7860
tgtatatata catgctcgaa catgcttaga tacatgaagt aacatgctac tacggtttaa  7920
tcgttcttga gtacctatat attctaataa atcagtatgt cttaaattat cttgatttta  7980
ctggtactta gatagatgta tatacatgct tagatacatg aagtaacatg ctactatgat  8040
ttaatcgttc ttgagtacct atatattcta ataaatcagt atgtttttaa ttattttgat  8100
tttactggta cttagataga tgtatatata catgctcgaa catgcttaga tacatgaagt  8160
aacatgctac tacggtttaa tcattcttga gtacctatat attctaataa atcagtatgt  8220
ttttaattat tttgatatta ctggtactta acatgtttag atacatcata tagcatgcac  8280
atgctgctac tgtttaatca ttcgtgaata cctatatatt ctaatatatc agtatgtctt  8340
ctaattatta tgattttgat gtacttgtat ggtggcatat gctgcagcta tgtgtagatt  8400
ttgaataccc agtgtgatga gcatgcatgg cgccttcata gttcatatgc tgtttatttc  8460
ctttgagact gttctttttt gttgatagtc accctgttgt ttggtgattc ttatgcagat  8520
ccagatcttc gtaaaccatg gctctggtgg ctaggccagt gctgtctgct agagtggctg  8580
cttctaggcc aagggtggcc gctagaaagg ctgtgagggt gagcgctgcc agtcacggcg  8640
ctagctctag gccagccacc gctaggaagt ccagcggcct gagcggcacc gtgcgcatcc  8700
caggcgacaa gagcatcagt caccgcagct tcatgttcgg cggcctggcc agcggcgaga  8760
ctaggatcac cggcctgctc gagggcgagg acgtgatcaa caccggcaag gccatgcagg  8820
ctatgggcgc tcgcatccgc aaggagggcg acacctggat catcgacggc gtgggtaatg  8880
gcggcctgct ggccccagag gccccactgg acttcggcaa cgccgccacc ggctgcaggc  8940
tgactatggg cctggtgggc gtgtacgact tcgacagcac ctttatcggc gacgccagcc  9000
tgaccaagag gccgatgggc agggtgctga acccgctgcg cgagatgggc gtgcaggtca  9060
agagcgagga cggcgacagg ctgccggtga ccctgagggg cccaaagacc ccgaccccga  9120
tcacctaccg cgtgccaatg gccagcgccc aggtgaagtc agccgtgctg ctggccggcc  9180
tgaacacccc aggcatcacc accgtgatcg agccgatcat gacccgcgat cacaccgaga  9240
agatgctgca gggcttcggc gccaacctga ccgtcgagac tgacgctgac ggcgtgagga  9300
ccatcaggct cgagggcagg ggcaagctga ccggccaggt gatcgacgtg ccgggcgacc  9360
caagcagcac cgccttccca ctggtggccg ccctgctggt gccaggctct gacgtgacca  9420
tcctgaacgt gctgatgaac ccgagccgca ccggcctgat cctgaccctg caggagatgg  9480
gcgccgatat cgaggtgatc aacccgaggc tggctggcgg cgaggacgtc gccgacctga  9540
gggtgaggtc cagcaccctg aagggcgtga ccgtgccaga ggacagggcc ccgagtatga  9600
ttgacgagta cccgatcctg gccgtggccg ctgccttcgc cgagggcgcc accgtgatga  9660
acggcctcga ggagctgcgc gtgaaggaga gcgacaggct gagcgctgtg gccaacggcc  9720
tgaagctgaa cggcgtggac tgcgacgagg gcgagactag cctggtggtg aggggcaggc  9780
cagacggcaa gggcctgggc aacgcttccg gcgctgccgt ggccacccac ctggatcaca  9840
ggatcgccat gtcgttcctc gtgatgggcc tcgtgagcga gaacccggtg accgtggacg  9900
acgccaccat gatcgccacc agcttccccg agttcatgga cctgatggcc ggcctgggcg  9960
ctaagatcga gctgagcgac accaaggccg cctgatcatc tagagctcgc caaggttcaa  10020
ttaagctgct gctgtacctg ggtatctgcg tcgtctggtg ccctctggtg tacctctata  10080
tggatgtcgt cgtctaataa acatctgtgg tttgtgtgtc atgaatcgtg gttgtggctt  10140
cgttggttta atggacctgt tgtgtcctct gtgttgtacc caaaactctt ctgcagcagt  10200
atggcttgaa tccttatgaa gtttgatatt tgaacttaaa agtctgctca ttatgttttt  10260
ttctggttat atctcctaat taactgcctg ggatcaaatt tgattcgctg gtgtttattg  10320
gacccctccc aggttcttgc tttctaccgt ttcttgctga atgttaactt gattctgtca  10380
ggctcagttt cccactatgg cttacagctt aacgtgtttg gtttgttgaa tgttaacttg  10440
gttttgtcaa gctcagtttt ttactctggc ttacagcata acatgtttga cttttggttt  10500
tgctgctttg ttattgggtt ctgggtagtt cttgatgaat ccaaaagatc atgtgcacag  10560
ccatattatc tatttaagcg atccaggtta ttactatgaa aggatgcctt ctagctaagg  10620
agtagttagg ttttttcttc aaggttaaat ttctcgatg ctctagtgtt cctgtgacca  10680
taatcataat aattcctttg aaagctctat ggtccctgga agcagggcat acaatgcaag  10740
acagcaactt gatcacatca actgaagtat acagggttct cttaactctt ggtgacttcg  10800
gtttaatgga ccggttgtac tcgtgttcta tccgtaaccg ttgtgatgtc ttgtgtgttt  10860
ggttgcggga tagctgggac cacgacgttt ccgtctaatt ctgatggata gctatagacg  10920
gcactgagat ggttatatta taacctctga tcctgaactc tacgagatcg tctcatccgt  10980
cattgccacc aaatacacca ttaaattact aattagctaa cggacccctt gcctcggtta  11040
caattgagtt tgtcataaga aagaatgaga aagaaaagaa gcaatccaag cgcaagagct  11100
caaaggaaca caagtcactc tctcactagt cactattgat tggaattgaa ctagggactt  11160
gggagaggat tttatctctt tggtgtgtct tgtattgaat gctatagctc ttgtaatgtg  11220
tagaatgttg gaaacttgga tgccattgaa tgtggggtgg ttggggtatt tatagcccca  11280
accaccacaa tgtggtcgtt ggaagtctgc tgtcgcatgg cgcaccggat agtccgatgc  11340
gccaccggac actgtccggt gcgccagcca cgtcagccag ccgttggggt tcgaccgttg  11400
gagctctgac ttgtggggcc tctgggctgt ccggtggtgc accggacagg tcctgtagac  11460
tgtccggtgc accaactgcg cgtgctctga cctctgcgcg cgcaggcgcg cattaaatgc  11520
gttgcagtcg accgttgcgc ttgaagtagt cgttgctccg ctggcacacc ggacagtgtc  11580
cggtgaatta tagcggagcg gcctccattt tcccgaaggt agcgagttca gcgtcgagtt  11640
ccctggtgca ccggacactg tccggtggca caccggacag tccggtgcgc cagaccaggg  11700
cacacttcgg ttgtctttgg ctctctttgt ttgaaccctt tcttggtctt tttattggtc  11760
tattgtgaac ctttggcacc tgtaaaactt ataatctaga gtaaactagt tagtccaatt  11820
atttgtgttg ggcaattcaa ccaccaaaat caattaggaa aaggtgtaag cctatttccc  11880
tttcaggagg cgtacgtgag agggagaggt gaaaaggaac aacgcgtata ccagataagg  11940
tcccacagcc taagtaggta gccttctaat atctctacta actattaagg agagagtgta  12000
gactgccccc gctccctacc caacgccccc cgctacctgt tcaccgcgcg ccagcgaaac  12060
ctccgcacgc ccactgccca tctgttcccc gtgcgccagc gaaacatccg cacgcccgcg  12120
gcccgcctgt tccccgcgca tcccgctgca cgacttctgc taccgcaacg gccacccacg  12180
cacgcccgcc tgttcaccgc gcatcccgct gacctcccct tcacgctcgc acacgctccg  12240
ttcccccacc ccaccgcaat ccccgacgct ataagagcgg taaccaactc catctccctg  12300
gtgccacgca ttgttgagtt cttaaggtgc gtttcgttga ggacttgttc atttttgttg  12360
gtcatgtatt ccattttact gctctaccat tttgtggaat aaagggagga atgttttcac  12420
tagaagagtt catcaatctt atgttggttt cttggatcag ttttgctcta tggctaaatg  12480
gtcgaattga gcctatttca ttataaagtt agcgagcgaa taattgttca gcctcttcct  12540
```

```
agaactcatt accagtagaa tcagttacta actgcttttc tttttcttgg attagaatgg  12600
ctggggctat ctctcaccat gcgctagcat tttcacaatc ccactggtgc agtgcgaaga  12660
actctagatt cggaaagagg acgggcaatg ctcgcctggt ttatctaaaa ggaagatgtg  12720
gttcaggcag cagaaaactg ggtttgatgt gggcctcgag ctcgcagtct tctgtcatgg  12780
agccgacgca cctaccatct gatggcaaca gcagccacac cccaaaaaaa tcaagtaatt  12840
ttaacgacct cctatggtgg ttatttgttt ttaatttgag aaaactatcc atttgacaca  12900
tttaactttg ggcttctcag aatttggggg catataataa gatctgctaa tctgttatct  12960
ctatgtcgtt gtaggtgaaa gcgctcttat attgatttgg catggtgaat ccctgtggaa  13020
cgagaaaaat ctatttcctg gctgcatcga tgtacccctg acaccgaagg gtgttgagga  13080
ggccattgag gcaggtaaaa ggatatgcaa tatcccaatc gatgtgatat atacttcatc  13140
actgatttgt gctcagatga ccgcaatgct tgccatgatg cagcatcgac gcaagaaggt  13200
ttgtgtcttt cctttgaaat tccagtaatt tcttctagca tttgtatgaa cttgccggag  13260
aaatcatgct ttgctggtga tatatgtatt tatagatcct agttatcacg cataatgaga  13320
gtgaacaagc tcacaggtgg agtcagatat acagtgagga gacaatgaaa cagtccattc  13380
ctgtcatcac agcttggcaa ttgaatgaac ggatgtaata ctttctccat actctttgat  13440
ttgctaatta ctccctctgt ctcaaaatag tattaatttt agctcttgat ttttatgtct  13500
atattcaaat agatgatgat aaatctagat tctagacaca aatataaaac atatacatca  13560
agtattatat gaatctatta atttactaag accaatttta atttgggaca gagggagtat  13620
acgattataa tagttgtttg actgtgcttc tctttaaata tcccttgaca tttctaggta  13680
tggtgagcta caaggcctta acaagcaaga aactgtagat cgatttggca aagaacaagt  13740
tcatgagtgg cgccgcagtt atgatattcc tccgccaaat ggagaaagtc tagagaagtg  13800
tgctgagaga gctgttgctt atttcaaaga tcaggcacat ctagcaaggc cactttacac  13860
taattgaaag atacactttt tacttgggtt attggtcttg ctgcagtatt ggtatgcatg  13920
ctaaaggtta ttcttgaatc gatgaattcc tctactatgg gatgcagaaa tgcatgtgct  13980
tagttttctt tctattgtgc tagctcatat caaatttata acctgaattt tttatttatg  14040
ttcgactcta aaaaacagtt ttttctagct cgatttgacc tatagtaatt tttccgtaat  14100
agattattcc acaacttgtg gctggaaaac atgtgatggt tgctgcacat gggaattcac  14160
ttcgttcaat tataatgcat ctggacaaat taacttctca gaaggtaatt cactgtcgtt  14220
tttgtctttc catcaaaaag gactcggcta aacagaacat gtagcattat gttaagtttg  14280
ggagtgagcc tttcgtccct tcaggtaata agccttgagc tgtctactgg cattcccatg  14340
ctttacatat tcaaagaggg aaagtttatt cgacgtggga ctccagtagg accttcggag  14400
gccagtgttt atgcttatac cagggtaaga ttctttcccc cacatgttct accataggac  14460
gatactccag tttacaaacc ttatctgtac agaccaaacg atttgctgag cacattacat  14520
ttcagaacaa attggcctag aagataaggg gtgtttggtt tgagaaatca ctctattcaa  14580
aatgagatgg tgtatcatgg gtccatttct caaatttggt gggatgaccc tattcctcat  14640
attagtacta actaggtgag tgtccgtgcg ttgcaacggg aacatataat aacatgataa  14700
cttatataca aaatgtgtct tatattgtta taagaaaatg tttcataatc catttgtaat  14760
cctggccata cataaatttt gttattttaa tttagctgtt tcactactac attgcaacca  14820
tcagtatcat gcagacttcg atatatgtca cgatttgcat agtcttatca ttgaagagca  14880
cgtgtcacac ctaccggtag aagttccctc gtacattgtc agggggacct catggtcgtc  14940
gctaaagccg gcgactctct ggttgttctg ggcaccgcat ccgacgacaa caccgtcacg  15000
ctgtccagct catcatccac ctgaagatca acctgccacg taagtcggta gtgaccggcc  15060
atgaattctt gtgcgctggg gcaacgggcg ttgcattccg ttgtgtgagt gttttagaac  15120
aagatgtatg taaaggagta gcacatccgg tggtgcaatg gctaggtgta ctacctcgct  15180
gatgagctcg cggtgcactt cgtttagcag cccagccaag agtcatcggt acttgccatg  15240
tcgtgcgtgt tcgacgacta ctatatcaag gactgtggcg tcctcttggc gccagaggtg  15300
aggagtaccg acagcaatga cctctcgcca tcgtcggggt agcttttgtg ctggcccgcc  15360
tttaattctc ttcgtaaaca catacacttg cctttttgt ttaagcaagt gagtatagtg  15420
gtgcgtacct gatgactgac aatgtacgag gaaacttcta ctggcaggtg tggcacgtgc  15480
tcttcaatga tgagaccatg taaatcgtga catatatcga agtctgcatg atactgatcg  15540
gaccgcctgc aggcccgggg gcgcgcccta attagctaac ggccaggatc gccgcgtgag  15600
cctttagcaa ctagctagat taattaacgc aatctgttat taagttgtct aagcgtcaat  15660
ttgtttacac cacaatatat cctgccacca gccagccaac agctccccga ccggcagctc  15720
ggcacaaaat caccactcga tacaggcagc ccatcag                          15757
```

```
SEQ ID NO: 95          moltype = DNA  length = 15355
FEATURE                Location/Qualifiers
misc_feature           1..15355
                       note = Expression cassett of construct 22503
regulatory             214..407
                       note = enhancer - eFMV
                       regulatory_class = enhancer
regulatory             414..706
                       note = enhancer - e35S
                       regulatory_class = enhancer
regulatory             714..4707
                       note = promoter - Ubi
                       regulatory_class = promoter
gene                   4708..6165
                       note = EPSPS
regulatory             6179..7178
                       note = terminator - Ubi
                       regulatory_class = terminator
regulatory             7198..9285
                       note = promoter - pPLA2m
                       regulatory_class = promoter
stem_loop              9298..10212
                       note = targeting exon2 of PLA2
regulatory             10223..11218
```

```
                         note = terminator - tPLA2
                         regulatory_class = terminator
regulatory               11226..13349
                         regulatory_class = promoter
gene                     13352..14131
misc_feature             14039..14128
regulatory               14138..15136
                         regulatory_class = terminator
source                   1..15355
                         mol_type = other DNA
                         organism = synthetic construct
SEQUENCE: 95
cctgtggttg gcatgcacat acaaatggac gaacggataa acctttcac gcccttttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga cccagctgct tgtggggacc agacaaaaaa  240
ggaatggtgc agaattgtta ggcgcaccta ccaaaagcaa ctttgccttt attgcaaaga  300
taaagcagat tcctctagta caagtgggga acaaaataac gtggaaaaga gctgtcctga  360
cagcccactc actattgcgt ttgacgaacg cagtgacgac cacaaaactc gagacttttc  420
aacaaagggt attatccgga aacctcctcg gattccattg cccagctatc tgtcacttta  480
ttgtgaagat agtggaaaag gaaggtggct cctacaaatg ccatcattgc gataaaggaa  540
aggctatcgt tgaagatgcc tctgccgaca gtggtcccaa agatggaccc ccacccacga  600
ggagcatcgt ggaaaaagaa gacgttccaa ccacgtcttc aaagcaagtg gattgatgtg  660
atatctccac tgacgtaagg gttgacgaac aatcccacta tccttcaagc tttggaaaac  720
caaaacaacg aataagcaaa ctgcaggaaa agtatgcagt ggaaaccaac ccagattcgg  780
acgataggaa agtatcaagt gaatgatttg ccaggaaaag gagaggggta aaaaggggcg  840
aagatttaga agatctaaag cacaagaacc agagattaga ttgaacaata gggaacttgg  900
agcatccttt ttttcttcag ggaaaaactg aaaatccaaa ccatgttgag caaaaccgag  960
tgggattgga aaccaaaaaa cccgagataa agaaactcga gaaaaagcat gaaatcgaaa  1020
ccaacttcag taaaacaaaa ggaggacaga aaagaaagtc ggaagctata aagaatacat  1080
taacattcag tgaaacagca tgctgtcttc ttcttttttt atgcacaaca gagcatacat  1140
atataccttc ccaggctgag gacttggcgg aggagagccg cggataggtt ggcggtgcag  1200
acggtctgga cgggcccgaa gacggagacg aacagcgggc ccttcctgcc caggcaccac  1260
gcttggaacg ccaagcacgc gccaaccgcg gccccgccga ggacgacgat ccccgcgaca  1320
agcgtggcgt cgatcctggg cgaccccaag ccgaggaacc tcccttccag gacgagccgt  1380
aggacggcgg tgagaggcgc acccgtcgcg gaggtggcgc agcacaaggt gagcagcgcg  1440
gggaaggcgg cgagcgtggc ggcctgcagg acggtgacga gcgcgaagac ggtgacgccg  1500
gcgacgaggc agcagcagcc gaggatccag tcgtaggagg aagccggacc aaaccgggca  1560
atgcaacctg cagatgcact agacggaggt aacgaggagg aggagaaaac agagcaagag  1620
caggcggaga gaagatagag caaaacacga gtgaggcaca gcgtaagcac tcggtagaag  1680
tctccagagg cgaggtgcgc acaggagaac agatgagtaa agtcagccaa ggatccacga  1740
tccaacggct acgaattttt ggagtgacgt ggataggctc aaaggcgcca tttccatccg  1800
gctttatagt attttaaaaa aattcatttt cctccctcta gtgtgtgcgg aggcgtgagc  1860
ccgtttaacg gcgttgagaa gtctaacgga caccaaccac aaccaggaac cagcgccggc  1920
cgcgccgccg agtgaagcag actgcatacg gcacggcgcg gcatctctct ggctgcctct  1980
cgagagttcc gcccccacct tcccgcggta gcgtggtggt ttcgctttcc gctgtcggca  2040
tccggaagtt gcgtggcaga gtggacggag acgaggccgg gtcctccagc tcctctcaaa  2100
cgtcacggca ccggcatccg gcagccagcg cggtccttcc caaccactcg ttcccaaccc  2160
atccccctc ctcgcccgcc gtcataaata gccagcccca tccccagctt ctttccccaa  2220
cctcatcttc tctcctttg ctctgaacgc acacaccgcc cggtctccga tctccgatcc  2280
ccgatcccct cgtcgatcct aggtacggcg accatcctac cccccccccc cccccctctc  2340
tctctgcctt ctctagatcg gcgatccgat ccatgcttac ttggttaggg cctgctaact  2400
atgttcatgt ttgcgttaga tccgtgcatg gacgcgatct gtacacacca gacgcgttct  2460
gattgctagc taactcgcca gtacctggga atcctgggat ggctgtagcc ggccccgcac  2520
gcagacggga ccgatttcat gattctctat ttttttcttt gtttcgttgc ctagggtttc  2580
gttcgatcga tccgcgttat tctttatttc catatattct ggtacgatgt tgatacggtt  2640
cgaccgtgct gcttacgttc tgtgcgcttg tttgccgggt catttttacc ttgccttttt  2700
tgtatggttt ggttgtggcg atgtggtctg gtcgggctgt cgttctagat cggagtagag  2760
tgctgtttca aactgtctag cggatctatt agatttggat ctgcatgtgt gacatatatc  2820
ttcgtagtta agatgatgca tctgtatgtg tgacatgcgg atctattaga tttggatctg  2880
tatgtgtgac atatatcttc gtagttgaga tgatgcatct gtatgtgtga catatatctt  2940
cgtagttaag attatgcatg gaaatatcaa tcctttagat aaggacgggt atacttgttg  3000
ctgtgggttt tactggtact tcgatagatg catatacatg atctaacatg cttagataca  3060
tgaagtaaca tgctgctacg gtttaataat tcttgagttg atttttactg gtacttagat  3120
agatgtatat acatgcttag atacatgaag taacatgctc ctacagttcc tttaatcatt  3180
attgagtacc tatatattct aataaatcag tatgttttaa attattttga ttttactggt  3240
acttagatag atgtatatat acatgctcaa acatgcttag atacatgaag taacatgctg  3300
ctacggttta gtcattattg agtgcctata tattctaata aatcagtatg ttttaaatta  3360
ttttgatttt actggtactt agatagatgt atatatacat gctcaaacat gcttagatac  3420
atgaagtaat atgctactac ggtttaattg ttcttgagta cctatatatt ctaataaatc  3480
agtatgtttt aaattatttc gattttactg gtacttagat agatgtatat atacatgctt  3540
agatacatga agtaacatgc tactacggtt taattgttct tgaataccta tatattctaa  3600
taaatcagta tgttttaaat tatttcgatt ttactggtac ttagatagat gtatatatac  3660
atgctcgaac atgcttagat acatgaagta acatgctaca tatatattat aataaatcag  3720
tatgtcttaa attattttga ttttactggt acttagatag atgtatatac atgctcaaac  3780
atgcttagat acatgaagta acatgctact acggtttaat cattattgag tacctatata  3840
ttctaataaa tcagtatgtt ttcaattgtt ttgattttac tggtacttag atatatgtat  3900
atatacatgc tcgaacatgc ttagatacgt gaagtaacat gctactatgg ttaattgttc  3960
ttgagtacct atatattcta ataaatcagt atgttttaaa ttatttcgat tttactggta  4020
```

-continued

```
cttagataga tgtatatata catgctcgaa catgcttaga tacatgaagt aacatgctac  4080
tacggtttaa tcgttcttga gtacctatat attctaataa atcagtatgt cttaaattat  4140
cttgatttta ctggtactta gatagatgta tatacatgct tagatacatg aagtaacatg  4200
ctactatgat ttaatcgttc ttgagtacct atatattcta ataaatcagt atgtttttaa  4260
ttatttgat tttactggta cttagataga tgtatatata catgctcgaa catgcttaga  4320
tacatgaagt aacatgctac tacggtttaa tcattcttga gtacctatat attctaataa  4380
atcagtatgt ttttaattat tttgatatta ctggtactta acatgtttag atacatcata  4440
tagcatgcac atgctgctac tgtttaatca ttcgtgaata cctatatatt ctaatatatc  4500
agtatgtctt ctaattatta tgattttgat gtacttgtat ggtggcatat gctgcagcta  4560
tgtgtagatt ttgaataccc agtgtgatga gcatgcatgg cgccttcata gttcatatgc  4620
tgtttatttc ctttgagact gttctttttt gttgatagtc accctgttgt ttggtgattc  4680
ttatgcagat ccagatcttc gtaaaccatg gctctggtgg ctaggccagt gctgtctgct  4740
agagtggctg cttctaggcc aagggtggcc gctagaaagg ctgtgagggt gagcgctgcc  4800
agtcacggcg ctagctctag gccagccacc gctaggaagt ccagcggcct gagcggcacc  4860
gtgcgcatcc caggcgacaa gagcatcagt caccgcagct tcatgttcgg cggcctggcc  4920
agcggcgaga ctaggatcac cggcctgctc gagggcgagg acgtgatcaa caccggcaag  4980
gccatgcagg ctatgggcgc tcgcatccgc aaggagggcg acacctggat catcgacggc  5040
gtgggtaatg gcggcctgct ggccccagag gccccactgg acttcggcaa cgccgccacc  5100
ggctgcaggc tgactatggg cctggtgggc gtgtacgact tcgacagcac ctttatcggc  5160
gacgccagcc tgaccaagag gccgatgggc agggtgctga acccgctgcg cgagatgggc  5220
gtgcaggtca agagcgagga cggcgacagg ctgccggtga ccctgagggg cccaaagacc  5280
ccgaccccga tcacctaccg cgtgccaatg gccagcgccc aggtgaagtc agccgtgctg  5340
ctggccggcc tgaacacccc aggcatcacc accgtgatcg agccgatcat gacccgcgat  5400
cacaccgaga agatgctgca gggcttcggc gccaacctga ccgtcgagac tgacgctgac  5460
ggcgtgagga ccatcaggct cgagggcagg ggcaagctga ccggccaggt gatcgacgtg  5520
ccgggcgacc caagcagcac cgccttccca ctggtggccg ccctgctggt gccaggctct  5580
gacgtgacca tcctgaacgt gctgatgaac ccgagccgca ccggcctgat cctgaccctg  5640
caggagatgg gcgccgatat cgaggtgatc aacccgaggc tggctggcgg cgaggacgtc  5700
gccgacctga gggtgaggtc cagcaccctg aagggcgtga ccgtgccaga ggacagggcc  5760
ccgagtatga ttgacgagta cccgatcctg gccgtggccg ctgccttcgc cgagggcgcc  5820
accgtgatga acggcctcga ggagctgcgc gtgaaggaga gcgacaggct gagcgctgtg  5880
gccaacggcc tgaagctgaa cggcgtggac tgcgacgagg gcgagactag cctggtggtg  5940
aggggcaggc cagacggcaa gggcctgggc aacgcttccg gcgctgccgt ggccacccac  6000
ctggatcaca ggatcgccat gtcgttcctc gtgatgggcc tcgtgagcga gaacccggtg  6060
accgtggacg acgccaccat gatcgccacc agcttccccg agttcatgga cctgatggcc  6120
ggcctgggcg ctaagatcga gctgagcgac accaaggccg cctgatcatc tagagctcgc  6180
caaggttcaa ttaagctgct gctgtacctg ggtatctgcg tcgtctggtg ccctctggtg  6240
tacctctata tggatgtcgt cgtctaataa acatctgtgg tttgtgtgtc atgaatcgtg  6300
gttgtggctt cgttggttta atggacctgt tgtgtcctct gtgttgtacc caaaactctt  6360
ctgcagcagt atggcttgaa tccttatgaa gtttgatatt tgaacttaaa agtctgctca  6420
ttatgttttt ttctggttat atctcctaat taactgcctg ggatcaaatt tgattcgctg  6480
gtgtttattg gacccctccc aggttcttgc tttctaccgt ttcttgctga atgttaactt  6540
gattctgtca ggctcagttt cccactatgg cttacagctt aacgtgtttg gtttgttgaa  6600
tgttaacttg gttttgtcaa gctcagtttt ttactctggc ttacagcata acatgtttga  6660
cttttggttt tgctgctttg ttattgggtt ctgggtagtt cttgatgaat ccaaaagatc  6720
atgtgcacag ccatattatc tatttaagcg atccaggtta ttactatgaa aggatgcctt  6780
ctagctaagg agtagttagg tttttttcttc aaggttaaat tttctcgatg ctctagtgtt  6840
cctgtgacca taatcataat aattcctttg aaagctctat ggtccctgga agcagggcat  6900
acaatgcaag acagcaactt gatcacatca actgaagtat acagggttct cttaactctt  6960
ggtgacttcg gtttaatgga ccggttgtac tcgtgttcta tccgtaaccg ttgtgatgtc  7020
ttgtgtgttt ggttgcggga tagctgggac cacgacgttt ccgtctaatt ctgatggata  7080
gctatagacg gcactgagat ggttatatta taacctctga tcctgaactc tacgagatcg  7140
tctcatccgt cattgccacc aaatacacca ttaaattact aattagctaa cggaccctat  7200
ttgtactcat tccatgtctc ataaactttg ggcaccatcc atccaacaca tccaatctaa  7260
acacaccaaa cgatggggaa tggaaagagc agtattcgat tcaacaatgg caaacaaata  7320
tcactgaatt agaccaagaa taaacctaat tagacaacga cctcccaacc atcattcgtc  7380
aggctgtaaa gaagataaag ctgccttggg gcatggatca agcagaacac cagagatgaa  7440
tccaaacaca cagaaaatca cgcgcgctgt ctacaatgac aacaagcccc acatttcatt  7500
gcagtacact gggctacaaa ggcacgtaca acaaagagct agggaaacat tgcggagggc  7560
acgagagagc agctaacttg acaatatagc agactgagct tgcactgtta gcaggcgagg  7620
aagggaatca tggggacgga gaatggggtc catgcccgcg aaggagaagg cggacgccgc  7680
cacggtggca ccggcgcacg cgcacacagg gaacccgcac aggcagccaa ggatgctgcc  7740
tcgccattgc gccggtcgtc tctgccacgc tcctctctct ctcccgctgc atcgccgtgg  7800
atggggcaag cagagagcag ggactgcgac gatctgggcg gaggactcgc cttggagagc  7860
gcggacgcag acgggattct agggagagag cgaagacggg gcgcgcgcgg cgctcgcgcg  7920
gcgtggtggc ggcgagatta gcgggggtgg ggggagggcg gagccgtggt gagggtgtgg  7980
acgccctcct taccctctta agtagtagta gagatataat ccgttccaaa atatccatcc  8040
gttcaattta tatttcgttt gatcttttta ccctaaattt gattgactca tcttattaaa  8100
aaagttcata actattatta atctttattg agatatcatt tagcatataa tatactttaa  8160
gtgtggtttt agattttttt taaaaaaaaa aattcgcaaa aattaaatga aacgacccaa  8220
tcaaacttga aaagtaaaac taattataaa tttgaacgga aggagtaaga ggatgtttga  8280
atgtactaga gctaatagtt ggttgcttta aaatttgcta gtagaattag ctagctaata  8340
aatatctaga taactattag ctaatttgct aaaacagcta atagttgaac tattagctag  8400
attgtttgga tgtattcggc taattttaat ggctaactat tagctatagt acaatattca  8460
aacacctcct aattaaaatg gacaaatatc tcttcttttg gtcccttgcg ttagattttt  8520
catatctcct tatttagtat aaaagaatca tcaaaaagtg gacaacccct agtggaacac  8580
cattttagta gtggttgcat gaaacctttc gcgcaccagt ttctatgtgt cactctaaaa  8640
atgggacagc atgtacgtag tgcctatata tatacaagtc atctatcgtt gcctcctcag  8700
ttcatcacta atcacactta ttgtgccctc gacgagtatc tatagctagc tcattaatcg  8760
```

-continued

```
attcgggggt gtgttgtcga aggcggcatt ggcgagctac tcgtcgcggc gtccaagcaa  8820
tacctgtagc acgaaggcga tcgccgggag cgtggtcggc gagcccgtcg tgctggggca  8880
gagggtgacg gtgctgacgg tggacggcgg cggcgtccgg ggtctcatcc cgggaaccat  8940
cctcgccttc ctggaggcca ggctgcagga gctggacgca ccggaggcga ggctggcgga  9000
ctacttcgac tacatcgccg gaaccagcac cggcggtctc atcaccgcct tgctgaccgc  9060
gcccggcaag gacaagcggc ctctctaggc tgccaaggac atcaaccact tttacatcca  9120
taactgcccg cgcatctttc ctcagaagtg agtccgatgc tgccgccatt gttcttgcat  9180
ccatccagca tcgtacgtac gtcctctata catctgcgga tcatcatgtg cgcatgtttg  9240
tggcatgcat gcatgcatgt gagcaggagc aggcttgcga aaaccccatg gagatctgaa  9300
caggcttgcg gccgccgtgt ccgcgctgag gaagccaaag tacaacggca agtgcatgcg  9360
cagcctgatt aggagcatcc tcggcgagac gaggggtcga ctcgggagca tgccctttgt  9420
gcttatgcct ccgttctgcc ttctgacgaa tttggtactg gaagcagatg agttttggtt  9480
cactatcatt ctgaatttac acctgcgctt gctgtcagac taggcaacca agtgactttt  9540
gtgactttga tcatgttcag tgtgtttcca agtcctaatc aatcaaaaag aaaaacagtt  9600
tgttaacgat tgtttgccat gtctatataa taaagttgct tttatagtag cttagaattc  9660
aatcggccaa ctttatctcg tacgctgaca gtaaaggtac atttaaaagg tgacaatgga  9720
tagtctaata cttgaactga caatagagac acattacatg tcagttgatt aagtttgtaa  9780
cagaaaaata aacaatacta cataattgca aagtttcttt gatgtctttc tttcaagaaa  9840
cacaaatata tcaatgctac agtattgctg atgaatttat ccatgttgag atgtttttct  9900
ggtttctgat ctgatcagtc tcaattggtg tgctgtttca ttttcatttg ctgatgatcg  9960
tccgagtagt taattcttac taatatttag ataatttggc atacaagcga atcacgtaga  10020
acatgatact tttgaatgaa tttatcaaag ttttatcact tggtgagttg tttcatggtt  10080
ttcctactga tgtctcttct tcagatttct cgagccctcg tctcgccgag gatgctccta  10140
atcaggctgc gcatgcactt gccgttgtac tttggcttcc tcagcgcgga catggcggcc  10200
gcaagcctgc tcggatccat gggacaagtg gctttactgt cagtcacatg cttgtaaata  10260
agtagacttt attttaataa aacataaaaa tatatatatg ttcttgaata taaaattgat  10320
aaccaaatta aaattcgaac catcacttat acataatttt actttatttt ttataaaacg  10380
tgaacgggaa ggactaccgt gaatgactat agaaccaatc atactagtat aaaatatatg  10440
atgacactac gggagagaca aactttgtct ggcgctaaat attttgccga gtgtgaattc  10500
acgggcacta ggcaaagatc ttctttgccg agtgttacgc tgggcaaagt aagacactag  10560
gtaaatcagt catttgccga gtgtccgcca ctaggcaaag caaaacactg gcaaatcaaa  10620
agtttaccta gtgccagaca ctaggcaaaa aaaaaacgct cggcaaatcg gaagtttccc  10680
tagtgccaga cactagacaa agaaaaacac ttgataaact agcgtcgtca gctaacacca  10740
tccaccaacc gttaacgttg ccgagtatct gacttcgaca ctcggcaaag aaggtctctt  10800
tgcctagtgt cggtctggaa cactaggcaa agaggcactt tacctagtgt cgtattttga  10860
cactcagtaa aataattttt tttctttctg cttccaaact ttttatgatg tgttcctata  10920
gcacctagaa ctacatgtca agttttggta aaatttttga agtttttgct atatttactt  10980
aatttatttt atttaattga atttcttttg ataattcaaa tttgaactcg gcaaggtaag  11040
aagcgagggt agcctggaaa cacactttgc ctagtgttac actcggtaca ggagcctccc  11100
ctgcctagtg ctgcactcga caaaagattc gcctttgcct agcgctgcac tcggcacagg  11160
agtcgccttt gcctagtgct gcactaggca aagcctccgt taccgtgcct tccatcgtcg  11220
gaccctggag aggcatgaac ccatcatgta tactcctgga cttggaagag gaaatgtcaa  11280
ccaaagtgaa aggttttctt ctagttgctg ctaagagata aattgaatac tagatctctc  11340
ctaagacatc ggggcattcg tctggactac tacacatgcg aaaattgcat cttacagtgg  11400
gaagaaacta tatctcacct cttcttgcgg tgtaactttg cccgaagatg ttggctcact  11460
gttggaatca ctccgccccg aacgttggat ctagcgcttg cagtgctaca tattagagca  11520
agactgacat tgtcgtggag aatggaaggt attataacca tgcatgtcat ggtacatatg  11580
gaaatgtcaa aataactgga tattcgaaaa cataccgcca acggtggcgg tctgcaagga  11640
aatgttcaag attgaaatga actacatatg caaccaggtt aagcttgaga caggagataa  11700
aagtagaaac tggatacaac actttgtaac atagcgacac tctctccttc ctttctttta  11760
ccttagaact atacatagaa tctacattca ataaaaatac agtaggtacg ccgagagatt  11820
taaaatgagt aagctaacat accaactaag gccctgtttg tttcggatta taatctctcc  11880
agattatata atccagcgta aataattcag cagataaaca aacacctaaa ttatatgttc  11940
agattatata atctatagcg gagattatga taatctcgta atctcctaag agtagcttat  12000
ttgagatttt tttggcaaaa gacccactac ccaaggttat gtaaatagaa ttacaatata  12060
tgacatcctt ctttcttcac ctcaaataaa caaacaaggg tactgttgtc tttatgaata  12120
atctacattt atataatcta gactaacaaa caactacata tagattataa tatgtctaga  12180
ttataatcta gattatataa tttaaattat agtccatatt atataatcta taagctaaaa  12240
caaataggcc ctaattatta gctattagtt gttagctatt taaatctaag ctaaaaccaa  12300
ctaatagctt attagttgaa ttacaattag ctcaacggaa ttctctgttt ttctaaaaaa  12360
aaactgcccc tctcttacag caaattgtcc gctgcccgtc gtccagatac aatgaacgta  12420
cctagtagga actcttttac acgctcggtc gctcgccgcg gatcggagtc cccggaacac  12480
gacaccactg tggaacacga caaagtctgc tcagaggcgg ccacaccctg gcgtgcaccg  12540
agccggagcc cggataagca cggtaaggag agtacggcgg gacgtggcga cccgtgtgtc  12600
tgctgccacg cagccttcct ccacgtagcc gcgcggccgc gccacgtacc agggcccggc  12660
gctggtataa cgcgccacct ccgctttagt tctgcataca gccaacccaa cacacacccg  12720
agcatatcac agtgacagac actacacggt gagcgccaga atcgttgtcc tcctcgccac  12780
cctcctatcc gctgccgccg cagtcgcgtc gtcctgggag gacgacaacc tccaccacca  12840
cgggggccac aagtccgggc gtagcgtgcg gcggtgcgag gaccggccct ggcaccagcg  12900
cccccggtgc ctggagcagt gcagggagga ggagcgggag aagcggcaag agcggagcag  12960
gctagaggcc gacgaccgca gcggcaaggg ttcgtcggag gtagagcgcg agcgagagca  13020
ggaggaggag aagcagaagg accggcggcc gtacgtgttc gaccggcgca gcttccgtcg  13080
cgtggtccgg agcgagcagg ggtctctgag ggtgctccgg ccgttcgacg aggtgtccag  13140
gctcctccgc ggcatccggg actaccgcgt ggcggtccta gaggcgaacc cgcgctcgtt  13200
cgtggtgccc agccataccg tagcgcactg catctgctac gtggtggaag gtacgttcgt  13260
ccggtccctg agaccacata gatcgagggc gacgccggcc gtgcacgtta gctgatctgt  13320
tgttgcctcg tgactaggcg agggataaac catggcctcc tccgagaacg tcatcaccga  13380
gttcatgcgc ttcaaggtgc gcatggaggg caccgtgaac ggccacgagt tcgagatcga  13440
gggcgagggc gagggccgcc cctacgaggg ccacaacacc gtgaagctga aggtgaccaa  13500
```

```
gggcggcccc ctgcccttcg cctgggacat cctgtccccc cagttccagt acggctccaa  13560
ggtgtacgtg aagcaccccg ccgacatccc cgactacaag aagctgtcct tccccgaggg  13620
cttcaagtgg gagcgcgtga tgaacttcga ggacggcggc gtggcgaccg tgacccagga  13680
ctcctccctg caggacggct gcttcatcta caaggtgaag ttcatcggcg tgaacttccc  13740
ctccgacggc cccgtgatgc agaagaagac aatgggctgg gaggcctcca ccgagcgcct  13800
gtacccccgc gacggcgtgc tgaagggcga gacccacaag gccctgaagc tgaaggacgg  13860
cggccactac ctggtggagt tcaagtccat ctacatggcc aagaagcccg tgcagctgcc  13920
cggctactac tacgtggacg ccaagctgga catcacctcc cacaacgagg actacaccat  13980
cgtggagcag tacgagcgca ccgagggccg ccaccacctg ttcctgagat ctcgagctga  14040
tccaaaaaag aagagaaagg tagatccaaa aaagaagaga aaggtagatc caaaaaagaa  14100
gagaaaggta ggctccaccg gatctagata agagctcggc cgccgcgctc gccaaaacga  14160
gcaagaagca acaagagggt ggcgcgcgac cgacgtgcgt acgtagctga gcctgagtgg  14220
agacgttgga cgtgtatgta tatacctctc tgcgtgttaa ctatgtacgt aagcggcagg  14280
cagtgcaata agtgtggctc tgtagtatgt acgtgcggat acgatgctgt atgctactga  14340
ggcaagtccc ataaataaat aatgacacgt gcgtgttcta taatctcttc gcttcttcag  14400
tgtccccttg cggagtttgg catccattga tgccgttaca ctgagaacat aacggacaca  14460
gtagacgaac cacttgagtt cttgtatgaa attctgaccc ttttttttga aggatcagga  14520
gggggaaacc cctactggcc tggtcctttt acaatcaata aaaagaaaag aaaaagaaag  14580
aaaaaggaag agctatttct atatttgcca caaatttagc cagttcggga ttgaggtgtc  14640
gaattctccc cgtgctctgt gaatgattag tcgcaattct ctactaaatt cctgagtaca  14700
gcggagcacg gagggatctc tatttgaaaa caaccactcg tttcggcttt tccagatgct  14760
ccaagtcata agaatagtga tctccataga gaagggaacg ttgagctggt gtttgaggtt  14820
cacagatgcc tcttcaaggt tggaaattct gggtggggta atgccaattg agttccagca  14880
ggctttcgcg aagttgcatc tgaggaaaag atgataaagg gtctcctctc tttgccaaag  14940
gcagttttcg caagagtagg aatctagctc catgtttctc cttctcaaca tatttctggt  15000
gtttagcctg ttcttaagcc acagccaata gaagactcta tgcttaggct gacacttact  15060
tttccaaact agtttgtaga taggatgagt ttgcatctgg cccatgaaag atctgtaagc  15120
tttttgggac gagaatcgga ccgcctgcag gcccgggggc gcgccctaat tagctaacgg  15180
ccaggatcgc cgcgtgagcc tttagcaact agctagatta attaacgcaa tctgttatta  15240
agttgtctaa gcgtcaattt gtttacacca caatatatcc tgccaccagc cagccaacag  15300
ctccccgacc ggcagctcgg cacaaaatca ccactcgata caggcagccc atcag       15355
```

```
SEQ ID NO: 96           moltype = DNA  length = 15441
FEATURE                 Location/Qualifiers
misc_feature            1..15441
                        note = Expression cassette of construct 22513
regulatory              214..407
                        note = enhancer - eFMV
                        regulatory_class = enhancer
regulatory              414..706
                        note = enhancer - e35S
                        regulatory_class = enhancer
regulatory              714..4707
                        note = promoter - Ubi
                        regulatory_class = promoter
gene                    4708..6165
                        note = EPSPS
regulatory              6179..7178
                        note = terminator - Ubi
                        regulatory_class = terminator
regulatory              7198..9285
                        note = promoter - pPLA2
                        regulatory_class = promoter
stem_loop               9292..10386
                        note = targeting exon4 of PLA2
regulatory              10397..11392
                        note = terminator - tPLA2
                        regulatory_class = terminator
regulatory              11400..13526
                        regulatory_class = promoter
gene                    13527..14204
regulatory              14210..15222
                        regulatory_class = terminator
source                  1..15441
                        mol_type = other DNA
                        organism = synthetic construct
SEQUENCE: 96
cctgtggttg gcatgcacat acaaatggac gaacggataa accttttcac gcccttttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga cccagctgct tgtggggacc agacaaaaaa  240
ggaatggtgc agaattgtta ggcgcaccta ccaaaagcaa ctttgccttt attgcaaaga  300
taaagcagat tcctctagta caagtgggga acaaaataac gtggaaaaga gctgtcctga  360
cagcccactc actattgcgt ttgacgaacg cagtgacgac cacaaaactc gagacttttc  420
aacaaagggt attatccgga aacctcctcg gattccattg cccagctatc tgtcacttta  480
ttgtgaagat agtggaaaag gaaggtggct cctacaaatg ccatcattgc gataaaggaa  540
aggctatcgt tgaagatgcc tctgccgaca gtggtcccaa agatggaccc ccacccacga  600
ggagcatcgt ggaaaaagaa gacgttccaa ccacgtcttc aaagcaagtg gattgatgtg  660
atatctccac tgacgtaagg gttgacgaac aatcccacta tccttcaagc tttggaaaac  720
```

```
caaaacaacg aataagcaaa ctgcaggaaa agtatgcagt ggaaaccaac ccagattcgg  780
acgataggaa agtatcaagt gaatgatttg ccaggaaaag gagaggggta aaaaggggcg  840
aagatttaga agatctaaag cacaagaacc agagattaga ttgaacaata gggaacttgg  900
agcatccttt ttttcttcag ggaaaaactg aaaatccaaa ccatgttgag caaaaccgag  960
tgggattgga aaccaaaaaa cccgagataa agaaactcga gaaaaagcat gaaatcgaaa  1020
ccaacttcag taaaacaaaa ggaggacaga aaagaaagtc ggaagctata aagaatacat  1080
taacattcag tgaaacagca tgctgtcttc ttcttttttt atgcacaaca gagcatacat  1140
atataccttc ccaggctgag gacttggcgg aggagagccg cggataggtt ggcggtgcag  1200
acggtctgga cgggcccgaa gacggagacg aacagcgggc ccttcctgcc caggcaccac  1260
gcttggaacg ccaagcacgc gccaaccgcg gccccgccga ggacgacgat ccccgcgaca  1320
agcgtggcgt cgatcctggg cgaccccaag ccgaggaacc tcccttccag gacgagccgt  1380
aggacggcgg tgagagaggc acccgtcgcg gaggtggcgc agcacaaggt gagcagcgcg  1440
gggaaggcgg cgagcgtggc ggcctgcagg acggtgacga gcgcgaagac ggtgacgccg  1500
gcgacgaggc agcagcagcc gaggatccag tcgtaggagg aagccggacc aaaccgggca  1560
atgcaacctg cagatgcact agacggaggt aacgaggagg aggagaaaac agagcaagag  1620
caggcggaga gaagatagag caaaacacga gtgaggcaca gcgtaagcac tcggtagaag  1680
tctccagagg cgaggtgcgc acaggagaac agatgagtaa agtcagccaa ggatccacga  1740
tccaacggct acgaattttt ggagtgacgt ggataggctc aaaggcgcca tttccatccg  1800
gctttatagt attttaaaaa aattcatttt cctccctcta gtgtgtgcgg aggcgtgagc  1860
ccgtttaacg gcgttgagaa gtctaacgga caccaaccac aaccaggaac cagcgccggc  1920
cgcgccgccg agtgaagcag actgcatacg gcacggcgcg gcatctctct ggctgcctct  1980
cgagagttcc gcccccacct tcccgcggta gcgtggtggt ttcgctttcc gctgtcggca  2040
tccggaagtt gcgtggcaga gtggacggag acgaggccgg gtcctccagc tcctctcaaa  2100
cgtcacggca ccggcatccg gcagccagcg cggtccttcc caaccactcg ttcccaaccc  2160
atccccctc ctcgcccgcc gtcataaata gccagcccca tccccagctt ctttccccaa  2220
cctcatcttc tctcctttg ctctgaacgc acacaccgcc cggtctccga tctccgatcc  2280
ccgatcccct cgtcgatcct aggtacggcg accatcctac cccccccccc ccccctctc  2340
tctctgcctt ctctagatcg gcgatccgat ccatgcttac ttggttaggg cctgctaact  2400
atgttcatgt ttgcgttaga tccgtgcatg gacgcgatct gtacacacca gacgcgttct  2460
gattgctagc taactcgcca gtacctggga atcctgggat ggctgtagcc ggccccgcac  2520
gcagacggga ccgatttcat gattctctat tttttcttt gtttcgttgc ctagggtttc  2580
gttcgatcga tccgcgttat tctttatttc catatattct ggtacgatgt tgatacggtt  2640
cgaccgtgct gcttacgttc tgtgcgcttg tttgccgggt cattttacc ttgcctttt  2700
tgtatggttt ggttgtggcg atgtggtctg gtcgggctgt cgttctagat cggagtagag  2760
tgctgtttca aactgtctag cggatctatt agatttggat ctgcatgtgt gacatatatc  2820
ttcgtagtta agatgatgca tctgtatgtg tgacatgcgg atctattaga tttggatctg  2880
tatgtgtgac atatatcttc gtagttgaga tgatgcatct gtatgtgtga catatatctt  2940
cgtagttaag attatgcatg gaaatatcaa tcctttagat aaggacgggt atacttgttg  3000
ctgtgggttt tactggtact tcgatagatg catatacatg atctaacatg cttagataca  3060
tgaagtaaca tgctgctacg gtttaataat tcttgagttg atttttactg gtacttagat  3120
agatgtatat acatgcttag atacatgaag taacatgctc ctacagttcc tttaatcatt  3180
attgagtacc tatatattct aataaatcag tatgttttaa attattttga ttttactggt  3240
acttagatag atgtatatat acatgctcaa acatgcttag atacatgaag taacatgctg  3300
ctacggttta gtcattattg agtgcctata tattctaata aatcagtatg ttttaaatta  3360
ttttgatttt actggtactt agatagatgt atatatacat gctcaaacat gcttagatac  3420
atgaagtaat atgctactac ggtttaattg ttcttgagta cctatatatt ctaataaatc  3480
agtatgtttt aaattatttc gattttactg gtacttagat agatgtatat atacatgctt  3540
agatacatga agtaacatgc tactacggtt taattgttct tgaataccta tatattctaa  3600
taaatcagta tgttttaaat tatttcgatt ttactggtac ttagatagat gtatatatac  3660
atgctcgaac atgcttagat acatgaagta acatgctaca tatatattat aataaatcag  3720
tatgtcttaa attattttga ttttactggt acttagatag atgtatatac atgctcaaac  3780
atgcttagat acatgaagta acatgctact acggtttaat cattattgag tacctatata  3840
ttctaataaa tcagtatgtt ttcaattgtt ttgattttac tggtacttag atatatgtat  3900
atatacatgc tcgaacatgc ttagatacgt gaagtaacat gctactatgg ttaattgttc  3960
ttgagtacct atatattcta ataaatcagt atgttttaaa ttatttcgat tttactggta  4020
cttagataga tgtatatata catgctcgaa catgcttaga tacatgaagt aacatgctac  4080
tacggtttaa tcgttcttga gtacctatat attctaataa atcagtatgt cttaaattat  4140
cttgatttta ctggtactta gatagatgta tatacatgct tagatacatg aagtaacatg  4200
ctactatgat ttaatcgttc ttgagtacct atatattcta ataaatcagt atgtttttaa  4260
ttattttgat tttactggta cttagataga tgtatatata catgctcgaa catgcttaga  4320
tacatgaagt aacatgctac tacggtttaa tcattcttga gtacctatat attctaataa  4380
atcagtatgt ttttaattat tttgatatta ctggtactta acatgtttag atacatcata  4440
tagcatgcac atgctgctac tgtttaatca ttcgtgaata cctatatatt ctaatatatc  4500
agtatgtctt ctaattatta tgattttgat gtacttgtat ggtggcatat gctgcagcta  4560
tgtgtagatt ttgaataccc agtgtgatga gcatgcatgg cgccttcata gttcatatgc  4620
tgtttatttc ctttgagact gttctttttt gttgatagtc accctgttgt ttggtgattc  4680
ttatgcagat ccagatcttc gtaaaccatg gctctggtgg ctaggccagt gctgtctgct  4740
agagtggctg cttctaggcc aagggtggcc gctagaaagg ctgtgagggt gagcgctgcc  4800
agtcacggcg ctagctctag gccagccacc gctaggaagt ccagcggcct gagcggcacc  4860
gtgcgcatcc caggcgacaa gagcatcagt caccgcagct tcatgttcgg cggcctggcc  4920
agcggcgaga ctaggatcac cggcctgctc gagggcgagg acgtgatcaa caccggcaag  4980
gccatgcagg ctatgggcgc tcgcatccgc aaggagggcg acacctggat catcgacggc  5040
gtgggtaatg gcggcctgct ggccccagag gccccactgg acttcggcaa cgccgccacc  5100
ggctgcaggc tgactatggg cctggtgggc gtgtacgact tcgacagcac ctttatcggc  5160
gacgccagcc tgaccaagag gccgatgggc agggtgctga acccgctgcg cgagatgggc  5220
gtgcaggtca agagcgagga cggcgacagg ctgccggtga ccctgagggg cccaaagacc  5280
ccgaccccga tcacctaccg cgtgccaatg gccagcgccc aggtgaagtc agccgtgctg  5340
ctggccggcc tgaacaccc aggcatcacc accgtgatcg agccgatcat gacccgcgat  5400
cacaccgaga agatgctgca gggcttcggc gccaacctga ccgtcgagac tgacgctgac  5460
```

-continued

```
ggcgtgagga ccatcaggct cgagggcagg ggcaagctga ccggccaggt gatcgacgtg  5520
ccgggcgacc caagcagcac cgccttccca ctggtggccg ccctgctggt gccaggctct  5580
gacgtgacca tcctgaacgt gctgatgaac ccgagccgca ccggcctgat cctgaccctg  5640
caggagatgg gcgccgatat cgaggtgatc aacccgaggc tggctggcgg cgaggacgtc  5700
gccgacctga gggtgaggtc cagcaccctg aagggcgtga ccgtgccaga ggacagggcc  5760
ccgagtatga ttgacgagta cccgatcctg gccgtggccg ctgccttcgc cgagggcgcc  5820
accgtgatga acggcctcga ggagctgcgc gtgaaggaga gcgacaggct gagcgctgtg  5880
gccaacggcc tgaagctgaa cggcgtggac tgcgacgagg gcgagactag cctggtggtg  5940
aggggcaggc cagacggcaa gggcctgggc aacgcttccg gcgctgccgt ggccaccccac  6000
ctggatcaca ggatcgccat gtcgttcctc gtgatgggcc tcgtgagcga gaacccggtg  6060
accgtggacg acgccaccat gatcgccacc agcttccccg agttcatgga cctgatggcc  6120
ggcctgggcg ctaagatcga gctgagcgac accaaggccg cctgatcatc tagagctcgc  6180
caaggttcaa ttaagctgct gctgtacctg ggtatctgcg tcgtctggtg ccctctggtg  6240
tacctctata tggatgtcgt cgtctaataa acatctgtgg tttgtgtgtc atgaatcgtg  6300
gttgtggctt cgttggttta atggacctgt tgtgtcctct gtgttgtacc caaaactctt  6360
ctgcagcagt atggcttgaa tccttatgaa gtttgatatt tgaacttaaa agtctgctca  6420
ttatgttttt ttctggttat atctcctaat taactgcctg ggatcaaatt tgattcgctg  6480
gtgtttattg gacccctccc aggttcttgc tttctaccgt ttcttgctga atgttaactt  6540
gattctgtca ggctcagttt cccactatgg cttacagctt aacgtgtttg gtttgttgaa  6600
tgttaacttg gttttgtcaa gctcagtttt ttactctggc ttacagcata acatgtttga  6660
cttttggttt tgctgctttg ttattgggtt ctgggtagtt cttgatgaat ccaaaagatc  6720
atgtgcacag ccatattatc tatttaagcg atccaggtta ttactatgaa aggatgcctt  6780
ctagctaagg agtagttagg tttttttcttc aaggttaaat tttctcgatg ctctagtgtt  6840
cctgtgacca taatcataat aattcctttg aaagctctat ggtccctgga agcagggcat  6900
acaatgcaag acagcaactt gatcacatca actgaagtat acagggttct cttaactctt  6960
ggtgacttcg gtttaatgga ccggttgtac tcgtgttcta tccgtaaccg ttgtgatgtc  7020
ttgtgtgttt ggttgcggga tagctgggac cacgacgttt ccgtctaatt ctgatggata  7080
gctatagacg gcactgagat ggttatatta taacctctga tcctgaactc tacgagatcg  7140
tctcatccgt cattgccacc aaatacacca ttaaattact aattagctaa cggaccctat  7200
ttgtactcat tccatgtctc ataaactttg ggcaccatcc atccaacaca tccaatctaa  7260
acacaccaaa cgatggggaa tggaaagagc agtattcgat tcaacaatgg caaacaaata  7320
tcactgaatt agaccaagaa taaacctaat tagacaacga cctcccaacc atcattcgtc  7380
aggctgtaaa gaagataaag ctgccttggg gcatggatca agcagaacac cagagatgaa  7440
tccaaacaca cagaaaatca cgcgcgctgt ctacaatgac aacaagcccc acatttcatt  7500
gcagtacact gggctacaaa ggcacgtaca acaaagagct agggaaacat tgcggagggc  7560
acgagagagc agctaacttg acaatatagc agactgagct tgcactgtta gcaggcgagg  7620
aagggaatca tggggacgga gaatggggtc catgcccgcg aaggagaagg cggacgccgc  7680
cacggtggca ccggcgcacg cgcacacagg gaacccgcac aggcagccaa ggatgctgcc  7740
tcgccattgc gccggtcgtc tctgccacgc tcctctctct ctcccgctgc atcgccgtgg  7800
atggggcaag cagagagcag ggactgcgac gatctgggcg gaggactcgc cttggagagc  7860
gcggacgcag acgggattct agggagagag cgaagacggg gcgcgcgcgg cgctcgcgcg  7920
gcgtggtggc ggcgagatta gcgggggtgg ggggagggcg gagccgtggt gagggtgtgg  7980
acgccctcct taccctctta agtagtagta gagatataat ccgttccaaa atatccatcc  8040
gttcaattta tatttcgttt gatcttttta ccctaaattt gattgactca tcttattaaa  8100
aaagttcata actattatta atctttattg agatatcatt tagcatataa tatactttaa  8160
gtgtggtttt agattttttt taaaaaaaaa aattcgcaaa aattaaatga aacgacccaa  8220
tcaaacttga aaagtaaaac taattataaa tttgaacgga aggagtaaga ggatgtttga  8280
atgtactaga gctaatagtt ggttgcttta aaatttgcta gtagaattag ctagctaata  8340
aatatctaga taactattag ctaatttgct aaaacagcta atagttgaac tattagctag  8400
attgtttgga tgtattcggc taattttaat ggctaactat tagctatagt acaatattca  8460
aacacctcct aattaaaatg gacaaatatc tcttcttttg gtcccttgcg ttagattttt  8520
catatctcct tatttagtat aaaagaatca tcaaaaagtg gacaacccct agtggaacac  8580
cattttagta gtggttgcat gaaacctttc gcgcaccagt ttctatgtgt cactctaaaa  8640
atgggacagc atgtacgtag tgcctatata tatacaagtc atctatcgtt gcctcctcag  8700
ttcatcacta atcacactta ttgtgccctc gacgagtatc tatagctagc tcattaatcg  8760
attcgggggt gtgttgtcga aggcggcatt ggcgagctac tcgtcgcggc gtccaagcaa  8820
tacctgtagc acgaaggcga tcgccgggag cgtggtcggc gagcccgtcg tgctggggca  8880
gagggtgacg gtgctgacgg tggacggcgg cggcgtccgg ggtctcatcc cgggaaccat  8940
cctcgccttc ctggaggcca ggctgcagga gctggacgca ccggaggcga ggctggcgga  9000
ctacttcgac tacatcgccg gaaccagcac cggcggtctc atcaccgcct tgctgaccgc  9060
gcccggcaag gacaagcggc ctctctaggc tgccaaggac atcaaccact tttacatcca  9120
taactgcccg cgcatctttc ctcagaagtg agtccgatgc tgccgccatt gttcttgcat  9180
ccatccagca tcgtacgtac gtcctctata catctgcgga tcatcatgtg cgcatgtttg  9240
tggcatgcat gcatgcatgt gagcaggagc aggcttgcga aaaccccatg gagatctttg  9300
cgatggcgca gatcaccaaa aagatgcttg ccaacaagga caaggccgag gagctgtacc  9360
cagtgaagcc gtcgaactgc cgcaggttcc tggtgctgtc catcgggacg gggtcgacgt  9420
ccgagcaggg cctctacacg gcgcggcagt gctcccggtg gggtatctgc cggtggctcc  9480
gcgtcgactc gggagcatgc cctttgtgct tatgcctccg ttctgccttc tgacgaattt  9540
ggtactggaa gcagatgagt tttggttcac tatcattctg aatttacacc tgcgcttgct  9600
gtcagactag gcaaccaagt gactttttgtg actttgatca tgttcagtgt gtttccaagt  9660
cctaatcaat caaaaagaaa aacagtttgt taacgattgt ttgccatgtc tatataataa  9720
agttgctttt atagtagctt agaattcaat cggccaactt tatctcgtac gctgacagta  9780
aaggtacatt taaaaggtga caatggatag tctaatactt gaactgacaa tagagacaca  9840
ttacatgtca gttgattaag tttgtaacag aaaaataaac aatactacat aattgcaaag  9900
tttctttgat gtctttcttt caagaaacac aaatatatca atgctacagt attgctgatg  9960
aatttatcca tgttgagatg tttttctggt ttctgatctg atcagtctca attggtgtgc  10020
tgtttcattt tcatttgctg atgatcgtcc gagtagttaa ttcttactaa tatttagata  10080
atttggcata caagcgaatc acgtagaaca tgatactttt gaatgaattt atcaaagttt  10140
tatcacttgg tgagttgttt catggttttc ctactgatgt ctcttcttca gatttctcga  10200
```

-continued

```
ggcggagcca ccggcagata ccccaccggg agcactgccg cgccgtgtag aggccctgct  10260
cggacgtcga ccccgtcccg atggacagca ccaggaacct gcggcagttc gacggcttca  10320
ctgggtacag ctcctcggcc ttgtccttgc tggcaagcat ctttttggtg atctgcgtca  10380
tcgcaaggat ccatgggaca agtggcttta ctgtcagtca catgcttgta aataagtaga  10440
ctttatttta ataaaacata aaaatatata tatgttcttg aatataaaat tgataaccaa  10500
attaaaattc gaaccatcac ttatacataa ttttacttta ttttttataa aacgtgaacg  10560
ggaaggacta ccgtgaatga ctatagaacc aatcatacta gtataaaata tatgatgaca  10620
ctacgggaga gacaaacttt gtctggcgct aaatattttg ccgagtgtga attcacgggc  10680
actaggcaaa gatcttcttt gccgagtgtt acgctgggca aagtaagaca ctaggtaaat  10740
cagtcatttg ccgagtgtcc gccactaggc aaagcaaaac actggcaaat caaaagttta  10800
cctagtgcca gacactaggc aaaaaaaaaa cgctcggcaa atcggaagtt tccctagtgc  10860
cagacactag acaaagaaaa acacttgata aactagcgtc gtcagctaac accatccacc  10920
aaccgttaac gttgccgagt atctgacttc gacactcggc aaagaaggtc tctttgccta  10980
gtgtcggtct ggaacactag gcaaagaggc actttaccta gtgtcgtatt ttgacactca  11040
gtaaaataat tttttttctt tctgcttcca aactttttat gatgtgttcc tatagcacct  11100
agaactacat gtcaagtttt ggtaaaattt ttgaagtttt tgctatattt acttaattta  11160
ttttatttaa ttgaatttct tttgataatt caaatttgaa ctcggcaagg taagaagcga  11220
gggtagcctg gaaacacact ttgcctagtg ttacactcgg tacaggagcc tcccctgcct  11280
agtgctgcac tcgacaaaag attcgccttt gcctagcgct gcactcggca caggagtcgc  11340
ctttgcctag tgctgcacta ggcaaagcct ccgttaccgt gccttccatc gtcggacccg  11400
aaagtagcaa acaacaggtt catgtgcact ataaaaagac aaaattctcg agtttcatct  11460
tttattccac ataagcctta tattttccat tttcatatga tttttagttt aagtttgtgt  11520
cttaactttt tcgttaatac gtaattctat gcattatgga tgcgtgaagt atttttgttt  11580
aaaaaaatga aatgtcaaaa tacgttttgt gatctatttc catgttttca cctaacaggt  11640
ggtttttact atatattctg ccataactct agccttagat gtaaatcgaa aaaaaatgag  11700
agatgagctg gagatagcct tagatgaagc gtctgaaata taaaagaaag agtaatgttg  11760
aacgcagtag gtgtagcagc tgtagttcca tctctaggaa agggaactgc aatccgggct  11820
ccgggcctcg cgcaatctgg cctgtcgtgt agatgcagcc ctgtccatga cggcccaagc  11880
aacgcccgcg gctctcgatc caccacggaa cccactccga cacacactga cacacacatg  11940
ctggatgtgg atgtgctgtc caattattag tagcaattcg gtaggcacag gcacgtactg  12000
gccggtgttt tagctgtaag taccgaacca atcacggtta agaaccgatt aatccgtgcc  12060
cagccgccga gtgcgttcgt acgtgcatcg gatgcactgc atgaattgag agcatcatca  12120
tatcatacgc aggagtagta cgacgccgct gctgtcttgt ccggctaatg ctttgctcac  12180
agattagtcc atcgcccacg gtcggtgtgg tgtggatcgc tgatgccact gctttttgtt  12240
tggtttttat tcccctgata atcctccgcg tccctgaatg tatctattta ttttcattcc  12300
gaaatccctt tcacgaaaaa gaaaacgaat aaaaagagag ttacgaatac gcttccggcg  12360
gcccacatca ccttccagcg aacatcgcgc cgcgctgacg tgtcgcccat cgcggccgtc  12420
catatcgcca tccgacgacc gtggaagctg gcagcggccg ctccgttccg tcgaaggggc  12480
aggtcagtca ggtcacccac acggccacac ccgcgcgggg gatacgcggt ggaaaacccg  12540
gcgaccacat caaaacacga ggcgtctccc gcaggactgg tcactcggca cgcaggcaga  12600
ggcagcacag cagcagccag ctccatccat cctctttccc ctcctcgctt cgcttcctcg  12660
gcggattcct cctccctcgg ccgtccccgt ccccttcttc gccgcgccag ctcgcccgag  12720
ttggtacgcc catcctctgc tgtactcccc ccgttcctgc tgtgcgaaac cgagcaccca  12780
aaccctagcc taagctattc gcatcgcaaa ctctattgag cgacggatcg cgaaacgcgc  12840
gccgccgcat tcggacgaga cctcgtggcc cgtaccttcc tactctaccg tcgtcgccgg  12900
agaccagctc accggttagg gtttcgggat taggggcttg gggcttggat tcccggggga  12960
ctccataccc ggtggcctta gaaggggaag ggggcccagc ggtggtggtg gttcgactgt  13020
cagcgagcga gacggcgggg caccgccgat cgggcgtcgc tggacatttg attgagctgg  13080
gcaggcgaag gcgtggagct tgctcttcga ttgggattag aggagggcgg aggtggtatg  13140
gtgggcggct cggctggctc aatggagccg ctggccggtg gtggggcagg cgagatcacg  13200
ctctctcata gagcgtaatg ggttgcgtaa cacactcctg tttgtatttc gatccgatct  13260
aataattaaa gtttatttac gtggtgcaca tgtagaattt tcccatgccc actgctaact  13320
tggattggat ttttgccaaa aaaacgggtg tgcacccaat cacttatagt gaaaccgttg  13380
tgtgtttgat gtgcttctaa ccaagtacaa atccagtgaa aacacaccta ccattcaaca  13440
atccacattt tggttgcaat tatcagcatt ctagaaaggt gcatgtgccc attgatacac  13500
ttgctattgg tgcaggcaaa cccaccatgg cctcctccga gaacgtcatc accgagttca  13560
tgcgcttcaa ggtgcgcatg gagggcaccg tgaacggcca cgagttcgag atcgagggcg  13620
agggcgaggg ccgcccctac gagggccaca acaccgtgaa gctgaaggtg accaagggcg  13680
gccccctgcc cttcgcctgg gacatcctgt ccccccagtt ccagtacggc tccaaggtgt  13740
acgtgaagca ccccgccgac atccccgact acaagaagct gtccttcccc gagggcttca  13800
agtgggagcg cgtgatgaac ttcgaggacg gcggcgtggc gaccgtgacc caggactcct  13860
ccctgcagga cggctgcttc atctacaagg tgaagttcat cggcgtgaac ttccccctccg  13920
acggccccgt gatgcagaag aagaccatgg gctgggaggc ctccaccgag cgcctgtacc  13980
cccgcgacgg cgtgctgaag ggcgagaccc acaaggccct gaagctgaag gacggcggcc  14040
actacctggt ggagttcaag tccatctaca tggccaagaa gcccgtgcag ctgcccggct  14100
actactacgt ggacgccaag ctggacatca cctcccacaa cgaggactac accatcgtgg  14160
agcagtacga gcgcaccgag ggccgccacc acctgttcct gtaggagctc gcatcatgat  14220
catgcatcat ggactcggcc tactactgtg gatttgtatg ccattataga cttggtgctg  14280
tgaaagactg cttgatgatt tgcgggtttg ttgctgtgta aaaaaaggtc ccttggctcc  14340
cagaagacca tgaaggttcg gatctatcat gtaattcctt gttatctgcc aattatgtat  14400
ggactatgga catgtgttgc gctgttcaac ttactactac aaataagtaa tcgatatgtt  14460
cccttcccat gtctcggtga caattgtctg gagaagctta ggggtcgttt gtttgggatt  14520
atgtctggag aaacttattt taaactaagt gtgagttcaa gttaagttag attatataat  14580
ctaggcagat tataattcca agcgaacagg tccttagtgt ttttggaaaa tcctaggtgt  14640
tcttttggct acattgttgt gtgtgcagat cccttgttgg tctgtaagcg tggggaagta  14700
agaatcgtcc gtttctactg aagacctgct cgagttaggc accgaggatg ccggtaacca  14760
aacagagcaa tagtgtctct gtgggcacag tggagtgtga atctgtgtga tgcaaatccg  14820
tcatttgttt agcaaaattt ccagcgttgc atgatgcagt ttctttaaca cggacttaag  14880
ggaagggaaa aaaatgttga gccaggagat ccttcaatgt gttagactga cgtgatagcc  14940
```

```
aactaaacca cgacgcaatg ttgtcgttaa tgacaaaaaa actatttgtt cctaaatcct  15000
tggcgacatt gcatggctgt ctcatgagat aatggtctca tctcttattt atctcttatt  15060
tatagccgga agtggtagtg acccctgctt gattgctcgt atgccatctc aagttctcaa  15120
ccgtgtcgag cagccatttt cccatctcaa gcgcatcatc gtttcgtttg acctcatctg  15180
ctatcctgct cctagtgcaa atcacatgcg acagaaagtg tgcggaccgc ctgcaggccc  15240
gggggcgcgc cctaattagc taacggccag gatcgccgcg tgagccttta gcaactagct  15300
agattaatta acgcaatctg ttattaagtt gtctaagcgt caatttgttt acaccacaat  15360
atatcctgcc accagccagc caacagctcc ccgaccggca gctcggcaca aaatcaccac  15420
tcgatacagg cagcccatca g                                            15441

SEQ ID NO: 97          moltype = DNA  length = 10671
FEATURE                Location/Qualifiers
misc_feature           1..10671
                       note = Expression cassette of construct 22807
regulatory             165..256
                       note = enhancer - eNOS
                       regulatory_class = enhancer
regulatory             301..2097
                       note = promoter - Ubi
                       regulatory_class = promoter
gene                   2114..6283
                       note = Cas9
misc_feature           6218..6274
                       note = NLS-TAG
regulatory             6289..6541
                       note = terminator - tNOS
                       regulatory_class = terminator
regulatory             6548..6922
                       note = promoter - pU3
                       regulatory_class = promoter
misc_feature           6924..6941
misc_feature           6924..7026
                       note = sgRNA
regulatory             7037..9028
                       note = promoter - Ubi
                       regulatory_class = promoter
gene                   9045..10223
                       note = PMI
regulatory             10246..10498
                       note = terminator - tNOS
                       regulatory_class = terminator
source                 1..10671
                       mol_type = other DNA
                       organism = synthetic construct
SEQUENCE: 97
cctgtggttg gcatgcacat acaaatggac gaacggataa acctttcac gccctttttaa  60
atatccgatt attctaataa acgctctttt ctcttaggtt tacccgccaa tatatcctgt  120
caaacactga tagtttaaac tgaaggcggg aaacgacaat ctgatcatga gcggagaatt  180
aagggagtca cgttatgacc cccgccgatg acgcgggaca agccgtttta cgtttggaac  240
tgacagaacc gcaacgctgc aggaattggc cgcagcggcc atttaaacaa agcttggtac  300
cattatgtgg tctaggtagg ttctatatat aagaaaactt gaaatgttct aaaaaaaaat  360
tcaagcccat gcatgattga agcaaacggt atagcaacgg tgttaacctg atctagtgat  420
ctcttgcaat ccttaacggc cacctaccgc aggtagcaaa cggcgtcccc ctcctcgata  480
tctccgcggc gacctctggc tttttccgcg gaattgcgcg gtggggacgg attccacgag  540
accgcgacgc aaccgcctct cgccgctggg ccccacaccg ctcggtgccg tagcctcacg  600
ggactctttc tccctcctcc cccgttataa attggcttca tcccctcctt gcctcatcca  660
tccaaatccc agtccccaat cccatccctt cgtaggagaa attcatcgaa gctaagcgaa  720
tcctcgcgat cctctcaagg tactgcgagt tttcgatccc cctctcgacc cctcgtatgt  780
ttgtgtttgt cgtagcgttt gattaggtat gctttccctg tttgtgttcg tcgtagcgtt  840
tgattaggta tgctttccct gttcgtgttc atcgtagtgt ttgattaggt cgtgtgaggc  900
gatggcctgc tcgcgtcctt cgatctgtag tcgatttgcg ggtcgtggtg tagatctgcg  960
ggctgtgatg aagttatttg gtgtgatctg ctcgcctgat tctgcgggtt ggctcgagta  1020
gatatgatgg ttggaccggt tggttcgttt accgcgctag ggttgggctg ggatgatgtt  1080
gcatgcgccg ttgcgcgtga tcccgcagca ggacttgcgt ttgattgcca gatctcgtta  1140
cgattatgtg atttggtttg gactttttag atctgtagct tctgcttatg tgccagatgc  1200
gcctactgct catatgcctg atgataatca taaatggctg tggaactaac tagttgattg  1260
cggagtcatg tatcagctac aggtgtaggg actagctaca ggtgtaggga cttgcgtcta  1320
attgtttggt cctttactca tgttgcaatt atgcaattta gtttagattg tttgttccac  1380
tcatctaggc tgtaaaaggg acactgctta gattgctgtt taatcttttt agtagattat  1440
attatattgg taacttatta cccctattac atgccatacg tgacttctgc tcatgcctga  1500
tgataatcat agatcactgt ggaattaatt agttgattgt tgaatcatgt ttcatgtaca  1560
taccacggca caattgctta gttccttaac aaatgcaaat tttactgatc catgtatgat  1620
ttgcgtggtt ctctaatgtg aaatactata gctacttgtt agtaagaatc aggttcgtat  1680
gcttaatgct gtatgtgcct tctgctcatg cctgatgata atcatatatc actggaatta  1740
attagttgat cgtttaatca tatatcaagt acataccatg ccacaatttt tagtcactta  1800
acccatgcag attgaactgg tccctgcatg ttttgctaaa ttgttctatt ctgattagac  1860
catatatcat gtattttttt ttggtaatgg ttctcttatt ttaaatgcta tatagttctg  1920
gtacttgtta gaaagatctg cttcatagtt tagttgccta tccctcgaat taggatgctg  1980
agcagctgat cctatagctt tgtttcatgt atcaattctt ttgtgttcaa cagtcagttt  2040
```

-continued

```
ttgttagatt cattgtaact tatggtcgct tactcttctg gtcctcaatg cttgcaggat  2100
cgcggccgct catatggaca agaagtacag catcggcctg gacatcggca ccaacagcgt  2160
gggctgggcc gtgatcaccg acgagtacaa ggtgccgagc aagaagttca aggtgctggg  2220
caacaccgac aggcacagca tcaagaagaa cctgatcggc gccctgctgt tcgacagcgg  2280
cgagaccgcc gaggccacca ggctgaagag gaccgccagg aggaggtaca ccaggaggaa  2340
gaacaggatc tgctacctgc aggagatctt cagcaacgag atggccaagg tggacgacag  2400
cttcttccac aggctggagg agagcttcct ggtggaggag gacaagaagc acgagaggca  2460
cccgatcttc ggcaacatcg tggacgaggt ggcctaccac gagaagtacc cgaccatcta  2520
ccacctgagg aagaagctgg tggacagcac cgacaaggcc gacctgaggc tgatctacct  2580
ggccctggcc cacatgatca agttcagggg ccacttcctg atcgagggcg acctgaaccc  2640
ggacaacagc gacgtggaca agctgttcat ccagctggtg cagacctaca accagctgtt  2700
cgaggagaac ccgatcaacg ccagcggcgt ggacgccaag gccatcctga gcgccaggct  2760
gagcaagagc aggaggctgg agaacctgat cgcccagctg ccgggcgaga agaagaacgg  2820
cctgttcggc aacctgatcg ccctgagcct gggcctgacc ccgaacttca agagcaactt  2880
cgacctggcc gaggacgcca agctgcagct gagcaaggac acctacgacg acgacctgga  2940
caacctgctg gcccagatcg gcgaccagta cgccgacctg ttcctggccg ccaagaacct  3000
gagcgacgcc atcctgctga gcgacatcct gagggtgaac accgagatca ccaaggcccc  3060
gctgagcgcc agcatgatca agaggtacga cgagcaccac caggacctga ccctgctgaa  3120
ggccctggtg aggcagcagc tgccggagaa gtacaaggag atcttcttcg accagagcaa  3180
gaacggctac gccggctaca tcgacggcgg cgccagccag gaggagttct acaagttcat  3240
caagccgatc ctggagaaga tggacggcac cgaggagctg ctggtgaagc tgaacaggga  3300
ggacctgctg aggaagcaga ggaccttcga caacggcagc atcccgcacc agatccacct  3360
gggcgagctg cacgccatcc tgaggaggca ggaggacttc tacccgttcc tgaaggacaa  3420
cagggagaag atcgagaaga tcctgacctt ccgcatcccg tactacgtgg gcccgctggc  3480
caggggcaac agcaggttcg cctggatgac caggaagagc gaggagacca tcaccccgtg  3540
gaacttcgag gaggtggtgg acaagggcgc cagcgcccag agcttcatcg agaggatgac  3600
caacttcgac aagaacctgc cgaacgagaa ggtgctgccg aagcacagcc tgctgtacga  3660
gtacttcacc gtgtacaacg agctgaccaa ggtgaagtac gtgaccgagg gcatgaggaa  3720
gccggccttc ctgagcggcg agcagaagaa ggccatcgtg gacctgctgt tcaagaccaa  3780
caggaaggtg accgtgaagc agctgaagga ggactacttc aagaagatcg agtgcttcga  3840
cagcgtggag atcagcggcg tggaggacag gttcaacgcc agcctgggca cctaccacga  3900
cctgctgaag atcatcaagg acaaggactt cctggacaac gaggagaacg aggacatcct  3960
ggaggacatc gtgctgaccc tgaccctgtt cgaggacagg gagatgatcg aggagaggct  4020
gaagacctac gcccacctgt tcgacgacaa ggtgatgaag cagctgaaga ggaggaggta  4080
caccggctgg ggcaggctga gcaggaagct gatcaacggc atcagggaca agcagagcgg  4140
caagaccatc ctggacttcc tgaagagcga cggcttcgcc aacaggaact tcatgcagct  4200
gatccacgac gacagcctga ccttcaagga ggacatccag aaggcccagg tgagcggcca  4260
gggcgacagc ctgcacgagc acatcgccaa cctggccggc agcccggcca tcaagaaggg  4320
catcctgcag accgtgaagg tggtggacga gctggtgaag gtgatgggca ggcacaagcc  4380
ggagaacatc gtgatcgaga tggccaggga gaaccagacc acccagaagg gccagaagaa  4440
cagcagggag aggatgaaga ggatcgagga gggcatcaag gagctgggca gccagatcct  4500
gaaggagcac ccggtggaga acacccagct gcagaacgag aagctgtacc tgtactacct  4560
gcagaacggc agggacatgt acgtggacca ggagctggac atcaacaggc tgagcgacta  4620
cgacgtggac cacatcgtgc cgcagagctt cctgaaggac gacagcatcg acaacaaggt  4680
gctgaccagg agcgacaaga acaggggcaa gagcgacaac gtgccgagcg aggaggtggt  4740
gaagaagatg aaaaactact ggaggcagct gctgaacgcc aagctgatca cccagaggaa  4800
gttcgacaac ctgaccaagg ccgagagggg cggcctgagc gagctggaca aggccggctt  4860
cattaaaagg cagctggtgg agaccaggca gatcaccaag cacgtggccc agatcctgga  4920
cagcaggatg aacaccaagt acgacgagaa cgacaagctg atcagggagg tgaaggtgat  4980
caccctgaag agcaagctgg tgagcgactt caggaaggac ttccagttct acaaggtgag  5040
ggagatcaat aattaccacc acgcccacga cgcctacctg aacgccgtgg tgggcaccgc  5100
cctgattaaa aagtacccga agctggagag cgagttcgtg tacggcgact acaaggtgta  5160
cgacgtgagg aagatgatcg ccaagagcga gcaggagatc ggcaaggcca ccgccaagta  5220
cttcttctac agcaacatca tgaacttctt caagaccgag atcaccctgg ccaacggcga  5280
gatcaggaag aggccgctga tcgagaccaa cggcgagacc ggcgagatcg tgtgggacaa  5340
gggcagggac ttcgccaccg tgaggaaggt gctgtccatg ccgcaggtga acatcgtgaa  5400
gaagaccgag gtgcagaccg gcggcttcag caaggagagc atcctgccga agaggaacag  5460
cgacaagctg atcgccagga agaaggactg ggacccgaag aagtacggcg gcttcgacag  5520
cccgaccgtg gcctacagcg tgctggtggt ggccaaggtg gagaagggca agagcaagaa  5580
gctgaagagc gtgaaggagc tggtgggcat caccatcatg gagaggagca gcttcgagaa  5640
gaacccagtg gacttcctgg aggccaaggg ctacaaggag gtgaagaagg acctgatcat  5700
taaactgccg aagtacagcc tgttcgagct ggagaacggc aggaagagga tgctggccag  5760
cgccggcgag ctgcagaagg gcaacgagct ggccctgccg agcaagtacg tgaacttcct  5820
gtacctggcc agccactacg agaagctgaa gggcagcccg gaggacaacg agcagaagca  5880
gctgttcgtg gagcagcaca agcactacct ggacgagatc atcgagcaga tcagcgagtt  5940
cagcaagagg gtgatcctgg ccgacgccaa cctggacaag gtgctgagcg cctacaacaa  6000
gcacagggac aagccgatca gggagcaggc cgagaacatc atccacctgt tcaccctgac  6060
caacctgggc gccccggccg ccttcaagta cttcgacacc accatcgaca ggaagaggta  6120
caccagcacc aaggaggtgc tggacgccac cctgatccac cagagcatca ccggcctgta  6180
cgagaccagg atcgacctga gccagctggg cggcgacagc agcccgccga agaagaagag  6240
gaaggtgagc tggaaggacg ccagcggctg gagcaggatg tgaagcttga tcgttcaaac  6300
atttggcaat aaagtttctt aagattgaat cctgttgccg gtcttgcgat gattatcata  6360
taatttctgt tgaattacgt taagcatgta ataattaaca tgtaatgcat gacgttattt  6420
atgagatggg tttttatgat tagagtcccg caattataca tttaatacgc gatagaaaac  6480
aaaatatagc gcgcaaacta ggataaatta tcgcgcgcgg tgtcatctat gttactagat  6540
cttcgaaggg atctttaaac atacgaacag atcacttaaa gttcttctga agcaacttaa  6600
agttatcagg catgcatgga tcttggagga atcagatgtg cagtcaggga ccatagcaca  6660
ggacaggcgt cttctactgg tgctaccagc aaatgctgga agccgggaac actgggtacg  6720
ttggaaacca cgtgatgtgg agtaagataa actgtaggag aaaagcattt cgtagtgggc  6780
```

-continued

```
catgaagcct ttcaggacat gtattgcagt atgggccggc ccattacgca attggacgac  6840
aacaaagact agtattagta ccacctcggc tatccacata gatcaaagct ggtttaaaag  6900
agttgtgcag atgatccgtg gcagtcaacg tggagacagg ggttttagag ctagaaatag  6960
caagttaaaa taaggctagt ccgttatcaa cttgaaaaag tggcaccgag tcggtgcttt  7020
tttttcgga ccgcgcctgc agtgcagcgt gacccggtcg tgcccctctc tagagataat  7080
gagcattgca tgtctaagtt ataaaaaatt accacatatt tttttgtca cacttgtttg  7140
aagtgcagtt tatctatctt tatacatata tttaaacttt actctacgaa taatataatc  7200
tatagtacta caataatatc agtgttttag agaatcatat aaatgaacag ttagacatgg  7260
tctaaaggac aattgagtat tttgacaaca ggactctaca gttttatctt tttagtgtgc  7320
atgtgttctc cttttttttt gcaaatagct tcacctatat aatacttcat ccattttatt  7380
agtacatcca tttagggttt agggttaatg gtttttatag actaattttt ttagtacatc  7440
tattttattc tattttagcc tctaaattaa gaaaactaaa actctatttt agttttttta  7500
tttaataatt tagatataaa atagaataaa ataaagtgac taaaaattaa acaaataccc  7560
tttaagaaat taaaaaaact aaggaaacat ttttcttgtt tcgagtagat aatgccagcc  7620
tgttaaacgc cgtcgacgag tctaacggac accaaccagc gaaccagcag cgtcgcgtcg  7680
ggccaagcga agcagacggc acggcatctc tgtcgctgcc tctggacccc tctcgagagt  7740
tccgctccac cgttggactt gctccgctgt cggcatccag aaattgcgtg gcggagcggc  7800
agacgtgagc cggcacggca ggcggcctcc tcctcctctc acggcaccgg cagctacggg  7860
ggattccttt cccaccgctc cttcgctttc ccttcctcgc ccgccgtaat aaatagacac  7920
cccctccaca ccctctttcc ccaacctcgt gttgttcgga gcgcacacac acacaaccag  7980
atctccccca aatccacccg tcggcacctc cgcttcaagg tacgccgctc gtcctccccc  8040
cccccccctct ctaccttctc tagatcggcg ttccggtcca tggttagggc ccggtagttc  8100
tacttctgtt catgtttgtg ttagatccgt gtttgtgtta gatccgtgct gctagcgttc  8160
gtacacggat gcgacctgta cgtcagacac gttctgattg ctaacttgcc agtgtttctc  8220
tttggggaat cctgggatgg ctctagccgt tccgcagacg ggatcgattt catgattttt  8280
tttgtttcgt tgcatagggt ttggtttgcc cttttccttt atttcaatat atgccgtgca  8340
cttgtttgtc gggtcatctt ttcatgcttt tttttgtctt ggttgtgatg atgtggtctg  8400
gttgggcggt cgttctagat cggagtagaa ttctgtttca aactacctgg tggatttatt  8460
aattttggat ctgtatgtgt gtgccataca tattcatagt tacgaattga agatgatgga  8520
tggaaatatc gatctaggat aggtatacat gttgatgcgg gttttactga tgcatataca  8580
gagatgcttt ttgttcgctt ggttgtgatg atgtggtgtg gttgggcggt cgttcattcg  8640
ttctagatcg gagtagaata ctgtttcaaa ctacctggtg tatttattaa ttttggaact  8700
gtatgtgtgt gtcatacatc ttcatagtta cgagtttaag atggatggaa atatcgatct  8760
aggataggta tacatgttga tgtgggtttt actgatgcat atacatgatg gcatatgcag  8820
catctattca tatgctctaa ccttgagtac ctatctatta taataaacaa gtatgtttta  8880
taattatttt gatcttgata tacttggatg atggcatatg cagcagctat atgtggattt  8940
ttttagccct gccttcatac gctatttatt tgcttggtac tgtttctttt gtcgatgctc  9000
accctgttgt ttggtgttac ttctgcaggg atccggcagc agccatgcag aagctgatca  9060
acagcgtgca gaactacgcc tggggcagca agaccgccct gaccgagctg tacggcatgg  9120
agaaccccag cagccagccc atggccgagc tgtggatggg cgcccacccc aagagcagca  9180
gccgcgtgca gaacgccgcc ggcgacatcg tgagcctgcg cgacgtgatc gagagcgaca  9240
agagcaccct gctgggcgag gccgtggcca agcgcttcgg cgagctgccc ttcctgttca  9300
aggtgctgtg cgccgcccag cccctgagca tccaggtgca ccccaacaag cacaacagcg  9360
agatcggctt cgccaaggag aacgccgccg gcatccccat ggacgccgcc gagcgcaact  9420
acaaggaccc caaccacaag cccgagctgg tgttcgccct gacccccttc ctggccatga  9480
acgccttccg cgagttcagc gagatcgtga gcctgctgca gcccgtggcc ggcgcccacc  9540
ccgccatcgc ccacttcctg cagcagcccg acgccgagcg cctgagcgag ctgttcgcca  9600
gcctgctgaa catgcagggc gaggagaaga gccgcgccct ggccatcctg aagagcgccc  9660
tggacagcca gcagggcgag ccctggcaga ccatccgcct gatcagcgag ttctaccccg  9720
aggacagcgg cctgttcagc cccctgctgc tgaacgtggt gaagctgaac cccggcgagg  9780
ccatgttcct gttcgccgag accccccacg cctacctgca gggcgtggcc ctggaggtga  9840
tggccaacag cgacaacgtg ctgcgcgccg gcctgacccc caagtacatc gacatccccg  9900
agctggtggc caacgtgaag ttcgaggcca agcccgccaa ccagctgctg acccagcccg  9960
tgaagcaggg cgccgagctg gacttcccca tccccgtgga cgacttcgcc ttcagcctgc  10020
acgacctgag cgacaaggag accaccatca gccagcagag cgccgccatc ctgttctgcg  10080
tggagggcga cgccaccctg tggaagggca gccagcagct gcagctgaag cccggcgaga  10140
gcgccttcat cgccgccaac gagagccccg tgaccgtgaa gggccacggc cgcctggccc  10200
gcgtgtacaa caagctgtga taggagctcg atccgtcgac ctgcagatcg ttcaaacatt  10260
tggcaataaa gtttcttaag attgaatcct gttgccggtc ttgcgatgat tatcatataa  10320
tttctgttga attacgttaa gcatgtaata attaacatgt aatgcatgac gttatttatg  10380
agatgggttt ttatgattag agtcccgcaa ttatacattt aatacgcgat agaaaacaaa  10440
atatagcgcg caaactagga taaattatcg cgcgcggtgt catctatgtt actagatcgg  10500
cgcgccgcaa ttgaagtttg ggcggccagc atggccgtat ccgcaatgtg ttattaagtt  10560
gtctaagcgt caatttgttt acaccacaat atatcctgcc accagccagc caacagctcc  10620
ccgaccggca gctcggcaca aaatcaccac tcgatacagg cagcccatca g           10671
```

SEQ ID NO: 98 moltype = DNA length = 14475
FEATURE Location/Qualifiers
misc_feature 1..14475
note = Expression cassette of construct 22808
regulatory 165..256
note = enhancer - eNOS
regulatory_class = enhancer
regulatory 301..2097
note = promoter - Ubi
regulatory_class = promoter
gene 2116..5190
note = TNFw
regulatory 2116..5190

```
                        note = terminator - tNOS
                        regulatory_class = terminator
regulatory              5483..7475
                        note = promoter - Ubi
                        regulatory_class = promoter
gene                    7489..10563
                        note = TNRv
regulatory              10570..10822
                        note = terminator - tNOS
                        regulatory_class = terminator
regulatory              10841..12832
                        note = promoter - Ubi
                        regulatory_class = promoter
gene                    12849..14027
                        note = PMI
regulatory              14050..14302
                        note = terminator - tNOS
                        regulatory_class = terminator
source                  1..14475
                        mol_type = other DNA
                        organism = synthetic construct
SEQUENCE: 98
cctgtggttg gcatgcacat acaaatggac gaacggataa accttttcac gcccttttaa  60
atatccgatt attctaataa acgctctttt ctcttaggtt tacccgccaa tatatcctgt  120
caaacactga tagtttaaac tgaaggcggg aaacgacaat ctgatcatga gcggagaatt  180
aagggagtca cgttatgacc cccgccgatg acgcgggaca agccgtttta cgtttggaac  240
tgacagaacc gcaacgctgc aggaattggc cgcagcggcc atttaaacaa agcttggtac  300
cattatgtgg tctaggtagg ttctatatat aagaaaactt gaaatgttct aaaaaaaaat  360
tcaagcccat gcatgattga agcaaacggt atagcaacgg tgttaacctg atctagtgat  420
ctcttgcaat ccttaacggc cacctaccgc aggtagcaaa cggcgtcccc ctcctcgata  480
tctccgcggc gacctctggc tttttccgcg gaattgcgcg gtggggacgg attccacgag  540
accgcgacgc aaccgcctct cgccgctggg ccccacaccg ctcggtgccg tagcctcacg  600
ggactctttc tccctcctcc cccgttataa attggcttca tcccctcctt gcctcatcca  660
tccaaatccc agtccccaat cccatccctt cgtaggagaa attcatcgaa gctaagcgaa  720
tcctcgcgat cctctcaagg tactgcgagt tttcgatccc cctctcgacc cctcgtatgt  780
ttgtgtttgt cgtagcgttt gattaggtat gctttccctg tttgtgttcg tcgtagcgtt  840
tgattaggta tgctttccct gttcgtgttc atcgtagtgt ttgattaggt cgtgtgaggc  900
gatggcctgc tcgcgtcctt cgatctgtag tcgatttgcg ggtcgtggtg tagatctgcg  960
ggctgtgatg aagttatttg gtgtgatctg ctcgcctgat tctgcgggtt ggctcgagta  1020
gatatgatgg ttggaccggt tggttcgttt accgcgctag ggttgggctg ggatgatgtt  1080
gcatgcgccg ttgcgcgtga tcccgcagca ggacttgcgt ttgattgcca gatctcgtta  1140
cgattatgtg atttggtttg gacttttag atctgtagct tctgcttatg tgccagatgc  1200
gcctactgct catatgcctg atgataatca taaatggctg tggaactaac tagttgattg  1260
cggagtcatg tatcagctac aggtgtaggg actagctaca ggtgtaggga cttgcgtcta  1320
attgtttggt cctttactca tgttgcaatt atgcaattta gtttagattg tttgttccac  1380
tcatctaggc tgtaaaaggg acactgctta gattgctgtt taatcttttt agtagattat  1440
attatattgg taacttatta cccctattac atgccatacg tgacttctgc tcatgcctga  1500
tgataatcat agatcactgt ggaattaatt agttgattgt tgaatcatgt ttcatgtaca  1560
taccacggca caattgctta gttccttaac aaatgcaaat tttactgatc catgtatgat  1620
ttgcgtggtt ctctaatgtg aaatactata gctacttgtt agtaagaatc aggttcgtat  1680
gcttaatgct gtatgtgcct tctgctcatg cctgatgata atcatatatc actggaatta  1740
attagttgat cgtttaatca tatatcaagt acataccatg ccacaatttt tagtcactta  1800
acccatgcag attgaactgg tccctgcatg ttttgctaaa ttgttctatt ctgattagac  1860
catatatcat gtattttttt ttggtaatgg ttctcttatt ttaaatgcta tatagttctg  1920
gtacttgtta gaaagatctg cttcatagtt tagttgccta tccctcgaat taggatgctg  1980
agcagctgat cctatagctt tgtttcatgt atcaattctt ttgtgttcaa cagtcagttt  2040
ttgttagatt cattgtaact tatggtcgct tactcttctg gtcctcaatg cttgcaggat  2100
cgcggccgcg ccaccatggg aaaacctatt cctaatcctc tgctgggcct ggattctacc  2160
ggaggcatgg ccccctaagaa aaagcggaag gtggacggcg gagtggacct gagaacactg  2220
ggatattctc agcagcagca ggagaagatc aagcccaagg tgagatctac agtggcccag  2280
caccacgaag ccctggtggg acacggattt acacacgccc acattgtggc cctgtctcag  2340
caccctgccg ccctgggaac agtggccgtg aaatatcagg atatgattgc cgccctgcct  2400
gaggccacac acgaagccat tgtgggagtg ggaaaacagt ggtctggagc cagagccctg  2460
gaagccctgc tgacagtggc cggagaactg agaggacctc ctctgcagct ggatacagga  2520
cagctgctga agattgccaa aaggggcgga gtgaccgcgg tggaagccgt gcacgcctgg  2580
agaaatgccc tgacaggagc ccctctgaac ctgacccccg aacaggtggt ggccattgcc  2640
agccacgacg gcggcaagca ggccctggaa accgtgcaga gactgctgcc cgtgctgtgc  2700
caggcccatg gcctgacacc tgaacaggtg gtggctatcg cctctcacga cggaggaaaa  2760
caggctctgg aaacagtgca gcggctgctg cctgtgctgt gtcaggctca cggcttgact  2820
ccagaacagg tggtggctat tgcttccaat attgggggga aacaggccct ggaaactgtg  2880
cagcgcctgc tgccagtgct gtgccaggct cacggactga cccccgaaca ggtggtggcc  2940
attgccagca acaacggcgg caagcaggcc ctggaaaccg tgcagagact gctgcccgtg  3000
ctgtgccagg cccatggcct gacacctgaa caggtggtgg ctatcgcctc taacaacgga  3060
ggaaaacagg ctctggaaac agtgcagcgg ctgctgcctg tgctgtgtca ggctcacggc  3120
ttgactccag aacaggtggt ggctattgct tccaacaacg gggggaaaca ggccctggaa  3180
actgtgcagc gcctgctgcc agtgctgtgc caggctcacg ggctgacccc cgaacaggtg  3240
gtggccattg ccagcaacgg cggcggcaag caggccctgg aaaccgtgca gagactgctg  3300
cccgtgctgt gccaggccca tggcctgaca cctgaacagg tggtggctat cgcctctcac  3360
gacggaggaa aacaggctct ggaaacagtg cagcggctgc tgcctgtgct gtgtcaggct  3420
```

```
cacggcttga ctccagaaca ggtggtggct attgcttcca atattggggg gaaacaggcc  3480
ctggaaactg tgcagcgcct gctgccagtg ctgtgccagg ctcacggcct cactcccgaa  3540
caggtggtgg ccattgccag caacatcggc ggcaagcagg ccctggaaac cgtgcagaga  3600
ctgctgcccg tgctgtgcca ggcccatggc ctgacacctg aacaggtggt ggctatcgcc  3660
tctcacgacg gaggaaaaca ggctctggaa acagtgcagc ggctgctgcc tgtgctgtgt  3720
caggctcacg gcttgactcc agaacaggtg gtggctattg cttccaacaa cggggggaaa  3780
caggccctgg aaactgtgca gcgcctgctg ccagtgctgt gccaggctca cggactgacc  3840
cccgaacagg tggtggccat tgccagcaac ggcggcggca agcaggccct ggaaaccgtg  3900
cagagactgc tgcccgtgct gtgccaggcc catggcctga cacctgaaca ggtggtggct  3960
atcgcctcta acaacggagg aaaacaagca ctcgagacag tgcagcggct gctgcctgtg  4020
ctgtgtcagg ctcacggctt gactccagaa caggtggtgg ctattgcttc caacaacggg  4080
gggaaacagg ccctggaaac tgtgcagcgc ctgctgccag tgctgtgcca ggctcacggg  4140
ctgacccccg aacaggtggt ggccattgcc agcaacatcg gcggcaagca ggccctggaa  4200
accgtgcaga gactgctgcc cgtgctgtgc caggcccatg gcctgacacc tgaacaggtg  4260
gtggctatcg cctctaacaa cggaggaaaa caggctctgg aaacagtgca gcggctgctg  4320
cctgtgctgt gtcaggctca cggcttgact ccacagcagg tcgtggcaat tgctagcaat  4380
atcggcggac ggcccgccct ggagagcatt gtggcccagc tgtctagacc tgatcctgcc  4440
ctggccgccc tgacaaatga tcacctggtg gccctggcct gtctgggagg cagacctgcc  4500
ctggatgccg tgaaaaaagg actgcctcac gcccctgccc tgattaaaag aacaaataga  4560
agaatccccg agcggacctc tcacagagtg gccggatccc agctggtgaa atctgagctg  4620
gaggagaaga agtctgagct gagacacaag ctgaagtacg tgcctcacga gtacatcgag  4680
ctgatcgaga tcgccagaaa tagcacccag gatagaatcc tggagatgaa ggtgatggag  4740
ttcttcatga agtgtacgg ctacagagga aagcatctgg gaggaagcag aaaacctgac  4800
ggagccattt atacagtggg cagccctatc gattatggcg tgatcgtgga tacaaaggcc  4860
tacagcggag gctacaatct gcctattgga caggccgatg agatgcagag atacgtggag  4920
gagaaccaaa ccaggaacaa gcatatcaac cctaacgagt ggtggaaggt gtacccttct  4980
agcgtgaccg agttcaagtt cctgtttgtg agcggccact tcaagggcaa ttataaggcc  5040
cagctgacca ggctgaacca catcacaaat tgtaatggcg ccgtgctgtc tgtggaggaa  5100
ctgctgattg gaggagagat gattaaggcc ggaacactga cactggagga ggtgagaaga  5160
aagttcaaca acggcgagat caacttctga aagcttgatc gttcaaacat ttggcaataa  5220
agtttcttaa gattgaatcc tgttgccggt cttgcgatga ttatcatata atttctgttg  5280
aattacgtta agcatgtaat aattaacatg taatgcatga cgttatttat gagatgggtt  5340
tttatgatta gagtcccgca attatacatt taatacgcga tagaaaacaa aatatagcgc  5400
gcaaactagg ataaattatc gcgcgcggtg tcatctatgt tactagatct tcgaacccta  5460
gtcgaagaca accggtgcat gcctgcagtg cagcgtgacc cggtcgtgcc cctctctaga  5520
gataatgagc attgcatgtc taagttataa aaaattacca catatttttt ttgtcacact  5580
tgtttgaagt gcagtttatc tatctttata catatattta aactttactc tacgaataat  5640
ataatctata gtactacaat aatatcagtg ttttagagaa tcatataaat gaacagttag  5700
acatggtcta aaggacaatt gagtattttg acaacaggac tctacagttt tatcttttta  5760
gtgtgcatgt gttctccttt ttttttgcaa atagcttcac ctatataata cttcatccat  5820
tttattagta catccattta gggtttaggg ttaatggttt ttatagacta atttttttag  5880
tacatctatt ttattctatt ttagcctcta aattaagaaa actaaaactc tattttagtt  5940
tttttattta ataatttaga tataaaatag aataaaataa agtgactaaa aattaaacaa  6000
ataccettta agaaattaaa aaaactaagg aaacattttt cttgtttcga gtagataatg  6060
ccagcctgtt aaacgccgtc gacgagtcta acggacacca accagcgaac cagcagcgtc  6120
gcgtcgggcc aagcgaagca gacggcacgg catctctgtc gctgcctctg gacccctctc  6180
gagagttccg ctccaccgtt ggacttgctc cgctgtcggc atccagaaat tgcgtggcgg  6240
agcggcagac gtgagccggc acggcaggcg gcctcctcct cctctcacgg caccggcagc  6300
tacgggggat tcctttccca ccgctccttc gctttccctt cctcgcccgc cgtaataaat  6360
agacaccccc tccacaccct ctttccccaa cctcgtgttg ttcggagcgc acacacacac  6420
aaccagatct cccccaaatc cacccgtcgg cacctccgct tcaaggtacg ccgctcgtcc  6480
tccccccccc cccctctcta ccttctctag atcggcgttc cggtccatgg ttagggcccg  6540
gtagttctac ttctgttcat gtttgtgtta gatccgtgtt tgtgttagat ccgtgctgct  6600
agcgttcgta cacggatgcg acctgtacgt cagacacgtt ctgattgcta acttgccagt  6660
gtttctcttt ggggaatcct gggatggctc tagccgttcc gcagacggga tcgatttcat  6720
gatttttttt gtttcgttgc atagggtttg gtttgccctt ttcctttatt tcaatatatg  6780
ccgtgcactt gtttgtcggg tcatcttttc atgctttttt ttgtcttggt tgtgatgatg  6840
tggtctggtt gggcggtcgt tctagatcgg agtagaattc tgtttcaaac tacctggtgg  6900
atttattaat tttggatctg tatgtgtgtg ccatacatat tcatagttac gaattgaaga  6960
tgatggatgg aaatatcgat ctaggatagg tatacatgtt gatgcgggtt ttactgatgc  7020
atatacagag atgctttttg ttcgcttggt tgtgatgatg tggtgtggtt gggcggtcgt  7080
tcattcgttc tagatcggag tagaatactg tttcaaacta cctggtgtat ttattaattt  7140
tggaactgta tgtgtgtgtc atacatcttc atagttacga gtttaagatg gatggaaata  7200
tcgatctagg ataggtatac atgttgatgt gggttttact gatgcatata catgatggca  7260
tatgcagcat ctattcatat gctctaacct tgagtaccta tctattataa taaacaagta  7320
tgttttataa ttattttgat cttgatatac ttggatgatg gcatatgcag cagctatatg  7380
tggatttttt tagccctgcc ttcatacgct atttatttgc ttggtactgt ttcttttgtc  7440
gatgctcacc ctgttgtttg gtgttacttc tgcagcggcc gcgccaccat gggaaaacct  7500
attcctaatc ctctgctggg cctggattct accggaggca tggcccctaa gaaaaagcgg  7560
aaggtggacg gcggagtgga cctgagaaca ctgggatatt ctcagcagca gcaggagaag  7620
atcaagccca aggtgagatc tacagtggcc cagcaccacg aagccctggt gggacacgga  7680
tttacacacg cccacattgt ggccctgtct cagcaccctg ccgccctggg aacagtggcc  7740
gtgaaatatc aggatatgat tgccgccctg cctgaggcca cacacgaagc cattgtggga  7800
gtgggaaaac agtggtctgg agccagagcc ctggaagccc tgctgacagt ggccggagaa  7860
ctgagaggac ctcctctgca gctggataca ggacagctgc tgaagattgc caaaaggggc  7920
ggagtgaccg cggtggaagc cgtgcacgcc tggagaaatg ccctgacagg agcccctctg  7980
aacctgaccc ccgaacaggt ggtggccatt gccagcaaca acggcggcaa gcaggccctg  8040
gaaaccgtgc agagactgct gcccgtgctg tgccaggccc atggcctgac acctgaacag  8100
gtggtggcta tcgcctctca cgacggagga aaacaggctc tggaaacagt gcagcggctg  8160
```

-continued

```
ctgcctgtgc tgtgtcaggc tcacggcttg actccagaac aggtggtggc tattgcttcc  8220
aacggcgggg ggaaacaggc cctggaaact gtgcagcgcc tgctgccagt gctgtgccag  8280
gctcacggac tgacccccga acaggtggtg gccattgcca gcaacggcgg cggcaagcag  8340
gccctggaaa ccgtgcagag actgctgccc gtgctgtgcc aggcccatgg cctgacacct  8400
gaacaggtgg tggctatcgc ctctcacgac ggaggaaaac aggctctgga aacagtgcag  8460
cggctgctgc ctgtgctgtg tcaggctcac ggcttgactc cagaacaggt ggtggctatt  8520
gcttcccacg acggggggaa acaggccctg gaaactgtgc agcgcctgct gccagtgctg  8580
tgccaggctc acgggctgac ccccgaacag gtggtggcca ttgccagcaa cggcggcggc  8640
aagcaggccc tggaaaccgt gcagagactg ctgcccgtgc tgtgccaggc ccatggcctg  8700
acacctgaac aggtggtggc tatcgcctct aacggcggag gaaaacaggc tctggaaaca  8760
gtgcagcggc tgctgcctgt gctgtgtcag gctcacggct tgactccaga acaggtggtg  8820
gctattgctt cccacgacgg ggggaaacag gccctggaaa ctgtgcagcg cctgctgcca  8880
gtgctgtgcc aggctcacgg cctcactccc gaacaggtgg tggccattgc cagcaacaac  8940
ggcggcaagc aggccctgga aaccgtgcag agactgctgc ccgtgctgtg ccaggcccat  9000
ggcctgacac ctgaacaggt ggtggctatc gcctctcacg acggaggaaa acaggctctg  9060
gaaacagtgc agcggctgct gcctgtgctg tgtcaggctc acggcttgac tccagaacag  9120
gtggtggcta ttgcttccca cgacgggggg aaacaggccc tggaaactgt gcagcgcctg  9180
ctgccagtgc tgtgccaggc tcacggactg acccccgaac aggtggtggc cattgccagc  9240
aacatcggcg gcaagcaggc cctggaaacc gtgcagagac tgctgcccgt gctgtgccag  9300
gcccatggcc tgacacctga acaggtggtg gctatcgcct ctaacaacgg aggaaaacaa  9360
gcactcgaga cagtgcagcg gctgctgcct gtgctgtgtc aggctcacgg cttgactcca  9420
gaacaggtgg tggctattgc ttccaacggc ggggggaaac aggccctgga aactgtgcag  9480
cgcctgctgc cagtgctgtg ccaggctcac gggctgaccc ccgaacaggt ggtggccatt  9540
gccagccacg acggcggcaa gcaggccctg gaaaccgtgc agagactgct gcccgtgctg  9600
tgccaggccc atggcctgac acctgaacag gtggtggcta tcgcctctaa tatcggagga  9660
aaacaggctc tggaaacagt gcagcggctg ctgcctgtgc tgtgtcaggc tcacggcttg  9720
actccacagc aggtcgtggc aattgctagc cacgacggcg gacggcccgc cctggagagc  9780
attgtggccc agctgtctag acctgatcct gccctggccg ccctgacaaa tgatcacctg  9840
gtggccctgg cctgtctggg aggcagacct gccctggatg ccgtgaaaaa aggactgcct  9900
cacgcccctg ccctgattaa aagaacaaat agaagaatcc ccgagcggac ctctcacaga  9960
gtggccggat cccagctggt gaaatctgag ctggaggaga agaagtctga gctgagacac  10020
aagctgaagt acgtgcctca cgagtacatc gagctgatcg agatcgccag aaatagcacc  10080
caggatagaa tcctggagat gaaggtgatg gagttcttca tgaaagtgta cggctacaga  10140
ggaaagcatc tgggaggaag cagaaaacct gacggagcca tttatacagt gggcagccct  10200
atcgattatg gcgtgatcgt ggatacaaag gcctacagcg gaggctacaa tctgcctatt  10260
ggacaggccg atgagatgca gagatacgtg gaggagaacc aaaccaggaa caagcatatc  10320
aaccctaacg agtggtggaa ggtgtaccct tctagcgtga ccgagttcaa gttcctgttt  10380
gtgagcggcc acttcaaggg caattataag gcccagctga ccaggctgaa ccacatcaca  10440
aattgtaatg gcgccgtgct gtctgtggag gaactgctga ttggaggaga gatgattaag  10500
gccggaacac tgacactgga ggaggtgaga agaaagttca acaacggcga gatcaacttc  10560
tgaaagcttg atcgttcaaa catttggcaa taaagtttct taagattgaa tcctgttgcc  10620
ggtcttgcga tgattatcat ataatttctg ttgaattacg ttaagcatgt aataattaac  10680
atgtaatgca tgacgttatt tatgagatgg gtttttatga ttagagtccc gcaattatac  10740
atttaatacg cgatagaaaa caaaatatag cgcgcaaact aggataaatt atcgcgcgcg  10800
gtgtcatcta tgttactaga tcttcgaaga cggaccgcgc ctgcagtgca gcgtgacccg  10860
gtcgtgcccc tctctagaga taatgagcat tgcatgtcta agttataaaa aattaccaca  10920
tattttttt gtcacacttg tttgaagtgc agtttatcta tctttataca tatatttaaa  10980
ctttactcta cgaataatat aatctatagt actacaataa tatcagtgtt ttagagaatc  11040
atataaatga acagttagac atggtctaaa ggacaattga gtattttgac aacaggactc  11100
tacagtttta tctttttagt gtgcatgtgt tctccttttt ttttgcaaat agcttcacct  11160
atataatact tcatccattt tattagtaca tccatttagg gtttagggtt aatggttttt  11220
atagactaat ttttttagta catctatttt attctatttt agcctctaaa ttaagaaaac  11280
taaaactcta ttttagtttt tttatttaat aatttagata taaaatagaa taaaataaag  11340
tgactaaaaa ttaaacaaat accctttaag aaattaaaaa aactaaggaa acatttttct  11400
tgtttcgagt agataatgcc agcctgttaa acgccgtcga cgagtctaac ggacaccaac  11460
cagcgaacca gcagcgtcgc gtcgggccaa gcgaagcaga cggcacggca tctctgtcgc  11520
tgcctctgga cccctctcga gagttccgct ccaccgttgg acttgctccg ctgtcggcat  11580
ccagaaattg cgtggcggag cggcagacgt gagccggcac ggcaggcggc ctcctcctcc  11640
tctcacggca ccggcagcta cgggggattc ctttcccacc gctccttcgc tttcccttcc  11700
tcgcccgccg taataaatag acaccccctc cacaccctct ttccccaacc tcgtgttgtt  11760
cggagcgcac acacacacaa ccagatctcc cccaaatcca cccgtcggca cctccgcttc  11820
aaggtacgcc gctcgtcctc cccccccccc ctctctacct tctctagatc ggcgttccgg  11880
tccatggtta gggcccggta gttctacttc tgttcatgtt tgtgttagat ccgtgtttgt  11940
gttagatccg tgctgctagc gttcgtacac ggatgcgacc tgtacgtcag acacgttctg  12000
attgctaact tgccagtgtt tctctttggg gaatcctggg atggctctag ccgttccgca  12060
gacgggatcg atttcatgat ttttttttgtt tcgttgcata gggtttggtt tgcccttttc  12120
ctttatttca atatatgccg tgcacttgtt tgtcgggtca tcttttcatg cttttttttg  12180
tcttggttgt gatgatgtgg tctggttggg cggtcgttct agatcggagt agaattctgt  12240
ttcaaactac ctggtggatt tattaatttt ggatctgtat gtgtgtgcca tacatattca  12300
tagttacgaa ttgaagatga tggatggaaa tatcgatcta ggataggtat acatgttgat  12360
gcgggtttta ctgatgcata tacagagatg ctttttgttc gcttggttgt gatgatgtgg  12420
tgtggttggg cggtcgttca ttcgttctag atcggagtag aatactgttt caaactacct  12480
ggtgtattta ttaattttgg aactgtatgt gtgtgtcata catcttcata gttacgagtt  12540
taagatggat ggaaatatcg atctaggata ggtatacatg ttgatgtggg ttttactgat  12600
gcatatacat gatggcatat gcagcatcta ttcatatgct ctaaccttga gtacctatct  12660
attataataa acaagtatgt tttataatta ttttgatctt gatatacttg gatgatggca  12720
tatgcagcag ctatatgtgg atttttttag ccctgccttc atacgctatt tatttgcttg  12780
gtactgtttc ttttgtcgat gctcaccctg ttgtttggtg ttacttctgc agggatccgg  12840
cagcagccat gcagaagctg atcaacagcg tgcagaacta cgcctggggc agcaagaccg  12900
```

```
ccctgaccga gctgtacggc atggagaacc ccagcagcca gcccatggcc gagctgtgga  12960
tgggcgccca ccccaagagc agcagccgcg tgcagaacgc cgccggcgac atcgtgagcc  13020
tgcgcgacgt gatcgagagc gacaagagca ccctgctggg cgaggccgtg gccaagcgct  13080
tcggcgagct gcccttcctg ttcaaggtgc tgtgcgccgc ccagcccctg agcatccagg  13140
tgcaccccaa caagcacaac agcgagatcg gcttcgccaa ggagaacgcc gccggcatcc  13200
ccatggacgc cgccgagcgc aactacaagg accccaacca caagcccgag ctggtgttcg  13260
ccctgacccc cttcctggcc atgaacgcct tccgcgagtt cagcgagatc gtgagcctgc  13320
tgcagcccgt ggccggcgcc cacccccgcca tcgcccactt cctgcagcag cccgacgccg  13380
agcgcctgag cgagctgttc gccagcctgc tgaacatgca gggcgaggag aagagccgcg  13440
ccctggccat cctgaagagc gccctggaca gccagcaggg cgagccctgg cagaccatcc  13500
gcctgatcag cgagttctac cccgaggaca gcggcctgtt cagcccctg ctgctgaacg  13560
tggtgaagct gaaccccggc gaggccatgt tcctgttcgc cgagaccccc cacgcctacc  13620
tgcagggcgt ggccctggag gtgatggcca acagcgacaa cgtgctgcgc gccggcctga  13680
cccccaagta catcgacatc cccgagctgg tggccaacgt gaagttcgag gccaagcccg  13740
ccaaccagct gctgacccag cccgtgaagc agggcgccga gctggacttc cccatccccg  13800
tggacgactt cgccttcagc ctgcacgacc tgagcgacaa ggagaccacc atcagccagc  13860
agagcgccgc catcctgttc tgcgtggagg gcgacgccac cctgtggaag ggcagccagc  13920
agctgcagct gaagcccggc gagagcgcct tcatcgccgc caacgagagc cccgtgaccg  13980
tgaagggcca cggccgcctg gcccgcgtgt acaacaagct gtgataggag ctcgatccgt  14040
cgacctgcag atcgttcaaa catttggcaa taaagtttct taagattgaa tcctgttgcc  14100
ggtcttgcga tgattatcat ataatttctg ttgaattacg ttaagcatgt aataattaac  14160
atgtaatgca tgacgttatt tatgagatgg gtttttatga ttagagtccc gcaattatac  14220
atttaatacg cgatagaaaa caaaatatag cgcgcaaact aggataaatt atcgcgcgcg  14280
gtgtcatcta tgttactaga tcggcgcgcc gcaattgaag tttgggcggc cagcatggcc  14340
gtatccgcaa tgtgttatta agttgtctaa gcgtcaattt gtttacacca caatatatcc  14400
tgccaccagc cagccaacag ctccccgacc ggcagctcgg cacaaaatca ccactcgata  14460
caggcagccc atcag                                                   14475
```

```
SEQ ID NO: 99          moltype = DNA  length = 10668
FEATURE                Location/Qualifiers
misc_feature           1..10668
                       note = Expression cassette of construct 22873
regulatory             165..256
                       note = enhancer - eNOS
                       regulatory_class = enhancer
regulatory             301..2097
                       note = promoter - Ubi
                       regulatory_class = promoter
gene                   2114..6280
                       note = Cas9m
misc_feature           6215..6271
                       note = NLS-TAG
regulatory             6286..6538
                       note = terminator - tNOS
                       regulatory_class = terminator
regulatory             6545..6919
                       note = promoter - pU3
                       regulatory_class = promoter
misc_feature           6921..6938
misc_feature           6921..7023
                       note = sgRNA
regulatory             7034..9025
                       note = promoter - Ubi
                       regulatory_class = promoter
gene                   9042..10220
                       note = PMI
regulatory             10243..10495
                       note = terminator - tNOS
                       regulatory_class = terminator
source                 1..10668
                       mol_type = other DNA
                       organism = synthetic construct
SEQUENCE: 99
cctgtggttg gcatgcacat acaaatggac gaacggataa acctttcac gcccttttaa  60
atatccgatt attctaataa acgctctttt ctcttaggtt tacccgccaa tatatcctgt  120
caaacactga tagtttaaac tgaaggcggg aaacgacaat ctgatcatga gcggagaatt  180
aagggagtca cgttatgacc cccgccgatg acgcgggaca agccgtttta cgtttggaac  240
tgacagaacc gcaacgctgc aggaattggc cgcagcggcc atttaaacaa agcttggtac  300
cattatgtgg tctaggtagg ttctatatat aagaaaactt gaaatgttct aaaaaaaaat  360
tcaagcccat gcatgattga agcaaacggt atagcaacgg tgttaacctg atctagtgat  420
ctcttgcaat ccttaacggc cacctaccgc aggtagcaaa cggcgtcccc ctcctcgata  480
tctccgcggc gacctctggc tttttccgcg gaattgcgcg gtggggacgg attccacgag  540
accgcgacgc aaccgcctct cgccgctggg ccccacaccg ctcggtgccg tagcctcacg  600
ggactctttc tccctcctcc cccgttataa attggcttca tcccctcctt gcctcatcca  660
tccaaatccc agtccccaat cccatccctt cgtaggagaa attcatcgaa gctaagcgaa  720
tcctcgcgat cctctcaagg tactgcgagt tttcgatccc cctctcgacc cctcgtatgt  780
ttgtgtttgt cgtagcgttt gattaggtat gctttccctg tttgtgttcg tcgtagcgtt  840
tgattaggta tgctttccct gttcgtgttc atcgtagtgt ttgattaggt cgtgtgaggc  900
gatggcctgc tcgcgtcctt cgatctgtag tcgatttgcg ggtcgtggtg tagatctgcg  960
```

-continued

```
ggctgtgatg aagttatttg gtgtgatctg ctcgcctgat tctgcgggtt ggctcgagta  1020
gatatgatgg ttggaccggt tggttcgttt accgcgctag ggttgggctg ggatgatgtt  1080
gcatgcgccg ttgcgcgtga tcccgcagca ggacttgcgt ttgattgcca gatctcgtta  1140
cgattatgtg atttggtttg gactttttag atctgtagct tctgcttatg tgccagatgc  1200
gcctactgct catatgcctg atgataatca taaatggctg tggaactaac tagttgattg  1260
cggagtcatg tatcagctac aggtgtaggg actagctaca ggtgtaggga cttgcgtcta  1320
attgtttggt cctttactca tgttgcaatt atgcaattta gtttagattg tttgttccac  1380
tcatctaggc tgtaaaaggg acactgctta gattgctgtt taatcttttt agtagattat  1440
attatattgg taacttatta cccctattac atgccatacg tgacttctgc tcatgcctga  1500
tgataatcat agatcactgt ggaattaatt agttgattgt tgaatcatgt ttcatgtaca  1560
taccacggca caattgctta gttccttaac aaatgcaaat tttactgatc catgtatgat  1620
ttgcgtggtt ctctaatgtg aaatactata gctacttgtt agtaagaatc aggttcgtat  1680
gcttaatgct gtatgtgcct tctgctcatg cctgatgata atcatatatc actggaatta  1740
attagttgat cgtttaatca tatatcaagt acataccatg ccacaatttt tagtcactta  1800
acccatgcag attgaactgg tccctgcatg ttttgctaaa ttgttctatt ctgattagac  1860
catatatcat gtattttttt ttggtaatgg ttctcttatt ttaaatgcta tatagttctg  1920
gtacttgtta gaaagatctg cttcatagtt tagttgccta tccctcgaat taggatgctg  1980
agcagctgat cctatagctt tgtttcatgt atcaattctt ttgtgttcaa cagtcagttt  2040
ttgttagatt cattgtaact tatggtcgct tactcttctg gtcctcaatg cttgcaggat  2100
cgcggccgct aaaatggata agaagtactc tattggcctc gatattggaa ccaactctgt  2160
gggctgggcc gtgatcaccg atgagtacaa ggtgccatct aagaagttca aggtgctcgg  2220
caacaccgat aggcactcta tcaagaagaa cctcatcggt gccctcctct tcgattctgg  2280
cgagaccgcc gaggccacca ggctcaagag gaccgccagg aggaggtaca ccaggaggaa  2340
gaacaggatc tgctacctcc aggagatctt ctctaacgag atggccaagg tggatgattc  2400
tttcttccac aggctcgagg agtctttcct cgtggaggag gataagaagc acgagaggca  2460
cccaatcttc ggcaacatcg tggatgaggt ggcctaccac gagaagtacc caaccatcta  2520
ccacctcagg aagaagctcg tggattctac cgataaggcc gatctcaggc tcatctacct  2580
cgccctcgcc cacatgatca agttcagggg ccacttcctc atcgagggcg atctcaaccc  2640
agataactct gatgtggata agctcttcat ccagctcgtg cagacctaca accagctctt  2700
cgaggagaac ccaatcaacg cctctggcgt ggatgccaag gccatcctct ctgccaggct  2760
ctctaagtct aggaggctcg agaacctcat cgcccagctc ccaggcgaga agaagaacgg  2820
cctcttcggc aacctcatcg ccctctctct cggcctcacc ccaaacttca agtctaactt  2880
cgatctcgcc gaggatgcca agctccagct ctctaaggat acctacgatg atgatctcga  2940
taacctcctc gcccagatcg gcgatcagta cgccgatctc ttcctcgccg ccaagaacct  3000
ctctgatgcc atcctcctct ctgatatcct cagggtgaac accgagatca ccaaggcccc  3060
actctctgcc tctatgatca agaggtacga tgagcaccac caggatctca ccctcctcaa  3120
ggccctcgtg aggcagcagc tcccagagaa gtacaaggag atcttcttcg atcagtctaa  3180
gaacggctac gccggctaca tcgatggcgg cgcctctcag gaggagttct acaagttcat  3240
caagccaatc ctcgagaaga tggatggcac cgaggagctc ctcgtgaagc tcaacaggga  3300
ggatctcctc aggaagcaga ggaccttcga taacggctct atcccacacc agatccacct  3360
cggcgagctc cacgccatcc tcaggaggca ggaggatttc tacccattcc tcaaggataa  3420
cagggagaag atcgagaaga tcctcacctt ccgcatccca tactacgtgg gcccactcgc  3480
caggggcaac tctaggttcg cctggatgac caggaagtct gaggagacca tcaccccttg  3540
gaacttcgag gaggtggtgg ataagggcgc ctctgcccag tctttcatcg agaggatgac  3600
caacttcgat aagaacctcc caaacgagaa ggtgctccca aagcactctc tcctctacga  3660
gtacttcacc gtgtacaacg agctcaccaa ggtgaagtac gtgaccgagg gcatgaggaa  3720
gccagccttc ctctctggcg agcagaagaa ggccatcgtg gatctcctct tcaagaccaa  3780
caggaaggtg accgtgaagc agctcaagga ggattacttc aagaagatcg agtgcttcga  3840
ttctgtggag atctctggcg tggaggatag gttcaacgcc tctctcggca cctaccacga  3900
tctcctcaag atcatcaagg ataaggattt cctcgataac gaggagaacg aggatatcct  3960
cgaggatatc gtgctcaccc tcaccctctt cgaggatagg gagatgatcg aggagaggct  4020
caagacctac gcccacctct tcgatgataa ggtgatgaag cagctcaaga ggaggaggta  4080
caccggctgg ggcaggctct ctaggaagct catcaacggc atcagggata agcagtctgg  4140
caagaccatc ctcgatttcc tcaagtctga tggcttcgcc aacaggaact tcatgcagct  4200
catccacgat gattctctca ccttcaagga ggatatccag aaggctcagg tgtctggcca  4260
gggccactct ctccacgagc agatcgccaa cctcgccggc tctccagcca tcaagaaggg  4320
catcctccag accgtgaagg tggtggatga gctcgtgaag gtgatgggcc acaagccaga  4380
gaacatcgtg atcgagatgg ccagggagaa ccagaccacc cagaagggcc agaagaactc  4440
tagggagagg atgaagagga tcgaggaggg catcaaggag ctcggctctc agatcctcaa  4500
ggagcaccca gtggagaaca cccagctcca gaacgagaag ctctacctct actacctcca  4560
gaacggcagg gatatgtacg tggatcagga gctcgatatc aacaggctct ctgattacga  4620
tgtggatcac atcgtgccac agtctttcct caaggatgat tctatcgata acaaggtgct  4680
caccaggtct gataagaaca ggggcaagtc tgataacgtg ccatctgagg aggtggttaa  4740
gaagatgaag aactactgga ggcagctcct caacgccaag ctcatcaccc agaggaagtt  4800
cgataacctc accaaggccg agaggggcgg cctctctgag ctcgataagg ccggcttcat  4860
caagaggcag ctcgtggaga ccaggcagat cactaagcac gtggcccaga tcctcgattc  4920
taggatgaac accaagtacg atgagaacga taagctcatc agggaggtga aggtgatcac  4980
cctcaagtct aagctcgtgt ctgatttcag gaaggatttc cagttctaca aggtgaggga  5040
gatcaacaac taccaccacg cccacgatgc ctacctcaac gccgtggtgg gcaccgccct  5100
catcaagaag tacccaaaac tcgagtctga gttcgtgtac ggcgattaca aggtgtacga  5160
tgtgaggaag atgatcgcca agtctgagca ggagatcggc aaggccaccg ccaagtactt  5220
cttctactct aacatcatga acttcttcaa gaccgagatc accctcgcca acggcgagat  5280
caggaagagg ccactcatcg agaccaacgg cgagaccggc gagatcgtgt gggataaggg  5340
cagggatttc gccaccgtga ggaaggtgct ctctatgcca caggtgaaca tcgtgaagaa  5400
gaccgaggtg cagaccggcg gcttctctaa ggagtctatc ctcccaaaga ggaactctga  5460
taagctcatc gccaggaaga aggattggga cccgaagaag tacggcggct tcgacagccc  5520
gaccgtggcc tacagcgtgc tggtggtggc caaggtggag aagggcaaga gcaagaagct  5580
gaagagcgtg aaggagctgg tgggcatcac catcatggag aggagcagct tcgagaagaa  5640
cccagtggac ttcctggagg ccaagggcta caaggaggtg aagaaggacc tgatcattaa  5700
```

```
actgccgaag tacagcctgt tcgagctgga gaacggcagg aagaggatgc tggccagcgc  5760
cggcgagctg cagaagggca acgagctggc cctgccgagc aagtacgtga acttcctgta  5820
cctggccagc cactacgaga agctgaaggg cagcccggag gacaacgagc agaagcagct  5880
gttcgtggag cagcacaagc actacctgga cgagatcatc gagcagatca gcgagttcag  5940
caagagggtg atcctggccg acgccaacct ggacaaggtg ctgagcgcct acaacaagca  6000
cagggacaag ccgatcaggg agcaggccga gaacatcatc cacctgttca ccctgaccaa  6060
cctgggcgcc ccggccgcct tcaagtactt cgacaccacc atcgacagga agaggtacac  6120
cagcaccaag gaggtgctgg acgccaccct gatccaccag agcatcaccg gcctgtacga  6180
gaccaggatc gacctgagcc agctgggcgg cgacagcagc ccgccgaaga agaagaggaa  6240
ggtgagctgg aaggacgcca gcggctggag caggatgtga agcttgatcg ttcaaacatt  6300
tggcaataaa gtttcttaag attgaatcct gttgccggtc ttgcgatgat tatcatataa  6360
tttctgttga attacgttaa gcatgtaata attaacatgt aatgcatgac gttatttatg  6420
agatgggttt ttatgattag agtcccgcaa ttatacattt aatacgcgat agaaaacaaa  6480
atatagcgcg caaactagga taaattatcg cgcgcggtgt catctatgtt actagatctt  6540
cgaagggatc tttaaacata cgaacagatc acttaaagtt cttctgaagc aacttaaagt  6600
tatcaggcat gcatggatct tggaggaatc agatgtgcag tcagggacca tagcacagga  6660
caggcgtctt ctactggtgc taccagcaaa tgctggaagc cgggaacact gggtacgttg  6720
gaaaccacgt gatgtggagt aagataaact gtaggagaaa agcatttcgt agtgggccat  6780
gaagcctttc aggacatgta ttgcagtatg ggccggccca ttacgcaatt ggacgacaac  6840
aaagactagt attagtacca cctcggctat ccacatagat caaagctggt ttaaaagagt  6900
tgtgcagatg atccgtggca gtcaacgtgg agacaggggt tttagagcta gaaatagcaa  6960
gttaaaataa ggctagtccg ttatcaactt gaaaaagtgg caccgagtcg gtgctttttt  7020
tttcggaccg cgcctgcagt gcagcgtgac ccggtcgtgc ccctctctag agataatgag  7080
cattgcatgt ctaagttata aaaaattacc acatattttt tttgtcacac ttgtttgaag  7140
tgcagtttat ctatctttat acatatattt aaactttact ctacgaataa tataatctat  7200
agtactacaa taatatcagt gttttagaga atcatataaa tgaacagtta gacatggtct  7260
aaaggacaat tgagtatttt gacaacagga ctctacagtt ttatcttttt agtgtgcatg  7320
tgttctcctt tttttttgca aatagcttca cctatataat acttcatcca ttttattagt  7380
acatccattt agggtttagg gttaatggtt tttatagact aattttttta gtacatctat  7440
tttattctat tttagcctct aaattaagaa aactaaaact ctattttagt tttttttattt  7500
aataatttag atataaaata gaataaaata aagtgactaa aaattaaaca aatacccttt  7560
aagaaattaa aaaaactaag gaaacatttt tcttgtttcg agtagataat gccagcctgt  7620
taaacgccgt cgacgagtct aacggacacc aaccagcgaa ccagcagcgt cgcgtcgggc  7680
caagcgaagc agacggcacg gcatctctgt cgctgcctct ggacccctct cgagagttcc  7740
gctccaccgt tggacttgct ccgctgtcgg catccagaaa ttgcgtggcg gagcggcaga  7800
cgtgagccgg cacggcaggc ggcctcctcc tcctctcacg gcaccggcag ctacgggga  7860
ttcctttccc accgctcctt cgctttccct tcctcgcccg ccgtaataaa tagacacccc  7920
ctccacaccc tctttcccca acctcgtgtt gttcggagcg cacacacaca caaccagatc  7980
tcccccaaat ccacccgtcg gcacctccgc ttcaaggtac gccgctcgtc ctcccccccc  8040
cccctctcta ccttctctag atcggcgttc cggtccatgg ttagggcccg gtagttctac  8100
ttctgttcat gtttgtgtta gatccgtgtt tgtgttagat ccgtgctgct agcgttcgta  8160
cacggatgcg acctgtacgt cagacacgtt ctgattgcta acttgccagt gtttctcttt  8220
ggggaatcct gggatggctc tagccgttcc gcagacggga tcgatttcat gatttttttt  8280
gtttcgttgc atagggtttg gtttgccctt ttcctttatt tcaatatatg ccgtgcactt  8340
gtttgtcggg tcatcttttc atgctttttt ttgtcttggt tgtgatgatg tggtctggtt  8400
gggcggtcgt tctagatcgg agtagaattc tgtttcaaac tacctggtgg atttattaat  8460
tttggatctg tatgtgtgtg ccatacatat tcatagttac gaattgaaga tgatggatgg  8520
aaatatcgat ctaggatagg tatacatgtt gatgcgggtt ttactgatgc atatacagag  8580
atgctttttg ttcgcttggt tgtgatgatg tggtgtggtt gggcggtcgt tcattcgttc  8640
tagatcggag tagaatactg tttcaaacta cctggtgtat ttattaattt tggaactgta  8700
tgtgtgtgtc atacatcttc atagttacga gtttaagatg gatggaaata tcgatctagg  8760
ataggtatac atgttgatgt gggttttact gatgcatata catgatggca tatgcagcat  8820
ctattcatat gctctaacct tgagtaccta tctattataa taaacaagta tgttttataa  8880
ttattttgat cttgatatac ttggatgatg gcatatgcag cagctatatg tggatttttt  8940
tagccctgcc ttcatacgct atttatttgc ttggtactgt ttcttttgtc gatgctcacc  9000
ctgttgtttg gtgttacttc tgcagggatc cggcagcagc catgcagaag ctgatcaaca  9060
gcgtgcagaa ctacgcctgg ggcagcaaga ccgccctgac cgagctgtac ggcatggaga  9120
accccagcag ccagcccatg gccgagctgt ggatgggcgc ccacccccaag agcagcagcc  9180
gcgtgcagaa cgccgccggc gacatcgtga gcctgcgcga cgtgatcgag agcgacaaga  9240
gcaccctgct gggcgaggcc gtggccaagc gcttcggcga gctgcccttc ctgttcaagg  9300
tgctgtgcgc cgcccagccc ctgagcatcc aggtgcaccc caacaagcac aacagcgaga  9360
tcggcttcgc caaggagaac gccgccggca tccccatgga cgccgccgag cgcaactaca  9420
aggaccccaa ccacaagccc gagctggtgt tcgccctgac cccttcctg gccatgaacg  9480
ccttccgcga gttcagcgag atcgtgagcc tgctgcagcc cgtggccggc gcccaccccg  9540
ccatcgccca cttcctgcag cagcccgacg ccgagcgcct gagcgagctg ttcgccagcc  9600
tgctgaacat gcagggcgag gagaagagcc gcgccctggc catcctgaag agcgccctgg  9660
acagccagca gggcgagccc tggcagacca tccgcctgat cagcgagttc taccccgagg  9720
acagcggcct gttcagcccc ctgctgctga acgtggtgaa gctgaacccc ggcgaggcca  9780
tgttcctgtt cgccgagacc ccccacgcct acctgcaggg cgtggccctg gaggtgatgg  9840
ccaacagcga caacgtgctg cgcgccggcc tgacccccaa gtacatcgac atccccgagc  9900
tggtggccaa cgtgaagttc gaggccaagc ccgccaacca gctgctgacc cagcccgtga  9960
agcagggcgc cgagctggac ttccccatcc ccgtggacga cttcgccttc agcctgcacg  10020
acctgagcga caaggagacc accatcagcc agcagagcgc cgccatcctg ttctgcgtgg  10080
agggcgacgc caccctgtgg aagggcagcc agcagctgca gctgaagccc ggcgagagcg  10140
ccttcatcgc cgccaacgag agccccgtga ccgtgaaggg ccacggccgc ctggcccgcg  10200
tgtacaacaa gctgtgatag gagctcgatc cgtcgacctg cagatcgttc aaacatttgg  10260
caataaagtt tcttaagatt gaatcctgtt gccggtcttg cgatgattat catataattt  10320
ctgttgaatt acgttaagca tgtaataatt aacatgtaat gcatgacgtt atttatgaga  10380
tgggttttta tgattagagt cccgcaatta tacatttaat acgcgataga aaacaaaata  10440
```

```
tagcgcgcaa actaggataa attatcgcgc gcggtgtcat ctatgttact agatcggcgc  10500
gccgcaattg aagtttgggc ggccagcatg gccgtatccg caatgtgtta ttaagttgtc  10560
taagcgtcaa tttgtttaca ccacaatata tcctgccacc agccagccaa cagctccccg  10620
accggcagct cggcacaaaa tcaccactcg atacaggcag cccatcag               10668

SEQ ID NO: 100          moltype = DNA  length = 10673
FEATURE                 Location/Qualifiers
misc_feature            1..10673
                        note = Expression cassette of construct 23123
regulatory              165..256
                        note = enhancer - eNOS
                        regulatory_class = enhancer
regulatory              301..2097
                        note = promoter - Ubi
                        regulatory_class = promoter
gene                    2114..6283
                        note = Cas9
misc_feature            6218..6274
                        note = NLS-TAG
regulatory              6289..6541
                        note = terminator - tNOS
                        regulatory_class = terminator
regulatory              6548..6922
                        note = promoter - pU3
                        regulatory_class = promoter
misc_feature            6924..6943
misc_feature            6924..7028
                        note = sgRNA
regulatory              7039..9030
                        note = promoter - Ubi
                        regulatory_class = promoter
gene                    9047..10225
                        note = PMI
regulatory              10248..10500
                        note = terminator - tNOS
                        regulatory_class = terminator
source                  1..10673
                        mol_type = other DNA
                        organism = synthetic construct
SEQUENCE: 100
cctgtggttg gcatgcacat acaaatggac gaacggataa accttttcac gcccttttaa  60
atatccgatt attctaataa acgctctttt ctcttaggtt tacccgccaa tatatcctgt  120
caaacactga tagtttaaac tgaaggcggg aaacgacaat ctgatcatga gcggagaatt  180
aagggagtca cgttatgacc cccgccgatg acgcgggaca agccgtttta cgtttggaac  240
tgacagaacc gcaacgctgc aggaattggc cgcagcggcc atttaaacaa agcttggtac  300
cattatgtgg tctaggtagg ttctatatat aagaaaactt gaaatgttct aaaaaaaaat  360
tcaagcccat gcatgattga agcaaacggt atagcaacgg tgttaacctg atctagtgat  420
ctcttgcaat ccttaacggc cacctaccgc aggtagcaaa cggcgtcccc ctcctcgata  480
tctccgcggc gacctctggc tttttccgcg gaattgcgcg gtggggacgg attccacgag  540
accgcgacgc aaccgcctct cgccgctggg ccccacaccg ctcggtgccg tagcctcacg  600
ggactctttc tccctcctcc cccgttataa attggcttca tcccctcctt gcctcatcca  660
tccaaatccc agtccccaat cccatccctt cgtaggagaa attcatcgaa gctaagcgaa  720
tcctcgcgat cctctcaagg tactgcgagt tttcgatccc cctctcgacc cctcgtatgt  780
ttgtgtttgt cgtagcgttt gattaggtat gctttccctg tttgtgttcg tcgtagcgtt  840
tgattaggta tgctttccct gttcgtgttc atcgtagtgt ttgattaggt cgtgtgaggc  900
gatggcctgc tcgcgtcctt cgatctgtag tcgatttgcg ggtcgtggtg tagatctgcg  960
ggctgtgatg aagttatttg gtgtgatctg ctcgcctgat tctgcgggtt ggctcgagta  1020
gatatgatgg ttggaccggt tggttcgttt accgcgctag ggttgggctg ggatgatgtt  1080
gcatgcgccg ttgcgcgtga tcccgcagca ggacttgcgt ttgattgcca gatctcgtta  1140
cgattatgtg atttggtttg gactttttag atctgtagct tctgcttatg tgccagatgc  1200
gcctactgct catatgcctg atgataatca taaatggctg tggaactaac tagttgattg  1260
cggagtcatg tatcagctac aggtgtaggg actagctaca ggtgtaggga cttgcgtcta  1320
attgtttggt cctttactca tgttgcaatt atgcaattta gtttagattg tttgttccac  1380
tcatctaggc tgtaaaaggg acactgctta gattgctgtt taatcttttt agtagattat  1440
attatattgg taacttatta cccctattac atgccatacg tgacttctgc tcatgcctga  1500
tgataatcat agatcactgt ggaattaatt agttgattgt tgaatcatgt ttcatgtaca  1560
taccacggca caattgctta gttccttaac aaatgcaaat tttactgatc catgtatgat  1620
ttgcgtggtt ctctaatgtg aaatactata gctacttgtt agtaagaatc aggttcgtat  1680
gcttaatgct gtatgtgcct tctgctcatg cctgatgata atcatatatc actggaatta  1740
attagttgat cgtttaatca tatatcaagt acataccatg ccacaatttt tagtcactta  1800
acccatgcag attgaactgg tccctgcatg ttttgctaaa ttgttctatt ctgattagac  1860
catatatcat gtattttttt ttggtaatgg ttctcttatt ttaaatgcta tatagttctg  1920
gtacttgtta gaaagatctg cttcatagtt tagttgccta tccctcgaat taggatgctg  1980
agcagctgat cctatagctt tgtttcatgt atcaattctt ttgtgttcaa cagtcagttt  2040
ttgttagatt cattgtaact tatggtcgct tactcttctg gtcctcaatg cttgcaggat  2100
cgcggccgct catatggaca agaagtacag catcggcctg gacatcggca ccaacagcgt  2160
gggctgggcc gtgatcaccg acgagtacaa ggtgccgagc aagaagttca aggtgctggg  2220
caacaccgac aggcacagca tcaagaagaa cctgatcggc gccctgctgt tcgacagcgg  2280
cgagaccgcc gaggccacca ggctgaagag gaccgccagg aggaggtaca ccaggaggaa  2340
```

-continued

```
gaacaggatc tgctacctgc aggagatctt cagcaacgag atggccaagg tggacgacag  2400
cttcttccac aggctggagg agagcttcct ggtggaggag gacaagaagc acgagaggca  2460
cccgatcttc ggcaacatcg tggacgaggt ggcctaccac gagaagtacc cgaccatcta  2520
ccacctgagg aagaagctgg tggacagcac cgacaaggcc gacctgaggc tgatctacct  2580
ggccctggcc cacatgatca agttcagggg ccacttcctg atcgagggcg acctgaaccc  2640
ggacaacagc gacgtggaca agctgttcat ccagctggtg cagacctaca accagctgtt  2700
cgaggagaac ccgatcaacg ccagcggcgt ggacgccaag gccatcctga gcgccaggct  2760
gagcaagagc aggaggctgg agaacctgat cgcccagctg ccgggcgaga agaagaacgg  2820
cctgttcggc aacctgatcg ccctgagcct gggcctgacc ccgaacttca agagcaactt  2880
cgacctggcc gaggacgcca agctgcagct gagcaaggac acctacgacg acgacctgga  2940
caacctgctg gcccagatcg gcgaccagta cgccgacctg ttcctggccg ccaagaacct  3000
gagcgacgcc atcctgctga gcgacatcct gagggtgaac accgagatca ccaaggcccc  3060
gctgagcgcc agcatgatca agaggtacga cgagcaccac caggacctga ccctgctgaa  3120
ggccctggtg aggcagcagc tgccggagaa gtacaaggag atcttcttcg accagagcaa  3180
gaacggctac gccggctaca tcgacggcgg cgccagccag gaggagttct acaagttcat  3240
caagccgatc ctggagaaga tggacggcac cgaggagctg ctggtgaagc tgaacaggga  3300
ggacctgctg aggaagcaga ggaccttcga caacggcagc atcccgcacc agatccacct  3360
gggcgagctg cacgccatcc tgaggaggca ggaggacttc tacccgttcc tgaaggacaa  3420
cagggagaag atcgagaaga tcctgacctt ccgcatcccg tactacgtgg gcccgctggc  3480
caggggcaac agcaggttcg cctggatgac caggaagagc gaggagacca tcaccccgtg  3540
gaacttcgag gaggtggtgg acaagggcgc cagcgcccag agcttcatcg agaggatgac  3600
caacttcgac aagaacctgc cgaacgagaa ggtgctgccg aagcacagcc tgctgtacga  3660
gtacttcacc gtgtacaacg agctgaccaa ggtgaagtac gtgaccgagg gcatgaggaa  3720
gccggccttc ctgagcggcg agcagaagaa ggccatcgtg gacctgctgt tcaagaccaa  3780
caggaaggtg accgtgaagc agctgaagga ggactacttc aagaagatcg agtgcttcga  3840
cagcgtggag atcagcggcg tggaggacag gttcaacgcc agcctgggca cctaccacga  3900
cctgctgaag atcatcaagg acaaggactt cctggacaac gaggagaacg aggacatcct  3960
ggaggacatc gtgctgaccc tgaccctgtt cgaggacagg gagatgatcg aggagaggct  4020
gaagacctac gcccacctgt tcgacgacaa ggtgatgaag cagctgaaga ggaggaggta  4080
caccggctgg ggcaggctga gcaggaagct gatcaacggc atcagggaca agcagagcgg  4140
caagaccatc ctggacttcc tgaagagcga cggcttcgcc aacaggaact tcatgcagct  4200
gatccacgac gacagcctga ccttcaagga ggacatccag aaggcccagg tgagcggcca  4260
gggcgacagc ctgcacgagc acatcgccaa cctggccggc agcccggcca tcaagaaggg  4320
catcctgcag accgtgaagg tggtggacga gctggtgaag gtgatgggca ggcacaagcc  4380
ggagaacatc gtgatcgaga tggccaggga gaaccagacc acccagaagg gccagaagaa  4440
cagcagggag aggatgaaga ggatcgagga gggcatcaag gagctgggca gccagatcct  4500
gaaggagcac ccggtggaga acacccagct gcagaacgag aagctgtacc tgtactacct  4560
gcagaacggc agggacatgt acgtggacca ggagctggac atcaacaggc tgagcgacta  4620
cgacgtggac cacatcgtgc cgcagagctt cctgaaggac gacagcatcg acaacaaggt  4680
gctgaccagg agcgacaaga acaggggcaa gagcgacaac gtgccgagcg aggaggtggt  4740
gaagaagatg aaaaactact ggaggcagct gctgaacgcc aagctgatca cccagaggaa  4800
gttcgacaac ctgaccaagg ccgagagggg cggcctgagc gagctggaca aggccggctt  4860
cattaaaagg cagctggtgg agaccaggca gatcaccaag cacgtggccc agatcctgga  4920
cagcaggatg aacaccaagt acgacgagaa cgacaagctg atcagggagg tgaaggtgat  4980
caccctgaag agcaagctgg tgagcgactt caggaaggac ttccagttct acaaggtgag  5040
ggagatcaat aattaccacc acgcccacga cgcctacctg aacgccgtgg tgggcaccgc  5100
cctgattaaa aagtacccga agctggagag cgagttcgtg tacggcgact acaaggtgta  5160
cgacgtgagg aagatgatcg ccaagagcga gcaggagatc ggcaaggcca ccgccaagta  5220
cttcttctac agcaacatca tgaacttctt caagaccgag atcaccctgg ccaacggcga  5280
gatcaggaag aggccgctga tcgagaccaa cggcgagacc ggcgagatcg tgtgggacaa  5340
gggcagggac ttcgccaccg tgaggaaggt gctgtccatg ccgcaggtga acatcgtgaa  5400
gaagaccgag gtgcagaccg gcggcttcag caaggagagc atcctgccga agaggaacag  5460
cgacaagctg atcgccagga agaaggactg ggacccgaag aagtacggcg gcttcgacag  5520
cccgaccgtg gcctacagcg tgctggtggt ggccaaggtg gagaagggca agagcaagaa  5580
gctgaagagc gtgaaggagc tggtgggcat caccatcatg gagaggagca gcttcgagaa  5640
gaacccagtg gacttcctgg aggccaaggg ctacaaggag gtgaagaagg acctgatcat  5700
taaactgccg aagtacagcc tgttcgagct ggagaacggc aggaagagga tgctggccag  5760
cgccggcgag ctgcagaagg gcaacgagct ggccctgccg agcaagtacg tgaacttcct  5820
gtacctggcc agccactacg agaagctgaa gggcagcccg gaggacaacg agcagaagca  5880
gctgttcgtg gagcagcaca agcactacct ggacgagatc atcgagcaga tcagcgagtt  5940
cagcaagagg gtgatcctgg ccgacgccaa cctggacaag gtgctgagcg cctacaacaa  6000
gcacagggac aagccgatca gggagcaggc cgagaacatc atccacctgt tcaccctgac  6060
caacctgggc gcccccggccg ccttcaagta cttcgacacc accatcgaca ggaagaggta  6120
caccagcacc aaggaggtgc tggacgccac cctgatccac cagagcatca ccggcctgta  6180
cgagaccagg atcgacctga gccagctggg cggcgacagc agcccgccga agaagaagag  6240
gaaggtgagc tggaaggacg ccagcggctg gagcaggatg tgaagcttga tcgttcaaac  6300
atttggcaat aaagtttctt aagattgaat cctgttgccg gtcttgcgat gattatcata  6360
taatttctgt tgaattacgt taagcatgta ataattaaca tgtaatgcat gacgttattt  6420
atgagatggg tttttatgat tagagtcccg caattataca tttaatacgc gatagaaaac  6480
aaaatatagc gcgcaaacta ggataaatta tcgcgcgcgg tgtcatctat gttactagat  6540
cttcgaaggg atctttaaac atacgaacag atcacttaaa gttcttctga agcaacttaa  6600
agttatcagg catgcatgga tcttggagga atcagatgtg cagtcaggga ccatagcaca  6660
ggacaggcgt cttctactgg tgctaccagc aaatgctgga agccgggaac actgggtacg  6720
ttggaaacca cgtgatgtgg agtaagataa actgtaggag aaaagcattt cgtagtgggc  6780
catgaagcct ttcaggacat gtattgcagt atgggccggc ccattacgca attggacgac  6840
aacaaagact agtattagta ccacctcggc tatccacata gatcaaagct ggtttaaaag  6900
agttgtgcag atgatccgtg gcagggtcaa cgtggagaca ggggttttag agctagaaat  6960
agcaagttaa aataaggcta gtccgttatc aacttgaaaa agtggcaccg agtcggtgct  7020
tttttttcg gaccgcgcct gcagtgcagc gtgacccggt cgtgcccctc tctagagata  7080
```

-continued

```
atgagcattg catgtctaag ttataaaaaa ttaccacata tttttttgt cacacttgtt  7140
tgaagtgcag tttatctatc tttatacata tatttaaact ttactctacg aataatataa  7200
tctatagtac tacaataata tcagtgtttt agagaatcat ataaatgaac agttagacat  7260
ggtctaaagg acaattgagt attttgacaa caggactcta cagttttatc tttttagtgt  7320
gcatgtgttc tcctttttt ttgcaaatag cttcacctat ataatacttc atccatttta  7380
ttagtacatc catttagggt ttagggttaa tggtttttat agactaattt ttttagtaca  7440
tctattttat tctattttag cctctaaatt aagaaaacta aaactctatt ttagtttttt  7500
tatttaataa tttagatata aaatagaata aaataaagtg actaaaaatt aaacaaatac  7560
cctttaagaa attaaaaaaa ctaaggaaac atttttcttg tttcgagtag ataatgccag  7620
cctgttaaac gccgtcgacg agtctaacgg acaccaacca gcgaaccagc agcgtcgcgt  7680
cgggccaagc gaagcagacg gcacggcatc tctgtcgctg cctctggacc cctctcgaga  7740
gttccgctcc accgttggac ttgctccgct gtcggcatcc agaaattgcg tggcggagcg  7800
gcagacgtga gccggcacgg caggcggcct cctcctcctc tcacggcacc ggcagctacg  7860
ggggattcct ttcccaccgc tccttcgctt tcccttcctc gcccgccgta ataaatagac  7920
acccccctcca caccctcttt ccccaacctc gtgttgttcg gagcgcacac acacacaacc  7980
agatctcccc caaatccacc cgtcggcacc tccgcttcaa ggtacgccgc tcgtcctccc  8040
cccccccct ctctaccttc tctagatcgg cgttccggtc catggttagg gcccggtagt  8100
tctacttctg ttcatgtttg tgttagatcc gtgtttgtgt tagatccgtg ctgctagcgt  8160
tcgtacacgg atgcgacctg tacgtcagac acgttctgat tgctaacttg ccagtgtttc  8220
tctttgggga atcctgggat ggctctagcc gttccgcaga cgggatcgat ttcatgattt  8280
tttttgtttc gttgcatagg gtttggtttg cccttttcct ttatttcaat atatgccgtg  8340
cacttgtttg tcgggtcatc ttttcatgct ttttttgtc ttggttgtga tgatgtggtc  8400
tggttgggcg gtcgttctag atcggagtag aattctgttt caaactacct ggtggattta  8460
ttaattttgg atctgtatgt gtgtgccata catattcata gttacgaatt gaagatgatg  8520
gatggaaata tcgatctagg ataggtatac atgttgatgc gggttttact gatgcatata  8580
cagagatgct ttttgttcgc ttggttgtga tgatgtggtg tggttgggcg gtcgttcatt  8640
cgttctagat cggagtagaa tactgtttca aactacctgg tgtatttatt aattttggaa  8700
ctgtatgtgt gtgtcataca tcttcatagt tacgagttta agatggatgg aaatatcgat  8760
ctaggatagg tatacatgtt gatgtgggtt ttactgatgc atatacatga tggcatatgc  8820
agcatctatt catatgctct aaccttgagt acctatctat tataataaac aagtatgttt  8880
tataattatt ttgatcttga tatacttgga tgatggcata tgcagcagct atatgtggat  8940
tttttagcc ctgccttcat acgctattta tttgcttggt actgtttctt ttgtcgatgc  9000
tcaccctgtt gtttggtgtt acttctgcag ggatccggca gcagccatgc agaagctgat  9060
caacagcgtg cagaactacg cctggggcag caagaccgcc ctgaccgagc tgtacggcat  9120
ggagaacccc agcagccagc ccatggccga gctgtggatg ggcgcccacc ccaagagcag  9180
cagccgcgtg cagaacgccg ccggcgacat cgtgagcctg cgcgacgtga tcgagagcga  9240
caagagcacc ctgctgggcg aggccgtggc caagcgcttc ggcgagctgc ccttcctgtt  9300
caaggtgctg tgcgccgccc agcccctgag catccaggtg caccccaaca agcacaacag  9360
cgagatcggc ttcgccaagg agaacgccgc cggcatcccc atggacgccg ccgagcgcaa  9420
ctacaaggac cccaaccaca agcccgagct ggtgttcgcc ctgacccccct tcctggccat  9480
gaacgccttc cgcgagttca gcgagatcgt gagcctgctg cagcccgtgg ccggcgccca  9540
ccccgccatc gcccacttcc tgcagcagcc cgacgccgag cgcctgagcg agctgttcgc  9600
cagcctgctg aacatgcagg gcgaggagaa gagccgcgcc ctggccatcc tgaagagcgc  9660
cctggacagc cagcagggcg agccctggca gaccatccgc ctgatcagcg agttctaccc  9720
cgaggacagc ggcctgttca gcccccctgct gctgaacgtg gtgaagctga accccggcga  9780
ggccatgttc ctgttcgccg agacccccca cgcctacctg cagggcgtgg ccctggaggt  9840
gatggccaac agcgacaacg tgctgcgcgc cggcctgacc cccaagtaca tcgacatccc  9900
cgagctggtg gccaacgtga agttcgaggc caagcccgcc aaccagctgc tgacccagcc  9960
cgtgaagcag ggcgccgagc tggacttccc catccccgtg gacgacttcg ccttcagcct  10020
gcacgacctg agcgacaagg agaccaccat cagccagcag agcgccgcca tcctgttctg  10080
cgtggagggc gacgccaccc tgtggaaggg cagccagcag ctgcagctga agcccggcga  10140
gagcgccttc atcgccgcca acgagagccc cgtgaccgtg aagggccacg gccgcctggc  10200
ccgcgtgtac aacaagctgt gataggagct cgatccgtcg acctgcagat cgttcaaaca  10260
tttggcaata aagtttctta agattgaatc ctgttgccgg tcttgcgatg attatcatat  10320
aatttctgtt gaattacgtt aagcatgtaa taattaacat gtaatgcatg acgttattta  10380
tgagatgggt ttttatgatt agagtcccgc aattatacat ttaatacgcg atagaaaaca  10440
aaatatagcg cgcaaactag gataaattat cgcgcgcggt gtcatctatg ttactagatc  10500
ggcgcgccgc aattgaagtt tgggcggcca gcatggccgt atccgcaatg tgttattaag  10560
ttgtctaagc gtcaatttgt ttacaccaca atatatcctg ccaccagcca gccaacagct  10620
ccccgaccgg cagctcggca caaaatcacc actcgataca ggcagcccat cag         10673
```

```
SEQ ID NO: 101          moltype = DNA  length = 10693
FEATURE                 Location/Qualifiers
misc_feature            1..10693
                        note = Expression cassette of construct 23501, gRNA target
                         1 dual guides
regulatory              214..734
                        note = promoter - 35S
                        regulatory_class = promoter
gene                    748..4917
                        note = Cas9
misc_feature            4852..4908
                        note = NLS-TAG
regulatory              4923..5175
                        note = terminator - tNOS
                        regulatory_class = terminator
regulatory              5196..5570
                        note = promoter - pU3
                        regulatory_class = promoter
```

```
misc_feature          5572..5591
misc_feature          5592..5636
                      note = crRNA
regulatory            5643..6158
                      note = promoter - pU6
                      regulatory_class = promoter
misc_feature          6159..6246
                      note = tracrRNA
regulatory            6253..8245
                      note = promoter - Ubi
                      regulatory_class = promoter
gene                  8257..9435
                      note = PMI
regulatory            9440..10474
                      note = terminator - Ubi
                      regulatory_class = terminator
source                1..10693
                      mol_type = other DNA
                      organism = synthetic construct
SEQUENCE: 101
cctgtggttg gcatgcacat acaaatggac gaacggataa accttttcac gccctttttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga ccgagtcaaa gattcaaata gaggacctaa  240
cagaactcgc cgtaaagact ggcgaacagt tcatacagag tctcttacga ctcaatgaca  300
agaagaaaat cttcgtcaac ttggtggagc acgacacgct agtctactcc aaaaatatca  360
aagatacagt ctcagaagac caaagggcaa ttgagacttt tcaacaaagg gtaatatccg  420
gaaacctcct cggattccat tgcccagcta tctgtcactt aattgtgaag atagtggaaa  480
aggaaggtgg ctcctacaaa tgccatcatt gcgataaagg aaaggccatc gttgaagatg  540
cctctgccga cagtggtccc aaagatggac ccccacccac gaggagcatc gtggtaaaag  600
aagacgttcc aaccacgtct tcaaagcaag tggattgatg tgatatctcc actgacgtaa  660
gggatgacgc acaatcccac tatccttcgc aagacccttc ctctatataa ggaagttcat  720
ttcatttgga gaggataatt atccaccatg gacaagaagt acagcatcgg cctggacatc  780
ggcaccaaca gcgtgggctg ggccgtgatc accgacgagt acaaggtgcc gagcaagaag  840
ttcaaggtgc tgggcaacac cgacaggcac agcatcaaga agaacctgat cggcgccctg  900
ctgttcgaca gcggcgagac cgccgaggcc accaggctga agaggaccgc caggaggagg  960
tacaccagga ggaagaacag gatctgctac ctgcaggaga tcttcagcaa cgagatggcc  1020
aaggtggacg acagcttctt ccacaggctg gaggagagct tcctggtgga ggaggacaag  1080
aagcacgaga ggcacccgat cttcggcaac atcgtggacg aggtggccta ccacgagaag  1140
tacccgacca tctaccacct gaggaagaag ctggtggaca gcaccgacaa ggccgacctg  1200
aggctgatct acctggccct ggcccacatg atcaagttca ggggccactt cctgatcgag  1260
ggcgacctga acccggacaa cagcgacgtg gacaagctgt tcatccagct ggtgcagacc  1320
tacaaccagc tgttcgagga gaacccgatc aacgccagcg gcgtggacgc caaggccatc  1380
ctgagcgcca ggctgagcaa gagcaggagg ctggagaacc tgatcgccca gctgccgggc  1440
gagaagaaga acggcctgtt cggcaacctg atcgccctga gcctgggcct gaccccgaac  1500
ttcaagagca acttcgacct ggccgaggac gccaagctgc agctgagcaa ggacacctac  1560
gacgacgacc tggacaacct gctggcccag atcggcgacc agtacgccga cctgttcctg  1620
gccgccaaga acctgagcga cgccatcctg ctgagcgaca tcctgagggt gaacaccgag  1680
atcaccaagg ccccgctgag cgccagcatg atcaagaggt acgacgagca ccaccaggac  1740
ctgaccctgc tgaaggccct ggtgaggcag cagctgccgg agaagtacaa ggagatcttc  1800
ttcgaccaga gcaagaacgg ctacgccggc tacatcgacg gcggcgccag ccaggaggag  1860
ttctacaagt tcatcaagcc gatcctggag aagatggacg gcaccgagga gctgctggtg  1920
aagctgaaca gggaggacct gctgaggaag cagaggacct tcgacaacgg cagcatcccg  1980
caccagatcc acctgggcga gctgcacgcc atcctgagga ggcaggagga cttctacccg  2040
ttcctgaagg acaacaggga gaagatcgag aagatcctga ccttccgcat cccgtactac  2100
gtgggcccgc tggccagggg caacagcagg ttcgcctgga tgaccaggaa gagcgaggag  2160
accatcaccc cgtggaactt cgaggaggtg gtggacaagg gcgccagcgc ccagagcttc  2220
atcgagagga tgaccaactt cgacaagaac ctgccgaacg agaaggtgct gccgaagcac  2280
agcctgctgt acgagtactt caccgtgtac aacgagctga ccaaggtgaa gtacgtgacc  2340
gagggcatga ggaagccggc cttcctgagc ggcgagcaga agaaggccat cgtggacctg  2400
ctgttcaaga ccaacaggaa ggtgaccgtg aagcagctga aggaggacta cttcaagaag  2460
atcgagtgct tcgacagcgt ggagatcagc ggcgtggagg acaggttcaa cgccagcctg  2520
ggcacctacc acgacctgct gaagatcatc aaggacaagg acttcctgga caacgaggag  2580
aacgaggaca tcctggagga catcgtgctg accctgaccc tgttcgagga cagggagatg  2640
atcgaggaga ggctgaagac ctacgcccac ctgttcgacg acaaggtgat gaagcagctg  2700
aagaggagga ggtacaccgg ctggggcagg ctgagcagga agctgatcaa cggcatcagg  2760
gacaagcaga gcggcaagac catcctggac ttcctgaaga gcgacggctt cgccaacagg  2820
aacttcatgc agctgatcca cgacgacagc ctgaccttca aggaggacat ccagaaggcc  2880
caggtgagcg gccagggcga cagcctgcac gagcacatcg ccaacctggc cggcagcccg  2940
gccatcaaga agggcatcct gcagaccgtg aaggtggtgg acgagctggt gaaggtgatg  3000
ggcaggcaca agccggagaa catcgtgatc gagatggcca gggagaacca gaccacccag  3060
aagggccaga agaacagcag ggagaggatg aagaggatcg aggagggcat caaggagctg  3120
ggcagccaga tcctgaagga gcacccggtg gagaacaccc agctgcagaa cgagaagctg  3180
tacctgtact acctgcagaa cggcagggac atgtacgtgg accaggagct ggacatcaac  3240
aggctgagcg actacgacgt ggaccacatc gtgccgcaga gcttcctgaa ggacgacagc  3300
atcgacaaca aggtgctgac caggagcgac aagaacaggg gcaagagcga caacgtgccg  3360
agcgaggagg tggtgaagaa gatgaaaaac tactggaggc agctgctgaa cgccaagctg  3420
atcacccaga ggaagttcga caacctgacc aaggccgaga ggggcggcct gagcgagctg  3480
gacaaggccg gcttcattaa aaggcagctg gtggagacca ggcagatcac caagcacgtg  3540
```

-continued

```
gcccagatcc tggacagcag gatgaacacc aagtacgacg agaacgacaa gctgatcagg  3600
gaggtgaagg tgatcaccct gaagagcaag ctggtgagcg acttcaggaa ggacttccag  3660
ttctacaagg tgagggagat caataattac caccacgccc acgacgccta cctgaacgcc  3720
gtggtgggca ccgccctgat taaaaagtac ccgaagctgg agagcgagtt cgtgtacggc  3780
gactacaagg tgtacgacgt gaggaagatg atcgccaaga gcgagcagga gatcggcaag  3840
gccaccgcca agtacttctt ctacagcaac atcatgaact tcttcaagac cgagatcacc  3900
ctggccaacg gcgagatcag gaagaggccg ctgatcgaga ccaacggcga gaccggcgag  3960
atcgtgtggg acaagggcag ggacttcgcc accgtgagga aggtgctgtc catgccgcag  4020
gtgaacatcg tgaagaagac cgaggtgcag accggcggct tcagcaagga gagcatcctg  4080
ccgaagagga acagcgacaa gctgatcgcc aggaagaagg actgggatcc gaagaagtac  4140
ggcggcttcg acagcccgac cgtggcctac agcgtgctgg tggtggccaa ggtggagaag  4200
ggcaagagca agaagctgaa gagcgtgaag gagctggtgg gcatcaccat catggagagg  4260
agcagcttcg agaagaaccc agtggacttc ctggaggcca agggctacaa ggaggtgaag  4320
aaggacctga tcattaaact gccgaagtac agcctgttcg agctggagaa cggcaggaag  4380
aggatgctgg ccagcgccgg cgagctgcag aagggcaacg agctggccct gccgagcaag  4440
tacgtgaact tcctgtacct ggccagccac tacgagaagc tgaagggcag cccggaggac  4500
aacgagcaga agcagctgtt cgtggagcag cacaagcact acctggacga gatcatcgag  4560
cagatcagcg agttcagcaa gagggtgatc ctggccgacg ccaacctgga caaggtgctg  4620
agcgcctaca acaagcacag ggacaagccg atcagggagc aggccgagaa catcatccac  4680
ctgttcaccc tgaccaacct gggcgccccg gccgccttca agtacttcga caccaccatc  4740
gacaggaaga ggtacaccag caccaaggag gtgctggacg ccaccctgat ccaccagagc  4800
atcaccggcc tgtacgagac caggatcgac ctgagccagc tgggcggcga cagcagcccg  4860
ccgaagaaga agaggaaggt gagctggaag gacgccagcg gctggagcag gatgtgaagc  4920
ttgatcgttc aaacatttgg caataaagtt tcttaagatt gaatcctgtt gccggtcttg  4980
cgatgattat catataattt ctgttgaatt acgttaagca tgtaataatt aacatgtaat  5040
gcatgacgtt atttatgaga tgggttttta tgattagagt cccgcaatta tacatttaat  5100
acgcgataga aaacaaaata tagcgcgcaa actaggataa attatcgcgc gcggtgtcat  5160
ctatgttact agatcgggac cggaattcgg gacccgggat ctttaaacat acgaacagat  5220
cacttaaagt tcttctgaag caacttaaag ttatcaggca tgcatggatc ttggaggaat  5280
cagatgtgca gtcagggacc atagcacagg acaggcgtct tctactggtg ctaccagcaa  5340
atgctggaag ccgggaacac tgggtacgtt ggaaaccacg tgatgtggag taagataaac  5400
tgtaggagaa aagcatttcg tagtgggcca tgaagccttt caggacatgt attgcagtat  5460
gggccggccc attacgcaat tggacgacaa caaagactag tattagtacc acctcggcta  5520
tccacataga tcaaagctgg tttaaaagag ttgtgcagat gatccgtggc atgcagtcga  5580
agtaatcggc ggttttagag ctatgctgtt ttgaatggtc ccaaaacttt ttttttacta  5640
gttttgtgaa agttgaatta cggcatagcc gaaggaataa cagaatcgtt tcacactttc  5700
gtaacaaagg tcttcttatc atgtttcaga cgatggaggc aaggctgatc aaagtgatca  5760
agcacataaa cgcatttttt taccatgttt cactccataa gcgtctgaga ttatcacaag  5820
tcacgtctag tagtttgatg gtacactagt gacaatcagt tcgtgcagac agagctcata  5880
cttgactact tgagcgatta caggcgaaag tgtgaaacgc atgtgatgtg ggctgggagg  5940
aggagaatat atactaatgg gccgtatcct gatttgggct gcgtcggaag gtgcagccca  6000
cgcgcgccgt accgcgcggg tggcgctgct acccacttta gtccgttgga tggggatccg  6060
atggtttgcg cggtggcgtt gcgggggatg tttagtacca catcggaaac cgaaagacga  6120
tggaaccagc ttataaaccc gcgcgctgta gtcagcttgg aaccattcaa aacagcatag  6180
caagttaaaa taaggctagt ccgttatcaa cttgaaaaag tggcaccgag tcggtgcttt  6240
tttttcccta ggctgcagtg cagcgtgacc cggtcgtgcc cctctctaga gataatgagc  6300
attgcatgtc taagttataa aaaattacca catatttttt ttgtcacact tgtttgaagt  6360
gcagtttatc tatctttata catatattta aactttactc tacgaataat ataatctata  6420
gtactacaat aatatcagtg ttttagagaa tcatataaat gaacagttag acatggtcta  6480
aaggacaatt gagtattttg acaacaggac tctacagttt tatcttttta gtgtgcatgt  6540
gttctccttt ttttttgcaa atagcttcac ctatataata cttcatccat tttattagta  6600
catccattta gggtttaggg ttaatggttt ttatagacta attttttag tacatctatt  6660
ttattctatt ttagcctcta aattaagaaa actaaaactc tattttagtt tttttattta  6720
ataatttaga tataaaatag aataaaataa agtgactaaa aattaaacaa ataccctta   6780
agaaattaaa aaaactaagg aaacattttt cttgtttcga gtagataatg ccagcctgtt  6840
aaacgccgtc gacgagtcta acggacacca accagcgaac cagcagcgtc gcgtcgggcc  6900
aagcgaagca gacggcacgg catctctgtc gctgcctctg gacccctctc gagagttccg  6960
ctccaccgtt ggacttgctc cgctgtcggc atccagaaat tgcgtggcgg agcggcagac  7020
gtgagccggc acggcaggcg gcctcctcct cctctcacgg caccggcagc tacgggggat  7080
tcctttccca ccgctccttc gctttccctt cctcgcccgc cgtaataaat agacaccccc  7140
tccacaccct ctttccccaa cctcgtgttg ttcggagcgc acacacacac aaccagatct  7200
cccccaaatc cacccgtcgg cacctccgct tcaaggtacg ccgctcgtcc tccccccccc  7260
cccctctcta ccttctctag atcggcgttc cggtccatgg ttagggcccg gtagttctac  7320
ttctgttcat gtttgtgtta gatccgtgtt tgtgttagat ccgtgctgct agcgttcgta  7380
cacggatgcg acctgtacgt cagacacgtt ctgattgcta acttgccagt gtttctcttt  7440
ggggaatcct gggatggctc tagccgttcc gcagacggga tcgatttcat gatttttttt  7500
gtttcgttgc atagggtttg gtttgccctt ttcctttatt tcaatatatg ccgtgcactt  7560
gtttgtcggg tcatcttttc atgctttttt ttgtcttggt tgtgatgatg tggtctggtt  7620
gggcggtcgt tctagatcgg agtagaattc tgtttcaaac tacctggtgg atttattaat  7680
tttggatctg tatgtgtgtg ccatacatat tcatagttac gaattgaaga tgatggatgg  7740
aaatatcgat ctaggatagg tatacatgtt gatgcgggtt ttactgatgc atatacagag  7800
atgctttttg ttcgcttggt tgtgatgatg tggtgtggtt gggcggtcgt tcattcgttc  7860
tagatcggag tagaatactg tttcaaacta cctggtgtat ttattaattt tggaactgta  7920
tgtgtgtgtc atacatcttc atagttacga gtttaagatg gatggaaata tcgatctagg  7980
ataggtatac atgttgatgt gggttttact gatgcatata catgatggca tatgcagcat  8040
ctattcatat gctctaacct tgagtaccta tctattataa taaacaagta tgttttataa  8100
ttattttgat cttgatatac ttggatgatg gcatatgcag cagctatatg tggatttttt  8160
tagccctgcc ttcatacgct atttatttgc ttggtactgt ttcttttgtc gatgctcacc  8220
ctgttgtttg gtgttacttc tgcagtgact aaatagatgc agaagctgat caacagcgtg  8280
```

-continued

```
cagaactacg cctggggcag caagaccgcc ctgaccgagc tgtacggcat ggagaacccc  8340
agcagccagc ccatggccga gctgtggatg ggcgcccacc ccaagagctc aagccgcgtg  8400
cagaacgccg ccggcgatat cgttagcctg cgcgacgtga tcgagagcga caagagcacc  8460
ctgctgggcg aggccgtggc caagcgcttc ggcgagctgc ccttcctgtt caaggtgctg  8520
tgcgccgctc agcccctgag catccaggtg caccctaaca agcacaacag cgagatcggc  8580
ttcgccaagg agaacgccgc cggcatcccc atggacgccg ccgagcgcaa ctacaaggac  8640
cccaaccaca agcccgagct ggtgttcgcc ctgaccccct tcctggccat gaacgccttc  8700
cgcgagttca gcgagatcgt tagcctgctg cagcccgtgg ccggcgccca ccccgctatc  8760
gcccacttcc ttcagcagcc cgacgccgag cgcctgagcg agctgttcgc cagcctgctg  8820
aacatgcagg gtgaggagaa gtcacgcgcc ctggccatcc tgaagagcgc cctggacagc  8880
cagcagggcg agccctggca gacaatccgc ctgatcagcg agttctaccc cgaggatagc  8940
ggcctgttca gcccccctgct gctgaacgtg gtgaagctga accccggcga ggccatgttc  9000
ctgttcgccg agaccccccca cgcctacctg cagggcgtgg ccctggaggt gatggccaac  9060
agcgacaacg tgctgcgcgc cggcctgacc cccaagtaca tcgacatccc cgagctggtg  9120
gccaacgtga agttcgaggc taagcccgcc aaccagctgc tgacccagcc cgtgaagcag  9180
ggcgccgagc tggacttccc tatccccgtt gacgacttcg ccttcagcct gcacgacctg  9240
agcgacaagg agaccactat cagccagcag agcgccgcga tcctgttctg cgtggagggc  9300
gacgccaccc tgtggaaggg cagccagcag ctgcagctga agcccggcga gagcgccttt  9360
atcgccgcca acgagagccc cgtgaccgtg aagggccacg gccgcctggc ccgcgtgtac  9420
aacaagctgt gatagctacg tcatgggtcg tttaagctgc cgatgtgcct gcgtcgtctg  9480
gtgccctctc tccatatgga ggttgtcaaa gtatctgctg ttcgtgtcat gagtcgtgtc  9540
agtgttggtt taataatgga ccggttgtgt tgtgtgtgcg tactacccag aactatgaca  9600
aatcatgaat aagtttgatg tttgaaatta aagcctgtgc tcattatgtt ctgtctttca  9660
gttgtctcct aatatttgcc tgcaggtact ggctatctac cgtttcttac ttaggaggtg  9720
tttgaatgca ctaaaactaa tagttagtgg ctaaaattag ttaaaacatc caaacaccat  9780
agctaatagt tgaactatta gctatttttg gaaaattagt taatagtgag gtagttattt  9840
gttagctagc taattcaact aacaattttt agccaactaa caattagttt cagtgcattc  9900
aaacaccccc ttaatgttaa cgtggttcta tctaccgtct cctaatatat ggttgattgt  9960
tcggtttgtt gctatgctat tgggttctga ttgctgctag ttcttgctga atccagaagt  10020
tctcgtagta tagctcagat tcatattatt tatttgagtg ataagtgatc caggttatta  10080
ctatgttagc taggtttttt ttacaaggat aaattatctg tgatcataat tcttatgaaa  10140
gctttatgtt tcctggaggc agtggcatgc aatgcatgac agcaacttga tcacaccagc  10200
tgaggtagat acggtaacaa ggttcttaaa tctgttcacc aaatcattgg agaacacaca  10260
tacacattct tgccagtctt ggttagagaa atttcatgac aaaatgccaa agctgtcttg  10320
actcttcact tttggccatg agtcgtgact tagtttggtt taatggaccg gttctcctag  10380
cttgttctac tcaaaactgt tgttgatgcg aataagttgt gatggttgat ctctggattt  10440
tgttttgctc tcaatagtgg acgagattag atagcggacc gcctgcaggc ccgggggcgc  10500
gccctaatta gctaacggcc aggatcgccg cgtgagcctt tagcaactag ctagattaat  10560
taacgcaatc tgttattaag ttgtctaagc gtcaatttgt ttacaccaca atatatcctg  10620
ccaccagcca gccaacagct ccccgaccgg cagctcggca caaaatcacc actcgataca  10680
ggcagcccat cag                                                     10693
```

```
SEQ ID NO: 102          moltype = DNA  length = 10264
FEATURE                 Location/Qualifiers
misc_feature            1..10264
                        note = Expression cassette of construct 23501, gRNA target
                         1 single guide
regulatory              214..734
                        note = promoter - 35S
                        regulatory_class = promoter
gene                    748..4917
                        note = Cas9
misc_feature            4852..4908
                        note = NLS-TAG
regulatory              4923..5175
                        note = terminator - tNOS
                        regulatory_class = terminator
regulatory              5196..5711
                        note = promoter - pU6
                        regulatory_class = promoter
misc_feature            5712..5817
                        note = sgRNA
misc_feature            5713..5732
regulatory              5824..7816
                        note = promoter - Ubi promoter
                        regulatory_class = promoter
gene                    7828..9006
                        note = PMI
regulatory              9011..10045
                        note = terminator - Ubi terminator
                        regulatory_class = terminator
source                  1..10264
                        mol_type = other DNA
                        organism = synthetic construct
SEQUENCE: 102
cctgtggttg gcatgcacat acaaatggac gaacggataa accttttcac gcccttttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga ccgagtcaaa gattcaaata gaggacctaa  240
```

-continued

```
cagaactcgc cgtaaagact ggcgaacagt tcatacagag tctcttacga ctcaatgaca  300
agaagaaaat cttcgtcaac ttggtggagc acgacacgct agtctactcc aaaaatatca  360
aagatacagt ctcagaagac caaagggcaa ttgagacttt tcaacaaagg gtaatatccg  420
gaaacctcct cggattccat tgcccagcta tctgtcactt aattgtgaag atagtggaaa  480
aggaaggtgg ctcctacaaa tgccatcatt gcgataaagg aaaggccatc gttgaagatg  540
cctctgccga cagtggtccc aaagatggac ccccacccac gaggagcatc gtggtaaaag  600
aagacgttcc aaccacgtct tcaaagcaag tggattgatg tgatatctcc actgacgtaa  660
gggatgacgc acaatcccac tatccttcgc aagacccttc ctctatataa ggaagttcat  720
ttcatttgga gaggatattt atccaccatg gacaagaagt acagcatcgg cctggacatc  780
ggcaccaaca gcgtgggctg ggccgtgatc accgacgagt acaaggtgcc gagcaagaag  840
ttcaaggtgc tgggcaacac cgacaggcac agcatcaaga agaacctgat cggcgccctg  900
ctgttcgaca gcggcgagac cgccgaggcc accaggctga agaggaccgc caggaggagg  960
tacaccagga ggaagaacag gatctgctac ctgcaggaga tcttcagcaa cgagatggcc  1020
aaggtggacg acagcttctt ccacaggctg gaggagagct tcctggtgga ggaggacaag  1080
aagcacgaga ggcacccgat cttcggcaac atcgtggacg aggtggccta ccacgagaag  1140
tacccgacca tctaccacct gaggaagaag ctggtggaca gcaccgacaa ggccgacctg  1200
aggctgatct acctggccct ggcccacatg atcaagttca ggggccactt cctgatcgag  1260
ggcgacctga acccggacaa cagcgacgtg gacaagctgt tcatccagct ggtgcagacc  1320
tacaaccagc tgttcgagga gaacccgatc aacgccagcg gcgtggacgc caaggccatc  1380
ctgagcgcca ggctgagcaa gagcaggagg ctggagaacc tgatcgccca gctgccgggc  1440
gagaagaaga acggcctgtt cggcaacctg atcgccctga gcctgggcct gaccccgaac  1500
ttcaagagca acttcgacct ggccgaggac gccaagctgc agctgagcaa ggacacctac  1560
gacgacgacc tggacaacct gctggcccag atcggcgacc agtacgccga cctgttcctg  1620
gccgccaaga acctgagcga cgccatcctg ctgagcgaca tcctgagggt gaacaccgag  1680
atcaccaagg ccccgctgag cgccagcatg atcaagaggt acgacgagca ccaccaggac  1740
ctgaccctgc tgaaggccct ggtgaggcag cagctgccgg agaagtacaa ggagatcttc  1800
ttcgaccaga gcaagaacgg ctacgccggc tacatcgacg gcggcgccag ccaggaggag  1860
ttctacaagt tcatcaagcc gatcctggag aagatggacg gcaccgagga gctgctggtg  1920
aagctgaaca gggaggacct gctgaggaag cagaggacct tcgacaacgg cagcatcccg  1980
caccagatcc acctgggcga gctgcacgcc atcctgagga ggcaggagga cttctacccg  2040
ttcctgaagg acaacaggga gaagatcgag aagatcctga ccttccgcat cccgtactac  2100
gtgggcccgc tggccagggg caacagcagg ttcgcctgga tgaccaggaa gagcgaggag  2160
accatcaccc cgtggaactt cgaggaggtg gtggacaagg gcgccagcgc ccagagcttc  2220
atcgagagga tgaccaactt cgacaagaac ctgccgaacg agaaggtgct gccgaagcac  2280
agcctgctgt acgagtactt caccgtgtac aacgagctga ccaaggtgaa gtacgtgacc  2340
gagggcatga ggaagccggc cttcctgagc ggcgagcaga agaaggccat cgtggacctg  2400
ctgttcaaga ccaacaggaa ggtgaccgtg aagcagctga aggaggacta cttcaagaag  2460
atcgagtgct tcgacagcgt ggagatcagc ggcgtggagg acaggttcaa cgccagcctg  2520
ggcacctacc acgacctgct gaagatcatc aaggacaagg acttcctgga caacgaggag  2580
aacgaggaca tcctggagga catcgtgctg accctgaccc tgttcgagga cagggagatg  2640
atcgaggaga ggctgaagac ctacgcccac ctgttcgacg acaaggtgat gaagcagctg  2700
aagaggagga ggtacaccgg ctggggcagg ctgagcagga agctgatcaa cggcatcagg  2760
gacaagcaga gcggcaagac catcctggac ttcctgaaga gcgacggctt cgccaacagg  2820
aacttcatgc agctgatcca cgacgacagc ctgaccttca aggaggacat ccagaaggcc  2880
caggtgagcg gccagggcga cagcctgcac gagcacatcg ccaacctggc cggcagcccg  2940
gccatcaaga agggcatcct gcagaccgtg aaggtggtgg acgagctggt gaaggtgatg  3000
ggcaggcaca agccggagaa catcgtgatc gagatggcca gggagaacca gaccacccag  3060
aagggccaga agaacagcag ggagaggatg aagaggatcg aggagggcat caaggagctg  3120
ggcagccaga tcctgaagga gcacccggtg gagaacaccc agctgcagaa cgagaagctg  3180
tacctgtact acctgcagaa cggcagggac atgtacgtgg accaggagct ggacatcaac  3240
aggctgagcg actacgacgt ggaccacatc gtgccgcaga gcttcctgaa ggacgacagc  3300
atcgacaaca aggtgctgac caggagcgac aagaacaggg gcaagagcga caacgtgccg  3360
agcgaggagg tggtgaagaa gatgaaaaac tactggaggc agctgctgaa cgccaagctg  3420
atcacccaga ggaagttcga caacctgacc aaggccgaga ggggcggcct gagcgagctg  3480
gacaaggccg gcttcattaa aaggcagctg gtggagacca ggcagatcac caagcacgtg  3540
gcccagatcc tggacagcag gatgaacacc aagtacgacg agaacgacaa gctgatcagg  3600
gaggtgaagg tgatcaccct gaagagcaag ctggtgagcg acttcaggaa ggacttccag  3660
ttctacaagg tgagggagat caataattac caccacgccc acgacgccta cctgaacgcc  3720
gtggtgggca ccgccctgat taaaaagtac ccgaagctgg agagcgagtt cgtgtacggc  3780
gactacaagg tgtacgacgt gaggaagatg atcgccaaga gcgagcagga gatcggcaag  3840
gccaccgcca agtacttctt ctacagcaac atcatgaact tcttcaagac cgagatcacc  3900
ctggccaacg gcgagatcag gaagaggccg ctgatcgaga ccaacggcga gaccggcgag  3960
atcgtgtggg acaagggcag ggacttcgcc accgtgagga aggtgctgtc catgccgcag  4020
gtgaacatcg tgaagaagac cgaggtgcag accggcggct tcagcaagga gagcatcctg  4080
ccgaagagga acagcgacaa gctgatcgcc aggaagaagg actgggatcc gaagaagtac  4140
ggcggcttcg acagcccgac cgtggcctac agcgtgctgg tggtggccaa ggtggagaag  4200
ggcaagagca agaagctgaa gagcgtgaag gagctggtgg gcatcaccat catggagagg  4260
agcagcttcg agaagaaccc agtggacttc ctggaggcca agggctacaa ggaggtgaag  4320
aaggacctga tcattaaact gccgaagtac agcctgttcg agctggagaa cggcaggaag  4380
aggatgctgg ccagcgccgg cgagctgcag aagggcaacg agctggccct gccgagcaag  4440
tacgtgaact tcctgtacct ggccagccac tacgagaagc tgaagggcag cccggaggac  4500
aacgagcaga agcagctgtt cgtggagcag cacaagcact acctggacga gatcatcgag  4560
cagatcagcg agttcagcaa gagggtgatc ctggccgacg ccaacctgga caaggtgctg  4620
agcgcctaca acaagcacag ggacaagccg atcagggagc aggccgagaa catcatccac  4680
ctgttcaccc tgaccaacct gggcgccccg gccgccttca agtacttcga caccaccatc  4740
gacaggaaga ggtacaccag caccaaggag gtgctggacg ccaccctgat ccaccagagc  4800
atcaccggcc tgtacgagac caggatcgac ctgagccagc tgggcggcga cagcagcccg  4860
ccgaagaaga agaggaaggt gagctggaag gacgccagcg gctggagcag gatgtgaagc  4920
ttgatcgttc aaacatttgg caataaagtt tcttaagatt gaatcctgtt gccggtcttg  4980
```

-continued cgatgattat catataattt ctgttgaatt acgttaagca tgtaataatt aacatgtaat 5040
gcatgacgtt atttatgaga tgggttttta tgattagagt cccgcaatta tacatttaat 5100
acgcgataga aaacaaaata tagcgcgcaa actaggataa attatcgcgc gcggtgtcat 5160
ctatgttact agatcgggac cggaattcgg gaccctttgt gaaagttgaa ttacggcata 5220
gccgaaggaa taacagaatc gtttcacact ttcgtaacaa aggtcttctt atcatgtttc 5280
agacgatgga ggcaaggctg atcaaagtga tcaagcacat aaacgcattt ttttaccatg 5340
tttcactcca taagcgtctg agattatcac aagtcacgtc tagtagtttg atggtacact 5400
agtgacaatc agttcgtgca gacagagctc atacttgact acttgagcga ttacaggcga 5460
aagtgtgaaa cgcatgtgat gtgggctggg aggaggagaa tatatactaa tgggccgtat 5520
cctgatttgg gctgcgtcgg aaggtgcagc ccacgcgcgc cgtaccgcgc gggtggcgct 5580
gctacccact ttagtccgtt ggatggggat ccgatggttt gcgcggtggc gttgcggggg 5640
atgtttagta ccacatcgga aaccgaaaga cgatggaacc agcttataaa cccgcgcgct 5700
gtagtcagct tgtgcagtcg aagtaatcgg cggttttaga gctagaaata gcaagttaaa 5760
ataaggctag tccgttatca acttgaaaaa gtggcaccga gtcggtgctt ttttttcct 5820
aggctgcagt gcagcgtgac ccggtcgtgc ccctctctag agataatgag cattgcatgt 5880
ctaagttata aaaaattacc acatattttt tttgtcacac ttgtttgaag tgcagtttat 5940
ctatctttat acatatattt aaactttact ctacgaataa tataatctat agtactacaa 6000
taatatcagt gttttagaga atcatataaa tgaacagtta gacatggtct aaaggacaat 6060
tgagtatttt gacaacagga ctctacagtt ttatcttttt agtgtgcatg tgttctcctt 6120
tttttttgca aatagcttca cctatataat acttcatcca ttttattagt acatccattt 6180
agggtttagg gttaatggtt tttatagact aattttttta gtacatctat tttattctat 6240
tttagcctct aaattaagaa aactaaaact ctattttagt ttttttattt aataatttag 6300
atataaaata gaataaaata aagtgactaa aaattaaaca aataccettt aagaaattaa 6360
aaaaactaag gaaacatttt tcttgtttcg agtagataat gccagcctgt taaacgccgt 6420
cgacgagtct aacggacacc aaccagcgaa ccagcagcgt cgcgtcgggc caagcgaagc 6480
agacggcacg gcatctctgt cgctgcctct ggacccctct cgagagttcc gctccaccgt 6540
tggacttgct ccgctgtcgg catccagaaa ttgcgtggcg gagcggcaga cgtgagccgg 6600
cacggcaggc ggcctcctcc tcctctcacg gcaccggcag ctacggggga ttcctttccc 6660
accgctcctt cgctttccct tcctcgcccg ccgtaataaa tagacacccc ctccacaccc 6720
tctttcccca acctcgtgtt gttcggagcg cacacacaca caaccagatc tcccccaaat 6780
ccacccgtcg gcacctccgc ttcaaggtac gccgctcgtc ctcccccccc cccctctct 6840
accttctcta gatcggcgtt ccggtccatg gttagggccc ggtagttcta cttctgttca 6900
tgtttgtgtt agatccgtgt ttgtgttaga tccgtgctgc tagcgttcgt acacggatgc 6960
gacctgtacg tcagacacgt tctgattgct aacttgccag tgtttctctt tggggaatcc 7020
tgggatggct ctagccgttc cgcagacggg atcgatttca tgattttttt tgtttcgttg 7080
catagggttt ggtttgccct tttcctttat ttcaatatat gccgtgcact tgtttgtcgg 7140
gtcatctttt catgcttttt tttgtcttgg ttgtgatgat gtggtctggt tgggcggtcg 7200
ttctagatcg gagtagaatt ctgtttcaaa ctacctggtg gatttattaa ttttggatct 7260
gtatgtgtgt gccatacata ttcatagtta cgaattgaag atgatggatg gaaatatcga 7320
tctaggatag gtatacatgt tgatgcgggt tttactgatg catatacaga gatgcttttt 7380
gttcgcttgg ttgtgatgat gtggtgtggt tgggcggtcg ttcattcgtt ctagatcgga 7440
gtagaatact gtttcaaact acctggtgta tttattaatt ttggaactgt atgtgtgtgt 7500
catacatctt catagttacg agtttaagat ggatggaaat atcgatctag gataggtata 7560
catgttgatg tgggttttac tgatgcatat acatgatggc atatgcagca tctattcata 7620
tgctctaacc ttgagtacct atctattata ataaacaagt atgttttata attattttga 7680
tcttgatata cttggatgat ggcatatgca gcagctatat gtggattttt ttagccctgc 7740
cttcatacgc tatttatttg cttggtactg tttcttttgt cgatgctcac cctgttgttt 7800
ggtgttactt ctgcagtgac taaatagatg cagaagctga tcaacagcgt gcagaactac 7860
gcctggggca gcaagaccgc cctgaccgag ctgtacggca tggagaaccc cagcagccag 7920
cccatggccg agctgtggat gggcgcccac cccaagagct caagccgcgt gcagaacgcc 7980
gccggcgata tcgttagcct gcgcgacgtg atcgagagcg acaagagcac cctgctgggc 8040
gaggccgtgg ccaagcgctt cggcgagctg cccttcctgt tcaaggtgct gtgcgccgct 8100
cagcccctga gcatccaggt gcaccctaac aagcacaaca gcgagatcgg cttcgccaag 8160
gagaacgccg ccggcatccc catggacgcc gccgagcgca actacaagga ccccaaccac 8220
aagcccgagc tggtgttcgc cctgaccccc ttcctggcca tgaacgcctt ccgcgagttc 8280
agcgagatcg ttagcctgct gcagcccgtg gccggcgccc accccgctat cgcccacttc 8340
cttcagcagc ccgacgccga gcgcctgagc gagctgttcg ccagcctgct gaacatgcag 8400
ggtgaggaga agtcacgcgc cctggccatc ctgaagagcg ccctggacag ccagcagggc 8460
gagccctggc agacaatccg cctgatcagc gagttctacc ccgaggatag cggcctgttc 8520
agccccctgc tgctgaacgt ggtgaagctg aaccccggcg aggccatgtt cctgttcgcc 8580
gagaccccc acgcctacct gcagggcgtg gccctggagg tgatggccaa cagcgacaac 8640
gtgctgcgcg ccggcctgac ccccaagtac atcgacatcc ccgagctggt ggccaacgtg 8700
aagttcgagg ctaagcccgc caaccagctg ctgacccagc ccgtgaagca gggcgccgag 8760
ctggacttcc ctatccccgt tgacgacttc gccttcagcc tgcacgacct gagcgacaag 8820
gagaccacta tcagccagca gagcgccgcg atcctgttct gcgtggaggg cgacgccacc 8880
ctgtggaagg gcagccagca gctgcagctg aagcccggcg agagcgcctt tatcgccgcc 8940
aacgagagcc ccgtgaccgt gaagggccac ggccgcctgg cccgcgtgta caacaagctg 9000
tgatagctac gtcatgggtc gtttaagctg ccgatgtgcc tgcgtcgtct ggtgccctct 9060
ctccatatgg aggttgtcaa agtatctgct gttcgtgtca tgagtcgtgt cagtgttggt 9120
ttaataatgg accggttgtg ttgtgtgtgc gtactaccca gaactatgac aaatcatgaa 9180
taagtttgat gtttgaaatt aaagcctgtg ctcattatgt tctgtctttc agttgtctcc 9240
taatatttgc ctgcaggtac tggctatcta ccgtttctta cttaggaggt gtttgaatgc 9300
actaaaacta atagttagtg gctaaaatta gttaaaacat ccaaacacca tagctaatag 9360
ttgaactatt agctattttt ggaaaattag ttaatagtga ggtagttatt tgttagctag 9420
ctaattcaac taacaatttt tagccaacta acaattagtt tcagtgcatt caaacacccc 9480
cttaatgtta acgtggttct atctaccgtc tcctaatata tggttgattg ttcggtttgt 9540
tgctatgcta ttgggttctg attgctgcta gttcttgctg aatccagaag ttctcgtagt 9600
atagctcaga ttcatattat ttatttgagt gataagtgat ccaggttatt actatgttag 9660
ctaggttttt tttacaagga taaattatct gtgatcataa ttcttatgaa agctttatgt 9720

```
ttcctggagg cagtggcatg caatgcatga cagcaacttg atcacaccag ctgaggtaga  9780
tacggtaaca aggttcttaa atctgttcac caaatcattg gagaacacac atacacattc  9840
ttgccagtct tggttagaga aatttcatga caaaatgcca aagctgtctt gactcttcac  9900
ttttggccat gagtcgtgac ttagtttggt ttaatggacc ggttctccta gcttgttcta  9960
ctcaaaactg ttgttgatgc gaataagttg tgatggttga tctctggatt ttgttttgct  10020
ctcaatagtg gacgagatta gatagcggac cgcctgcagg cccgggggcg cgccctaatt  10080
agctaacggc caggatcgcc gcgtgagcct ttagcaacta gctagattaa ttaacgcaat  10140
ctgttattaa gttgtctaag cgtcaatttg tttacaccac aatatatcct gccaccagcc  10200
agccaacagc tccccgaccg gcagctcggc acaaaatcac cactcgatac aggcagccca  10260
tcag                                                              10264

SEQ ID NO: 103          moltype = DNA  length = 10692
FEATURE                 Location/Qualifiers
misc_feature            1..10692
                        note = Expression cassette of construct 23501, gRNA target
                         2 dual guides
regulatory              214..734
                        note = promoter - 35S
                        regulatory_class = promoter
gene                    748..4917
                        note = Cas9
misc_feature            4852..4908
                        note = NLS-TAG
regulatory              4923..5175
                        note = terminator - tNOS
                        regulatory_class = terminator
regulatory              5196..5570
                        note = promoter - pU3
                        regulatory_class = promoter
misc_feature            5572..5590
misc_feature            5591..5635
                        note = crRNA
regulatory              5642..6157
                        note = promoter - pU6
                        regulatory_class = promoter
misc_feature            6158..6245
                        note = tracrRNA
regulatory              6252..8244
                        note = promoter - Ubi promoter
                        regulatory_class = promoter
gene                    8256..9434
                        note = PMI
regulatory              9439..10473
                        note = terminator - Ubi terminator
                        regulatory_class = terminator
source                  1..10692
                        mol_type = other DNA
                        organism = synthetic construct
SEQUENCE: 103
cctgtggttg gcatgcacat acaaatggac gaacggataa accttttcac gcccttttaa  60
atatccgatt attctaataa acgctctttt ctcttaggtt tacccgccaa tatatcctgt  120
caaacactga tagtttaaac tggcactagc ctaacggtgt tgactaacta ggccgcttcc  180
ctaattagct aacccggggg cgcgccggga ccgagtcaaa gattcaaata gaggacctaa  240
cagaactcgc cgtaaagact ggcgaacagt tcatacagag tctcttacga ctcaatgaca  300
agaagaaaat cttcgtcaac ttggtggagc acgacacgct agtctactcc aaaaatatca  360
aagatacagt ctcagaagac caaagggcaa ttgagacttt tcaacaaagg gtaatatccg  420
gaaacctcct cggattccat tgcccagcta tctgtcactt aattgtgaag atagtggaaa  480
aggaaggtgg ctcctacaaa tgccatcatt gcgataaagg aaaggccatc gttgaagatg  540
cctctgccga cagtggtccc aaagatggac ccccacccac gaggagcatc gtggtaaaag  600
aagacgttcc aaccacgtct tcaaagcaag tggattgatg tgatatctcc actgacgtaa  660
gggatgacgc acaatcccac tatccttcgc aagacccttc ctctatataa ggaagttcat  720
ttcatttgga gaggataatt atccaccatg gacaagaagt acagcatcgg cctggacatc  780
ggcaccaaca gcgtgggctg ggccgtgatc accgacgagt acaaggtgcc gagcaagaag  840
ttcaaggtgc tgggcaacac cgacaggcac agcatcaaga agaacctgat cggcgccctg  900
ctgttcgaca gcggcgagac cgccgaggcc accaggctga agaggaccgc caggaggagg  960
tacaccagga ggaagaacag gatctgctac ctgcaggaga tcttcagcaa cgagatggcc  1020
aaggtggacg acagcttctt ccacaggctg gaggagagct tcctggtgga ggaggacaag  1080
aagcacgaga ggcacccgat cttcggcaac atcgtggacg aggtggccta ccacgagaag  1140
tacccgacca tctaccacct gaggaagaag ctggtggaca gcaccgacaa ggccgacctg  1200
aggctgatct acctggccct ggcccacatg atcaagttca ggggccactt cctgatcgag  1260
ggcgacctga acccggacaa cagcgacgtg gacaagctgt tcatccagct ggtgcagacc  1320
tacaaccagc tgttcgagga gaacccgatc aacgccagcg gcgtggacgc caaggccatc  1380
ctgagcgcca ggctgagcaa gagcaggagg ctggagaacc tgatcgccca gctgccgggc  1440
gagaagaaga acggcctgtt cggcaacctg atcgccctga gcctgggcct gaccccgaac  1500
ttcaagagca acttcgacct ggccgaggac gccaagctgc agctgagcaa ggacacctac  1560
gacgacgacc tggacaacct gctggcccag atcggcgacc agtacgccga cctgttcctg  1620
gccgccaaga acctgagcga cgccatcctg ctgagcgaca tcctgagggt gaacaccgag  1680
atcaccaagg ccccgctgag cgccagcatg atcaagaggt acgacgagca ccaccaggac  1740
ctgaccctgc tgaaggccct ggtgaggcag cagctgccgg agaagtacaa ggagatcttc  1800
```

-continued

```
ttcgaccaga gcaagaacgg ctacgccggc tacatcgacg gcggcgccag ccaggaggag  1860
ttctacaagt tcatcaagcc gatcctggag aagatggacg gcaccgagga gctgctggtg  1920
aagctgaaca gggaggacct gctgaggaag cagaggacct tcgacaacgg cagcatcccg  1980
caccagatcc acctgggcga gctgcacgcc atcctgagga ggcaggagga cttctacccg  2040
ttcctgaagg acaacaggga gaagatcgag aagatcctga ccttccgcat cccgtactac  2100
gtgggcccgc tggccagggg caacagcagg ttcgcctgga tgaccaggaa gagcgaggag  2160
accatcaccc cgtggaactt cgaggaggtg gtggacaagg gcgccagcgc ccagagcttc  2220
atcgagagga tgaccaactt cgacaagaac ctgccgaacg agaaggtgct gccgaagcac  2280
agcctgctgt acgagtactt caccgtgtac aacgagctga ccaaggtgaa gtacgtgacc  2340
gagggcatga ggaagccggc cttcctgagc ggcgagcaga agaaggccat cgtggacctg  2400
ctgttcaaga ccaacaggaa ggtgaccgtg aagcagctga aggaggacta cttcaagaag  2460
atcgagtgct tcgacagcgt ggagatcagc ggcgtggagg acaggttcaa cgccagcctg  2520
ggcacctacc acgacctgct gaagatcatc aaggacaagg acttcctgga caacgaggag  2580
aacgaggaca tcctggagga catcgtgctg accctgaccc tgttcgagga cagggagatg  2640
atcgaggaga ggctgaagac ctacgcccac ctgttcgacg acaaggtgat gaagcagctg  2700
aagaggagga ggtacaccgg ctggggcagg ctgagcagga agctgatcaa cggcatcagg  2760
gacaagcaga gcggcaagac catcctggac ttcctgaaga gcgacggctt cgccaacagg  2820
aacttcatgc agctgatcca cgacgacagc ctgaccttca aggaggacat ccagaaggcc  2880
caggtgagcg gccagggcga cagcctgcac gagcacatcg ccaacctggc cggcagcccg  2940
gccatcaaga agggcatcct gcagaccgtg aaggtggtgg acgagctggt gaaggtgatg  3000
ggcaggcaca agccggagaa catcgtgatc gagatggcca gggagaacca gaccacccag  3060
aagggccaga agaacagcag ggagaggatg aagaggatcg aggagggcat caaggagctg  3120
ggcagccaga tcctgaagga gcacccggtg gagaacaccc agctgcagaa cgagaagctg  3180
tacctgtact acctgcagaa cggcagggac atgtacgtgg accaggagct ggacatcaac  3240
aggctgagcg actacgacgt ggaccacatc gtgccgcaga gcttcctgaa ggacgacagc  3300
atcgacaaca aggtgctgac caggagcgac aagaacaggg gcaagagcga caacgtgccg  3360
agcgaggagg tggtgaagaa gatgaaaaac tactggaggc agctgctgaa cgccaagctg  3420
atcacccaga ggaagttcga caacctgacc aaggccgaga ggggcggcct gagcgagctg  3480
gacaaggccg gcttcattaa aaggcagctg gtggagacca ggcagatcac caagcacgtg  3540
gcccagatcc tggacagcag gatgaacacc aagtacgacg agaacgacaa gctgatcagg  3600
gaggtgaagg tgatcaccct gaagagcaag ctggtgagcg acttcaggaa ggacttccag  3660
ttctacaagg tgagggagat caataattac caccacgccc acgacgccta cctgaacgcc  3720
gtggtgggca ccgccctgat taaaaagtac ccgaagctgg agagcgagtt cgtgtacggc  3780
gactacaagg tgtacgacgt gaggaagatg atcgccaaga gcgagcagga gatcggcaag  3840
gccaccgcca agtacttctt ctacagcaac atcatgaact tcttcaagac cgagatcacc  3900
ctggccaacg gcgagatcag gaagaggccg ctgatcgaga ccaacggcga gaccggcgag  3960
atcgtgtggg acaagggcag ggacttcgcc accgtgagga aggtgctgtc catgccgcag  4020
gtgaacatcg tgaagaagac cgaggtgcag accggcggct tcagcaagga gagcatcctg  4080
ccgaagagga acagcgacaa gctgatcgcc aggaagaagg actgggatcc gaagaagtac  4140
ggcggcttcg acagcccgac cgtggcctac agcgtgctgg tggtggccaa ggtggagaag  4200
ggcaagagca agaagctgaa gagcgtgaag gagctggtgg gcatcaccat catggagagg  4260
agcagcttcg agaagaaccc agtggacttc ctggaggcca agggctacaa ggaggtgaag  4320
aaggacctga tcattaaact gccgaagtac agcctgttcg agctggagaa cggcaggaag  4380
aggatgctgg ccagcgccgg cgagctgcag aagggcaacg agctggccct gccgagcaag  4440
tacgtgaact tcctgtacct ggccagccac tacgagaagc tgaagggcag cccggaggac  4500
aacgagcaga agcagctgtt cgtggagcag cacaagcact acctggacga gatcatcgag  4560
cagatcagcg agttcagcaa gagggtgatc ctggccgacg ccaacctgga caaggtgctg  4620
agcgcctaca acaagcacag ggacaagccg atcagggagc aggccgagaa catcatccac  4680
ctgttcaccc tgaccaacct gggcgccccg gccgccttca agtacttcga caccaccatc  4740
gacaggaaga ggtacaccag caccaaggag gtgctggacg ccaccctgat ccaccagagc  4800
atcaccggcc tgtacgagac caggatcgac ctgagccagc tgggcggcga cagcagcccg  4860
ccgaagaaga agaggaaggt gagctggaag gacgccagcg gctggagcag gatgtgaagc  4920
ttgatcgttc aaacatttgg caataaagtt tcttaagatt gaatcctgtt gccggtcttg  4980
cgatgattat catataattt ctgttgaatt acgttaagca tgtaataatt aacatgtaat  5040
gcatgacgtt atttatgaga tgggttttta tgattagagt cccgcaatta tacatttaat  5100
acgcgataga aaacaaaata tagcgcgcaa actaggataa attatcgcgc gcggtgtcat  5160
ctatgttact agatcgggac cggaattcgg gacccgggat ctttaaacat acgaacagat  5220
cacttaaagt tcttctgaag caacttaaag ttatcaggca tgcatggatc ttggaggaat  5280
cagatgtgca gtcagggacc atagcacagg acaggcgtct tctactggtg ctaccagcaa  5340
atgctggaag ccgggaacac tgggtacgtt ggaaaccacg tgatgtggag taagataaac  5400
tgtaggagaa aagcatttcg tagtgggcca tgaagccttt caggacatgt attgcagtat  5460
gggccggccc attacgcaat tggacgacaa caaagactag tattagtacc acctcggcta  5520
tccacataga tcaaagctgg tttaaaagag ttgtgcagat gatccgtggc agagaccggc  5580
aggtacgtcg gttttagagc tatgctgttt tgaatggtcc caaaactttt tttttactag  5640
ttttgtgaaa gttgaattac ggcatagccg aaggaataac agaatcgttt cacactttcg  5700
taacaaaggt cttcttatca tgtttcagac gatggaggca aggctgatca aagtgatcaa  5760
gcacataaac gcattttttt accatgtttc actccataag cgtctgagat tatcacaagt  5820
cacgtctagt agtttgatgg tacactagtg acaatcagtt cgtgcagaca gagctcatac  5880
ttgactactt gagcgattac aggcgaaagt gtgaaacgca tgtgatgtgg gctgggagga  5940
ggagaatata tactaatggg ccgtatcctg atttgggctg cgtcggaagg tgcagcccac  6000
gcgcgccgta ccgcgcgggt ggcgctgcta cccactttag tccgttggat ggggatccga  6060
tggtttgcgc ggtggcgttg cgggggatgt ttagtaccac atcggaaacc gaaagacgat  6120
ggaaccagct tataaacccg cgcgctgtag tcagcttgga accattcaaa acagcatagc  6180
aagttaaaat aaggctagtc cgttatcaac ttgaaaaagt ggcaccgagt cggtgctttt  6240
tttttcctag gctgcagtgc agcgtgaccc ggtcgtgccc ctctctagag ataatgagca  6300
ttgcatgtct aagttataaa aaattaccac atattttttt tgtcacactt gtttgaagtg  6360
cagtttatct atctttatac atatatttaa actttactct acgaataata taatctatag  6420
tactacaata atatcagtgt tttagagaat catataaatg aacagttaga catggtctaa  6480
aggacaattg agtattttga caacaggact ctacagtttt atctttttag tgtgcatgtg  6540
```

-continued

```
ttctcctttt tttttgcaaa tagcttcacc tatataatac ttcatccatt ttattagtac  6600
atccatttag ggtttagggt taatggtttt tatagactaa ttttttttagt acatctattt  6660
tattctattt tagcctctaa attaagaaaa ctaaaactct attttagttt ttttatttaa  6720
taatttagat ataaaataga ataaaataaa gtgactaaaa attaaacaaa taccctttaa  6780
gaaattaaaa aaactaagga aacatttttc ttgtttcgag tagataatgc cagcctgtta  6840
aacgccgtcg acgagtctaa cggacaccaa ccagcgaacc agcagcgtcg cgtcgggcca  6900
agcgaagcag acggcacggc atctctgtcg ctgcctctgg acccctctcg agagttccgc  6960
tccaccgttg gacttgctcc gctgtcggca tccagaaatt gcgtggcgga gcggcagacg  7020
tgagccggca cggcaggcgg cctcctcctc ctctcacggc accggcagct acgggggatt  7080
cctttcccac cgctccttcg ctttcccttc ctcgcccgcc gtaataaata gacaccccct  7140
ccacaccctc tttccccaac ctcgtgttgt tcggagcgca cacacacaca accagatctc  7200
ccccaaatcc acccgtcggc acctccgctt caaggtacgc cgctcgtcct cccccccccc  7260
ccctctctac cttctctaga tcggcgttcc ggtccatggt tagggcccgg tagttctact  7320
tctgttcatg tttgtgttag atccgtgttt gtgttagatc cgtgctgcta gcgttcgtac  7380
acggatgcga cctgtacgtc agacacgttc tgattgctaa cttgccagtg tttctctttg  7440
gggaatcctg ggatggctct agccgttccg cagacgggat cgatttcatg atttttttttg  7500
tttcgttgca tagggtttgg tttgcccttt tcctttattt caatatatgc cgtgcacttg  7560
tttgtcgggt catcttttca tgcttttttt tgtcttggtt gtgatgatgt ggtctggttg  7620
ggcggtcgtt ctagatcgga gtagaattct gtttcaaact acctggtgga tttattaatt  7680
ttggatctgt atgtgtgtgc catacatatt catagttacg aattgaagat gatggatgga  7740
aatatcgatc taggataggt atacatgttg atgcgggttt tactgatgca tatacagaga  7800
tgctttttgt tcgcttggtt gtgatgatgt ggtgtggttg ggcggtcgtt cattcgttct  7860
agatcggagt agaatactgt ttcaaactac ctggtgtatt tattaatttt ggaactgtat  7920
gtgtgtgtca tacatcttca tagttacgag tttaagatgg atggaaatat cgatctagga  7980
taggtataca tgttgatgtg ggttttactg atgcatatac atgatggcat atgcagcatc  8040
tattcatatg ctctaacctt gagtacctat ctattataat aaacaagtat gttttataat  8100
tattttgatc ttgatatact tggatgatgg catatgcagc agctatatgt ggattttttt  8160
agccctgcct tcatacgcta tttatttgct tggtactgtt tcttttgtcg atgctcaccc  8220
tgttgtttgg tgttacttct gcagtgacta aatagatgca gaagctgatc aacagcgtgc  8280
agaactacgc ctggggcagc aagaccgccc tgaccgagct gtacggcatg gagaacccca  8340
gcagccagcc catggccgag ctgtggatgg gcgcccaccc caagagctca agccgcgtgc  8400
agaacgccgc cggcgatatc gttagcctgc gcgacgtgat cgagagcgac aagagcaccc  8460
tgctgggcga ggccgtggcc aagcgcttcg gcgagctgcc cttcctgttc aaggtgctgt  8520
gcgccgctca gcccctgagc atccaggtgc accctaacaa gcacaacagc gagatcggct  8580
tcgccaagga gaacgccgcc ggcatcccca tggacgccgc cgagcgcaac tacaaggacc  8640
ccaaccacaa gcccgagctg gtgttcgccc tgaccccctt cctggccatg aacgccttcc  8700
gcgagttcag cgagatcgtt agcctgctgc agcccgtggc cggcgcccac cccgctatcg  8760
cccacttcct tcagcagccc gacgccgagc gcctgagcga gctgttcgcc agcctgctga  8820
acatgcaggg tgaggagaag tcacgcgccc tggccatcct gaagagcgcc ctggacagcc  8880
agcagggcga gccctggcag acaatccgcc tgatcagcga gttctacccc gaggatagcg  8940
gcctgttcag ccccctgctg ctgaacgtgg tgaagctgaa ccccggcgag gccatgttcc  9000
tgttcgccga gaccccccac gcctacctgc agggcgtggc cctggaggtg atggccaaca  9060
gcgacaacgt gctgcgcgcc ggcctgaccc ccaagtacat cgacatcccc gagctggtgg  9120
ccaacgtgaa gttcgaggct aagcccgcca accagctgct gacccagccc gtgaagcagg  9180
gcgccgagct ggacttccct atccccgttg acgacttcgc cttcagcctg cacgacctga  9240
gcgacaagga gaccactatc agccagcaga gcgccgcgat cctgttctgc gtggagggcg  9300
acgccaccct gtggaagggc agccagcagc tgcagctgaa gcccggcgag agcgccttta  9360
tcgccgccaa cgagagcccc gtgaccgtga agggccacgg ccgcctggcc cgcgtgtaca  9420
acaagctgtg atagctacgt catgggtcgt ttaagctgcc gatgtgcctg cgtcgtctgg  9480
tgccctctct ccatatggag gttgtcaaag tatctgctgt tcgtgtcatg agtcgtgtca  9540
gtgttggttt aataatggac cggttgtgtt gtgtgtgcgt actacccaga actatgacaa  9600
atcatgaata agtttgatgt ttgaaattaa agcctgtgct cattatgttc tgtctttcag  9660
ttgtctccta atatttgcct gcaggtactg gctatctacc gtttcttact taggaggtgt  9720
ttgaatgcac taaaactaat agttagtggc taaaattagt taaaacatcc aaacaccata  9780
gctaatagtt gaactattag ctatttttgg aaaattagtt aatagtgagg tagttatttg  9840
ttagctagct aattcaacta acaattttta gccaactaac aattagtttc agtgcattca  9900
aacacccccct taatgttaac gtggttctat ctaccgtctc ctaatatatg gttgattgtt  9960
cggtttgttg ctatgctatt gggttctgat tgctgctagt tcttgctgaa tccagaagtt  10020
ctcgtagtat agctcagatt catattattt atttgagtga taagtgatcc aggttattac  10080
tatgttagct aggttttttt tacaaggata aattatctgt gatcataatt cttatgaaag  10140
ctttatgttt cctggaggca gtggcatgca atgcatgaca gcaacttgat cacaccagct  10200
gaggtagata cggtaacaag gttcttaaat ctgttcacca aatcattgga gaacacacat  10260
acacattctt gccagtcttg gttagagaaa tttcatgaca aaatgccaaa gctgtcttga  10320
ctcttcactt ttggccatga gtcgtgactt agtttggttt aatggaccgg ttctcctagc  10380
ttgttctact caaaactgtt gttgatgcga ataagttgtg atggttgatc tctggatttt  10440
gttttgctct caatagtgga cgagattaga tagcggaccg cctgcaggcc cgggggcgcg  10500
ccctaattag ctaacggcca ggatcgccgc gtgagccttt agcaactagc tagattaatt  10560
aacgcaatct gttattaagt tgtctaagcg tcaatttgtt tacaccacaa tatatcctgc  10620
caccagccag ccaacagctc cccgaccggc agctcggcac aaaatcacca ctcgatacag  10680
gcagcccatc ag                                                       10692
```

```
SEQ ID NO: 104          moltype = DNA  length = 10262
FEATURE                 Location/Qualifiers
misc_feature            1..10262
                        note = Expression cassette of construct 23501, gRNA target
                         2 single guide
regulatory              214..734
                        note = promoter - 35S promoter
                        regulatory_class = promoter
```

-continued gene 748..4917
note = Cas9
regulatory 4923..5175
note = terminator - tNOS
regulatory_class = terminator
regulatory 5196..5711
regulatory_class = promoter
misc_feature 5712..5730
misc_feature 5712..5815
note = sgRNA
regulatory 5822..7814
note = promoter - Ubi promoter
regulatory_class = promoter
gene 7826..9004
note = PMI
regulatory 9009..10043
note = terminator - Ubi terminator
regulatory_class = terminator
source 1..10262
mol_type = other DNA
organism = synthetic construct

SEQUENCE: 104 cctgtggttg gcatgcacat acaaatggac gaacggataa acctttcac gcccttttaa 60
atatccgatt attctaataa acgctctttt ctcttaggtt tacccgccaa tatatcctgt 120
caaacactga tagtttaaac tggcactagc ctaacggtgt tgactaacta ggccgcttcc 180
ctaattagct aacccggggg cgcgccggga ccgagtcaaa gattcaaata gaggacctaa 240
cagaactcgc cgtaaagact ggcgaacagt tcatacagag tctcttacga ctcaatgaca 300
agaagaaaat cttcgtcaac ttggtggagc acgacacgct agtctactcc aaaaatatca 360
aagatacagt ctcagaagac caaagggcaa ttgagacttt tcaacaaagg gtaatatccg 420
gaaacctcct cggattccat tgcccagcta tctgtcactt aattgtgaag atagtggaaa 480
aggaaggtgg ctcctacaaa tgccatcatt gcgataaagg aaaggccatc gttgaagatg 540
cctctgccga cagtggtccc aaagatggac ccccacccac gaggagcatc gtggaaaaag 600
aagacgttcc aaccacgtct tcaaagcaag tggattgatg tgatatctcc actgacgtaa 660
gggatgacgc acaatcccac tatccttcgc aagacccttc ctctatataa ggaagttcat 720
ttcatttgga gaggataatt atccaccatg gacaagaagt acagcatcgg cctggacatc 780
ggcaccaaca gcgtgggctg ggccgtgatc accgacgagt acaaggtgcc gagcaagaag 840
ttcaaggtgc tgggcaacac cgacaggcac agcatcaaga agaacctgat cggcgccctg 900
ctgttcgaca gcggcgagac cgccgaggcc accaggctga agaggaccgc caggaggagg 960
tacaccagga ggaagaacag gatctgctac ctgcaggaga tcttcagcaa cgagatggcc 1020
aaggtggacg acagcttctt ccacaggctg gaggagagct tcctggtgga ggaggacaag 1080
aagcacgaga ggcacccgat cttcggcaac atcgtggacg aggtggccta ccacgagaag 1140
tacccgacca tctaccacct gaggaagaag ctggtggaca gcaccgacaa ggccgacctg 1200
aggctgatct acctggccct ggcccacatg atcaagttca ggggccactt cctgatcgag 1260
ggcgacctga acccggacaa cagcgacgtg gacaagctgt tcatccagct ggtgcagacc 1320
tacaaccagc tgttcgagga gaacccgatc aacgccagcg gcgtggacgc caaggccatc 1380
ctgagcgcca ggctgagcaa gagcaggagg ctggagaacc tgatcgccca gctgccgggc 1440
gagaagaaga acggcctgtt cggcaacctg atcgccctga gcctgggcct gaccccgaac 1500
ttcaagagca acttcgacct ggccgaggac gccaagctgc agctgagcaa ggacacctac 1560
gacgacgacc tggacaacct gctggcccag atcggcgacc agtacgccga cctgttcctg 1620
gccgccaaga acctgagcga cgccatcctg ctgagcgaca tcctgagggt gaacaccgag 1680
atcaccaagg ccccgctgag cgccagcatg atcaagaggt acgacgagca ccaccaggac 1740
ctgaccctgc tgaaggccct ggtgaggcag cagctgccgg agaagtacaa ggagatcttc 1800
ttcgaccaga gcaagaacgg ctacgccggc tacatcgacg gcggcgccag ccaggaggag 1860
ttctacaagt tcatcaagcc gatcctggag aagatggacg gcaccgagga gctgctggtg 1920
aagctgaaca gggaggacct gctgaggaag cagaggacct tcgacaacgg cagcatcccg 1980
caccagatcc acctgggcga gctgcacgcc atcctgagga ggcaggagga cttctacccg 2040
ttcctgaagg acaacaggga gaagatcgag aagatcctga ccttccgcat cccgtactac 2100
gtgggcccgc tggccagggg caacagcagg ttcgcctgga tgaccaggaa gagcgaggag 2160
accatcaccc cgtggaactt cgaggaggtg gtggacaagg gcgccagcgc ccagagcttc 2220
atcgagagga tgaccaactt cgacaagaac ctgccgaacg agaaggtgct gccgaagcac 2280
agcctgctgt acgagtactt caccgtgtac aacgagctga ccaaggtgaa gtacgtgacc 2340
gagggcatga ggaagccggc cttcctgagc ggcgagcaga agaaggccat cgtggacctg 2400
ctgttcaaga ccaacaggaa ggtgaccgtg aagcagctga aggaggacta cttcaagaag 2460
atcgagtgct tcgacagcgt ggagatcagc ggcgtggagg acaggttcaa cgccagcctg 2520
ggcacctacc acgacctgct gaagatcatc aaggacaagg acttcctgga caacgaggag 2580
aacgaggaca tcctggagga catcgtgctg accctgaccc tgttcgagga cagggagatg 2640
atcgaggaga ggctgaagac ctacgcccac ctgttcgacg acaaggtgat gaagcagctg 2700
aagaggagga ggtacaccgg ctggggcagg ctgagcagga agctgatcaa cggcatcagg 2760
gacaagcaga gcggcaagac catcctggac ttcctgaaga gcgacggctt cgccaacagg 2820
aacttcatgc agctgatcca cgacgacagc ctgaccttca aggaggacat ccagaaggcc 2880
caggtgagcg gccagggcga cagcctgcac gagcacatcg ccaacctggc cggcagcccg 2940
gccatcaaga agggcatcct gcagaccgtg aaggtggtgg acgagctggt gaaggtgatg 3000
ggcaggcaca agccggagaa catcgtgatc gagatggcca gggagaacca gaccacccag 3060
aagggccaga agaacagcag ggagaggatg aagaggatcg aggagggcat caaggagctg 3120
ggcagccaga tcctgaagga gcacccggtg gagaacaccc agctgcagaa cgagaagctg 3180
tacctgtact acctgcagaa cggcagggac atgtacgtgg accaggagct ggacatcaac 3240
aggctgagcg actacgacgt ggaccacatc gtgccgcaga gcttcctgaa ggacgacagc 3300
atcgacaaca aggtgctgac caggagcgac aagaacaggg gcaagagcga caacgtgccg 3360
agcgaggagg tggtgaagaa gatgaaaaac tactggaggc agctgctgaa cgccaagctg 3420

```
atcacccaga ggaagttcga caacctgacc aaggccgaga ggggcggcct gagcgagctg  3480
gacaaggccg gcttcattaa aaggcagctg gtggagacca ggcagatcac caagcacgtg  3540
gcccagatcc tggacagcag gatgaacacc aagtacgacg agaacgacaa gctgatcagg  3600
gaggtgaagg tgatcaccct gaagagcaag ctggtgagcg acttcaggaa ggacttccag  3660
ttctacaagg tgagggagat caataattac caccacgccc acgacgccta cctgaacgcc  3720
gtggtgggca ccgccctgat taaaaagtac ccgaagctgg agagcgagtt cgtgtacggc  3780
gactacaagg tgtacgacgt gaggaagatg atcgccaaga gcgagcagga gatcggcaag  3840
gccaccgcca agtacttctt ctacagcaac atcatgaact tcttcaagac cgagatcacc  3900
ctggccaacg gcgagatcag gaagaggccg ctgatcgaga ccaacggcga gaccggcgag  3960
atcgtgtggg acaagggcag ggacttcgcc accgtgagga aggtgctgtc catgccgcag  4020
gtgaacatcg tgaagaagac cgaggtgcag accggcggct tcagcaagga gagcatcctg  4080
ccgaagagga acagcgacaa gctgatcgcc aggaagaagg actgggatcc gaagaagtac  4140
ggcggcttcg acagcccgac cgtggcctac agcgtgctgg tggtggccaa ggtggagaag  4200
ggcaagagca agaagctgaa gagcgtgaag gagctggtgg gcatcaccat catggagagg  4260
agcagcttcg agaagaaccc agtggacttc ctggaggcca agggctacaa ggaggtgaag  4320
aaggacctga tcattaaact gccgaagtac agcctgttcg agctggagaa cggcaggaag  4380
aggatgctgg ccagcgccgg cgagctgcag aagggcaacg agctggccct gccgagcaag  4440
tacgtgaact tcctgtacct ggccagccac tacgagaagc tgaagggcag cccggaggac  4500
aacgagcaga agcagctgtt cgtggagcag cacaagcact acctggacga gatcatcgag  4560
cagatcagcg agttcagcaa gagggtgatc ctggccgacg ccaacctgga caaggtgctg  4620
agcgcctaca acaagcacag ggacaagccg atcagggagc aggccgagaa catcatccac  4680
ctgttcaccc tgaccaacct gggcgccccg gccgccttca agtacttcga caccaccatc  4740
gacaggaaga ggtacaccag caccaaggag gtgctggacg ccaccctgat ccaccagagc  4800
atcaccggcc tgtacgagac caggatcgac ctgagccagc tgggcggcga cagcagcccg  4860
ccgaagaaga agaggaaggt gagctggaag gacgccagcg gctggagcag gatgtgaagc  4920
ttgatcgttc aaacatttgg caataaagtt tcttaagatt gaatcctgtt gccggtcttg  4980
cgatgattat catataattt ctgttgaatt acgttaagca tgtaataatt aacatgtaat  5040
gcatgacgtt atttatgaga tgggttttta tgattagagt cccgcaatta tacatttaat  5100
acgcgataga aaacaaaata tagcgcgcaa actaggataa attatcgcgc gcggtgtcat  5160
ctatgttact agatcgggac cggaattcgg gaccctttgt gaaagttgaa ttacggcata  5220
gccgaaggaa taacagaatc gtttcacact ttcgtaacaa aggtcttctt atcatgtttc  5280
agacgatgga ggcaaggctg atcaaagtga tcaagcacat aaacgcattt ttttaccatg  5340
tttcactcca taagcgtctg agattatcac aagtcacgtc tagtagtttg atggtacact  5400
agtgacaatc agttcgtgca gacagagctc atacttgact acttgagcga ttacaggcga  5460
aagtgtgaaa cgcatgtgat gtgggctggg aggaggagaa tatatactaa tgggccgtat  5520
cctgatttgg gctgcgtcgg aaggtgcagc ccacgcgcgc cgtaccgcgc gggtggcgct  5580
gctacccact ttagtccgtt ggatggggat ccgatggttt gcgcggtggc gttgcggggg  5640
atgtttagta ccacatcgga aaccgaaaga cgatggaacc agcttataaa cccgcgcgct  5700
gtagtcagct tgagaccggc aggtacgtcg gttttagagc tagaaatagc aagttaaaat  5760
aaggctagtc cgttatcaac ttgaaaaagt ggcaccgagt cggtgctttt tttttcctag  5820
gctgcagtgc agcgtgaccc ggtcgtgccc ctctctagag ataatgagca ttgcatgtct  5880
aagttataaa aaattaccac atattttttt tgtcacactt gtttgaagtg cagtttatct  5940
atctttatac atatatttaa actttactct acgaataata taatctatag tactacaata  6000
atatcagtgt tttagagaat catataaatg aacagttaga catggtctaa aggacaattg  6060
agtattttga caacaggact ctacagtttt atctttttag tgtgcatgtg ttctcctttt  6120
tttttgcaaa tagcttcacc tatataatac ttcatccatt ttattagtac atccatttag  6180
ggtttagggt taatggtttt tatagactaa ttttttagt acatctattt tattctattt  6240
tagcctctaa attaagaaaa ctaaaactct attttagttt ttttatttaa taatttagat  6300
ataaaataga ataaaataaa gtgactaaaa attaaacaaa taccctttaa gaaattaaaa  6360
aaactaagga aacatttttc ttgtttcgag tagataatgc cagcctgtta aacgccgtcg  6420
acgagtctaa cggacaccaa ccagcgaacc agcagcgtcg cgtcgggcca agcgaagcag  6480
acggcacggc atctctgtcg ctgcctctgg acccctctcg agagttccgc tccaccgttg  6540
gacttgctcc gctgtcggca tccagaaatt gcgtggcgga gcggcagacg tgagccggca  6600
cggcaggcgg cctcctcctc ctctcacggc accggcagct acgggggatt cctttcccac  6660
cgctccttcg ctttcccttc ctcgcccgcc gtaataaata gacacccct ccacaccctc  6720
tttccccaac ctcgtgttgt tcggagcgca cacacacaca accagatctc ccccaaatcc  6780
acccgtcggc acctccgctt caaggtacgc cgctcgtcct cccccccccc ccctctctac  6840
cttctctaga tcggcgttcc ggtccatggt tagggcccgg tagttctact tctgttcatg  6900
tttgtgttag atccgtgttt gtgttagatc cgtgctgcta gcgttcgtac acggatgcga  6960
cctgtacgtc agacacgttc tgattgctaa cttgccagtg tttctctttg gggaatcctg  7020
ggatggctct agccgttccg cagacgggat cgatttcatg attttttttg tttcgttgca  7080
tagggtttgg tttgcccttt tcctttattt caatatatgc cgtgcacttg tttgtcgggt  7140
catcttttca tgcttttttt tgtcttggtt gtgatgatgt ggtctggttg ggcggtcgtt  7200
ctagatcgga gtagaattct gtttcaaact acctggtgga tttattaatt ttggatctgt  7260
atgtgtgtgc catacatatt catagttacg aattgaagat gatggatgga aatatcgatc  7320
taggataggt atacatgttg atgcgggttt tactgatgca tatacagaga tgctttttgt  7380
tcgcttggtt gtgatgatgt ggtgtggttg ggcggtcgtt cattcgttct agatcggagt  7440
agaatactgt ttcaaactac ctggtgtatt tattaatttt ggaactgtat gtgtgtgtca  7500
tacatcttca tagttacgag tttaagatgg atggaaatat cgatctagga taggtataca  7560
tgttgatgtg ggttttactg atgcatatac atgatggcat atgcagcatc tattcatatg  7620
ctctaacctt gagtacctat ctattataat aaacaagtat gttttataat tattttgatc  7680
ttgatatact tggatgatgg catatgcagc agctatatgt ggattttttt agccctgcct  7740
tcatacgcta tttatttgct tggtactgtt tcttttgtcg atgctcaccc tgttgtttgg  7800
tgttacttct gcagtgacta aatagatgca gaagctgatc aacagcgtgc agaactacgc  7860
ctggggcagc aagaccgccc tgaccgagct gtacggcatg gagaacccca gcagccagcc  7920
catggccgag ctgtggatgg gcgcccaccc caagagctca agccgcgtgc agaacgccgc  7980
cggcgatatc gttagcctgc gcgacgtgat cgagagcgac aagagcaccc tgctgggcga  8040
ggccgtggcc aagcgcttcg gcgagctgcc cttcctgttc aaggtgctgt gcgccgctca  8100
gcccctgagc atccaggtgc accctaacaa gcacaacagc gagatcggct tcgccaagga  8160
```

```
gaacgccgcc ggcatcccca tggacgccgc cgagcgcaac tacaaggacc ccaaccacaa  8220
gcccgagctg gtgttcgccc tgaccccctt cctggccatg aacgccttcc gcgagttcag  8280
cgagatcgtt agcctgctgc agcccgtggc cggcgcccac cccgctatcg cccacttcct  8340
tcagcagccc gacgccgagc gcctgagcga gctgttcgcc agcctgctga acatgcaggg  8400
tgaggagaag tcacgcgccc tggccatcct gaagagcgcc ctggacagcc agcagggcga  8460
gccctggcag acaatccgcc tgatcagcga gttctacccc gaggatagcg gcctgttcag  8520
ccccctgctg ctgaacgtgg tgaagctgaa ccccggcgag gccatgttcc tgttcgccga  8580
gacccccccac gcctacctgc agggcgtggc cctggaggtg atggccaaca gcgacaacgt  8640
gctgcgcgcc ggcctgaccc ccaagtacat cgacatcccc gagctggtgg ccaacgtgaa  8700
gttcgaggct aagcccgcca accagctgct gacccagccc gtgaagcagg gcgccgagct  8760
ggacttccct atccccgttg acgacttcgc cttcagcctg cacgacctga gcgacaagga  8820
gaccactatc agccagcaga gcgccgcgat cctgttctgc gtggagggcg acgccaccct  8880
gtggaagggc agccagcagc tgcagctgaa gcccggcgag agcgccttta tcgccgccaa  8940
cgagagcccc gtgaccgtga agggccacgg ccgcctggcc cgcgtgtaca acaagctgtg  9000
atagctacgt catgggtcgt ttaagctgcc gatgtgcctg cgtcgtctgg tgccctctct  9060
ccatatggag gttgtcaaag tatctgctgt tcgtgtcatg agtcgtgtca gtgttggttt  9120
aataatggac cggttgtgtt gtgtgtgcgt actacccaga actatgacaa atcatgaata  9180
agtttgatgt ttgaaattaa agcctgtgct cattatgttc tgtctttcag ttgtctccta  9240
atatttgcct gcaggtactg gctatctacc gtttcttact taggaggtgt ttgaatgcac  9300
taaaactaat agttagtggc taaaattagt taaaacatcc aaacaccata gctaatagtt  9360
gaactattag ctatttttgg aaaattagtt aatagtgagg tagttatttg ttagctagct  9420
aattcaacta acaattttta gccaactaac aattagtttc agtgcattca aacacccccct  9480
taatgttaac gtggttctat ctaccgtctc ctaatatatg gttgattgtt cggtttgttg  9540
ctatgctatt gggttctgat tgctgctagt tcttgctgaa tccagaagtt ctcgtagtat  9600
agctcagatt catattattt atttgagtga taagtgatcc aggttattac tatgttagct  9660
aggttttttt tacaaggata aattatctgt gatcataatt cttatgaaag ctttatgttt  9720
cctggaggca gtggcatgca atgcatgaca gcaacttgat cacaccagct gaggtagata  9780
cggtaacaag gttcttaaat ctgttcacca aatcattgga gaacacacat acacattctt  9840
gccagtcttg gttagagaaa tttcatgaca aaatgccaaa gctgtcttga ctcttcactt  9900
ttggccatga gtcgtgactt agtttggttt aatggaccgg ttctcctagc ttgttctact  9960
caaaactgtt gttgatgcga ataagttgtg atggttgatc tctggatttt gttttgctct  10020
caatagtgga cgagattaga tagcggaccg cctgcaggcc cgggggcgcg ccctaattag  10080
ctaacggcca ggatcgccgc gtgagccttt agcaactagc tagattaatt aacgcaatct  10140
gttattaagt tgtctaagcg tcaatttgtt tacaccacaa tatatcctgc caccagccag  10200
ccaacagctc cccgaccggc agctcggcac aaaatcacca ctcgatacag gcagcccatc  10260
ag                                                                 10262
```

```
SEQ ID NO: 105          moltype = DNA  length = 1366
FEATURE                 Location/Qualifiers
misc_feature            1..1366
                        note = TALEN-induced mutation in Event 38A ID 22808-4108
                         allele 2
source                  1..1366
                        mol_type = other DNA
                        organism = synthetic construct
SEQUENCE: 105
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaggacgaa ccggtgactg gcgaaggaag caatgccgat gccctcggtg ggctcgctag  1200
gcagctctcc gaggagagga gaacaaggct cgcgcgccgc gtctctgcca tcaacccaag  1260
aggctctaga tgtgcgtcgt acgatatcta agacaagtgg ctttactgtc agtcacatgc  1320
ttgtaaataa gtagacttta ttttaataaa acataaaaat atatat               1366
```

```
SEQ ID NO: 106          moltype = DNA  length = 1366
FEATURE                 Location/Qualifiers
misc_feature            1..1366
                        note = CRISPR-induced MTL mutation in Event 27A ID
                         22807-4073 allele 2
source                  1..1366
                        mol_type = other DNA
                        organism = synthetic construct
SEQUENCE: 106
```

```
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggagaa ccggtgactg gcgaaggaag caatgccgat gccctcggtg ggctcgctag  1200
gcagctctcc gaggagagga gaacaaggct cgcgcgccgc gtctctgcca tcaacccaag  1260
aggctctaga tgtgcgtcgt acgatatcta agacaagtgg ctttactgtc agtcacatgc  1320
ttgtaaataa gtagacttta ttttaataaa acataaaaat atatat  1366
```

```
SEQ ID NO: 107         moltype = DNA  length = 1363
FEATURE                Location/Qualifiers
misc_feature           1..1363
                       note = CRISPR-induced MTL mutation in Event 27A ID
                        22807-4081 allele 2
source                 1..1363
                       mol_type = other DNA
                       organism = synthetic construct
SEQUENCE: 107
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acaggaaccg gtgactggcg aaggaagcaa tgccgatgcc ctcggtgggc tcgctaggca  1200
gctctccgag gagaggagaa caaggctcgc gcgccgcgtc tctgccatca acccaagagg  1260
ctctagatgt gcgtcgtacg atatctaaga caagtggctt tactgtcagt cacatgcttg  1320
taaataagta gactttattt taataaaaca taaaaatata tat  1363
```

```
SEQ ID NO: 108         moltype = DNA  length = 1371
FEATURE                Location/Qualifiers
source                 1..1371
                       mol_type = genomic DNA
                       organism = Zea mays
SEQUENCE: 108
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctata gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
```

```
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 109          moltype = DNA  length = 1371
FEATURE                 Location/Qualifiers
source                  1..1371
                        mol_type = genomic DNA
                        organism = Zea mays
SEQUENCE: 109
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagctcgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 110          moltype = DNA  length = 1371
FEATURE                 Location/Qualifiers
source                  1..1371
                        mol_type = genomic DNA
                        organism = Zea mays
SEQUENCE: 110
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc tgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 111          moltype = DNA  length = 1371
FEATURE                 Location/Qualifiers
source                  1..1371
                        mol_type = genomic DNA
                        organism = Zea mays
SEQUENCE: 111
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
```

-continued

```
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttacg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 112         moltype = DNA  length = 1371
FEATURE                Location/Qualifiers
source                 1..1371
                       mol_type = genomic DNA
                       organism = Zea mays
SEQUENCE: 112
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatacgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 113         moltype = DNA  length = 1371
FEATURE                Location/Qualifiers
source                 1..1371
                       mol_type = genomic DNA
                       organism = Zea mays
SEQUENCE: 113
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gattggcgaa ggaagcaatg ccgatgccct cggtgggctc  1200
gctaggcagc tctccgagga gaggagaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371
```

```
SEQ ID NO: 114         moltype = DNA  length = 1371
FEATURE                Location/Qualifiers
source                 1..1371
                       mol_type = genomic DNA
                       organism = Zea mays
SEQUENCE: 114
agttcatcac taatcacact tattgttccc tcgacgagta tctagctagc tcattaatcg  60
atcaatcggg gtgtgcggtc gaaggcggca atggcgagct actcgtcgcg gcgtccatgc  120
aatacctgta gcacgaaggc gatggccggg agcgtggtcg gcgagcccgt cgtgctgggg  180
cagagggtga cggtgctgac ggtggacggc ggcggcgtcc ggggtctcat cccgggaacc  240
atcctcgcct tcctcgaggc caggctgcag gagctggacg gaccggaggc gaggctggcg  300
gactacttcg actacatcgc cggaaccagc accggcggtc tcatcaccgc catgctcacc  360
gcgcccggca aggacaagcg gcctctctac gctgccaagg acatcaacca cttttacatg  420
gagaactgcc cgcgcatctt ccctcagaag agcaggcttg cggccgccat gtccgcgctg  480
aggaagccaa agtacaacgg caagtgcatg cgcagcctga ttaggagcat cctcggcgag  540
acgagggcca agagcacgcc tctgaagaac gctctgctct cggacgtgtg cattggcacg  600
tccgccgcgc cgacctacct cccggcgcac tacttccaga ctgaagacgc caacggcaag  660
gagcgcgaat acaacctcat cgacggcggt gtggcggcca acaacccgac gatggttgcg  720
atgacgcaga tcaccaaaaa gatgcttgcc agcaaggaca aggccgagga gctgtaccca  780
gtgaagccgt cgaactgccg caggttcctg gtgctgtcca tcgggacggg gtcgacgtcc  840
gagcagggcc tctacacggc gcggcagtgc tcccggtggg gtatctgccg gtggctccgc  900
aacaacggca tggcccccat catcgacatc ttcatggcgg ccagctcgga cctggtggac  960
atccacgtcg ccgcgatgtt ccagtcgctc cacagcgacg gcgactacct gcgcatccag  1020
gacaactcgc tccgtggcgc cgcggccacc gtggacgcgg cgacgccgga gaacatgcgg  1080
acgctcgtcg ggatcgggga gcggatgctg gcacagaggg tgtccagggt caacgtggag  1140
acagggaggt acgaaccggt gactggcgaa ggaagcaatg ccgatgccct cggtgggctc  1200
gctaggcagc tctccgagga gaggaaaaca aggctcgcgc gccgcgtgtc tgccatcaac  1260
ccaagaggct ctagatgtgc gtcgtacgat atctaagaca agtggcttta ctgtcagtca  1320
catgcttgta aataagtaga ctttatttta ataaaacata aaaatatata t           1371

SEQ ID NO: 115         moltype = AA  length = 401
FEATURE                Location/Qualifiers
source                 1..401
                       mol_type = protein
                       organism = Zea mays
SEQUENCE: 115
MASYSSRRPC NTYSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                     401

SEQ ID NO: 116         moltype = AA  length = 401
FEATURE                Location/Qualifiers
source                 1..401
                       mol_type = protein
                       organism = Zea mays
SEQUENCE: 116
MASYSSRRPC NTCSTKAMAG SVVGELVVLG QRVTVLTVDG GGVRGLIPGT ILAFLEARLQ  60
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                     401

SEQ ID NO: 117         moltype = AA  length = 401
FEATURE                Location/Qualifiers
source                 1..401
                       mol_type = protein
                       organism = Zea mays
SEQUENCE: 117
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM ENCLRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                     401

SEQ ID NO: 118         moltype = AA  length = 401
FEATURE                Location/Qualifiers
source                 1..401
                       mol_type = protein
                       organism = Zea mays
SEQUENCE: 118
MASYSSRRPC NTCSTKAMAG SVVGEPVVLG QRVTVLTVDG GGVRGLIPGT ILAFLEARLQ  60
```

```
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVT MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERRT RLARRVSAIN PRGSRCASYD I                     401

SEQ ID NO: 119         moltype = AA  length = 401
FEATURE                Location/Qualifiers
source                 1..401
                       mol_type = protein
                       organism = Zea mays
SEQUENCE: 119
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENIR TLVGIGERML AQRVSRVNVE TGRYEPVTGE  360
GSNADALGGL ARQLSEERRT RLARRVSAIN PRGSRCASYD I                     401

SEQ ID NO: 120         moltype = AA  length = 401
FEATURE                Location/Qualifiers
source                 1..401
                       mol_type = protein
                       organism = Zea mays
SEQUENCE: 120
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVIGE  360
GSNADALGGL ARQLSEERRT RLARRVSAIN PRGSRCASYD I                     401

SEQ ID NO: 121         moltype = AA  length = 401
FEATURE                Location/Qualifiers
source                 1..401
                       mol_type = protein
                       organism = Zea mays
SEQUENCE: 121
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM ENCPRIFPQK  120
SRLAAAMSAL RKPKYNGKCM RSLIRSILGE TRAKSTPLKN ALLSDVCIGT SAAPTYLPAH  180
YFQTEDANGK EREYNLIDGG VAANNPTMVA MTQITKKMLA SKDKAEELYP VKPSNCRRFL  240
VLSIGTGSTS EQGLYTARQC SRWGICRWLR NNGMAPIIDI FMAASSDLVD IHVAAMFQSL  300
HSDGDYLRIQ DNSLRGAAAT VDAATPENMR TLVGIGERML AQRVSRVNVE TGRYEPVTGE  360
GSNADALGGL ARQLSEERKT RLARRVSAIN PRGSRCASYD I                     401

SEQ ID NO: 122         moltype = AA  length = 379
FEATURE                Location/Qualifiers
source                 1..379
                       mol_type = protein
                       organism = Zea mays
SEQUENCE: 122
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVENR                                              379

SEQ ID NO: 123         moltype = AA  length = 396
FEATURE                Location/Qualifiers
source                 1..396
                       mol_type = protein
                       organism = Zea mays
SEQUENCE: 123
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGR TGDWRRKQCR CPRWAR                           396

SEQ ID NO: 124         moltype = AA  length = 379
FEATURE                Location/Qualifiers
```

```
source                1..379
                      mol_type = protein
                      organism = Zea mays
SEQUENCE: 124
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVENR                                               379

SEQ ID NO: 125        moltype = AA  length = 394
FEATURE               Location/Qualifiers
source                1..394
                      mol_type = protein
                      organism = Zea mays
SEQUENCE: 125
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETTG DWRRKQCRCP RWAR                              394

SEQ ID NO: 126        moltype = AA  length = 395
FEATURE               Location/Qualifiers
source                1..395
                      mol_type = protein
                      organism = Zea mays
SEQUENCE: 126
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGT GDWRRKQCRC PRWAR                             395

SEQ ID NO: 127        moltype = AA  length = 393
FEATURE               Location/Qualifiers
source                1..393
                      mol_type = protein
                      organism = Zea mays
SEQUENCE: 127
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETTG DWRRKQCRCP RWA                               393

SEQ ID NO: 128        moltype = AA  length = 395
FEATURE               Location/Qualifiers
source                1..395
                      mol_type = protein
                      organism = Zea mays
SEQUENCE: 128
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGT GDWRRKQCRC PRWAR                             395

SEQ ID NO: 129        moltype = AA  length = 398
FEATURE               Location/Qualifiers
source                1..398
                      mol_type = protein
                      organism = Zea mays
SEQUENCE: 129
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
```

```
MAPIIDIFMA ASSDLVDIHV AAMFQSLHSD GDYLRIQDNS LRGAAATVDA ATPENMRTLV  360
GIGERMLAQR VSRVNVETRE VRTGDWRRKQ CRCPRWAR                          398

SEQ ID NO: 130          moltype = AA  length = 398
FEATURE                 Location/Qualifiers
source                  1..398
                        mol_type = protein
                        organism = Zea mays
SEQUENCE: 130
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETRE VRTGDWRRKQ CRCPRWAR                          398

SEQ ID NO: 131          moltype = AA  length = 384
FEATURE                 Location/Qualifiers
source                  1..384
                        mol_type = protein
                        organism = Zea mays
SEQUENCE: 131
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETKG GTNR                                         384

SEQ ID NO: 132          moltype = AA  length = 383
FEATURE                 Location/Qualifiers
source                  1..383
                        mol_type = protein
                        organism = Zea mays
SEQUENCE: 132
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGG TNR                                          383

SEQ ID NO: 133          moltype = AA  length = 396
FEATURE                 Location/Qualifiers
source                  1..396
                        mol_type = protein
                        organism = Zea mays
SEQUENCE: 133
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGR TGDWRRKQCR CPRWAR                            396

SEQ ID NO: 134          moltype = AA  length = 396
FEATURE                 Location/Qualifiers
source                  1..396
                        mol_type = protein
                        organism = Zea mays
SEQUENCE: 134
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGR TGDWRRKQCR CPRWAR                            396

SEQ ID NO: 135          moltype = AA  length = 395
FEATURE                 Location/Qualifiers
source                  1..395
                        mol_type = protein
                        organism = Zea mays
SEQUENCE: 135
```

```
MASYSSRRPC NTCSTKAMAG SVVGEPVVLG QRVTVLTVDG GGVRGLIPGT ILAFLEARLQ  60
ELDGPEARLA DYFDYIAGTS TGGLITAMLT APGKDKRPLY AAKDINHFYM QNCPRIFPQK  120
SRLAAAMSAL RKPKYNGKCM RSLIRSILGE TRVSETLTNV IIPAFDIRLL QPIIFSTYDA  180
KSTPLKNALL SDVCIGTSAA PTYLPAHYFQ TEDANGKERE YNLIDGGVAA NNPTMVAMTQ  240
ITKKMLASKD KAEELYPVNP SNCRRFLVLS IGTGTSTSEQG LYTARQCSRW GICRWLRNNG  300
MAPIIDIFMA ASSDLVDIHV AAMFQSLHSD GDYLRIQDNS LRGAAATVDA ATPENMRTLV  360
GIGERMLAQR VSRVNVETGT GDWRRKQCRC PRWAR                            395

SEQ ID NO: 136         moltype = AA  length = 437
FEATURE                Location/Qualifiers
source                 1..437
                       mol_type = protein
                       organism = Sorghum bicolor
SEQUENCE: 136
MATYYSSRRP CNACSTKAMA GSVVGEPVVL GQRVTVLTVD GGGIRGLIPG TILAFLEARL  60
QELDGPEVRL ADYFDYIAGT STGGLITAML TAPGKDRRPL YAAKDINQFY MENCPRIFPQ  120
KSSRLAAAMS ALRKPRYNGK CLRNLIMSML GETRVSDTLT NVIIPTFDVR LLQPIIFSTY  180
DAKSMPLKNA LLSDVCIGTS AAPTYLPAHY FQTKDAGSGK EREYNLIDGG VAANNPTMVA  240
MTQITKKMLA SKEKAEELYP VKPWNCRKFL VLSIGTGSTS EQGLYTARQC SRWGICRWIR  300
NNGMAPIIDI FMAASSDLVD IHVAAMFQSL HSDGDYLRIQ DNSLHGAAAT VDAATPENMR  360
TLVGIGERML AQRVSRVNVE TGRYEPVPGE GSNADALAGI ARQLSEERRT RLARRTSAIV  420
SSGGASRRTC ASKVSNV                                                437

SEQ ID NO: 137         moltype = AA  length = 421
FEATURE                Location/Qualifiers
source                 1..421
                       mol_type = protein
                       organism = Setaria italica
SEQUENCE: 137
MASYSSRRPC NACRTKAMAG SVVGEPVVPG QRVTVLTIDG GGIRGLIPGT ILAFLEARLQ  60
ELDGPEARLA DYFDCIAGTS TGGLITAMIT TPGEDKRPLF AARDINRFYF DNCPRIFPQS  120
RSSLAAAMSA LRKPRYNGKY LRSTIRSMLG ETRVSDALTN VVIPTFDIKL IQPIIFSTYD  180
VKNMPLKNAL LSDVCISTSA APTYLPAHYF QIQDAGGKTR EYNLIDGGVA ANNPTMVAMT  240
QITKMMLAKD KEELYPVKPE DCRKFLVLSI GTGSTSDEGL FTARQCSRWG VVRWLRNNGM  300
APIIDIFMAA SSDLVDIHAA VLFQSLHSDG HSLRGAAATV DAATPENMRT LVGIGERMLA  360
QRVSRVNVET GRYEPVPGEG SNADALVALA RQLSDERRAR IARRAAAACA GGSRCCSPVK  420
T                                                                 421

SEQ ID NO: 138         moltype = AA  length = 422
FEATURE                Location/Qualifiers
source                 1..422
                       mol_type = protein
                       organism = Hordeum vulgare
SEQUENCE: 138
MASYWCRRPC ESCSTRAMAG SVVGQPVAPG QRVTVLTIDG GGIRGLIPGT ILAFLEARLQ  60
ELDGPDARLA DYFDCIAGTS TGGLITAMLT APGQDGRPLF AAKDVNRFYL DNGPYIFPQR  120
RCALAAVTAS LRRPRYSGKY LHGKIRSMLG ETRLCDALTD VVIPTFDVKL LQPIIFSTYD  180
ARNMPLKNAR LADICIGTSA APTYLPAHHF HTQDDNGKER EYNLIDGGVA ANNPTMVTMT  240
QITKKMMVKD REELYPVKPS DCGKFLVLSI GTGSTSDQGL YTAKQCSQWG IIRWLRNKGM  300
APIIDIFMAA SSDLVDIHAA VLFQSLHSDG NYLRIQDNSL HGPAATVDAA TPENMAELLR  360
IGERMLAQRV SRVNVETGRY EEIRGAGSNA DALAGFAKQL SDERRTRLGR RRVGAGRLKS  420
RR                                                                422

SEQ ID NO: 139         moltype = AA  length = 423
FEATURE                Location/Qualifiers
source                 1..423
                       mol_type = protein
                       organism = Brachypodium distachyon
SEQUENCE: 139
MASYACRRPC ESCRTRAMAG GVVGEPTTPG QRVTVLTIDG GGIRGLIPGT ILAFLEDRLQ  60
ELDGPDARLA DYFDCIAGTS TGGLITAMIT APGEEGRPLF AAEDINRFYL DNGPQIFPQK  120
RSSLMSVLAS LTRPRYNGKF LHGKIRSMLG ETRVCDTLTD VVIPTFDVRL LQPIIFSTYD  180
AKSMPLKNAL LSDVCISTSA APTFLPAHYF QTEDDNGKVR EYNLIDGGVA ANNPTMVAMT  240
QITKKIMAKD KEELYPVKPS DCGKFLVLSI GTGSTSDQGL YTAKQCSRWG IIRWLRNKGM  300
APIIDIFMAA SSDLVDIHAA VLFQSLHSDG DCYLRIQDNS LRGAAATVDT ATPDNMRELV  360
RIGERMLAQR VSKVNVETGR YEEMQGAGTN ADALAGFARQ LSDERRARFG PRDGAPANGK  420
SRC                                                               423

SEQ ID NO: 140         moltype = AA  length = 414
FEATURE                Location/Qualifiers
source                 1..414
                       mol_type = protein
                       organism = Oryza sativa
SEQUENCE: 140
MAGCVVGEPA SAPGQRVTLL AIDGGGIRGL IPGTILAFLE ARLQELDGPD ARLADYFDCI  60
AGTSTGGLIT AMLAAPGDHG RPLFAASDIN RFYLDNGPRI FPQKRCGMAA AMAALTRPRY  120
NGKYLQGKIR KMLGETRVRD TLTNVVIPTF DVRLLQPTIF STYDAKSMPL KNALLSDICI  180
STSAAPTYLP AHCFQTTDDA TGKVREFDLI DGGVAANNPT MVAMTQITKK IMVKDKEELY  240
PVKPSDCGKF LVLSLGTGST SDQGMYTARQ CSRWGIVRWL RNKGMAPIID IFMAASSDLV  300
```

-continued

```
DIHAAVMFQS LHSDGDYLRI QDNTLHGDAA TVDAATRDNM RALVGIGERM LAQRVSRVNV  360
ETGRYVEVPG AGSNADALRG FARQLSEERR ARLGRRNACG GGGEGEPSGV ACKR        414

SEQ ID NO: 141         moltype = AA  length = 275
FEATURE                Location/Qualifiers
source                 1..275
                       mol_type = protein
                       organism = Triticum aestivum
SEQUENCE: 141
MLGETRLSDA LTDVVIPTFD VKLLQPIIFS TYDAKSMPLK NARLADVCIG TSAAPTYLPA  60
HHFHTHDGNG KEREYNLIDG GVAANNPTMV AMTQITKKMM GKDREELYPV EPSDCGKFLV  120
LSVGTGSTSD QGLYTAKQCS QWGIISWLRN KGMAPIIDIF MAASSDLVDI HAAVLFQSLH  180
SDANYLRIQD NSLHGPAATV DAATPENMAE LLRIGERMLA QRVSRVNVET GRYEEVKGAG  240
NNADALAGFA RQLSDERRTR LGSRRGGAGR LKSSR                             275

SEQ ID NO: 142         moltype = AA  length = 416
FEATURE                Location/Qualifiers
source                 1..416
                       mol_type = protein
                       organism = Musa acuminata
SEQUENCE: 142
MASDQTPPAT ADAPISTPPP SFGKRVTVLC IDGGGVRGLI PATIIAFLEA ELQKLDGPEA  60
RIADYFDVIA GTSTGGLVTA MLTAPNKEKR PLFAAKDIVQ FYLDNSPKIF PQKNAGLFNS  120
ALNLVGAVSG PKYDGKYLHA IIRQLLGDTR LSQTLTNVVI PTFDIKFLQP TIFSTYQTKS  180
TPLKDALLSD ICIGTSAAPT YLPGHYFETK DDNGNKRSFN LVDGGVAANN PTLTAMTEVS  240
KEILLSNPDF FSYQPVEYDR FLVISLGTGA PKQEEKFTAQ ESAKWGVLGW LLNKGTTPLI  300
DIFTQASADM VDIHASVLFQ ALNKGKNYLR IEDDTLTGQT SSVDVSTKKN LQDLVDIGNS  360
LLKKPVSRVN IETGHSEAVD GEGTNEAALT GFAKKLSDEK RRRQSKQLTS SDATQH      416

SEQ ID NO: 143         moltype = AA  length = 402
FEATURE                Location/Qualifiers
source                 1..402
                       mol_type = protein
                       organism = Elaeis guineensis
SEQUENCE: 143
MGSNESPVAN PPPCKGKVVT ILSIDGGGVR GIIPGTILEF LEAKLQELDG PDARIADYFD  60
IIAGTSTGGL VTTMLTAPNK DNRPLFSAKD IIQFYLENCP KIFPQRTGLL AGALNLFGAV  120
SGPKYDGKFL HSKVKELLGD TKLHQTLTNI VIPAFDIKLL QPVIFSTFET KTDPSKDALL  180
SDICISTSAA PTYLPAHYFE TKDSQGKTRS FNLVDGGVAA NNPMLIATSQ ITKQIFWNNE  240
DFSKFKPTDF AKFLVVSLGT GSPKQEQKFT APESAKWGLL GWLQNKGSTP IIDIFSQSSA  300
DMVDIHASIL FQALRSEKNY LRIQDDTLEG DTASVDVSTS ENLRKLVQVG QDLLKKPVSR  360
VNLETGVSEA CDVEGTNEDA LIRFAKMLSN ERKSRNAKMS AA                     402

SEQ ID NO: 144         moltype = AA  length = 407
FEATURE                Location/Qualifiers
source                 1..407
                       mol_type = protein
                       organism = Arabidopsis thaliana
SEQUENCE: 144
MQMDSPKSPL QPPTYGNLVT ILSIDGGGIR GLIPAVILGF LESELQKLDG EEARLADYFD  60
VIAGTSTGGL VTAMLTAPNK EGRPLFAASE IKDFYLEQCP KIFPQDHFPF SAAKKLVKSL  120
TGPKYDGKYL HQLIHAKLGD TKLSQTLTNV VIPTFDIKHL QPTIFSSYEV KNHPLKDAAL  180
ADIAISTSAA PTYLPAHFFK VEDLNGNAKE YNLIDGGVAA NNPALLAIGE VTNEISGGSS  240
DFFPIRPNDY GRFLVLSLGT GNHKAEEKFN AKEVAGWGLL NWLTHDNSTP IIDAFSQASS  300
DMVDFHLSAV FRALHSEANY IRIQDDTLTG DAASVDIATV ENLDILAKTG DELLKKPVAR  360
VNLDSGCNEN AYETTNEHAL IKLAGILSKE KKIRDIRSPH AKAPIRI                407
```

HAPLOID INDUCTION COMPOSITIONS AND METHODS FOR USE THEREFOR

STATEMENT OF PRIORITY

This application is a divisional of U.S. application Ser. No. 17/691,549, now U.S. Pat. No. 12,035,666, and claims the benefit thereof under 35 U.S.C. § 120 and 37 C.F.R. § 1.53 (b), which is a divisional of U.S. patent application Ser. No. 17/174,515, now U.S. Pat. No. 11,840,697, which is a divisional of U.S. patent application Ser. No. 16/218,529, now U.S. Pat. No. 10,954,523, which is a divisional of U.S. patent application Ser. No. 15/586,649, now U.S. Pat. No. 10,190,125, which is a divisional of U.S. patent application Ser. No. 14/212,504, now U.S. Pat. No. 9,677,082, which itself claims the benefit, under 35 U.S.C. § 119(e), of U.S. Provisional Application No. 61/852,428 filed on Mar. 15, 2013, the entire contents of all are incorporated by reference herein.

STATEMENT REGARDING ELECTRONIC FILING OF A SEQUENCE LISTING

A Sequence Listing in XML format, submitted under 37 C.F.R. § 1.821, entitled 80225 Div6_ST26.xml, 598 kilobytes in size, generated on Nov. 13, 2023 and filed via EFS-Web, is provided in lieu of a paper copy. This Sequence Listing is hereby incorporated herein by reference into the specification for its disclosures.

TECHNICAL FIELD

The presently disclosed subject matter relates to the diagnostic detection of haploid induction (HI) or its absence and/or presence in plants which are, or are not haploid inducers. More particularly, the presently disclosed subject matter relates to nucleic acids that can be employed for inducing HI in plants and/or the biological activities which can be modified in order to produce or prevent HI in either a plant that would otherwise exhibit HI or in a plant that would otherwise not exhibit HI. Even more particularly, the presently disclosed subject matter relates to a nucleic acid molecule that encodes a biologically active molecule as well as methods for using the same to regulate HI in plants.

BACKGROUND

Maize breeders have been crossing inbred parent lines, one acting as a male and one as a female to form hybrid seed. The process of developing inbred parent lines which are substantially homozygous usually required a hybrid cross to be selected and self-pollinated (selfed) for numerous generations to become nearly homozygous. This was a time consuming and expensive process. To shorten the time to develop homozygous inbreds in maize, maize breeders have been using a process of using a haploid inducer line to induce haploid seed on a hybrid parent. The chromosomes of the haploid plants are doubled to form double haploid homozygous inbred lines.

A high haploid induction rate allows a higher frequency of haploid seeds to be formed on the parent plant of interest. The parent plants can be pre-screened with genetic markers associated with desired traits or phenotypic observed traits to enrich the genetic potential of the parent plants. When these desired parent plants are pollinated by a haploid inducer that has a higher haploid induction rate, a higher potential of desired doubled haploids can be obtained with the desired genotype and phenotype.

Although the doubled haploid process resulted in faster production of homozygous inbreds, the volume of doubled haploid inbreds that could be produced was limited. The inducer lines had a low frequency of induction of haploids. A number of known haploid-inducing maize lines exist including but not limited to: stock 6, MHI (Moldovian Haploid Inducer), indeterminate gametophyte (ig) mutation, KEMS, RWK, ZEM, ZMS, KMS. The standard inducer lines such as Stock 6 were inducing only 1-3% haploid seeds. Induction of haploids was a rate limiting step in the process of producing doubled haploid lines.

Haploid induction (HI) is a class of plant phenomena characterized by loss of the male inducer chromosomes during embryo development. WO2012/030893 describes a slightly different region of chromosome (1) that is found responsible for haploid induction. The identified markers in the region responsible for haploid induction and increased haploid induction was described as being between 48,249, 509-51,199,249 which is associated with a public marker umc1169 that has the physical position of (60,213,661). This region apparently aligns with the Haploid Induction region in Stock 6. Dong et al. (2013) Theor. Appl. Genet. 126: 1713-1720 describe a QTL located in bin 1.04 which explains up to 66% of the genotypic variance for haploid induction rate.

Haploid induction has been observed in numerous plant species, such as sorghum, rice, and other grasses. The HI appears to be a result of rearrangements of, mutations in, and/or recombinations, insertion, or deletions within a region of chromosome 1. Purported HI-lines have been studied and roughly identified. However, experimental evidence demonstrating a causative genetic agent of HI in maize has not been presented. Nor have the markers listed herein that associate with this trait been previously identified.

The presently disclosed subject matter provides isolated cDNA. In some embodiments, the isolated cDNA are selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

In other embodiments, a synthetic hairpin nucleic acid construct comprising between 15 and 1000 nucleotides from SEQ ID NO. 33, 37, 52 or 53 and the antisense-complement thereof, such that the first and the second polynucleotide sequences hybridize when transcribed into a ribonucleic acid to form the hairpin-like double stranded ribonucleotide molecule. In further embodiments, the synthetic hairpin nucleic acid construct is selected from the group consisting of SEQ ID NC): 60 and SEQ ID NO: 61.

In other embodiments, an expression cassette for RNAi comprises a promoter operably linked to the synthetic hairpin. In further embodiments, the promoter is a constitutive promoter, optionally a maize ubiquitin-1 promoter, a rice actin-1 promoter, a rice ubiquitin-3 promoter, a rice alpha tubulin (tubA1) promoter, a cauliflower mosaic virus (CaMV) 35S promoter, a cestrum yellow leaf curling virus (CmYLCV) CMP promoter, a super MAS promoter, a sorghum ubiquitin-3 promoter, or a sugarcane ubiquitin-4 promoter. In other embodiments, the promoter is a stamen-, anther-, and/or pollen-specific promoter, optionally selected from the group consisting of SEQ ID NO: 58, a *Triticum aestivum* P19 promoter, a maize B200 promoter, a maize prCDPK-01 promoter, a maize prCDPK-02 promoter, a rice alpha-N-acetylglucosaminidase (prOsANG) promoter, a rice MADS box gene promoter (optionally a prOsMADS1 promoter, a prOsMADS2 promoter, a prOsMADS6 promoter, a prOsMADS14 promoter, or a prOsMADS16 promoter), a rice anther specific-promoter (optionally a prRA8 promoter or a prOsG6 promoter). In other embodiments, the expression vector may optionally comprise a terminator. In further embodiments, the terminator may be SEQ ID NO: 59. In some embodiments consist of a plant comprising hairpin nucleic acid construct of the previous embodiments. This plant could be a monocot such as a maize plant.

Some embodiments consist of a method of creating a new haploid inducer plant with a silenced patatin-like phospholipase 2A, comprising transcribing a polynucleotide sequence capable of silencing the patatin-like phospholipase 2A, wherein said polynucleotide sequence is selected from the group consisting of: a polynucleotide sequence comprising the nucleic acid sequence set forth in SEQ ID NOs 33, 37, 52, 53 or the complement thereof, a functional fragment comprising at least 15 contiguous bases of any one of SEQ ID NOs 33, 52, 53 or the complement thereof, a polynucleotide sequence having at least 95% sequence identity as determined using the BLASTN alignment tool to the nucleic acid sequence set forth in any one of SEQ ID NOs 33, 37, 52, 53 or the complement thereof, and a double-stranded ribonucleotide sequence produced from the expression of a polynucleotide sequence of any one of the above polynucleotide sequences, wherein silencing of the patatin-like phospholipase 2A creates a new haploid inducer plant.

Other embodiments are a plant made by the above method. The plant may be a maize plant or other monocot. Other embodiments are a method of inducing haploid embryos by using the pollen of the plant made by the above method to fertilize another plant, wherein the fertilization induces haploid embryos. Other embodiments are a method of identifying a maize plant that comprises a genotype associated with an increased haploid induction phenotype, comprising: isolating DNA from a maize plant, providing a reaction mixture comprising the DNA from a maize plant, the pair of primers comprising SEQ ID NO: 64 and SEQ ID NO 65 wherein the first primer is complementary to a sequence on the first strand of the target DNA and the second primer is complementary to a sequence on the second strand of the target DNA, Taq polymerase, and a plurality of free nucleotides comprising adenine, thymine, cytosine and guanine; heating the reaction mixture to a first predetermined temperature for a first predetermined time to separate the strands of the target DNA from each other; cooling the reaction mixture to a second predetermined temperature for a second predetermined time under conditions to allow the first and second primers to hybridize with their complementary sequences on the first and second strands of the target DNA, and to allow the Taq polymerase to extend the primers; and repeating steps (b) and (c) at least 20 times, wherein an amplification product of about 822 nucleotides indicates a maize plant that comprises a genotype associated with an increased haploid induction phenotype.

Some embodiments consist of an expression cassette for expression of a fertility restoring polypeptide in a plant, the expression cassette comprising an isolated nucleic acid of SEQ ID NO. 33 or 52 operably linked to a promoter that regulates transcription of the isolated nucleic acid of SEQ ID NO. 33 or 52 in a plant cell and/or tissue of interest, wherein the isolated cDNA of claim 1 encodes an amino acid sequence that is at least 95% identical to SEQ ID NO: 54 or 55, optionally wherein the percent identity is calculated over the entire length of SEQ ID NO: 54 or 55.

Other embodiments consist of a kit for detecting the presence of absence of a HI-inducing allele in a plant, the kit comprising one or more nucleic acid- and/or amino acid-based reagents derived from the maize HI locus or from a locus linked thereto wherein the one or more nucleic acid- and/or amino acid-based reagents are designed to be employed in a nucleic acid- and/or amino acid-based assay for the presence or absence in the plant of: a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33; a nucleic acid having at least 95% identity over nucleotides 91-1452 of SEQ ID NO: 33; a nucleic acid that is the reverse complement of either of (a) or (b); and/or a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57, or nucleic acid comprising nucleotides 1230-1233 of SEQ ID NO: 53.

In some embodiments, the isolated nucleic acids are selected from the group consisting of: a sequence having at least 90% identity to the listed SEQ ID NOs which comprise at least one sequence evidencing an association with a haploid inducing trait by its presence or absence selected from the group consisting of genes identified as GRMZM2G305400, GRMZM2G082836, GRMZM2G382717, GRMZM2G120587, GRMZM2G471240, GRMZM2G866758, and GRMZM2G003530.

The presently disclosed subject matter also provides expression cassettes for expression of the gene products made by the gene which is absent in HI plants. In some embodiments, an expression cassette of the presently disclosed subject matter comprises a nucleic acid sequence as described herein as a synthetic hairpin nucleic acid construct comprising between 15 and 1000 nucleotides from SEQ ID NO: 33, SEQ ID NO: 37, SEQ ID NO: 52 or SEQ ID NO: 53 (such as, but not limited to SEQ ID NO: 60 or 61) operably linked to a promoter that regulates transcription of the isolated nucleic acid in a plant cell and/or tissue of interest, and/or an organelle or subcellular structure thereof. In some embodiments, the isolated nucleic acid present in the expression cassette encodes an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57. In some embodiments, the promoter is a native promoters associated with the genes within this haploid induction region (such as, but not limited to SEQ ID NO: 58). In some embodiments, constitutive promoter, which can optionally be selected from the group consisting of the native promoter, a constitutive promoter such as ZmUbi1, ZmUbi158, ZmUbi361, SbUbiCh3, SbUbiCh4, a maize ubiquitin-1 promoter, a rice actin-1 promoter, a rice ubiquitin-3 promoter, a cauliflower mosaic virus (CaMV) 35S promoter, a sorghum ubiquitin-3 promoter, or a sugarcane ubiquitin-4 promoter, or a promoter that is pollen specific. Examples of pollen promoters are shown in the art in pollen-specific expression cassettes. Pollen-specific genes have been described for maize (Lopez I, Anthony, R. G., Maciver, S. K., Jaing, C.-J., Khan, S., Weeds, A. G., Hussey, P. J. (1996). Pollen specific expression of maize genes encoding actin depolymerizing factor-like proteins. Proc Natl Acad Sci USA 93:7415-7420.) Such information can be used to identify other maize pollen-specific genes, and promoters and produce pollen-specific expression cassettes. In some embodiments, the expression cassette further comprises a transcription terminator operably linked to the promoter and/or coding sequence. Some embodiments are a promoter for anther, stamen or pollen specific expression comprising SEQ ID NO:58.

In some embodiments, the plant cell and/or tissue of interest is selected from the group consisting of a stamen cell, a microspore, a meiotic cell, a cell that differentiates into a stamen cell or a progeny cell thereof, an anther cell, a cell that differentiates into an anther cell or a progeny cell thereof. In some embodiments, the organelle or subcellular structure of the plant cell and/or tissue of interest is a microspore. Thus, in some embodiments, the promoter is a stamen-, anther-, and/or pollen-specific promoter, which in some embodiments is selected from the group consisting of a *Triticum aestivum* P19 promoter, a maize B200 promoter, a maize prCDPK-01 and prCDPK-02 promoter, a rice α-N-acetylglucosaminidase (prOsANG) promoter, a rice MADS box gene promoter (including, but not limited to a prOsMADS1 promoter, a prOsMADS2 promoter, a prOsMADS6 promoter, prOsMADS7 promoter a prOsMADS14 promoter, or a prOsMADS16 promoter), a rice anther-specific promoter (such as, but not limited to a prRA8 promoter or a prOsG6 promoter), a rice stamen-specific promoter (such as, but not limited to the promoters disclosed in U.S. Pat. No. 5,639,948); and a corn stamen-specific promoter (such as, but not limited to the promoters disclosed in U.S. Pat. No. 5,589,610). In some embodiments, the promoter is a promoter that is transcriptionally active in a plant mitochondrion. Exemplary such promoters include, but are not limited to those disclosed in Fey & Maréchal-Drouard, 1999 and Binder et al., 1996.

In some embodiments, the expression cassette further comprises a transcription terminator, optionally a Nos or ags terminator.

In some embodiments, the expression cassette further comprises a targeting peptide (TP) coding sequence that is operably linked to and in frame with a sequence that encodes an amino acid sequence that is at least 95% identical to SEQ ID NO: 54, SEQ ID NO: 55, SEQ ID NO: 56 or SEQ ID NO: 57.

The presently disclosed subject matter also provides vectors comprising an expression cassette as disclosed herein.

The presently disclosed subject matter also provides transgenic plant cells comprising the presently disclosed expression cassettes, as well as plants, plant parts, and seeds comprising or derived from the presently disclosed transgenic plant cells.

The presently disclosed subject matter also provides isolated polypeptides comprising amino acid sequences that are at least 95% identical to SEQ ID NO: 54, SEQ ID NO: 55, SEQ ID NO: 56 or SEQ ID NO: 57. In some embodiments, wherein the percent identity is calculated over the entire length of SEQ ID NO: 54, SEQ ID NO: 55, SEQ ID NO: 56 or SEQ ID NO: 57. In some embodiments, the isolated polypeptides comprise amino acid sequences that comprise all or substantially all of amino acids 1-429 of SEQ ID NO: 54 locus.

The presently disclosed subject matter also provides subsequences, amplicons, and informative fragments of SEQ ID NO: 33, SEQ ID NO: 37, SEQ ID NO: 52 or SEQ ID NO: 53, as well as allelic variations thereof, wherein the subsequences, amplicons, informative fragments, and/or allelic variations can be used to identify the presence or absence of an allele associated with HI in a plant, or plant tissue, or plant cell.

The presently disclosed subject matter also provides compositions comprising amplification primer pairs capable of amplifying plant nucleic acid templates to generate marker amplicons, wherein the marker amplicons correspond to markers comprising informative subsequences of any of SEQ ID NO: 33, SEQ ID NO: 37, SEQ ID NO: 52 or SEQ ID NO: 53, or of the listed SEQ ID NOs. from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), GRMZM2G003530, and GRMZM2G866758 (two) wherein the informative subsequences permit identification of the presence or absence of an allele associated with HI in plants. In some embodiments, the amplification primers are designed to amplify a subsequence of SEQ ID NO: 33, SEQ ID NO: 37, SEQ ID NO: 52 or SEQ ID NO: 53 (exemplary primers, but not limited to SEQ ID NO: 64, SEQ ID NO: 65, SEQ ID NO: 66 or SEQ ID NO: 67). The presently disclosed subject matter also provides methods for producing plants that exhibit a new or increased HI trait. In some embodiments, the methods comprise (a) transforming a plant cell with an expression cassette comprising a nucleic acid as disclosed herein to produce a transformed plant cell; and (b) generating a plant from the transformed plant cell.

The presently disclosed subject matter also provides methods for identifying the presence or absence of allele associated with HI in plants. In some embodiments, the methods comprise (a) obtaining a sample from the plant comprising genomic and/or nuclear DNA and/or an RNA product derived therefrom; (b) contacting the sample with a pair of primers that, when used in a nucleic acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences or haplotypes into plants. In some embodiments, the methods comprise crossing a first plant with a second plant to produce a third plant, wherein the genome of the first plant or the second plant comprises a nucleic acid sequence (in some embodiments a recombinant nucleic acid sequence) encoding a HI-associated gene product of the presently disclosed subject matter and selecting those plants that do not exhibit production of the gene product, or a gene product at substantially reduced levels. In some embodiments, the methods further comprise assaying the genome of the third plant for the presence or absence of the nucleic acid sequence (in some embodiments, the recombinant nucleic acid sequence) encoding the HI-associated gene product. A HI-associated gene product, can be a negative or positive association. In this instance the association is a negative association, i.e. the presence of the gene product is associated with the absence of the haploid induction trait. In some embodiments, the recombinant nucleic acid comprises SEQ ID NO: 33, SEQ ID NO: 37, SEQ ID NO: 52 or SEQ ID NO: 53, and/or encodes a polypeptide that is at least 95% identical to SEQ ID NO: 54, SEQ ID NO: 55, SEQ ID NO: 56 or SEQ ID NO: 57. In some embodiments, the genome of the third plant that is assayed is the third plant's genome.

The presently disclosed subject matter also provides methods for selecting $F_0$ parental plants predicted to produce haploid inducing plants that exhibit inducible HI traits. In some embodiments, the methods comprise identifying in the genome of an $F_0$ plant the present or absence of a nucleic acid comprising a nucleotide sequence selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 1-1452 of SEQ ID NO: 33; (c) a nucleic acid that is the reverse complement of either of (a) or (b); and (d) a nucleic acid that encodes a polypeptide comprising an amino acid sequence that is at least 95% identical to SEQ ID NO: 54, SEQ ID NO: 55, SEQ ID NO: 56 or SEQ ID NO: 57, optionally wherein the percent identity is calculated over the entire length of SEQ ID NO: 54, SEQ ID NO: 55, SEQ ID NO: 56 or SEQ ID NO: 57.

In some embodiments, the methods comprise identifying in the genome of an $F_0$ plant the present or absence of a nucleic acid comprising a nucleotide sequence selected from the group consisting of the listed SEQ ID NOs. 3, 9-46 from this 0.6 MB region which comprise at least one sequence evidencing an association with a haploid inducing trait in this by its presence or absence selected from the group consisting of genes identified as GRMZM2G305400, GRMZM2G082836, GRMZM2G382717, GRMZM2G120587, GRMZM2G471240 (two), and GRMZM2G866758 (two) wherein the nucleic acid has at least 90% identity to the selected SEQ ID NO. optionally wherein the percent identity is calculated over the entire length of the selected SEQ ID NO.

Thus, it is an object of the presently disclosed subject matter to identify and/or introgress and/or provide nucleic acids for inducing and/or inhibiting the HI trait in a plant.

BRIEF DESCRIPTION OF THE FIGURES

FIG. 7A: Pollen tube germination rate was similar in inducers and non-inducers (n=200). FIG. 7B: Initial pollen tube elongation was also similar (n=25). FIG. 7C: RWK but not RWK-NIL is subject to segregation distortion (SD) based on low (25%) trait transmission in germinated progeny (n=300). FIG. 7D: MTL/0 complementation lines also exhibit SD against mtl in germinated progeny (n=400). FIG. 7E: Venn diagram showing RNA-seq profiling results of two haploid inducer-near isogenic pairs (left, RWK versus RWK-NIL; right, NP2222-HI versus NP2222; red text, up-regulated; green text, down-regulated). Only 60 genes were found significantly changed in the same direction.

BRIEF DESCRIPTION OF THE SEQUENCE LISTING

SEQ ID NO: 1 is a cDNA nucleotide sequence from the maize NIL-genome of SEQ ID NO:3

Figure 1:
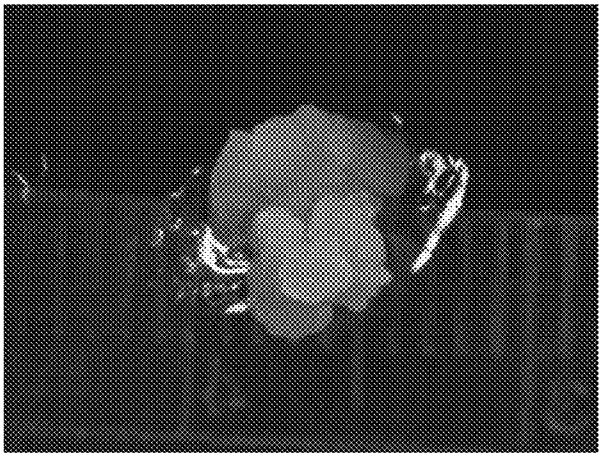
FIG. 1 shows a Maize callus transformed with an *agrobacterium* binary vector carrying the RNAi expression cassette comprising SEQ ID NO: 61 are surviving selection indicating successful transformation.

SEQ ID NO: 2 is an amino acid sequence of a polypeptide encoded by SEQ ID NO: 1 which is a cDNA from the NIL-genome designated GRMZM2G062320-B SEQ ID NO: 3 is the NIL-genome genomic nucleotide sequence SEQ ID NO: 4 is the sequence of ZmABP2-GRMZM2G062320 shown in the vector used in the tissue depicted in FIG. 1.

SEQ ID NOs: 5-8 are amino acid sequences for maize GRMZM2G062320-A, GRMZM2G062320-C, GRMZM2G062320-D, GRMZM2G062320-E SEQ ID NO: 9 GRMZM2G305400 gDNA (from B73 genome)

SEQ ID NO: 10 GRMZM2G305400 cDNA (from B73 genome)

SEQ ID NO: 11 GRMZM2G082836 gDNA (from the B73 genome)

SEQ ID NO: 12 GRMZM2G082836 cDNA1 (from the B73 genome)

SEQ ID NO: 13 GRMZM2G082836 cDNA2 (from the B73 genome)

SEQ ID NO: 14 GRMZM2G082836 cDNA3 (from the B73 genome)

SEQ ID NO: 15 GRMZM2G082836 gDNA (from the NIL genome)

SEQ ID NO: 16 GRMZM2G082836 gDNA (from the Stock 6 genome)

SEQ ID NO: 17 GRMZM2G082836 gDNA (from the RWK genome)

SEQ ID NO: 18 GRMZM2G382717 gDNA (from B73 genome)

SEQ ID NO: 19 GRMZM2G382717 cDNA2 (from B73 genome)

SEQ ID NO: 20 GRMZM2G382717 gDNA (from NIL genome)

SEQ ID NO: 21 GRMZM2G382717 gDNA (from RWK genome)

SEQ ID NO: 22 GRMZM2G382717 gDNA (991832 from Stock 6 genome)

SEQ ID NO: 23 GRMZM2G382717 gDNA (989131 from Stock 6 genome)

SEQ ID NO: 24 GRMZM2G382717 protein coding sequence (from RWK genome)

SEQ ID NO: 25 GRMZM2G120587 gDNA (from the B73 genome)

SEQ ID NO: 26 GRMZM2G120587 cDNA1 (from the B73 genome)

SEQ ID NO: 27 GRMZM2G120587 cDNA2 (from the B73 genome)

SEQ ID NO: 28 GRMZM2G120587 cDNA3 (from the B73 genome)

SEQ ID NO: 29 GRMZM2G120587 GDNA (from the Stock 6 genome)

SEQ ID NO: 30 GRMZM2G120587 GDNA (from the RWK genome)

SEQ ID NO: 31 GRMZM2G120587 GDNA (from the Stock 6/RWK genome)

SEQ ID NO: 32 GRMZM2G471240 gDNA (from the B73 genome)

SEQ ID NO: 33 GRMZM2G471240 cDNA long splice variant (from the B73 genome)

SEQ ID NO: 34 GRMZM2G471240 gDNA (from the NIL genome)

SEQ ID NO: 35 GRMZM2G471240 gDNA (from the maize Stock 6 genome)

SEQ ID NO: 36 GRMZM2G471240 gDNA (from the maize RWK genome)

SEQ ID NO: 37 GRMZM2G471240 cDNA short splice variant (from the Stock6/RWK genome)

SEQ ID NO: 38 GRMZM5G866758 gDNA (from the B73 genome)

SEQ ID NO: 39 GRMZM5G866758 cDNA1 (from the B73 genome)

SEQ ID NO: 40 GRMZM5G866758 cDNA2 (from the B73 genome)

SEQ ID NO: 41 GRMZM5G866758 cDNA-1780 (from the B73 maize genome)

SEQ ID NO: 42 GRMZM5G866758 gDNA (from the NIL maize genome)

SEQ ID NO: 43 GRMZM5G866758 cDNA (from the NIL genome)

SEQ ID NO: 44 GRMZM5G866758 gDNA (from the Stock 6 genome)

SEQ ID NO: 45 GRMZM5G866758 gDNA (from the RWK genome)

SEQ ID NO: 46 GRMZM5G866758 gDNA (from the Stock 6/RWK genome)

SEQ ID NO: 47 GRMZM2G382717 cDNA1 (from B73 genome).

SEQ ID NO: 48 GRMZM2G003530 gDNA (from B73 genome).

SEQ ID NO: 49 GRMZM2G003530 gDNA (from NIL genome).

SEQ ID NO: 50 GRMZM2G003530 gDNA (from RWK genome).

SEQ ID NO: 51 GRMZM2G003530 gDNA (from Stock 6 genome).

SEQ ID NO: 52 GRMZM2G471240 cDNA short splice variant (from the B73 genome)

SEQ ID NO: 53 GRMZM2G471240 cDNA long splice variant (from the RWK genome)

SEQ ID NO: 54 is an amino acid sequence of a polypeptide encoded by SEQ ID NO: 33

SEQ ID NO: 55 is an amino acid sequence of a polypeptide encoded by SEQ ID NO: 52

SEQ ID NO: 56 is an amino acid sequence of a polypeptide encoded by SEQ ID NO: 37

SEQ ID NO: 57 is an amino acid sequence of a polypeptide encoded by SEQ ID NO: 53

SEQ ID NO: 58 is the promoter of the GRMZM2G471240 gene

SEQ ID NO: 59 is the terminator of the GRMZM2G471240 gene

SEQ ID NO: 60 is a synthetic hairpin designed to SEQ ID NO 33 nt 450-547 with 2 mismatches, a spacer sequence and the reverse compliment of SEQ ID NO 33 nt 450-547

SEQ ID NO: 61 is a synthetic hairpin designed to SEQ ID NO 33 nt 797-987 with 2 mismatches, a spacer sequence and the reverse compliment of SEQ ID NO 33 nt 797-987

SEQ ID NO: 62 is the reverse compliment of SEQ ID NO 33

SEQ ID NO: 63 is the reverse compliment of SEQ ID NO 52

SEQ ID NO: 64 is primer rwk.F1

SEQ ID NO: 65 is primer rwk.R1

SEQ ID NO: 66 is primer nil.F1

SEQ ID NO: 67 is primer nil.R1

SEQ ID NO: 68 is the nucleotide sequence of unmutated GRMZM2G471240-NIL.

SEQ ID NO: 69 is the amino acid sequence encoded by SEQ ID NO: 68.

SEQ ID NO: 70 is the nucleotide sequence of GRMZM2G471240-mtl, comprising a 4 base pair insertion, herein renamed matrilineal.

SEQ ID NO: 71 is the amino acid sequence encoded by SEQ ID NO: 70.

SEQ ID NO: 72 is the nucleotide sequence for the TALEN-induced MTL mutation in Event 39A ID 22808-3954 allele 1.

SEQ ID NO: 73 is the nucleotide sequence for the TALEN-induced MTL mutation in Event 23A ID 22808-3924 allele 1.

SEQ ID NO: 74 is the nucleotide sequence for the TALEN-induced MTL mutation in Event 81A ID 22808-3932, Event 81A ID 22808-3317, and Event 81A ID 22808-3303.

SEQ ID NO: 75 is the nucleotide sequence for the TALEN-induced MTL mutation in Event 39A ID 22808-3954 allele 2.

SEQ ID NO: 76 is the nucleotide sequence for the TALEN-induced MTL mutation in Event 23A ID 22808-3924 allele 2.

SEQ ID NO: 77 is the nucleotide sequence for the TALEN-induced MTL mutation in Event 38A ID 22808-4108 allele 1.

SEQ ID NO: 78 is the nucleotide sequence for the CRISPR-induced MTL mutation in Event 18A ID 22807-4016.

SEQ ID NO: 79 is the nucleotide sequence for the CRISPR-induced MTL mutation in Event 27A ID 22807-4073 allele 1.

SEQ ID NO: 80 is the nucleotide sequence for the CRISPR-induced MTL mutation in Event 27A ID 22807-4081 allele 1.

SEQ ID NO: 81 is the nucleotide sequence for the CRISPR-induced MTL mutation in Event 76A ID 22873-3999.

SEQ ID NO: 82 is the nucleotide sequence for the CRISPR-induced MTL mutation in Event 32A ID 22873-3991.

SEQ ID NO: 83 is the nucleotide sequence for a CRISPR guide RNA.

SEQ ID NO: 84 is the nucleotide sequence for Os03g27610, the rice PLA ortholog.

SEQ ID NO: 85 is the cDNA sequence for SEQ ID NO: 84.

SEQ ID NO: 86 is the amino acid sequence encoded by SEQ ID NO: 85.

SEQ ID NO: 87 is the nucleotide sequence of unmutated GRMZM2G471240-B73.

SEQ ID NO: 88 is the nucleotide sequence of unmutated GRMZM2G471240-RWK.

SEQ ID NO: 89 is the nucleotide sequence of unmutated GRMZM2G471240-ST6.

SEQ ID NO: 90 is the amino acid sequence encoded by SEQ ID NO: 87.

SEQ ID NO: 91 is the amino acid sequence encoded by SEQ ID NO: 88.

SEQ ID NO: 92 is the amino acid sequence encoded by SEQ ID NO: 89.

SEQ ID NO: 93 is the nucleotide sequence for the expression cassette of construct 22466.

SEQ ID NO: 94 is the nucleotide sequence for the expression cassette of construct 22467.

SEQ ID NO: 95 is the nucleotide sequence for the expression cassette of construct 22503.

SEQ ID NO: 96 is the nucleotide sequence for the expression cassette of construct 22513.

SEQ ID NO: 97 is the nucleotide sequence for the expression cassette of construct 22807.

SEQ ID NO: 98 is the nucleotide sequence for the expression cassette of construct 22808.

SEQ ID NO: 99 is the nucleotide sequence for the expression cassette of construct 22873.

SEQ ID NO: 100 is the nucleotide sequence for the expression cassette of construct 23123.

SEQ ID NO: 101 is the nucleotide sequence for the expression cassette of construct 23501, rice gRNA target 1 dual guides.

SEQ ID NO: 102 is the nucleotide sequence for the expression cassette of construct 23501, rice gRNA target 1 single guide.

SEQ ID NO: 103 is the nucleotide sequence for the expression cassette of construct 23501, rice gRNA target 2 dual guides.

SEQ ID NO: 104 is the nucleotide sequence for the expression cassette of construct 23501, rice gRNA target 2 single guide.

SEQ ID NO: 105 is the nucleotide sequence for the TALEN-induced MTL mutation in Event 38A ID 22808-4108 allele 2.

SEQ ID NO: 106 is the nucleotide sequence for the CRISPR-induced MTL mutation in Event 27A ID 22807-4073 allele 2.

SEQ ID NO: 107 is the nucleotide sequence for the CRISPR-induced MTL mutation in Event 27A ID 22807-4081 allele 2.

SEQ ID NO: 108 is the nucleotide sequence for TILLING line 1139.

SEQ ID NO: 109 is the nucleotide sequence for TILLING line 3594.

SEQ ID NO: 110 is the nucleotide sequence for TILLING line 0505.

SEQ ID NO: 111 is the nucleotide sequence for TILLING line 2658.

SEQ ID NO: 112 is the nucleotide sequence for TILLING line 1983.

SEQ ID NO: 113 is the nucleotide sequence for TILLING line 2732.

SEQ ID NO: 114 is the nucleotide sequence for TILLING line 2414.

SEQ ID NO: 115 is the amino acid sequence encoded by SEQ ID NO: 108.

SEQ ID NO: 116 is the amino acid sequence encoded by SEQ ID NO: 109.

SEQ ID NO: 117 is the amino acid sequence encoded by SEQ ID NO: 110.

SEQ ID NO: 118 is the amino acid sequence encoded by SEQ ID NO: 111.

SEQ ID NO: 119 is the amino acid sequence encoded by SEQ ID NO: 112.

SEQ ID NO: 120 is the amino acid sequence encoded by SEQ ID NO: 113.

SEQ ID NO: 121 is the amino acid sequence encoded by SEQ ID NO: 114.

SEQ ID NO: 122 is the amino acid sequence encoded by SEQ ID NO: 72.

SEQ ID NO: 123 is the amino acid sequence encoded by SEQ ID NO: 73.

SEQ ID NO: 124 is the amino acid sequence encoded by SEQ ID NO: 74.

SEQ ID NO: 125 is the amino acid sequence encoded by SEQ ID NO: 75.

SEQ ID NO: 126 is the amino acid sequence encoded by SEQ ID NO: 76.

SEQ ID NO: 127 is the amino acid sequence encoded by SEQ ID NO: 77.

SEQ ID NO: 128 is the amino acid sequence encoded by SEQ ID NO: 78.

SEQ ID NO: 129 is the amino acid sequence encoded by SEQ ID NO: 79.

SEQ ID NO: 130 is the amino acid sequence encoded by SEQ ID NO: 80.

SEQ ID NO: 131 is the amino acid sequence encoded by SEQ ID NO: 81.

SEQ ID NO: 132 is the amino acid sequence encoded by SEQ ID NO: 82.

SEQ ID NO: 133 is the amino acid sequence encoded by SEQ ID NO: 105.

SEQ ID NO: 134 is the amino acid sequence encoded by SEQ ID NO: 106.

SEQ ID NO: 135 is the amino acid sequence encoded by SEQ ID NO: 107.

SEQ ID NO: 136 is the amino acid sequence for MTL ortholog found in *Sorghum bicolor.*

SEQ ID NO: 137 is the amino acid sequence for MTL ortholog found in *Setaria italica.*

SEQ ID NO: 138 is the amino acid sequence for MTL ortholog found in *Hordeum vulgare.*

SEQ ID NO: 139 is the amino acid sequence for MTL ortholog found in *Brachypodium distachyon.*

SEQ ID NO: 140 is the amino acid sequence for MTL ortholog found in *Oryza sativa* v. *indica.*

SEQ ID NO: 141 is the amino acid sequence for MTL ortholog found in *Triticum aestivum.*

SEQ ID NO: 142 is the amino acid sequence for MTL ortholog found in *Musa acuminata.*

SEQ ID NO: 143 is the amino acid sequence for MTL ortholog found in *Elaeis guineensis.*

SEQ ID NO: 144 is the amino acid sequence for MTL ortholog found in *Arabidopsis thaliana.*

DETAILED DESCRIPTION

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques and/or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. For example, the phrase "a cell" refers to one or more cells, and in some embodiments can refer to a tissue and/or an organ. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to all whole number values between 1 and 100 as well as whole numbers greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the discloses compositions, nucleic acids, polypeptides, etc. Accordingly, unless indicated to the contrary, the numerical parameters set forth in this specification and attached claims are approximations that can vary depending upon the desired properties sought to be obtained by the presently disclosed subject matter.

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D (e.g., AB, AC, AD, BC, BD, CD, ABC, ABD, and BCD). In some embodiments, one of more of the elements to which the "and/or" refers can also individually be present in single or multiple occurrences in the combinations(s) and/or subcombination(s).

As used herein, the phrase "associated with" refers to a recognizable and/or assayable relationship between two entities. For example, the phrase "associated with HI" refers to a trait, locus, gene, allele, marker, phenotype, etc., or the expression thereof, the presence or absence of which can influence an extent and/or degree at which a plant or its progeny exhibits HI. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with HI" refers to a marker whose presence or absence can be used to predict whether and/or to what extent a plant will display haploid induction.

The term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter.

With respect to the terms "comprising", "consisting essentially of", and "consisting of", where one of these three terms is used herein, the presently disclosed and claimed subject matter can include in some embodiments the use of either of the other two terms. For example, if a subject matter relates in some embodiments to nucleic acids that encode polypeptides comprising amino acid sequences that are at least 95% identical to a SEQ ID NO: 55. It is understood that the disclosed subject matter thus also encompasses nucleic acids that encode polypeptides that in some embodiments consist essentially of amino acid sequences that are at least 95% identical to that SEQ ID NO: 55 as well as nucleic acids that encode polypeptides that in some embodiments consist of amino acid sequences that are at least 95% identical to that SEQ ID NO: 55 Similarly, it is also understood that in some embodiments the methods for the disclosed subject matter comprise the steps that are disclosed herein, in some embodiments the methods for the presently disclosed subject matter consist essentially of the steps that are disclosed, and in some embodiments the methods for the presently disclosed subject matter consist of the steps that are disclosed herein.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombination events between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, SNPs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome (in some embodiments, including the nuclear genome, the mitochondrial genome, plastid genome or all three). Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety, or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the terms "informative fragment" and "informative subsequence" refer to nucleotide sequences comprising a fragment of a larger nucleotide sequence, wherein detecting of the presence of absence of the fragment allows for the detecting of the presence of absence of the larger nucleotide sequence. For example, an informative fragment of the nucleotide sequence of SEQ ID NO: 33 comprises a fragment of the nucleotide sequence of SEQ ID NO: 33 that permits the accurate identification of whether or not SEQ ID NO: 33 is present in a sample. This non HI locus lacks the 4 nucleotide insertion that is present in the HI germplasm as found in SEQ ID NO: 53 nucleotides 1230-1233. In some embodiments, an informative fragment of SEQ ID NO: 53 allows identification of the presence or absence of the HI locus. In some embodiments, informative fragments of SEQ ID NO: 53 containing nucleotides 1230-1233 allow identification of the presence or absence of the HI locus.

As used herein, the term "isolated" refers to a nucleotide sequence that is free of sequences that normally flank one or both sides of the nucleotide sequence in a plant genome. Thus, isolated nucleic acids include, without limitation, a recombinant DNA that exists as a separate molecule with no flanking sequences present, as well as a recombinant DNA that is incorporated into a vector, an autonomously replicating plasmid, or into the genomic DNA of a plant as part of a hybrid or fusion nucleic acid molecule.

As used herein, the term "linkage" refers to a phenomenon wherein alleles on the same chromosome tend to be transmitted together more often than expected by chance if their transmission were independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a HI locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a locus associated with HI). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., HI. The degree of linkage of a molecular marker to a phenotypic trait is measured, e.g., as a statistical probability of co-segregation of that molecular marker with the phenotype.

As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium. Linkage disequilibrium is most commonly assessed using the measure r2, which is calculated using the formula described by Hill & Robertson, 1968. When r2=1, complete linkage disequilibrium exists between the two marker loci, meaning that the markers have not been separated by recombination and have the same allele frequency. In some embodiments, values for r2 above 0.33 indicate sufficiently strong linkage disequilibrium to be useful for mapping. See Ardlie et al., 2002. Hence, alleles are in linkage disequilibrium when r2 values between pairwise marker loci are greater than or equal to about 0.33, 0.4, 0.5, 0.6, 0.7, 0.8, 0.9, or 1.0.

As used herein, the terms "marker", "genetic marker", and 'molecular marker" are used interchangeably to refer to an identifiable position on a DNA molecule (e.g., a chromosome or a nuclear genome) the inheritance of which can be monitored and/or a reagent that is used in methods for visualizing differences in nucleic acid sequences present at such identifiable positions on a DNA molecule. Thus, in some embodiments a marker comprises a known or detectable nucleic acid sequence. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS; Rafalski & Tingey, 1993), an amplified fragment length polymorphism (AFLP; Vos et al., 1995), a single nucleotide polymorphism (SNP) (Brookes, 1993), a sequence-characterized amplified region (SCAR; Paran & Michelmore, 1993), a sequence-tagged site (STS; Onozaki et al., 2004), a single-stranded conformation polymorphism (SSCP; Orita et al., 1989), an inter-simple sequence repeat (ISSR; Blair et al., 1999), an inter-retrotransposon amplified polymorphism (TRAP), a retrotransposon-microsatellite amplified polymorphism (REMAP; Kalendar et al., 1999) or an RNA cleavage product (such as a Lynx tag). A marker can be present in genomic (including but not limited to nuclear genomic and/or 1 genomic) or expressed nucleic acids (e.g., ESTs). In some embodiments, a marker is an informative fragment of SEQ ID NO: 33, SEQ ID NO: 37, SEQ ID NO: 52 or SEQ ID NO: 53 that permits the specific identification of nucleic acids comprising or lacking SEQ ID NO: 33, SEQ ID NO: 37, SEQ ID NO: 52 or SEQ ID NO: 53 in samples.

The term marker can also refer to nucleic acids used as probes or primers (e.g., primer pairs) for use in amplifying, hybridizing to, and/or detecting nucleic acid molecules according to methods well known in the art. In some embodiments, a nucleic acid marker that can be employed to detect the presence or absence of SEQ ID NO: 33, SEQ ID NO: 37, SEQ ID NO: 52 or SEQ ID NO: 53 is a primer pair that comprises a forward primer that comprises a subsequence of nucleotides of SEQ ID NO: 33, SEQ ID NO: 37, SEQ ID NO: 52 or SEQ ID NO: 53 and a reverse primer that is the reverse complement of a subsequence of nucleotides of SEQ ID NO: 33, SEQ ID NO: 37, SEQ ID NO: 52 or SEQ ID NO: 53 and/or is an amplicon that is generated by using such a primer pair to amplify a subsequence of SEQ ID NO: 33, SEQ ID NO: 37, SEQ ID NO: 52 or SEQ ID NO: 53 (i.e., the subsequence of SEQ ID NO: 33, SEQ ID NO: 37, SEQ ID NO: 52 or SEQ ID NO: 53 that comprises nucleotides, optionally including 1, 2, 3, 4, 5, 6, 7, 8, 9, 10, or more nucleotides of SEQ ID NO: 33, SEQ ID NO: 37, SEQ ID NO: 52 or SEQ ID NO: 53 that are 5' to and/or 3' to nucleotides selected nucleotides from the positions listed in the Table on Fine Mapping in Example 3 and a part of SEQ ID NO: 1-47).

As used herein, the terms "marker probe" and "probe" refer to a nucleotide sequence or nucleic acid molecule that can be used to detect the presence or absence of sequence within SEQ ID NO: 33, SEQ ID NO: 37, SEQ ID NO: 52 or SEQ ID NO: 53 (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization.

As used herein, the term "molecular marker" can be used to refer to a genetic marker, as defined above, or an encoded product thereof (e.g., a protein) used as a point of reference when identifying the presence/absence of a HI-associated locus. A molecular marker can be derived from genomic nucleotide sequences or from expressed nucleotide sequences (e.g., from an RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution (e.g., according to Watson-Crick base pairing rules). This term also refers to the genetic markers that indicate a trait by the absence of the nucleotide sequences complementary to or flanking the marker sequences, such as nucleotide sequences used as probes and/or primers capable of amplifying the marker sequence.

As used herein, the terms "nucleotide sequence", "polynucleotide", "nucleic acid sequence", "nucleic acid molecule", and "nucleic acid fragment" refer to a polymer of RNA or DNA that is single- or double-stranded, optionally containing synthetic, non-natural, and/or altered nucleotide bases. A "nucleotide" is a monomeric unit from which DNA or RNA polymers are constructed and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

As used herein, the term "nucleotide sequence identity" refers to the presence of identical nucleotides at corresponding positions of two polynucleotides. Polynucleotides have "identical" sequences if the sequence of nucleotides in the two polynucleotides is the same when aligned for maximum correspondence (e.g., in a comparison window). Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" for polynucleotides, such as about 50, 55, 60, 65, 70, 75, 80, 85, 90, 95, 98, 99 or 100 percent sequence identity, can be determined by comparing two optimally aligned sequences over a comparison window, wherein the portion of the polynucleotide sequence in the comparison window can include additions or deletions (i.e., gaps) as compared to the reference sequence for optimal alignment of the two sequences. In some embodiments, the percentage is calculated by: (a) determining the number of positions at which the identical nucleic acid base occurs in both sequences; (b) dividing the number of matched positions by the total number of positions in the window of comparison; and (c) multiplying the result by 100. Optimal alignment of sequences for comparison can also be conducted by computerized implementations of known algorithms, or by visual inspection. Readily available sequence comparison and multiple sequence alignment algorithms are, respectively, the Basic Local Alignment Search Tool (BLAST) and ClustalW/ClustalW2/Clustal Omega programs available on the Internet (e.g., the website of the EMBL-EBI). Other suitable programs include, but are not limited to, GAP, BestFit, Plot Similarity, and FASTA, which are part of the Accelrys GCG Package available from Accelrys, Inc. of San Diego, California, United States of America. See also Smith & Waterman, 1981; Needleman & Wunsch, 1970; Pearson & Lipman, 1988; Ausubel et al., 1988; and Sambrook & Russell, 2001.

One example of an algorithm that is suitable for determining percent sequence identity and sequence similarity is the BLAST algorithm, which is described in Altschul et al., 1990. In some embodiments, a percentage of sequence identity refers to sequence identity over the full length of one of the gDNA, cDNA, or the predicted protein sequences in the largest ORF of SEQ ID No: 33 being compared (e.g., the full length of any of SEQ ID NOs. 1-47 respectively). In some embodiments, a calculation to determine a percentage of nucleic acid sequence identity does not include in the calculation any nucleotide positions in which either of the compared nucleic acids includes an "N" (i.e., where any nucleotide could be present at that position).

The term "open reading frame" (ORF) refers to a nucleic acid sequence that encodes a polypeptide. In some embodiments, an ORF comprises a translation initiation codon, a translation termination (i.e., stop) codon, and the nucleic acid sequence there between that encodes the amino acids present in the polypeptide. The terms "initiation codon" and "termination codon" refer to a unit of three adjacent nucleotides ('codon') in a coding sequence that specifies initiation and chain termination, respectively, of protein synthesis (mRNA translation).

As used herein, the terms "phenotype," "phenotypic trait" or "trait" refer to one or more traits of a plant or plant cell. The phenotype can be observable to the naked eye, or by any other means of evaluation known in the art, e.g., microscopy, biochemical analysis, or an electromechanical assay. In some cases, a phenotype is directly controlled by a single gene or genetic locus (i.e., corresponds to a "single gene trait"). In the case of haploid induction use of color markers, such as R Navajo, and other markers including transgenes visualized by the presences or absences of color within the seed evidence if the seed is an induced haploid seed. The use of R Navajo as a color marker and the use of transgenes is well known in the art as means to detect induction of haploid seed on the female plant. In other cases, a phenotype is the result of interactions among several genes, which in some embodiments also results from an interaction of the plant and/or plant cell with its environment.

As used herein, the term "plant" can refer to a whole plant, any part thereof, or a cell or tissue culture derived from a plant. Thus, the term "plant" can refer to any of: whole plants, plant components or organs (e.g., leaves, stems, roots, etc.), plant tissues, seeds and/or plant cells.

A plant cell is a cell of a plant, taken from a plant, or derived through culture from a cell taken from a plant. Thus, the term "plant cell" includes without limitation cells within seeds, suspension cultures, embryos, meristematic regions, callus tissue, leaves, shoots, gametophytes, sporophytes, pollen, and microspores. The phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "primer" refers to an oligonucleotide which is capable of annealing to a nucleic acid target (in some embodiments, annealing specifically to a nucleic acid target) allowing a DNA polymerase and/or reverse transcriptase to attach thereto, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, one or more pluralities of primers are employed to amplify plant nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. In haploid induction the seed on the female parent is haploid, thus not a progeny of the inducing haploid line. The progeny of the haploid seed is what is the desired progeny. There is also the HI seed and subsequent plant and seed progeny of the haploid inducing plant. Both the haploid seed and the HI seed can be progeny. A progeny plant can be obtained by cloning or selfing a single parent plant, or by crossing two or more parental plants. For instance, a progeny plant can be obtained by cloning or selfing of a parent plant or by crossing two parental plants and include selfings as well as the $F_1$ or F2 or still further generations. An $F_1$ is a first-generation progeny produced from parents at least one of which is used for the first time as donor of a trait, while progeny of second generation ($F_2$) or subsequent generations ($F_3$, $F_4$, and the like) are specimens produced from selfings, intercrosses, backcrosses, and/or other crosses of $F_1$s, $F_2$s, and the like. An $F_1$ can thus be (and in some embodiments is) a hybrid resulting from a cross between two true breeding parents (i.e., parents that are true-breeding are each homozygous for a trait of interest or an allele thereof), while an $F_2$ can be (and in some embodiments is) a progeny resulting from self-pollination of the $F_1$ hybrids.

As used herein, the phrase "recombination" refers to an exchange of DNA fragments between two DNA molecules or chromatids of paired chromosomes (a "crossover") over in a region of similar or identical nucleotide sequences. A "recombination event" is herein understood to refer in some embodiments to a meiotic crossover.

As used herein, the term "reference sequence" refers to a defined nucleotide sequence used as a basis for nucleotide sequence comparison. In some embodiments, any of SEQ ID NOs: 1 and 3 can serve as a reference sequence for comparing to other sequences obtained from plants.

As used herein, the term "regenerate", and grammatical variants thereof, refers to the production of a plant from tissue culture.

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances.

Longer sequences typically hybridize specifically at higher temperatures. An extensive guide to the hybridization of nucleic acids is found in Sambrook & Russell, 2001. Generally, stringent conditions are selected to be about 5-10° C. lower than the thermal melting point (T m) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Exemplary stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides).

Stringent conditions can also be achieved with the addition of destabilizing agents such as formamide. Additional exemplary stringent hybridization conditions include 50% formamide, 5×SSC, and 1% SDS incubating at 42° C.; or SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "trait" refers to a phenotype of interest, a gene that contributes to a phenotype of interest, as well as a nucleic acid sequence associated with a gene that contributes to a phenotype of interest. For example, a "HI trait" refers to a haploid induction phenotype as well as a gene that contributes to a haploid induction and a nucleic acid sequence (e.g., a HI-associated gene product) that is associated with the presence or absence of the haploid induction phenotype.

As used herein, the term "transgene" refers to a nucleic acid molecule introduced into an organism or one or more of its ancestors by some form of artificial transfer technique. The artificial transfer technique thus creates a "transgenic organism" or a "transgenic cell". It is understood that the artificial transfer technique can occur in an ancestor organism (or a cell therein and/or that can develop into the ancestor organism) and yet any progeny individual that has the artificially transferred nucleic acid molecule or a fragment thereof is still considered transgenic even if one or more natural and/or assisted breedings result in the artificially transferred nucleic acid molecule being present in the progeny individual.

Maize haploid inducer plants produce pollen which when crossed onto non-inducer germplasm results in the gynogenic development of haploid seeds. Unfortunately, this process often yields a low frequency of haploid kernels. Inefficient haploid induction frequency is a limiting factor in maize doubled haploid breeding programs. The present invention identifies a locus that identifies haploid induction in a plant; and a four nucleotide insertion at positions 1230-1233 of SEQ ID NO: 53 the presence or absence of which distinguishes haploid inducer germplasm from non-inducer germplasm. This locus or the presence or absence of the four nucleotide insertion at positions 1230-1233 of SEQ ID NO: 53 can be employed for selecting, and/or introgressing, and/or transforming the haploid inducing trait into plants.

More specifically, the present invention produces new maize haploid-inducing lines. A number of known haploid-inducing maize lines exist including but not limited to: stock 6, MHI (Moidovian Haploid Inducer), indeterminate gametophyte (ig) mutation, KEMS, ZEM, ZMS, KMS, RWS and RWK, The present invention relates to a method of identifying, and/or selecting germplasm which can or cannot induce haploids. The present invention also relates to increasing and further development of the selected haploid inducing germplasm. The invention further relates to a method of improving haploid inducing germplasm to increase the induction of haploids on the seed producing parent.

The initial step in the production of haploid seeds from a hybrid or segregating maternal parent plant derives from the pollination with pollen from a haploid inducer on to the ear from a seed producing plant. A result of this hybridization process is the production of diploid and maternal haploid (In) kernels. The induced haploid (in) kernels are often distinguished from the diploid seed by the use of color markers which indicate embryo ploidy. The diploid seeds are generally discarded, while haploid kernels or embryos are often subjected to chromosome doubling processes to produce doubled haploid plants.

More specifically, the haploid genetic material is treated with one or more mitotic arrest agents to allow the haploid (In) chromosome complement in one or more cells to produce homolog pairs. After the chemical treatment procedure, the chromosome doubling chemical(s) are removed. The now-doubled haploid maize is allowed to mature and the resulting doubled haploid seeds when planted will produce homozygous plants (also called inbred plant or lines). These inbred lines are the materials that breeders utilize to pursue their hybrid development programs.

The locus for the haploid induction trait was fine mapped. Although a major QTL on chromosome 1 responsible for haploid induction has been mapped and published, Dong et al. Theor, Appl. Genet (2013) 126: 1713-1720, the exact gene/genetic element responsible for the induction process has not been identified until now. The haploid induction locus is fine-mapped to be within a small region of 0.60 Mb (between the markers SM2363 (Chromosome 1, 67851018 nt Maize genome assembly version 3) and SM2712 (Chromosome 1, 68453157 nt Maize genome assembly version 3)). By comparing inducer and non-inducer germplasm, it was determined that a four nucleotide insertion present in haploid inducers which shifts the frame for amino acid coding of GRMZM2G471240 is not present in non-inducer germplasm. Therefore, the present invention has identified a gene with a frameshift mutation in inducer germplasm as being responsible for maize haploid induction. The candidate gene corresponding to gene model GRMZM2G471240 encodes a patatin-like phospholipase 2A.

Also notable are several secondary candidate genes identified as GRMZM2G305400, GRMZM2G082836, GRMZM2G382717, GRMZM2G120587, GRMZM2G062320, and GRMZM2G866758 that also may show differences between inducer and non-inducer lines. The secondary candidate genes may themselves be responsible for improved efficiency in HI. Crossing different HI inducers with these secondary candidate genes such as Stock 6 and RWK lines (each of which lack the candidate gene) can unexpectedly increase haploid induction, which may imply other genetic factors are also contributing to the HI trait. However, improved haploid induction germplasm can be difficult to maintain because it also results in significant seed abortion upon self-pollination and thus, makes HI line maintenance difficult.

DNA sequence was generated for each candidate gene from the two inducer lines and one non-inducer line. In addition, the public B73 genome data was used as a second non-inducer line. Gene model information was compared to EST/cDNA data to confirm the structure of each gene. The annotated sequence data were compared to catalog differences between the four alleles of each gene. The notable exceptions included GRMZM2G:305400 which is only identified in the B73 genome and GRMZM2G062320 which is only detected in this study in the NIL and B73 genomes. PCR experiments show that it is present in RWK and Stock 6.

The sequence comparisons revealed that B73 and NIL alleles were similar to each other, and RWK and Stock 6 alleles were similar to each other. Most sequence differences were single nucleotide polymorphisms that do not alter protein coding sequence. There were some insertions and some deletions, most of which are in non-protein coding sequence.

The exceptional sequence difference identified by the method used to generate the sequence data is in GRMZM2G471240, which contains a four nucleotide insertion in RWK and Stock 6. GRMZM2G471240 (annotated as a patatin-like phospholipase 2A protein) has a frame-shift mutation in the RWK and Stock6 lines resulting from a four base pair insertion in the fourth (and last) exon. When the nucleotide sequence is translated, the mutation shifts the coding frame by one base pair, changing the amino acid (AA) identity for each codon after the mutation. This results in 20 incorrect AA followed by a new, premature stop codon. The entire protein lesion thus constitutes a 30 AA truncation of the protein from the C-terminus, in addition to 20 AA of incorrect sequence between the mutation and the premature stop codon.

The presently disclosed subject matter provides the isolated nucleic acids, the genomic sequence and the protein sequence, the presence or absence, showed an association with HI, as well as any subsequences and informative fragments therefrom. In some embodiments, The presently disclosed subject matter provides isolated cDNA selected from the group consisting of: (a) a nucleic acid having at least 90% identity to SEQ ID NO: 33, SEQ ID NO: 37, SEQ ID NO: 52 or SEQ ID NO: 53, optionally wherein the percent identity is calculated over the entire length of SEQ ID NO: 33, SEQ ID NO: 37, SEQ ID NO: 52 or SEQ ID NO: 53; (b) a nucleic acid having at least 95% identity over nucleotides 91-1452 of SEQ ID NO: 33; (c) a nucleic acid that is the reverse complement of either of (a) or (b); and (d)

a nucleic acid that encodes a polypeptide comprising an amino acid sequence that is at least 95% identical to SEQ ID NO: 54, or SEQ ID NO: 55, or SEQ ID NO: 56, or SEQ ID NO: 57 optionally wherein the percent identity is calculated over the entire length of SEQ ID NO: 54, or SEQ ID NO: 55, or SEQ ID NO: 56, or SEQ ID NO: 57.

Comparisons of an amino acid sequence encoded thereby (i.e., SEQ ID NO: 54, SEQ ID NO: 55, SEQ ID NO: 56 and SEQ ID NO: 57) to sequences present in the GENBANK® biosequence database indicated the following this was a patatin-like phospholipase 2A protein. The table below lists gene identities in the interval shown in the tables below. This information is from chromosome 1, and lists a short description of the other encoded proteins from the genes within the haploid inducing locus.

| gene_id | transcript_ start | transcript_ end | Query length | Subject length | Score | Identity | Similarity | Align length | Short_description |
|---|---|---|---|---|---|---|---|---|---|
| GRMZM2G305400 | 67991172 | 67994092 | 308 | 362 | 385 | 33.3 | 53.33752 | 314 | Cyclin D2; 1 |
| GRMZM2G082836 | 68107606 | 68110989 | 202 | 205 | 729 | 71.2 | 83.33333 | 198 | GTP-binding protein 1 |
| GRMZM2G382717 | 68113455 | 68115168 | 396 | 464 | 489 | 38.77 | 53.17371 | 314 | Chaperone DnaJ-domain superfamily protein |
| GRMZM2G120587 | 68133178 | 68136953 | 458 | 461 | 1329 | 55 | 71.23894 | 452 | serine carboxypeptidase-like 51 |
| GRMZM2G471240 | 68240862 | 68242656 | 428 | 407 | 1049 | 51.5 | 72.36181 | 398 | phospholipase A 2A |
| GRMZM2G471240 | 68240862 | 68242656 | 401 | 407 | 961 | 50.15 | 70.0938 | 395 | phospholipase A 2A |
| GRMZM2G062320 | 68318898 | 68321409 | 335 | 334 | 1064 | 73.3 | 84.21053 | 285 | Phosphoglycerate mutase family protein |
| GRMZM5G866758 | 68430654 | 68436197 | 401 | 403 | 1678 | 80.4 | 90.45226 | 398 | acetoacetyl-CoA thiolase 2 |
| GRMZM5G866758 | 68430654 | 68436197 | 303 | 403 | 1248 | 78.4 | 89.40397 | 302 | acetoacetyl-CoA thiolase 2 |
| GRMZM2G003530 | 68435670 | 68439997 | 360 | 344 | 1063 | 60.5 | 76.41791 | 335 | P-loop containing nucleoside triphosphate hydrolases superfamily protein |
| GRMZM2G077991 | 68543246 | 68546264 | 94 | 95 | 424 | 79.7 | 91.48936 | 94 | Zinc-binding ribosomal protein family protein |
| GRMZM2G077991 | 68543694 | 68546264 | 94 | 95 | 424 | 79.7 | 91.48936 | 94 | Zinc-binding ribosomal protein family protein |
| GRMZM2G077991 | 68543805 | 68546269 | 147 | 95 | 419 | 79.5 | 91.39785 | 93 | Zinc-binding ribosomal protein family protein |
| GRMZM2G077960 | 68554980 | 68559182 | 438 | 478 | 1422 | 65.3 | 79.80998 | 421 | Protein phosphatase 2C family protein |
| GRMZM2G077897 | 68561209 | 68565155 | 784 | 807 | 1561 | 48.1 | 65.69848 | 723 | Plant protein of unknown function (DUF827) |
| GRMZM2G347583 | 68660278 | 68665995 | 1651 | 2156 | 1201 | 41.37 | 55.70954 | 1375 | |
| GRMZM2G173030 | 68668900 | 68671460 | 626 | 2156 | 858 | 35.6 | 48.30299 | 586 | |
| GRMZM2G022061 | 68876150 | 68882226 | 203 | 556 | 618 | 64.9 | 79.89691 | 194 | |
| GRMZM2G022061 | 68876150 | 68882226 | 322 | 556 | 1004 | 66 | 77.47748 | 333 | |
| GRMZM2G022061 | 68876150 | 68882226 | 142 | 556 | 547 | 79.6 | 89.84375 | 128 | |
| GRMZM2G022061 | 68876150 | 68882226 | 322 | 556 | 1004 | 66 | 77.47748 | 333 | |
| GRMZM2G022061 | 68876150 | 68882226 | 534 | 556 | 1802 | 67.7 | 79.81651 | 545 | |
| GRMZM2G340286 | 68928213 | 68929600 | 378 | 403 | 570 | 37.83 | 55.75713 | 407 | |
| GRMZM2G340279 | 68934652 | 68937080 | 746 | 937 | 3095 | 29.34 | 50.31745 | 2517 | Tetratricopeptide repeat (TPR)-like superfamily protein |
| GRMZM2G347808 | 69005208 | 69012612 | 589 | 455 | 1115 | 50.4 | 66.60178 | 423 | S-adenosyl-L-methionine-dependent methyltransferases superfamily protein |

RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs), The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or “guide strand”) of the RNA is loaded. This guide strand acts as a template for the recognition and destruction of the duplex sequences. This process is repeated each time the siRNA hybridizes to its complementary-RNA target, effectively preventing those mRNAs from being translated, and thus “silencing” the expression of specific genes from which the mRNAs were transcribed. Most plant miRNAs show extensive base pairing to, and guide cleavage of their target mRNAs (Jones-Rhoades et al, (2006) Annu. Rev. Plant Biol. 57, 19-53; Llave et al. (2002) Proc. Natl. Acad. Sci. USA 97, 13401-13406). In other instances, interfering RNAs may bind to target RNA molecules having imperfect complementarity, causing translational repression without mRNA degradation. The majority of the animal miRNAs studied so far appear to function in this manner.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.
RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 18 to about 25 base pairs, optionally a sequence of about 18 to about 50 base pairs, optionally a sequence of about 50 to about 100 base pairs, optionally a sequence of about 1.00 to about 200 base pairs, optionally a sequence of about 200 to about 500, and optionally a sequence of about 500 to about 1000 or more base pairs, up to molecule that is double stranded for its full length, corresponding in size to a full length target RNA molecule.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term “specifically reduce the level of a target RNA and/or the production of a target protein encoded by the RNA”, and variations thereof, refers to the sequence of a portion of one strand of the dsRNA being sufficiently identical to the target RNA such that the presence of the dsRNA in a cell reduces the steady state level and/or the production of said RNA, In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, Cell, 116:281-297 (2004); Zhang et al, Dev. Biol. 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. Genes Dev. 16:1616-1626 (2002), Park et al. Curr. Biol. 12:1484-1495 (2002)) many hundreds have been identified. Furthermore, many plant miRNAs have been shown to be highly conserved across very divergent taxa. (Floyd et al. Nature 428:485-486 (2004): Zhang et al. Plant J. 46:243-259 (2006)). Many microRNA genes (MI R genes) have been identified and made publicly available in a data base (miRBase; microrna.sanger.ac.uk/sequences) miRNAs are also described in U.S. Patent Publications 2005/0120415 and 2005/144669A1, the entire contents of which are incorporated by reference herein.

Genes encoding miRNAs yield primary miRNAs (termed a “pri-miRNA”) oaf 70 to 300 bp in length that can form imperfect stem-loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. Proc. Natl. Acad. Sci. 105:9851-9852 (2008)). Many reviews on microRNA biogenesis and function are available, for example, see, Bartel Cell 116:281-297 (2004), Murchison et al. Curr. Opin. Cell Biol. 16:223-229 (2004), Dugas et al. Curt. Opin. Plant Biol. 7:512-520 (2004) and Kim Nature Rev. Mol. Cell 6:376-385 (2005).

The term “plant microRNA precursor molecule” as used herein describes a small (~70-300 nt) non-coding RNA sequence that is processed by plant enzymes to yield a ~19-24 nucleotide product known as a mature microRNA sequence. The mature sequences have regulatory roles through complementarity to messenger RNA. The term “artificial plant microRNA precursor molecule” describes the non-coding miRNA precursor sequence prior to processing that is employed as a backbone sequence for the delivery of a siRNA molecule via substitution of the endogenous native miRNA/miRNA* duplex of the miRNA precursor molecule with that or a non-native, heterologous miRNA (amiRNA/amiRNA*; e.g. siRNA/siRNA*) that is then processed into the mature miRNA sequence with the siRNA sequence.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, "complementary" polynucleotides are those that are capable of base pairing according to the standard Watson-Crick complementarily rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

The terms "complementary" or "complementarily," as used herein, refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "substantially complementary" or "partially complementary mean that two nucleic acid sequences are complementary at least a bout 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art In some embodiments, the dsRNA molecule can comprise, consist essentially of or consist of from at least 18 to a bout 25 consecutive nucleotides (e.g. 18, 19, 20, 21, 22, 23, 24 or 25) to at least about 400 consecutive nucleotides. In some embodiments the dsRNA molecule can comprise, consist essentially of or consist of about 500, or about 50 or about 543 consecutive nucleotides, Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the portion of the mRNA polynucleotide transcribable from a GRMZM2G471240 gene that the antisense strand is complementary to comprises at least 18 consecutive nucleotides of SEQ ID NO:33, SEQ ID NO:37, SEQ ID NO:52 or SEQ In other embodiments, the portion of mRNA comprises, consists essentially of or consists of at least from 19, 20 or 21 consecutive nucleotides to at least 400 consecutive nucleotides of SEQ ID NO:33, SEQ ID NO:37, SEQ ID NO:52 or SEQ ID NO:53, In other embodiments, the portion of mRNA comprises, consists essentially of or consists of at least about 500, or at least about 98 or at least about 185 consecutive nucleotides of SEQ ID NO:33.

In other embodiments, the portion of the mRNA polynucleotide that is complementary to the antisense strand of a dsRNA of the invention comprises any 19-mer subsequence of SEQ ID NO:33 (GRMZM2G471240) consisting of N to N+18 nucleotides, wherein N is nucleotide 1 to 1452 of SEQ ID NO:33. In other words, the portion of the mRNA that is targeted comprises any of the 1452 19 consecutive nucleotide subsequences (i.e. 19-mer) of SEQ ID NO:33, for example, bases 1-19 (5'-AGTTCATCACTAATCACAC-3'), bases 2-20 (5'-GTTCATCACTAATCACACT-3'), bases 3-21 (5'-TTCATCACTAATCACACTT-3') and so forth to bases 1434-1452 (5'-AAAACATAAAAATATATAT-3').

In other embodiments, the nucleotide sequence of the antisense strand can consist essentially of the nucleotide sequence of any 19-mer subsequence of SEQ ID NO:62 consisting of N to N±18 nucleotides, wherein N is nucleotide 1 to nucleotide 1452 of SEQ ID NO:62, In other words, the antisense strand consists essentially of the nucleotide sequence of any of the 1452 19 consecutive nucleotide subsequences (i.e. 19-mer) of SEQ ID NO:62, for example, bases 1-19 (5'-ATATATATTTTTATGTTTT-3'), bases 2-20 (5'-TATATATTTTTATGTTTTA-3'), bases 3-21 (5'-ATATATTTTTATGTTTTAT-3') and so forth to bases 1434-1452 (5'-GTGTGATTAGTGATGAACT-3').

It would be understood that the deletion of the one nucleotide or the addition of up to six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3; end may be present, which is used to stabilize the siRNA duplex and does not affect the specificity of the siRNA.

In some embodiments of this invention, the antisense strand of the double stranded RNA molecule can be fully complementary to the target RNA polynucleotide or the antisense strand can be substantially complementary or partially complementary to the target RNA polynucleotide. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allele" Acta Pharmacol. Sin. 29:211-216 (2008'; Schwarz et al. "Asymmetry in the assembly of the RNAi enzyme complex" Cell 115:199-208 (2003)), Other such mismatches can be introduced into the antisense strand due to eliminating fortuitous open reading frames created in making dsRNA encoding expression cassettes. Such open reading frames are eliminated by making point mutations in the dsRNA encoding nucleotide sequence thus creating some mismatches in the dsRNA compared to the target gene. In some embodiments of this invention, the dsRNA molecule of the invention is a short hairpin RNA (shRNA) molecule. Expression of shRNA in cells is typically accomplished by delivery of plasmids or recombinant vectors, for example in transgenic plants such as transgenic corn.

The invention encompasses a nucleic acid molecule encoding at least one strand of a dsRNA molecule of the invention. The invention further encompasses a nucleic acid construct comprising at least one strand of a dsRNA molecule of the invention or comprising the nucleic acid molecule encoding the at least one strand of a dsRNA molecule of the invention. In one embodiment of the invention, the nucleic acid molecule encodes a short hairpin RNA. In another embodiment, the nucleic acid molecule that encodes the short hairpin RNA comprises SEQ ID NO:62 or SEQ ID NO:63

The invention further encompasses chimeric nucleic acid molecules comprising an antisense strand of a dsRNA of the invention operably linked with a plant microRNA precursor molecule. In some embodiments, the chimeric nucleic acid molecule comprises an antisense strand having the nucleotide sequence of any of the 19-mer subsequences of SEQ ID NO:33, SEQ ID NO:37, SEQ ID NO:52 or SEQ ID NO:53 operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA molecule of the invention. In other embodiments, the artificial plant microRNA precursor molecule comprises an antisense strand having the nucleotide sequence of any of the 19-mer subsequences of SEQ ID NO:62, or SEQ ID NO:63. The use of artificial plant microRNAs to deliver a nucleotide sequence of interest (e.g an artificial miRNA; siRNA/siRNA*) into a plant is known in the art (see, e.g., Schwab et al. 2006, The Plant Cell 18:1121-1133 and Examples section herein). In the invention, the artificial microRNAs are chimeric or hybrid molecules, having a plant microRNA precursor backbone and an insect (i.e. animal siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Nonlimiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses nucleic acid constructs, nucleic acid molecules or recombinant vectors comprising at least one strand of a dsRNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

In some embodiments, the invention encompasses compositions comprising two or more dsRNA molecules of the invention wherein the two or more RNA molecules each comprise a different antisense strand. In some embodiments the two or more dsRNA molecules are present on the same nucleic acid construct, on different nucleic acid constructs or any combination thereof. In other embodiments, the composition comprises an RNA molecule comprising an antisense strand consisting essentially of the nucleotide sequence of SEQ ID NO:62 and an RNA molecule comprising an antisense strand consisting essentially of the nucleotide sequence of SEQ ID NO:63. In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

RNA interference (RNAi) can be used to produce genetically modified plants that are tolerant or resistant to abiotic and biotic stresses. In the past decade, RNAi has been described and characterized in organisms as diverse as plants, fungi, nematodes, hydra, and humans. Zamore and Haley (2005) Science 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) Trends Genet. 15,358-363.

RNA interference occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs, Jones-Rhoades et al. (2006) Annu. Rev. Plant Biel 57, 19-53; Llave et al. (2002) Proc. Natl. Acad. Sci, USA 97, 1340140406. In other instances, interfering RNAs may bind to target RNA molecules having imperfect complementarity, causing translational repression without mRNA degradation.

The mode of action for silencing a plant gene generally includes a double stranded RNA (dsRNA) that associates with a dicer enzyme that cuts the dsRNA into ds fragments 19-24 bps in length (siRNA). There may be more than one dicer enzyme, depending on the organism. Meister and Tuschl, 2004). The siRNA is typically degraded into two single stranded RNAs (ssRNAs), referred to as the passenger strand and the guide strand. A RNA-interference silencing complex (RISC complex) loads the guide strand. The RISC complex associates with a target mRNA that has partial or complete homology to the guide strand. The catalytic RISC component agronaute causes cleavage of the target mRNA preventing it from being used as a translation template. Ahlquist P (2002) RNA-dependent RNA polymerases, viruses, and RNA silencing, Science 296 (5571): 1270-3. The RNAi pathway is exploited in plants by using recombinant technology, which entails transforming a plant with a vector comprising DNA that when expressed produces a dsRNA homologous or nearly homologous to a gene target.

The gene target can be homologous to a endogenous plant gene or an insect gene. If the target is an insect gene, the insect eats the plant thereby ingesting the dsRNA, at which the RNAi RISC complex of the insect causes cleavage and targeting of the homologous mRNA, causing disruption of a vital insect process.

To date, plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are not known in the art. Such methods and formulations represent a significant development for gene silencing technology. Known methods for delivering exogenous dsRNA into plant cells are via particle bombardment or viral RNA infection through wounding the plant tissue (e.g. tobacco and rice leaf tissues). Application by spray or brush of RNA molecules, or other non-tissue evasive techniques, resulting in assimilation of the exogenous RNA molecules into plant tissue, thereby causing endogenous and/or pest gene silencing, has not been reported.

The present invention is directed to methods and formulations to incorporate exogenous RNA, by application to external tissue surface(s) of plants, into the plant cells causing silencing of plant endogenous target gene(s) or of the target genes of plant pests.

The present invention is not directed to any particular RNAi mechanism or mode of action of gene silencing, and should not be construed as limited to any such mechanisms, known or unknown.

The terms "silencing" and "suppression" are used interchangeably to generally describe substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

MicroRNAs are encoded by genes that are transcribed but not translated into protein (non-coding DNA), although sonic miRNAs are encoded by sequences that overlap protein-coding genes. By way of background, miRNAs are processed from primary transcripts known as pri-miRNAs to short stem loop structures called pre-miRNAs that are further processed by action of dicer enzyme(s) creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-WatsonCrick base pairs (i.e., G-U wobble base pairs), and other features are frequently observed in pre-miRNAs and such characteristics are thought to be important for processing. Mature miRNA molecules are partially complementary to one or more mRNA molecules, and they function to regulate gene expression. siRNAs of the present invention have structural and functional properties of endogenous miRNAs (e.g., gene silencing and suppressive functions). Thus, in various aspects of the invention, siRNAs of the invention can derived from miRNAs, from target gene sequence information, or can be produced synthetically based on predictive models known in the art. The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism, but not in a non-target organism, such as a host organism (the organism expressing or producing the miRNA) or a consumer of the host organism. Consequently, "target-specific siRNAs" only produce phenotypes in target organisms and do not produce phenotypes in non-target organisms. In the present invention, the target-specific siRNAs selectively hybridize to nucleic acids that are endogenous to the host organism, which are plants. MicroRNAs (miRNAs) are non-protein coding RNAs, generally of between about 19 to about 25 nucleotides (commonly about 20-24 nucleotides in plants), miRNAs direct cleavage in trans of target transcripts, regulating the expression of genes involved in various regulation and development pathways (Bartel, Cell, 116:281-297 (2004); Zhang et al. Dev. Biol. 289:3-16 (2006)). miRNAs have been shown to be involved in different aspects of plant growth and development as well as in signal transduction and protein degradation. In addition, growing evidence indicates that small endogenous mRNAs including miRNAs may also be involved in biotic stress responses such as parasite attack, Since the first miRNAs were discovered in plants (Reinhart et al. Genes Dev. 16:1616-1626 (2002), Park et al. Curr. Biol. 12:1484-1495 (2002)), many hundreds have been identified. Further, many plant miRNAs have been shown to be highly conserved across very divergent taxa. (Floyd et al. Nature 428:485-486 (2004); Zhang et al. Plant J. 46:243-259 (2006)). Many microRNA genes (MIR genes) have been identified and made publicly available in a database ("miRBase," available on line at microrna.sanger.ac.uk/sequences). miRNAs are also described in U.S. Patent Publications 2005/0120415 and 2005/144669A1, the entire contents of which are incorporated by reference herein.

Further encompassed within the presently disclosed subject matter are expression cassettes according to the embodiments of the presently disclosed subject matter as well as expression vectors (see FIG. 3) comprising the same. Also encompassed are plant cells comprising expression cassettes according to the present disclosure, and plants comprising these plant cells. In some embodiments, the plant is a dicot. In some embodiments, the plant is a monocot. In some embodiments, the monocot is a cereal. The plant can be, for example, rice, maize, grass, wheat, maize, barley, brome, oats, rye, millet, sorghum, triticale, secale, einkorn, spelt, emmer, teff, milo, flax, gramma grass, *Tripsacum*, or teosinte.

Thus, the compositions of the presently disclosed subject matter can comprise nucleic acid sequences for transformation and expression in a plant of interest. The expression is of the primary candidate gene and HI trait is desired the expression may also be for down regulated expression or induced expression in some or all of the female portion of the plant and no expression in the male flowering plant parts.

The nucleic acid sequences can be present in DNA constructs or expression cassettes. "Expression cassette" as used herein means a nucleic acid molecule capable of directing expression of a particular nucleotide sequence, or iRNA in an appropriate host cell, comprising a promoter operatively linked to the sequence of interest (e.g., a sequence encoding a gene product or iRNA associated with HI) which is optionally also operatively linked to termination signals. It also typically comprises sequences required for proper translation of the nucleotide sequence. The coding region usually codes for a protein of interest but can also code for a functional RNA of interest, for example antisense RNA or a nontranslated RNA such as, but not limited to a siRNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression. In some embodiments, the expression cassette is heterologous with respect to the host (i.e., the particular DNA sequence of the expression cassette, or a subsequence thereof, does not occur naturally in the host cell and must have been introduced into the host cell or an ancestor of the host cell by a transformation event). The expression of the nucleotide sequence in the expression cassette can be under the control of a constitutive promoter, a tissue specific promoter, and/or an inducible promoter that initiates transcription only when the host cell is exposed to some particular external stimulus, a minimal promoter, etc. Additionally, the promoter can also be specific to a particular cell type, tissue, organ, and/or stage of development. In some embodiments, an expression cassette is present in a vector that permits replication of the expression cassette in a host cell.

The present presently disclosed subject matter encompasses the transformation of plants with expression cassettes capable of expressing a polynucleotide of interest (e.g., a polynucleotide encoding a gene product or iRNA associated with HI) alone or in combination with one or more additional nucleic acid molecules encoding polypeptides that confer desirable traits. However, if the polynucleotide is the primary gene, GRMZM2G062320, it maybe preferred that the cassette is adapted to down regulate or knock out the gene in nonhaploid inducing material. Or expressed in an inducible matter so that the pollen used to self the HI plant is expressing the gene product that occurs in B73 and other non haploid inducing material. In some embodiments, the expression cassette includes at least the following basic elements oriented in the 5'-3' direction of transcription: a transcriptional and translational initiation region (i.e., a promoter) and a polynucleotide of interest. The expression cassette can optionally comprise a transcriptional and translational termination region (e.g., termination region) functional in plants. In some embodiments, the expression cassette comprises a selectable marker gene to allow for selection for stable transformants.

In some embodiments, the regulatory sequences of the expression construct are operably linked to the polynucleotide of interest. By "operably linked" is intended a functional linkage between a first sequence (e.g., a promoter) and a second sequence (e.g., a coding sequence), wherein the first sequence influences a biological event (e.g., transcription, transcription, replication, etc.) that occurs with respect to the second sequence. Generally, operably linked means that the nucleotide sequences being linked are contiguous in a single molecule.

Any promoter capable of driving expression in the plant of interest can be used in the practice of the presently disclosed subject matter. In some embodiments, the expression cassette is expressed throughout the plant. In some embodiments, the expression cassette is expressed in a specific location and/or tissue of a plant, or at a certain time during the development of the plant. In some embodiments, the location and/or tissue includes, but is not limited to, anther, ovule, plastid, pollen, mitochondrion, chloroplast, epidermis, root, vascular tissue, meristem, cambium, cortex, pith, leaf, flower, and combinations thereof. In another embodiment, the location and/or tissue is a seed.

The promoter can be native or analogous, or can be heterologous or exogenous, to the plant or plant cell in which it is intended to be active. The terms "heterologous" and "exogenous" when used herein to refer to a nucleic acid sequence (e.g., a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, in some embodiments the terms refer to a DNA segment that is foreign or heterologous to the cell, or homologous to the cell but in a position within the host cell nucleic acid in which the element is not ordinarily found. In some embodiments, an exogenous DNA segment is expressed to yield an exogenous polypeptide in a cell or tissue type of interest. In some embodiments, a heterologous or exogenous nucleic acid is referred to herein as a transgene.

A "homologous" nucleic acid (e.g., DNA) sequence is a nucleic acid (e.g., DNA or RNA) sequence that is naturally associated with a host cell into which it is introduced. As such, and by way of example and not limitation, a nucleic acid that is derived from (i.e., isolated from with or without subsequent modification) a plant cell or tissue could be considered a homologous nucleic acid when reintroduced into a plant cell or tissue of the same species, but could be considered heterologous or exogenous when introduced into a cell or tissue of a plant other than the plant species from which it was derived. In some embodiments, a homologous nucleic acid can also be referred to herein as a heterologous or a transgene when the homologous nucleic acid is operatively linked to a nucleotide sequence to which it is not naturally operatively linked.

The choice of promoters to be included depends in some embodiments upon several factors, including, but not limited to, efficiency, selectability, inducibility, desired expression level, and/or cell- or tissue-preferential and/or -specific expression. It is a routine matter for one of skill in the art to modulate the expression of a sequence by appropriately selecting and positioning promoters and other regulatory regions relative to that sequence. The promoters that are used for expression of the transgene(s) can be in some embodiments a strong plant promoter, in some embodiments a viral promoter, and in some embodiments a chimeric promoter comprising such basic transcriptional regulatory elements such as but not limited to a TATA box from any gene (or synthetic, based on analysis of plant gene TATA boxes), optionally fused to the region 5' to the TATA box of plant promoters (which direct tissue and temporally appropriate gene expression), optionally fused to one or more enhancers (such as the 35S enhancer, FMV enhancer, CMP enhancer, etc.).

For example, the selection of the promoter used in expression cassettes can determine the spatial and temporal expression pattern of the transgene in the transgenic plant. Selected promoters can express transgenes in specific cell types and/or in specific tissues or organs, and the selection can reflect the desired location for accumulation of the gene product. Alternatively, the selected promoter can drive expression of the gene under various inducing conditions. Promoters vary in their strength; i.e., their abilities to promote transcription. Depending upon the host cell system utilized, any one of a number of suitable promoters can be used, including the gene's native promoter. The following are non-limiting examples of promoters that can be used in expression cassettes.

Promoters which are directing expression of the gene are referred to herein as "constitutive" promoters and are active under most environmental conditions and states of development or cell differentiation. Examples of constitutive promoters include the 1'- or 2'-promoter derived from T-DNA of *Agrobacterium tumefaciens*, and other transcription initiation regions from various plant genes known to those of ordinary skill in the art. Such genes include, but are not limited to, the inducible promoters of AP2 gene; ACT11 from *Arabidopsis* (Huang et al., 1996); Cat3 from *Arabidopsis* (GENBANK® Accession No. U43147; Thong et al., 1996); the gene encoding stearoyl-acyl carrier protein desaturase from *Brassica napus* (GENBANK® Accession No. X74782; Solocombe et al., 1994); GPc1 from maize (GENBANK® Accession No. X15596; Martinez et al., 1989); and Gpc2 from maize (GENBANK® Accession No. U45855; Manjunath et al., 1997). Additional non-limiting examples of constitutive promoters include, for example, the core promoter of the Rsyn7 promoter and other constitutive promoters disclosed in PCT International Patent Application Publication No. WO 1999/43838 and U.S. Pat. No. 6,072,050; various ubiquitin promoters (see e.g., U.S. Pat. Nos. 5,641,876 and 8,168,859; Christensen et al., 1989; Christensen et al., 1992; Wei et al., 2003; Lu et al., 2008); the core CaMV 35S promoter (Odell et al., 1985; Benfey & Chua, 1990); the CaMV 19S promoter; the figwort mosaic virus (FMV) promoter; the rice actin-1 promoter (McElroy et al., 1990); the rice alpha tubulin (tubA1) promoter (Fiume et al., 2004); pEMU (Last et al., 1991); the Cestrum yellow leaf curling virus (CmYLCV) CMP promoter (Hohn et al., 2007; U.S. Pat. No. 7,166,770); the MAS promoter (Velten et al., 1984); the Super MAS promoter (Ni et al., 1995; Lee et al., 2007); the ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

The present invention shows a frame shift mutation in GRMZM2G471240 in the Haploid inducing material, thus RNAi silencing of GRMZM2G471240 will create a HI line. The silencing can be accomplished in numerous ways including expression of a hairpin or artificial microRNA to target GRMZM2G471240. The down regulated expression transformants will allow various types of germplasm to act as HI lines.

It should also be possible to compensate the defect in a HI line. Transgenic material with the non haploid inducing sequence when expressed (SEQ ID NO: 33) should if joined with an inducible promoter make the HI line switchable between being a HI line and a non HI line. Therefore, transformation methods, cassettes, vectors and transgenic plant with the non HI sequence are described herein.

Appropriate plant or chimeric promoters are useful for applications such as expression of transgenes and/or other heterologous or homologous nucleic acids in certain tissues, while minimizing expression (including but not limited to a level of expression that is below detection using routine techniques) in other tissues, in some embodiments such as but not limited to seeds and/or female reproductive tissues. In some embodiments, expression of a nucleic acid designed to silence a gene product associated with HI of the current presently disclosed subject matter can optionally be localized to seed, or fruit tissues and preferably no expression in the anther or pollen or very downregulated expression if this gene product is present at all in the anther or pollen. The data suggests that expression of the expression is most likely important in early reproductive structures, particularly female structures. Exemplary cell type- or tissue-preferential (in some embodiments, tissue-specific) promoters drive expression preferentially (or in some embodiments essentially specifically) in the target tissue, but can also lead to some expression in other cell types or tissues as well. Methods for identifying and characterizing promoter regions in plant genomic DNA include, for example, those described in the following references: Green et al., 1988; Bustos et al., 1989; Jordano et al., 1989; Meier et al., 1991; and Zhang et al., 1996.

Alternatively, the plant promoter can direct expression of the nucleic acid molecules of the presently disclosed subject matter in a specific tissue or can be otherwise under more precise environmental or developmental control. Examples of environmental conditions that can effect transcription by inducible promoters include anaerobic conditions, elevated temperature, or the presence of light. Such promoters are referred to herein as "inducible", "cell type-specific", or "tissue-specific" promoters. Those of ordinary skill in the art will recognize that a tissue-specific promoter can drive expression of operatively linked sequences in tissues other than the target tissue. Thus, as used herein a "tissue-specific" promoter is one that drives expression preferentially in the target tissue, but can also lead to some expression in other tissues as well.

Examples of promoters under developmental control include promoters that initiate transcription preferentially or exclusively in certain tissues, such as pollen, anthers, fruit, seeds, or flowers. Promoters that direct expression of nucleic acids in pollen, anthers, and the like and possibly in ovules, flowers, or seeds are particularly useful in the presently disclosed subject matter. As used herein a seed-specific promoters are active in cells destined to produce the ovule and tend to direct expression specifically or preferentially in the seed tissues. And reproduction specific promoters are promoters that are active in cells destined to produce the male parts such as the anther, pollen and microspores and the female parts such as the ovule, silks, embryo, and seed. And male Reproductive specific promoters are promoters that are active in cells destined to produce the male parts like pollen.

Seed specific promoters can be, for example, ovule-specific, embryo-specific, endosperm-specific, integument-specific, seed coat-specific, or some combination thereof. Examples include a promoter from the ovule-specific BELL gene described in Reiser et al., 1995 (GENBANK® Accession No. U39944). Non-limiting examples of seed specific promoters are derived from the following genes: MAC1 from maize (Sheridan et al., 1996); Cat3 from maize (GENBANK® Accession No. L05934; Abler et al., 1993); the gene encoding oleosin 18 kD from maize (GENBANK® Accession No. J05212; Lee & Huang, 1994); vivparous-1 from *Arabidopsis* (GENBANK® Accession No. U93215);

the gene encoding oleosin from *Arabidopsis* (GENBANK® Accession No. Z17657); Atmycl from *Arabidopsis* (Urao et al., 1996); the 2s seed storage protein gene family from *Arabidopsis* (Conceicao et al., 1994); the gene encoding oleosin kD from *Brassica napus* (GENBANK® Accession No. M63985); napA from *Brassica napus* (GENBANK® Accession No. J02798; Josefsson et al., 1987); the napin gene family from *Brassica napus* (Sjodahl et al., 1995); the gene encoding the 2S storage protein from *Brassica napus* (Dasgupta et al., 1993); the genes encoding oleosin A (GENBANK® Accession No. U09118) and oleosin B (GENBANK® Accession No. U09119) from soybean; and the gene encoding low molecular weight sulfur rich protein from soybean (Choi et al., 1995). Additional cell type- and/or tissue-specific promoters include, but are not limited to the *Triticum aestivum* pistil specific P19 promoter (see Japanese Patent Application JP 2001512988-A/13); the maize silk promoter prB200 (see Japanese Patent Application JP 001512988-A/13), the maize prCDPK-01 and prCDPK-02 promoters (Estruch et al., 1994); the rice α-N-acetylglucosaminidase (prOsANG) promoter (U.S. Pat. No. 7,550,578); the rice MADS box gene promoters prOsMADS1, prOsMADS2, prOsMADS6, prOsMADS7, prOsMADS14; and prOsMADS16 (U.S. Patent Application Publication Nos. 2007/0006344, 2010/0205692 A1, and 2012/0021506 A1); the rice anther-specific promoter prRA8 (see Japanese Patent Application JP 2001512988-A/13); the rice prOsG6 promoter (Tsuchiya et al., 1994); the whole seed-specific promoter disclosed in U.S. Patent Application Publication No. 2012/0036595; and the endosperm promoter disclosed in U.S. Patent Application Publication No. 2012/0036593.

Additional promoters that can be employed with the presently disclosed subject matter include, but are not limited to those described in U.S. Pat. No. 7,151,201; the PsEND1 promoter described in Roque et al., 2007; the corn stamen-specific promoters described in PCT International Patent Application Publication No. WO 1992/013957; and the APETALA3 promoter described in U.S. Pat. No. 7,253,340.

In some embodiments, an inducible promoter might be desired. Inducible promoters drive transcription in response to external stimuli such as chemical agents or environmental stimuli. For example, inducible promoters can confer transcription in response to hormones such as gibberellic acid or ethylene, or in response to light, heat or drought.

In some embodiments, an expression construct further comprises a transcription terminator operably linked to the nucleic acid of interest. These are responsible for the termination of transcription beyond the transgene and/or correct mRNA polyadenylation. A variety of transcriptional terminators are available for use in expression cassettes. The termination region can be native with respect to the transcriptional initiation region/promoter (i.e., the promoter and transcription terminator can be derived from the same genetic locus), can be native with the operably linked DNA sequence of interest, can be native with the plant host, and/or can be derived from another source (e.g., can be foreign or heterologous to the promoter, the DNA sequence of interest, the plant host, or any combination thereof). Exemplary transcriptional terminators are those that are known to function in plants and include the CAMV 35S terminator, the tml terminator, the nopaline synthase (Nos) terminator, and the pea rbcs E9 terminator. These can be used in both monocotyledons and dicotyledons. In addition, a gene's native transcription terminator can be used.

In some embodiments, an expression cassette comprises a selectable marker gene for the selection of transformed cells.

Additionally, various sequences have been found to enhance gene expression from within the transcriptional unit, and in some embodiments these sequences are used in conjunction with the nucleic acids of the presently disclosed subject matter to increase their expression in transgenic plants. For example, certain intron sequences have been shown to enhance expression, particularly in monocotyledonous cells. For example, the introns of the maize Adhl gene have been found to significantly enhance the expression of the wild type gene under its cognate promoter when introduced into maize cells. Intron 1 was found to be particularly effective and enhanced expression in fusion constructs with the chloramphenicol acetyltransferase gene (Callis et al., 1987). In the same experimental system, the intron from the maize bronze 1 gene had a similar effect in enhancing expression of an operably linked nucleic acid sequence. Intron sequences have been routinely incorporated into plant transformation vectors, typically within the non-translated leader.

Expression constructs of the presently disclosed subject matter can also comprise a leader sequence and/or a sequence allowing for inducible expression of the polynucleotide of interest. See e.g., Guo et al., 2003; Chen et al., 2003 for examples of sequences allowing for inducible expression.

A number of non-translated leader sequences derived from viruses are also known to enhance expression of operably linked nucleic acid sequences, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (see e.g., Gallie et al., 1987; Skuzeski et al., 1990). Other leader sequences known in the art include, but are not limited to, picornavirus leaders (e.g., the EMCV leader (the encephalomyocarditis 5'-noncoding region); Elroy-Stein et al., 1989); potyvirus leaders (e.g., the Tobacco Etch Virus (TEV) leader; Allison et al., 1986); the Maize Dwarf Mosaic Virus (MDMV) leader (see GENBANK® Accession No. NC_003377); the human immunoglobulin heavy-chain binding protein (BiP) leader (Macejak & Samow, 1991); the untranslated leader from the coat protein mRNA of alfalfa mosaic virus (AMV RNA 4; Jobling & Gehrke, 1987); the tobacco mosaic virus leader (TMV) leader (Gallie et al., 1989); and the Maize Chlorotic Mottle Virus (MCMV) leader (Lommel et al., 1991). See also, Della-Cioppa et al., 1987.

Alternatively or in addition, an expression construct of the present invention can include a presequence that directs the localization polypeptide encoded by the expression construct to an organelle within a plant cell. A nucleotide sequence encoding a presequence can be introduced in frame at the 5' end of a coding sequence in order to target the polypeptide encoded by the presequence/coding sequence hybrid to the target area. In some embodiments, the coding sequence encodes a subsequence or the entire sequence set forth in SEQ ID NO: 54. In some embodiments 454 amino acids of SEQ ID NO: 54 or a subsequence thereof that comprised amino acids non HI trait or less consecutive amino acids or more consecutive amino acids or an amino acid sequence that is 95% identical thereto can be fused to any presequence using standard molecular cloning techniques.

The transformation of non HI; or HI germplasm can include transformants in monocots and dicots which may be for example orthologs. Species that have orthologues to this sequence can readily be employed in the transformation process these include but are not limited to the species: *Sorghum bicolor*, maize, wheat, millet, *Setaria Italica, Oryza brachyantha, Oryza indica, Oryza glaberrima, Hordeum vulgare, Oryza sativa, Solanum lycopersicum* (tomato), and *Brachypodium distachyon.*

In some embodiments, the presently disclosed subject matter provides markers for detecting and/or assaying for the presence or absence of gene products associated with HI in a plant cell or other source of biomolecules. In some embodiments, a marker is intended to detect the presence of a nucleic acid molecule that includes the deletion junction where the maize HI sequences show an insertion in the sequence in SEQ ID NO. 53 to allow for the specific detection of the presence or absence of a chimeric nucleic acid comprising SEQ ID NO: 33, SEQ ID NO: 37, SEQ ID NO: 52 or SEQ ID NO: 53 in a sample. The number of nucleotides 5' and/or 3' of the deletion junction that allow for specific detection of the presence of absence of a chimeric nucleic acid comprising SEQ ID NO: 53 in a sample can vary based on the identification method employed, but can be in some embodiments at least about 5 nucleotides, in some embodiments at least about 10 nucleotides, in some embodiments at least about 15 nucleotides, in some embodiments at least about 20 nucleotides, in some embodiments at least about 25 nucleotides, and in some embodiments at least about 50 nucleotides 5' and/or 3' to the insertion junction on either side of nucleotides 1230-1233 in SEQ ID NO: 53 should have fit within the HI Locus and does appear in the nonHI locus at this position. In some embodiments, an informative fragment of SEQ ID NO: 33, SEQ ID NO: 37, SEQ ID NO: 52 or SEQ ID NO: 53 can be a marker as defined herein below. A marker which tracks the lesion which causes the phenotype will be superior to any marker which is merely linked because the marker to the causative lesion will never disassociate from the phenotype. Linked markers can and become disassociated by a recombination event.

The presently disclosed subject matter also provides reagents for use in detecting and/or assaying for the presence of gene products associated with HI in a plant cell or other source of biomolecules. Such reagents can include in some embodiments an amplification primer pair capable of amplifying a plant nucleic acid template to generate a marker amplicon, wherein the marker amplicon corresponds to a marker comprising an informative subsequence of SEQ ID NO: 33, SEQ ID NO: 37, SEQ ID NO: 52 or SEQ ID NO: 53, wherein the informative subsequence permits identification of the presence or absence of an allele associated with HI in a plant. By way of example and not limitation, such a amplification primer pair can be designed with a forward primer that is located 5' to the fusion junction and a reverse primer that is located 3' to the fusion junction present in SEQ ID NO: 53. Such an amplification primer pair would not be expected to amplify a gene product derived from a wildtype maize non HI locus.

In some embodiments, one or more amplification primer pairs of the presently disclosed subject matter are provided in the form of a kit, wherein the kit further comprises one or more positive and/or negative amplification primer pairs (such as but not limited to an amplification primer pair designed to amplify a wild type (HI) gene product), instructions for employing the amplification primer pairs, and/or one or more additional reagents necessary for performing an amplification reaction (e.g., a DNA polymerase, a reverse transcriptase, a buffer solution, etc.).

Thus, in some embodiments, a method for detecting and/or assaying for the presence of gene products associated with HI in a plant cell or other source of biomolecules can employ the polymerase chain reaction (PCR) using appropriately designed primers to detect the presence in a plant cell or other source of biomolecules of a gene product associated with HI (including, but not limited to a gene product comprising SEQ ID NO: 33, SEQ ID NO: 37, SEQ ID NO: 52 or SEQ ID NO: 53 or an informative fragment thereof. It is understood that other molecular biological techniques can also be employed for this purpose including, but not limited to TAQMAN® assays, KASPAR™ assays, ILLUMINA® GOLDENGATE® assays, etc.

In some embodiments, the presently disclosed subject matter provides methods for diagnostic determination of whether a plant having such DNA will or will not exhibit HI and/or producing plants that exhibit HI. In some embodiments, the methods comprise (a) transforming a plant cell with an expression cassette as disclosed herein to produce a transformed plant cell; and (b) generating a plant from the transformed plant cell.

In some embodiments, a plant cell is stably transformed with an expression cassette of the presently disclosed subject matter. "Stable transformation" or "stably transformed" is intended to mean that a polynucleotide, for example, an expression cassette as described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the nucleic acids pertinent to the presently disclosed subject matter can be used in conjunction with any such vectors. The selection of a vector will depend upon the transformation technique to be employed and the target species for transformation. For certain target species, different antibiotic or herbicide selection markers might be preferred. Selection markers used routinely in transformation include the nptII gene, which confers resistance to kanamycin and related antibiotics (Viera & Messing, 1982; Bevan et al., 1983); the pat and bar genes, which confer resistance to the herbicide glufosinate (also called phosphinothricin; see White et al., 1990; Spencer et al., 1990; and U.S. Pat. Nos. 5,561,236 and 5,276,268); the hph gene, which confers resistance to the antibiotic hygromycin (Blochinger & Diggelmann, 1984), and the dhfr gene, which confers resistance to methatrexate (Bourouis & Jarry, 1983); the EPSPS gene, which confers resistance to glyphosate (U.S. Pat. Nos. 4,940,935 and 5,188,642); the glyphosate N-acetyltransferase (GAT) gene, which also confers resistance to glyphosate (Castle et al., 2004; U.S. Patent Application Publication Nos. 2005/0060767, 2005/0246798, and 2007/0004912); and the mannose-6-phosphate isomerase gene, which provides the ability to metabolize mannose (U.S. Pat. Nos. 5,767,378 and 5,994,629), the gene encoding a mutant D-amino acid oxidase which can be derived from *Rhodotorula gracilis*, with a lysine at position 58 rather than a phenylalanine which interacts with D-phosphinothricin to produce a toxin (U.S. Pat. No. 7,939,709).

Thus, in some embodiments the presently disclosed subject matter relates to inducing HI in a plant. In some embodiments, a general technique for producing plants that exhibit HI comprises transforming a plant cell with an expression cassette to produce a transformed plant cell, wherein the expression cassette encodes an RNAi construct targeted to a gene associated with HI; and (b) generating a plant from the transformed plant cell. After a plant cell is transformed with an expression vector or expression cassette encodes an RNAi construct targeted to a gene associated with HI, a whole plant or plant tissue can be regenerated, if desired. Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, 1984). For the construction of vectors useful in *Agrobacterium* transformation, see e.g., U.S. Patent Application Publication No. 2006/0260011. See also Lee & Glevin, 2008.

Transformation without the use of *Agrobacterium tumefaciens* circumvents the requirement for T-DNA sequences in the chosen transformation vector and consequently vectors lacking these sequences can be utilized in addition to vectors such as the ones described above which contain one or more T-DNA sequences. Transformation techniques that do not rely on *Agrobacterium* include transformation via particle bombardment, protoplast uptake (e.g., PEG and electroporation), whiskering, and microinjection. The choice of vector depends largely on the chosen selection for the species being transformed. For the construction of such vectors, see e.g., U.S. Patent Application Publication No. 2006/0260011.

For expression of a nucleotide sequence of the presently disclosed subject matter in plant plastids, plastid transformation vector pPH143 (PCT International Patent Application Publication No. WO 1997/32011, example 36) can be used. The nucleotide sequence is inserted into pPH143 thereby replacing the PROTOX coding sequence.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, and/or microinjection. Examples of these techniques are described by Paszkowski et al., 1984; Potrykus et al., 1985; Reich et al., 1986; and Klein et al., 1987. In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g., pCIB200 or pCIB2001) to an appropriate *Agrobacterium* strain which may depend of the complement of vir genes carried by the host *Agrobacterium* strain either on a co-resident Ti plasmid or chromosomally (e.g., strain CIB542 for pCIB200 and pCIB2001 (Uknes et al., 1993). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, 1988).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. Variations of this technique are disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium, or a bacteriophage, each containing DNA sought to be introduced) can also be propelled into plant cell tissue.

Transformation of most monocotyledon species has now also become routine. Exemplary techniques include direct gene transfer into protoplasts using PEG or electroporation techniques, and particle bombardment into callus tissue. Transformations can be undertaken with a single DNA species or multiple DNA species (i.e., co-transformation), and both of these techniques are suitable for use with the presently disclosed subject matter. Co-transformation can have the advantage of avoiding complete vector construction and of generating transgenic plants with unlinked loci for the gene of interest and the selectable marker, thereby permitting the removal of the selectable marker in subsequent generations, should this be regarded desirable. However, a disadvantage of the use of co-transformation can be the less than 100% frequency with which separate DNA species are integrated into the genome (Schocher et al. Biotechnology 4: 1093-1096 (1986)).

European Patent Applications EP 0 292 435 and EP 0 392 225, and PCT International Patent Application Publication No. WO 1993/07278 describe techniques for the preparation of callus and protoplasts from an elite inbred line of maize, transformation of protoplasts using PEG or electroporation, and the regeneration of maize plants from transformed protoplasts. Gordon-Kamm et al., 1990) and Fromm et al., 1990 have published techniques for transformation of A188-derived maize line using particle bombardment. Furthermore, PCT International Patent Application Publication No. WO 1993/07278 and Koziel et al., 1993 describe techniques for the transformation of elite inbred lines of maize by particle bombardment. This technique utilizes immature maize embryos of 1.5-2.5 mm length excised from a maize ear 14-15 days after pollination and a BIOLISTIC® PDS-1000/He (Bio-Rad Laboratories, Hercules, California, United States of America) device for bombardment.

Transformation of rice can also be undertaken by direct gene transfer techniques utilizing protoplasts or particle bombardment. Protoplast-mediated transformation has been described for *Japonica*-types and *Indica*-types (Zhang et al., 1988; Shimamoto et al., 1989; Datta et al., 1990). Both types are also routinely transformable using particle bombardment (Christou et al., 1991). Furthermore, PCT International Patent Application Publication No. WO 1993/21335 describes techniques for the transformation of rice via electroporation.

European Patent Application EP 0 332 581 describes techniques for the generation, transformation and regeneration of Pooideae protoplasts. These techniques allow the transformation of *Dactylis* and wheat. Furthermore, wheat transformation has been described by Vasil et al., 1992 using particle bombardment into cells of type C long-term regenerable callus, and also by Vasil et al., 1993 and Weeks et al., 1993 using particle bombardment of immature embryos and immature embryo-derived callus. An exemplary technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashige & Skoog, 1962) and 3 mg/l 2,4-D for induction of somatic embryos, which is allowed to proceed in the dark. On the chosen day of bombardment, embryos are removed from the induction medium and placed onto the osmoticum (i.e., induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hours, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See e.g., PCT International Patent Application Publication No. WO 1994/00977 and U.S. Pat. No. 5,591,616. See also Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994; Dong et al., 1996; Hiei et al., 1997). Also, the various media constituents described below can be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; PHYTAGEL™ plant tissue culture reagent, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is resuspended in liquid MS-CIM medium. The *Agrobacterium* culture is diluted to an $OD_{600}$ of 0.2-0.3 and acetosyringone is added to a final concentration of 200 μM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., 2001), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin, 2% Mannose, and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (To generation) grown to maturity, and the $T_1$ seed is harvested.

The plants obtained via transformation with a nucleic acid sequence of interest in the presently disclosed subject matter can be any of a wide variety of plant species, including those of monocots and dicots. The plants used in the methods of the presently disclosed subject matter are in some embodiments selected from the list of agronomically important target crops set forth elsewhere herein. The expression of a nucleic acid of the presently disclosed subject matter in combination with other characteristics important for production and quality can be incorporated into plant lines through breeding. Breeding approaches and techniques are known in the art. See e.g., Welsh, 1981; Wood, 1983; Mayo, 1987; Singh, 1986; and Wricke & Weber, 1986.

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad Laboratories, Hercules, California, United States of America) coated with DNA from plasmids pPH143 and pPH145 essentially as described in Svab & Maliga, 1993. Bombarded seedlings are incubated on T medium for two days after which leaves are excised and placed abaxial side up in bright light (350-500 μmol photons/$m^2$/s) on plates of RMOP medium (see Svab et al., 1990) containing 500 μg/ml spectinomycin dihydrochloride (Sigma, St. Louis, Missouri, United States of America). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (see Sambrook & Russell, 2001). BamHI/EcoRI-digested total cellular DNA (Mettler, 1987) is separated on 1% Tris-borate (TBE) agarose gels, transferred to nylon or nitrocellulose membranes, and probed with $^{32}P$-labeled random-primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride et al., 1994) and transferred to the greenhouse.

To test the haploid induction capacity of newly created lines, the pollen from each line is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%, and for high stringency, a good cutoff off is greater than 1% haploids. This is because a natural 'background' haploid induction rate of around 0.1% exists in maize Because haploidy is only induced through the male parent during in vivo maize haploid induction, the female simply serves as a "tester" and thus, the female germplasm could be any number of lines. The female tester could be the inducer line itself (and the cross would thus be a self hybridization), or the tester could be any inbred, hybrid, or backcrossed maize line. The ploidy analysis can involve different methods, as described below.

One method of plant ploidy analysis is to evaluate the phenotypic characteristics of the plant, paying attention to those characteristics associated with haploidy, including but not limited to short plant stature, altered phylotaxy, smaller leaf width, low overall body mass, and male sterility. Plants could be given a score on each characteristic and then the scores could be added together and compared to known haploid and diploid controls. In another embodiment, the embryos resulting from a haploid induction cross may be extracted mechanically from immature kernels anytime between day 9 and day 20 after pollination, and then subjected to ploidy analysis by a ploidy analyzer (Partec) which uses DAPI stain combined with flow cytometry to quantify the total DNA amount per cell. In one embodiment, embryonic and/or scutellar tissue is used for processing; in another embodiment, adult plant tissues including roots, leaves, stems, or flowers are used. In one embodiment, the selected tissues are chopped up with a razor blade, incubated in an extraction buffer, filtered through a nylon mesh filter and then incubated in a DAPI stain before loading into the ploidy analyzer. In another embodiment, embryonic or adult tissue including those described above is first digested into protoplasts using a combination of cellulose and maceroenzyme in a buffer solution, then filtered and incubated in DAPI.

In yet another method of ploidy analysis, microscopic imaging of mature, juvenile, or embryonic plant tissues can be used to identify the ploidy by counting the number of chromosomes in certain cells that are undergoing mitosis. The DNA in this case may be stained with DAPI or any other common DNA stain such as propidium iodide. In maize a diploid plant will have 20 chromosomes per cell while a haploid plant will have 10 per cell. In such an approach, the embryos can be incubated on media for anywhere from zero to fourteen days, during which many embryos may germinate and grow small rootlets.

Alone or in combination with any of the ploidy analysis methods described above, the putative novel haploid induction line may be first crossed to a marker line, including but not limited to lines that contain the R1-navajo (R 1-nj) or R1-scutellum2 (R1-Scm2) markers, or any line having DNA that encode for protein products that confer a visual identifier, such as a color visible to the human eye (e.g. anthocyanin) or a fluorescence-based marker visible only via fluorescent microscopy. Such markers, having been introgressed into the putative haploid inducer line, can serve as evidence of the existence of the paternal genome in progeny indicating a diploid state, with absence indicating a haploid state. The presence or absence of the marker may be detected using a visual test or microscopy.

The presently disclosed subject matter also provides methods for identifying the presence or absence of an allele associated with HI in a plant. In some embodiments, the methods comprise (a) obtaining a sample from the plant comprising genomic and/or nuclear DNA and/or an RNA product derived therefrom; (b) contacting the sample with a pair of primers that, when used in a nucleic-acid amplification reaction with a nucleic acid sample from the plant, produces an amplicon that can be used to identify the presence or absence of an allele associated with HI; (c) amplifying a fragment from said sample using the primer pair of (b), wherein the primer pair is complementary and binds to the nucleotide sequence of (b); and (d) detecting an amplicon that can be used to identify the presence or absence of an allele associated with HI in the plant.

The presently disclosed subject matter also provides methods for introgressing HI-inducing nucleotide sequences into plants. In some embodiments, the methods comprise crossing a first plant with a second plant to produce a third plant, wherein the genome of the first plant or the second plant comprises a recombinant nucleic acid sequence encoding a HI-associated gene product of the presently disclosed subject matter. In some embodiments, the methods further comprise assaying the genome of the third plant for the presence of the recombinant nucleic acid sequence encoding the HI-associated gene product. In some embodiments, the recombinant nucleic acid comprises (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

The presently disclosed subject matter also provides methods for selecting $F_0$ parental plants that are predicted to produce subsequent (e.g., $F_1$, $F_2$, $F_3$, etc.) generations with plants that exhibit HI. In some embodiments, the methods comprise identifying in the absence of sequence in the genome of an $F_0$ plant a nucleic acid comprising a sequence selected from the group consisting of The presently disclosed subject matter also provides kits for detecting the presence or absence of a HI-inducing allele in a plant. In some embodiments, the kits comprise one or more nucleic acid- and/or amino acid-based reagents derived from the maize HI locus or from a locus linked thereto, wherein the one or more nucleic acid- and/or amino acid-based reagents are designed to be employed in a nucleic acid- and/or amino acid-based assay for the presence or absence in the plant (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

In some embodiments, the one or more nucleic acid- and/or amino acid-based reagents derived from the maize HI locus or from a locus linked thereto comprise one or more oligonucleotide primers that are diagnostic of the presence in the plant of in the plant of the nucleic acid having at (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

As used herein, a "nucleic acid- or amino acid-based reagent" of the presently disclosed subject matter refers to any nucleic acid, peptide, or polypeptide that can be used to detect the presence or absence of SEQ ID NO: 33, SEQ ID NO: 37, SEQ ID NO: 52 or SEQ ID NO: 53 or an informative fragment thereof in a plant in any type of assay. By way of example and not limitation, a nucleic acid-based reagent of the presently disclosed subject matter can be an oligonucleotide primer pair that is designed to flank the deletion junction such that an amplification product will occur only if (a) a nucleic acid having at least 90% identity to SEQ ID NO: 33, optionally wherein the percent identity is calculated over the entire length of SEQ ID NO: 33; (b) a nucleic acid having at least 95% identity over nucleotides 91-1452 of SEQ ID NO: 33; (c) a nucleic acid that is the reverse complement of either of (a) or (b); (d) a nucleic acid that encodes a polypeptide comprising an amino acid sequence that is at least 95% identical to SEQ ID NO: 54, SEQ ID NO: 55, SEQ ID NO: 56 or SEQ ID NO: 57 optionally wherein the percent identity is calculated over the entire length of SEQ ID NO: 54, SEQ ID NO: 55, SEQ ID NO: 56 or SEQ ID NO: 57 respectively; and, (e) a sequence having at least 90% identity to SEQ ID NO: 32, optionally wherein the percent identity is calculated over the entire length of SEQ ID NO: 32; (f) a sequence having at least 95% identity over nucleotides 1-1795 of SEQ ID NO: 32; (g) a nucleic acid sequence that is the reverse complement of either of (e) or (f). In some embodiments, the recombinant nucleic acid encodes an amino acid sequence that comprises all or substantially all of amino acids 1-454 of SEQ ID NO: 54.

Similarly, an amino acid-based reagent of the presently disclosed subject matter can be, but is not limited to, an antibody that binds to a polypeptide having SEQ ID NO: 54, SEQ ID NO: 55, SEQ ID NO: 56 or SEQ ID NO: 57 or an informative fragment thereof. In some embodiments, an antibody that binds to both a polypeptide of SEQ ID NO: 54, SEQ ID NO: 55, SEQ ID NO: 56 or SEQ ID NO: 57 and a maize HI gene product can be employed, wherein in an appropriate assay (e.g., a Western blot or an SDS-PAGE gel), the polypeptide of SEQ ID NO: 54, SEQ ID NO: 55, SEQ ID NO: 56 or SEQ ID NO: 57 and its absence or presence shows the maize HI gene product can be distinguished. In some embodiments, the kit further comprises a set of instructions for performing an assay with the nucleic acid- or amino acid-based reagent. In some embodiments, the kit further comprises one or more additional reagents that can be employed in the performance of the assay with the nucleic acid- or amino acid-based reagent.

EXAMPLE

The following Examples provide illustrative embodiments of the presently disclosed subject matter. In light of the present disclosure and the general level of skill in the art, those of skill will appreciate that the following examples are intended to be exemplary only and that numerous changes, modifications, and alterations can be employed without departing from the scope of the presently disclosed subject matter.

Example 1

QTL Mapping Material Choices

Two mapping populations involving a haploid inducer inbred (RWK) and two non-inducer inbreds (NP2391, NP2460) were generated. RWK was selected because of its high haploid induction ability compared to stock 6. The two non-inducer lines were selected due to existence of extensive data relevant to them. The recombinant inbred populations were backcross populations (BC1) such that the theoretical allele content was 75% RWK and 25% NP2391 for the first population (138 RILs, Recombinant Inbred Lines) and 75% RWK and 25% NP2460 for the second population (123 RILs). The mapping populations were self-pollinated two generations to make the BC1F3. The subsequent BC1F4 plants were testcrossed onto eight plants in two tester rows. The testcrosses were harvested and bulk shelled. Approximately 500 kernels of testcross seed were planted for each entry to observe the number of haploid and diploid plants and thereby determine the haploid induction rate of each recombinant inbred entry within that population.

QTL analysis was performed for both the populations using a version of "QTL Cartographer" software by combining the testcross induction rates with the SNP genotyping data of RILs. QTLs were declared when the LOD score is higher than 2. In total about −70% variation in haploid induction rate was explained by QTL Bin 1.04. A number of other QTLs were also detected but these accounted for less of the variation. The two important values in QTL studies are the LOD (logarithm of odds) and the $R^2$. A high LOD value represents greater statistical evidence for the present of a QTL, and a higher $R^2$ indicates that the particular QTL has more effect on the trait of interest. The major QTL detected was on Chromosome 1, in a somewhat different region of Chromosome 1 than what was previously indicated by a patent application publication. Additional information about the fine mapping is provided in the subsequent examples.

TABLE 2

Breeding-Mapping Strategy

| Season | What | Result |
|---|---|---|
| Year 0 | F1 | Two non-inducers inbreds (NP2391; P2460) were crossed with RWK |
| Year 0 | F1->BC1 | Both F1 backcrossed to RWK |
| Year 1 | BC1F1->BC1F2 | |
| Year 1 | BC1F2->BC1F3 | |
| Year 1 | BC1F4 testcrosses made X 2 testers | Two mapping Populations x two testers |
| Year 1 | BC1F4 testcrosses phenotyped | QTL Bin 1.04 identified, ~70% variation explained |
| Year 1 | BC2 made | |
| Year 2 | BC3 made | |
| Year 2 | BC3F2 made | |
| Year 2 | BC3F3 testcrosses made X 2 testers | Two fine mapping Populations X two testers |
| Year 3 | BC3F3 testcrosses phenotyped | First fine mapping completed |
| Year 3 | BC3F4 testcrosses made X 2 testers | |
| Year 3 | BC3F4 testcrosses phenotyped | Second fine mapping completed |
| Year 4 | BC3F5 testcrosses made X 2 testers | |

TABLE 2-continued

Breeding-Mapping Strategy

| Season | What | Result |
|---|---|---|
| Year 5 | BC3F5 testcrosses phenotyped | Fine mapping completed |
| Year 5 | RWK, RWK-NIL, Stock 6 gemones sequences | Annotations |

Example 2

Development of Near Isogenic Lines

To accurately position and fine-map the QTL for Haploid induction, near isogenic lines (NIL's) are created by back-crossing to RWK for three generations and followed by selfing for another 3 generations. During this process several NIL's were created in RWK background with regions from NP2391 and NP2460 in the target QTL region. This particular strategy was utilized to create NIL's because, haploid induction efficiency can change with the background and also to keep the rest of the RWK genome mostly uniform while focusing on the small non-inducer chromosome regions that were back-crossed into RWK.

Example 3

Fine Mapping

When the experiment was initiated, the haploid induction locus was localized in a region of 3.3 MB containing approximately 90 putative genes within that interval. The fine mapping process reduced the haploid induction locus to a 0.88 MB region with twenty five annotated genes. Additional fine mapping reduced the haploid induction locus to a 0.60 region.

The BC3F3 plants described in the above examples, which were heterozygous at the region of interest were selfed to create additional recombinations. These BC3F4 recombinants were testcrossed with two different testers and phenotypic information was gathered by measuring their haploid induction (HI) ability. The genotypic information from this localized haploid induction region and the phenotypic information taken concerning these line's haploid induction ability were correlated to fine-map the haploid induction locus to a 0.60 MB region with fewer than 7 annotated genes.

TABLE 3

FINE MAPPING

| Old interval | New Confidence interval | Refined interval | Gene_ID | transcript_start | transcript_end | transcript_strand |
|---|---|---|---|---|---|---|
| x | x | x | GRMZM2G305400 | 67991172 | 67994092 | −1 |
| x | x | x | GRMZM2G082836 | 68107606 | 68110989 | 1 |
| x | x | x | GRMZM2G382717 | 68113455 | 68115168 | −1 |
| x | x | x | GRMZM2G120587 | 68133178 | 68136953 | −1 |
| x | x | x | GRMZM2G471240 | 68240862 | 68242656 | 1 |
| x | x | x | GRMZM2G471240 | 68240862 | 68242656 | 1 |
| x | x | x | GRM2M2G062320 | 68318898 | 68321409 | 1 |
| x | x | | GRMZM5G866758 | 68430654 | 68436197 | 1 |
| x | x | | GRMZM5G866758 | 68430654 | 68436197 | 1 |
| x | x | | GRMZM2G003530 | 68435670 | 68439997 | −1 |
| x | | | GRMZM2G077991 | 68543246 | 68546264 | −1 |
| x | | | GRMZM2G077991 | 68543694 | 68546264 | −1 |
| x | | | GRMZM2G077991 | 68543805 | 68546269 | −1 |
| x | | | GRMZM2G077960 | 68554980 | 68559182 | 1 |
| x | | | GRMZM2G077897 | 68561209 | 68565155 | −1 |

TABLE 3-continued

| FINE MAPPING | | | | | | |
|---|---|---|---|---|---|---|
| Old interval | New Confidence interval | Refined interval | Gene_ID | transcript_start | transcript_end | transcript_strand |
| x | | | GRMZM2G347583 | 68660278 | 68665995 | 1 |
| x | | | GRMZM2G173030 | 68668900 | 68671460 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G022061 | 68876150 | 68882226 | 1 |
| x | | | GRMZM2G340286 | 68928213 | 68929600 | 1 |
| x | | | GRMZM2G340279 | 68934652 | 68937080 | −1 |
| x | | | GRMZM2G347808 | 69005208 | 69012612 | 1 |

Example 4

Markers for Refining Fine Mapping

The Table shown in example four shows the marker or locus name on the far left of the table. The limiting factor for further refining the locus was the availability of markers and not the maize line recombinants. Thus additional taqman assays were developed for gathering genotypic information from the haploid induction region. The Table shows the SNPs and their map positions. Each of these markers identifies an allele. The desirable nucleotides for a haploid inducing allele in the RWK (haploid inducing line) are also listed. These markers can be utilized in a marker assisted breeding program to select for or against the haploid induction ability in germplasm.

TABLE 4

| MARKER TABLE | | | |
|---|---|---|---|
| Marker or Locus Name | Chromosome | Map Position | RWK Allele |
| SM0262A | 1 | 45441103 | G/G |
| SM0390D | 1 | 45514003 | G/G |
| SM0657AQ | 1 | 56221199 | A/A |
| SM0103A | 1 | 60144794 | A/A |
| SM2317 | 1 | 60806574 | G/G |
| SM2318 | 1 | 60808690 | A/A |
| SM2315 | 1 | 60834691 | A/A |
| SM2322 | 1 | 61019467 | G/G |
| SM1994CQ | 1 | 61940683 | C/C |
| SM1994AQ | 1 | 61948232 | A/A |
| SM2014DQ | 1 | 62141179 | A/A |
| SM2014CQ | 1 | 62141297 | G/G |
| SM1208A | 1 | 62890212 | C/C |
| SM1208BQ | 1 | 62890343 | C/C |
| SM2332 | 1 | 62890343 | C/C |
| SM2331 | 1 | 62918261 | C/C |
| SM2542 | 1 | 65086371 | A/A |
| SM2543 | 1 | 65086379 | A/A |
| SM2547 | 1 | 65086882 | C/C |
| SM2548 | 1 | 65087687 | G/G |
| SM2359 | 1 | 65222457 | C/C |
| SM2366 | 1 | 65223245 | C/C |
| SM2333 | 1 | 65657736 | G/G |
| SM2338 | 1 | 66955942 | C/C |
| SM2340 | 1 | 67130654 | G/G |
| SM2339 | 1 | 67130683 | A/A |
| SM2356 | 1 | 67645465 | A/A |
| SM2357 | 1 | 67645486 | G/G |
| SM2361 | 1 | 67850657 | G/G |
| SM2363 | 1 | 67851018 | A/A |
| SM2587 | 1 | 68128675 | A/A |
| SM2589 | 1 | 68128928 | G/G |

TABLE 4-continued

| MARKER TABLE | | | |
|---|---|---|---|
| Marker or Locus Name | Chromosome | Map Position | RWK Allele |
| SM2593 | 1 | 68129217 | G/G |
| SM2594 | 1 | 68129237 | C/C |
| SM2602 | 1 | 68130522 | A/A |
| SM2607 | 1 | 68424731 | A/A |
| SM2608 | 1 | 68428500 | A/A |
| SM2365 | 1 | 68431623 | G/G |
| SM2362 | 1 | 68431768 | C/C |
| SM2712 | 1 | 68453157 | A/A |
| SM2709 | 1 | 68454360 | G/G |
| SM2706 | 1 | 68455010 | A/A |
| SM2710 | 1 | 68565361 | C/C |
| SM2707 | 1 | 68658060 | G/G |
| SM2550 | 1 | 68670604 | C/C |
| SM2551 | 1 | 68670713 | C/C |
| SM2708 | 1 | 68678452 | A/A |
| SM2610 | 1 | 69012158 | A/A |
| SM2613 | 1 | 69158347 | A/A |
| SM2552 | 1 | 69543214 | A/A |
| SM2553 | 1 | 69587711 | G/G |
| SM2554 | 1 | 69881293 | C/C |
| SM2556 | 1 | 69887955 | A/A |
| SM2557 | 1 | 69889226 | G/G |
| SM2558 | 1 | 70155695 | A/A |
| SM2616 | 1 | 70158847 | A/A |
| SM2617 | 1 | 70159265 | A/A |
| SM2559 | 1 | 70162230 | A/A |
| SM2621 | 1 | 70164485 | A/A |
| SM2624 | 1 | 70213152 | A/A |
| SM2626 | 1 | 70244705 | A/A |
| SM2560 | 1 | 70251144 | A/A |
| SM2628 | 1 | 70347954 | A/A |
| SM2629 | 1 | 70512212 | G/G |
| SM2013BQ | 1 | 71020438 | C/C |
| SM2573 | 1 | 71066077 | C/C |
| SM2575 | 1 | 71541039 | A/A |
| SM2576 | 1 | 71590349 | A/A |
| SM2579 | 1 | 71794881 | G/G |
| SM2580 | 1 | 71794974 | C/C |
| SM2581 | 1 | 72013466 | A/A |
| SM2347 | 1 | 72233113 | G/G |
| SM2349 | 1 | 72233448 | G/G |
| SM2368 | 1 | 73246562 | G/G |
| SM2352 | 1 | 73379493 | A/A |
| SM2369 | 1 | 73380804 | C/C |
| SM2351 | 1 | 73635946 | G/G |
| SM2354 | 1 | 73966550 | G/G |
| SM2353 | 1 | 73966557 | G/G |
| SM2345 | 1 | 73967645 | A/A |
| SM0118A | 1 | 75203350 | G/G |
| SM0251A | 1 | 82575679 | G/G |
| SM0241C | 1 | 147159831 | A/A |

TABLE 4-continued

| MARKER TABLE | | | |
|---|---|---|---|
| Marker or Locus Name | Chromosome | Map Position | RWK Allele |
| SM0201B | 1 | 178008426 | A/A |
| SM1990AQ | 1 | 184012848 | G/G |
| SM0376B | 1 | 195332392 | G/G |

Example 5

New Interval Developed with Fine Mapping

As indicated in Example 4, the limiting factor for further refinement of the haploid induction QTL region was resolved with the development of additional markers for the haploid induction region on Chromosome 1. The recombinants were screened with these newly developed markers. The original haploid induction locus was reduced from a starting interval containing ~64 genes, which was then reduced its size to 17-25 genes. Further fine mapping resolved the region to 0.60 MB with 8 genes in the interval. The eight genes include two genes GRMZ2G471240, and GRMZ2G866758 which appear twice because expression data suggests alternative transcripts. Each of the genes are listed in the Table below and are identified by the public Gene ID with the transcript start and end identified. The new refined haploid induction locus is indicated in the new confidence level. With the data from a single recombinant, a subset of approximately 8 genes were identified to be highly likely to have impact on the haploid induction trait. These are indicated by the highlighted section of the third column from the left of the Haploid Interval Table below.

TABLE 5

| Describing Haploid Induction QTL Interval | | | |
|---|---|---|---|
| New Confidence interval | Refined interval | Sequencing data analysis | gene_id |
| x | x | Appears to be missing from all three lines | GRMZM2G305400 |
| x | x | NIL and B73 gDNAs align in coding region. RWK/Stock 6 gDNAs are very similar. All protein coding sequences appear similar. | GRMZM2G082836 |
| x | x | NIL/B73 are identical. RWK differs at several bases and three AA residues. It also has a 21 base insert just downstream of the stop codon. Stock 6 data not so good at amino terminus, but suggests its similar to RWK at the carboxy terminus. | GRMZM2G382717 |
| x | x | Stock 6, RWK and NIL differ from B73 outside protein coding region. RWK and Stock 6 have 2 additional amino acids | GRMZM2G120587 |
| x | x | NIL and B73 are virtually identical. Stock 6 and RWK are identical and a frame shift results in 20 incorrect AA followed by a new, premature stop codon | GRMZM2G471240 |
| | x | | GRMZM2G471240 |
| x | x | Not present in Stock 6/RWK. NIL/B73 are virtually identical. Some evidence this is a transcribed gene. | GRMZM2G062320 |
| x | | NIL and B73 are virtually identical. Stock 6 and RWK are identical. The pairs differ slightly at the protein level and outside the coding region. | GRMZM5G866758 |
| x | | | GRMZM5G866758 |
| x | | NIL is 97-98% identical to B73; RWK/Stock 6 95-99% similar to B73. Adjacent to GRMZM5G866758 but transcribed from opposite strand. All 4 encode the same protein. | GRMZM2G003530 |

Example 6

Sequence Analysis of Inducer and Non-Inducer Genomes

The maize haploid induction locus was understood to be present in a 2.2 Mb QTL located on Chromosome 1. This QTL represents approximately 70% of the variation associated with the haploid induction trait, and is therefore required for haploid induction. To date, no one has identified the genetic element responsible for haploid induction. As indicated in the earlier examples the haploid induction QTL was fine-mapped to reduce its size to 0.60 Mb In order to further identify the genes in this Haploid Induction region, the genomes of two haploid inducer lines, Stock 6 and RWK, and an RWK-NIL line were sequenced. Stock 6 is a maize haploid inducer line which is available from the Maize Genetics Stock Center in Champaign Ill. RWK is a maize line which is a haploid inducer line available from the University of Hohenhiem in Germany. B73 is a stiff stalk maize line produced and is broadly available from many sources including the Iowa State University in Ames, IA Genomic DNA from the leaf tissue of RWK, RWK-NIL, and Stock 6, was prepared and fragmented to produce two short-insert paired end (SIPE) libraries and one long-insert paired end (LIPE) library. Sufficient DNA sequence data were generated for 50× coverage of each genome, as indicated in the table below. The raw data were trimmed and compiled into sequence contigs. B73 sequence data for the Haploid Induction QTL on Chromosome 1 was used as a scaffold to enrich and refine contigs corresponding to this region from each genome.

TABLE 6

Sequence Coverage

| | SIPE data | | LIPE data | | | | |
|---|---|---|---|---|---|---|---|
| | total Mb | Coverage | total Mb | coverage | total % cov | % SIPE | % LIPE |
| Stock6 | 185,117 | 74.0 | 47,301 | 18.9 | 93.0 | 80% | 20% |
| NIL | 117,060 | 46.8 | 17,649 | 7.1 | 53.9 | 87% | 13% |
| RNK | 215,666 | 86.3 | 28,108 | 11.2 | 97.5 | 88% | 12% |

Total = total Mb of sequence data
coverage = average depth of sequence coverage (based on maize genome estimate of 2.5 Gb)
SIPE = short insert paired end library data (average insert size ~330 bp)
LIPE = long insert paired end library data (average insert size ~5000 bp)
Sequencing target was >= 50x coverage, >=10% of data from LIPE reads The contigs were assembled and analyzed. The process produced ~300 contigs. These were then BLASTed against the 25 genes found within the HI interval. The candidate sequence from each line was annotated and compared. Expression was verified by cDNA/EST analysis, and the annotation was verified by cDNA/gDNA alignment. The differences between the lines were noted and distinguished. (see Tables in earlier examples.)

Example 7

Sequence Analysis of Inducer and Non-Inducer Genomes

The assembled Stock 6, RWK and NIL (RWK-NIL) sequence contigs were compared to corresponding B73 sequence data. Gene models for each candidate gene were confirmed with additional sequence data from public and proprietary databases. The sequence data for each gene in the reduced HI interval were compared.

TABLE 7

Structural Variants in Haploid Induction Interval

| Gene | structural variants? | # SNPs altering protein sequence | annotation |
|---|---|---|---|
| GRMZM2G120587 | No | 3 | Serine carboxypeptidase |
| GRMZM2G471240 | No | 4 | Patatin-like phospholipase |
| GRMZM2G062320 | Yes | 1 | Histidine phosphatase superfamily, Phosphoglycerate mutase family |
| AC213048.3 | No | 0 | pseudogene/hypothetical protein |
| GRMZM5G866758 | Yes | 2 | acetyl-CoA acetyltransferase, cytosolic 1 [Zea mays] |
| GRMZM2G003530 | Yes | 2 | Putative uncharacterized protein |
| GRMZM2G077991 | Yes | 2 | Ribosomal protein L37e |
| GRMZM2G077960 | No | 0 | Protein phosphatase 2C family protein |
| GRMZM2G077897 | No | 15 | Plant protein of unknown function, paramyosin, |
| GRMZM2G347583 | No | 2 | uncharacterized protein |
| GRMZM2G173030 | No | 0 | hypothetical protein |
| GRMZM2G031591 | Yes | 0 | hypothetical protein |
| GRMZM2G070462 | Yes | 0 | FHA domain-containing protein |
| GRMZM2G022061 | No | 5 | hypothetical protein LOC100279962 (LOC100279962 |
| GRMZM2G340286 | No | 4 | uncharacterized protein |
| GRMZM2G340279 | Yes | 8 | pentatricopeptide repeat-containing protein |
| GRMZM2G347808 | No | 4 | uncharacterized protein |

The experiment did not find DNA sequence evidence that GRMZM2G305400 is present in the Stock 6, RWK or Nil genomes.

The gene GRMZM2G062320 is encoding a phosphoglycerate mutase and is absent in RWK and Stock 6 but present in NIL and B73. This result will be tested by PCR. This gene product has expression in most plant tissues and stages of development. The gene product can be classified as a phosphoglycerate mutase and has sequence that places it in the histidine phosphatase superfamily.

We noted that other genes in the refined HI interval differ in sequence between the various genomes we examined. GRMZM2G471240 encodes a phospholipase that is exclusively expressed in meiotic anthers, and has a four nucleotide insertion resulting in 20 incorrect AA followed by a new, premature stop codon.

GRMZM2G120587 encodes a serine carboxypeptidase-like 51 (SCPL51) that is expressed in anthers and is a good candidate for a haploid induction because proteolysis has been shown to contribute towards centromere-specific localization of CENH3 proteins. The proteins encoded by RWK and Stock 6 have 2 additional amino acids.

GRMZM2G305400 encodes a cyclin and this gene was not present in the inducers or NIL, but it was present in B73.

GRMZM2G082836 gDNAs in Stock 6 and RWK are more similar to each other, and the GRMZM2G082836 gDNAs in NIL and B73 gene are more similar to each other. However the GRMZM2G082836 protein coding sequences of Stock 6, RWK, NIL and B73 are identical. This gene encodes a GTP-binding protein 1.

GRMZM2G382717 gDNAs in the NIL and B73 lines are identical. Sequence coverage for Stock 6 was not complete, but the available data align precisely to the RWK sequence data. RWK differs from NIL/B73 at several bases and at three amino acids, and there is an additional 21 base pair insertion in RWK downstream of the translation stop codon. This gene encodes a chaperone DnaJ-domain superfamily protein.

GRMZM5G866758 gDNAs from the B73 and NIL lines are virtually identical. GRMZM5G866758 gDNAs from the inducer lines, RWK and Stock 6, are identical. The data indicate some sequence differences between RWK/stock 6 and B73/NIL at the protein level and outside the protein coding sequence. This gene encodes an acetoacetyl-CoA thiolase 2.

Example 8

A Method to Knock Out GRMZM2G062320 Expression in Pollen

Any unique GRMZM2G062320 transcript sequence ranging from 200-500 contiguous bases can be used to make an RNAi molecule targeting this gene. Sequences comprising the double stranded RNA can separate by an intron, or other DNA strand that doesn't constrain formation of the GRMZM2G062320 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. An effective expression cassette to accomplish this in pollen is shown in FIG. 1. A general expression cassette design strategy is given in U.S. Pat. No. 8,129,58. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.).

Example 9

Example Demonstrating Conservation of GRMZM2G062320 Protein Sequence in Maize Syngenta's Maize Solexa Association panel is a collection of RNA-seq data derived from 790 lines. Lines in this collection were chosen based on their phenotypic and genotypic diversity from a larger collection of maize germplasm. Seedling leaf tissue was used to generate the data. The largest open reading frame for each cDNA was translated to the encoded protein for each line. The proteins were then compared to establish diversity across all lines. This evidence shows that there are five GRMZM2G062320 variants in this collection. Sequence analysis of these 790 diverse maize lines showed that version A, SEQ ID NO: 5 is present in 784 lines, version B, SEQ ID NO: 2 is present in 3 lines and versions C SEQ ID NO: 6, D SEQ ID NO: 7, and E SEQ ID NO: 8 are present in one line each. The protein sequences are derived from RNA-seq data.

The alignment shown in FIG. 1 show these proteins differ at four positions. The evidence suggests the GRMZM2G062320 protein is highly conserved.

```
GRMZM2G062320-A
                                                   >SEQ ID NO: 5
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ
```

-continued

```
LVAGKHVMVAAHGNSLRSIIMHLDKLTSQKVISLELSTGIPMLYIFKEGK

FIRRGTPVGPSEASVYAYTRTKRFAEHITFQNKLA

GRMZM2G062320-B
                                                   >SEQ ID NO: 2
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKILVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

GRMZM2G062320-C
                                                   >SEQ ID NO: 6
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

PGCIDVPLTPKGVEEAIEAGKRICNIPIDVIYTSSLICAQMTAMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

GRMZM2G062320-D
                                                   >SEQ ID NO: 7
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWHRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA

GRMZM2G062320-E
                                                   >SEQ ID NO: 8
MAGAISHHALAFSQSHWCSAKNSRFGKRTGNARLVYLKGRCGSGSRKLGL

MWASSSQSSVMEPTHLPSDGNSSHTPKKSSESALILIWHGESLWNEKNLF

TGCIDVPLTPKGVEEAIEAGKRICNIPIDVIYTSSLICAQMTSMLAMMQH

RRKKIPVITHNESEQAHRWSQIYSEETMKQSIPVITAWQLNERMYGELQG

LNKQETVDRFGKEQVHEWRRSYDIPPPNGESLEKCAERAVAYFKDQIIPQ

LVAGKHVMVAAHGNSLRSIIMHLDKLTSQKVISLELSTGIPMLYIFKEGK

FIRRGTPVGPSEASVYAYTRTKRFAEHITFQNKLA
```

Example 10

PCR Experiments to Determine the Presence or Absence of GRMZM2G062320 in the Haploid Inducer Lines These pairs worked as expected on NIL, RWK, and Stock6 DNA: NIL gDNA only amplified the NIL primer pair. RWK and Stock6 gDNA only amplified the RWK/Stock6 primer pair, which specifically detects the frameshift allele. The PCR products were sequenced and the sequences were identical to that from whole genome sequencing. The primer pairs are "nil.F1/R1" and "rwk.F1/R1".

Three PCR reactions spanning all but the first two exons of the gene model amplified in RWK and Stock6, and the amplicons had the correct size PCR gel band. These bands were excised from the gel, sub-cloned and sequenced, and were found to be nearly identical in sequence to the B73 and NIL amplicons, except for a few single nucleotide polymorphisms (SNPs). These SNPs may represent normal genetic drift because none of them caused non-conservative amino acid substitutions. The 5' end of the gene model could not be detected by PCR in RWK, Stock6, or NIL DNA samples. After multiple rounds of PCR and primer redesign, the 5' end was never amplified or cloned in any of the lines. Overall, this data contradicts the genome assemblies, suggesting that at least part of the gene model exists in RWK and Stock6 inducers.

One primer pair, designed to amplify a ~400 bp amplicon spanning exons 6-8, not only amplified in all lines tested, but the DNA sequence also matched B73 with 100% nucleotide identity. This primer pair was used to query a panel of high, low, and non-inducer maize plants. The high inducers all give greater than 7% haploid embryos upon outcrossing through the male (>7% haploid induction rate (HIR)). The low inducers have a HIR between 1 and 3%, and the non-inducers have a HIR of <0.1%. All of the high and low inducer lines were derived from the original Stock6 line, and thus it is assumed that the lesion responsible for haploid induction should be present in all high and low inducers, and absent in non-inducers.

When the exon 6-8 PCR primers were tested on these DNA samples, a band of the correct size and sequence was found in 9/9 non-inducers, 8/12 high inducers, and 6/7 low inducers. No band was present in 4/12 high inducers and 1/7 low inducers (Table 1). This indicates that, contrary to the sequencing data, this gene does exist in RWK and Stock6, but in various other induction lines, there may be presence/absence variation but it does not correlate with induction capacity. This makes it difficult to explain how GRMZM2G062320 is responsible for haploid induction.

TABLE 8

| GRMZM2G062320<br>PCR test for presence of amplicon exon 6-8 | Induction Rate | Band present? |
|---|---|---|
| Controls: | | |
| Stock 6 (low) | 2.50% | + |
| RWK (high) | 12% | + |
| RWK-NIL (non) | <1% | + |
| High Inducers: | | |
| ZMS | 7% | − |
| Z19-PR | 7% | − |
| RWS-Z86 | 10% | + |
| K13 | 9% | + |
| (ID3002/Z22)B > 29-5 > 2-5-1-B- | 7% | − |
| Z-19-//AF4031PR//Z-19-)1-1-2-3-1-3-B- | 9.5% | + |
| ZR86 | 12% | + |
| ZR53 | 12% | − |
| ZR75 | 13% | + |
| (Z21/RWS)B(GS)-75-1-2-3-B- | ~8% | + |
| AX5707 inducer-good | ~9% | + |
| Poor Inducers: | | |
| Stock6 R1-nj | 2.5% | + |
| (Z21/RWS//[RWS]B$)33-5- | <2% | + |
| (K-13-/(ZMS/SEW-PR)B > 2 > B-9//K-13-)2-4-1- | <2% | + |

TABLE 8-continued

| GRMZM2G062320<br>PCR test for presence of amplicon exon 6-8 | Induction Rate | Band present? |
|---|---|---|
| (K-13-/(ZMS/SEW-PR)B > 2 > B-9//K-13-)6-1-2- | <2% | + |
| (ZMS/SEW-PR)B > 2 > B-7-2-1-2- | <2% | − |
| AX5707 inducer-low | ~3% | + |
| Non-inducers: | | |
| Stock6 R1-nj B1Pl1 | <0.1% | + |
| (Z-21-/AF4031PR//Z-21-1-B-)1-1-1-1-B- | <0.1% | + |
| FF6096 | <0.1% | + |
| ID5829 | <0.1% | + |
| XO5744 | <0.1% | + |
| ID3002 | <0.1% | + |
| AF4031PR | <0.1% | + |
| AX5707 | <0.1% | + |

Example 11

PCR Experiments to Determine the Presence or Absence of GRMZM2G471240 in the Haploid Inducer Lines In order to develop a PCR test that would distinguish between RWK/Stock6 and NIL haplotypes, two primer pairs were designed: one pair should amplify the RWK/Stock6 frame-shift allele, while the other should amplify the B73/NIL allele.

```
For STOCK6/RWK allele (mutant,
frameshift allele):
rwk.F1       TACGCCGTGCGCTAACATA

rwk.R1       GTACCTCGCTCCCTGTCTCC
SIZE:        822 bp

FOR B73/RWK-NIL
nil.F1       GTACGCCGTGCGCTAACA

nil.R1       TCGTACCTCCCTGTCTCCAC
SIZE:        821
```

Use: In a PCR reaction, these would be used at 500 nMol final concentration. The reaction may also contain:

1×PCR reaction buffer
200 uM of dNTPs (dATP, dCTP, dGTP, and dTTP)
<250 ng of genomic DNA
deionized water
Taq enzyme (1 unit—many different types available—usually 0.2 uL or 0.5 uL depending on the units/uL
magnesium chloride or magnesium sulfate (1 mM)
Reaction volume: 25 or 50 uL Recommended Reaction:

1. 95 degrees C. 3'
2. 95 degrees C. 30" (denature)
3. 62 degrees C. 30" (anneal)
4. 72 degrees C. 1' (extend)
5. Repeat steps 2-4, 35 times
6. 72 degrees C., 10" (final extension)
7. 4 degrees C., forever These pairs worked as expected on NIL, RWK, and Stock6 DNA, NIL gDNA only amplified the NIL primer pair. RWK and Stock6 gDNA only amplified the RWK/Stock6 primer pair, which specifically detects the frame-shift allele. The PCR products were sequenced and the sequences were identical to that from whole genome sequencing. SNPs that were identified in the whole genome sequencing were confirmed in the PCR products (data not shown). The primer pairs are "nil.F1/R1" and "rwk.F1/R1".

Example 12

A Method to Knock Out GRMZM2G471240 Expression

Any unique GRMZM2G471240 transcript sequence ranging from 200-1000 contiguous bases can be used to make an RNAi molecule targeting this gene. Sequences comprising the double stranded RNA can separate by an intron, or other DNA strand that doesn't constrain formation of the GRMZM2G471240 double-strand RNA. Any number of constitutive promoters could be selected. A short list of some constitutive promoters include ZmUbi1, ZmUbi158, ZmUbi361, SbUbiCh3, SbUbiCh4. Pollen specific: Pollen-specific genes have been described for maize (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.) Such information can be used to identify other maize pollen-specific genes and produce pollen-specific expression cassettes. An effective expression cassette to accomplish this in pollen is shown in FIG. 1. A general expression cassette design strategy is given in U.S. Pat. No. 8,129,58. Use of the NOS, AGS terminator components in the design is optional. The gene regulatory sequences are derived from the ZmABP2 gene (Lopez I, Anthony, R. G., Maciver, S. K., Jaing, C.-J., Khan, S., Weeds, A. G., Hussey, P. J. (1996) Pollen specific expression of maize genes encoding actin depolymerizing factor-like proteins. Proc Natl Acad Sci USA 93:7415-7420.). Expression constructs have been built comprising The promoter of GRMZM2G471240 as in SEQ ID NO: 58 operably linked to the hairpin construct in SEQ ID NO: 60 operably linked to the terminator of SEQ ID NO:59. Another construct was made with The promoter of GRMZM2G471240 as in SEQ ID NO: 58 operably linked to the hairpin construct in SEQ ID NO: 61 operably linked to the terminator of SEQ ID NO:59.

Example 13

Generation of Transgenic Maize Plants

Transformation of immature maize embryos is performed essentially as described in Negrotto et al., Plant Cell Reports 19:798-803 (2000). Various media constituents described therein can be substituted.
Agrobacterium strain LBA4404 (Invitrogen) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately 0.8×109 Agrobacteria are suspended in LS-inf media supplemented with 100 µM acetosyringone (As) (LSAs medium) (Negrotto et al., Plant Cell Rep 19:798-803 (2000)). Bacteria are pre-induced in this medium for 30-60 minutes.
Immature embryos from maize line, A188, or other suitable maize genotypes are excised from 8-12 day old ears into liquid LS-inf+100 µM As (LSAs). Embryos are vortexed for 5 seconds and rinsed once with fresh infection medium. Infection media is removed and Agrobacterium solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/1) and silver nitrate (1.6 mg/1) (Negrotto et al., Plant Cell Rep 19:798-803 (2000)) and cultured in the dark for 28° C. for 10 days. Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., Plant Cell Rep 19:798-803 (2000)). Calli transformed with an agrobacterium binary vector carrying the RNAi expression cassette comprising or SEQ ID NO: 61 are surviving selection indicating successful transformation. See FIG. 1. An agrobacterium binary vector carrying the RNAi expression cassette comprising or SEQ ID NO: 60 will be transformed into maize Following culturing in the light (16 hour light/8 hour dark regiment), green tissues will be transferred to Reg2 medium without growth regulators (as described in Negrotto et al., Plant Cell Rep 19:798-803 (2000)) and incubated for 1-2 weeks. Plantlets will be transferred to Magenta GA-7 boxes (Magenta Corp, Chicago Ill.) containing Reg3 medium (as described in Negrotto et al. (2000)) and grown in the light. Plants that are PCR positive for PMI and negative for Spectinomycin will be transferred to soil and grown in the greenhouse.

Example 14

Haploid Induction

T0 transgenic plants expressing an RNAi construct which silences GRMZM2G471240 will be tested for haploid induction capacity. The pollen from each plant is to be crossed onto an ear to induce fertilization, and the resulting progeny of the cross subjected to ploidy analysis. Ploidy analysis can be defined in this case as any experimental test where the ploidy level of an individual plant is determined. In crosses between two non-inducing lines, the resulting progeny should be almost exclusively diploid, or 2N. However, if a haploid induction line is the male parent, the resulting progeny will be a mixed population of haploids (1N), diploids (2N), aneuploids (somewhere between 1N and 2N), and chimeras (containing tissues with mixed ploidy). The determination of haploid induction capacity can be made binary by setting a cutoff value for the haploid induction rate, which is defined as the number of haploid embryos over the total number of viable embryos. The rate should be at least greater than 0.5%.

Example 15. Identifying the Frameshift Mutation in PLA

The present invention identifies a series of independent human-induced mutations found in at least one patatin-like phospholipase AIIα (pPLAIIα) gene of maize; maize plants having these mutations in at least one of their PLA genes; and a method of creating and identifying similar and/or additional mutations in the PLA gene by screening pooled and/or individual rice and maize plants. The rice and maize plants of the present invention induce haploidy as a result of non-transgenic mutations in at least one of their PLA genes.

More specifically, the present invention produces new maize haploid inducing lines. A number of known haploid-inducing maize lines exist including but not limited to: Stock 6, MHI (Moldovian Haploid Inducer), indeterminate gametophyte ("ig") mutation, KEMS, ZEM, ZMS, KMS, RWS, and RWK. The present invention relates to a method of identifying, and/or selecting germplasm which can or cannot induce haploids. The present invention also relates to increasing and further development of the selected haploid inducing germplasm. The invention further relates to a method of improving haploid inducing germplasm to increase the induction of haploids on the seed producing parent.

The initial step in the production of haploid seeds from a hybrid or segregating maternal parent plant derives from the pollination with pollen from a haploid inducer onto the ear from a seed producing plant. A result of this hybridization process is the production of diploid and maternal haploid (1n) kernels. The induced haploid (1n) kernels are often distinguished from the diploid seed by the use of color markers which indicate embryo ploidy. The diploid seeds are generally discarded, while haploid kernels or embryos are often subjected to chromosome doubling processes to produce doubled haploid plants. More specifically, the haploid genetic material is treated with one or more mitotic arrest agents to allow the haploid (1n) chromosome complement in one or more cells to produce homolog pairs. After the chemical treatment procedure, the chromosome doubling chemical(s) are removed. The now-doubled haploid maize is allowed to mature and the resulting doubled haploid seeds when planted will produce homozygous plants (also called inbred plant or lines). These inbred lines are the materials that breeders utilize to pursue their hybrid development programs.

Figure 2:
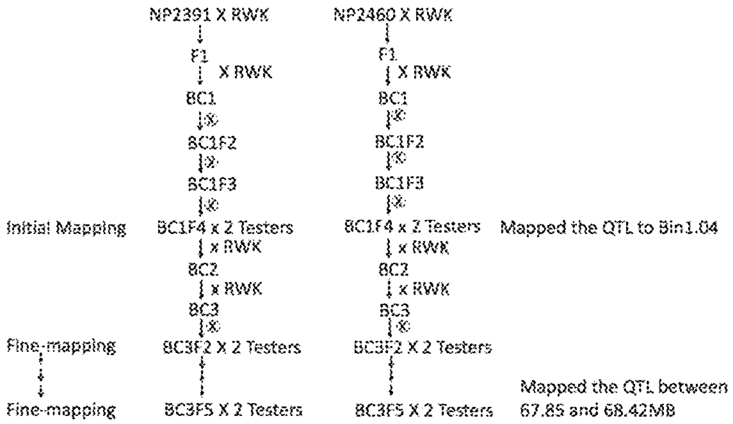
FIG. 2 is a mapping scheme used to map the haploid induction trait in RWK.

The locus for the haploid induction trait was fine mapped. Although a major QTL on chromosome 1 responsible for haploid induction has been mapped and published, Dong et al. Theor. Appl. Genet (2013) 126: 1713-1720, the exact gene/genetic element responsible for the induction process has not been identified until now. To clarify the developmental genetics underlying haploid induction, the Stock 6 derivative RWK (~13% HIR) was obtained from the University of Hohenheim in 2006, crossed to inbreds NP2460 and NP2391, and subsequently backcrossed to RWK to generate mapping populations. See FIG. 2.

Elevated HIR in both populations co-segregated with marker SM020SDQ in bin 1.04, consistent with recent reports on a QTL called qhir1. See Prigge, et al., New Insights into the Genetics of in Vivo Induction of Maternal Haploids, the Backbone of Doubled Haploid Technology in Maize, GENETICS (2012) 190:781-793 (discussing major QTL for HI in Bin 1.04 [qhir1] and minor QTLs for HI in Bins 3.02 [qhir2], 3.06 [qhir3], 4.03 [qhir4], 5.01 [qhir5], 5.04 [qhir6], 7.01 [qhir7], and 9.01 [qhir8]); Liu, et al., Fine mapping of qhir8 affecting in vivo haploid induction in maize, THEOR. APPL. GENET. (2015) 128:2507-2515 (fine mapping thirty-five genes to qhir8); Hu, et al., The Genetic Basis of Haploid Induction in Maize Identified with a Novel Genome-Wide Association Method, GENETICS (2016) 202:1267-1276 (asserting that qhir1 is two QTLs: qhir11 and qhir12, and fine mapping qhir6 to a 1.1 Mb region). We did several rounds of fine mapping and narrowed the QTL to an approximately 0.57 Mb region between 67.85 Mb and 68.42 Mb that lies within qhir11. This region has seven annotated genes.

Using the Illumina HiSeq2000, we sequenced RWK, Stock 6, and a BC3F5 non-inducer "RWK-NIL" that is near-isogenic to RWK but has NP2391 haplotypes in the qhir11 interval. By comparing inducer and non-inducer germplasm, it was determined that a four nucleotide insertion present in haploid inducers which shifts the frame for amino acid coding of GRMZM2G471240 is not present in non-inducer germplasm. Therefore, the present invention has identified a gene with a frameshift mutation in inducer germplasm as being responsible for maize haploid induction. The candidate gene corresponding to gene model GRMZM2G471240 encodes patatin-like phospholipase AIIα (pPLAIIα), which we have renamed MATRILINEAL (MTL) to represent the wildtype allele and the frameshift allele is referred to as matrilineal (mtl).

DNA sequence was generated for each candidate gene from the two inducer lines (Stock6 and RWK) and one non-inducer line (RWK-NIL). In addition, the public B73 genome data was used as a second non-inducer line. Gene model information was compared to EST/cDNA data to confirm the structure of each gene. The annotated sequence data were compared to catalog differences between the four alleles of each gene.

The sequence comparisons revealed that B73 and RWK-NIL alleles were similar to each other, and RWK and Stock 6 alleles were similar to each other. Most sequence differences were single nucleotide polymorphisms that do not alter protein coding sequence. There were some insertions and some deletions, most of which are in non-protein coding sequence.

Figure 3:
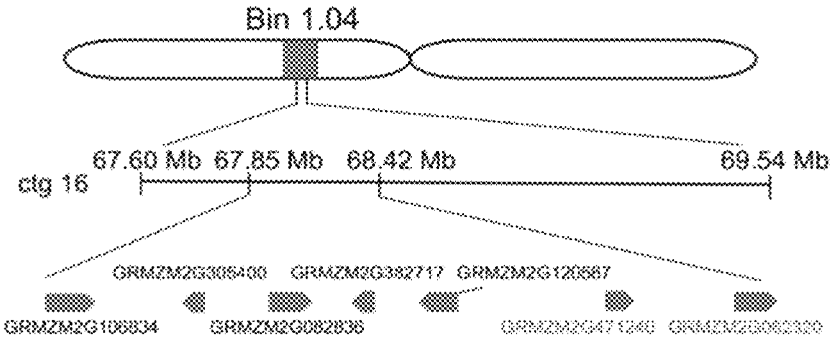
FIG. 3 shows fine mapping narrowed the major QTL to a very small interval in bin 1.04, between 67.85 Mb and 68.42 Mb. This region has seven annotated genes. We sequenced and assembled the genes in this interval in several lines. The two genes with the most dramatic mutations in the haploid inducer lines are shown on the bottom right (GRMZM2G471240 and GRMZM2G062320).

Having completed fine mapping of the haploid inducer trait to an interval containing only seven genes, we focused on those in the sequence assembly and analysis. The sequences for the seven genes were nearly identical between B73 and RWK-NIL, but RWK and Stock 6 lacked GRMZM2G062320, a PHOSPHOGLYCERATE MUTASE (PGM), and had a 4 basepair ("bp") insertion in the fourth exon of GRMZM2G471240, a PATATIN-LIKE PHOSPHOLIPASE AIIα (pPLAIIα) (FIG. 3). We found that RWK and Stock6 both have the same 4 bp insertion in the fourth exon of pPLAIIα, and that this gene is specifically expressed in pollen (see maizegdb.org/gene_center/gene?id=GRMZM2G471240 incorporated herein by reference). The unmutated GRMZM2G471240 is represented by SEQ ID NO: 68. GRMZM2G471240, comprising the 4 bp insertion in the fourth exon, is represented by SEQ ID NO: 70.

Most of the haploids that were identified were found using a taqman marker test. This marker test takes advantage of a difference in the pPLAIIα gene between RWK×NP2222. In crosses where we use RWK as the female, and NP2222 as the male, the RWK parent is homozygous for the mtl allele, while NP2222 is homozygous for the MTL allele. Diploid progeny are MTL/mtl and haploid gynogenetic haploid progeny are mtl/0. Therefore when this test is done the taqman results show 1 copy of the mtl allele and one copy of MTL allele in the diploid progeny, and 1 copy of the mtl but no copies of MTL in the haploid progeny. When this type of cross is performed, ears are harvested between 12-21 days following pollination, the embryos are extracted and a small sample of the embryos are taken for taqman marker analysis. Alternatively the embryos are plated on solid media and germinated in the dark so that a larger sample of the extended shoot or root can be taken between 2-10 days later for marker analysis. At the same time some of the tissue is saved for ploidy analysis. In this latter case after the molecular test is used, the larger samples of the haploids can be run on a CyFlow Space ploidy analyzer and confirmed as haploids. In most cases this results in the positive identification of haploids. In a few rarer cases this results in the overturning of the false positive marker results and correction of the call as a diploid.

Another way we test for haploids is via dominant marker assay. In this case, an X26 male line is used. This line is homozygous for a marker that acts in a dominant fashion. In such a cross any line can be used as a female as long as it doesn't have a marker or any genes or alleles that work to inhibit the marker phenotype. The X26 line is a non-inducer and is homozygous for MTL. Using such a line, the progeny are dissected between 12-21 days after pollination and evaluated for the presence of the marker, or they are examined directly on the ear, or the dried kernels are harvested and evaluated for the presence of the marker. Diploid progeny show the marker phenotype because they have a single copy of the marker gene from the X26 male parent, whereas gynogenic haploid progeny do not show the marker phenotype. The penetrance of the marker and the spontaneous haploid induction rate of X26 was tested in numerous control crosses. Using this system we screen for haploids and then test them on the ploidy analyzer to confirm that they are truly haploids.

We developed PCR tests to specifically detect the "wild-type" and "mutant" alleles for screening of nineteen Stock 6-derived inducers, including NP2222-Haploid Inducer (NP2222-HI), a BC3 introgression of RWK into Syngenta's standard transformable inbred line NP2222. We also screened nine non-inducer control lines.

To develop a PCR test that would distinguish between RWK/Stock6 and RWK-NIL haplotypes, two primer pairs were designed: one pair should amplify the RWK/Stock6 frame-shift allele, while the other should amplify the B73/RWK-NIL allele. These pairs worked as expected on RWK-NIL, RWK, and Stock6 DNA: RWK-NIL gDNA only amplified the RWK-NIL primer pair. RWK and Stock6 gDNA only amplified the RWK/Stock6 primer pair, which specifically detects the frame-shift allele. The PCR products were sequenced and the sequences were identical to that from whole genome sequencing. SNPs that were identified in the whole genome sequencing were confirmed in the PCR products. Below, in FIG. 3, the DNA used in each reaction is in capital letters. The primers are "nil.F1/R1" and "rwk.F1/R1."

```
GRMZM2G471240_nil.F1:
                                   (SEQ ID NO: 66)
GTACGCCGTGCGCTAACA.

GRMZM2G471240_nil.R1:
                                   (SEQ ID NO: 67)
TCGTACCTCCCTGTCTCCAC.

GRMZM2G471240_rwk.F1:
                                   (SEQ ID NO: 64)
TACGCCGTGCGCTAACATA.

GRMZM2G471240_rwk.R1:
                                   (SEQ ID NO: 65)
GTACCTCGCTCCCTGTCTCC.
```

The "rwk.F1/R1" and "nil.F1/R1" primer pairs were used to genotype the panel of high, low, and non-inducers. We found that all 19 haploid inducer lines had the 4 bp insertion, including Stock6 (3% haploid induction rate ["HIR"]), RWK (line derived from the University of Honheim stocks, 10-15% HIR), RWS, and Z22, among others. In contrast, the wild-type allele was found in all nine non-haploid inducer lines (average HIR of 0.1%). The data indicates that homozygosity for the frame-shift allele correlates with induction capacity: 12/12 high and 7/7 low inducers amplified the frame-shift assay, but not the wild type assay, while 9/9 non-inducers amplified the wild type but not frame-shift assay. This indicates that induction capacity correlates with the GRMZM2G471240 mutation, and that pPLAIIα underlies qhir11 and is the primary mutation responsible for haploid induction in these lines.

TABLE 9

GRMZM2G471240 PCR test results.

| | Induction Rate | RWK amplicon | RWK-NIL amplicon |
|---|---|---|---|
| Controls: | | | |
| Stock 6 (low inducer) | 2.50% | + | − |
| RWK (high inducer) | 12% | + | − |
| RWK-NIL (non-inducer) | <1% | − | + |
| Good Inducers: | | | |
| ZMS | 7% | + | − |
| Z19-PR | 7% | + | − |
| RWS-Z86 | 10% | + | − |
| K13 | 9% | + | − |
| (ID3002/Z22)B > 29-5 > 2-5-1-B- | 7% | + | − |
| Z-19-//AF4031PR//Z-19-) 1-1-2-3-1-3-B- | 9.50% | + | − |
| ZR86 | 12% | + | − |
| ZR53 | 12% | + | − |
| ZR75 | 13% | + | − |
| (Z21/RWS)B(GS)-75-1-2-3-B- | ~8% | + | − |
| NP2222 inducer-good | ~9% | + | − |
| Poor Inducers: | | | |
| Stock6 R1-nj | 2.50% | + | − |
| (Z21/RWS//[RWS]B$)33-5- | <2% | + | − |
| (K-13-/(ZMS/SEW-PR)B > 2 > B-9//K-13-)2-4-1- | <2% | + | − |
| (K-13-/(ZMS/SEW-PR)B > 2 > B-9//K-13-)6-1-2- | <2% | + | − |
| (ZMS/SEW-PR)B > 2 > B-7-2-1-2- | <2% | + | − |
| NP2222 inducer-low | ~3% | + | − |
| Non-inducer Lines and Donors: | | | |
| Stock6 R1-nj B1P11 | <0.1% | − | + |
| (Z-21-/AF4031PR// Z-21-1-B-)1-1-1-1-B- | <0.1% | − | + |
| FF6096 | <0.1% | − | + |
| ID5829 | <0.1% | − | + |
| XO5744 | <0.1% | − | + |
| ID3002 | <0.1% | − | + |
| AF4031PR | <0.1% | − | + |
| NP2222 | <0.1% | − | + |

We also identified a number of single nucleotide polymorphisms ("SNPs") between the frame-shift allele and that of RWK-NIL. For many of these SNPs, the STOCK6 and RWK sequences agreed with other inbreds we have sequenced, and thus likely represent natural variation. Indeed most of these SNPs did not alter the amino acid sequence and thus likely do not contribute to the haploid induction phenotype. Two SNPs did result in amino acid changes (H107Y; K232N) and these are not highly conservative changes, so they may have a small contribution to the phenotype, but mostly like they do not impact the phenotype because the frame-shift causes a loss of function.

We renamed pPLAIIα "MATRILINEAL" (MTL; i.e., SEQ ID NO: 68) and the native 4 bp insertion allele "matrilineal" (mtl; of which the cDNA is SEQ ID NO: 70). According to the predicted protein sequence, the 4 bp insertion causes a shift in the open reading frame of the protein at amino acid ("AA") 352 out of 401. The frame-shift leads to a premature stop codon.

After finding the frame-shift knock-out mutation we directly tested the effect it had on haploid induction by complementing a haploid inducer line with a wild-type pPLAIIα transgene. Heterologous complementation of NP2222-HI (10.2% HIR) with a wild-type copy of MATRILINEAL virtually eliminated haploid induction and kernel abortion. Compared to controls the HIR decreased 50-fold, from 10% to 0.23%. It also decreases the embryo abortion rate to 0.65%. Full length functional reporter lines were also made using transgenic fusions of the wild type MTL gene to GFP as well as the mutant allele mtl to GFP, in order to both visualize subcellular localization of wild-type MTL, but also to see if the mutant version of the protein localizes correctly or is produced at all. These lines also served as additional material to test for complementation. Haploid inducer material (NP2222-HI) that was homozygous for the MTL-GFP transgene also did not exhibit the haploid inducer phenotype. The induction rate of NP2222-HI falls to 0.60% when it is homozygous for MTL-GFP. Additionally, the MTL-GFP transgene also knocked down embryo abortion to 4.86%. Finally we tested whether the mutant mtl allele fused to GFP complements the haploid induction phenotype, and it does not. Haploid induction and embryo abortion rates were very similar in NP2222-HI compared to NP2222-HI that was homozygous for the mutant fusion transgene mtl-GFP. See Table 10. This represents conclusive evidence that the MATRILINEAL frame-shift is responsible and required for haploid induction. To apply this knowledge, we demonstrate that mutating or modulating the expression of pPLAIIα in a wild type line leads to the creation of new haploid induction lines.

TABLE 10

Reproductive characteristics of haploid inducer, complementation and edited lines. This table shows the haploid induction and kernel abortion rates of inducer lines in the NP2222 background. The number testcrosses is listed first ("ears") and then the kernel and embryo statistics are listed. Embryo abortion and haploid induction generally comes together on the same ear. That is why the embryo abortion rate is so high in an ear crossed by the NP2222-HI male, which has a 10.17% haploid induction rate (HIR). Both the WT transgenes, including one without GFP and one fused to GFP, complemented the haploid induction phenotype. Meanwhile, the mutant mtl fused to GFP did not complement.

| | Complementation Assays | | | Kernel characteristics | | Embryos tested | | |
|---|---|---|---|---|---|---|---|---|
| Male parent | ears | viable | aborted | % aborted | embryos | haploids | diploids | HIR |
| NP2222-HI | 4 | 548 | 498 | 47.61% | 531 | 54 | 477 | 10.17% |
| NP2222-HI + MTL/MTL | 17 | 4403 | 29 | 0.65% | 4321 | 11 | 4310 | 0.25% |
| NP2222-HI + mtl-GFP/mtl-GFP | 3 | 371 | 298 | 44.54% | 360 | 34 | 326 | 9.44% |
| NP2222-HI + MTL-GFP/MTI-GFP | 3 | 1019 | 52 | 4.86% | 836 | 5 | 831 | 0.60% |

Several mtl-like alleles were generated in the inbred NP2222 by introducing small deletions in MTL close to the 4 bp insertion site in mtl, using transcription activator-like effector nucleases (TALEN) (Boch, J. et al., Breaking the code of DNA binding specificity of TAL-type III effectors, Science 326:1509-1512 (2009), incorporated herein by reference). Several mutant events were self-pollinated and T1 plants lacking the TALEN T-DNA insert but homozygous for small deletions in MTL were outcrossed onto NP2222. Edited lines homozygous for frame-shift deletions in MTL (hereafter called MTL TAL-F S) exhibited an HIR of 4.0-12.5% (average 6.65%) (Table 11). The ploidy status of 118/127 putative haploids was confirmed by Flow Cytometry, and phenotypic evaluations indicated these plants were haploids. These results prove that a frame-shift in MTL is sufficient to induce high rates of haploid induction. Other contributors to the phenotype have been mapped including the neighboring qhir12 (see Liu, 2016)), which may account for the difference between the HIR of $MTL^{TAL-FS}$ and NP2222-HI. It reasonable to infer that seed set, HIR and kernel abortion rates are set through mtl by paternal and maternal genotype-specific interactions.

TABLE 11

Reproductive characteristics of MTL edited lines (generally referred to as MTL$^{TAL-FS}$ lines). This table shows the haploid induction and kernel abortion rates of inducer lines in the NP2222 background. The transgenic events tested are given on the left followed by the number of testcrosses made ("ears") and the progeny statistics.

| | | | | Kernel Characteristics | | | Ploidy Analysis Data | | | |
|---|---|---|---|---|---|---|---|---|---|---|
| Event | ID | Mutation(s) | Ears | Avg. viable | Avg. aborted | % aborted | Total Embryos | Putative Haploids | Confirmed Haploids | HIR |
| 39A | 3954 | Biallelic (13 bp & 28 bp dels) | 4 | 162 | 128 | 44.10% | 579 | 37 | 35 | 6.04% |
| 23A | 3924 | Biallelic (8 bp & 5 bp dels) | 2 | 114 | 116 | 50.40% | 128 | 18 | 16 | 12.50% |
| 81A | 3932 | Homozygous (13 bp del) | 2 | 165 | 129 | 43.90% | 169 | 18 | 15 | 8.88% |
| 81A | 3317 | Homozygous (13 bp del) | 2 | 183 | 108 | 37.10% | 343 | 19 | 19 | 5.54% |
| 81A | 3303 | Homozygous (13 bp del) | 1 | 189 | 100 | 34.60% | 176 | 7 | 7 | 3.98% |
| 38A | 4108 | Biallelic (11 bp & 5 bp dels) | 4 | 147 | 102 | 40.10% | 379 | 28 | 26 | 6.86% |
| 18A | 22807-4016 | Homozygous (8 bp del) | 8 | 144 | 97 | 40.20% | 1025 | 47 | 44 | 4.29% |
| 27A | 22807-4073 | Biallelic (1 bp insert & 5 bp del) | 2 | 161 | 92 | 36.40% | 180 | 18 | 18 | 10.00% |
| 27A | 22807-4081 | Biallelic (1 bp insert & 8 bp del) | 6 | 176 | 116 | 39.80% | 931 | 45 | 44 | 4.73% |
| 76A | 22873-3999 | Homozygous (2 bp insert) | 2 | 175 | 95 | 35.20% | 117 | 17 | 16 | 13.68% |
| 32A | 22873-3991 | Homozygous (1 bp del) | 2 | 140 | 105 | 42.90% | 260 | 14 | 14 | 5.38% |
| Total | | Totals | 15 | 160 | 108 | 40% | 390 | 24 | 23 | 7% |

Figure 4:
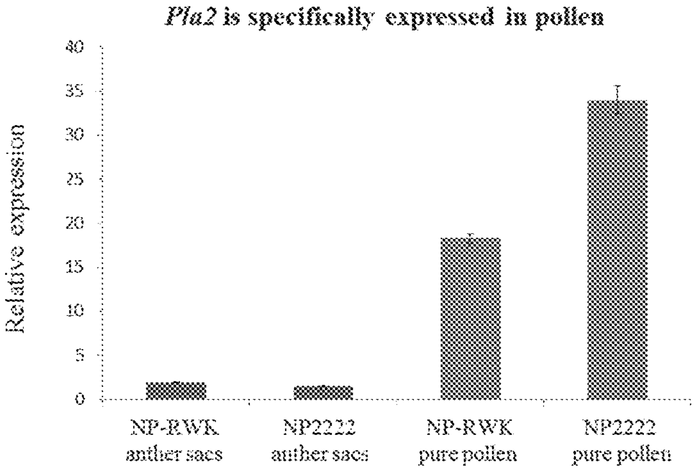
FIG. 4 shows the difference in expression of GRMZM2G471240 in haploid inducer and non-inducer pollen and post-anthesis anther sacs (sporophytic tissue with the pollen grains removed). This gene is specifically expressed in the male gametophyte.
Figure 5A:
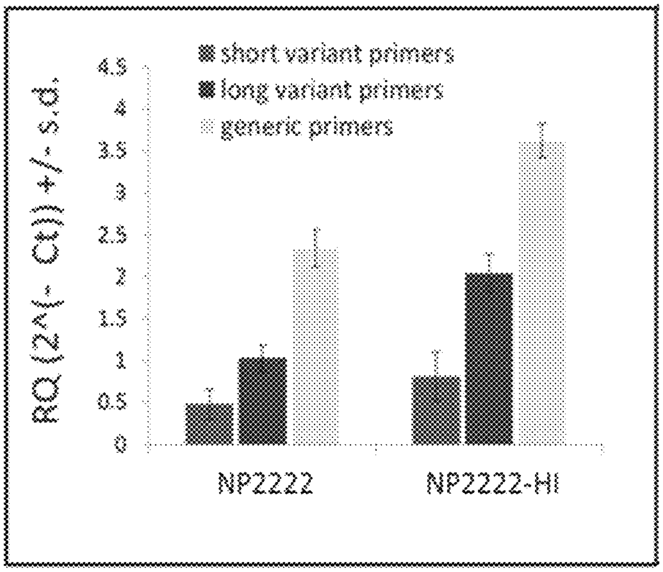
FIG. 5A shows splice-specific qRT-PCR results for GRMZM2G471240. Three biological replicates of R1-staged anthers were tested in technical triplicate, and the average Ct and standard deviation was calculated for each reaction. The relative quantity of each transcript type was compared to the endogenous control using a $\log_2$ regression of the delta Ct. Two sets of primers were used to assess the relative abundance of each of the two annotated splice variants compared to a primer set that is agnostic with respect to the splice variants. The shorter transcript variant had relatively low abundance compared to the long transcript in both NP2222 (wild type) and NP2222-HI (haploid inducer) genotypes. Expression of the mutant copies of the gene in NP2222-HI was significantly higher for all three primer pairs tested.
Figure 5B:
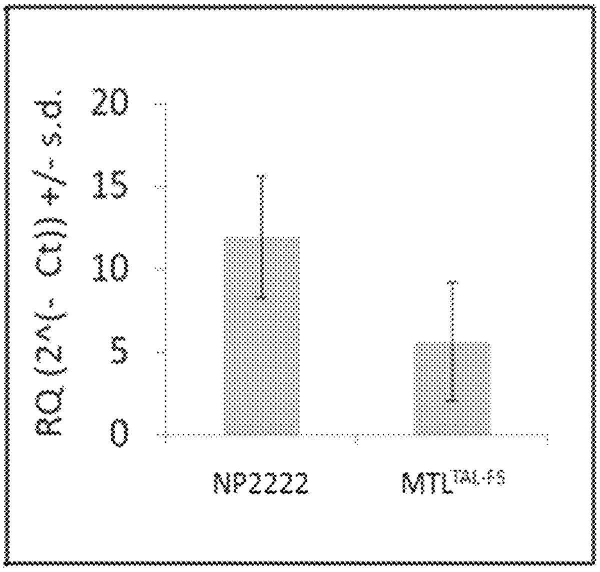
FIG. 5B shows five biological replicates of fresh pollen from NP2222 and $MTL^{TAL-FS}$ plants (T1 plants that are homozygous for edited mtl-like alleles) were tested in technical triplicate on the generic primer, and the average Ct and standard deviation was calculated for each reaction. The relative quantity of each transcript type was compared to the endogenous control using a $\log_2$ regression of the delta Ct. $MTL^{TAL-FS}$ pollen has lower transcript abundance than NP2222 (wild type) pollen.

Haploid seed formation in maize is a post-zygotic character triggered by a defective male gametophyte. This fact is reflected in MTL expression data. Public RNA-seq profiles indicate the wild-type MTL transcript is specific to anthesis-staged anthers (see Sekhon, R. S., et al. *Genome-wide atlas of transcription during maize development*, Plant Journal, 66, 553-563 (2011), incorporated herein by reference), in agreement with a developmental profile that found it exclusively in pre-dehiscent anthers (see Thai, J., et al. *Spatiotemporally dynamic, cell-type-dependent premeiotic and meiotic phasiRNAs in maize anthers*, PNAS 112, 3146-3151 (2015), incorporated herein by reference). We found that wild-type pollen had 18× more MTL transcript than post-anthesis anther sacs, indicating the gene is male gametophyte-specific (FIG. 4). Attempts to knockdown MTL by RNAi led to elevated rates of haploid formation for MTL$^{R\text{-}NAi}$ only (Table 12). There are two annotated splice variants of MTL, reflecting an alternative splice site 81 nucleotides prior to the 3' end of exon 2. Compared to NP2222, Mtl was elevated in NP2222-HI but not MTL$^{TAL-FS}$ pollen (FIG. 5), while the abundance of the two annotated splice variants was consistent.

TABLE 12

RNAi construct 22503 (SEQ ID NO: 95) to knockdown Mtl led to haploid induction.

| GRMZM2G471240 RNAi | | | Kernel Characteristics | | | | | | |
|---|---|---|---|---|---|---|---|---|---|
| Individual | Event | | | | % | Embryos tested for ploidy | | | |
| ID | ID | ears | viable | aborted | aborted | embryos | haploids | diploids | HIR |
| 5148 | 001 | 2 | 701 | 43 | 5.78% | 369 | 3 | 366 | 0.81% |
| 5149 | 001 | 2 | 186 | 22 | 10.58% | 166 | 1 | 165 | 0.60% |
| 5153 | 001 | 2 | 625 | 61 | 8.89% | 323 | 7 | 316 | 2.17% |
| 5161 | 001 | 3 | 1116 | 87 | 7.23% | 485 | 4 | 481 | 0.82% |
| 5170 | 028 | 2 | 629 | 23 | 3.53% | 324 | 1 | 323 | 0.31% |
| 5173 | 028 | 2 | 551 | 33 | 5.65% | 322 | 0 | 322 | 0.00% |
| 5187 | 028 | 3 | 379 | 27 | 6.65% | 333 | 9 | 324 | 2.70% |
| 3731 | 014 | 2 | 894 | 23 | 2.51% | 263 | 4 | 259 | 1.52% |
| 3732 | 014 | 2 | 648 | 49 | 7.03% | 351 | 0 | 351 | 0.00% |
| 3736 | 007 | 1 | 277 | 21 | 7.05% | 277 | 0 | 277 | 0.00% |
| 3737 | 007 | 1 | 223 | 49 | 18.01% | 175 | 3 | 172 | 1.71% |
| 3751 | 0055 | 1 | 133 | 6 | 4.32% | 118 | 0 | 118 | 0.00% |
| TOTALS | events | 23 | 6362 | 444 | 6.52% | 3506 | 32 | 3474 | 0.91% |

The frame-shift in mtl occurs at amino acid 380, leading to 20 altered amino acids followed by a premature stop codon which truncates the protein by 29 amino acids (FIG.

Figure 6A:
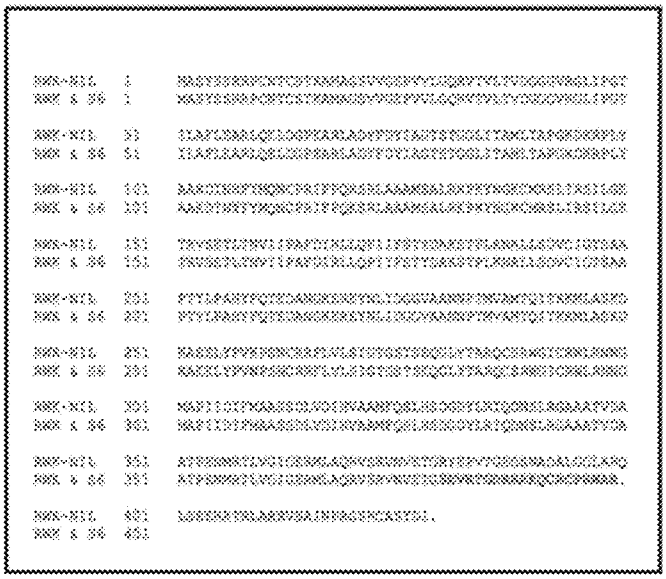
FIG. 6A shows an amino acid alignment of the B73 predicted protein sequence of the long splice variant of the GRMZM2G471240 gene in B73 and RWK-NIL (i.e., SEQ ID NO: 69), with the predicted sequence of the mtl allele found in RWK and Stock 6 (S6) (i.e., SEQ ID NO: 71). Stop codons are indicated with a full stop. Two point mutations result in amino acid substitutions, a histidine (H) to a tyrosine (Y), and a lysine (K) to an arginine (N). These changes are not conservative; it is possible that one or both of these modifies the haploid induction phenotype—suggesting that an allelic series could be uncovered with further investigation of variants.
Figure 6B:
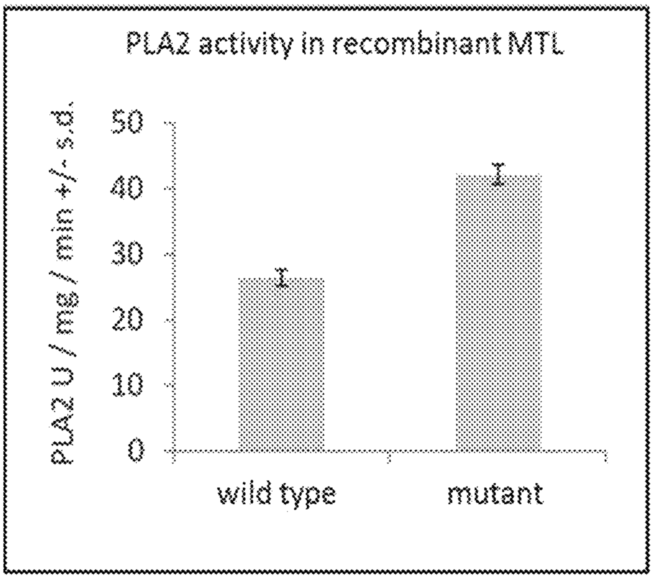
FIG. 6B shows wild type MTL and mutant (truncated) MTL encoded by the mtl allele have in vitro phospholipase activity. PLA2 phospholipase activity as measured by fluorescent liposome assay on recombinant, purified protein produced using the MTL and mtl cDNAs. Error bars indicate standard error based on the average of four replicates.

6A). The wild-type MTL protein was found in LS-MS profiles of RWK-NIL and NP2222 pollen, but was below the detection limit in three out of three RWK and 3 out of 3 NP2222-HI samples (Table 13). This demonstrates that even though there is mutant mtl transcript produced in pollen, the protein is not detected, confirming this is a loss of function mutation. Both mutant and wild type recombinant MTL proteins exhibited phospholipase activity in vitro in pPLAIIα-like fluorescent liposome cleavage assays (FIG. 6B). This demonstrates that the functional annotation of the MTL gene (i.e. that it codes for a phospholipase protein) is correct.

Figure 7A:
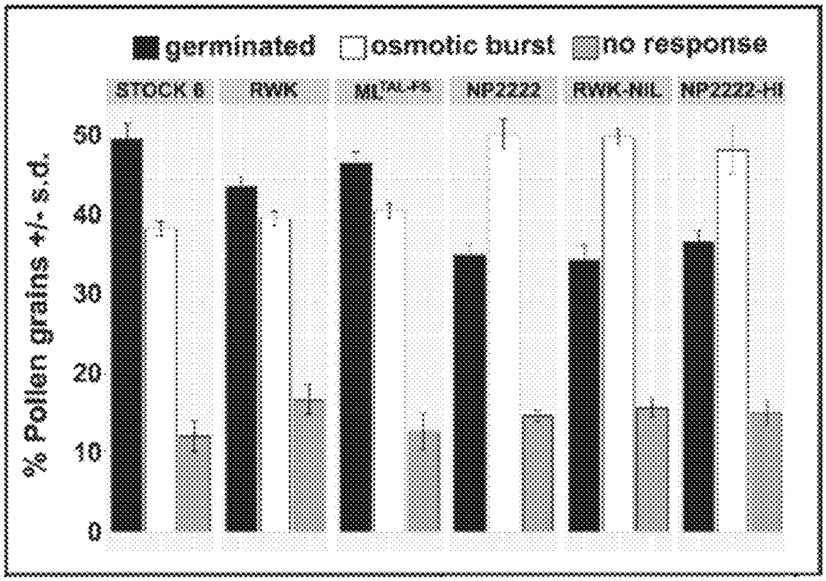
FIG. 7A-E shows mtl is responsible for pleiotropic phenotypes associated with haploid induction.
Figure 7B:
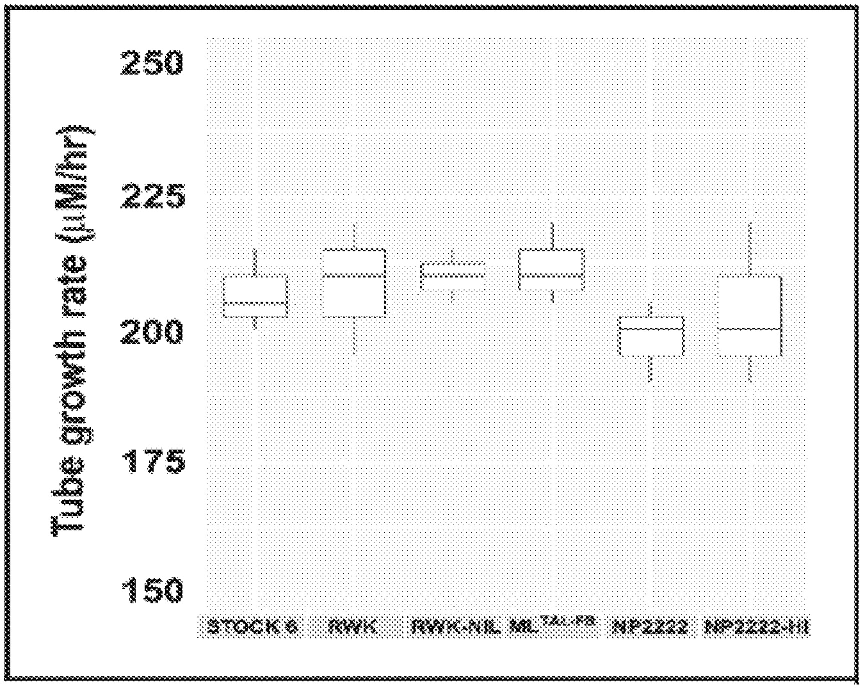
Figure 7C:
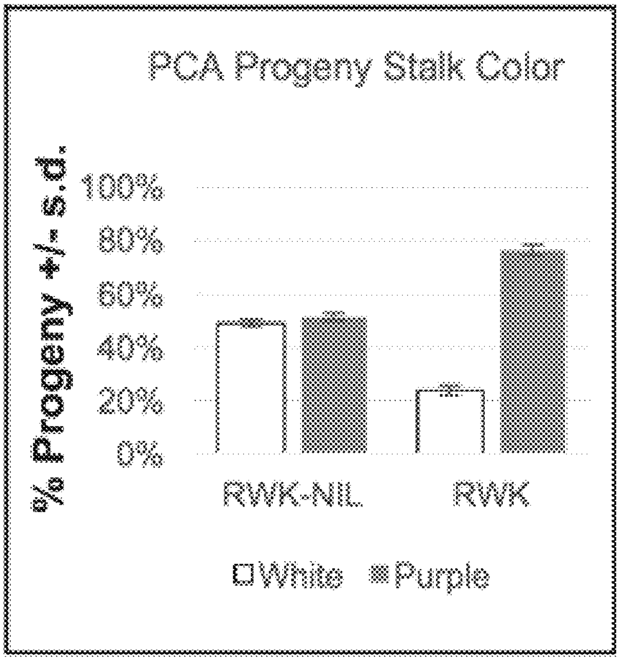
Figure 7D:
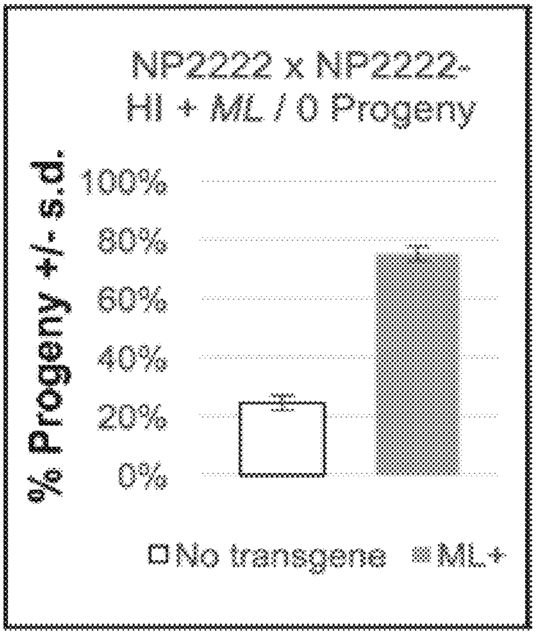
Figure 7E:
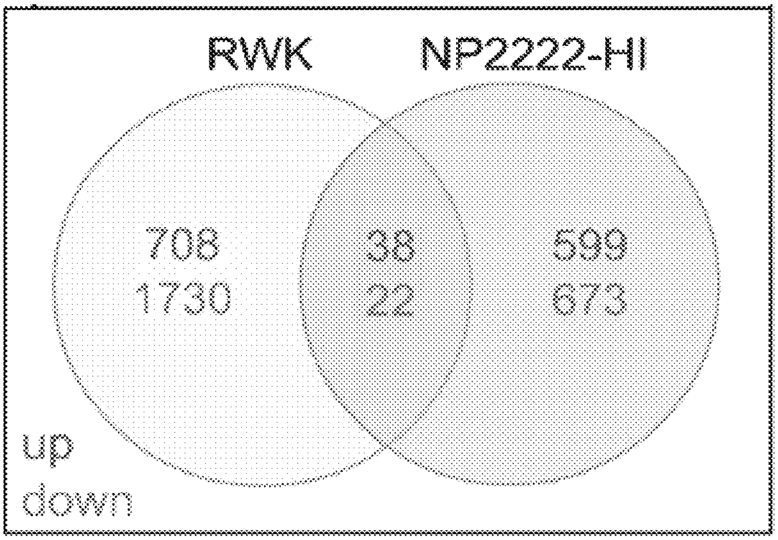

RWK, Stock 6 and $MTL^{TAL-FS}$ lines (FIG. 7A, 7B). Ears pollinated with NP2222-HI and $MTL^{TAL-FS}$ pollen exhibit ~10-25% fertilization failure, and a pollen competition assay showed that RWK is subject to segregation distortion (SD) (FIG. 7C), consistent with prior reports (see Xu, X., et al. *Gametophytic and zygotic selection leads to segregation distortion through in vivo induction of a maternal haploid in maize*, J. Exp. Bot. 64, 1083-1096 (2013)). Crosses with hemizygous NP2222-HI+MTL/0 pollen produced a proportional bias towards MTL+ progeny (FIG. 7D), indicating that inducer SD is attributable to mtl. Embryo abortion, a persistent byproduct of haploid induction linked to endosperm proliferation failure, occurred at similar rates in native and $MTL^{TAL-FS}$ inducers (Table 4). Collectively these data implicate mtl in every reproductive defect associated with haploid induction. The two mechanisms typically proffered to explain haploid formation are single fertilization and post-zygotic genome elimination (see Sarkar, K. R. & Coe, E. H, *A genetic analysis of the origin of maternal haploids in maize*, Genetics 54, 453-464 (1966); Zhang, Z., et al., *Chromosome elimination and in vivo haploid production induced by Stock 6-derived inducer line in maize (Zea mays* L.), Plant Cell Rep. 27, 1851-1860 (2008); and Barret, P., Brinkmann, M., & Beckert, M., *A major locus expressed in the male gametophyte with incomplete penetrance is responsible for in situ gynogenesis in maize*, Theor. Appl. Genet. 117, 581-594 (2008)). In the former, haploids result from fertilization of the central cell but not the egg, which subsequently develops via parthenogenesis. In the latter, double fertilization precedes male chromosome elimination. Clarifying the precise mechanism will require careful embryology after $MTL^{TAL-FS}$ pollinations, along with quantitative data tracking the rare persistence of male DNA in maize haploids.

Haploid induction was recently engineered in *Arabidopsis* via manipulation of CENTROMERIC HISTONES, which causes uniparental genome elimination through post-zygotic centromere imbalance between hybridized genomes. An attempt to replicate this in maize was successful (see Ravi, M. & Chan, S. W. L. *Haploid plants produced by cen-*

TABLE 13

Proteins off and on in NP2222 and NP2222-HI pollen samples, including MTL, which is found in NP2222 but not NP2222-HI pollen.

| | log2 LFQ | | | | | | | |
|---|---|---|---|---|---|---|---|---|
| | NP2222 | | | NP2222-HI | | | | |
| | rep 1 | rep 2 | rep 3 | rep 1 | rep 2 | rep 3 | Majority protein ID | best BlastP match (S prot plants) |
| Absent in NP2222-HI | 23.3 | 23.3 | 23.4 | ND | ND | ND | GRMZM2G028905 | L-fucose alpha-1,3-D-xylosyltransferase |
| | 22.9 | 24.1 | 23.9 | ND | ND | ND | GRMZM2G046743 | Lysine histidine transporter 1 |
| | 23.2 | 23.1 | 23.2 | ND | ND | ND | GRMZM2G310362 | Polyadenylate-binding protein 5 |
| | 24.2 | 24.2 | 24.1 | ND | ND | ND | GRMZM2G130121 | Chaperone protein ClpB2, chloroplastic |
| | 23.5 | 23.5 | 23.6 | ND | ND | ND | GRMZM2G375807 | ABC transporter D; COMATOSE |
| | 24.1 | 23.7 | 23.9 | ND | ND | ND | GRMZM2G396212 | Phospho-2-dehydro-3-deoxyheptonate aldolase 1 |
| | 23.7 | 23.8 | 23.9 | ND | ND | ND | GRMZM2G467907 | RNA-binding protein 47 |
| | 23.8 | 23.8 | 23.9 | ND | ND | ND | GRMZM2G471240 | Matrilineal |
| Absent in NP2222 | ND | ND | ND | 23.9 | 23.8 | 23.9 | GRMZM2G013607 | Ferredoxin-6, chloroplastic |
| | ND | ND | ND | 22.1 | 22.1 | 22.2 | GRMZM2G030971 | Phospholipase A I |
| | ND | ND | ND | 24.5 | 24.6 | 24 | GRMZM2G064967 | Mannan endo-1,4-beta-mannosidase |
| | ND | ND | ND | 24 | 24.3 | 24.2 | GRMZM2G143613 | F-box protein |
| | ND | ND | ND | 24.4 | 24.3 | 24.1 | GRMZM2G166906 | HOTHEAD (synth long-chain a-dicarboxylic FAs) |
| | ND | ND | ND | 23.2 | 23.5 | 23.6 | GRMZM2G181259 | beta-D-xylosidase 2 |

*ND, Not detected

Example 16. Pollen Germination and Localization Experiments

Full length functional reporter lines were used to characterize MTL localization. No signal was found in the pollen of NP2222 or NP2222+mtl-GFP/mtl-GFP. In contrast, NP2222+MTL-GFP/MTL-GFP pollen exhibited a strong signal in the cytoplasm of the two sperm cells. This signal was found in the stringy gamete cytoplasm within germinated pollen tubes. NP2222 embryo sacs fixed 18 hours after pollination with MTL-GFP pollen had signal in the area of the degenerating synergid consistent with that of SCs delivered during fertilization. This indicates MTL is part of the male germ unit that is deposited in the embryo sac after pollen tube burst. MTL-GFP but not mtl-GFP eliminated haploid induction in NP2222-HI (Table 10). Collectively these data indicate that MTL is a phospholipase specific to the SC cytoplasm, and that the frame-shift in mtl compromises MTL localization or stability in haploid inducer pollen.

The identification of MTL as the causative gene in maize haploid induction permitted dissection of the pleiotropic phenotypes historically associated with the trait. Phospholipase mutations are associated with delayed pollen germination and tube growth (see Kim, H. J., et al. *Endoplasmic reticulum- and golgi-localized phospholipase A2 plays critical roles in Arabidopsis pollen development and germination*, Plant Cell 23, 94-110 (2011)), but these were normal in

Figure 8:
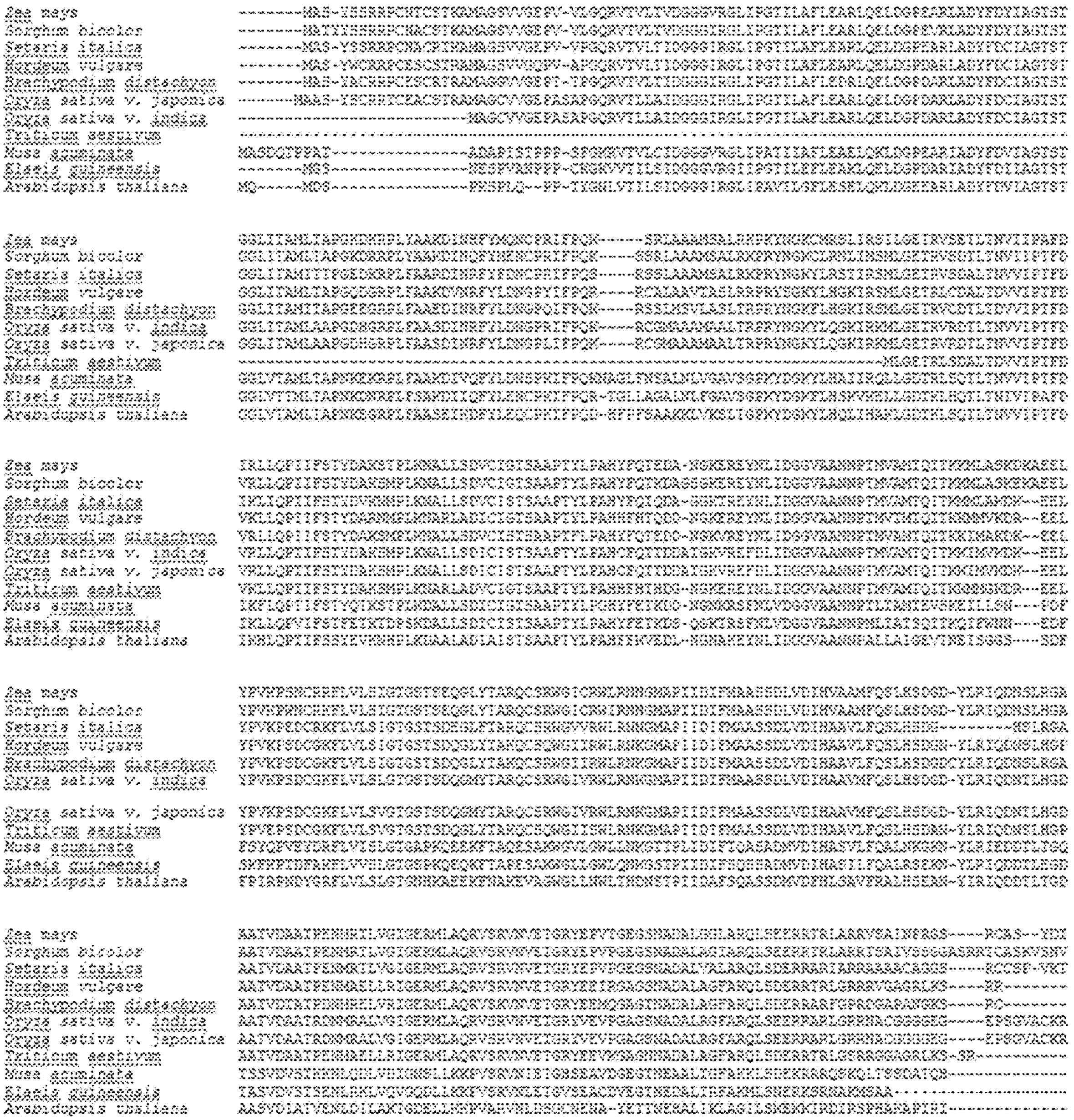
FIG. 8 shows an amino acid alignment of the maize MTL gene to publically available MTL orthologs in eight grasses, two non-grass monocots, and *Arabidopsis* (thale cress). This alignment includes maize (*Zea mays*, SEQ ID NO: 69), sorghum (*Sorghum bicolor,* 92% sequence identity to MTL, SEQ ID NO: 136), foxtail millet (*Setaria italica,* 85% identity, SEQ ID NO: 137), barley (*Hordeum vulgare,* 78% identity, SEQ ID NO: 138), *Brachypodium distachyon* (78% identity, SEQ ID NO: 139), Indica and *Japonica* variety rice (*Oryza sativa* v. indica (SEQ ID NO: 86) and *japonica* (SEQ ID NO: 140), Os3g27610, 78 and 79% identity, respectively), bread wheat (*Triticum aestivum,* 55% identity, SEQ ID NO: 141), banana (*Musa acuminata,* 57% identity, SEQ ID NO: 142), oil palm (*Elaeis guineesnsis,* 56% identity, SEQ ID NO: 143), and *Arabidopsis thaliana* (52% identity, SEQ ID NO: 144).

*tromere-mediated genome elimination*, Nature 464, 615-618 (2010)), but this filing is the first instance of a haploid inducer system triggered by a cytoplasmic protein that does not bind chromatin. Thus, this work highlights the importance of non-nuclear sperm components in reproductive success and faithful genome transmittance. The conservation of MTL in the grasses (see FIG. 8), especially in rice where the closest homolog is pollen-specific and also found in sperm, suggests these findings will lead to the development of novel intra-specific haploid inducer lines in important crop plants.

Example 17. Mutagenesis and Knockouts of PLA

In an effort to alter the haploid induction rate or decrease the embryo abortion rate during haploid induction crosses, we created or obtained several mutant lines by several methods, including GM RNAi lines, TILLING lines, CRISPR lines, and TALEN lines. First, we sought evidence that targeted mutagenesis of pPLAIIα is a viable strategy to create new haploid inducer lines. Therefore, we tested both CRISPR/CAS9 and TALEN maize targeted mutation strategy aimed at the same sequence that contains the frame-shift in the mutant haploid inducer allele. This led to the generation of lines with novel mutations, which we tested for haploid induction.

There are three key components to the CRISPR process. See U.S. Pat. No. 8,697,359 B1, incorporated herein by reference in its entirety. The first key component is the target sequence. The second is the Cas9, which is the endonuclease. The third key component is the guide RNA ("gRNA"), which is complementary to the target sequence and is responsible for recruiting Cas9 to the desired location. The target sequence is 18 to 20 bp long, and optimally should be sitting just 5' to a protospacer adjacent motif ("PAM") in the plant genome. For Cas9 from *Streptococcus pyogenes*, the PAM sequence should be 5'-NGG-3'. Transcription of the gRNA can be driven by the Pol III promoter U3 (RNA starts with an A) or U6 (RNA starts with a G). The gRNA should carry target sequence at the 5' end right after the A (U3) or G (U6). Cas9 will generate a double-stranded break ("DSB") at the target sequence three base pairs 5' to the PAM sequence. The amino acid sequence of Cas9 is the same as Cas9 from *Streptococcus pyogenes* strain SF370, with two amino acid changes, L1164V and I1179V in the PI domain (1099-1368) in NUC lobe. Cas9 activity has been demonstrated in transformation experiments to have approximately a 90% mutation frequency of tested target sequence in corn. Generally, it is advisable to identify multiple candidate PAMs and target sequences in the target region, then look for the best one by seeing which of the sequences is unique in the genome of the target. The target plant is maize, rice, or any monocot plant.

This strategy was followed to identify CRISPR target sequences that overlap with the existing frame-shift mutation. The precise cut site is just two base pairs away from the insertion point in the frame-shift. Constructs containing both the Cas9 and the gRNA were transformed into maize plants. Generally, biallelic or homozygous mutant plants are recoverable from the multiple events generated, but heterozygous mutant plants are also useful. The heterozygous plants were selfed, then the T1 seed was grown up, screened for homozygosity of the mutation, and outcrossed. Homozygous or biallelic mutant T0 transformants were simply selfed and outcrossed to untransformed NP2222. All outcrossed embryos were isolated for ploidy analysis to find haploids.

Three different targeted mutagenesis constructs created: CRISPR/CAS9 I, CRISPR/CAS9 II, and TALEN. The difference between CRISPR/CAS9 I and II is minor. The target site locus for all three constructs was the same region where the frame-shift was found in haploid inducer lines. For the CRISPR constructs, the guide RNA sequence starts at nucleotide+1560: -GTCAACGTGGAGACAGGG- (i.e., SEQ ID NO: 83). The -AGG- PAM site of SEQ ID NO: 83 is underlined and italicized. The four basepair insertion in haploid inducer lines is at that exact site, at nucleotide+1576. After transformation, several different CRISPR I events (comprising the expression construct found in SEQ ID NO: 97), CRISPR II events (comprising the expression construct found in SEQ ID NO: 99), and TALEN events (comprising the expression construct found in SEQ ID NO: 98) were selected, grown to maturity, and set viable seed. In the T0 generation, we performed PCR at the target site and sequenced the PCR products after sub-cloning. We identified many unique mutations amongst those events (and many of the events were chimeras or had multiple alleles).

Many plants were chimeric, as evidenced by multiple different sequences appearing in the T1 generation. After T0 self-pollination, the T1 plants segregated 1:2:1 for the target mutagenesis construct, and many had novel mutations at the target locus in either a biallelic or homozygous state. We screened seedlings at the DNA level using TAQMAN markers, identified the biallelics that lacked the Cas9 or TALEN transgenes, and performed PCR sequencing to produce PCR product reading basepairs+1494 to +1691 in the GRMZM2G471240 gene sequence. We then tested homozygous mutants for haploid induction capacity. See SEQ ID NOs: 9-19 and 42-44 for the sequences of the new T1 plants at the mtl gene.

The HIR was measured for the putative new lines. See Table 11, above. This HIR data is from crosses where the male was a putative haploid inducer line and the female was our standard inbred transformation line NP2222. The putative haploid inducer lines were created using either TALEN- or CRISPR/CAS9-mediated targeted mutation of the pPLAIIα locus. Among those shown here, there are eleven different putative inducer plants comprising eight different events from three distinct transformation constructs. Event 39A was a TALEN event. Events 18A and 27A were CRISPR events. The latter was a chimera as a T0 plant, and after it was self-pollinated, multiple mutations were found in the T1 population, including "biallelic" plants (by biallelic, we mean that when we sequenced the region of pPLAIIα that was mutated, we found two different novel alleles—such that it is clear that both wild type copies of the gene had been mutated, but they were mutated differently, so there are two novel alleles). Each of these eleven individual plants thus had distinct combinations of mutations in pPLAIIα. What they all had in common is that none of the eleven plants had a wild type copy of pPLAIIα. Therefore, these are all "homozygous mutant" for the pPLAIIα gene. The mutations were all frameshifts in exon 4, mimicking the original mutation in the native haploid inducer lines. Using these five plants as males, we crossed onto either one or several female ears, generating thousands of embryos. We dissected and did ploidy analysis on those progeny and discovered that each of the progeny sets had at least 3.98% haploids with a maximum of 12.5% haploids. This demonstrates that generating mutations in pPLAIIα will lead to haploid induction. We think that other types of mutations, besides frameshifts, will also lead to haploid induction. Those mutations could be anywhere in the gene, and they could be point mutations or insertions or deletions or other types of mutations.

Figure 9:
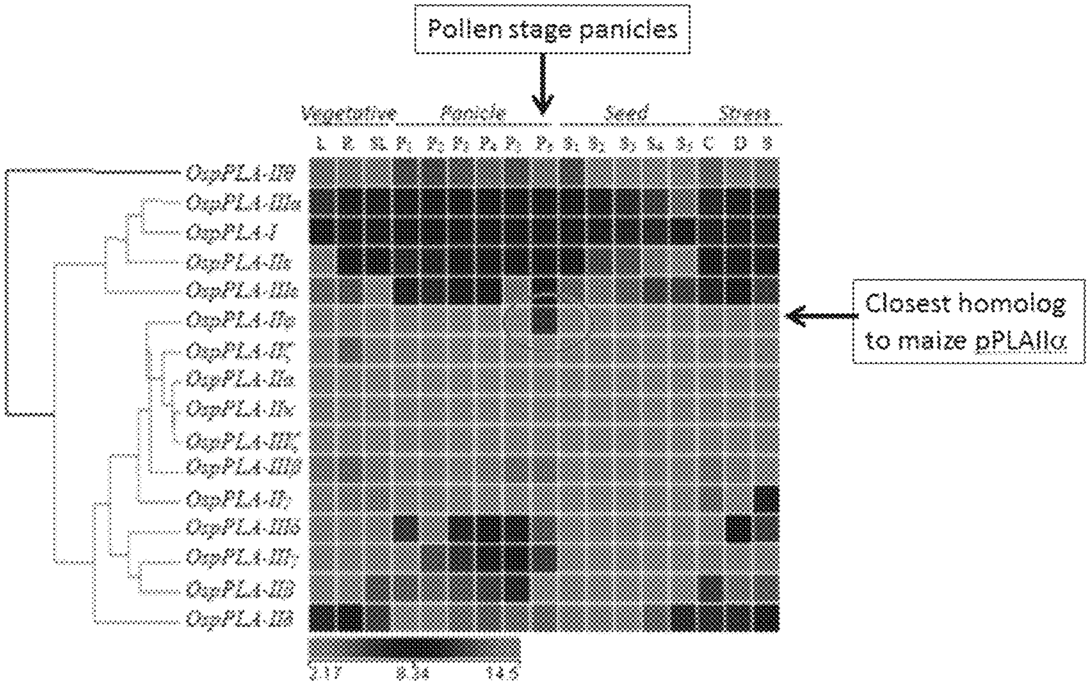
FIG. 9. Expression profile of rice phospholipases (adapted from Singh, A., et al., *Rice phospholipase A superfamily: organization, phylogenetic and expression analysis during abiotic stresses and development*, PLoS One 7: e30947 (2012)). The closest homolog to MTL is the rice gene OspPLAIIφ (053 g27610).
Figure 10:
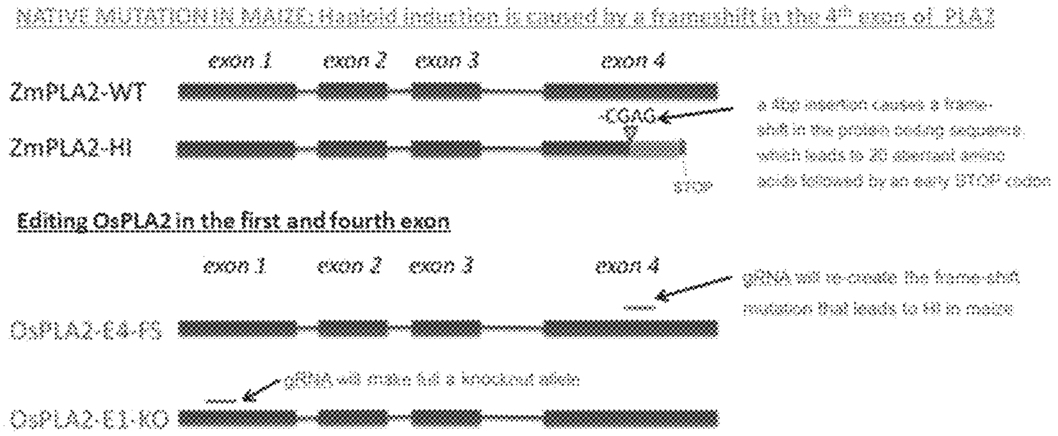
FIG. 10. Diagram showing a route to editing Os3g27610 in order to make haploid inducer lines. One could target any part of the gene (shown here—targeting the first and fourth exons) and expect to create frame-shift mutations that would lead to knockout and loss of function of the gene, and that will lead to haploid induction.

RNAi was also used to generate haploid inducer lines. For the RNAi, two hairpin constructs were made; one mapping to the border between exon 1 and 2, and the other mapping to exon 4 (FIGS. 9 and 10). The constructs were transformed into wild-type and the T0 plants were selfed. The T1 seed from three events per construct were grown, screened for homozygosity of the transgene, and outcrossed onto several ears as tests for haploid induction. After examining over 1500 kernels from these outcrosses, we found both events induce haploids at a rate of approximately 1% to 2%. The highest rate of haploid induction obtained on a single ear was 4.3%. That ear had about 300 kernels, so we can conclude that the embryo abortion rate was also lower than a typical high-inducer line. This work demonstrates than an RNAi+GM strategy can be used to create new haploid inducer lines in otherwise-typically wild-type lines by altering the expression of pPLAIIα.

The TILLING mutagenesis method was also used to create and identify the phospholipase mutations and maize of the present invention. Publications describing TILLING are available for crop plants such as rice: Till et al., *BMC Plant Biology* 7:19 (2007), tomato: Rigola et al. PLOS ONE Mar. 13, 2009, and maize Till et al. *BMC Plant Biol.* 2004 Jul. 28; 4:12 (2004), all of which are incorporated herein by reference. In the basic TILLING methodology, plant material, such as seed, is subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of maize having at least one phospholipase gene with substantial homology to SEQ ID NO: 68 may be used in accordance with the present invention. As used herein, "substantial homology" means that the DNA sequence of the gene is sufficiently similar to SEQ ID NO: 68 at the nucleotide level to code for the equivalent protein as SEQ ID NO: 68, allowing for allelic differences between cultivars. In accordance with one aspect of an exemplary embodiment of the invention, "substantial homology" may be present when the homology between the phospholipase gene and SEQ ID NO: 68 is as low as about 85%, provided that the homology in the conserved regions of the gene is higher (e.g., at least about 90%). Preferably, the percent identity in the coding region is 85-90%, more preferably 90-95%, and optimally, it is above 95%. One of skill in the art may prefer a maize cultivar having commercial popularity or one having specific desired characteristics in which to create the phospholipase-mutated maize. Alternatively, one of skill in the art may prefer a maize cultivar having few polymorphisms, such as an in-bred cultivar, in order to facilitate screening for mutations within the phospholipase loci.

In accordance with one aspect of an exemplary embodiment of the present invention, seeds from rice and maize were mutagenized and then grown into M1 plants. The M1 plants were then allowed to self-pollinate and seeds from the M1 plant were grown into M2 plants, which were then screened for mutations in their phospholipase locus. While M1 plants may be screened for mutations, an advantage of screening the M2 plants is that all somatic mutations correspond to the germline mutations. One of skill in the art would recognize that a variety of maize plant materials, including, but not limited to, seeds, pollen, plant tissue or plant cells, may be mutagenized in order to create the phospholipase-mutated maize of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for phospholipase mutations instead of waiting until the M2 generation.

Mutagens that create primarily point mutations and short deletions, insertions, transversions, and or transitions (about 1 to about 5 nucleotides), such as chemical mutagens or radiation, may be used to create the mutations of the present invention. Mutagens conforming with the method of the present invention include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitro so guanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloro-ethyl)aminopropylamino]acridine dihydrochloride (ICR-170), and formaldehyde. Spontaneous mutations in the nucleolar organizing region ("NOR") that may not have been directly caused by the mutagen can also be identified in accordance with various embodiments of the present invention.

Any suitable method of plant DNA preparation now known or hereafter devised may be used to prepare the maize plant DNA for phospholipase mutation screening. For example, see Chen and Ronald, Plant Molecular Biology Reporter 17:53-57, 1999; Stewart and Via, Bio Techniques 14:748-749, 1993. Additionally, several commercial kits are available, including kits from Qiagen (Valencia, Calif.) and Qbiogene (Carlsbad, Calif.).

In accordance with one aspect of an exemplary embodiment of the invention, DNA samples from individual maize plants are prepared and then pooled in order to expedite screening for mutations in phospholipase of the entire population of plants originating from the mutagenized plant tissue. The size of the pooled group may be dependent upon the sensitivity of the screening method used. In accordance with one aspect of an exemplary embodiment of the invention, groups of four or more individual maize plants are pooled.

In accordance with another aspect of an exemplary embodiment, after the DNA samples are pooled, the pools are subjected to phospholipase sequence-specific amplification techniques, such as Polymerase Chain Reaction (PCR). For a general overview of PCR, see PCR Protocols: A Guide to Methods and Applications (Innis, Gelfand, Sninsky, J., and White, eds.), Academic Press, San Diego, 1990, which is incorporated herein by reference. Any primer specific to the phospholipase locus or the sequences immediately adjacent to the phospholipase locus may be utilized to amplify the phospholipase sequences within the pooled DNA sample. Preferably, the primer is designed to amplify the regions of the phospholipase locus where useful mutations are most likely to arise. Most preferably, the primer is designed to detect mutations in the coding region of the phospholipase gene. Additionally, it is preferable for the primer to avoid known polymorphic sites in order to ease screening for point mutations. To facilitate detection of PCR products on a gel, the PCR primer may be labeled using any conventional or hereafter devised labeling method.

In accordance with one aspect of an exemplary embodiment of the invention, the PCR amplification products may be screened for phospholipase mutations using any method that identifies nucleotide differences between wild type and mutant sequences. These may include, without limitation, sequencing, denaturing high pressure liquid chromatography (dHPLC), constant denaturant capillary electrophoresis (CDCE), temperature gradient capillary electrophoresis (TGCE) (see Li et al., Electrophoresis 23(10):1499-1511, 2002), or by fragmentation using enzymatic cleavage, such as used in the high throughput method described by Colbert et al., Plant Physiology 126:480-484, 2001. Preferably, the PCR amplification products are incubated with an endonuclease that preferentially cleaves mismatches in heteroduplexes between wild type and mutant sequences. In accordance with another aspect of an exemplary embodiment, cleavage products are electrophoresed using an automated sequencing gel apparatus, and gel images are analyzed with the aid of a standard commercial image-processing program.

31:3808-3811, 2003). For example, a SIFT score that is less than 0.05 and a large change in PSSM score (e.g., roughly 10 or above) indicate a mutation that is likely to have a deleterious effect on protein function.

In accordance with a further aspect of an exemplary embodiment, if the initial assessment of a mutation in an M2 plant indicates it to be of a useful nature and in a useful position within the phospholipase gene, then further phenotypic analysis of the maize plant containing that mutation is pursued. First, the M2 plant is backcrossed or outcrossed twice to create a BC1 plant in order to eliminate background mutations. Then the backcrossed or outcrossed BC1 plant is self-pollinated in order to create a BC1F2 plant that is homozygous for the phospholipase mutation.

Several physical characteristics of these homozygous phospholipase mutant plants are assessed to determine if the mutation results in a useful phenotypic change in the maize Mutant phospholipase maize are evaluated for haploid induction compared to normal (e.g., wild type) parental maize or to wild type sibling control maize Table 14 shows novel mutations obtained by TILLING.

TABLE 14

Novel pPLAIIα Mutations Obtained by TILLING & their HIR. The nucleotide change column represents the position from the start of the cDNA sequence (SEQUENCE No. 1), and the changed nucleotide is capitalized within its codon context. The amino acid change is then indicated followed by the impact of that change (Tolerated or Not Tolerated). Of the two alleles that were not tolerated, one induced haploids at a rate of 1.04% (3/288).

| Line | Nucleotide change | Exon | AA change | Tolerated? | Diploids | Haploids | PA confirmed | HIR |
|---|---|---|---|---|---|---|---|---|
| 1139 | bp + 128 tGt/tAt | 1 | C13Y | Yes | 389 | 0 | 0 | 0.00% |
| 3594 | bp + 167 cCc/cTc | 1 | P26L | Yes | 381 | 0 | 0 | 0.00% |
| 0505 | bp + 431 cCg/cTg | 1 | P114L | No | 235 | 0 | 0 | 0.00% |
| 2658 | bp + 718 Gcg/Acg | 4 | A237T | Yes | 379 | 0 | 0 | 0.00% |
| 1983 | bp + 1077 atG/atA | 4 | M356I | No | 285 | 3 | 3 | 1.04% |
| 2732 | bp + 1163 aCt/aTt | 4 | T385I | Yes | 383 | 0 | 0 | 0.00% |
| 2414 | bp + 1226 aGa/aAa | 4 | R406K | Yes | 392 | 0 | 0 | 0.00% |

The present inventors have determined that to achieve haploid induction in maize, mutations that alter phospholipase function are desirable. Preferred mutations include missense, nonsense and splice junction changes, including mutations that prematurely truncate the translation of the phospholipase protein from messenger RNA, such as those mutations that create a stop codon within the coding regions of the phospholipase gene. Such mutations include insertions, repeat sequences, modified open reading frames (ORFs) and, most preferably, point mutations.

In accordance with yet another aspect of an exemplary embodiment of the invention, once an M2 plant having a mutated phospholipase sequence is identified, the mutations are analyzed to determine its effect on the expression, translation, and/or activity of the protein. In accordance with one exemplary embodiment, the phospholipase fragment containing the mutation is sequenced, using standard sequencing techniques, in order to determine the exact location of the mutation in relation to the overall phospholipase sequence. Each mutation is evaluated in order to predict its impact on protein function (i.e., completely tolerated to loss-of-function) using bioinformatics tools such as SIFT (Sorting Intolerant from Tolerant; Ng et al., Nucleic Acids Research 31:3812-3814, 2003), PSSM (Position-Specific Scoring Matrix; Henikoff and Henikoff, Computer Applications in the Biosciences 12:135-143, 1996) and PARSESNP (Taylor and Greene, Nucleic Acids Research The nomenclature used in the Table 14 indicates the wild type nucleotide or amino acid, followed by its position according to the referenced SEQ ID NO: 68, followed by the changed nucleotide or amino acid at that position using standard genetic code terminology.

For maize, TILLING the maize pPLAIIα gene generates new alleles which have low rates of haploid induction. This enables the creation of an allelic series, including knockouts, of GRMZM2G471240. The sequence of two segments of this gene (maximum 1.5 kb, which equals amplicons per gene) are screened for mutations. These sequences included the genomic sequence including introns, plus the predicted cDNA sequence and coding sequences for the two splice variants. Relevant and unique amplicon sequences are designed based on those sequences, and mutation screening is performed in an existing bulked-M2 corn population. The identified mutants are characterized in terms of DNA sequence and consequences on translated protein sequence. The M3 seed is grown and selfed to generate M4 lines with putative mutant homozygous individuals segregating. These individuals are identified by PCR sequencing and outcrossed and selfed to test for these mutant lines' ability to induce haploids.

To execute the test crosses, the new lines are grown alongside a marker line which is homozygous recessive for a non-lethal color marker gene. Reciprocal crosses are used to test the specificity of induction to male vs. female transmission by evaluating the resulting plants for haploids, which exhibit the color phenotype. Positive hits are confirmed by the ploidy analysis as described above.

Individuals that are homozygous for the SNP mutations were crossed as males to the marker line female and led to the formation of a low rate of haploids in some instances. Positive hits are confirmed by the ploidy analysis as described above. In particular, a line that led to haploid formation had a G to A mutation at base pair 1077 of the cDNA sequence. This mutation causes an amino acid substitution of a methionine (M) to an isoleucine (I) at amino acid 356. This is a non-conservative amino acid change that may disrupt the protein's activity leading to the formation of low rate of haploids. Among 288 progeny tested, we found three haploids, for an induction rate of 1% (3/288).

Example 18. Creating Haploid Inducing Lines in Rice

In rice, the closest homolog to the maize pPLAIIα is Os03g27610, a rice patatin-like phospholipase (OspPLAIIφ) with a similar annotation, gene structure and expression pattern, i.e., expressed in pollen and absent elsewhere (FIG. 10). SEQ ID NO: 84 comprises the genomic DNA sequence of Os03g27610, SEQ ID NO: 85 comprises the cDNA sequence, and SEQ ID NO: 86 comprises the amino acid sequence. The close agreement of these features, along with the short evolutionary distance between these two grasses, suggests that a mutation in the rice gene may also give rise to a haploid induction line. In a recent publication the rice protein was detected in sperm nuclei of pollen grains (Abiko et al., 2013), suggesting involvement of this protein in fertilization and/or zygote development.

To improve the haploid induction rate in maize and create the first haploid inducer lines in rice, a reverse genetics TILLING approach was used to obtain novel mutants in the maize GRMZM2G471240 gene and the rice Os03g27610 gene. See McCallum C M et al. (2000) *Targeting induced local lesions IN genomes* (*TILLING*) *for plant functional genomics*, Plant Physiol. 123: 439-42, incorporated herein by reference. TILLING provides an unbiased approach to generating new mutants as there is no control by the researcher of where the ethylmethanesulfonate (EMS) mutagen will create new mutations. A diversity and abundance of new alleles were generated and tested for haploid induction rate.

Thirteen different TILLING M3 lines were obtained. See Table 15. The PosGenomic column indicates the nucleotide position of the mutation and the change (e.g., G803A indicates that base pair G at position 803 was changed to an A). The effect is the amino acid change or other protein change that results from the mutation (e.g. A209T indicates that an Alanine at amino acid 209 was changed to a Threonine). The BLOSUM score is a prediction of the strength of the effect the amino acid change will have on the protein's conformation or fold (the more negative, the more severe the effect). The "Type" indicates the type of amino acid change ("NSM" means non-silent mutation; "PSM" means partially silent mutation; "silent" means silent mutation; "splice" means splice site mutation resulting in aberrant splicing; "intron" means mutation is in an intron). Finally the GSOR# is the line ID for the Genetic Stocks—*Oryza* collection at the USDA.

These thirteen lines were selfed to make the M4 and the M4 seed are grown and tested for homozygosity. Homozygous mutant individuals are selfed and outcrossed to test for haploid induction capacity. The resulting progeny are examined for DNA content per cell (ploidy) using the ploidy analyzer.

The non-conservative changes, such as the splice site changes and the changes with most negative BLOSUM scores have the greatest haploid induction potential. These should have the more destabilizing effects on the protein product, and so are the superior haploid induction TILLING alleles compared to the others, giving rise to more haploids per haploid induction cross and likely resulting in partially compromised seed set. Indeed, we have already started to see that in some of the T4 self-pollinations. The line with the lowest seed set was the splice site mutant G153A, with only 29 seeds being recovered per 12 homozygous mutant M4 plants crossed. The other lines had more than 100 recovered.

TABLE 15

TILLING alleles in rice Os03g27610.

| Gene | PosGen | PosTIL | Effect | BLOSUM | Type | GSOR# |
|---|---|---|---|---|---|---|
| Os03g27610 | G803A | G590A | A209T | 0 | NSM | 406317 |
| Os03g27610 | G761A | G548A | D195N | 1 | NSM | 405490 |
| Os03g27610 | G1163A | G950A | G293E | −2 | PSM | 403403 |
| Os03g27610 | G1189A | G976A | G302R | −2 | PSM | 406250 |
| Os03g27610 | T374C | T161C | intron | NA | intron | 403453 |
| Os03g27610 | G1026A | G813A | K247= | NA | silent | 406338 |
| Os03g27610 | C738T | C525T | P187L | −3 | PSM | 405205 |
| Os03g27610 | G1149A | G936A | Q288= | NA | silent | 405898 |
| Os03g27610 | G366A | G153A | splice | NA | splice | 403878 |
| Os03g27610 | G366A | G153A | splice | NA | splice | 405549 |
| Os03g27610 | C792T | C579T | T205I | −1 | PSM | 404794 |
| Os03g27610 | A1021G | A808G | T246A | 0 | NSM | 404534 |
| Os03g27610 | G558A | G345A | V156M | 1 | NSM | 404675 |

Alternately, the rice phospholipase gene found in Os03g27610 may be edited by CRISPR/Cas9 methods. As stated above, there are three key components to the CRISPR process. The first key component is the target sequence. The second is the Cas9, which is the endonuclease. The third key component is the guide RNA ("gRNA"), which is complementary to the target sequence and is responsible for recruiting Cas9 to the desired location. Guide RNAs can be in the form of single guide RNA (sgRNA) or double guide RNA (dgRNA). For rice, we created four constructs targeting the rice phospholipase gene. SEQ ID NO: 101 comprises an expression cassette that provides for dgRNA targeting Os03g27610, in exon 4 very near to where the native four base pair mutation is located in the maize homolog. In the rice gene, the guide RNA target site is GAGACCGGCAGGTACGTCGAGG. SEQ ID NO: 102 comprises an expression cassette that provides for sgRNA targeting Os03g27610, exon 4, at the same gRNA target site as is targeted in SEQ ID NO: 101. The frameshift mutations for both SEQ ID NOs: 101 and 102 are expected to occur where the vertical bar is placed between the G and the T in the sequence CAGGTACG I TCGAGG (at base pair +1150 of the gDNA sequence in the SEQ ID NO 85. Therefore, both of these constructs are expected to generate haploid inducer mutations that are only seven base pairs downstream from where the maize haploid inducer insertion is located. These mutations in most cases will be frame-shifting mutations that induce small insertions or deletions, for instance a deletion of a G or a T at the cut site, or any other similar mutation. SEQ ID NO: 103 comprises an expression cassette that provides for dgRNA targeting Os03g27610. SEQ ID NO: 104 comprises an expression cassette that provides for sgRNA targeting Os03g27610. Both of these harbor guide RNAs that target the sequence CCTCGCCGAT- TACTTCGACTGCA in Exon 1. This should generate a knockout of the majority of the coding sequence of the gene. The mutation that is generated should occur at the cut site where the vertical bar is placed between the C and the C in the sequence CCTCGC|CGATTAC (at base pair +215 of the cDNA sequence in SEQ ID NO 85). Therefore both construct 40 and 41 are expected to generate a high frequency of plants containing knockout mutations of the gene, which should also lead to high haploid induction rates in rice.

Rice plants are transformed with a transformation construct comprising a sequence selected from the group consisting of SEQ ID Nos: 101-104. Through the CRISPR/Cas9 machinery encoded in the transformation construct, new phospholipase alleles are generated in the transformants, i.e., the T0 rice plants. T0 rice plants, are grown and crossed (i.e., self-pollinated) to create T1 plants. The T1 rice plants are tested for homozygosity at the new phospholipase allele. Homozygous T1 rice plants are crossed with a rice line, and resulting progeny are tested for haploidy using a ploidy analyzer. Haploid embryos containing no detectable T1 DNA are identified and counted, and the HIR is measured. At least one haploid embryo is produced from the cross, and the HIR is elevated. Preferably, the HIR is at least 5%. The at least one haploid embryo is treated with a chromosome doubling agent, for example colchicine, and a doubled-haploid plant is grown therefrom.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Abler et al. (1993) Isolation and characterization of a genomic sequence encoding the maize Cat3 catalase gene. *Plant Mol Biol* 22: 1031-1038.

Allison et al. (1986) The nucleotide sequence of the coding region of tobacco etch virus genomic RNA: evidence for the synthesis of a single polyprotein. *Virology* 154:9-20.

Ardlie et al. (2002) Patterns of linkage disequilibrium in the human genome. *Nature Reviews Genetics* 3:299-309.

Ausubel et al. (1988) *Current Protocols in Molecular Biology*, John Wiley & Sons, New York, New York, United States of America.

Barret P, Brinkmann M, Beckert M. 2008. A major locus expressed in the male gametophyte with incomplete penetrance is responsible for in situ gynogenesis in maize. *Theoretical and Applied Genetics* 117, 581-594.

Benfey & Chua (1990) The Cauliflower Mosaic Virus 35S Promoter: Combinatorial Regulation of Transcription in Plants. *Science* 250: 959-966.

Bennett M D, Finch R A, Barclay I R. 1976. The time rate and mechanism of chromosome elimination in *Hordeum* hybrids. *Chromosoma* 54, 175-200.

Bevan (1984) Binary *Agrobacterium* vectors for plant transformation. *Nucl Acids Res* 12:8711-8721.

Bevan et al. (1983) A chimeric antibiotic resistance gene as a selectable marker for plant cell transformation. *Nature* 304:184-187.

Binder et al. (1996) Regulation of gene expression in plant nnuclear. *Plant Mol Biol* 32:303-314.

Birchler J A. 1993. Dosage analysis of maize endosperm development. *Annual Review of Genetics* 27, 181-204.

Birchler J A, Gao Z, Sharma A, Presting G G, Han F. 2011. Epigenetic aspects of centromere function in plants. *Current Opinion in Plant Biology* 14, 217-222.

Blair et al. (1999) Inter-simple sequence repeat (ISSR) amplification for analysis of microsatellite motif frequency and fingerprinting in rice (*Oryza sativa* L.). *Theor Appl Genet* 98:780-792.

Blochinger & Diggelmann (1984) Hygromycin B phosphotransferase as a selectable marker for DNA transfer experiments with higher eucaryotic cells. *Mol Cell Biol* 4:2929-2931.

Bourouis & Jarry (1983) Vectors containing a prokaryotic dihydrofolate reductase gene transform *Drosophila* cells to methotrexate-resistance. *EMBO J* 2:1099-1104.

Braun & Schmitz (1999) The protein-import apparatus of plant nnuclear. *PLANTA* 209:267-274.

Brookes (1994) The essence of SNPs. *Gene* 234:177-186.

Bustos et al. (1989) Regulation of beta-glucuronidase expression in transgenic tobacco plants by an A/T-rich, cis-acting sequence found upstream of a French bean beta-phaseolin gene. *Plant Cell* 1:839-854.

Callis et al. (1987) Introns increase gene expression in cultured maize cells. *Genes Develop* 1:1183-1200.

Castle et al. (2004) Discovery and directed evolution of a glyphosate tolerance gene. *Science* 304:1151-1154.

Chalyk, S. T., 1994 Properties of maternal haploid maize plants and potential application to maize breeding. Euphytica 79: 13-18.

Chalyk, S. T., A. Baumann, G. Daniel, and J. Eder, 2003 Aneuploidy as a possible cause of haploid-induction in maize. Maize Genet. Newsl. 77: 29-30.

Chang, M., and E. H. Coe, 2009 Doubled haploids, pp. 127-142 in Molecular Genetic Approaches to Maize Improvement, edited by A. L. Kritz and B. Larkins. Springer-Verlag, Berlin.

Chase (2007) Haploid induction: a window to the world of plant 1-nuclear interactions. *Trends in Genetics* 23:81-90.

Chase, S. S., 1952 Monoploids in maize, pp. 389-399 in Heterosis, edited by J. W. Gowen. Iowa State College Press, Ames, IA.

Chen et al. (2003) Temporal and spatial control of gene silencing in transgenic plants by inducible expression of double-stranded RNA. *Plant J* 36:731-740.

Choi et al. (1995) Tissue-specific and developmental regulation of a gene encoding a low molecular weight sulfur-rich protein in soybean seeds. *Mol Gen Genet* 246:266-268.

Christensen et al. (1989) Sequence analysis and transcriptional regulation by heat shock of polyubiquitin transcripts from maize. *Plant Mol Biol* 12:619-632.

Christensen et al. (1992) Maize polyubiquitin genes: structure, thermal perturbation of expression and transcript splicing, and promoter activity following transfer to protoplasts by electroporation. *Plant Mol Biol* 18:675-689.

Christou et al. (1991) Production of Transgenic Rice (*Oryza Sativa* L.) plants from agronomically important Indica and *Japonica* varieties via electric discharge particle acceleration of exogenous DNA into immature zygotic embryos. *Nature Biotechnol* 9:957-962.

Coe, E. H., 1959 A line of maize with high haploid frequency. *Am. Nat.* 93: 381-382.

Conceicao et al. (1994) A cotyledon regulatory region is responsible for the different spatial expression patterns of *Arabidopsis* 2S albumin genes. *Plant* 5:493-505.

Dasgupta et al. (1993) Cloning and sequencing of 5' flanking sequence from the gene encoding 2S storage protein, from two *Brassica* species. *Gene* 133:301-302.
Datta et al. (1990) Genetically engineered fertile Indica-rice recovered from protoplasts. *Nature Biotechnol* 8:736-740.
Deimling, S., F. K. Röber, and H. H. Geiger, 1997 Methodology and genetics of in vivo haploid induction in maize Vortr. Pflanzenziichtg. 38: 203-224.
Della-Cioppa et al. (1987) Protein trafficking in plant cells. *Plant Physiol* 84:965-968.
Dong et al. (1996) Characterization of rice transformed via an *Agrobacterium*-mediated inflorescence approach. *Molecular Breeding* 2:267-276.
Dong et al. (2013) Fine mapping of qhir1 influencing in vivo haploid induction in maize. *Theor Appl. Genet* 126: 17134720.
Dunwell J M. 2010. Haploids in flowering plants: origins and exploitation. *Plant Biotechnology Journal* 8, 377-424.
Eldar, A., V. K. Chary, P. Xenopoulos, M. E. Fontes, 0. C. Los& et al., 2009 Partial penetrance facilitates developmental evolution in bacteria. *Nature* 460: 510-514.
Elroy-Stein et al. (1989) Cap-independent translation of mRNA conferred by encephalomyocarditis virus 5' sequence improves the performance of the vaccinia virus/bacteriophage T7 hybrid expression system. *Proc Natl Acad Sci USA* 86:6126-6130.
Estruch et al. (1994) Cloning and characterization of a maize pollen-specific calcium-dependent calmodulin-independent protein kinase. *Proc Natl Acad Sci USA* 91:8837-8841.
European Patent Applications EP 0 292 435; EP 0 332 581; EP 0 392 225.
Evans M M S. 2007. The indeterminate gametophyte 1 gene of maize encodes a LOB domain protein required for embryo sac and leaf development. *The Plant Cell* 19, 46-62.
Fey & Maréchal-Drouard (1999) Compilation and analysis of plant nnuclearl promoter sequences: An illustration of a divergent evolution between monocot and dicot nuclear. *Biochem Biophys Res Commun* 256:409-414.
Fiume et al. (2004) Introns are key regulatory elements of rice tubulin expression. *Planta* 218: 693-703.
Fischer E. 2004. Molecular genetic studies on the occurrence of paternal DNA transmission during in vivo haploid induction in maize (*Zea mays*) [in German]. Dissertation, University of Hohenheim.
Fromm et al. (1990) Inheritance and expression of chimeric genes in the progeny of transgenic maize plants. *Nature Biotechnol* 8:833-839.
Gallie et al. (1987) A comparison of eukaryotic viral 5'-leader sequences as enhancers of mRNA expression in vivo. *Nucl Acids Res* 15:8693-8711.
Gallie et al. (1989) Eukaryotic viral 5'-leader sequences act as translational enhancers in eukaryotes and prokaryotes. In: *Molecular Biology of RNA*, Cech (ed.). UCLA Symposia on Molecular and Cellular Biology, New Series, Alan R. Liss, Inc., New York, New York, Volume 92, pp. 237-256.
Geiger, H. H., 2009 Doubled haploids, pp. 641-657 in Maize Handbook, Vol. 2, edited by J. L. Bennetzen, and S. Hake. Springer, New York.
GENBANK® Accession Nos. EF115541; NC_007579.
GENBANK® Accession Nos. J02798; J05212; L05934; M63985; NC_003377; U09118; U09119; U39944; U43147; U45855; U93215; X15596; X74782; YP_398418; YP_398423; Z17657.
Gordon-Kamm et al. (1990) Transformation of maize cells and regeneration of fertile transgenic plants. *Plant Cell* 2:603-618.
Green et al. (1988) Binding site requirements for pea nuclear protein factor GT-1 correlate with sequences required for light-dependent transcriptional activation of the rbcS-3A gene. *EMBO J* 7:4035-4044.
Guo et al. (2003) A chemical-regulated inducible RNAi system in plants. *Plant J* 34:383-392.
Hanson & Bentolila (2004) Interactions of nnuclearl and nuclear genes that affect male gametophyte development. *Plant Cell* 16 Suppl:S154-169
Hedgcoth et al. (2002) A chimeric open reading frame associated with haploid induction in alloplasmic wheat with *Triticum* timopheevi nnuclear is present in several *Triticum* and *Aegilops* species, maize, and rye. *Curr Genet* 41:357-365.
Hiei et al. (1994) Efficient transformation of rice (*Oryza sativa* L.) mediated by *Agrobacterium* and sequence analysis of the boundaries of the T-DNA. *Plant J* 6:271-282.
Hiei et al. (1997) Transformation of rice mediated by *Agrobacterium tumefaciens. Plant Mol Biol* 35:205-218.
Hill & Robertson (1968) Linkage disequilibrium in finite populations. Theor. Appl. Genet. 38, 226-231. *Theor Appl Genet* 38:226-231.
Hofgen & Willmitzer (1988) Storage of competent cells for *Agrobacterium* transformation. *Nucl Acids Res* 16:9877.
Huang et al. (1996) The *Arabidopsis* ACT11 actin gene is strongly expressed in tissues of the emerging inflorescence, pollen, and developing ovules. *Plant Mol Biol* 33:125-139.
Huang et al. (2009) Refining the Definition of Plant Nnuclearl Presequences through Analysis of Sorting Signals, N-Terminal Modifications, and Cleavage Motifs. *Plant Physiol* 150:1272-128.
Japanese Patent Application JP 2001512988-A/13.
Jing et al. (2012) A male sterility-associated cytotoxic protein ORF288 in *Brassica juncea* causes aborted pollen development. *J Exp Biol* 63:1285-1295.
Jobling & Gehrke (1987) Enhanced translation of chimaeric messenger RNAs containing a plant viral untranslated leader sequence. *Nature* 325:622-625.
Jordano et al. (1989) A sunflower helianthinin gene upstream sequence ensemble contains an enhancer and sites of nuclear protein interaction. *Plant Cell* 1:855-866.
Josefsson et al. (1987) Structure of a gene encoding the 1.7 S storage protein, napin, from *Brassica napus. J Biol Chem* 262:12196-1201.
Kalendar et al. (1999) IRAP and REMAP: two new retrotransposon-based DNA fingerprinting techniques. *Theor Appl Genet* 98:704-.
Kermicle J L. 1969. Androgenesis conditioned by a mutation in maize. *Science* 166, 1422-1424.
Klein et al. (1987) High-velocity microprojectiles for delivering nucleic acids into living cells. *Nature* 327:70-73.
Koziel et al. (1993) Field performance of elite transgenic maize plants expressing an insecticidal protein derived from *Bacillus thuringiensis. Nature Biotechnol* 11:194-200.
Lashermes, P., and M. Beckert, 1988 Genetic control of maternal haploidy in maize (*Zea mays* L.) and selection of haploid inducing lines. Theor. Appl. Genet. 76: 405-410.
Last et al. (1991) Emu: an improved promoter for gene expression in cereal cells. *Theor Appl Genet* 81:581-588.
Lee & Gelvin (2008) T-DNA Binary vectors and systems. *Plant Physiol* 146:325-332.

Lee & Huang (1994) Genes encoding oleosins in maize kernel of inbreds Mo17 and B73. *Plant Mol Biol* 26:1981-1987.

Lee et al. (2007) Novel Plant Transformation Vectors Containing the Superpromoter. *Plant Physiol* 1294-1300.

Lommel et al. (1991) Identification of the maize chlorotic mottle virus capsid protein cistron and characterization of its subgenomic messenger RNA. *Virology* 181:382-385.

Lu et al. (2008) Activity of the 5' regulatory regions of the rice polyubiquitin *rubi*3 gene in transgenic rice plants as analyzed by both GUS and GFP reporter genes. *Plant Cell Rep* 27:1587-600.

Li L, Xu X, Jin W, Chen S. 2009. Morphological and molecular evidences for DNA introgression in haploid induction via a high oil inducer CAUHOI in maize. *Planta* 230, 367-376.

Macejak & Samow (1991) Internal initiation of translation mediated by the 5' leader of a cellular mRNA. *Nature* 353:90-94.

Manjunath et al. (1997) Molecular characterization and promoter analysis of the maize cytosolic glyceraldehyde 3-phosphate dehydrogenase gene family and its expression during anoxia. *Plant Mol Biol* 33:97-112.

Martinez et al. (1989) Structure, evolution and anaerobic regulation of a nuclear gene encoding cytosolic glyceraldehyde-3-phosphate dehydrogenase from maize. *J Mol Biol* 208:551-565.

Mayo (1987) *The Theory of Plant Breeding*, Second Edition, Clarendon Press, Oxford, United Kingdom.

McBride et al. (1994) ontrolled expression of plastid transgenes in plants based on a nuclear DNA-encoded and plastid-targeted T7 RNA polymerase. *Proc Natl Acad Sci USA* 91:7301-7305.

McElroy et al. (1990) Isolation of an efficient actin promoter for use in rice transformation. *Plant Cell* 2:163-171.

Meier et al. (1991) Elicitor-inducible and constitutive in Vivo DNA footprints indicate novel cis-acting elements in the promoter of a parsley gene encoding pathogenesis-related protein 1. *Plant Cell* 3:309-316.

Mettler (1987) A simple and rapid method for minipreparation of DNA from tissue cultured plant cells. *Plant Mol Biol Reporter* 5:346-349.

Murashige & Skoog (1962) A revised medium for rapid growth and bioassays with tobacco tissue cultures. Physiologia *Plantarum* 15:473-497.

Nanda, D. K., and S. S. Chase, 1966 An embryo marker for detecting monoploids of maize (*Zea mays* L.). *Crop Sci.* 6: 213-215.

Needleman & Wunsch (1970) A general method applicable to the search for similarities in the amino acid sequence of two proteins. *J Mol Biol* 48:443-453.

Negrotto et al. (2000) The use of phosphomannose-isomerase as a selectable marker to recover transgenic maize plants (*Zea mays* L.) via *Agrobacterium* transformation. Plant Cell Reports 19:798-803.

Neuffer M G, Sheridan W F. 1980. Defective kernel mutants of maize. I. Genetic and lethality studies. *Genetics* 95, 929-944.

Ni et al. (1995) Strength and tissue specificity of chimeric promoters derived from the octopine and mannopine synthase genes. *Plant J* 7:661-676.

Odell et al. (1985) Identification of DNA sequences required for activity of the cauliflower mosaic virus 35S promoter. *Nature* 313:810-812.

Onozaki et al. (2004) A RAPD-derived STS marker is linked to a bacterial wilt (*Burkholderia caryophylli*) resistance gene in carnation. Euphytica 138:255-262.

Orita et al. (1989) Detection of polymorphisms of human DNA by gel electrophoresis as single-strand conformation polymorphisms. *Proc Natl Acad Sci USA* 86:2766-.

Paran & Michelmore (1993) Development of reliable PCR-based markers linked to downy mildew resistance genes in lettuce. *Theor Appl Genet* 85:985-993.

Paszkow ski et al. (1984) Direct gene transfer to plants. *EMBO J* 3:2717-2722.

PCT International Patent Application Publication Nos. WO 1992/013957; WO 1993/07278; WO 1993/21335; WO 1994/00977; WO 1997/32011; WO 1999/043838.

Pearson & Lipman (1988) Improved tools for biological sequence comparison. *Proc Natl Acad Sci US A* 85:2444-2448.

Potrykus et al. (1985) Molecular and general genetics of a hybrid foreign gene introduced into tobacco by direct gene transfer. *Mol Gen Genet* 199:169-177.

Prigge V, Melchinger A E. 2012. Production of haploids and doubled haploids in maize. *Methods in Molecular Biology* 877, 161-172.

Prigge, V., and A. E. Melchinger, 2012 Production of haploids and doubled haploids in maize, Plant Cell Culture Protocols, Ed. 3, edited by V. M. Loyola-Vargas and N. Ochoa-Alejo. Humana Press-Springer Verlag, Totowa, NJ (in press).

Prigge, V., C. Sánchez, B. S. Dhillon, W. Schipprack, J. L. Araus et al., 2011 Doubled haploids in tropical maize I Effects of inducers and source germplasm on in vivo haploid induction rates. Crop Sci. 51: 1498-1506.

Prigge V, Xu X, Li L, Babu R, Chen S, Atlin G N, Melchinger A E. 2012. New insights into the genetics of in vivo induction of maternal haploids, the backbone of doubled haploid technology in maize. *Genetics* 190, 781-793.

Rafalski & Tingey (1993) Genetic diagnostics in plant breeding: RAPDs, microsatellites and machines. *Trends Genet* 9:275-280.

Ravi, M., and S. W. L. Chan, 2010 Haploid plants produced by centromere-mediated genome elimination. *Nature* 464: 615-619

Reed et al. (2001) Phosphomannose isomerase: an efficient selectable marker for plant transformation. In *Vitro Cell Dev Biol-Plant* 37:127-132.

Reich et al. (1986) Efficient transformation of alfalfa protoplasts by the intranuclear microinjection of Ti plasmids. *Nature Biotechnol* 4:1001-1004.

Reiser et al. (1995) he BELL1 Gene Encodes a Homeodomain Protein Involved in Pattern Formation in the *Arabidopsis* Ovule Primordium. Cell 83:735-742.

Röber, F. K., G. A. Gordillo, and H. H. Geiger, 2005 In vivo haploid induction in maize: performance of new inducers and significance for doubled haploid lines in hybrid breeding. Maydica 50: 275-283

Roque et al. (2007) The PsEND1 promoter: a novel tool to produce genetically engineered male-sterile plants by early anther ablation. *Plant Cell Reports* 26:313-325.

Sambrook & Russell (2001) *Molecular Cloning: A Laboratory Manual* ($3^{rd}$ ed.), Cold Spring Harbor Library Press, Cold Spring Harbor, New York, United States of America.

Sarkar K, Coe E. 1966. A genetic analysis of the origin of maternal haploids in maize. *Genetics* 54, 453-464.

Schocher et al. (1986) Co-transformation of unlinked foreign genes into plants by direct gene transfer. *Nature Biotechnol* 4:1093-1096.

Sheridan et al. (1996) The mac 1 Gene: Controlling the Commitment to the Meiotic Pathway in Maize. *Genetics* 142:1009-1020.

Shimamoto et al. (1989) Fertile transgenic rice plants regenerated from transformed protoplasts. *Nature* 338:274-276.

Singh, (1986) *Breeding for Resistance to Diseases and Insect Pests*, Springer-Verlag, New York, New York, United States of America.

Sjodahl et al. (1995) Deletion analysis of *Brassica napus* cruciferin gene cru 1 promoter in transformed tobacco: promoter activity during early and late stages of embryogenesis is influenced by cis-acting elements in partially separate regions. *Planta* 197:264-274.

Sjoling & Glaser (1998) Nnuclearl targeting peptides in plants. *Trends Plant Sci* 3:136-140.

Skuzeski et al. (1990) Analysis of leaky viral translation termination codons in vivo by transient expression of improved beta-glucuronidase vectors. *Plant Mol Biol* 15:65-79.

Smith & Waterman (1981) "Comparison of biosequences. *Adv Appl Math* 2: 482-489.

Solocombe et al. (1994) Temporal and tissue-specific regulation of a *Brassica napus* stearoyl-acyl carrier protein de s atura se gene. *Plant Physiol* 104:1167-1176.

Song & Hedgcoth (1994) A chimeric gene (orf256) is expressed as protein only in cytoplasmic male-sterile lines of wheat. *Plant Mol Biol* 26:535-539.

Spencer et al. (1990) Bialaphos selection of stable transformants from maize cell cultures. *Theor Appl Genet* 79:625-631.

Svab & Maliga, (1993) High-frequency plastid transformation in tobacco by selection for a chimeric aadA gene. *Proc Natl Acad Sci USA* 90:913-917.

Svab et al. (1990) Stable transformation of plastids in higher plants. *Proc Natl Acad Sci USA* 87:8526-8530.

Tsuchiya et al. (1994) Molecular characterization of rice genes specifically expressed in the anther tapetum. *Plant Mol Biol* 26:1737-1746.

U.S. Patent Application Publication Nos. 2005/0060767; 2005/0246798; 2006/0260011; 2007/0004912; 2007/0006344; 2010/0205692; 2012/0021506; 2012/0036593.

U.S. Pat. Nos. 4,945,050; 4,940,935; 5,036,006; 5,100,792; 5,188,642; 5,268,463; 5,276,268; 5,399,680; 5,466,785; 5,569,597; 5,561,236; 5,589,610; 5,591,616; 5,604,121; 5,608,142; 5,608,144; 5,608,149; 5,639,948; 5,641,876; 5,659,026; 5,767,378; 5,994,629; 6,072,050; 6,177,611; 7,151,201; 7,166,770; 7,253,340; 7,550,578; 8,168,859.

Uknes et al. (1993) Regulation of pathogenesis-related protein-la gene expression in tobacco. *Plant Cell* 5:159-169.

Urao et al. (1996) Molecular cloning and characterization of a gene that encodes a MYC-related protein in *Arabidopsis. Plant Mol Biol* 32:571-576.

Vasil et al. (1992) Herbicide resistant fertile transgenic wheat plants obtained by microprojectile bombardment of regenerable embryogenic callus. *Nature Biotechnol* 10:667-674.

Vasil et al. (1993) Rapid production of transgenic wheat plants by direct bombardment of cultured immature embryos. *Nature Biotechnol* 11:1553-1558.

Velten et al. (1984) Isolation of a dual plant promoter fragment from the Ti plasmid of *Agrobacterium tumefaciens. EMBO J* 3:2723-2730.

Viera & Messing (1982) The pUC plasmids, an M13mp7-derived system for insertion mutagenesis and sequencing with synthetic universal primers. *Gene* 19:259-268.

Vos et al. (1995) AFLP: a new technique for DNA fingerprinting. *Nucleic Acids Res* 23:4407-4414.

Weeks et al. (1993) Rapid production of multiple independent lines of fertile transgenic wheat (*Triticum aestivum*). *Plant Physiol* 102:1077-1084.

Wei et al. (2003) Comparative expression analysis of two sugarcane polyubiquitin promoters and flanking sequences in transgenic plants. *J Plant Physiol* 160:1241-1251.

Welsh (1981) *Fundamentals of Plant Genetics and Breeding*, John Wiley & Sons, New York, New York, United States of America.

White et al. (1990) A cassette containing the bar gene of *S. hygroscopicus*: a selectable marker for plant transformation. *Nucl Acids Res* 18:1062.

Wood (ed) (1983) *Crop Breeding*, American Society of Agronomy, Madison, Wisconsin, United States of America.

Wricke & Weber (1986) *Quantitative Genetics and Selection Plant Breeding*, Walter de Gruyter and Co., Berlin, Germany.

Yang et al. (2010) Nnuclearlly-targeted expression of a haploid induction-associated orf220 gene causes male sterility in *Brassica juncea. BMC Plant Biol* 10:231.

Zhang & Glaser (2002) Interaction of plant nnuclearl and chloroplast signal peptides with the Hsp70 molecular chaperone. *Trends Plant Sci* 7:14-21.

Zhang, Z. L., F. Z. Qiu, Y. Z. Liu, K. J. Ma, Z. Y. Li et al., 2008 Chromosome elimination and in vivo haploid induction by stock 6-derived inducer line in maize (*Zea mays* L.). Plant Cell Rep. 27: 1851-1860.

Zhang et al. (1988) Transgenic rice plants produced by electroporation-mediated plasmid uptake into protoplasts. *Plant Cell Rep* 7:379-384.

Zhang et al. (1996) DNA sequences that activate isocitrate lyase gene expression during late embryogenesis and during postgerminative growth. *Plant Physiol* 110:1069-1079.

Zhong et al. (1996) The circadian clock gates expression of two *Arabidopsis* catalase genes to distinct and opposite circadian phases. *Mol Gen Genet* 251:196-203.

It will be understood that various details of the presently disclosed subject matter may be changed without departing from the scope of the presently disclosed subject matter. Furthermore, the foregoing description is for the purpose of illustration only, and not for the purpose of limitation.

What is claimed:

1. Method of creating a new haploid inducer plant with a silenced patatin-like phospholipase 2A, comprising transcribing a polynucleotide sequence that silences the patatin-like phospholipase 2A in maize, wherein said polynucleotide sequence is selected from the group consisting of:

a) a polynucleotide sequence comprising the nucleic acid sequence set forth in SEQ ID NO: 53 or the complement thereof:

b) a functional fragment comprising at least 22 contiguous nucleotides of SEQ ID NO: 53 or the complement thereof, and c) a polynucleotide sequence having at least 95% sequence identity as determined using the BLASTN alignment tool to the nucleic acid sequence set forth in SEQ ID NO: 53 or the complement thereof, and a second sequence that is the complement of the first sequence, wherein the polynucleotide sequence expresses a double-stranded ribonucleotide sequence which silences the patatin-like phospholipase 2A when contacted with a maize plant and thus creates a new haploid inducer maize plant.

2. The method of claim 1, wherein the contacting is achieved by transforming the plant with a polynucleotide sequence which when expressed produces a double-stranded ribonucleotide sequence that silences the patatin-like phospholipase 2A.

* * * * *